US008426184B2

(12) United States Patent
Blum et al.

(10) Patent No.: US 8,426,184 B2
(45) Date of Patent: Apr. 23, 2013

(54) CELLULASES, NUCLEIC ACIDS ENCODING THEM AND METHODS FOR MAKING AND USING THEM

(75) Inventors: David Blum, Nashville, TN (US); Joslin Gemsch Cuenca, San Diego, CA (US); Mark Dycaico, San Diego, CA (US)

(73) Assignees: BP Corporation North America, Houston, TX (US); Verenium Corporation, San Diego, CA (US)

(*) Notice: Subject to any disclaimer, the term of this patent is extended or adjusted under 35 U.S.C. 154(b) by 769 days.

(21) Appl. No.: 11/908,672

(22) PCT Filed: Jan. 13, 2006

(86) PCT No.: PCT/US2006/002516
§ 371 (c)(1),
(2), (4) Date: Sep. 21, 2009

(87) PCT Pub. No.: WO2006/101584
PCT Pub. Date: Sep. 28, 2006

(65) Prior Publication Data
US 2010/0003234 A1    Jan. 7, 2010

Related U.S. Application Data

(60) Provisional application No. 60/662,224, filed on Mar. 15, 2005.

(51) Int. Cl.
| C12N 9/42 | (2006.01) |
| C12N 9/14 | (2006.01) |
| C12N 15/00 | (2006.01) |
| C12N 1/20 | (2006.01) |
| C12P 21/06 | (2006.01) |
| C12P 19/00 | (2006.01) |
| C12P 7/06 | (2006.01) |
| A62D 3/00 | (2007.01) |
| C07H 21/04 | (2006.01) |
| A61K 38/47 | (2006.01) |
| A23C 17/00 | (2006.01) |
| A01H 5/00 | (2006.01) |

(52) U.S. Cl.
USPC ......... 435/209; 435/195; 435/69.1; 435/91.1; 435/320.1; 435/252.3; 435/254.11; 435/262.5; 435/72; 435/161; 536/23.1; 536/23.2; 530/350; 530/387.1; 424/94.61; 424/94.1; 424/130.1; 426/11; 426/16; 426/42; 800/278; 800/298

(58) Field of Classification Search ............... 435/209, 435/195, 69.1, 91.1, 320.1, 252.3, 254.11, 435/262.5, 72, 161; 536/23.1, 23.2; 530/350, 530/387.1; 424/94.61, 94.1, 130.1; 426/11, 426/16, 42; 800/278, 298
See application file for complete search history.

(56) References Cited

U.S. PATENT DOCUMENTS

| 4,788,066 | A | 11/1988 | Witt |
| 5,582,681 | A | 12/1996 | Back |
| 5,705,369 | A | 1/1998 | Torget |
| 5,709,796 | A | 1/1998 | Fuqua et al. |
| 5,747,320 | A | 5/1998 | Saha |
| 5,795,766 | A | 8/1998 | Suzuki |
| 5,833,857 | A | 11/1998 | Roth |
| 5,958,758 | A | 9/1999 | Miller |
| 5,973,228 | A | 10/1999 | Carlson |
| 6,022,725 | A | 2/2000 | Fowler |
| 6,066,233 | A | 5/2000 | Olsen |
| 6,077,316 | A | 6/2000 | Lund et al. |
| 6,087,131 | A | 7/2000 | Gunata |
| 6,090,595 | A | 7/2000 | Foody |
| 6,127,160 | A | 10/2000 | Yamanobe |
| 6,184,018 | B1 | 2/2001 | Li |
| 6,241,849 | B1 | 6/2001 | Franks |
| 6,251,643 | B1 | 6/2001 | Hansen |
| 6,409,841 | B1 | 6/2002 | Lombard |
| 6,423,145 | B1 | 7/2002 | Nguyen |
| 6,423,524 | B1 | 7/2002 | Hagen |
| 6,566,113 | B1 | 5/2003 | Takayama |
| 6,602,700 | B1 | 8/2003 | Li |
| 6,660,506 | B2 | 12/2003 | Nguyen |
| 6,921,655 | B1 | 7/2005 | Nakamura |

(Continued)

FOREIGN PATENT DOCUMENTS

| RU | 2127760 | 3/1999 |
| WO | WO 99/57325 | 11/1999 |

(Continued)

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Harjunpaa—Eur. J. Biochem (1996)—240—584-591.

(Continued)

*Primary Examiner* — Ganapathirama Raghu
(74) *Attorney, Agent, or Firm* — Kalim S. Fuzail

(57) ABSTRACT

This invention relates to molecular and cellular biology and biochemistry. In one aspect, the invention provides polypeptides having cellulase activity, e.g., endoglucanase, cellobiohydrolase, mannanase and/or β-glucosidase activity, polynucleotides encoding these polypeptides, and methods of making and using these polynucleotides and polypeptides. In one aspect, the invention is directed to polypeptides cellulase activity, e.g., endoglucanase, cellobiohydrolase, mannanase and/or β-glucosidase activity, including thermostable and thermotolerant activity, and polynucleotides encoding these enzymes, and making and using these polynucleotides and polypeptides. The polypeptides of the invention can be used in a variety of pharmaceutical, agricultural, food and feed processing and industrial contexts.

17 Claims, 15 Drawing Sheets

U.S. PATENT DOCUMENTS

| | | | |
|---|---|---|---|
| 6,979,733 | B2 | 12/2005 | Zhao |
| 7,129,069 | B2 | 10/2006 | Borchert |
| 7,220,542 | B2 | 5/2007 | Van Den Brink |
| 7,393,673 | B2 | 7/2008 | Adney |
| 2003/0233675 | A1 | 12/2003 | Cao |
| 2006/0147581 | A1 | 7/2006 | Svendsen |
| 2006/0257984 | A1 | 11/2006 | Borchert |

FOREIGN PATENT DOCUMENTS

| | | |
|---|---|---|
| WO | WO 01/70998 | 9/2001 |
| WO | WO 02/24882 | 3/2002 |
| WO | WO 02/099091 | 12/2002 |
| WO | WO 03/000941 | 1/2003 |
| WO | WO 03/012109 | 2/2003 |
| WO | WO 03/093420 | 11/2003 |
| WO | WO 2004/016760 | 2/2004 |
| WO | WO 2004/078919 | 9/2004 |
| WO | WO 2004/081185 | 9/2004 |
| WO | WO 2005/003319 | 1/2005 |
| WO | WO 2006/101584 | 9/2006 |
| WO | WO 01/70998 | 9/2010 |

OTHER PUBLICATIONS

Himmel—Curr. Opin. Biotechnol (1999)—10—358-364.
Zverlov—Microbiology (2002)—148—247-255.
Baker—J. Biochem. Biophys Methods (1991)—4—265-273.
Sharrock—J. Biochem. Biophys. Methods (1988)—2—81-105.
Carder—Anal. Biochem. (1986)—1—75-79.
Canevascini—Anal. Biochem. (1985)—2—419-27.
Huang—Anal. Biochem. (1976)—2—369-377.
PCT/US2006/046919—ISR & WO—Apr. 8, 2008.
Baker—Applied Biochemistry and Biotechnology (1994)—45-46—245-256.
Irwin—Biotechnology and Bioengineering (1993)—42—1002-1013.
Irwin—Journal of Bacteriology (1998)—180—1709-1714.
Johnston—Journal of Food Biochemistry (1998)—22—301-319.
Klyosov—Biochemistry (1990)—29—10577-10585.
Medve—Biotechnology and Bioengineering—(1998)—59—621-634.
Murashima—Journal of Bacteriology (2003)—185—1518-1524.
Parry—Archives of Biochemistry and Biophysics (2002)—404—243-253.
Saha—J. Ind. Microbiol Biotechnol (2003)—30—279-291.
Shallom—Current Opinion in Microbiology (2003)—6—219-228.
Wood—Methods in Enzymology (1988)—160—87-116.
Zhang—Biotechnology and Bioengineering (2004)—88—797-824.
Leibovitz—J. Bacteriol.(1997)—179—2519-2523.
Leibovitz—J. Bacteriol. (1996)—178—3077-3084.
Charnock—J. Biol. Chem. (1998)—273—32187-32199.
Coutinho—Recent Advances in Carbohydrate Bioeng. (1999)—3-12.
Coutinho—The modular structure of cellulases and other carbohydrate-active enzymes: an integrated database approach. "Genetics, Biochemistry and Ecology of Cellulose Degradation" (1999) K. Ohmiya, et al., eds., Uni Publishers Co., Tokyo, pp. 15-23.
Guttman—Anal. Biochem. (1996)—233—234-242.
Altschul—Journal of Molecular Biology (1990)—215—403-410.
Lynd—Microbiol. and Molecular Biol. Reviews (2002)—66—506-577.
Kikuchi—Science (2003)—301—376-379.
Sposato—Mol. Plant. Microbe Interact. (1995)—8—602-609.
Grabnitz et al., "Structure of the B-glucosidase gene bglA of Clostridium thermocellum" Eur. J. Biochem. (1991) 200:301-309.
Liebl et al. "Comparative amino acid sequence analysis of Thermotoga maritima B-glucosidase (BgIA) . . . " Mol. Gen. Genet. (1994) 242:111-115.

Mackenzie et al. "Crystal structure of the family 7 endoglucanase I (CeI7B) from Humicola insolens . . . " Biochem J. (1998) 335:409-416.
Sakon et al. "Structure and mechanism of endo/exocellulase E4 from Thermomonospora fusca" Nat. Struc. Biol. (1997) 4:810-818.
Varrot et al. "Crystal structure of the catalytic core domain of the family 6 cellobiohydrolase II, CeI6A, from Humicola insolens . . . " Biochem J. (1999) 337:297-304.
CIPO—Jan. 12, 2010—First Office Action—2,529,403.
EP06845040—Supplementary EP Search Report—Jul. 14, 2009.
EMBL Accession No. AY690482 (Aug. 23, 2004)—*Penicillium occitanis* cellobiohydrolase I gene.
UNIPROT Accession No. Q68HC2 (Oct. 11, 2004)—Cellobiohydrolase.
GENESEQ Accession No. AAF85588 (Jun. 25, 2001)—*Acremonium cellulolyticus* cellbiohydrolaseI.
GENESEQ Accession No. AAB81926 (Jun. 25, 2001)—*Acremonium cellulolyticus* cellobiohydrolaseI.
Demain—Microbiology and Molecular Biology Reviews (2005)—69—124-154.
Lin—Applied Microbiology and Biotechnology (2006)—69—627-642.
Lynd—Current Opinion in Biotechnology (2005)—16—577-583.
Doi—Chemical Record (2001)—1—24-32.
Poole—Mol Gen Genet (1990)—223—217-223.
USPTO—May 11, 2010—Office Action—U.S. Appl. No. 10/560,957.
Chica—Curr. Opin. Biotechnol. (2005)—16—378-384.
Witkowski—Biochemistry (1999)—38—11643-11650.
Seffernick—J. Bacteriol. (2001)—183—2405-2410.
JPO—May 10, 2010—Office Action—2006-518822.
Genbank Accession No. AAB42155 (Dec. 15, 2003).
Genbank Accession No. AAB61461 (Jan. 27, 2000).
Genbank Accession No. BAA74515 (May 5, 2010).
Wang—Molecular Genetics and Metabolism (1990)—222—265-269.
EA201000255—EAPO Search Report—May 5, 2010.
EP06733858—EP Supplementary Search Report—Nov. 6, 2009.
GENESEQ Accession No. ADQ79701 *Thermus filiformis*—Cho (2004).
UNIPROT Accession No. Q08638—Beta Glucosidase (1994).
UNIPROT Accession No. Q82M59—*Streptomyces avermitilis* (2003).
EP07875173—Supplemental EP Search Report—Nov. 12, 2009.
UNIPROT Accession No. 09X273—Endoglucanase—Nov. 1, 1999.
Gunnarsson—Protein Engineering Design and Selection (2004)—17(3)—213-221.
Tomme—FEBS Lett (1989)—243—239-243.
Gilkes—J. Biol. Chem. (1988)—263—10401-10407.
Tomme—Enzymatic Degradation of Insoluble Polysaccharides (1995, Saddler, J.N. & Penner; M., eds.)—142-163.
Henrissat—Curr. Op. Struct, Biol. (1997)—7—637-644.
Coutinho—J. Mol. Biol. (2003)—328—307-317.
Boraston—Biochem. J. (2004)—382—769-781.
Gunnarsson—Glycobiology (2006)—16—1171-1180.
Murashima—Jornal of Bacteriology (2005)—187—20—7146-7149.
Pages—Journal of Bacteriology (1996)—178—8—2279-2286.
Kakiuchi—Journal of Bacteriology (1998)—180—16—4303-4308.
Genbank Accession No. P23660—Endoglucanase (1991).
PCT/US2004/021492—ISR & WO—Jul. 25, 2008.
EP04777548—Supplementary EP Search Report—Apr. 27, 2009.

* cited by examiner

Figure 5 structure of cellobiose

Figure 6. TLC analysis of reaction products from cellohexaose

Figure 7. TLC analysis of reaction products from cellohexaose

Figure 8. Release of cellobiose from PASC by enzyme 22/22a

Figure 9. Release of cellobiose from Avicel MCC by CBH

CELLULASES, NUCLEIC ACIDS ENCODING THEM AND METHODS FOR MAKING AND USING THEM

CROSS-REFERENCE TO RELATED APPLICATIONS

This application is a national stage application claiming benefit of priority under 35 U.S.C. §371 to Patent Convention Treaty (PCT) International Application No. PCT/US2006/002516, filed Jan. 13, 2006 (published as WO 2006/101584, on Sep. 28, 2006), which claims the benefit of priority to U.S. Provisional Patent Application No. 60/662,224, filed Mar. 15, 2005. The aforementioned applications are explicitly incorporated herein by reference in their entirety and for all purposes.

GOVERNMENT SUPPORT

This invention was made with United States Government support under Contract Nos. DE-FG03-02ER83395 and DE-FG02-03ER83865, awarded by the Department of Energy. The Government has certain rights in this invention.

FIELD OF THE INVENTION

This invention relates to molecular and cellular biology and biochemistry. In one aspect, the invention provides polypeptides having cellulase activity, e.g., endoglucanase, cellobiohydrolase, mannanase and/or β-glucosidase activity, polynucleotides encoding these polypeptides, and methods of making and using these polynucleotides and polypeptides. In one aspect, the invention is directed to polypeptides having cellulase activity, e.g., endoglucanase, cellobiohydrolase, mannanase and/or β-glucosidase activity, including thermostable and thermotolerant activity, and polynucleotides encoding these enzymes, and making and using these polynucleotides and polypeptides. The polypeptides of the invention can be used in a variety of pharmaceutical, agricultural and industrial contexts.

BACKGROUND

Cellulose is the most abundant renewable resource on earth. It is composed of a linear chain of β 1-4 glucose units with the repeating unit being cellobiose, which is a glucose dimer having a structure as shown in FIG. 5. The polymer is degraded by a suite of enzymes which include endoglucanases (EG) which randomly hydrolyze the cellulose polymer, and cellobiohydrolases (CBH) which remove terminal cellobiose residues from cellulose. Cellobiose and cello-oligosaccharides are hydrolyzed to glucose by β-glucosidases (BG). All three of these enzymes are necessary for the complete breakdown of cellulose to glucose. For each of these three enzymes different structural variants exist that perform the same function. In addition, fungi and bacteria are known to produce multiple forms of the same structural variants in addition to different structural variants.

Further complicating this system is the fact that some anaerobic bacteria and fungi are known to produce these enzymes in multi-enzyme complexes which contain multiple enzymes all attached to an enzyme scaffold with molecular weights above 2 million daltons. Why is such a complex system of enzymes necessary for such a simple molecule? Some researchers believe that this complexity is due to the recalcitrant nature of the substrate. The cellulose chains form microfibrils that pack into a crystalline matrix via hydrogen bonding of adjacent chains. This structure is highly resistant to chemical or enzymatic degradation.

CBHs are thought to be the key enzyme in the degradation of this crystalline cellulose because of the nature of their enzymatic attack on cellulose. EGs unlike CBHs have an open cleft that attacks the cellulose chain at a perpendicular angle. CBHs attack the chain directly via a tunnel containing the active site. The current thought is that the cellulose chains enter the tunnel and at the same time, adjacent hydrogen bonding is disrupted. Once the cellobiohydrolases have established this "foothold" on the substrate, the EGs can then come in and more readily attack the substrate.

A major deficiency of known CBHs is their low catalytic activity. Some groups argue that the low activity stems from the fact that energy from hydrolysis is transferred to kinetic energy to disrupt hydrogen bonds and enable the enzyme to move along the substrate. CBHs are exo-acting enzymes and are found in 6 of the 90 families of glycosyl hydrolases. They include families 5, 6, 7, 9, 10 and 48. Family 5 contains many different types of glycosyl hydrolases including cellulases, mannanases and xylanases. Although most cellulases in this family are endoglucanases, there are examples of cellobiohydrolases, most notably CelO from *Clostridium thermocellum*. Family 6 contains only endoglucanases or cellobiohydrolases with more cellobiohydrolase members than endoglucanases. The enzymes have an inverting mechanism and crystallographic studies suggest that the enzyme has a distorted α/β barrel structure containing seven, not eight parallel β-strands. Family 7 enzymes are also composed of both endoglucanases and cellobiohydrolases with more cellobiohydrolases and only known members are from fungi. The enzyme has a retaining mechanism and the crystal structure suggests a β-jellyroll structure. Family 9 contains endoglucanases, cellobiohydrolases and β-glucosidases with a preponderance of endoglucanases. However, *Thermobifida fusca* produces an endo/exo-1,4-glucanase, the crystal structure of which suggests a $(\alpha/\alpha)_6$ barrel fold. The enzyme has characteristics of both endo and exo-glucanases CBHs. Family 10 contains only 2 members described as cellobiohydrolases with mainly the rest described as xylanases. Cellobiohydrolases and xylanases from family 10 have activity on methyl-umbelliferyl cellobioside. Family 48 contains mainly bacterial and anaerobic fungal cellobiohydrolases and endoglucanases. The structure is a $(\alpha/\alpha)_6$ barrel fold similar to family 9.

There is a need for less expensive and renewable sources of fuel for road vehicles. New fuel sources will be more attractive if they produce nonharmful endproducts after combustion. Ethanol offers an attractive alternative to petroleum based fuels and can be obtained through the fermentation of monomeric sugars derived from starch or lignocellulose. However, current economics do not support the widespread use of ethanol due to the high cost of generating it. One area of research aimed at decreasing costs is enhancement of the technical efficacy of the enzymes that can be used to generate fermentable sugars from lignocellulose. The development of enzymes that more efficiently digest feedstock will translate to decreased ethanol production costs. More efficient processes will decrease the United State's reliance on foreign oil and the price fluctuations that may be related to that reliance. Using cleaner fuels for transportation like bioethanol also may decrease net $CO_2$ emissions that are believed to be partially responsible for global warming.

SUMMARY

The invention provides cellulases, e.g., endoglucanases, cellobiohydrolases and/or β-glucosidase (beta-glucosidases), and methods for making and using them. In one aspect, the enzymes of the invention have an increased catalytic rate to improve the process of substrate hydrolysis. This increased efficiency in catalytic rate leads to an increased efficiency in producing sugars, which can be useful in industrial applications, e.g., the sugars so produced can be used by microorganisms for ethanol production. In one aspect, the invention provides highly active (e.g., having an increased catalytic rate) cellobiohydrolases, endoglucanases and beta-glucosidase. The invention provides industrial applications (e.g., biomass to ethanol) using enzymes of the invention having decreased enzyme costs, e.g., decreased costs in biomass to ethanol processes. Thus, the invention provides efficient processes for producing bioethanol and bioethanol-comprising compositions, including fuels comprising bioethanol, from any biomass.

In one aspect, the enzymes of the invention have a glucanase, e.g., an endoglucanase, activity, e.g., catalyzing hydrolysis of internal endo-β-1,4- and/or β-1,3-glucanase linkages. In one aspect, the endoglucanase activity (e.g., endo-1,4-beta-D-glucan 4-glucano hydrolase activity) comprises hydrolysis of 1,4- and/or β-1,3-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans or xyloglucans and other plant material containing cellulosic parts.

In one aspect, the enzymes of the invention have endoglucanase (e.g., endo-beta-1,4-glucanases, EC 3.2.1.4; endo-beta-1,3(1)-glucanases, EC 3.2.1.6; endo-beta-1,3-glucanases, EC 3.2.1.39) activity and can hydrolyze internal β-1,4- and/or β-1,3-glucosidic linkages in cellulose and glucan to produce smaller molecular weight glucose and glucose oligomers. The invention provides methods for producing smaller molecular weight glucose and glucose oligomers using these enzymes of the invention.

In one aspect, the enzymes of the invention are used to generate glucans, e.g., polysaccharides formed from 1,4-β- and/or 1,3-glycoside-linked D-glucopyranose. In one aspect, the endoglucanases of the invention are used in the food industry, e.g., for baking and fruit and vegetable processing, breakdown of agricultural waste, in the manufacture of animal feed, in pulp and paper production, textile manufacture and household and industrial cleaning agents. In one aspect, the enzymes, e.g., endoglucanases, of the invention are produced by a microorganism, e.g., by a fungi and/or a bacteria.

In one aspect, the enzymes, e.g., endoglucanases, of the invention are used to hydrolyze beta-glucans (β-glucans) which are major non-starch polysaccharides of cereals. The glucan content of a polysaccharide can vary significantly depending on variety and growth conditions. The physicochemical properties of this polysaccharide are such that it gives rise to viscous solutions or even gels under oxidative conditions. In addition glucans have high water-binding capacity. All of these characteristics present problems for several industries including brewing, baking, animal nutrition. In brewing applications, the presence of glucan results in wort filterability and haze formation issues. In baking applications (especially for cookies and crackers), glucans can create sticky doughs that are difficult to machine and reduce biscuit size. Thus, the enzymes, e.g., endoglucanases, of the invention are used to decrease the amount of β-glucan in a β-glucan-comprising composition, e.g., enzymes of the invention are used in processes to decrease the viscosity of solutions or gels; to decrease the water-binding capacity of a composition, e.g., a β-glucan-comprising composition; in brewing processes (e.g., to increase wort filterability and decrease haze formation), to decrease the stickiness of doughs, e.g., those for making coolies, breads, biscuits and the like.

In addition, carbohydrates (e.g., β-glucan) are implicated in rapid rehydration of baked products resulting in loss of crispiness and reduced shelf-life. Thus, the enzymes, e.g., endoglucanases, of the invention are used to retain crispiness, increase crispiness, or reduce the rate of loss of crispiness, and to increase the shelf-life of any carbohydrate-comprising food, feed or drink, e.g., a β-glucan-comprising food, feed or drink.

Enzymes, e.g., endoglucanases, of the invention are used to decrease the viscosity of gut contents (e.g., in animals, such as ruminant animals, or humans), e.g., those with cereal diets. Thus, in alternative aspects, enzymes, e.g., endoglucanases, of the invention are used to positively affect the digestibility of a food or feed and animal (e.g., human or domestic animal) growth rate, and in one aspect, are used to higher generate feed conversion efficiencies. For monogastric animal feed applications with cereal diets, beta-glucan is a contributing factor to viscosity of gut contents and thereby adversely affects the digestibility of the feed and animal growth rate. For ruminant animals, these beta-glucans represent substantial components of fiber intake and more complete digestion of glucans would facilitate higher feed conversion efficiencies. Accordingly, the invention provides animal feeds and foods comprising endoglucanases of the invention, and in one aspect, these enzymes are active in an animal digestive tract, e.g., in a stomach and/or intestine.

Enzymes, e.g., endoglucanases, of the invention are used to digest cellulose or any beta-1,4-linked glucan-comprising synthetic or natural material, including those found in any plant material. Enzymes, e.g., endoglucanases, of the invention are used as commercial enzymes to digest cellulose, e.g., in the wood processing, pulp and/or paper industry, in textile manufacture and in household and industrial cleaning agents, and/or in biomass waste processing.

In one aspect the invention provides compositions (e.g., pharmaceutical compositions, foods, feeds, drugs, dietary supplements) comprising the enzymes, polypeptides or polynucleotides of the invention. These compositions can be formulated in a variety of forms, e.g., as tablets, gels, pills, implants, liquids, sprays, powders, food, feed pellets or as any type of encapsulated form.

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, including SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163 and SEQ ID NO:165; see also Tables 1, 2, and 3, Examples 1 and 4, below, and Sequence Listing, over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues; and in alternative aspects, these nucleic acids encode at least one polypeptide having a cellulase activity, e.g., endoglucanase, cellobiohydrolase, mannanase and/or beta-glucosidase activity, or encode a polypeptide capable of generating an antibody that can specifically bind to a polypeptide of the invention, or, these nucleic acids can be used as probes for identifying or isolating cellulase-encoding nucleic acids, or to inhibit the expression of cellulase-expressing nucleic acids (all these aspects referred to as the "nucleic acids of the invention"). In one aspect, the sequence identities are determined by analysis with a sequence comparison algorithm or by a visual inspection.

Nucleic acids of the invention also include isolated or recombinant nucleic acids encoding an exemplary enzyme of the invention, including a polypeptide having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:143, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 and SEQ ID NO:166, see also Tables 1, 2, and 3, Examples 1 and 4, below, and the Sequence Listing, and subsequences thereof and variants thereof. In one aspect, the polypeptide has a cellulase activity, e.g., endoglucanase, cellobiohydrolase, mannanase and/or beta-glucosidase activity.

In one aspect, the invention provides cellulase-encoding, e.g., endoglucanase-, cellobiohydrolase- and/or beta-glucosidase-encoding nucleic acids having a common novelty in that they are derived from mixed cultures. The invention provides cellulose-degrading enzyme-encoding nucleic acids isolated from mixed cultures comprising a polynucleotide of the invention, e.g., a sequence having at least about 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:11, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163 and SEQ ID NO:165, and see Tables 1, 2, and 3, Examples 1 and 4, below, and Sequence Listing, over a region of at least about 50, 75, 100, 150, 200, 250, 300, 350, 400, 450, 500, 550, 600, 650, 700, 750, 800, 850, 900, 950, 1000, 1050, 1100, 1150, or more.

In one aspect, the invention provides cellulase enzyme-, e.g., endoglucanase enzyme-, cellobiohydrolase enzyme- and/or beta-glucosidase enzyme-encoding nucleic acids, including exemplary polynucleotide sequences of the invention, see also Tables 1, 2, and 3, Examples 1 and 4, below, and Sequence Listing, and the polypeptides encoded by them, including enzymes of the invention, e.g., exemplary polypeptides of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:143, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 or SEQ ID NO:166, see also Table 1 and Sequence Listing, having a common novelty in that they are derived from a common source, e.g., an environmental source. In one aspect, the invention also provides cellulase enzyme-, e.g., endoglucanase enzyme-, cellobiohydrolase enzyme- and/or beta-glucosidase enzyme-encoding nucleic acids with a common novelty in that they are derived from environmental sources, e.g., mixed environmental sources.

In one aspect, the sequence comparison algorithm is a BLAST version 2.2.2 algorithm where a filtering setting is set to blastall -p blastp -d "nr pataa" -F F, and all other options are set to default.

Another aspect of the invention is an isolated or recombinant nucleic acid including at least 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more consecutive bases of a nucleic acid sequence of the invention, sequences substantially identical thereto, and the sequences complementary thereto.

In one aspect, the isolated or recombinant nucleic acid encodes a polypeptide having a cellulase activity, e.g., endoglucanase, cellobiohydrolase, mannanase and/or beta-glucosidase activity, which is thermostable. The polypeptide can retain a cellulase activity under conditions comprising a temperature range of between about 37° C. to about 95° C.; between about 55° C. to about 85° C., between about 70° C. to about 95° C., or, between about 90° C. to about 95° C. The polypeptide can retain a cellulase activity in temperatures in the range between about 1° C. to about 5° C., between about 5° C. to about 15° C., between about 15° C. to about 25° C., between about 25° C. to about 37° C., between about 37° C. to about 95° C., 96° C., 97° C., 98° C. or 99° C., between about 55° C. to about 85° C., between about 70° C. to about 75° C., or between about 90° C. to about 99° C., or 95° C., 96° C., 97° C., 98° C. or 99° C., or more.

In another aspect, the isolated or recombinant nucleic acid encodes a polypeptide having a cellulase activity, e.g., endoglucanase, cellobiohydrolase, mannanase and/or beta-glucosidase activity, which is thermotolerant. The polypeptide can retain a cellulase activity after exposure to a temperature in the range from greater than 37° C. to about 95° C. or anywhere in the range from greater than 55° C. to about 85° C. The polypeptide can retain a cellulase activity after exposure to a temperature in the range between about 1° C. to about 5° C., between about 5° C. to about 15° C., between about 15° C. to about 25° C., between about 25° C. to about 37° C., between about 37° C. to about 95° C., 96° C., 97° C., 98° C. or 99° C., between about 55° C. to about 85° C., between about 70° C. to about 75° C., or between about 90° C. to about 95° C., or more. In one aspect, the polypeptide retains a cellulase activity after exposure to a temperature in the range from greater than 90° C. to about 99° C., or 95° C., 96° C., 97° C., 98° C. or 99° C., at about pH 4.5, or more.

The invention provides isolated or recombinant nucleic acids comprising a sequence that hybridizes under stringent conditions to a nucleic acid of the invention, including an exemplary sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO: 83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163 or SEQ ID NO:165 (see also Tables 1, 2, and 3, Examples 1 and 4, below), or fragments or subsequences thereof. In one aspect, the nucleic acid encodes a polypeptide having a cellulase activity, e.g., endoglucanase, cellobiohydrolase, mannanase and/or beta-glucosidase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In one aspect, the stringent conditions comprise a wash step comprising a wash in 0.2×SSC at a temperature of about 65° C. for about 15 minutes.

The invention provides a nucleic acid probe for identifying or isolating a nucleic acid encoding a polypeptide having a cellulase activity, e.g., endoglucanase, cellobiohydrolase, mannanase and/or beta-glucosidase activity, wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, or fragments or subsequences thereof.

The invention provides a nucleic acid probe for identifying or isolating a nucleic acid encoding a polypeptide having a cellulase activity, e.g., endoglucanase, cellobiohydrolase, mannanase and/or beta-glucosidase activity, wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues of a nucleic acid of the invention, e.g., a polynucleotide having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention. In one aspect, the sequence identities are determined by analysis with a sequence comparison algorithm or by visual inspection. In alternative aspects, the probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

The invention provides an amplification primer pair for amplifying (e.g., by PCR) a nucleic acid encoding a polypeptide having a cellulase activity, e.g., endoglucanase, cellobiohydrolase, mannanase and/or beta-glucosidase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50, or more, consecutive bases of the sequence, or about 10, 11, 12, 13, 14, 15, 16, 17, 18, 19, 20, 21, 22, 23, 24, 25, 26, 27, 28, 29, 30, 31, 32, 33, 34, 35, 36 or more consecutive bases of the sequence. The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36 or more residues of the complementary strand of the first member.

The invention provides cellulase-encoding, e.g., endoglucanase-, cellobiohydrolase- and/or beta-glucosidase-encoding nucleic acids generated by amplification, e.g., polymerase chain reaction (PCR), using an amplification primer pair of the invention. The invention provides cellulase-encoding, e.g., endoglucanase-, cellobiohydrolase- and/or beta-glucosidase-encoding nucleic acids generated by amplification, e.g., polymerase chain reaction (PCR), using an amplification primer pair of the invention. The invention provides methods of making a cellulase, e.g., endoglucanase, cellobiohydrolase, mannanase and/or beta-glucosidase enzyme by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having a cellulase activity, e.g., endoglucanase, cellobiohydrolase, mannanase and/or beta-glucosidase activity comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be soybeans, rapeseed, oilseed, tomato, cane sugar, a cereal, a potato, wheat, rice, corn, tobacco or barley cell.

The invention provides transgenic non-human animals comprising a nucleic acid of the invention or an expression cassette (e.g., a vector) of the invention. In one aspect, the animal is a mouse, a rat, a pig, a goat or a sheep.

The invention provides transgenic plants comprising a nucleic acid of the invention or an expression cassette (e.g., a vector) of the invention. The transgenic plant can be a cereal plant, a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid of the invention or an expression cassette (e.g., a vector) of the invention. The transgenic seed can be a cereal plant, a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of a cellulase, e.g., endoglucanase, cellobiohydrolase, mannanase and/or beta-glucosidase enzyme message in a cell comprising administering to the cell or expressing in the cell an antisense oligonucleotide comprising a nucleic acid sequence complementary to or capable of hybridizing under stringent conditions to a nucleic acid of the invention. In one aspect, the antisense oligonucleotide is between about 10 to 50, about 20 to 60, about 30 to 70, about 40 to 80, or about 60 to 100 bases in length, e.g., 10, 15, 20, 25, 30, 35, 40, 45, 50, 55, 60, 65, 70, 75, 80, 85, 90, 95, 100 or more bases in length. The invention provides methods of inhibiting the translation of a cellulase enzyme, e.g., endoglucanase, cellobiohydrolase, mannanase and/or beta-glucosidase enzyme message in a cell comprising administering to the cell or expressing in the cell an antisense oligonucleotide comprising a nucleic acid sequence complementary to or capable of hybridizing under stringent conditions to a nucleic acid of the invention.

The invention provides double-stranded inhibitory RNA (RNAi, or RNA interference) molecules (including small interfering RNA, or siRNAs, for inhibiting transcription, and microRNAs, or miRNAs, for inhibiting translation) comprising a subsequence of a sequence of the invention. In one aspect, the siRNA is between about 21 to 24 residues, or, about at least 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100 or more duplex nucleotides in length. The invention provides methods of inhibiting the expression of a cellulase enzyme, e.g., endoglucanase, cellobiohydrolase, mannanase and/or beta-glucosidase enzyme in a cell comprising administering to the cell or expressing in the cell a double-stranded inhibitory RNA (siRNA or miRNA), wherein the RNA comprises a subsequence of a sequence of the invention.

The invention provides isolated or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 10, 15, 20, 25, 30, 35, 40, 45, 50, 55, 60, 65, 70, 75, 80, 85, 90, 95, 100, 125, 150, 175, 200, 225, 250, 275, 300, 325, 350 or more residues, or over the full length of the polypeptide. In one aspect, the sequence identities are determined by analysis with a sequence comparison algorithm or by a visual inspection. Exemplary polypeptide or peptide sequences of the invention include SEQ ID NO:2, SEQ ID NO:4, SEQ ID NO:6, SEQ ID NO: 8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:143, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 and SEQ ID NO:166 (see also Tables 1, 2, and 3, Examples 1 and 4, below, and Sequence Listing), and subsequences thereof and variants thereof. Exemplary polypeptides also include fragments of at least about 10, 15, 20, 25, 30, 35, 40, 45, 50, 75, 80, 85, 90, 95, 100, 150, 200, 250, 300, 350, 400, 450, 500, 550, 600 or more residues in length, or over the full length of an enzyme. Polypeptide or peptide sequences of the invention include sequence encoded by a nucleic acid of the invention. Polypeptide or peptide sequences of the invention include polypeptides or peptides specifically bound by an antibody of the invention (e.g., epitopes), or polypeptides or peptides that can generate an antibody of the invention (e.g., an immunogen).

In one aspect, a polypeptide of the invention has at least one cellulase enzyme, e.g., endoglucanase, cellobiohydrolase, mannanase and/or beta-glucosidase enzyme activity. In alternative aspects, a polynucleotide of the invention encodes a polypeptide that has at least one cellulase enzyme, e.g., endoglucanase, cellobiohydrolase, mannanase and/or beta-glucosidase enzyme activity.

In one aspect, the cellulase, e.g., endoglucanase, cellobiohydrolase, mannanase and/or beta-glucosidase enzyme activity is thermostable. The polypeptide can retain a cellulase, e.g., endoglucanase, cellobiohydrolase, mannanase and/or beta-glucosidase enzyme activity under conditions comprising a temperature range of between about 1° C. to about 5° C., between about 5° C. to about 15° C., between about 15° C. to about 25° C., between about 25° C. to about 37° C., between about 37° C. to about 95° C., between about 55° C. to about 85° C., between about 70° C. to about 75° C., or between about 90° C. to about 95° C., or more. In another aspect, the cellulase, e.g., endoglucanase, cellobiohydrolase, mannanase and/or beta-glucosidase enzyme activity can be thermotolerant. The polypeptide can retain a cellulase, e.g., endoglucanase, cellobiohydrolase, mannanase and/or beta-glucosidase enzyme activity after exposure to a temperature in the range from greater than 37° C. to about 95° C., or in the range from greater than 55° C. to about 85° C. In one aspect, the polypeptide can retain a cellulase, e.g., endoglucanase, cellobiohydrolase, mannanase and/or beta-glucosidase enzyme activity after exposure to a temperature in the range from greater than 90° C. to about 95° C. at pH 4.5.

Another aspect of the invention provides an isolated or recombinant polypeptide or peptide comprising at least 10, 15, 20, 25, 30, 35, 40, 45, 50, 55, 60, 65, 70, 75, 80, 85, 90, 95, 100, 125, 150 or more consecutive bases of a polypeptide or peptide sequence of the invention, sequences substantially identical thereto, and the sequences complementary thereto. The peptide can be, e.g., an immunogenic fragment, a motif (e.g., a binding site), a signal sequence, a prepro sequence or an active site.

The invention provides isolated or recombinant nucleic acids comprising a sequence encoding a polypeptide having a cellulase, e.g., endoglucanase, cellobiohydrolase, mannanase and/or beta-glucosidase enzyme activity and a signal sequence, wherein the nucleic acid comprises a sequence of the invention. The signal sequence can be derived from another cellulase, e.g., endoglucanase, cellobiohydrolase, mannanase and/or beta-glucosidase enzyme or a non-cellulase, e.g., non-endoglucanase, non-cellobiohydrolase and/or non-beta-glucosidase enzyme (a heterologous) enzyme. The invention provides isolated or recombinant nucleic acids comprising a sequence encoding a polypeptide having a cellulase, e.g., endoglucanase, cellobiohydrolase, mannanase and/or beta-glucosidase enzyme activity, wherein the sequence does not contain a signal sequence and the nucleic acid comprises a sequence of the invention. In one aspect, the invention provides an isolated or recombinant polypeptide comprising a polypeptide of the invention lacking all or part of a signal sequence. In one aspect, the isolated or recombinant polypeptide can comprise the polypeptide of the invention comprising a heterologous signal sequence, such as a heterologous cellulase, e.g., endoglucanase, cellobiohydrolase, mannanase and/or beta-glucosidase enzyme signal sequence or non-cellulase, e.g., non-endoglucanase, non-cellobiohydrolase and/or non-beta-glucosidase enzyme signal sequence.

In one aspect, the invention provides chimeric proteins comprising a first domain comprising a signal sequence of the invention and at least a second domain. The protein can be a fusion protein. The second domain can comprise an enzyme. The enzyme can be a non-enzyme.

The invention provides chimeric polypeptides comprising at least a first domain comprising signal peptide (SP), a prepro sequence and/or a catalytic domain (CD) of the invention and at least a second domain comprising a heterologous polypeptide or peptide, wherein the heterologous polypeptide or peptide is not naturally associated with the signal peptide (SP), prepro sequence and/or catalytic domain (CD). In one aspect, the heterologous polypeptide or peptide is not a cellulase, e.g., endoglucanase, cellobiohydrolase, mannanase and/or beta-glucosidase enzyme. The heterologous polypeptide or peptide can be amino terminal to, carboxy terminal to or on both ends of the signal peptide (SP), prepro sequence and/or catalytic domain (CD).

The invention provides isolated or recombinant nucleic acids encoding a chimeric polypeptide, wherein the chimeric polypeptide comprises at least a first domain comprising signal peptide (SP), a prepro domain and/or a catalytic domain (CD) of the invention and at least a second domain comprising a heterologous polypeptide or peptide, wherein the heterologous polypeptide or peptide is not naturally associated with the signal peptide (SP), prepro domain and/or catalytic domain (CD).

The invention provides isolated or recombinant signal sequences (e.g., signal peptides) consisting of or comprising a sequence as set forth in residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43, 1 to 44, 1 to 45, 1 to 46 or 1 to 47, of a polypeptide of the invention, e.g., the exemplary SEQ ID NO:2, SEQ ID NO:4, SEQ ID NO:6, SEQ ID NO: 8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:143, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 or SEQ ID NO:166 (see Tables 1, 2, and 3, Examples 1 and 4, below, and Sequence Listing). In one aspect, the invention provides signal sequences comprising the first 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino terminal residues of a polypeptide of the invention.

In one aspect, the cellulase, e.g., endoglucanase, cellobiohydrolase, mannanase and/or beta-glucosidase enzyme activity comprises a specific activity at about 37° C. in the range from about 1 to about 1200 units per milligram of protein, or, about 100 to about 1000 units per milligram of protein. In another aspect, the cellulase, e.g., endoglucanase, cellobiohydrolase, mannanase and/or beta-glucosidase enzyme activity comprises a specific activity from about 100 to about 1000 units per milligram of protein, or, from about 500 to about 750 units per milligram of protein. Alternatively, the cellulase, e.g., endoglucanase, cellobiohydrolase, mannanase and/or beta-glucosidase enzyme activity comprises a specific activity at 37° C. in the range from about 1 to about 750 units per milligram of protein, or, from about 500 to about 1200 units per milligram of protein. In one aspect, the cellulase, e.g., endoglucanase, cellobiohydrolase, mannanase and/or beta-glucosidase enzyme activity comprises a specific activity at 37° C. in the range from about 1 to about 500 units per milligram of protein, or, from about 750 to about 1000 units per milligram of protein. In another aspect, the cellulase, e.g., endoglucanase, cellobiohydrolase, mannanase and/or beta-glucosidase enzyme activity comprises a specific activity at 37° C. in the range from about 1 to about 250 units per milligram of protein. Alternatively, the cellulase, e.g., endoglucanase, cellobiohydrolase, mannanase and/or beta-glucosidase enzyme activity comprises a specific activity at 37° C. in the range from about 1 to about 100 units per milligram of protein.

In another aspect, the thermotolerance comprises retention of at least half of the specific activity of the cellulase, e.g., endoglucanase, cellobiohydrolase, mannanase and/or beta-glucosidase enzyme at 37° C. after being heated to the elevated temperature. Alternatively, the thermotolerance can comprise retention of specific activity at 37° C. in the range from about 1 to about 1200 units per milligram of protein, or, from about 500 to about 1000 units per milligram of protein, after being heated to the elevated temperature. In another aspect, the thermotolerance can comprise retention of specific activity at 37° C. in the range from about 1 to about 500 units per milligram of protein after being heated to the elevated temperature.

The invention provides the isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a P. pastoris or a S. pombe.

In one aspect, the polypeptide can retain cellulase, e.g., endoglucanase, cellobiohydrolase, mannanase and/or beta-glucosidase enzyme activity under conditions comprising about pH 6.5, pH16, pH 5.5, pH 5, pH 4.5 or pH 4 or more acidic. In another aspect, the polypeptide can retain a cellulase, e.g., endoglucanase, cellobiohydrolase, mannanase and/or beta-glucosidase enzyme activity under conditions comprising about pH 7, pH 7.5 pH 8.0, pH 8.5, pH 9, pH 9.5, pH 10, pH 10.5 or pH 11 or more basic pH. In one aspect, the polypeptide can retain a cellulase, e.g., endoglucanase, cellobiohydrolase, mannanase and/or beta-glucosidase enzyme activity after exposure to conditions comprising about pH 6.5, pH 6, pH 5.5, pH 5, pH 4.5 or pH 4 or more acidic pH. In another aspect, the polypeptide can retain a cellulase, e.g., endoglucanase, cellobiohydrolase, mannanase and/or beta-glucosidase enzyme activity after exposure to conditions comprising about pH 7, pH 7.5 pH 8.0, pH 8.5, pH 9, pH 9.5, pH 10, pH 10.5 or pH11 or more basic pH.

In one aspect, the cellulase, e.g., endoglucanase, cellobiohydrolase, mannanase and/or beta-glucosidase enzyme of the invention has activity at under alkaline conditions, e.g., the alkaline conditions of the gut, e.g., the small intestine. In one aspect, the polypeptide can retains activity after exposure to the acidic pH of the stomach.

The invention provides protein preparations comprising a polypeptide (including peptides) of the invention, wherein the protein preparation comprises a liquid, a solid or a gel. The invention provides heterodimers comprising a polypeptide of the invention and a second protein or domain. The second member of the heterodimer can be a different cellulase, e.g., endoglucanase, cellobiohydrolase, mannanase and/or beta-glucosidase enzyme, a different enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides (including peptides) having cellulase, e.g., endoglucanase, cellobiohydrolase, mannanase and/or beta-glucosidase enzyme activity, wherein the immobilized polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention also provides arrays comprising an immobilized nucleic acid of the invention, including, e.g., probes of the invention. The invention also provides arrays comprising an antibody of the invention.

The invention provides isolated or recombinant antibodies that specifically bind to a polypeptide of the invention or to a polypeptide encoded by a nucleic acid of the invention. These antibodies of the invention can be a monoclonal or a polyclonal antibody. The invention provides hybridomas comprising an antibody of the invention, e.g., an antibody that specifically binds to a polypeptide of the invention or to a polypeptide encoded by a nucleic acid of the invention. The invention provides nucleic acids encoding these antibodies.

The invention provides method of isolating or identifying a polypeptide having cellulase, e.g., endoglucanase, cellobiohydrolase, mannanase and/or beta-glucosidase enzyme activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having a cellulase, e.g., endoglucanase, cellobiohydrolase, mannanase and/or beta-glucosidase enzyme activity.

The invention provides methods of making an anti-cellulase, e.g., anti-endoglucanase, anti-cellobiohydrolase and/or anti-beta-glucosidase enzyme antibody comprising administering to a non-human animal a nucleic acid of the invention or a polypeptide of the invention or subsequences thereof in an amount sufficient to generate a humoral immune response, thereby making an anti-cellulase, e.g., anti-endoglucanase, anti-cellobiohydrolase and/or anti-beta-glucosidase enzyme antibody. The invention provides methods of making an anti-cellulase, e.g., anti-endoglucanase, anti-cellobiohydrolase and/or anti-beta-glucosidase immune response (cellular or humoral) comprising administering to a non-human animal a nucleic acid of the invention or a polypeptide of the invention or subsequences thereof in an amount sufficient to generate an immune response (cellular or humoral).

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having cellulase, e.g., endoglucanase, cellobiohydrolase, mannanase and/or beta-glucosidase enzyme activity comprising the following steps: (a) providing a polypeptide of the invention; or a polypeptide encoded by a nucleic acid of the invention; (b) providing cellulase, e.g., endoglucanase, cellobiohydrolase, mannanase and/or beta-glucosidase enzyme substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having a cellulase, e.g., endoglucanase, cellobiohydrolase, mannanase and/or beta-glucosidase enzyme activity. In one aspect, the substrate is a cellulose-comprising compound.

The invention provides methods for identifying cellulase, e.g., endoglucanase, cellobiohydrolase, mannanase and/or beta-glucosidase enzyme substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a cellulase, e.g., endoglucanase, cellobiohydrolase, mannanase and/or beta-glucosidase enzyme substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of a cellulase, e.g., endoglucanase, cellobiohydrolase, mannanase and/or beta-glucosidase enzyme activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the cellulase, e.g., endoglucanase, cellobiohydrolase, mannanase and/or beta-glucosidase enzyme, wherein a change in the cellulase, e.g., endoglucanase, cellobiohydrolase, mannanase and/or beta-glucosidase enzyme activity measured in the presence of the test compound compared to the activity in the absence of the test compound provides a determination that the test compound modulates the cellulase, e.g., endoglucanase, cellobiohydrolase, mannanase and/or beta-glucosidase enzyme activity. In one aspect, the cellulase, e.g., endoglucanase, cellobiohydrolase, mannanase and/or beta-glucosidase enzyme activity can be measured by providing a cellulase, e.g., endoglucanase, cellobiohydrolase, mannanase and/or beta-glucosidase enzyme substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of cellulase, e.g., endoglucanase, cellobiohydrolase, mannanase and/or beta-glucosidase enzyme activity. An increase in the amount of the substrate or a decrease in the amount of the reaction product with the test compound as compared to the amount of substrate or reaction product without the test compound identifies the test compound as an inhibitor of cellulase, e.g., endoglucanase, cellobiohydrolase, mannanase and/or beta-glucosidase enzyme activity.

The invention provides computer systems comprising a processor and a data storage device wherein said data storage device has stored thereon a polypeptide sequence or a nucleic acid sequence of the invention (e.g., a polypeptide or peptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having a cellulase, e.g., endoglucanase, cellobiohydrolase, mannanase and/or beta-glucosidase enzyme activity from an environmental sample comprising the steps of: (a) providing an amplification primer sequence pair for amplifying a nucleic acid encoding a polypeptide having a cellulase, e.g., endoglucanase, cellobiohydrolase, mannanase and/or beta-glucosidase enzyme activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having a cellulase, e.g., endoglucanase, cellobiohydrolase, mannanase and/or beta-glucosidase enzyme activity from an environmental sample. One or each member of the amplification primer sequence pair can comprise an oligonucleotide comprising an amplification primer sequence pair of the invention, e.g., having at least about 10 to 50 consecutive bases of a sequence of the invention.

The invention provides methods for isolating or recovering a nucleic acid encoding a polypeptide having a cellulase, e.g., endoglucanase, cellobiohydrolase, mannanase and/or beta-glucosidase enzyme activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having a cellulase, e.g., endoglucanase, cellobiohydrolase, mannanase and/or beta-glucosidase enzyme activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having a cellulase, e.g., endoglucanase, cellobiohydrolase, mannanase and/or beta-glucosidase enzyme activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant cellulase, e.g., endoglucanase, cellobiohydrolase, mannanase and/or beta-glucosidase enzyme polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), Chromosomal Saturation Mutagenesis (CSM) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a cellulase, e.g., endoglucanase, cellobiohydrolase, mannanase and/or beta-glucosidase enzyme having an altered or different activity or an altered or different stability from that of a polypeptide encoded by the template nucleic acid is produced. In one aspect, the variant cellulase, e.g., endoglucanase, cellobiohydrolase, mannanase and/or beta-glucosidase enzyme polypeptide is thermotolerant, and retains some activity after being exposed to an elevated temperature. In another aspect, the variant cellulase, e.g., endoglucanase, cellobiohydrolase, mannanase and/or beta-glucosidase enzyme polypeptide has increased glycosylation as compared to the cellulase, e.g., endoglucanase, cellobiohydrolase, mannanase and/or beta-glucosidase enzyme encoded by a template nucleic acid. Alternatively, the variant cellulase, e.g., endoglucanase, cellobiohydrolase, mannanase and/or beta-glucosidase polypeptide has a cellulase, e.g., endoglucanase, cellobiohydrolase, mannanase and/or beta-glucosidase enzyme activity under a high temperature, wherein the cellulase, e.g., endoglucanase, cellobiohydrolase, mannanase and/or beta-glucosidase enzyme encoded by the template nucleic acid is not active under the high temperature. In one aspect, the method can be iteratively repeated until a cellulase, e.g., endoglucanase, cellobiohydrolase, mannanase and/or beta-glucosidase enzyme coding sequence having an altered codon usage from that of the template nucleic acid is produced. In another aspect, the method can be iteratively repeated until a cellulase, e.g., endoglucanase, cellobiohydrolase, mannanase and/or beta-glucosidase enzyme gene having higher or lower level of message expression or stability from that of the template nucleic acid is produced.

The invention provides methods for modifying codons in a nucleic acid encoding a polypeptide having a cellulase, e.g., endoglucanase, cellobiohydrolase, mannanase and/or beta-glucosidase enzyme activity to increase its expression in a host cell, the method comprising the following steps: (a) providing a nucleic acid of the invention encoding a polypeptide having a cellulase, e.g., endoglucanase, cellobiohydrolase, mannanase and/or beta-glucosidase enzyme activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having a cellulase, e.g., endoglucanase, cellobiohydrolase, mannanase and/or beta-glucosidase enzyme activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding a cellulase, e.g., endoglucanase, cellobiohydrolase, mannanase and/or beta-glucosidase enzyme.

The invention provides methods for modifying codons in a nucleic acid encoding a polypeptide having a cellulase, e.g., endoglucanase, cellobiohydrolase, mannanase and/or beta-glucosidase enzyme activity to increase its expression in a host cell, the method comprising the following steps: (a) providing a nucleic acid of the invention encoding a cellulase, e.g., endoglucanase, cellobiohydrolase, mannanase and/or beta-glucosidase enzyme polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a cellulase, e.g., endoglucanase, cellobiohydrolase, mannanase and/or beta-glucosidase enzyme activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified cellulase, e.g., endoglucanase, cellobiohydrolase, mannanase and/or beta-glucosidase enzyme active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes a cellulase, e.g., endoglucanase, cellobiohydrolase, mannanase and/or beta-glucosidase enzyme active site or a cellulase, e.g., endoglucanase, cellobiohydrolase, mannanase and/or beta-glucosidase enzyme substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified cellulase, e.g., endoglucanase, cellobiohydrolase, mannanase and/or beta-glucosidase enzyme active sites or substrate binding sites. In one aspect, the method comprises mutagenizing the first nucleic acid of step (a) by a method comprising an optimized directed evolution system, Gene Site Saturation Mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises a cellulase, e.g., endoglucanase, cellobiohydrolase, mannanase and/or beta-glucosidase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing a cellulase, e.g., endoglucanase, cellobiohydrolase, mannanase and/or beta-glucosidase enzyme, wherein the enzyme comprises a polypeptide of the invention, or, polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the cellulase, e.g., endoglucanase, cellobiohydrolase, mannanase and/or beta-glucosidase enzyme, thereby modifying a small molecule by a cellulase, e.g., endoglucanase, cellobiohydrolase, mannanase and/or beta-glucosidase enzymatic reaction. In one aspect, the method can comprise a plurality of small molecule substrates for the enzyme of step (a), thereby generating a library of modified small molecules produced by at least one enzymatic reaction catalyzed by the cellulase, e.g., endoglucanase, cellobiohydrolase, mannanase and/or beta-glucosidase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a cellulase, e.g., endoglucanase, cellobiohydrolase, mannanase and/or beta-glucosidase enzyme comprising the steps of: (a) providing a cellulase, e.g., endoglucanase, cellobiohydrolase, mannanase and/or beta-glucosidase enzyme, wherein the enzyme comprises a polypeptide of the invention, or a polypeptide encoded by a nucleic acid of the invention, or a subsequence thereof, and (b) deleting a plurality of amino acid residues from the sequence of step (a) and testing the remaining subsequence for a cellulase, e.g., endoglucanase, cellobiohydrolase, mannanase and/or beta-glucosidase enzyme activity, thereby determining a functional fragment of a cellulase, e.g., endoglucanase, cellobiohydrolase, mannanase and/or beta-glucosidase enzyme. In one aspect, the cellulase, e.g., endoglucanase, cellobiohydrolase, mannanase and/or beta-glucosidase enzyme activity is measured by providing a cellulase, e.g., endoglucanase, cellobiohydrolase, mannanase and/or beta-glucosidase enzyme substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods of increasing thermotolerance or thermostability of a cellulase, e.g., endoglucanase, cellobiohydrolase, mannanase and/or beta-glucosidase enzyme polypeptide, the method comprising glycosylating a cellulase, e.g., endoglucanase, cellobiohydrolase, mannanase and/or beta-glucosidase enzyme polypeptide, wherein the polypeptide comprises at least thirty contiguous amino acids of a polypeptide of the invention; or a polypeptide encoded by a nucleic acid sequence of the invention, thereby increasing the thermotolerance or thermostability of the cellulase, e.g., endoglucanase, cellobiohydrolase, mannanase and/or beta-glucosidase polypeptide. In one aspect, the cellulase, e.g., endoglucanase, cellobiohydrolase, mannanase and/or beta-glucosidase enzyme specific activity can be thermostable or thermotolerant at a temperature in the range from greater than about 37° C. to about 95° C.

The invention provides methods for overexpressing a recombinant cellulase, e.g., endoglucanase, cellobiohydrolase, mannanase and/or beta-glucosidase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a cane sugar, beet, soybean, tomato, potato, corn, rice, wheat, tobacco or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell. The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell.

The invention provides feeds or foods comprising a polypeptide of the invention, or a polypeptide encoded by a nucleic acid of the invention. In one aspect, the invention provides a food, feed, a liquid, e.g., a beverage (such as a fruit juice or a beer), a bread or a dough or a bread product, or a beverage precursor (e.g., a wort), comprising a polypeptide of the invention. The invention provides food or nutritional supplements for an animal comprising a polypeptide of the invention, e.g., a polypeptide encoded by the nucleic acid of the invention.

In one aspect, the polypeptide in the food or nutritional supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the cellulase, e.g., endoglucanase, cellobiohydrolase, mannanase and/or beta-glucosidase enzyme activity is thermotolerant. In another aspect, the cellulase, e.g., endoglucanase, cellobiohydrolase, mannanase and/or beta-glucosidase enzyme activity is thermostable.

The invention provides a food, a feed or a nutritional supplement comprising a polypeptide of the invention. The invention provides methods for utilizing a cellulase, e.g., endoglucanase, cellobiohydrolase, mannanase and/or beta-glucosidase enzyme as a nutritional supplement in an animal diet, the method comprising: preparing a nutritional supplement containing a cellulase, e.g., endoglucanase, cellobiohydrolase, mannanase and/or beta-glucosidase enzyme comprising at least thirty contiguous amino acids of a polypeptide of the invention; and administering the nutritional supplement to an animal. The animal can be a human, a ruminant or a monogastric animal. The cellulase, e.g., endoglucanase, cellobiohydrolase, mannanase and/or beta-glucosidase enzyme can be prepared by expression of a polynucleotide encoding the cellulase, e.g., endoglucanase, cellobiohydrolase, mannanase and/or beta-glucosidase enzyme in an organism selected from the group consisting of a bacterium, a yeast, a plant, an insect, a fungus and an animal. The organism can be selected from the group consisting of an *S. pombe, S. cerevisiae, Pichia pastoris, E. coli, Streptomyces* sp., *Bacillus* sp. and *Lactobacillus* sp.

The invention provides edible enzyme delivery matrix comprising a thermostable recombinant cellulase, e.g., endoglucanase, cellobiohydrolase, mannanase and/or beta-glucosidase enzyme, e.g., a polypeptide of the invention. The invention provides methods for delivering a cellulase, e.g., endoglucanase, cellobiohydrolase, mannanase and/or beta-glucosidase enzyme supplement to an animal, the method comprising: preparing an edible enzyme delivery matrix in the form of pellets comprising a granulate edible carrier and a thermostable recombinant cellulase, e.g., endoglucanase, cellobiohydrolase, mannanase and/or beta-glucosidase enzyme, wherein the pellets readily disperse the cellulase, e.g., endoglucanase, cellobiohydrolase, mannanase and/or beta-glucosidase enzyme contained therein into aqueous media, and administering the edible enzyme delivery matrix to the animal. The recombinant cellulase, e.g., endoglucanase, cellobiohydrolase, mannanase and/or beta-glucosidase enzyme can comprise a polypeptide of the invention. The cellulase, e.g., endoglucanase, cellobiohydrolase, mannanase and/or beta-glucosidase enzyme can be glycosylated to provide thermostability at pelletizing conditions. The delivery matrix can be formed by pelletizing a mixture comprising a grain germ and a cellulase, e.g., endoglucanase, cellobiohydrolase, mannanase and/or beta-glucosidase enzyme. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

In one aspect, invention provides a pharmaceutical composition comprising a cellulase, e.g., endoglucanase, cellobiohydrolase, mannanase and/or beta-glucosidase enzyme of the invention, or a polypeptide encoded by a nucleic acid of the invention. In one aspect, the pharmaceutical composition acts as a digestive aid.

In certain aspects, a cellulose-containing compound is contacted a polypeptide of the invention having a cellulase, e.g., endoglucanase, cellobiohydrolase, mannanase and/or beta-glucosidase enzyme activity at a pH in the range of between about pH 3.0 to 9.0, 10.0, 11.0 or more. In other aspects, a cellulose-containing compound is contacted with the cellulase, e.g., endoglucanase, cellobiohydrolase, mannanase and/or beta-glucosidase enzyme at a temperature of about 55° C., 60° C., 65° C., 70° C., 75° C., 80° C., 85° C., 90° C., or more.

The details of one or more aspects of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF DRAWINGS

The following drawings are illustrative of aspects of the invention and are not meant to limit the scope of the invention as encompassed by the claims.

Like reference symbols in the various drawings indicate like elements.

DETAILED DESCRIPTION

Figure 1:
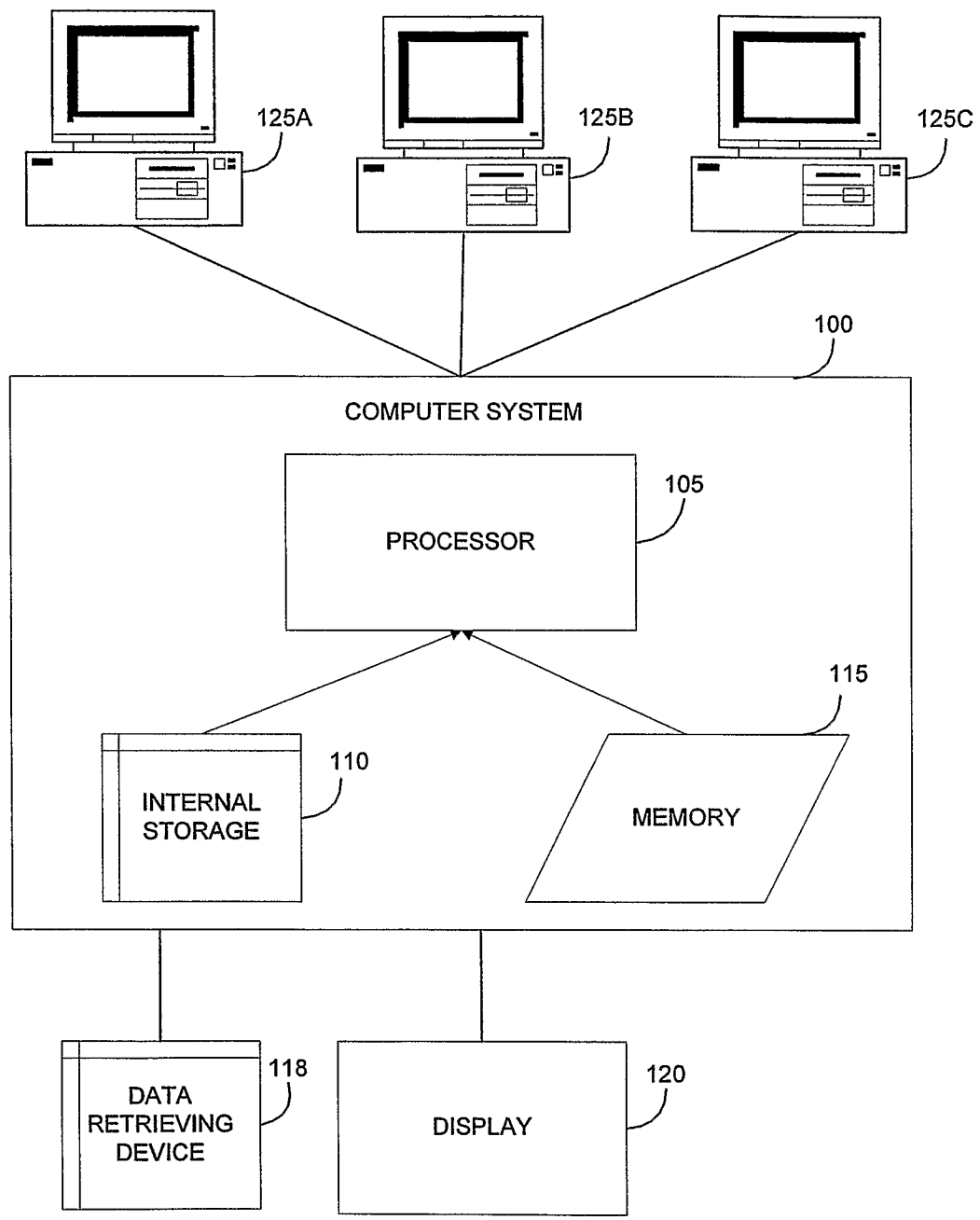
FIG. 1 is a block diagram of a computer system.

The invention provides polypeptides with cellulase, e.g., endoglucanase, cellobiohydrolase, mannanase and/or beta-glucosidase activity, polynucleotides encoding them, and methods of making and using these polynucleotides and polypeptides. The invention also provides cellulase enzymes, e.g., endoglucanase, cellobiohydrolase, mannanase and/or beta-glucosidase enzymes, polynucleotides encoding these enzymes, the use of such polynucleotides and polypeptides.

In one aspect, the invention provides a cellulase, e.g., endoglucanase, cellobiohydrolase, mannanase and/or beta-glucosidase, with an increased catalytic rate, improving the process of substrate hydrolysis. This increased efficiency in catalytic rate leads to an increased efficiency in producing sugars that will subsequently be used by microorganisms for ethanol production. In one aspect, microorganisms generating enzyme of the invention are used with ethanol-producing microorganisms. Thus, the invention provides methods for ethanol production and making "clean fuels" based on ethanol, e.g., for transportation using bioethanol.

In one aspect the invention provides compositions (e.g., enzyme preparations, feeds, drugs, dietary supplements) comprising the enzymes, polypeptides or polynucleotides of the invention. These compositions can be formulated in a variety of forms, e.g., as liquids, gels, pills, tablets, sprays, powders, food, feed pellets or encapsulated forms, including nanoencapsulated forms.

Assays for measuring cellulase activity, e.g., endoglucanase, cellobiohydrolase, mannanase and/or beta-glucosidase activity, e.g., for determining if a polypeptide has cellulase activity, e.g., endoglucanase, cellobiohydrolase, mannanase and/or beta-glucosidase activity, are well known in the art and are within the scope of the invention; see, e.g., Baker W L, Panow A, Estimation of cellulase activity using a glucose-oxidase-Cu(II) reducing assay for glucose, J Biochem Biophys Methods. 1991 December, 23(4):265-73; Sharrock K R, Cellulase assay methods: a review, J Biochem Biophys Methods. 1988 October, 17(2):81-105; Carder J H, Detection and quantitation of cellulase by Congo red staining of substrates in a cup-plate diffusion assay, Anal Biochem. 1986 Feb. 15, 153(1):75-9; Canevascini G., A cellulase assay coupled to cellobiose dehydrogenase, Anal Biochem. 1985 June, 147(2): 419-27; Huang J S, Tang J, Sensitive assay for cellulase and dextranase. Anal Biochem. 1976 June, 73(2):369-77.

The pH of reaction conditions utilized by the invention is another variable parameter for which the invention provides. In certain aspects, the pH of the reaction is conducted in the range of about 3.0 to about 9.0. In other aspects, the pH is about 4.5 or the pH is about 7.5 or the pH is about 9. Reaction conditions conducted under alkaline conditions also can be advantageous, e.g., in some industrial or pharmaceutical applications of enzymes of the invention.

The invention provides cellulase, e.g., endoglucanase, cellobiohydrolase, mannanase and/or beta-glucosidase polypeptides of the invention in a variety of forms and formulations. In the methods of the invention, cellulase, e.g., endoglucanase, cellobiohydrolase, mannanase and/or beta-glucosidase polypeptides of the invention are used in a variety of forms and formulations. For example, purified cellulase, e.g., endoglucanase, cellobiohydrolase, mannanase and/or beta-glucosidase polypeptides can be used in enzyme preparations deployed in bioethanol production or in pharmaceutical or dietary aid applications. Alternatively, the enzymes of the invention can be used directly in processes to produce bioethanol, make clean fuels, process biowastes, process foods, liquids or feeds, and the like.

Alternatively, the cellulase, e.g., endoglucanase, cellobiohydrolase, mannanase and/or beta-glucosidase polypeptides of the invention can be expressed in a microorganism using procedures known in the art. In other aspects, the cellulase, e.g., endoglucanase, cellobiohydrolase, mannanase and/or beta-glucosidase polypeptides of the invention can be immobilized on a solid support prior to use in the methods of the invention. Methods for immobilizing enzymes on solid supports are commonly known in the art, for example J. Mol. Cat. B: Enzymatic 6 (1999) 29-39; Chivata et al. Biocatalysis: Immobilized cells and enzymes, J Mol. Cat. 37 (1986) 1-24: Sharma et al., Immobilized Biomaterials Techniques and Applications, Angew. Chem. Int. Ed. Engl. 21 (1982) 837-54: Laskin (Ed.), Enzymes and Immobilized Cells in Biotechnology.

Nucleic Acids, Probes and Inhibitory Molecules

The invention provides isolated and recombinant nucleic acids, e.g., see Tables 1, 2, and 3, Examples 1 and 4, below, and Sequence Listing; nucleic acids encoding polypeptides, including the exemplary polynucleotide sequences of the invention, e.g., see Table 1 and Sequence Listing; including expression cassettes such as expression vectors and various cloning vehicles comprising nucleic acids of the invention. The invention also includes methods for discovering, identifying or isolated new cellulases, e.g., endoglucanase, cellobiohydrolase, mannanase and/or beta-glucosidase polypeptide sequences using the nucleic acids of the invention. The invention also includes methods for inhibiting the expression of cellulase, e.g., endoglucanase, cellobiohydrolase, mannanase and/or beta-glucosidase encoding genes and transcripts using the nucleic acids of the invention.

Also provided are methods for modifying the nucleic acids of the invention, including making variants of nucleic acids of the invention, by, e.g., synthetic ligation reassembly, optimized directed evolution system and/or saturation mutagenesis such as gene site saturation mutagenesis (GSSM). The term "saturation mutagenesis", Gene Site Saturation Mutagenesis, or "GSSM" includes a method that uses degenerate oligonucleotide primers to introduce point mutations into a polynucleotide, as described in detail, below. The term "optimized directed evolution system" or "optimized directed evolution" includes a method for reassembling fragments of related nucleic acid sequences, e.g., related genes, and explained in detail, below. The term "synthetic ligation reassembly" or "SLR" includes a method of ligating oligonucleotide fragments in a non-stochastic fashion, and explained in detail, below. The term "variant" refers to polynucleotides or polypeptides of the invention modified at one or more base pairs, codons, introns, exons, or amino acid residues (respectively) yet still retain the biological activity of a cellulase, e.g., endoglucanase, cellobiohydrolase, mannanase and/or beta-glucosidase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

The nucleic acids of the invention can be made, isolated and/or manipulated by, e.g., cloning and expression of cDNA libraries, amplification of message or genomic DNA by PCR, and the like. For example, exemplary sequences of the invention were initially derived from environmental sources. Thus, in one aspect, the invention provides cellulase, e.g., endoglucanase, cellobiohydrolase, mannanase and/or beta-glucosidase enzyme-encoding nucleic acids, and the polypeptides encoded by them, having a common novelty in that they are derived from a common source, e.g., an environmental, mixed culture, or a bacterial source.

In practicing the methods of the invention, homologous genes can be modified by manipulating a template nucleic acid, as described herein. The invention can be practiced in conjunction with any method or protocol or device known in the art, which are well described in the scientific and patent literature.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense (complementary) strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

A "coding sequence of" or a "nucleotide sequence encoding" a particular polypeptide or protein, is a nucleic acid sequence which is transcribed and translated into a polypeptide or protein when placed under the control of appropriate regulatory sequences. The term "gene" means the segment of DNA involved in producing a polypeptide chain; it includes regions preceding and following the coding region (leader and trailer) as well as, where applicable, intervening sequences (introns) between individual coding segments (exons). A promoter sequence is "operably linked to" a coding sequence when RNA polymerase which initiates transcription at the promoter will transcribe the coding sequence into mRNA. "Operably linked" as used herein refers to a functional relationship between two or more nucleic acid (e.g., DNA) segments. It can refer to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" as used herein refers to a nucleotide sequence which is capable of affecting expression of a structural gene (i.e., a protein coding sequence, such as a cellulase, e.g., endoglucanase, cellobiohydrolase, mannanase and/or beta-glucosidase enzyme of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers, alpha-factors. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "recombinant" encompasses nucleic acids adjacent to a "backbone" nucleic acid to which it is not adjacent in its natural environment. In one aspect, to be "enriched" the nucleic acids will represent about 5% or more of the number of nucleic acid inserts in a population of nucleic acid backbone molecules. Backbone molecules according to the invention include nucleic acids such as expression vectors, self-replicating nucleic acids, viruses, integrating nucleic acids and other vectors or nucleic acids used to maintain or manipulate a nucleic acid insert of interest. In one aspect, the enriched nucleic acids represent about 15% or more of the number of nucleic acid inserts in the population of recombinant backbone molecules. In one aspect, the enriched nucleic acids represent about 50% or more of the number of nucleic acid inserts in the population of recombinant backbone molecules. In a one aspect, the enriched nucleic acids represent about 90% or more of the number of nucleic acid inserts in the population of recombinant backbone molecules.

One aspect of the invention is an isolated or recombinant nucleic acid comprising one of the sequences of the invention, or a fragment comprising at least 10, 15, 20, 25, 30, 35, 40, 50, 75, 100, 150, 200, 300, 400, or 500 or more consecutive bases of a nucleic acid of the invention. The isolated or recombinant nucleic acids may comprise DNA, including cDNA, genomic DNA and synthetic DNA. The DNA may be double-stranded or single-stranded and if single stranded may be the coding strand or non-coding (anti-sense) strand. Alternatively, the isolated or recombinant nucleic acids comprise RNA.

The isolated or recombinant nucleic acids of the invention may be used to prepare one of the polypeptides of the invention, or fragments comprising at least 5, 10, 15, 20, 25, 30, 35, 40, 50, 75, 100, or 150 or more consecutive amino acids of one of the polypeptides of the invention. Accordingly, another aspect of the invention is an isolated or recombinant nucleic acid which encodes one of the polypeptides of the invention, or fragments comprising at least 5, 10, 15, 20, 25, 30, 35, 40, 50, 75, 100, or 150 or more consecutive amino acids of one of the polypeptides of the invention. The coding sequences of these nucleic acids may be identical to one of the coding sequences of one of the nucleic acids of the invention or may be different coding sequences which encode one of the of the invention having at least 5, 10, 15, 20, 25, 30, 35, 40, 50, 75, 100, or 150 or more consecutive amino acids of one of the polypeptides of the invention, as a result of the redundancy or degeneracy of the genetic code. The genetic code is well known to those of skill in the art and can be obtained, e.g., on page 214 of B. Lewin, Genes VI, Oxford University Press, 1997.

The nucleic acids encoding polypeptides of the invention include but are not limited to: the coding sequence of a nucleic acid of the invention and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes the coding sequence for the polypeptide as well as a polynucleotide which includes additional coding and/or non-coding sequence.

In one aspect, the nucleic acid sequences of the invention are mutagenized using conventional techniques, such as site directed mutagenesis, or other techniques familiar to those skilled in the art, to introduce silent changes into the polynucleotides o of the invention. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of the invention. Such nucleotide changes may be introduced using techniques such as site directed mutagenesis, random chemical mutagenesis, exonuclease III deletion and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of the invention (or the sequences complementary thereto) under conditions of high, moderate, or low stringency as provided herein.

General Techniques

The nucleic acids used to practice this invention, whether RNA, siRNA, miRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., cellulase, e.g., endoglucanase, cellobiohydrolase, mannanase and/or beta-glucosidase enzymes) generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

As used herein, the term "promoter" includes all sequences capable of driving transcription of a coding sequence in a cell, e.g., a plant or animal cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences can interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the α-factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express a cellulase, e.g., endoglucanase, cellobiohydrolase, mannanase and/or beta-glucosidase enzyme of the invention in a tissue-specific manner. The invention also provides plants or seeds that express a cellulase, e.g., endoglucanase, cellobiohydrolase, mannanase and/or beta-glucosidase enzyme of the invention in a tissue-specific manner. The tissue-specificity can be seed specific, stem specific, leaf specific, root specific, fruit specific and the like.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) *Plant Mol. Biol.* 33:125-139); Cat3 from *Arabidopsis* (GenBank No. U43147, Zhong (1996) *Mol. Gen. Genet.* 251:196-203); the gene encoding stearoyl-acyl carrier protein desaturase from *Brassica napus* (Genbank No. X74782, Solocombe (1994) *Plant Physiol.* 104: 1167-1176); GPc1 from maize (GenBank No. X15596; Martinez (1989) *J. Mol. Biol* 208:551-565); the Gpc2 from maize (GenBank No. U45855, Manjunath (1997) Plant Mol. Biol. 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

In one aspect, the plant promoter directs expression of cellulase, e.g., endoglucanase, cellobiohydrolase, mannanase and/or beta-glucosidase enzyme-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

In one aspect, tissue-specific promoters promote transcription only within a certain time frame of developmental stage within that tissue. See, e.g., Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fbl2A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

In one aspect, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, soybean, tomato, wheat, potato or other crops, inducible at any stage of development of the crop.

One of skill will recognize that a tissue-specific plant promoter may drive expression of operably linked sequences in tissues other than the target tissue. Thus, in one aspect, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the cellulase, e.g., endoglucanase, cellobiohydrolase, mannanase and/or beta-glucosidase enzyme-producing nucleic acids of the invention will allow the grower to select plants with the optimal cellulase, e.g., endoglucanase, cellobiohydrolase, mannanase and/or beta-glucosidase enzyme expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

In some aspects, proper polypeptide expression may require polyadenylation region at the 3'-end of the coding region. The polyadenylation region can be derived from the natural gene, from a variety of other plant (or animal or other) genes, or from genes in the Agrobacterial T-DNA.

Expression Vectors and Cloning Vehicles

The invention provides expression vectors and cloning vehicles comprising nucleic acids of the invention, e.g., sequences encoding the cellulase, e.g., endoglucanase, cellobiohydrolase, mannanase and/or beta-glucosidase enzymes of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE™ vectors (Qiagen), pBLUESCRIPT™ plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention. "Plasmids" can be commercially available, publicly available on an unrestricted basis, or can be constructed from available plasmids in accord with published procedures. Equivalent plasmids to those described herein are known in the art and will be apparent to the ordinarily skilled artisan.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

In one aspect, vectors for expressing the polypeptide or fragment thereof in eukaryotic cells contain enhancers to increase expression levels. Enhancers are cis-acting elements of DNA that can be from about 10 to about 300 bp in length. They can act on a promoter to increase its transcription. Exemplary enhancers include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBLUE-SCRIPT II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal minichromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, e.g., antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and tip. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors in one aspect contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Mammalian expression vectors may also comprise an origin of replication, any necessary ribosome binding sites, a polyadenylation site, splice donor and acceptor sites, transcriptional termination sequences and 5' flanking nontranscribed sequences. In some aspects, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin and the adenovirus enhancers.

In addition, the expression vectors can contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli* and the *S. cerevisiae* TRP1 gene.

In some aspects, the nucleic acid encoding one of the polypeptides of the invention, or fragments comprising at least about 5, 10, 15, 20, 25, 30, 35, 40, 50, 75, 100, or 150 or more consecutive amino acids thereof is assembled in appropriate phase with a leader sequence capable of directing secretion of the translated polypeptide or fragment thereof. In one aspect, the nucleic acid can encode a fusion polypeptide in which one of the polypeptides of the invention, or fragments comprising at least 5, 10, 15, 20, 25, 30, 35, 40, 50, 75, 100, or 150 or more consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2nd Ed., Cold Spring Harbor Laboratory Press (1989. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook, et al., Molecular Cloning: A Laboratory Manual, 2nd Ed., Cold Spring Harbor, N.Y., (1989).

Host Cells and Transformed Cells

The invention also provides a transformed cell comprising a nucleic acid sequence of the invention, e.g., a sequence encoding a cellulase, e.g., endoglucanase, cellobiohydrolase, mannanase and/or beta-glucosidase enzyme of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species of *Streptomyces, Staphylococcus* or *Bacillus*, or the exemplary species *E. coli, Bacillus subtilis, Bacillus cereus, Salmonella typhimurium*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Host cells containing the polynucleotides of interest, e.g., nucleic acids of the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan. The clones which are identified as having the specified enzyme activity may then be sequenced to identify the polynucleotide sequence encoding an enzyme having the enhanced activity.

The invention provides a method for overexpressing a recombinant cellulase, e.g., endoglucanase, cellobiohydrolase, mannanase and/or beta-glucosidase enzyme in a cell comprising expressing a vector comprising a nucleic acid of the invention, e.g., a nucleic acid comprising a nucleic acid sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to an exemplary sequence of the invention over a region of at least about 100 residues, wherein the sequence identities are determined by analysis with a sequence comparison algorithm or by visual inspection, or, a nucleic acid that hybridizes under stringent conditions to a nucleic acid sequence of the invention. The overexpression can be effected by any means, e.g., use of a high activity promoter, a dicistronic vector or by gene amplification of the vector.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention. The host cell may be any of the host cells familiar to those skilled in the art, including prokaryotic cells, eukaryotic cells, mammalian cells, insect cells, or plant cells. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981) and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of the invention, or fragments comprising at least 5, 10, 15, 20, 25, 30, 35, 40, 50, 75, 100, or 150 or more consecutive amino acids thereof can be synthetically produced by conventional peptide synthesizers, e.g., as discussed below. In other aspects, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of the invention, or fragments comprising at least 5, 10, 15, 20, 25, 30, 35, 40, 50, 75, 100, or 150 or more consecutive amino acids thereof using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

Amplification of Nucleic Acids

In practicing the invention, nucleic acids of the invention and nucleic acids encoding the cellulase, e.g., endoglucanase, cellobiohydrolase, mannanase and/or beta-glucosidase enzymes of the invention, or modified nucleic acids of the invention, can be reproduced by amplification, e.g., PCR. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

In one aspect, the invention provides a nucleic acid amplified by an amplification primer pair of the invention, e.g., a primer pair as set forth by about the first (the 5') 12, 13, 14, 15, 16, 17, 18, 19, 20, 21, 22, 23, 24, or 25 or more residues of a nucleic acid of the invention, and about the first (the 5') 15, 16, 17, 18, 19, 20, 21, 22, 23, 24, or 25 or more residues of the complementary strand. The invention provides amplification primer sequence pairs for amplifying a nucleic acid encoding a polypeptide having a cellulase, e.g., endoglucanase, cellobiohydrolase, mannanase and/or beta-glucosidase enzyme activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 or more consecutive bases of the sequence, or about 12, 13, 14, 15, 16, 17, 18, 19, 20, 21, 22, 23, 24, or 25 or more consecutive bases of the sequence. The invention provides amplification primer pairs, wherein the primer pair comprises a first member having a sequence as set forth by about the first (the 5') 12, 13, 14, 15, 16, 17, 18, 19, 20, 21, 22, 23, 24, or 25 or more residues of a nucleic acid of the invention, and a second member having a sequence as set forth by about the first (the 5') 12, 13, 14, 15, 16, 17, 18, 19, 20, 21, 22, 23, 24, or 25 or more residues of the complementary strand of the first member.

The invention provides cellulase, e.g., endoglucanase, cellobiohydrolase, mannanase and/or beta-glucosidase enzymes generated by amplification, e.g., polymerase chain reaction (PCR), using an amplification primer pair of the invention. The invention provides methods of making a cellulase, e.g., endoglucanase, cellobiohydrolase, mannanase and/or beta-glucosidase enzyme by amplification, e.g., PCR, using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining Sequence Identity in Nucleic Acids and Polypeptides

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to an exemplary nucleic acid of the invention (see also Tables 1, 2, and 3, Examples 1 and 4, below, and Sequence Listing) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention (see Tables 1, 2, and 3, Examples 1 and 4, below, and Sequence Listing). The extent of sequence identity (homology) may be determined using any computer program and associated parameters, including those described herein, such as BLAST 2.2.2. or FASTA version 3.0t78, with the default parameters.

Nucleic acid sequences of the invention can comprise at least 10, 15, 20, 25, 30, 35, 40, 50, 75, 100, 150, 200, 300, 400, or 500 or more consecutive nucleotides of an exemplary sequence of the invention and sequences substantially identical thereto. Homologous sequences and fragments of nucleic acid sequences of the invention can refer to a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to these sequences. Homology (sequence identity) may be determined using any of the computer programs and parameters described herein, including FASTA version 3.0t78 with the default parameters. Homologous sequences also include RNA sequences in which uridines replace the thymines in the nucleic acid sequences of the invention. The homologous sequences may be obtained using any of the procedures described herein or may result from the correction of a sequencing error. It will be appreciated that the nucleic acid sequences of the invention can be represented in the traditional single character format (See the inside back cover of Stryer, Lubert. Biochemistry, 3rd Ed., W.H. Freeman & Co., New York.) or in any other format which records the identity of the nucleotides in a sequence.

In various aspects, sequence comparison programs identified herein are used in this aspect of the invention, i.e., to determine if a nucleic acid or polypeptide sequence is within the scope of the invention. However, protein and/or nucleic acid sequence identities (homologies) may be evaluated using any sequence comparison algorithm or program known in the art. Such algorithms and programs include, but are by no means limited to, TBLASTN, BLASTP, FASTA, TFASTA and CLUSTALW (see, e.g., Pearson and Lipman, Proc. Natl. Acad. Sci. USA 85(8):2444-2448, 1988; Altschul et al., J. Mol. Biol. 215(3):403-410, 1990; Thompson Nucleic Acids Res. 22(2):4673-4680, 1994; Higgins et al., Methods Enzymol. 266:383-402, 1996; Altschul et al., J. Mol. Biol. 215(3): 403-410, 1990; Altschul et al., Nature Genetics 3:266-272, 1993).

In one aspect, homology or identity is measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. In one aspect, the terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. In one aspect, for sequence comparison, one sequence acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Nat'l. Acad. Sci. USA 85:2444, 1988, by computerized implementations of these algorithms (GAP, BESTFIT, FASTA and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997) and yeast (*S. cerevisiae*) (Mewes et al., 1997) and *D. melanogaster* (Adams et al., 2000). Significant progress has also been made in sequencing the genomes of model organism, such as mouse, *C. elegans* and *Arabidopsis* sp. Several databases containing genomic information annotated with some functional information are maintained by different organizations and may be accessible via the internet.

In one aspect, BLAST and BLAST 2.0 algorithms are used, which are described in Altschul et al., Nuc. Acids Res. 25:3389-3402, 1977 and Altschul et al., J. Mol. Biol. 215: 403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff, Proc. Natl. Acad. Sci. USA 89:10915, 1989) alignments (B) of 50, expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more in one aspect less than about 0.01 and most in one aspect less than about 0.001.

In one aspect, protein and nucleic acid sequence homologies are evaluated using the Basic Local Alignment Search Tool ("BLAST") In particular, five specific BLAST programs are used to perform the following task:
(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is in one aspect obtained from a protein or nucleic acid sequence database. High-scoring segment pairs are in one aspect identified (i.e., aligned) by means of a scoring matrix, many of which are known in the art. In one aspect, the scoring matrix used is the BLOSUM62 matrix (Gonnet (1992) Science 256:1443-1445; Henikoff and Henikoff (1993) Proteins 17:49-61). Less in one aspect, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some aspects, the parameters may be the default parameters used by the algorithms in the absence of instructions from the user.

Computer Systems and Computer Program Products

The invention provides computers, computer systems, computer readable mediums, computer programs products and the like recorded or stored thereon the nucleic acid and polypeptide sequences of the invention. Additionally, in practicing the methods of the invention, e.g., to determine and identify sequence identities (to determine whether a nucleic acid is within the scope of the invention), structural homologies, motifs and the like in silico, a nucleic acid or polypeptide sequence of the invention can be stored, recorded, and manipulated on any medium which can be read and accessed by a computer.

As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention. As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The polypeptides of the invention include exemplary sequences of the invention and sequences substantially identical thereto, and subsequences (fragments) of any of the preceding sequences. In one aspect, substantially identical, or homologous, polypeptide sequences refer to a polypeptide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to an exemplary sequence of the invention.

Homology (sequence identity) may be determined using any of the computer programs and parameters described herein. A nucleic acid or polypeptide sequence of the invention can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences of the invention, one or more of the polypeptide sequences of the invention. Another aspect of the invention is a computer readable medium having recorded thereon at least 2, 5, 10, 15, or 20 or more nucleic acid or polypeptide sequences of the invention.

Another aspect of the invention is a computer readable medium having recorded thereon one or more of the nucleic acid sequences of the invention. Another aspect of the invention is a computer readable medium having recorded thereon one or more of the polypeptide sequences of the invention. Another aspect of the invention is a computer readable medium having recorded thereon at least 2, 5, 10, 15, or 20 or more of the nucleic acid or polypeptide sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), e.g., computer systems which store and manipulate the sequence information described herein. One example of a computer system 100 is illustrated in block diagram form in FIG. 1. As used herein, "a computer system" refers to the hardware components, software components and data storage components used to analyze a nucleotide sequence of a nucleic acid sequence of the invention, or a polypeptide sequence of the invention. In one aspect, the computer system 100 includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

In one aspect, the computer system 100 is a general purpose system that comprises the processor 105 and one or more internal data storage components 110 for storing data and one or more data retrieving devices for retrieving the data stored on the data storage components. A skilled artisan can readily appreciate that any one of the currently available computer systems are suitable.

In one particular aspect, the computer system 100 includes a processor 105 connected to a bus which is connected to a main memory 115 (in one aspect implemented as RAM) and one or more internal data storage devices 110, such as a hard drive and/or other computer readable media having data recorded thereon. In some aspects, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some aspects, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence of the invention, or a polypeptide sequence of the invention, (such as search tools, compare tools and modeling tools etc.) may reside in main memory 115 during execution.

In some aspects, the computer system 100 may further comprise a sequence comparison algorithm for comparing a nucleic acid sequence of the invention, or a polypeptide sequence of the invention, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence of the invention, or a polypeptide sequence of the invention, stored on a computer readable medium to reference sequences stored on a computer readable medium to identify homologies or structural motifs.

Figure 2:
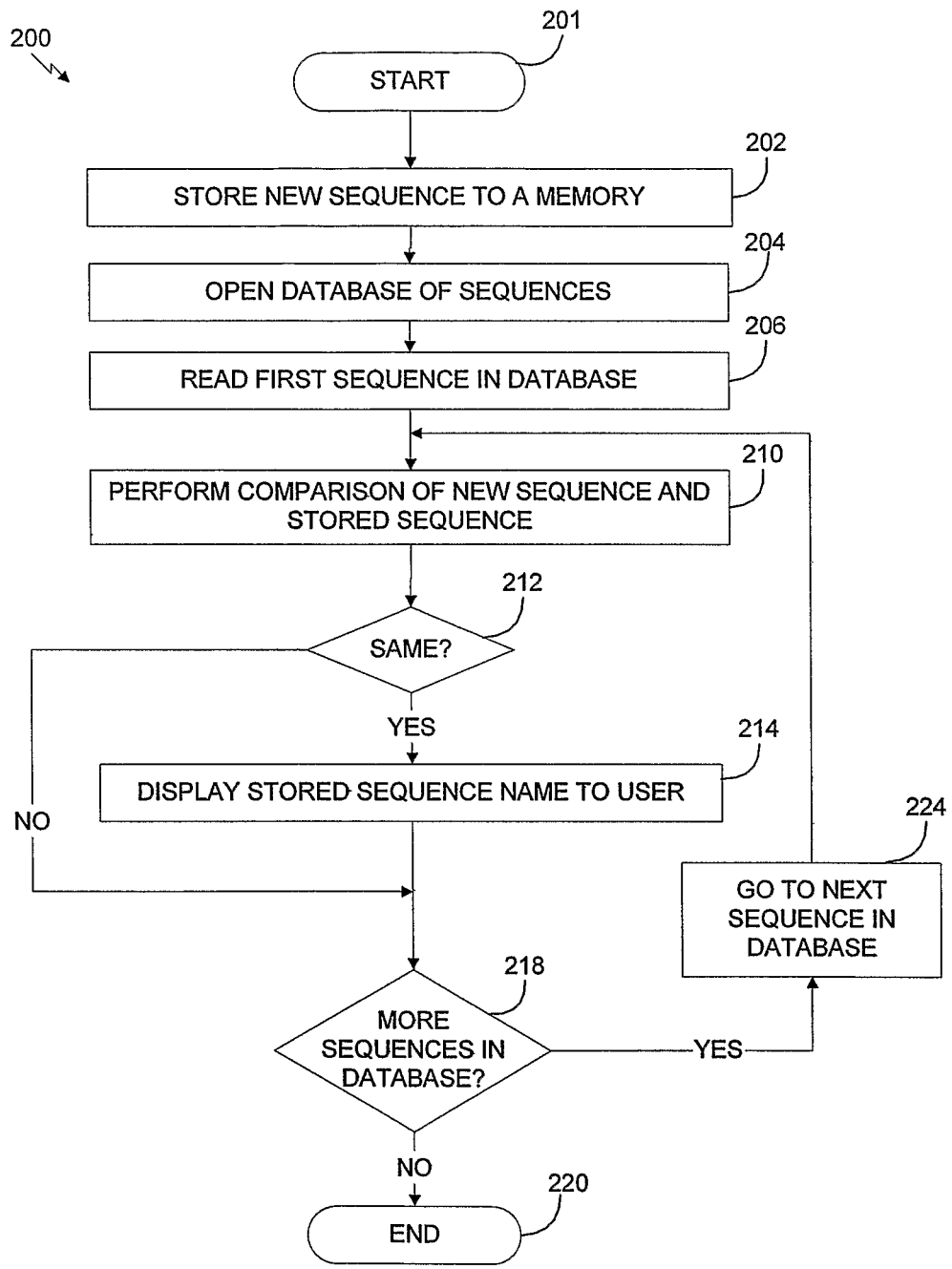
FIG. 2 is a flow diagram illustrating one aspect of a process for comparing a new nucleotide or protein sequence with a database of sequences in order to determine the homology levels between the new sequence and the sequences in the database.

FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence of the invention, or a polypeptide sequence of the invention, a data storage device having retrievably stored thereon reference nucleotide sequences or polypeptide sequences to be compared to a nucleic acid sequence of the invention, or a polypeptide sequence of the invention and a sequence comparer for conducting the comparison. The sequence comparer may indicate a homology level between the sequences compared or identify structural motifs in the above described nucleic acid code a nucleic acid sequence of the invention, or a polypeptide sequence of the invention, or it may identify structural motifs in sequences which are compared to these nucleic acid codes and polypeptide codes. In some aspects, the data storage device may have stored thereon the sequences of at least 2, 5, 10, 15, 20, 25, 30 or 40 or more of the nucleic acid sequences of the invention, or the polypeptide sequences of the invention.

Another aspect of the invention is a method for determining the level of homology between a nucleic acid sequence of the invention, or a polypeptide sequence of the invention and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences of the invention, or the polypeptide sequences of the invention through use of the computer program and determining homology between the nucleic acid codes or polypeptide codes and reference nucleotide sequences or polypeptide sequences.

Figure 3:
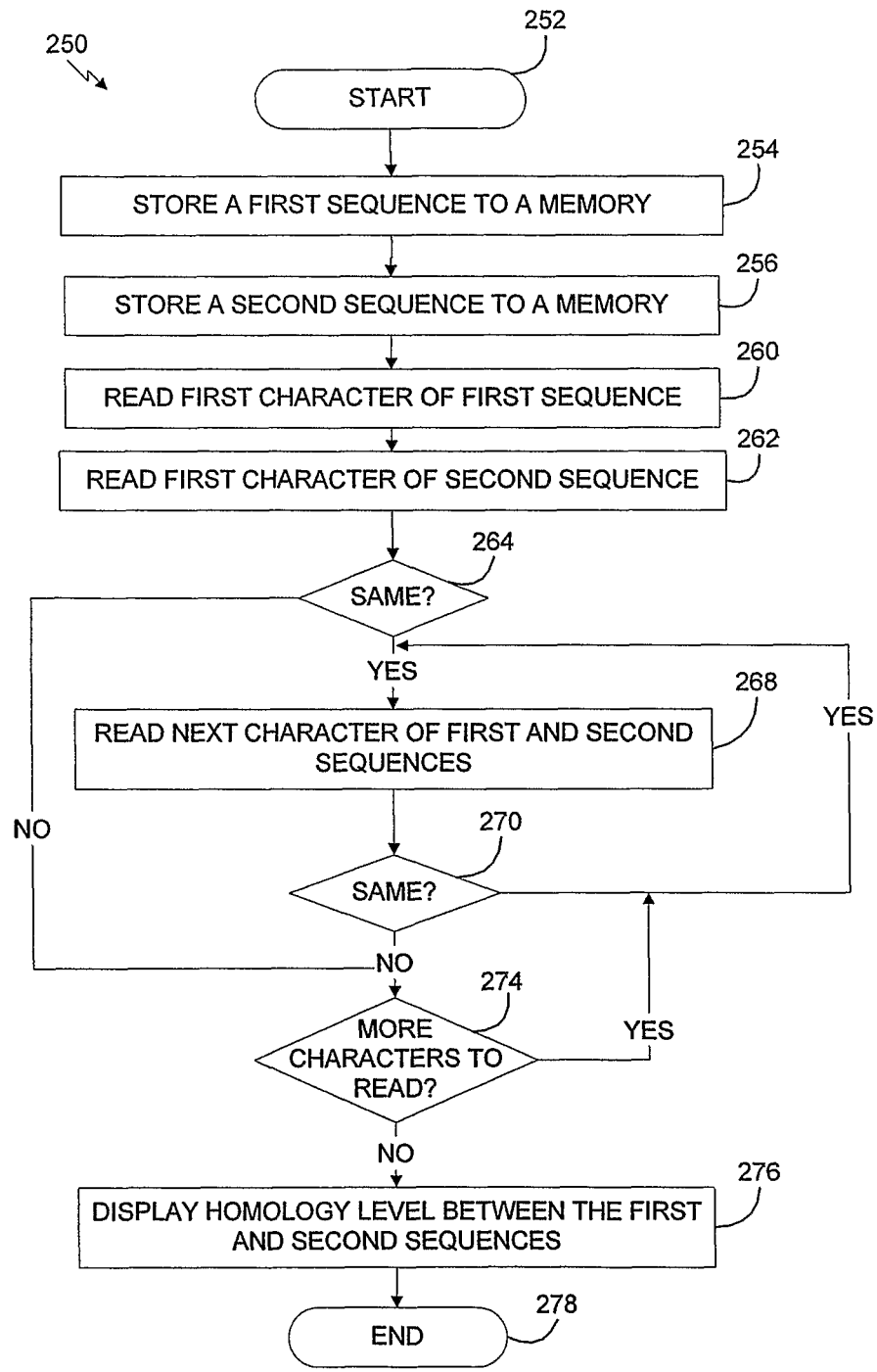
FIG. 3 is a flow diagram illustrating one aspect of a process in a computer for determining whether two sequences are homologous.

FIG. 3 is a flow diagram illustrating one aspect of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is in one aspect in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of the invention, differs from a reference nucleic acid sequence at one or more positions. Optionally such a program records the length and identity of inserted, deleted or substituted nucleotides with respect to the sequence of either the reference polynucleotide or a nucleic acid sequence of the invention. In one aspect, the computer program may be a program which determines whether a nucleic acid sequence of the invention, contains a single nucleotide polymorphism (SNP) with respect to a reference nucleotide sequence.

Accordingly, another aspect of the invention is a method for determining whether a nucleic acid sequence of the invention, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some aspects, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences of the invention and the reference nucleotide sequences through the use of the computer program and identifying differences between the nucleic acid codes and the reference nucleotide sequences with the computer program.

In other aspects the computer based system may further comprise an identifier for identifying features within a nucleic acid sequence of the invention or a polypeptide sequence of the invention. An "identifier" refers to one or more programs which identifies certain features within a nucleic acid sequence of the invention, or a polypeptide sequence of the invention. In one aspect, the identifier may comprise a program which identifies an open reading frame in a nucleic acid sequence of the invention.

Figure 4:
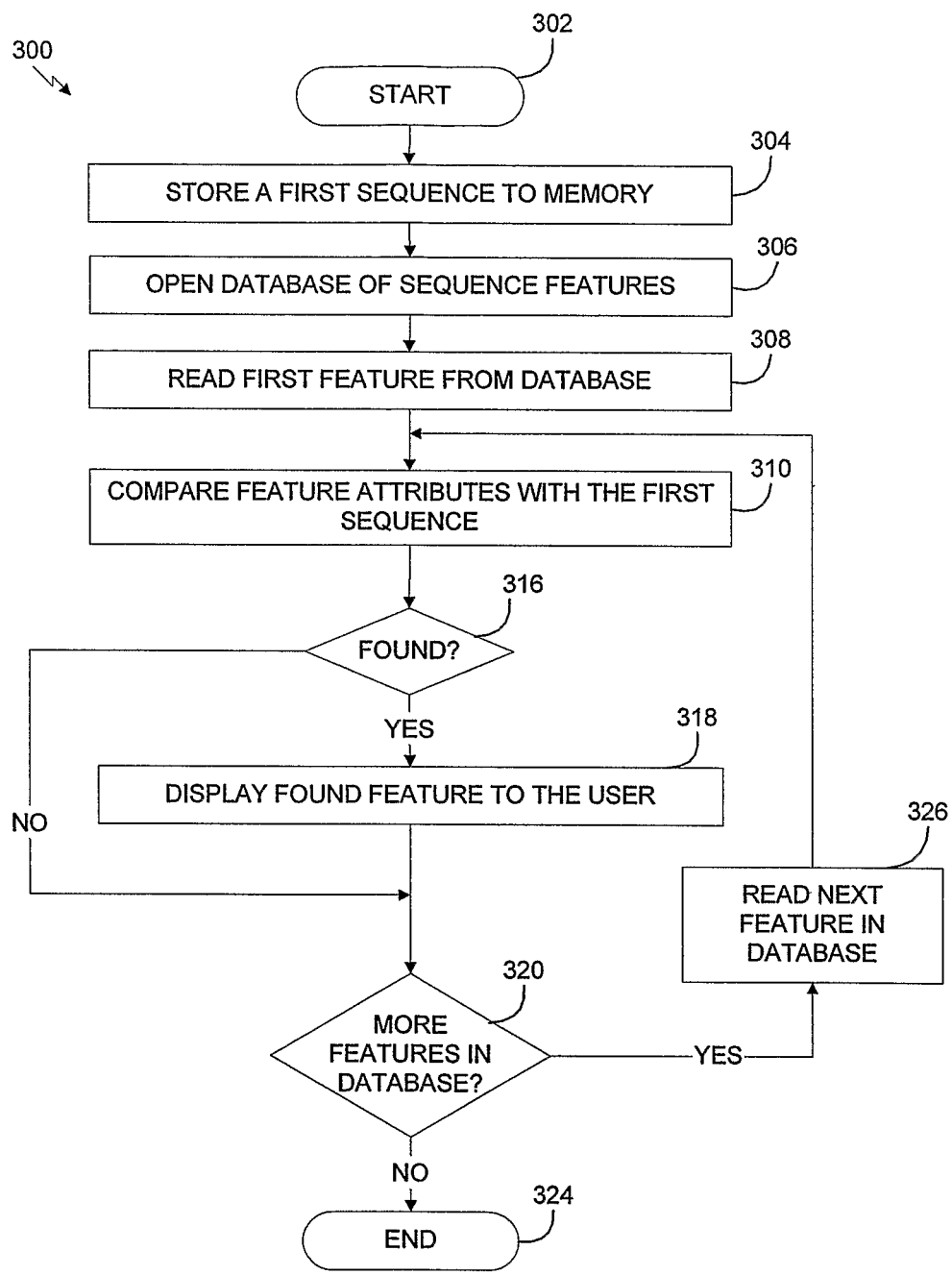
FIG. 4 is a flow diagram illustrating one aspect of an identifier process 300 for detecting the presence of a feature in a sequence.
Figure 5:
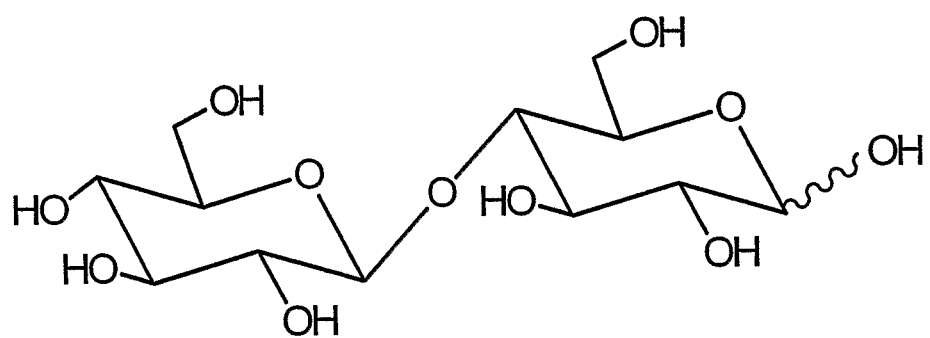
FIG. 5 is an illustration of the structure of cellobiose.

FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence of the invention, or a polypeptide sequence of the invention, comprising reading the nucleic acid code(s) or polypeptide code(s) through the use of a computer program which identifies features therein and identifying features within the nucleic acid code(s) with the computer program. In one aspect, computer program comprises a computer program which identifies open reading frames. The method may be performed by reading a single sequence or at least 2, 5, 10, 15, 20, 25, 30, or 40 or more of the nucleic acid sequences of the invention, or the polypeptide sequences of the invention, through the use of the computer program and identifying features within the nucleic acid codes or polypeptide codes with the computer program.

A nucleic acid sequence of the invention, or a polypeptide sequence of the invention, may be stored and manipulated in a variety of data processor programs in a variety of formats. For example, a nucleic acid sequence of the invention, or a polypeptide sequence of the invention, may be stored as text in a word processing file, such as Microsoft WORD™ or WORDPERFECT™ or as an ASCII file in a variety of database programs familiar to those of skill in the art, such as DB2™, SYBASE™, or ORACLE™. In addition, many computer programs and databases may be used as sequence comparison algorithms, identifiers, or sources of reference nucleotide sequences or polypeptide sequences to be compared to a nucleic acid sequence of the invention, or a polypeptide sequence of the invention. The following list is intended not to limit the invention but to provide guidance to programs and databases which are useful with the nucleic acid sequences of the invention, or the polypeptide sequences of the invention.

The programs and databases which may be used include, but are not limited to: MACPATTERN™ (EMBL), DISCOVERYBASE™ (Molecular Applications Group), GENEMINE™ (Molecular Applications Group), LOOK™ (Molecular Applications Group), MACLOOK™ (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), CATALYST™ (Molecular Simulations Inc.), Catalyst/SHAPE™ (Molecular Simulations Inc.), Cerius$^2$.DBAccess™ (Molecular Simulations Inc.), HYPOGEN™ (Molecular Simulations Inc.), INSIGHT II™, (Molecular Simulations Inc.), DISCOVER™ (Molecular Simulations Inc.), CHARMm™ (Molecular Simulations Inc.), FELIX™ (Molecular Simulations Inc.), DELPHI™, (Molecular Simulations Inc.), QuanteMM™, (Molecular Simulations Inc.), Homology (Molecular Simulations Inc.), MODELER™ (Molecular Simulations Inc.), ISIS™ (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices and beta sheets, signal sequences encoding signal peptides which direct the secretion of the encoded proteins, sequences implicated in transcription regulation such as homeoboxes, acidic stretches, enzymatic active sites, substrate binding sites and enzymatic cleavage sites.

Hybridization of Nucleic Acids

The invention provides isolated or recombinant nucleic acids that hybridize under stringent conditions to an exemplary sequence of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163 or SEQ ID NO:165 (see also Tables 1, 2, and 3, Examples 1 and 4, below, and Sequence Listing)). The stringent conditions can be highly stringent conditions, medium stringent conditions and/or low stringent conditions, including the high and reduced stringency conditions described herein. In one aspect, it is the stringency of the wash conditions that set forth the conditions which determine whether a nucleic acid is within the scope of the invention, as discussed below.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In alternative aspects, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

In one aspect, hybridization under high stringency conditions comprise about 50% formamide at about 37° C. to 42° C. In one aspect, hybridization conditions comprise reduced stringency conditions in about 35% to 25% formamide at about 30° C. to 35° C. In one aspect, hybridization conditions comprise high stringency conditions, e.g., at 42° C. in 50% formamide, 5×SSPE, 0.3% SDS and 200 n/ml sheared and denatured salmon sperm DNA. In one aspect, hybridization conditions comprise these reduced stringency conditions, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, siRNA or miRNA (single or double stranded), antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% or 40% formamide at a reduced temperature of 35° C. or 42° C.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content) and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's and 0.5 mg/ml polyriboadenylic acid. Approximately $2\times10^7$ cpm (specific activity $4\text{-}9\times10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m$-10° C. for the oligonucleotide probe. The membrane is then exposed to auto-radiographic film for detection of hybridization signals. All of the foregoing hybridizations would be considered to be under conditions of high stringency.

Following hybridization, a filter can be washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content) and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

In one aspect, hybridization conditions comprise a wash step comprising a wash for 30 minutes at room temperature in a solution comprising 1×150 mM NaCl, 20 mM Tris hydrochloride, pH 7.8, 1 mM $Na_2EDTA$, 0.5% SDS, followed by a 30 minute wash in fresh solution.

Nucleic acids which have hybridized to the probe are identified by autoradiography or other conventional techniques.

The above procedures may be modified to identify nucleic acids having decreasing levels of sequence identity (homology) to the probe sequence. For example, to obtain nucleic acids of decreasing sequence identity (homology) to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format may not be critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate or identify nucleic acids of the invention. For example, the preceding methods may be used to isolate or identify nucleic acids having a sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to a nucleic acid sequence selected from the group consisting of one of the sequences of the invention, or fragments comprising at least about 10, 15, 20, 25, 30, 35, 40, 50, 75, 100, 150, 200, 300, 400, or 500 consecutive bases thereof and the sequences complementary thereto. Sequence identity (homology) may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of the invention. Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% sequence identity (homology) to a polypeptide of the invention, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Oligonucleotides Probes and Methods for Using them

The invention also provides nucleic acid probes that can be used, e.g., for identifying, amplifying, or isolating nucleic acids encoding a polypeptide having a cellulase, e.g., endoglucanase, cellobiohydrolase, mannanase and/or beta-glucosidase enzyme activity or fragments thereof or for identifying cellulase, e.g., endoglucanase, cellobiohydrolase, mannanase and/or beta-glucosidase enzyme genes. In one aspect, the probe comprises at least about 10 consecutive bases of a nucleic acid of the invention. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The isolated or recombinant nucleic acids of the invention, the sequences complementary thereto, or a fragment comprising at least about 10, 15, 20, 25, 30, 35, 40, 50, 75, 100, 150, 200, 300, 400, or 500 consecutive bases of one of the sequences of the invention, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures and dot blots. Protocols for each of these procedures are provided in Ausubel et al. Current Protocols in Molecular Biology, John Wiley 503 Sons, Inc. (1997) and Sambrook et al., Molecular Cloning: A Laboratory Manual 2nd Ed., Cold Spring Harbor Laboratory Press (1989.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook, supra. Alternatively, the amplification may comprise a ligase chain reaction, 3 SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification—an Isothermal in vitro DNA Amplification Technique", *Nucleic Acid Research* 20:1691-1696, 1992). In such procedures, the nucleic acids in the sample are contacted with the probes, the amplification reaction is performed and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of the invention, may also be used in chromosome walking procedures to identify clones containing genomic sequences located adjacent to the sequences of the invention. Such methods allow the isolation of genes which encode additional proteins from the host organism.

In one aspect, the isolated or recombinant nucleic acids of the invention, the sequences complementary thereto, or a fragment comprising at least 10, 15, 20, 25, 30, 35, 40, 50, 75, 100, 150, 200, 300, 400, or 500 or more consecutive bases of one of the sequences of the invention, or the sequences complementary thereto are used as probes to identify and isolate related nucleic acids. In some aspects, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m = 81.5 + 16.6(\log [Na+]) + 0.41(\text{fraction } G+C) - (600/N)$ where N is the length of the probe.

If the hybridization is carried out in a solution containing formamide, the melting temperature may be calculated using the equation: $T_m = 81.5 + 16.6(\log [Na+]) + 0.41(\text{fraction } G+C) - (0.63\% \text{ formamide}) - (600/N)$ where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

In one aspect, hybridization is conducted by adding the detectable probe to the prehybridization solutions listed above. Where the probe comprises double stranded DNA, it is denatured before addition to the hybridization solution. In one aspect, the filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. In one aspect, for hybridizations in 6×SSC, the hybridization is conducted at approximately 68° C. Usually, for hybridizations in 50% formamide containing solutions, the hybridization is conducted at approximately 42° C.

Inhibiting Expression of Cellulase Enzymes

The invention provides nucleic acids complementary to (e.g., antisense sequences to) the nucleic acids of the invention, e.g., cellulase enzyme-encoding nucleic acids, e.g., nucleic acids comprising antisense, siRNA, miRNA, ribozymes. Nucleic acids of the invention comprising antisense sequences can be capable of inhibiting the transport, splicing or transcription of cellulase enzyme-encoding genes. The inhibition can be effected through the targeting of genomic DNA or messenger RNA. The transcription or function of targeted nucleic acid can be inhibited, for example, by hybridization and/or cleavage. One exemplary set of inhibitors provided by the present invention includes oligonucleotides which are able to either bind cellulase, e.g., endoglucanase, cellobiohydrolase, mannanase and/or beta-glucosidase enzyme gene or message, in either case preventing or inhibiting the production or function of a cellulase, e.g., endoglucanase, cellobiohydrolase, mannanase and/or beta-glucosidase enzyme. The association can be through sequence specific hybridization. Another useful class of inhibitors includes oligonucleotides which cause inactivation or cleavage of cellulase, e.g., endoglucanase, cellobiohydrolase, mannanase and/or beta-glucosidase enzyme message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of cellulase, e.g., endoglucanase, cellobiohydrolase, mannanase and/or beta-glucosidase enzyme expression on a nucleic acid and/or protein level, e.g., antisense, siRNA, miRNA and ribozymes comprising cellulase, e.g., endoglucanase, cellobiohydrolase, mannanase and/or beta-glucosidase enzyme sequences of the invention and the anti-cellulase, e.g., anti-endoglucanase, anti-cellobiohydrolase and/or anti-beta-glucosidase antibodies of the invention.

Inhibition of cellulase, e.g., endoglucanase, cellobiohydrolase, mannanase and/or beta-glucosidase enzyme expression can have a variety of industrial applications. For example, inhibition of cellulase, e.g., endoglucanase, cellobiohydrolase, mannanase and/or beta-glucosidase enzyme expression can slow or prevent spoilage. In one aspect, use of compositions of the invention that inhibit the expression and/or activity of cellulase, e.g., endoglucanase, cellobiohydrolase, mannanase and/or beta-glucosidase enzymes, e.g., antibodies, antisense oligonucleotides, ribozymes, siRNA and miRNA are used to slow or prevent spoilage. Thus, in one aspect, the invention provides methods and compositions comprising application onto a plant or plant product (e.g., a cereal, a grain, a fruit, seed, root, leaf, etc.) antibodies, antisense oligonucleotides, ribozymes, siRNA and miRNA of the invention to slow or prevent spoilage. These compositions also can be expressed by the plant (e.g., a transgenic plant) or another organism (e.g., a bacterium or other microorganism transformed with a cellulase, e.g., endoglucanase, cellobiohydrolase, mannanase and/or beta-glucosidase enzyme gene of the invention).

The compositions of the invention for the inhibition of cellulase, e.g., endoglucanase, cellobiohydrolase, mannanase and/or beta-glucosidase enzyme expression (e.g., antisense, iRNA, ribozymes, antibodies) can be used as pharmaceutical compositions, e.g., as anti-pathogen agents or in other therapies, e.g., as anti-microbials for, e.g., *Salmonella*.

Antisense Oligonucleotides

The invention provides antisense oligonucleotides capable of binding cellulase, e.g., endoglucanase, cellobiohydrolase, mannanase and/or beta-glucosidase enzyme message which, in one aspect, can inhibit cellulase, e.g., endoglucanase, cellobiohydrolase, mannanase and/or beta-glucosidase enzyme activity by targeting mRNA. Strategies for designing antisense oligonucleotides are well described in the scientific and patent literature, and the skilled artisan can design such cellulase, e.g., endoglucanase, cellobiohydrolase, mannanase and/or beta-glucosidase enzyme oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense cellulase, e.g., endoglucanase, cellobiohydrolase, mannanase and/or beta-glucosidase enzyme sequences of the invention (see, e.g., Gold (1995) J. of Biol. Chem. 270:13581-13584).

Inhibitory Ribozymes

The invention provides ribozymes capable of binding cellulase, e.g., endoglucanase, cellobiohydrolase, mannanase and/or beta-glucosidase enzyme message. These ribozymes can inhibit cellulase, e.g., endoglucanase, cellobiohydrolase, mannanase and/or beta-glucosidase enzyme activity by, e.g., targeting mRNA. Strategies for designing ribozymes and selecting the cellulase, e.g., endoglucanase, cellobiohydrolase, mannanase and/or beta-glucosidase enzyme-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In one aspect, a ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a cellulase, e.g., endoglucanase, cellobiohydrolase, mannanase and/or beta-glucosidase enzyme sequence of the invention. The RNAi molecule can comprise a double-stranded RNA (dsRNA) molecule, e.g., siRNA and/or miRNA. The RNAi molecule, e.g., siRNA and/or miRNA, can inhibit expression of a cellulase, e.g., endoglucanase, cellobiohydrolase, mannanase and/or beta-glucosidase enzyme gene. In one aspect, the RNAi molecule, e.g., siRNA and/or miRNA, is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's molecules, e.g., siRNA and/or miRNA, of the invention. The process may be practiced in vitro, ex vivo or in vivo. In one aspect, the RNAi molecules of the invention can be used to generate a loss-of-function mutation in a cell, an organ or an animal. Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Modification of Nucleic Acids—Making Variant Enzymes of the Invention

The invention provides methods of generating variants of the nucleic acids of the invention, e.g., those encoding a cellulase, e.g., endoglucanase, cellobiohydrolase, mannanase and/or beta-glucosidase enzyme. These methods can be repeated or used in various combinations to generate cellulase, e.g., endoglucanase, cellobiohydrolase, mannanase and/ or beta-glucosidase enzymes having an altered or different activity or an altered or different stability from that of a cellulase, e.g., endoglucanase, cellobiohydrolase, mannanase and/or beta-glucosidase enzyme encoded by the template nucleic acid. These methods also can be repeated or used in various combinations, e.g., to generate variations in gene/ message expression, message translation or message stability. In another aspect, the genetic composition of a cell is altered by, e.g., modification of a homologous gene ex vivo, followed by its reinsertion into the cell.

For example, in one aspect, the invention provides isolated or recombinant nucleic acids having a sequence comprising at least one nucleotide base residue modification of SEQ ID NO:163, wherein the modification comprises one or more of the following changes: a nucleotide at any one of positions 265 to 267 is modified to CGT, CGC, CGA, CGG, AGA or AGG; a nucleotide at any one of positions 307 to 309 is modified to GGT, GGC, GGA or GGG; a nucleotide at any one of positions 328 to 330 is modified to GGT, GGC, GGA or GGG; a nucleotide at any one of positions 340 to 342 is modified to TTA, TTG, CTT, CTC, CTA or CTG; a nucleotide at any one of positions 469 to 471 is modified to TCT, TCC, TCA, TCG, AGT or AGC; a nucleotide at any one of positions 1441 to 1443 is modified to TTT or TTC; a nucleotide at any one of positions 1648 to 1650 is modified to AAT or AAC; or, a nucleotide at any one of positions 1768 to 1770 is modified to CGT, CGC, CGA, CGG, AGA or AGG. In another aspect, the invention provides isolated or recombinant polypeptides having a sequence comprising at least one amino acid residue modification of SEQ ID NO:164, wherein the modification comprises one or more of the following changes: a methionine at amino acid position 89 is modified to arginine; a phenylalanine at amino acid position 103 is modified to glycine; a proline at amino acid position 110 is modified to glycine; a tyrosine at amino acid position 114 is modified to leucine; an alanine at amino acid position 157 is modified to serine; a tryptophan at amino acid position 481 is modified to phenylalanine; a proline at amino acid position 550 is modified to asparagine; or a glycine at amino acid position 590 is modified to arginine.

In another aspect, the invention provides isolated or recombinant nucleic acids having a sequence comprising a nucleotide residue sequence modification of an exemplary sequence of the invention (e.g., SEQ ID NO:1, SEQ ID NO:3, SEQ ID NO:5, SEQ ID NO:7, SEQ ID NO:9, SEQ ID NO:11, etc.) wherein the modification comprises one or more of the following changes: a nucleotide at the equivalent of any one of positions 265 to 267 of SEQ ID NO:163 are changed to CGT, CGC, CGA, CGG, AGA or AGG; a nucleotide at the equivalent of any one of positions 307 to 309 of SEQ ID NO:163 are changed to GGT, GGC, GGA or GGG; a nucleotide at the equivalent of any one of positions 328 to 330 of SEQ ID NO:163 are changed to GGT, GGC, GGA or GGG; a nucleotide at the equivalent of any one of positions 340 to 342 of SEQ ID NO:163 are changed to TTA, TTG, CTT, CTC, CTA or CTG; a nucleotide at the equivalent of any one of positions 469 to 471 of SEQ ID NO:163 are changed to TCT, TCC, TCA, TCG, AGT or AGC; a nucleotide at the equivalent of positions 1441 to 1443 of SEQ ID NO:163 are changed to TTT or TTC; a nucleotide at the equivalent of any one of positions 1648 to 1650 of SEQ ID NO:163 are changed to AAT or AAC; or a nucleotide at the equivalent of any one of positions 1768 to 1770 of SEQ ID NO:163 are changed to CGT, CGC, CGA, CGG, AGA or AGG. In another aspect, the invention provides isolated or recombinant nucleic acids having a sequence comprising a nucleotide residue sequence modification of any nucleic acid of the invention, wherein the modification comprises one or more of the following changes: a nucleotide at the equivalent of any one of positions 265 to 267 of SEQ ID NO:163 are changed to CGT, CGC, CGA, CGG, AGA or AGG; a nucleotide at the equivalent of any one of positions 307 to 309 of SEQ ID NO:163 are changed to GGT, GGC, GGA or GGG; a nucleotide at the equivalent of any one of positions 328 to 330 of SEQ ID NO:163 are changed to GGT, GGC, GGA or GGG; a nucleotide at the equivalent of any one of positions 340 to 342 of SEQ ID NO:163 are changed to TTA, TTG, CTT, CTC, CTA or CTG; a nucleotide at the equivalent of any one of positions 469 to 471 of SEQ ID NO:163 are changed to TCT, TCC, TCA, TCG, AGT or AGC; a nucleotide at the equivalent of positions 1441 to 1443 of SEQ ID NO:163 are changed to TTT or TTC; a nucleotide at the equivalent of any one of positions 1648 to 1650 of SEQ ID NO:163 are changed to AAT or AAC; or, a nucleotide at the equivalent of any one of positions 1768 to 1770 of SEQ ID NO:163 are changed to CGT, CGC, CGA, CGG, AGA or AGG.

In another aspect, the invention provides isolated or recombinant polypeptides having a sequence comprising an amino acid residue modification of an exemplary sequence of the invention (e.g., SEQ ID NO:2, SEQ ID NO:4, SEQ ID NO:6, SEQ ID NO: 8, SEQ ID NO:10, etc.) wherein the modification comprises one or more of the following changes: an amino acid at the equivalent of the methionine at amino acid position 89 of SEQ ID NO:164 is changed to an arginine; an amino acid at the equivalent of the phenylalanine at amino acid position 103 of SEQ ID NO:164 is changed to a glycine;

an amino acid at the equivalent of the proline at amino acid position 110 of SEQ ID NO:164 is changed to a glycine; an amino acid at the equivalent of the tyrosine at amino acid position 114 of SEQ ID NO:164 is changed to a leucine; an amino acid at the equivalent of the alanine at amino acid position 157 of SEQ ID NO:164 is changed to a serine; an amino acid at the equivalent of the tryptophan at amino acid position 481 of SEQ ID NO:164 is changed to a phenylalanine; an amino acid at the equivalent of the proline at amino acid position 550 of SEQ ID NO:164 is changed to an asparagine; or an amino acid at the equivalent of the glycine at amino acid position 590 of SEQ ID NO:164 is changed to an arginine.

In another aspect, the invention provides isolated or recombinant polypeptides having a sequence comprising an amino acid residue modification of any polypeptide of the invention, wherein the modification comprises one or more of the following changes: an amino acid at the equivalent of the methionine at amino acid position 89 of SEQ ID NO:164 is changed to an arginine; an amino acid at the equivalent of the phenylalanine at amino acid position 103 of SEQ ID NO:164 is changed to a glycine; an amino acid at the equivalent of the proline at amino acid position 110 of SEQ ID NO:164 is changed to a glycine; an amino acid at the equivalent of the tyrosine at amino acid position 114 of SEQ ID NO:164 is changed to a leucine; an amino acid at the equivalent of the alanine at amino acid position 157 of SEQ ID NO:164 is changed to a serine; an amino acid at the equivalent of the tryptophan at amino acid position 481 of SEQ ID NO:164 is changed to a phenylalanine; an amino acid at the equivalent of the proline at amino acid position 550 of SEQ ID NO:164 is changed to an asparagine; or an amino acid at the equivalent of the glycine at amino acid position 590 of SEQ ID NO:164 is changed to an arginine.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, Chromosomal Saturation Mutagenesis (CSM) and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller (1987) Oligonucleotide-directed mutagenesis: a simple method using two oligonucleotide primers and a single-stranded DNA template" Methods in Enzymol. 154: 329-350); phosphorothioate-modified DNA mutagenesis (Taylor (1985) "The use of phosphorothioate-modified DNA in restriction enzyme reactions to prepare nicked DNA" Nucl. Acids Res. 13: 8749-8764; Taylor (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer (1988) "Improved enzymatic in vitro reactions in the gapped duplex DNA approach to oligonucleotide-directed construction of mutations" Nucl. Acids Res. 16: 7207; and Fritz (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., saturation mutagenesis, such as Gene Site Saturation Mutagenesis (GSSM), synthetic ligation reassembly (SLR), or a combination thereof are used to modify the nucleic acids of the invention to generate cellulase, e.g., endoglucanase, cellobiohydrolase, mannanase and/or beta-glucosidase enzymes with new or altered properties (e.g., activity under highly acidic or alkaline conditions, high or low temperatures, and the like). Polypeptides encoded by the modified nucleic acids can be screened for an activity before testing for glucan hydrolysis or other activity. Any testing modality or protocol can be used, e.g., using a capillary array platform. See, e.g., U.S. Pat. Nos. 6,361,974; 6,280,926; 5,939,250.

Gene Site Saturation Mutagenesis, or, GSSM

The invention also provides methods for making enzyme using Gene Site Saturation mutagenesis, or, GSSM, as described herein, and also in U.S. Pat. Nos. 6,171,820 and 6,579,258. In one aspect, codon primers containing a degenerate N,N,G/T sequence are used to introduce point mutations into a polynucleotide, e.g., a cellulase, e.g., endoglucanase, cellobiohydrolase, mannanase and/or beta-glucosidase enzyme or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., cellulase, e.g., endoglucanase, cellobiohydrolase, mannanase and/or beta-glucosidase enzymes) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased glucan hydrolysis activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis (GSSM)). The oligos used are comprised contiguously of a first homologous sequence, a degenerate N,N,N sequence and in one aspect but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions and/or substitutions.

In one aspect, it is possible to simultaneously mutagenize two or more contiguous amino acid positions using an oligo that contains contiguous N,N,N triplets, i.e. a degenerate $(N,N,N)_n$ sequence. In another aspect, the present invention provides for the use of degenerate cassettes having less degeneracy than the N,N,N sequence. For example, it may be desirable in some instances to use (e.g. in an oligo) a degenerate triplet sequence comprised of only one N, where the N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

In one aspect, use of a degenerate triplet (such as N,N,G/T or an N,N, G/C triplet sequence) is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes and point mutations that cause the generation of stop codons and the corresponding expression of polypeptide fragments.

Thus, in one aspect of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

In one aspect, upon mutagenizing each and every amino acid position in a parental polypeptide using saturation mutagenesis as disclosed herein, a favorable amino acid changes is identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined—6 single point mutations (i.e., 2 at each of three positions) and no change at any position.

The invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is in one aspect every integer from 15 to 100,000. Thus, instead of mutagenizing every position along a molecule, one can subject every or a discrete number of bases (in one aspect a subset totaling from 15 to 100,000) to mutagenesis. In one aspect, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In one aspect, saturation mutagenesis is comprised of mutagenizing a complete set of mutagenic cassettes (wherein each cassette is in one aspect about 1-500 bases in length) in defined polynucleotide sequence to be mutagenized (wherein the sequence to be mutagenized is in one aspect from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

In one aspect, defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In one aspect, a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, e.g., cellulase, e.g., endoglucanase, cellobiohydrolase, mannanase and/or beta-glucosidase enzymes or antibodies of the invention, with new or altered properties.

SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773,900; 6,740,506; 6,713,282; 6,635,449; 6,605,449; 6,537,776. In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are in one aspect shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more in one aspect a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated in one aspect comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

Synthetic Gene Reassembly

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically. See, e.g., U.S. Pat. No. 6,537,776.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. The cellulase, e.g., endoglucanase, cellobiohydrolase, mannanase and/or beta-glucosidase enzymes of the present invention can be mutagenized in accordance with the methods described herein.

Thus according to one aspect of the invention, the sequences of a plurality of progenitor nucleic acid templates (e.g., polynucleotides of the invention) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

In one aspect, a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates and in one aspect at almost all of the progenitor templates. Even more in one aspect still a serviceable demarcation point is an area of homology that is shared by all of the progenitor templates.

In a one aspect, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated in one aspect comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

The invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one aspect, the recombination is facilitated by, or occurs at, areas of homology between the man-made, intron-containing gene and a nucleic acid, which serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

In one aspect, the synthetic gene reassembly method of the invention utilizes a plurality of nucleic acid building blocks, each of which in one aspect has two ligatable ends. The two ligatable ends on each nucleic acid building block may be two blunt ends (i.e. each having an overhang of zero nucleotides), or in one aspect one blunt end and one overhang, or more in one aspect still two overhangs. In one aspect, a useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block. A double-stranded nucleic acid building block can be of variable size. The sizes of these building blocks can be small or large. Exemplary sizes for building block range from 1 base pair (not including any overhangs) to 100,000 base pairs (not including any overhangs). Other exemplary size ranges are also provided, which have lower limits of from 1 bp to 10,000 bp (including every integer value in between) and upper limits of from 2 bp to 100,000 bp (including every integer value in between).

Many methods exist by which a double-stranded nucleic acid building block can be generated that is serviceable for the invention; and these are known in the art and can be readily performed by the skilled artisan. According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. In one aspect the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide. The approach of using recombination within a mixed population of genes can be useful for the generation of any useful proteins, for example, a cellulase of the invention or a variant thereof. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to make ribozymes or aptamers of the invention.

In one aspect the invention described herein is directed to the use of repeated cycles of reductive reassortment, recombination and selection which allow for the directed molecular evolution of highly complex linear sequences, such as DNA, RNA or proteins thorough recombination.

Optimized Directed Evolution System

The invention provides a non-stochastic gene modification system termed "optimized directed evolution system" to generate polypeptides, e.g., cellulase, e.g., endoglucanase, cellobiohydrolase, mannanase and/or beta-glucosidase enzymes or antibodies of the invention, with new or altered properties. In one aspect, optimized directed evolution is directed to the use of repeated cycles of reductive reassortment, recombination and selection that allow for the directed molecular evolution of nucleic acids through recombination.

Optimized directed evolution allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. Alternatively protocols for practicing these methods of the invention can be found in U.S. Pat. Nos. 6,773,900; 6,740,506; 6,713,282; 6,635,449; 6,605,449; 6,537,776; 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. See also U.S. Pat. Nos. 6,773, 900; 6,740,506; 6,713,282; 6,635,449; 6,605,449; 6,537,776; 6,361,974.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is in one aspect performed in MATLAB™ (The Mathworks, Natick, Mass.) a programming language and development environment for technical computing.

Iterative Processes

Any process of the invention can be iteratively repeated, e.g., a nucleic acid encoding an altered or new cellulase phenotype, e.g., endoglucanase, cellobiohydrolase, mannanase and/or beta-glucosidase enzyme of the invention, can be identified, re-isolated, again modified, re-tested for activity. This process can be iteratively repeated until a desired phenotype is engineered. For example, an entire biochemical anabolic or catabolic pathway can be engineered into a cell, including, e.g., cellulase, e.g., endoglucanase, cellobiohydrolase, mannanase and/or beta-glucosidase enzyme activity.

Similarly, if it is determined that a particular oligonucleotide has no affect at all on the desired trait (e.g., a new cellulase, e.g., endoglucanase, cellobiohydrolase, mannanase and/or beta-glucosidase enzyme phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In various aspects, in vivo shuffling of molecules is used in methods of the invention to provide variants of polypeptides of the invention, e.g., antibodies of the invention or cellulases of the invention, e.g., endoglucanase, cellobiohydrolase, mannanase and/or beta-glucosidase enzymes, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide (e.g., one, or both, being an exemplary cellulase, e.g., endoglucanase, cellobiohydrolase, mannanase and/or beta-glucosidase enzyme-encoding sequence of the invention) which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

In one aspect, vivo reassortment focuses on "inter-molecular" processes collectively referred to as "recombination"; which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

In another aspect of the invention, novel polynucleotides can be generated by the process of reductive reassortment. The method involves the generation of constructs containing consecutive sequences (original encoding sequences), their insertion into an appropriate vector and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences and results in the production of novel molecular species. Various treatments may be applied to enhance the rate of reassortment. These could include treatment with ultra-violet light, or DNA damaging chemicals and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In one aspect, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. In one aspect, the constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
  a) Primers that include a poly-A head and poly-T tail which when made single-stranded would provide orientation can be utilized. This is accomplished by having the first few bases of the primers made from RNA and hence easily removed RNaseH.
  b) Primers that include unique restriction cleavage sites can be utilized. Multiple sites, a battery of unique sequences and repeated synthesis and ligation steps would be required.
  c) The inner few bases of the primer could be thiolated and an exonuclease used to produce properly tailed molecules.

In one aspect, the recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
  1) The use of vectors only stably maintained when the construct is reduced in complexity.
  2) The physical recovery of shortened vectors by physical procedures. In this case, the cloning vector would be recovered using standard plasmid isolation procedures and size fractionated on either an agarose gel, or column with a low molecular weight cut off utilizing standard procedures.
  3) The recovery of vectors containing interrupted genes which can be selected when insert size decreases.
  4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates an exemplary method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (e.g., catalysts, solutes for increasing osmolarity of an aqueous solution and the like) and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a] anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-j]-quinoline ("N-hydroxy-IQ") and N-hydroxy-2-amino-1-methyl-6-phenylimidazo[4,5-j]-pyridine ("N-hydroxy-PhIP"). Exemplary means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

Producing Sequence Variants

The invention also provides additional methods for making sequence variants of the nucleic acid (e.g., cellulase, e.g., endoglucanase, cellobiohydrolase, mannanase and/or beta-glucosidase enzyme) sequences of the invention. The invention also provides additional methods for isolating cellulase, e.g., endoglucanase, cellobiohydrolase, mannanase and/or beta-glucosidase enzymes using the nucleic acids and polypeptides of the invention. In one aspect, the invention provides for variants of a cellulase, e.g., endoglucanase, cellobiohydrolase, mannanase and/or beta-glucosidase enzyme coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In one aspect of error prone PCR, the PCR is performed under conditions where the copying fidelity of the DNA polymerase is low, such that a high rate of point mutations is obtained along the entire length of the PCR product. Error prone PCR is described, e.g., in Leung (1989) Technique 1:11-15) and Caldwell (1992) PCR Methods Applic. 2:28-33. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids are evaluated.

In one aspect, variants are created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. In one aspect, clones containing the mutagenized DNA are recovered, expressed, and the activities of the polypeptide encoded therein assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

In one aspect, sexual PCR mutagenesis is an exemplary method of generating variants of the invention. In one aspect of sexual PCR mutagenesis forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/µl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

In one aspect, variants are created by in vivo mutagenesis. In some aspects, random mutations in a sequence of interest are generated by propagating the sequence of interest in a bacterial strain, such as an E. coli strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis" and U.S. Pat. No. 5,939,250, filed May 22, 1996, entitled, "Production of Enzymes Having Desired Activities by Mutagenesis.

The variants of the polypeptides of the invention may be variants in which one or more of the amino acid residues of the polypeptides of the sequences of the invention are substituted with a conserved or non-conserved amino acid residue (in one aspect a conserved amino acid residue) and such substituted amino acid residue may or may not be one encoded by the genetic code.

In one aspect, conservative substitutions are those that substitute a given amino acid in a polypeptide by another amino acid of like characteristics. In one aspect, conservative substitutions of the invention comprise the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of a polypeptide of the invention includes a substituent group. In one aspect, other variants are those in which the polypeptide is associated with another compound, such as a compound to increase the half-life of the polypeptide (for example, polyethylene glycol). Additional variants are those in which additional amino acids are fused to the polypeptide, such as a leader sequence, a secretory sequence, a proprotein sequence or a sequence which facilitates purification, enrichment, or stabilization of the polypeptide.

In some aspects, the fragments, derivatives and analogs retain the same biological function or activity as the polypeptides of the invention. In other aspects, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying cellulase, e.g., endoglucanase, cellobiohydrolase, mannanase and/or beta-glucosidase, enzyme-encoding nucleic acids to modify (e.g., optimize) codon usage. In one aspect, the invention provides methods for modifying codons in a nucleic acid encoding a cellulase, e.g., endoglucanase, cellobiohydrolase, mannanase and/or beta-glucosidase enzyme to increase or decrease its expression in a host cell. The invention also provides nucleic acids encoding a cellulase, e.g., endoglucanase, cellobiohydrolase, mannanase and/or beta-glucosidase enzyme modified to increase its expression in a host cell, cellulase, e.g., endoglucanase, cellobiohydrolase, mannanase and/or beta-glucosidase enzyme so modified, and methods of making the modified cellulase, e.g., endoglucanase, cellobiohydrolase, mannanase and/or beta-glucosidase enzymes. The method comprises identifying a "non-preferred" or a "less preferred" codon in cellulase, e.g., endoglucanase, cellobiohydrolase, mannanase and/or beta-glucosidase, enzyme-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells (see discussion, above). Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as *Streptomyces* sp., *Lactobacillus gasseri, Lactococcus lactis, Lactococcus cremoris, Bacillus subtilis, Bacillus cereus*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding a cellulase, e.g., endoglucanase, cellobiohydrolase, mannanase and/or beta-glucosidase enzyme isolated from a bacterial cell are modified such that the nucleic acid is optimally expressed in a bacterial cell different from the bacteria from which the cellulase, e.g., endoglucanase, cellobiohydrolase, mannanase and/or beta-glucosidase enzyme was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide (e.g., a cellulase, e.g., endoglucanase, cellobiohydrolase, mannanase and/or beta-glucosidase enzyme), an expression cassette or vector or a transfected or transformed cell of the invention. The invention also provides methods of making and using these transgenic non-human animals.

The transgenic non-human animals can be, e.g., dogs, goats, rabbits, sheep, pigs (including all swine, hogs and related animals), cows, rats and mice, comprising the nucleic acids of the invention. These animals can be used, e.g., as in vivo models to study cellulase, e.g., endoglucanase, cellobiohydrolase, mannanase and/or beta-glucosidase enzyme activity, or, as models to screen for agents that change the cellulase, e.g., endoglucanase, cellobiohydrolase, mannanase and/or beta-glucosidase enzyme activity in vivo. The coding sequences for the polypeptides to be expressed in the transgenic non-human animals can be designed to be constitutive, or, under the control of tissue-specific, developmental-specific or inducible transcriptional regulatory factors.

Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice. U.S. Pat. No. 6,187,992, describes making and using a transgenic mouse.

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing a cellulase, e.g., endoglucanase, cellobiohydrolase, mannanase and/or beta-glucosidase enzyme of the invention, or, a fusion protein comprising a cellulase, e.g., endoglucanase, cellobiohydrolase, mannanase and/or beta-glucosidase enzyme of the invention.

Transgenic Plants and Seeds

The invention provides transgenic plants and seeds comprising a nucleic acid, a polypeptide (e.g., a cellulase, e.g., endoglucanase, cellobiohydrolase, mannanase and/or beta-glucosidase enzyme), an expression cassette or vector or a transfected or transformed cell of the invention. The invention also provides plant products, e.g., oils, seeds, leaves, extracts and the like, comprising a nucleic acid and/or a polypeptide (e.g., a cellulase, e.g., endoglucanase, cellobiohydrolase, mannanase and/or beta-glucosidase enzyme) of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's cellulase, e.g., endoglucanase, cellobiohydrolase, mannanase and/or beta-glucosidase enzyme production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, tomato, soybean, beets, corn, wheat, rice, barley, and the like. Nucleic acids of the invention can be used to manipulate metabolic pathways of a plant in order to optimize or alter host's expression of cellulase, e.g., endoglucanase, cellobiohydrolase, mannanase and/or beta-glucosidase enzyme. The can change cellulase, e.g., endoglucanase, cellobiohydrolase, mannanase and/or beta-glucosidase enzyme activity in a plant. Alternatively, a cellulase, e.g., endoglucanase, cellobiohydrolase, mannanase and/or beta-glucosidase enzyme of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step involves selection and regeneration of whole plants capable of transmitting the incorporated target gene to the next generation. Such regeneration techniques may use manipulation of certain phytohormones in a tissue culture growth medium. In one aspect, the method uses a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

In one aspect, after the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a cellulase, e.g., endoglucanase, cellobiohydrolase, mannanase and/or beta-glucosidase enzyme) of the invention. The desired effects can be passed to future plant generations by standard propagation means.

In one aspect, the nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medi-* cago, *Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., a cellulase, e.g., endoglucanase, cellobiohydrolase, mannanase and/or beta-glucosidase enzyme or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity, or homology) to an exemplary sequence of the invention, e.g., proteins having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:10, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:143, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 or SEQ ID NO:166 (see also Tables 1, 2, and 3, Examples 1 and 4, below, and Sequence Listing)). The percent sequence identity can be over the full length of the polypeptide, or, the identity can be over a region of at least about 50, 60, 70, 80, 90, 100, 150, 200, 250, 300, 350, 400, 450, 500, 550, 600, 650, 700 or more residues.

Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as a cellulase, e.g., endoglucanase, cellobiohydrolase, mannanase and/or beta-glucosidase enzyme; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary cellulase, e.g., endoglucanase, cellobiohydrolase, mannanase and/or beta-glucosidase enzyme of the invention. Peptides of the invention (e.g., a subsequence of an exemplary polypeptide of the invention) can be useful as, e.g., labeling probes, antigens (immunogens), toleragens, motifs, cellulase, e.g., endoglucanase, cellobiohydrolase, mannanase and/or beta-glucosidase enzyme active sites (e.g., "catalytic domains"), signal sequences and/or prepro domains.

In alternative aspects, polypeptides of the invention having cellulase activity, e.g., endoglucanase, cellobiohydrolase, mannanase and/or beta-glucosidase activity are members of a genus of polypeptides sharing specific structural elements, e.g., amino acid residues, that correlate with cellulase activity, e.g., endoglucanase, cellobiohydrolase, mannanase and/or beta-glucosidase activity. These shared structural elements can be used for the routine generation of cellulase, e.g., endoglucanase, cellobiohydrolase, mannanase and/or beta-glucosidase variants. These shared structural elements of cellulase, e.g., endoglucanase, cellobiohydrolase, mannanase and/or beta-glucosidase enzymes of the invention can be used as guidance for the routine generation of cellulase, e.g., endoglucanase, cellobiohydrolase, mannanase and/or beta-glucosidase enzymes variants within the scope of the genus of polypeptides of the invention.

As used herein, the terms "cellulase, e.g., endoglucanase, cellobiohydrolase, mannanase and/or beta-glucosidase" encompass any polypeptide or enzymes capable of catalyzing the complete or partial breakdown and/or hydrolysis of cellulose (e.g., exemplary polypeptides of the invention, see also Tables 1, 2, and 3, Examples 1 and 4, below), or any modification of a cellulose or lignocellulotic material, e.g., a biomass material comprising lignocellulose.

In some aspects, a polypeptide of the invention can have an alternative enzymatic activity, for example, as set forth in Table 3, below. For example, the polypeptide having a sequence as set forth in SEQ ID NO:164, encoded, e.g., by SEQ ID NO:163, can have Alkaline endoglucanase/cellulase activity; the polypeptide having a sequence as set forth in SEQ ID NO:110, encoded, e.g., by SEQ ID NO:109, can have xylanase activity; the polypeptide having a sequence as set forth in SEQ ID NO:12, encoded, e.g., by SEQ ID NO:11, can have NAD binding oxidoreductase activity; the polypeptide having a sequence as set forth in SEQ ID NO:118, encoded, e.g., by SEQ ID NO:117, can have short chain dehydrogenase activity; the polypeptide having a sequence as set forth in SEQ ID NO:14, encoded, e.g., by SEQ ID NO:13, can have NADH dependent dehydrogenase activity; the polypeptide having a sequence as set forth in SEQ ID NO:138, encoded, e.g., by SEQ ID NO:137, can have peptidase activity; the polypeptide having a sequence as set forth in SEQ ID NO:162, encoded, e.g., by SEQ ID NO:161, can have Alkaline endoglucanase activity, in addition to cellulase activity; the polypeptide having a sequence as set forth in SEQ ID NO:42, encoded, e.g., by SEQ ID NO:41, can have cysteinyl tRNA synthetase activity; the polypeptide having a sequence as set forth in SEQ ID NO:32, encoded, e.g., by SEQ ID NO:31, can have cellodextrin phosphorylase activity; the polypeptide having a sequence as set forth in SEQ ID NO:50, encoded, e.g., by SEQ ID NO:49, can have fdhd/narq oxidoreductase activity; the polypeptide having a sequence as set forth in SEQ ID NO:54, encoded, e.g., by SEQ ID NO:53, can have a radical S-adenosylmethionine (SAM) activity; the polypeptide having a sequence as set forth in SEQ ID NO:58, encoded, e.g., by SEQ ID NO:57, can have a subtilisin like protease activity; etc., as set forth below:

TABLE 3

| SEQ ID NO: | Enzymatic Activity | Signaip Cleavage Site | Signal Sequence | Source | EC Number |
|---|---|---|---|---|---|
| 163, 164 | Alkaline endoglucanase/ cellulase | 1-30 | MSCRTLMSRRVGWGLLLWGGLFLRTGSVTG | Unknown | |
| 1, 2 | ORF 001-family 1 (β-glucosidase) | | | Unknown | 3.2.1.21 |
| 101, 102 | ORF 003-family 5 (cellulase) | 1-29 | MRNHLNVPFYFIFFFLIASIFTVCSSSTA | Unknown | 3.2.1.4 |
| 103, 104 | family 5 (cellulase) | 1-20 | MLIIGGLLVLLGFSSCGRQA | Unknown | 3.2.1.4 |
| 105, 106 | family 5 (cellulase) | | | Unknown | 3.2.1.4 |
| 107, 108 | family 5 (cellulase) | 1-32 | MEKQICSNVFSTMLIIGGLLVLLGFSSCGRQA | Unknown | 3.2.1.4 |
| 109, 110 | family 10 (xylanase) | 1-28 | MKTHSFNLRSRITLLTAALLFIGATAGA | Unknown | 3.2.1.8 |
| 11, 12 | ORF 003-NAD binding oxidoreductase | | | Unknown | 1.1.1.18 |
| 111, 112 | family 5 (cellulase) | 1-22 | MRRLITIILATAVAILSTTSCS | Unknown | 3.2.1.4 |
| 113, 114 | ORF 003-family 10 | 1-27 | MKVTRTAVAGIVAAAVLITIGTSTASA | Unknown | 3.2.1.8 |
| 115, 116 | ORF 004-short chain dehydrogenase | | | Unknown | 1.1.1.100 |
| 117, 118 | ORF 011-short chain dehydrogenase | 1-19 | MPKVMLVTGGSRGIGAAVA | Unknown | 1 . . . |
| 119, 120 | ORF 002-oxidoreductase | | | Unknown | 1.4.3.16 |
| 121, 122 | ORF 004-family 5 (cellulase | | | Unknown | 3.2.1.4 |
| 123, 124 | ORF 006-family 1 (β-glucosidase) | | | Unknown | 3.2.1.21 |
| 125, 126 | ORF 009-family 1 (β-glucosidase) | | | Unknown | 3.2.1.21 |
| 127, 128 | ORF 004-short chain dehydrogenase | | | Unknown | 1.1.1.100 |
| 129, 130 | ORF 010-short chain dehydrogenase | 1-19 | MPKVMLVTGGSRGIGAAVA | Unknown | 1 . . . |
| 13, 14 | ORF 005-NADH dependent dehydrogenase | | | Unknown | 1.1.1.18 |
| 131, 132 | ORF 007-family 5 (cellulase) | | | Unknown | 3.2.1.4 |
| 133, 134 | ORF 006-family 1 (β-glucosidase) | | | Unknown | 3.2.1.21 |
| 135, 136 | ORF 001-cellulase (glycosyl hydrolase family 5) | | | Unknown | 3.2.1.4 |
| 137, 138 | ORF 001-peptidase_M37 | | | Unknown | 3.5.1. |

TABLE 3-continued

| SEQ ID NO: | Enzymatic Activity | Signalp Cleavage Site | Signal Sequence | Source | EC Number |
|---|---|---|---|---|---|
| 139, 140 | ORF 001-threonine dehydrogenase | | | Unknown | 1 . . . |
| 141, 142 | ORF 005-family 1 (β-glucosidase) | | | Unknown | 3.2.1.21 |
| 143, 144 | ORF 003-family 1 (β-glucosidase) | | | Unknown | 3.2.1.21 |
| 145, 146 | ORF 002-family 1 (β-glucosidase) | | | Unknown | 3.2.1.21 |
| 147, 148 | family 10 (xylanase) | 1-26 | MLKVLRKPIISGLALALLLPAGAAGA | Unknown | 3.2.1.8 |
| 149, 150 | family 5 (cellulase) | | | Unknown | 3.2.1.4 |
| 15, 16 | ORF 007-family 1 (β-glucosidase) | | | Unknown | 3.2.1.21 |
| 151, 152 | family 5 (cellulase) | | | Unknown | 3.2.1.4 |
| 153, 154 | family 5 (cellulase) | | | Unknown | 3.2.1.4 |
| 155, 156 | family 5 (cellulase) | | | Unknown | 3.2.1.4 |
| 157, 158 | family 6 (cellulase) | | | Unknown | 3.2.1.4 |
| 159, 160 | family 10 (xylanase) | | | Unknown | 3.2.1.8 |
| 161, 162 | Alkaline endoglucanase/ cellulase | 1-30 | MSCRTLMSRRVGWGLLLWGGLFLRTGSVTG | Unknown | |
| 165, 166 | xylanase | | | | |
| 17, 18 | ORF 005-β-lactamase | 1-23 | MRYVLISCLALASLCAQPLPVST | Unknown | 3.5.2.6 |
| 19, 20 | ORF 008-family 10 (xylanase) | 1-20 | MPVLFALFLVASSCAAQSLA | Unknown | 3.2.1.8 |
| 21, 22 | ORF 001-family 5 (cellulase) | | | Clostridium thermocellum | 3.2.1.4 |
| 23, 24 | ORF 003-Family 16 + CBM | 1-26 | MYKRLLSSVLIIMLLLSAWSPISVQA | Clostridium thermocellum | 3.2.1. |
| 25, 26 | ORF 001-family 1 (β-glucosidase) | | | Clostridium thermocellum | 3.2.1.21 |
| 27, 28 | ORF 002-family 1 (β-glucosidase) | | | Unknown | 3.2.1.21 |
| 29, 30 | ORF 004-family 1 (β-glucosidase) | | | Unknown | 3.2.1.21 |
| 3, 4 | ORF 008-family 1 (β-glucosidase) | | | Unknown | 3.2.1.21 |
| 31, 32 | ORF 002-cellodextrin phosphorylase | | | Unknown | 2.4.1.20 |
| 33, 34 | ORF 006-family 1 (β-glucosidase) | | | Unknown | 3.2.1.21 |
| 35, 36 | ORF 007-family 5 (cellulase) | 1-23 | MNKILKLFSSLLLFAGICPALQA | Unknown | 3.2.1.4 |

TABLE 3-continued

| SEQ ID NO: | Enzymatic Activity | Signalp Cleavage Site | Signal Sequence | Source | EC Number |
|---|---|---|---|---|---|
| 37, 38 | ORF 011-family 1 (β-glucosidase) | | | Unknown | 3.2.1.21 |
| 39, 40 | ORF 004-putative oxidoreductase | | | Unknown | 4.1.1. |
| 41, 42 | ORF 004 -cysteinyl tRNA synthetase | | | Unknown | 6.1.1.16 |
| 43, 44 | ORF 011- | | | Unknown | |
| 45, 46 | ORF 006-family 1 (β-glucosidase) | | | Unknown | 3.2.1.21 |
| 47, 48 | ORF 002-family 1 (β-glucosidase) | | | Unknown | 3.2.1.21 |
| 49, 50 | ORF 006-fdhd/narq oxidoreductase | | | Unknown | |
| 5, 6 | ORF 012-family 6 (cellulase) | 1-29 | MTRRSIVRSSSNKWLVLAGAALLACTALG | Unknown | 3.2.1.91 |
| 51, 52 | ORF 001-family 5 (cellulase) | 1-20 | MSRGILILVMLSVLSGAALA | Unknown | 3.2.1.4 |
| 53, 54 | ORF 002-Radical SAM family | | | Unknown | 1 . . . |
| 55, 56 | ORF 004-family 1 (β-glucosidase) | | | Unknown | 3.2.1.21 |
| 57, 58 | ORF 001-subtilisin like protease | | | Unknown | |
| 59, 60 | family 5 (cellulase) | | | Unknown | 3.2.1.4 |
| 61, 62 | family 5 (cellulase) OFR 1 | 1-52 | MVWTPARSTLAGSSEIPLMTMNIFPNRKD SRMSLWIKLGILCMMAGTVMVHG | Unknown | 3.2.1.4 |
| 63, 64 | family 5 (cellulase) ORF 4 | 1-24 | MKRREFMLGGAGVAALASTLGVSA | Unknown | 3.2.1.4 |
| 65, 66 | family 10 (xylanase) | 1-39 | MNTLLPRRRLWSSTAILRTLAAGALAAGM VLAPVSAANa | Unknown | 3.2.1.8 |
| 67, 68 | family 5 (cellulase)-ORF 2 | 1-23 | MKYIFSYIIMMILIGFIPVYGFG | Unknown | 3.2.1.4 |
| 69, 70 | family 26 (mannanase)-ORF4 | 1-20 | MSFKNHILLSLLIVLLFFSA | Unknown | 3.2.1.78 |
| 7, 8 | ORF 003-Isocitrate dehydrogenase | | | Unknown | 1.1.1.42 |
| 71, 72 | family 5 (cellulase) | 1-21 | MKLLKLLIFLLITVIFSDVSA | Unknown | 3.2.1.4 |
| 73, 74 | family 10 (xylanase) | | | Unknown | 3.2.1.21 |
| 75, 76 | family 5 (cellulase) | 1-21 | MLRKLIVSVFGFVMLTSAAAA | Unknown | 3.2.1.4 |
| 77, 78 | family 5 (cellulase) | 1-28 | MKRKRVFIHSLIVFFLMIGSFTSCGSVA | Unknown | 3.2.1.4 |
| 79, 80 | family 5 (cellulase) | 1-25 | MKYKAIFIYLIVLILFYSINIYANA | Unknown | 3.2.1.4 |
| 81, 82 | family 5 (cellulase) | 1-25 | MNLLAQYFSGLFLIFLISIFFVSSA | Unknown | 3.2.1.4 |
| 83, | ORF 008-dehydrogenase | | | Unknown | 3.5.4.25 |

TABLE 3-continued

| SEQ ID NO: | Enzymatic Activity | Signalp Cleavage Site | Signal Sequence | Source | EC Number |
|---|---|---|---|---|---|
| 84 | | | | | |
| 85, 86 | ORF 008-family 1 (β-glucosidase) | | | Unknown | 3.2.1.21 |
| 87, 88 | family 5 (cellulase) | 1-23 | MRKSVFTLAVFLSALFAFTSCQN | Unknown | 3.2.1.4 |
| 89, 90 | family 5 (cellulase) | 1-29 | MKRSVSIFIACLLMTVLTISGVAAPEASA | Unknown | 3.2.1.4 |
| 9, 10 | ORF 004-family 10 (xylanase) | 1-26 | MRSVRIVTFALAAALAVPLVTSTATA | Unknown | 3.2.1.8 |
| 91, 92 | ORF 001-family 3 | | | Unknown | 3.2.1.52 |
| 93, 94 | ORF 002-alpha-rhamnosidase | | | Unknown | |
| 95, 96 | ORF 001-family 3 | | | Unknown | 3.2.1.21 |
| 97, 98 | ORF 003-beta-glucuronidase | | | Unknown | 3.2.1.31 |
| 99, 100 | ORF 012-family 1 (β-glucosidase) | | | Unknown | 3.2.1.21 |

"Amino acid" or "amino acid sequence" as used herein refer to an oligopeptide, peptide, polypeptide, or protein sequence, or to a fragment, portion, or subunit of any of these and to naturally occurring or synthetic molecules. "Amino acid" or "amino acid sequence" include an oligopeptide, peptide, polypeptide, or protein sequence, or to a fragment, portion, or subunit of any of these, and to naturally occurring or synthetic molecules. The term "polypeptide" as used herein, refers to amino acids joined to each other by peptide bonds or modified peptide bonds, i.e., peptide isosteres and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, glucan hydrolase processing, phosphorylation, prenylation, racemization, selenoylation, sulfation and transfer-RNA mediated addition of amino acids to protein such as arginylation. (See Creighton, T. E., Proteins—Structure and Molecular Properties 2nd Ed., W.H. Freeman and Company, New York (1993); *Posttranslational Covalent Modification of Proteins*, B. C. Johnson, Ed., Academic Press, New York, pp. 1-12 (1983)). The peptides and polypeptides of the invention also include all "mimetic" and "peptidomimetic" forms, as described in further detail, below.

As used herein, the term "isolated" means that the material (e.g., a protein or nucleic acid of the invention) is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment. As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. In one aspect, the term "purified" includes nucleic acids which have been purified from the remainder of the genomic DNA or from other sequences in a library or other environment by at least one order of magnitude, e.g., in one aspect, two or three orders, or, four or five orders of magnitude.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem.*

Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81:3998 (1984) and provide for synthesizing peptides upon the tips of a multitude of "rods" or "pins" all of which are connected to a single plate.

The phrase "substantially identical" in the context of two nucleic acids or polypeptides, refers to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one of the known sequence comparison algorithms or by visual inspection. In alternative aspects, the substantial identity exists over a region of at least about 100 or more residues and most commonly the sequences are substantially identical over at least about 150 to 200 or more residues. In some aspects, the sequences are substantially identical over the entire length of the coding regions.

Additionally a "substantially identical" amino acid sequence is a sequence that differs from a reference sequence by one or more conservative or non-conservative amino acid substitutions, deletions, or insertions. In one aspect, the substitution occurs at a site that is not the active site of the molecule, or, alternatively the substitution occurs at a site that is the active site of the molecule, provided that the polypeptide essentially retains its functional (enzymatic) properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a cellulase, e.g., endoglucanase, cellobiohydrolase, mannanase and/or beta-glucosidase polypeptide, resulting in modification of the structure of the polypeptide, without significantly altering its biological activity. For example, amino- or carboxyl-terminal amino acids that are not required for cellulase, e.g., endoglucanase, cellobiohydrolase, mannanase and/or beta-glucosidase enzyme biological activity can be removed. Modified polypeptide sequences of the invention can be assayed for cellulase, e.g., endoglucanase, cellobiohydrolase, mannanase and/or beta-glucosidase enzyme biological activity by any number of methods, including contacting the modified polypeptide sequence with a substrate and determining whether the modified polypeptide decreases the amount of specific substrate in the assay or increases the bioproducts of the enzymatic reaction of a functional cellulase, e.g., endoglucanase, cellobiohydrolase, mannanase and/or beta-glucosidase polypeptide with the substrate.

"Fragments" as used herein are a portion of a naturally occurring protein which can exist in at least two different conformations. Fragments can have the same or substantially the same amino acid sequence as the naturally occurring protein. Fragments which have different three dimensional structures as the naturally occurring protein are also included. An example of this, is a "pro-form" molecule, such as a low activity proprotein that can be modified by cleavage to produce a mature enzyme with significantly higher activity.

In one aspect, the invention provides crystal (three-dimensional) structures of proteins and peptides, e.g., cellulases, of the invention; which can be made and analyzed using the routine protocols well known in the art, e.g., as described in MacKenzie (1998) Crystal structure of the family 7 endoglucanase I (Cel7B) from *Humicola insolens* at 2.2 A resolution and identification of the catalytic nucleophile by trapping of the covalent glycosyl-enzyme intermediate, Biochem. J. 335: 409-416; Sakon (1997) Structure and mechanism of endo/exocellulase E4 from *Thermomonospora fusca*, Nat. Struct. Biol 4:810-818; Varrot (1999) Crystal structure of the catalytic core domain of the family 6 cellobiohydrolase II, Cel6A, from *Humicola insolens*, at 1.92 A resolution, Biochem. J. 337:297-304; illustrating and identifying specific structural elements as guidance for the routine generation of cellulase variants of the invention, and as guidance for identifying enzyme species within the scope of the invention.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants or members of a genus of polypeptides of the invention (e.g., having about 50% or more sequence identity to an exemplary sequence of the invention), routine experimentation will determine whether a mimetic is within the scope of the invention, i.e., that its structure and/or function is not substantially altered. Thus, in one aspect, a mimetic composition is within the scope of the invention if it has a cellulase, e.g., endoglucanase, cellobiohydrolase, mannanase and/or beta-glucosidase enzymes activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyrenylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholinyl-(4-ethyl)carbodiimide or 1-ethyl-3(4-azonia-4,4-dimethylpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propiolic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

In one aspect, a residue, e.g., an amino acid, of a polypeptide of the invention can also be replaced by an amino acid (or peptidomimetic residue) of the opposite chirality. In one aspect, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. In one aspect, modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The polypeptides of the invention include cellulase, e.g., endoglucanase, cellobiohydrolase, mannanase and/or beta-glucosidase enzymes in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include cellulase, e.g., endoglucanase, cellobiohydrolase, mannanase and/or beta-glucosidase enzymes inactive for other reasons, e.g., before "activation" by a post-translational processing event, e.g., an endo- or exo-peptidase or proteinase action, a phosphorylation event, an amidation, a glycosylation or a sulfation, a dimerization event, and the like. The polypeptides of the invention include all active forms, including active subsequences, e.g., catalytic domains or active sites, of the enzyme.

The invention includes immobilized cellulase, e.g., endoglucanase, cellobiohydrolase, mannanase and/or beta-glucosidase enzymes, anti-cellulase, e.g., anti-endoglucanase, anti-cellobiohydrolase and/or anti-beta-glucosidase antibodies and fragments thereof. The invention provides methods for inhibiting cellulase, e.g., endoglucanase, cellobiohydrolase, mannanase and/or beta-glucosidase enzyme activity, e.g., using dominant negative mutants or anti-cellulase, e.g., anti-endoglucanase, anti-cellobiohydrolase and/or anti-beta-glucosidase antibodies of the invention. The invention includes heterocomplexes, e.g., fusion proteins, heterodimers, etc., comprising the cellulase, e.g., endoglucanase, cellobiohydrolase, mannanase and/or beta-glucosidase enzymes of the invention.

Polypeptides of the invention can have a cellulase, e.g., endoglucanase, cellobiohydrolase, mannanase and/or beta-glucosidase enzyme activity under various conditions, e.g., extremes in pH and/or temperature, oxidizing agents, and the like. The invention provides methods leading to alternative cellulase, e.g., endoglucanase, cellobiohydrolase, mannanase and/or beta-glucosidase enzyme preparations with different catalytic efficiencies and stabilities, e.g., towards temperature, oxidizing agents and changing wash conditions. In one aspect, cellulase, e.g., endoglucanase, cellobiohydrolase, mannanase and/or beta-glucosidase enzyme variants can be produced using techniques of site-directed mutagenesis and/or random mutagenesis. In one aspect, directed evolution can be used to produce a great variety of cellulase, e.g., endoglucanase, cellobiohydrolase, mannanase and/or beta-glucosidase enzyme variants with alternative specificities and stability.

The proteins of the invention are also useful as research reagents to identify cellulase, e.g., endoglucanase, cellobiohydrolase, mannanase and/or beta-glucosidase enzyme modulators, e.g., activators or inhibitors of cellulase, e.g., endoglucanase, cellobiohydrolase, mannanase and/or beta-glucosidase enzyme activity. Briefly, test samples (compounds, broths, extracts, and the like) are added to cellulase, e.g., endoglucanase, cellobiohydrolase, mannanase and/or beta-glucosidase enzyme assays to determine their ability to inhibit substrate cleavage. Inhibitors identified in this way can be used in industry and research to reduce or prevent undesired proteolysis. As with cellulase, e.g., endoglucanase, cellobiohydrolase, mannanase and/or beta-glucosidase enzymes, inhibitors can be combined to increase the spectrum of activity.

The enzymes of the invention are also useful as research reagents to digest proteins or in protein sequencing. For example, the cellulase, e.g., endoglucanase, cellobiohydrolase, mannanase and/or beta-glucosidase enzymes may be used to break polypeptides into smaller fragments for sequencing using, e.g. an automated sequencer.

The invention also provides methods of discovering new cellulase, e.g., endoglucanase, cellobiohydrolase, mannanase and/or beta-glucosidase enzymes using the nucleic acids, polypeptides and antibodies of the invention. In one aspect, phagemid libraries are screened for expression-based discovery of cellulase, e.g., endoglucanase, cellobiohydrolase, mannanase and/or beta-glucosidase enzymes. In another aspect, lambda phage libraries are screened for expression-based discovery of cellulase, e.g., endoglucanase, cellobiohydrolase, mannanase and/or beta-glucosidase enzymes. Screening of the phage or phagemid libraries can allow the detection of toxic clones; improved access to substrate; reduced need for engineering a host, by-passing the potential for any bias resulting from mass excision of the library; and, faster growth at low clone densities. Screening of phage or phagemid libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174; U.S. Pat. No. 6,245,547.

In one aspect, polypeptides or fragments of the invention are obtained through biochemical enrichment or purification procedures. The sequence of potentially homologous polypeptides or fragments may be determined by cellulase, e.g., endoglucanase, cellobiohydrolase, mannanase and/or beta-glucosidase enzyme assays (see, e.g., Examples 1, 2 and 3, below), gel electrophoresis and/or microsequencing. The sequence of the prospective polypeptide or fragment of the invention can be compared to an exemplary polypeptide of the invention, or a fragment, e.g., comprising at least about 5, 10, 15, 20, 25, 30, 35, 40, 50, 75, 100, or 150 or more consecutive amino acids thereof using any of the programs described above.

Another aspect of the invention is an assay for identifying fragments or variants of the invention, which retain the enzymatic function of the polypeptides of the invention. For example the fragments or variants of said polypeptides, may be used to catalyze biochemical reactions, which indicate that the fragment or variant retains the enzymatic activity of a polypeptide of the invention. An exemplary assay for determining if fragments of variants retain the enzymatic activity of the polypeptides of the invention includes the steps of: contacting the polypeptide fragment or variant with a substrate molecule under conditions which allow the polypeptide fragment or variant to function and detecting either a decrease in the level of substrate or an increase in the level of the specific reaction product of the reaction between the polypeptide and substrate.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups and can react with many starting compounds containing this functional group.

In one aspect, the biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

In one aspect, procedural steps are performed using robotic automation enabling the execution of many thousands of biocatalytic reactions and/or screening assays per day as well as ensuring a high level of accuracy and reproducibility. Robotic automation can also be used to screen for cellulase activity to determine if a polypeptide is within the scope of the invention. As a result, in one aspect, a library of derivative compounds can be produced in a matter of weeks which would take years to produce using "traditional" chemical or enzymatic screening methods.

In a particular aspect, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library, which exhibits a desired activity. A specific biocatalytic reaction which produces the modified small molecule of desired activity is identified by systematically eliminating each of the biocatalytic reactions used to produce a portion of the library and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

Cellulase, e.g., Endoglicanase, Cellobiohydrolase and/or Beta-Glucosidase Enzyme Signal Sequences, Prepro and Catalytic Domains The invention provides cellulase, e.g., endoglucanase, cellobiohydrolase, mannanase and/or beta-glucosidase enzyme signal sequences (e.g., signal peptides (SPs)), prepro domains and catalytic domains (CDs). The SPs, prepro domains and/or CDs of the invention can be isolated or recombinant peptides or can be part of a fusion protein, e.g., as a heterologous domain in a chimeric protein. The invention provides nucleic acids encoding these catalytic domains (CDs), prepro domains and signal sequences (SPs, e.g., a peptide having a sequence comprising/consisting of amino terminal residues of a polypeptide of the invention).

The invention provides isolated or recombinant signal sequences (e.g., signal peptides) consisting of or comprising a sequence as set forth in residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43, 1 to 44, 1 to 45, 1 to 46, or 1 to 47, or more, of a polypeptide of the invention, e.g., exemplary polypeptides of the invention, see also Table 3, Examples 1 and 4, below, and Sequence Listing. For example, Table 3, above, sets forth exemplary signal (leader) sequences of the invention, e.g., as in the polypeptide having a sequence as set forth in SEQ ID NO:164, encoded, e.g., by SEQ ID NO:163, has a signal sequence comprising (or consisting of) the amino terminal 30 residues, or, MSCRTLMSRRVGWGLLLWGGLFLRTGSVTG. Additional signal sequences are similarly set forth in Table 3.

In one aspect, the invention provides signal sequences comprising the first 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more amino terminal residues of a polypeptide of the invention.

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated or recombinant signal sequences, prepro sequences and catalytic domains (e.g., "active sites") comprising sequences of the invention. The polypeptide comprising a signal sequence of the invention can be a cellulase, e.g., endoglucanase, cellobiohydrolase, mannanase and/or beta-glucosidase enzyme of the invention or another cellulase, e.g., endoglucanase, cellobiohydrolase, mannanase and/or beta-glucosidase enzyme or another enzyme or other polypeptide. Methods for identifying "prepro" domain sequences and signal sequences are well known in the art, see, e.g., Van de Ven (1993) Crit. Rev. Oncog. 4(2): 115-136. For example, to identify a prepro sequence, the protein is purified from the extracellular space and the N-terminal protein sequence is determined and compared to the unprocessed form.

The cellulase, e.g., endoglucanase, cellobiohydrolase, mannanase and/or beta-glucosidase enzyme signal sequences (SPs) and/or prepro sequences of the invention can be isolated or recombinant peptides, or, sequences joined to another cellulase, e.g., endoglucanase, cellobiohydrolase, mannanase and/or beta-glucosidase enzyme or a non-cellulase, e.g., non-endoglucanase, non-cellobiohydrolase and/or non-beta-glucosidase polypeptide, e.g., as a fusion (chimeric) protein. In one aspect, the invention provides polypeptides comprising cellulase, e.g., endoglucanase, cellobiohydrolase, mannanase and/or beta-glucosidase enzyme signal sequences of the invention. In one aspect, polypeptides comprising cellulase, e.g., endoglucanase, cellobiohydrolase, mannanase and/or beta-glucosidase enzyme signal sequences SPs and/or prepro of the invention comprise sequences heterologous to a cellulase, e.g., endoglucanase, cellobiohydrolase, mannanase and/or beta-glucosidase enzyme of the invention (e.g., a fusion protein comprising an SP and/or prepro of the invention and sequences from another cellulase, e.g., endoglucanase, cellobiohydrolase, mannanase and/or beta-glucosidase enzyme or a non-cellulase, e.g., non-endoglucanase, non-cellobiohydrolase and/or non-beta-glucosidase protein). In one aspect, the invention provides cellulase, e.g., endoglucanase, cellobiohydrolase, mannanase and/or beta-glucosidase enzymes of the invention with heterologous SPs and/or prepro sequences, e.g., sequences with a yeast signal sequence. A cellulase, e.g., endoglucanase, cellobiohydrolase, mannanase and/or beta-glucosidase enzyme of the invention can comprise a heterologous SP and/or prepro in a vector, e.g., a pPIC series vector (Invitrogen, Carlsbad, Calif.).

In one aspect, SPs and/or prepro sequences of the invention are identified following identification of novel cellulase, e.g., endoglucanase, cellobiohydrolase, mannanase and/or beta-glucosidase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from about 10 to 65, or more, amino acid residues. Various methods of recognition of signal sequences are known to those of skill in the art. For example, in one aspect, novel cellulase, e.g., endoglucanase, cellobiohydrolase, mannanase and/or beta-glucosidase enzyme signal peptides are identified by a method referred to as SignalP. SignalP uses a combined neural network which recognizes both signal peptides and their cleavage sites. (Nielsen (1997) "Identification of prokaryotic and eukaryotic signal peptides and prediction of their cleavage sites." Protein Engineering 10:1-6.

In some aspects cellulase, e.g., endoglucanase, cellobiohydrolase, mannanase and/or beta-glucosidase enzymes of the invention do not have SPs and/or prepro sequences or "domains." In one aspect, the invention provides the cellulase, e.g., endoglucanase, cellobiohydrolase, mannanase and/or beta-glucosidase enzymes of the invention lacking all or part of an SP and/or a prepro domain. In one aspect, the invention provides a nucleic acid sequence encoding a signal sequence (SP) and/or prepro from one cellulase, e.g., endoglucanase, cellobiohydrolase, mannanase and/or beta-glucosidase enzyme operably linked to a nucleic acid sequence of a different cellulase, e.g., endoglucanase, cellobiohydrolase, mannanase and/or beta-glucosidase enzyme or, optionally, a signal sequence (SPs) and/or prepro domain from a non-cellulase, e.g., non-endoglucanase, non-cellobiohydrolase and/or non-beta-glucosidase protein may be desired.

The invention also provides isolated or recombinant polypeptides comprising signal sequences (SPs), prepro domain and/or catalytic domains (CDs) of the invention and heterologous sequences. The heterologous sequences are sequences not naturally associated (e.g., to a enzyme) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., a cellulase, e.g., endoglucanase, cellobiohydrolase, mannanase and/or beta-glucosidase enzyme sequence). Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Hybrid (Chimeric) Cellulase, e.g., Endoglucanase, Cellobiohydrolase and/or Beta-Glucosidase Enzymes and Peptide Libraries In one aspect, the invention provides hybrid cellulase, e.g., endoglucanase, cellobiohydrolase, mannanase and/or beta-glucosidase enzymes and fusion proteins, including peptide libraries, comprising sequences of the invention. The peptide libraries of the invention can be used to isolate peptide modulators (e.g., activators or inhibitors) of targets, such as cellulase, e.g., endoglucanase, cellobiohydrolase, mannanase and/or beta-glucosidase enzyme substrates, receptors, enzymes.

The peptide libraries of the invention can be used to identify formal binding partners of targets, such as ligands, e.g., cytokines, hormones and the like. In one aspect, the invention provides chimeric proteins comprising a signal sequence (SP), prepro domain and/or catalytic domain (CD) of the invention or a combination thereof and a heterologous sequence (see above).

In one aspect, the fusion proteins of the invention (e.g., the peptide moiety) are conformationally stabilized (relative to linear peptides) to allow a higher binding affinity for targets. The invention provides fusions of cellulase, e.g., endoglucanase, cellobiohydrolase, mannanase and/or beta-glucosidase enzymes of the invention and other peptides, including known and random peptides. They can be fused in such a manner that the structure of the cellulase, e.g., endoglucanase, cellobiohydrolase, mannanase and/or beta-glucosidase enzymes is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of a cellulase, e.g., endoglucanase, cellobiohydrolase, mannanase and/or beta-glucosidase enzyme sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed cellulase, e.g., endoglucanase, cellobiohydrolase, mannanase and/or beta-glucosidase enzyme variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, e.g., assays of glucan hydrolysis. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides cellulase, e.g., endoglucanase, cellobiohydrolase, mannanase and/or beta-glucosidase enzymes where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e., a cellulase, e.g., endoglucanase, cellobiohydrolase, mannanase and/or beta-glucosidase enzyme activity) although variants can be selected to modify the characteristics of the cellulase, e.g., endoglucanase, cellobiohydrolase, mannanase and/or beta-glucosidase enzymes as needed.

In one aspect, cellulase, e.g., endoglucanase, cellobiohydrolase, mannanase and/or beta-glucosidase enzymes of the invention comprise epitopes or purification tags, signal sequences or other fusion sequences, etc. In one aspect, the cellulase, e.g., endoglucanase, cellobiohydrolase, mannanase and/or beta-glucosidase enzymes of the invention can be fused to a random peptide to form a fusion polypeptide. By "fused" or "operably linked" herein is meant that the random peptide and the cellulase, e.g., endoglucanase, cellobiohydrolase, mannanase and/or beta-glucosidase enzyme are linked together, in such a manner as to minimize the disruption to the stability of the cellulase, e.g., endoglucanase, cellobiohydrolase, mannanase and/or beta-glucosidase enzyme structure, e.g., it retains cellulase, e.g., endoglucanase, cellobiohydrolase, mannanase and/or beta-glucosidase enzyme activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

In one aspect, a cellulase, e.g., endoglucanase, cellobiohydrolase, mannanase and/or beta-glucosidase enzyme of the invention is a multidomain enzyme that comprises a signal peptide, a carbohydrate binding module, a cellulase, e.g., endoglucanase, cellobiohydrolase, mannanase and/or beta-glucosidase enzyme catalytic domain, a linker and/or another catalytic domain.

The invention provides a methods and sequences for generating chimeric polypeptides which may encode biologically active hybrid polypeptides (e.g., hybrid cellulase, e.g., endoglucanase, cellobiohydrolase, mannanase and/or beta-glucosidase enzymes). In one aspect, the original polynucleotides (e.g., an exemplary nucleic acid of the invention)

encode biologically active polypeptides. In one aspect, a method of the invention produces new hybrid polypeptides by utilizing cellular processes which integrate the sequence of the original polynucleotides such that the resulting hybrid polynucleotide encodes a polypeptide demonstrating activities derived, but different, from the original biologically active polypeptides (e.g., cellulase or antibody of the invention). For example, the original polynucleotides may encode a particular enzyme (e.g., cellulase) from or found in different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide of the invention may function effectively under environmental conditions shared by each of the enzymes encoded by the first and second polynucleotides, e.g., high salinity and extreme temperatures.

In one aspect, a hybrid polypeptide generated by a method of the invention may exhibit specialized enzyme activity not displayed in the original enzymes. For example, following recombination and/or reductive reassortment of polynucleotides encoding cellulase, e.g., endoglucanase, cellobiohydrolase, mannanase and/or beta-glucosidase enzymes, the resulting hybrid polypeptide encoded by a hybrid polynucleotide can be screened for specialized non-cellulase, e.g., non-endoglucanase, non-cellobiohydrolase and/or non-beta-glucosidase enzyme activities, e.g., hydrolase, peptidase, phosphorylase, etc., activities, obtained from each of the original enzymes. In one aspect, the hybrid polypeptide is screened to ascertain those chemical functionalities which distinguish the hybrid polypeptide from the original parent polypeptides, such as the temperature, pH or salt concentration at which the hybrid polypeptide functions.

In one aspect, the invention relates to a method for producing a biologically active hybrid polypeptide and screening such a polypeptide for enhanced activity by:

1) introducing at least a first polynucleotide in operable linkage and a second polynucleotide in operable linkage, the at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Isolating and Discovering Cellulase Enzymes

The invention provides methods for isolating and discovering cellulases, e.g., endoglucanase, cellobiohydrolase, mannanase and/or beta-glucosidase enzymes and the nucleic acids that encode them. Polynucleotides or enzymes may be isolated from individual organisms ("isolates"), collections of organisms that have been grown in defined media ("enrichment cultures"), or, uncultivated organisms ("environmental samples"). The organisms can be isolated by, e.g., in vivo biopanning (see discussion, below). The use of a culture-independent approach to derive polynucleotides encoding novel bioactivities from environmental samples is most preferable since it allows one to access untapped resources of biodiversity. Polynucleotides or enzymes also can be isolated from any one of numerous organisms, e.g. bacteria. In addition to whole cells, polynucleotides or enzymes also can be isolated from crude enzyme preparations derived from cultures of these organisms, e.g., bacteria.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

In one aspect, gene libraries generated from one or more uncultivated microorganisms are screened for an activity of interest. Potential pathways encoding bioactive molecules of interest are first captured in prokaryotic cells in the form of gene expression libraries. In one aspect, polynucleotides encoding activities of interest are isolated from such libraries and introduced into a host cell. The host cell is grown under conditions which promote recombination and/or reductive reassortment creating potentially active biomolecules with novel or enhanced activities.

In vivo biopanning may be performed utilizing a FACS-based and non-optical (e.g., magnetic) based machines. In one aspect, complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

In one aspect, subcloning is performed to further isolate sequences of interest. In subcloning, a portion of DNA is amplified, digested, generally by restriction enzymes, to cut out the desired sequence, the desired sequence is ligated into a recipient vector and is amplified. At each step in subcloning, the portion is examined for the activity of interest, in order to ensure that DNA that encodes the structural protein has not been excluded. The insert may be purified at any step of the subcloning, for example, by gel electrophoresis prior to ligation into a vector or where cells containing the recipient vector and cells not containing the recipient vector are placed on selective media containing, for example, an antibiotic, which will kill the cells not containing the recipient vector. Specific methods of subcloning cDNA inserts into vectors are well-known in the art (Sambrook et al., Molecular Cloning: A Laboratory Manual, 2nd Ed., Cold Spring Harbor Laboratory Press (1989)). In another aspect, the enzymes of the invention are subclones. Such subclones may differ from the parent clone by, for example, length, a mutation, a tag or a label.

The microorganisms from which the polynucleotide may be discovered, isolated or prepared include prokaryotic microorganisms, such as Eubacteria and Archaebacteria and lower eukaryotic microorganisms such as fungi, some algae and protozoa. Polynucleotides may be discovered, isolated or prepared from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms can be used. Enzymes of this invention can function at temperatures above 100° C., e.g., as those found in terrestrial hot springs and deep sea thermal vents, or at temperatures below 0° C., e.g., as those found in arctic waters, in a saturated salt environment, e.g., as those found in the Dead Sea, at pH values around 0, e.g., as those found in coal deposits and geothermal sulfur-rich springs, or at pH values greater than 11, e.g., as those found in sewage sludge. In one aspect, enzymes of the invention have high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are in one aspect already in a vector which includes appropriate control sequences. The host cell can be a higher eukaryotic cell, such as a mammalian cell, or a lower eukaryotic cell, such as a yeast cell, or in one aspect, the host cell can be a prokaryotic cell, such as a bacterial cell. Introduction of the construct into the host cell can be effected by calcium phosphate transfection, DEAE-Dextran mediated transfection, or electroporation.

Exemplary hosts include bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells; see discussion, above. The selection of an appropriate host is deemed to be within the scope of those skilled in the art from the teachings herein.

Various mammalian cell culture systems can be employed to express recombinant protein; examples of mammalian expression systems include the COS-7 lines of monkey kidney fibroblasts, described in "SV40-transformed simian cells support the replication of early SV40 mutants" (Gluzman, 1981) and other cell lines capable of expressing a compatible vector, for example, the C127, 3T3, CHO, HeLa and BHK cell lines. Mammalian expression vectors can comprise an origin of replication, a suitable promoter and enhancer and also any necessary ribosome binding sites, polyadenylation site, splice donor and acceptor sites, transcriptional termination sequences and 5' flanking nontranscribed sequences. DNA sequences derived from the SV40 splice and polyadenylation sites may be used to provide the required nontranscribed genetic elements.

In another aspect, nucleic acids, polypeptides and methods of the invention are used in biochemical pathways, or to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function (an example of a biochemical pathway encoded by gene clusters are polyketides).

In one aspect, gene cluster DNA is isolated from different organisms and ligated into vectors, e.g., vectors containing expression regulatory sequences which can control and regulate the production of a detectable protein or protein-related array activity from the ligated gene clusters. Use of vectors which have an exceptionally large capacity for exogenous DNA introduction can be appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. One aspect is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Methods for screening for various enzyme activities are known to those of skill in the art and are discussed throughout the present specification, see, e.g., Examples 1, 2 and 3, below. Such methods may be employed when isolating the polypeptides and polynucleotides of the invention.

In one aspect, the invention provides methods for discovering and isolating cellulases, e.g., endoglucanase, cellobiohydrolase, mannanase and/or beta-glucosidase, or compounds to modify the activity of these enzymes, using a whole cell approach (see discussion, below). Putative clones encoding cellulase, e.g., endoglucanase, cellobiohydrolase, mannanase and/or beta-glucosidase from genomic DNA library can be screened.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for cellulase, e.g., endoglucanase, cellobiohydrolase, mannanase and/or beta-glucosidase enzyme activity, to screen compounds as potential modulators, e.g., activators or inhibitors, of a cellulase, e.g., endoglucanase, cellobiohydrolase, mannanase and/or beta-glucosidase enzyme activity, for antibodies that bind to a polypeptide of the invention, for nucleic acids that hybridize to a nucleic acid of the invention, to screen for cells expressing a polypeptide of the invention and the like. In addition to the array formats described in detail below for screening samples, alternative formats can also be used to practice the methods of the invention. Such formats include, for example, mass spectrometers, chromatographs, e.g., high-throughput HPLC and other forms of liquid chromatography, and smaller formats, such as 1536-well plates, 384-well plates and so on. High throughput screening apparatus can be adapted and used to practice the methods of the invention, see, e.g., U.S. Patent Application Nos. 20020001809; 20050272044.

Capillary Arrays

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays, such as the GIGAMATRIX™, Diversa Corporation, San Diego, Calif.; and arrays described in, e.g., U.S. Patent Application No. 20020080350 A1; WO 0231203 A; WO 0244336 A, provide an alternative apparatus for holding and screening samples. In one aspect, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a Microtiter® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, e.g., a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a cellulase, e.g., endoglucanase, cellobiohydrolase, mannanase and/or beta-glucosidase enzyme gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

In practicing the methods of the invention, any known array and/or method of making and using arrays can be incorporated in whole or in part, or variations thereof, as described, for example, in U.S. Pat. Nos. 6,277,628; 6,277,489; 6,261, 776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to a cellulase, e.g., endoglucanase, cellobiohydrolase, mannanase and/or beta-glucosidase enzyme of the invention. These antibodies can be used to isolate, identify or quantify the cellulase, e.g., endoglucanase, cellobiohydrolase, mannanase and/or beta-glucosidase enzymes of the invention or related polypeptides. These antibodies can be used to isolate other polypeptides within the scope the invention or other related cellulase, e.g., endoglucanase, cellobiohydrolase, mannanase and/or beta-glucosidase enzymes. The antibodies can be designed to bind to an active site of a cellulase, e.g., endoglucanase, cellobiohydrolase, mannanase and/or beta-glucosidase enzyme. Thus, the invention provides methods of inhibiting cellulase, e.g., endoglucanase, cellobiohydrolase, mannanase and/or beta-glucosidase enzymes using the antibodies of the invention (see discussion above regarding applications for anti-cellulase, e.g., anti-endoglucanase, anti-cellobiohydrolase and/or anti-beta-glucosidase enzyme compositions of the invention).

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The invention provides fragments of the enzymes of the invention (e.g., peptides) including immunogenic fragments (e.g., subsequences) of a polypeptide of the invention. The invention provides compositions comprising a polypeptide or peptide of the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides of the invention or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of the invention, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays and Western Blots.

Polyclonal antibodies generated against the polypeptides of the invention, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained can bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al., Immunology Today 4:72, 1983) and the EBV-hybridoma technique (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides of the invention, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of the invention, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87-116.

Kits

The invention provides kits comprising the compositions, e.g., nucleic acids, expression cassettes, vectors, cells, transgenic seeds or plants or plant parts, polypeptides (e.g., a cellulase enzyme) and/or antibodies of the invention. The kits also can contain instructional material teaching the methodologies and industrial, medical and dietary uses of the invention, as described herein.

Whole Cell Engineering and Measuring Metabolic Parameters

The methods of the invention provide whole cell evolution, or whole cell engineering, of a cell to develop a new cell strain having a new phenotype, e.g., a new or modified cellulase, e.g., endoglucanase, cellobiohydrolase, mannanase and/or beta-glucosidase enzyme activity, by modifying the genetic composition of the cell. See U.S. patent application no. 20040033975.

The genetic composition can be modified by addition to the cell of a nucleic acid of the invention, e.g., a coding sequence for an enzyme of the invention. See, e.g., WO0229032; WO0196551.

To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the cellulase, e.g., endoglucanase, cellobiohydrolase, mannanase and/or beta-glucosidase enzymes of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., a cellulase, e.g., endoglucanase, cellobiohydrolase, mannanase and/or beta-glucosidase enzyme message) or generating new (e.g., cellulase, e.g., endoglucanase, cellobiohydrolase, mannanase and/or beta-glucosidase enzyme) transcripts in a cell. This increased or decreased expression can be traced by testing for the presence of a cellulase, e.g., endoglucanase, cellobiohydrolase, mannanase and/or beta-glucosidase enzyme of the invention or by cellulase, e.g., endoglucanase, cellobiohydrolase, mannanase and/or beta-glucosidase enzyme activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., a cellulase, e.g., endoglucanase, cellobiohydrolase, mannanase and/or beta-glucosidase enzyme) or generating new polypeptides in a cell. This increased or decreased expression can be traced by determining the amount of cellulase, e.g., endoglucanase, cellobiohydrolase, mannanase and/or beta-glucosidase enzyme present or by cellulase, e.g., endoglucanase, cellobiohydrolase, mannanase and/or beta-glucosidase enzyme activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g., immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial, Energy, Pharmaceutical and Other Applications

Polypeptides of the invention (e.g., having cellulase, e.g., endoglucanase, cellobiohydrolase, mannanase and/or beta-glucosidase) can catalyze the breakdown of cellulose. The enzymes of the invention can be highly selective catalysts. The invention provides industrial processes using enzymes of the invention, e.g., in the pharmaceutical or nutrient (diet) supplement industry, the energy industry (e.g., to make "clean" biofuels), in the food and feed industries, e.g., in methods for making food and feed products and food and feed additives. In one aspect, the invention provides processes using enzymes of the invention in the medical industry, e.g., to make pharmaceuticals or dietary aids or supplements, or food supplements and additives. In addition, the invention provides methods for using the enzymes of the invention in bioethanol, including "clean" fuel, production.

The enzymes of the invention can catalyze reactions with exquisite stereo-, regio- and chemo-selectivities. The cellulase, e.g., endoglucanase, cellobiohydrolase, mannanase and/or beta-glucosidase enzymes of the invention can be engineered to function in various solvents, operate at extreme pHs (for example, high pHs and low pHs) extreme temperatures (for example, high temperatures and low temperatures), extreme salinity levels (for example, high salinity and low salinity) and catalyze reactions with compounds that are structurally unrelated to their natural, physiological substrates.

Biomass Conversion and Production of Clean Biofuels

The invention provides enzymes and methods for the conversion of biomass (e.g., lignocellulosic materials) to fuels (e.g., bioethanol) and chemicals. Thus, the compositions and methods of the invention provide effective and sustainable alternatives to use of petroleum-based products. The invention provides organisms expressing enzymes of the invention for participation in chemical cycles involving natural biomass conversion. In one aspect, enzymes and methods for the conversion are used in enzyme ensembles for the efficient depolymerization of cellulosic and hemicellulosic polymers to metabolizable carbon moieties. As discussed above, the invention provides methods for discovering and implementing the most effective of enzymes to enable these important new "biomass conversion" and alternative energy industrial processes.

In one aspect, the polypeptides of the invention, e.g., proteins having cellulase activity, e.g., endoglucanase, cellobiohydrolase, mannanase and/or beta-glucosidase activity, are used in processes for converting lignocellulosic biomass to ethanol. The invention also provides processes for making ethanol ("bioethanol") from compositions comprising lignocellulosic biomass. The lignocellulose biomass material can be obtained from agricultural crops, as a byproduct of food or feed production, or as lignocellulosic waste products, such as plant residues and waste paper. Examples of suitable plant residues for treatment with polypeptides of the invention include stems, leaves, hulls, husks, cobs and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials.

In one aspect, the enzymes and methods of the invention can be used in conjunction with more "traditional" means of making ethanol from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506; 6,423,145.

Another exemplary method that incorporated use of enzymes of the invention comprises hydrolyzing lignocellulosic material containing hemicellulose, cellulose and lignin by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention can be added at any stage of this exemplary process.

Another exemplary method that incorporated use of enzymes of the invention comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention comprises prehydrolyzing lignocellulosic material in a prehydrolysis reactor, adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

Methods of the invention for the enzymatic degradation of lignocellulose, e.g., for production of ethanol from lignocellulosic material, can also comprise use of ultrasonic treatment of the biomass material; see, e.g., U.S. Pat. No. 6,333,181.

Another exemplary process for making a biofuel comprising ethanol using enzymes of the invention comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for cellulase hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

Animal Feeds and Food or Feed Additives

In addition to providing dietary aids or supplements, or food supplements and additives for human use, the invention also provides compositions and methods for treating animal feeds and foods and food or feed additives using a polypeptide of the invention, e.g., a protein having cellulase activity, e.g., endoglucanase, cellobiohydrolase, mannanase and/or beta-glucosidase enzymes of the invention, and/or the antibodies of the invention. The invention provides animal feeds, foods, and additives comprising cellulase, e.g., endoglucanase, cellobiohydrolase, mannanase and/or beta-glucosidase enzymes of the invention and/or antibodies of the invention. The animal can be any farm animal or any animal.

The animal feed additive of the invention may be a granulated enzyme product that may readily be mixed with feed components. Alternatively, feed additives of the invention can form a component of a pre-mix. The granulated enzyme product of the invention may be coated or uncoated. The particle size of the enzyme granulates can be compatible with that of feed and pre-mix components. This provides a safe and convenient mean of incorporating enzymes into feeds. Alternatively, the animal feed additive of the invention may be a stabilized liquid composition. This may be an aqueous or oil-based slurry. See, e.g., U.S. Pat. No. 6,245,546.

Cellulase, e.g., endoglucanase, cellobiohydrolase, mannanase and/or beta-glucosidase enzymes of the present invention, in the modification of animal feed or a food, can process the food or feed either in vitro (by modifying components of the feed or food) or in vivo. Polypeptides of the invention can be added to animal feed or food compositions.

In one aspect, an enzyme of the invention is added in combination with another enzyme, e.g., beta-galactosidases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases. These enzyme digestion products are more digestible by the animal. Thus, cellulase, e.g., endoglucanase, cellobiohydrolase, mannanase and/or beta-glucosidase enzymes of the invention can contribute to the available energy of the feed or food, or to the digestibility of the food or feed by breaking down cellulose.

In another aspect, cellulase, e.g., endoglucanase, cellobiohydrolase, mannanase and/or beta-glucosidase enzyme of the invention can be supplied by expressing the enzymes directly in transgenic feed crops (as, e.g., transgenic plants, seeds and the like), such as grains, cereals, corn, soy bean, rape seed, lupin and the like. As discussed above, the invention provides transgenic plants, plant parts and plant cells comprising a nucleic acid sequence encoding a polypeptide of the invention. In one aspect, the nucleic acid is expressed such that the cellulase, e.g., endoglucanase, cellobiohydrolase, mannanase and/or beta-glucosidase enzyme of the invention is produced in recoverable quantities. The cellulase, e.g., endoglucanase, cellobiohydrolase, mannanase and/or beta-glucosidase enzyme can be recovered from any plant or plant part. Alternatively, the plant or plant part containing the recombinant polypeptide can be used as such for improving the quality of a food or feed, e.g., improving nutritional value, palatability, etc.

In one aspect, the enzyme delivery matrix of the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Since the matrix is itself approved for use in animal feed, it can be used as a diluent for delivery of enzymes in animal feed.

In one aspect, the cellulase, e.g., endoglucanase, cellobiohydrolase, mannanase and/or beta-glucosidase enzyme contained in the invention enzyme delivery matrix and methods is a thermostable cellulase, e.g., endoglucanase, cellobiohydrolase, mannanase and/or beta-glucosidase enzyme, as described herein, so as to resist inactivation of the cellulase, e.g., endoglucanase, cellobiohydrolase, mannanase and/or beta-glucosidase enzyme during manufacture where elevated temperatures and/or steam may be employed to prepare the palletized enzyme delivery matrix. During digestion of feed containing the invention enzyme delivery matrix, aqueous digestive fluids will cause release of the active enzyme. Other types of thermostable enzymes and nutritional supplements that are thermostable can also be incorporated in the delivery matrix for release under any type of aqueous conditions.

In one aspect, a coating is applied to the enzyme matrix particles for many different purposes, such as to add a flavor or nutrition supplement to animal feed, to delay release of animal feed supplements and enzymes in gastric conditions, and the like. In one aspect, the coating is applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise a cellulase, e.g., endoglucanase, cellobiohydrolase, mannanase and/or beta-glucosidase enzyme encoded by an amino acid sequence of the invention. In one aspect, the process includes compacting or compressing the particles of enzyme-releasing matrix into granules, which most in one aspect is accomplished by pelletizing. The mold inhibitor and cohesiveness agent, when used, can be added at any suitable time, and in one aspect are mixed with the grain-based substrate in the desired proportions prior to pelletizing of the grain-based substrate. Moisture content in the pellet mill feed in one aspect is in the ranges set forth above with respect to the moisture content in the finished product, and in one aspect is about 14-15%. In one aspect, moisture is added to the feedstock in the form of an aqueous preparation of the enzyme to bring the feedstock to this moisture content. The temperature in the pellet mill in one aspect is brought to about 82° C. with steam. The pellet mill may be operated under any conditions that impart sufficient work to the feedstock to provide pellets. The pelleting process itself is a cost-effective process for removing water from the enzyme-containing composition.

The compositions and methods of the invention can be practiced in conjunction with administration of prebiotics, which are high molecular weight sugars, e.g., fructo-oligosaccharides (FOS); galacto-oligosaccharides (GOS), GRAS (Generally Recognized As Safe) material. These prebiotics can be metabolized by some probiotic lactic acid bacteria (LAB). They are non-digestible by the majority of intestinal microbes.

Treating Foods and Food Processing

The invention provides foods and feeds comprising enzymes of the invention, and methods for using enzymes of the invention in processing foods and feeds. Cellulases, e.g., endoglucanase, cellobiohydrolase, mannanase and/or beta-glucosidase enzymes of the invention have numerous applications in food processing industry. The invention provides methods for hydrolyzing cellulose-comprising compositions, including, e.g., a plant cell, a bacterial cell, a yeast cell, an insect cell, or an animal cell, or any plant or plant part, or any food or feed, a waste product and the like.

For example, the invention provides feeds or foods comprising a cellulase, e.g., endoglucanase, cellobiohydrolase, mannanase and/or beta-glucosidase enzyme the invention, e.g., in a feed, a liquid, e.g., a beverage (such as a fruit juice or a beer), a bread or a dough or a bread product, or a drink (e.g., a beer) or a beverage precursor (e.g., a wort).

The food treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

In one aspect, the invention provides enzymes and processes for hydrolyzing liquid (liquefied) and granular starch. Such starch can be derived from any source, e.g., beet, cane sugar, potato, corn, wheat, milo, sorghum, rye or bulgher. The invention applies to any plant starch source, e.g., a grain starch source, which is useful in liquefaction (for example, to make bioethanol), including any other grain or vegetable source known to produce starch suitable for liquefaction. The methods of the invention comprise liquefying starch (e.g., making bioethanol) from any natural material, such as rice, germinated rice, corn, barley, milo, wheat, legumes, potato, beet, cane sugar and sweet potato. The liquefying process can substantially hydrolyze the starch to produce a syrup. The temperature range of the liquefaction can be any liquefaction temperature which is known to be effective in liquefying starch. For example, the temperature of the starch can be between about 80° C. to about 115° C., between about 100° C. to about 110° C., and from about 105° C. to about 108° C. The bioethanols made using the enzymes and processes of the invention can be used as fuels or in fuels (e.g., auto fuels), e.g., as discussed below, in addition to their use in (or for malting) foods and feeds, including alcoholic beverages.

Waste Treatment

The invention provides enzymes for use in waste treatment. Cellulases, e.g., endoglucanase, cellobiohydrolase, mannanase and/or beta-glucosidase enzymes of the invention can be used in a variety of waste treatment or related industrial applications, e.g., in waste treatment related to biomass conversion to generate fuels. For example, in one aspect, the invention provides a solid and/or liquid waste digestion process using cellulase, e.g., endoglucanase, cellobiohydrolase, mannanase and/or beta-glucosidase enzymes of the invention. The methods can comprise reducing the mass and volume of substantially untreated solid waste. Solid waste can be treated with an enzymatic digestive process in the presence of an enzymatic solution (including cellulase, e.g., endoglucanase, cellobiohydrolase, mannanase and/or beta-glucosidase enzymes of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

In one aspect, the compositions and methods of the invention are used for odor removal, odor prevention or odor reduction, e.g., in animal waste lagoons, e.g., on swine farms, in other animal waste management systems, or in any industrial or food processing application.

The enzymes and methods for the conversion of biomass (e.g., lignocellulosic materials) to fuels (e.g., bioethanol) can incorporate the treatment/recycling of municipal solid waste material, including waste obtained directly from a municipality or municipal solid waste that was previously land-filled and subsequently recovered, or sewage sludge, e.g., in the form of sewage sludge cake which contains substantial amounts of cellulosic material. Since sewage sludge cakes will normally not contain substantial amounts of recyclable materials (aluminum, glass, plastics, etc.), they can be directly treated with concentrated sulfuric acid (to reduce the heavy metal content of the cellulosic component of the waste) and processed in the ethanol production system. See, e.g., U.S. Pat. Nos. 6,267,309; 5,975,439.

Another exemplary method using enzymes of the invention for recovering organic and inorganic matter from waste material comprises sterilizing a solid organic matter and softening it by subjecting it to heat and pressure. This exemplary process may be carried out by first agitating waste material and then subjecting it to heat and pressure, which sterilizes it and softens the organic matter contained therein. In one aspect, after heating under pressure, the pressure may be suddenly released from a perforated chamber to forces the softened organic matter outwardly through perforations of the container, thus separating the organic matter from the solid inorganic matter. The softened sterilized, organic matter is then fermented in fermentation chamber, e.g., using enzymes of the invention, e.g., to form a mash. The mash may be subjected to further processing by centrifuge, distillation column and/or anaerobic digester to recover fuels such as ethanol and methane, and animal feed supplements. See, e.g., U.S. Pat. No. 6,251,643.

Enzymes of the invention can also be used in processes, e.g., pretreatments, to reduce the odor of an industrial waste, or a waste generated from an animal production facility, and the like. For example, enzymes of the invention can be used to treat an animal waste in a waste holding facility to enhance efficient degradation of large amounts of organic matter with reduced odor. The process can also include inoculation with sulfide-utilizing bacteria and organic digesting bacteria and lytic enzymes (in addition to an enzyme of the invention). See, e.g., U.S. Pat. No. 5,958,758.

Enzymes of the invention can also be used in mobile systems, e.g., batch type reactors, for bioremediation of aqueous, hazardous wastes, e.g., as described in U.S. Pat. No. 5,833,857. Batch type reactors can be large vessels having circulatory capability wherein bacteria (e.g., expressing an enzyme of the invention) are maintained in an efficient state by nutrients being feed into the reactor. Such systems can be used where effluent can be delivered to the reactor or the reactor is built into a waste water treatment system. Enzymes of the invention can also be used in treatment systems for use at small or temporary remote locations, e.g., portable, high volume, highly efficient, versatile waste water treatment systems.

The waste treatment processes of the invention can include the use of any combination of other enzymes such as other cellulase, e.g., endoglucanase, cellobiohydrolase, mannanase and/or beta-glucosidase enzymes, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, phytases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Detergent Compositions

The invention provides detergent compositions comprising one or more polypeptides of the invention (e.g., enzymes having cellulase, endoglucanase, cellobiohydrolase, mannanase and/or beta-glucosidase activity) and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Enzymes of the invention can facilitate the removal of starchy stains by means of catalytic hydrolysis of the starch polysaccharide. Enzymes of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of glucosidase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Enzymes of the present invention (e.g., enzymes having cellulase, endoglucanase, cellobiohydrolase, mannanase and/or beta-glucosidase activity) can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of enzymes of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A polypeptide of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations. In alternative aspects, detergent additives and detergent compositions of the invention may comprise one or more other enzymes such as a protease, a lipase, a cutinase, another glucosidase, a carbohydrase, another cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

The detergents and related processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Treating Fabrics and Textiles

The invention provides methods of treating fabrics and textiles using one or more polypeptides of the invention, e.g., enzymes having cellulase, endoglucanase, cellobiohydrolase, mannanase and/or beta-glucosidase activity. The polypeptides of the invention can be used in any fabric-treating method, which are well known in the art, see, e.g., U.S. Pat. No. 6,077,316. For example, in one aspect, the feel and appearance of a fabric is improved by a method comprising contacting the fabric with an enzyme of the invention in a solution. In one aspect, the fabric is treated with the solution under pressure.

In one aspect, the enzymes of the invention are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes of the invention can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. The invention provides a method of desizing comprising enzymatic hydrolysis of the size by the action of an enzyme of the invention.

The enzymes of the invention (e.g., enzymes having cellulase, endoglucanase, cellobiohydrolase, mannanase and/or beta-glucosidase activity) can be used to desize fabrics, including cotton-containing fabrics, as detergent additives, e.g., in aqueous compositions. The invention provides methods for producing a stonewashed look on indigo-dyed denim fabric and garments. For the manufacture of clothes, the fabric can be cut and sewn into clothes or garments, which is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments (e.g., a "bio-stoning process"), enzymatic desizing and providing softness to fabrics using the Enzymes of the invention. The invention provides methods for quickly softening denim garments in a desizing and/or finishing process.

The invention also provides disinfectants comprising enzymes of the invention (e.g., enzymes having cellulase, endoglucanase, cellobiohydrolase, mannanase and/or beta-glucosidase activity).

The fabric or textile treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Paper or Pulp Treatment

The enzymes of the invention (e.g., enzymes having cellulase, endoglucanase, cellobiohydrolase, mannanase and/or beta-glucosidase activity) can be in paper or pulp treatment or paper deinking. For example, in one aspect, the invention provides a paper treatment process using enzymes of the invention. In one aspect, the enzymes of the invention can be used to modify starch in the paper thereby converting it into a liquefied form. In another aspect, paper components of recycled photocopied paper during chemical and enzymatic deinking processes. In one aspect, Enzymes of the invention can be used in combination with other enzymes, including other cellulases (including other endoglucanases, cellobiohydrolases and/or beta-glucosidases). The wood, paper, paper product or pulp can be treated by the following three processes: 1) disintegration in the presence of an enzyme of the invention, 2) disintegration with a deinking chemical and an enzyme of the invention, and/or 3) disintegration after soaking with an enzyme of the invention. The recycled paper treated with an enzyme of the invention can have a higher brightness due to removal of toner particles as compared to the paper treated with just cellulase. While the invention is not limited by any particular mechanism, the effect of an enzyme of the invention may be due to its behavior as surface-active agents in pulp suspension.

The invention provides methods of treating paper and paper pulp using one or more polypeptides of the invention. The polypeptides of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of an enzyme of the invention (other enzymes can also be added). In another aspect, the invention provides a method for enhancing the freeness of pulp, e.g., pulp made from secondary fiber, by adding an enzymatic mixture comprising an enzyme of the invention (can also include other enzymes, e.g., pectinase enzymes) to the pulp and treating under conditions to cause a reaction to produce an enzymatically treated pulp. The freeness of the enzymatically treated pulp is increased from the initial freeness of the secondary fiber pulp without a loss in brightness.

The paper, wood or pulp treatment or recycling processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Repulping: Treatment of Lignocellulosic Materials

The invention also provides a method for the treatment of lignocellulosic fibers, wherein the fibers are treated with a polypeptide of the invention (e.g., enzymes having cellulase, endoglucanase, cellobiohydrolase, mannanase and/or beta-glucosidase activity), in an amount which is efficient for improving the fiber properties. The enzymes of the invention may also be used in the production or recycling of lignocellulosic materials such as pulp, paper and cardboard, from starch reinforced waste paper and cardboard, especially where repulping or recycling occurs at pH above 7 and where the enzymes of the invention can facilitate the disintegration of the waste material through degradation of the reinforcing starch. The enzymes of the invention can be useful in a process for producing a papermaking pulp from starch-coated printed paper. The process may be performed as described in, e.g., WO 95/14807. An exemplary process comprises disintegrating the paper to produce a pulp, treating with a starch-degrading enzyme before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein the polypeptide is applied in an amount which is efficient for effective de-inking of the fiber surface.

Brewing and Fermenting

The invention provides methods of brewing (e.g., fermenting) beer comprising an enzyme of the invention, e.g., enzymes having cellulase, endoglucanase, cellobiohydrolase, mannanase and/or beta-glucosidase activity. In one exemplary process, starch-containing raw materials are disintegrated and processed to form a malt. An enzyme of the invention is used at any point in the fermentation process. For example, enzymes of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15-25° C. for 3 to 6 days when enzyme synthesis is stimulated under the control of gibberellins. During this time enzyme levels rise significantly. In one aspect, enzymes of the invention are added at this (or any other) stage of the process. The action of the enzyme results in an increase in fermentable reducing sugars. This can be expressed as the diastatic power, DP, which can rise from around 80 to 190 in 5 days at 12° C.

Enzymes of the invention can be used in any beer producing process, as described, e.g., in U.S. Pat. Nos. 5,762,991; 5,536,650; 5,405,624; 5,021,246; 4,788,066.

Increasing the Flow of Production Fluids from a Subterranean Formation

The invention also includes a method using an enzyme of the invention (e.g., enzymes having cellulase, endoglucanase, cellobiohydrolase, mannanase and/or beta-glucosidase activity), wherein the method increases the flow of production fluids from a subterranean formation by removing viscous, starch-containing, damaging fluids formed during production operations; these fluids can be found within the subterranean formation which surrounds a completed well bore. Thus, this method of the invention results in production fluids being able to flow from the well bore. This method of the invention also addresses the problem of damaging fluids reducing the flow of production fluids from a formation below expected flow rates. In one aspect, the invention provides for formulating an enzyme treatment (using an enzyme of the invention) by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

The subterranean formation enzyme treatment processes of the invention can also include the use of any combination of other enzymes such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Pharmaceutical Compositions and Dietary Supplements

The invention also provides pharmaceutical compositions and dietary supplements (e.g., dietary aids) comprising a cellulase of the invention (e.g., enzymes having endoglucanase, cellobiohydrolase, mannanase and/or beta-glucosidase activity). The cellulase activity comprises endoglucanase, cellobiohydrolase, mannanase and/or beta-glucosidase activity. In one aspect, the pharmaceutical compositions and dietary supplements (e.g., dietary aids) are formulated for oral ingestion, e.g., to improve the digestibility of foods and feeds having a high cellulose or lignocellulosic component.

Periodontal treatment compounds can comprise an enzyme of the invention, e.g., as described in U.S. Pat. No. 6,776,979. Compositions and methods for the treatment or prophylaxis of acidic gut syndrome can comprise an enzyme of the invention, e.g., as described in U.S. Pat. No. 6,468,964.

In another aspect, wound dressings, implants and the like comprise antimicrobial (e.g., antibiotic-acting) enzymes, including an enzyme of the invention (including, e.g., exemplary sequences of the invention). Enzymes of the invention can also be used in alginate dressings, antimicrobial barrier dressings, burn dressings, compression bandages, diagnostic tools, gel dressings, hydro-selective dressings, hydrocellular (foam) dressings, hydrocolloid dressings, I.V dressings, incise drapes, low adherent dressings, odor absorbing dressings, paste bandages, post operative dressings, scar management, skin care, transparent film dressings and/or wound closure. Enzymes of the invention can be used in wound cleansing, wound bed preparation, to treat pressure ulcers, leg ulcers, burns, diabetic foot ulcers, scars, IV fixation, surgical wounds and minor wounds. Enzymes of the invention can be used to in sterile enzymatic debriding compositions, e.g., ointments. In various aspects, the cellulase is formulated as a tablet, gel, pill, implant, liquid, spray, powder, food, feed pellet or as an encapsulated formulation.

Biodefense Applications

In other aspects, cellulases of the invention (e.g., enzymes having endoglucanase, cellobiohydrolase, mannanase and/or beta-glucosidase activity) can be used in biodefense (e.g., destruction of spores or bacteria comprising a lignocellulosic material). Use of cellulases of the invention in biodefense applications offer a significant benefit, in that they can be very rapidly developed against any currently unknown or biological warfare agents of the future. In addition, cellulases of the invention can be used for decontamination of affected environments. In aspect, the invention provides a biodefense or bio-detoxifying agent comprising a polypeptide having a cellulase activity, wherein the polypeptide comprises a sequence of the invention (including, e.g., exemplary sequences of the invention), or a polypeptide encoded by a nucleic acid of the invention (including, e.g., exemplary sequences of the invention), wherein optionally the polypeptide has activity comprising endoglucanase, cellobiohydrolase, mannanase and/or beta-glucosidase activity.

REFERENCE LIST

1. Sambrook, J. and Russell, D. W. 2001. Molecular Cloning: A Laboratory Manual. Third Edition. Cold Spring Harbor Laboratory Press, New York.
2. Benhar, I. Biotechnological applications of phage and cell display. Biotechnology Advances 19, 1-13. 2001.
3. Coutinho, P. M. and Henrissat, B. Carbohydrate-Active Enzymes server at URL: afmb.cnrs-mrs.fr/~cazy/CAZY/index.html. 1999.
4. Felix, C. R. and L. G. Ljungdahl. 1993. The cellulosome: the exocellular organelle of *Clostridium*. Annu. Rev. Microbiol 47:791-819:791-819.
5. Gray, K. A., T. H. Richardson, K. Kretz, J. M. Short, F. Bartnek, Knowles R., L. Kan, Swanson P. E., and Robertson D. E. 2001. Rapid evolution of reversible denaturation and elevated melting temperature in a microbial haloalkane dehalogenase. Advanced Synthesis and Catalysis 343:607-617.
6. Guttman, A., F. T. Chen, R. A. Evangelista, and N. Cooke. 1996. High-resolution capillary gel electrophoresis of reducing oligosaccharides labeled with 1-aminopyrene-3,6,8-trisulfonate. Anal. Biochem 233:234-242.
7. Hajunpaa, V., A. Teleman, A. Koivula, L. Ruohonen, T. T. Teeri, O. Teleman, and T. Drakenberg. 1996. Cello-oligosaccharide hydrolysis by cellobiohydrolase II from *Trichoderma reesei*. Association and rate constants derived from an analysis of progress curves. Eur. J Biochem 240:584-591.
8. Himmel, M. E., M. F. Ruth, and C. E. Wyman. 1999. Cellulase for commodity products from cellulosic biomass. Curr. Opin. Biotechnol 10:358-364.
9. Kerr, R. A. 1998. GEOLOGY: The Next Oil Crisis Looms Large—and Perhaps Close. Science 281:1128.
10. Kerr, R. A. 2000. OIL OUTLOOK: USGS Optimistic on World Oil Prospects. Science 289:237.
11. King, R. W., K. D. Lustig, P. T. Stukenberg, T. J. McGarry, and M. W. Kirschner. 1997. Expression cloning in the test tube. Science 277:973-974.
12. Kuritz, T. 1999. An easy colorimetric assay for screening and qualitative assessment of deiodination and dehalogenation by bacterial cultures. Lett. Appl Microbiol 28:445-447.
13. Lundberg, K. S., P. L. Kretz, G. S. Provost, and J. M. Short. 1993. The use of selection in recovery of transgenic targets for mutation analysis. Mutat. Res. 301:99-105.
14. MacKenzie, L. F., G. Sulzenbacher, C. Divne, T. A. Jones, H. F. Woldike, M. Schulein, S. G. Withers, and G. J. Davies. 1998. Crystal structure of the family 7 endoglucanase I (Cel7B) from *Humicola insolens* at 2.2 A resolution and identification of the catalytic nucleophile by trapping of the covalent glycosyl-enzyme intermediate. Biochem J 335:409-416.
15. Richardson, T. H., X. Tan, G. Frey, W. Callen, M. Cabell, D. Lam, J. Macomber, J. M. Short, D. E. Robertson, and C. Miller. 2002. A novel, high performance enzyme for starch liquefaction. Discovery and optimization of a low pH, thermostable alpha-amylase. J Biol Chem 277:26501-26507.
16. Sakon, J., D. Irwin, D. B. Wilson, and P. A. Karplus. 1997. Structure and mechanism of endo/exocellulase E4 from *Thermomonospora fusca*. Nat. Struct. Biol 4:810-818.
17. Short, J. M., J. M. Fernandez, J. A. Sorge, and W. D. Huse. 1988. Lambda ZAP: a bacteriophage lambda expression vector with in vivo excision properties. Nucleic Acids Res. 16:7583-7600.
18. Snustad, D. P., S. P. Hunsperger, B. M. Chereskin, and J. Messing. 1988. Maize glutamine synthetase cDNAs: isolation by direct genetic selection in *Escherichia coli*. Genetics 120:1111-1123.
19. Varrot, A., S. Hastrup, M. Schulein, and G. J. Davies. 1999. Crystal structure of the catalytic core domain of the family 6 cellobiohydrolase II, Cel6A, from *Humicola insolens*, at 1.92 A resolution. Biochem J 337:297-304.
20. Yano, T., S. Oue, and H. Kagamiyama. 1998. Directed evolution of an aspartate aminotransferase with new substrate specificities. Proc. Natl. Acad. Sci U.S. A 95:5511-5515.
21. Zverlov, V. V., G. A. Velikodvorskaya, and W. H. Schwarz. 2002. A newly described cellulosomal cellobiohydrolase, CelO, from *Clostridium thermocellum*: investigation of the exo-mode of hydrolysis, and binding capacity to crystalline cellulose. Microbiology 148:247-255.

The following examples are offered to illustrate, but not to limit the claimed invention.

EXAMPLES

Example 1

GIGAMATRIX™ Screen

In one aspect, the methods of the invention use Diversa Corporation's proprietary GIGAMATRIX™ platform; see PCT Patent Publication No. WO 01/38583; U.S. patent application no. 20050046833; 20020080350; U.S. Pat. No. 6,918,738; Design Pat. No. D480,814. For example, in one aspect, GIGAMATRIX™ is used in methods to determine if a polypeptide has cellulase activity and is within the scope of the invention, or, to identify and isolate a polypeptide having cellulase activity.

A GIGAMATRIX™ platform can include an ultra-high throughput screen based on a 100,000 well microplate with the dimensions of a conventional 96 well plate. In this example, the GIGAMATRIX™ screen was implemented using 2 substrates based on previously shown activity by CBHs. Methyl-umbelliferyl cellobioside (MUC) and methyl-lumbelliferyl lactoside (MUL) were tested. Phagemid versions of the different clones were screened because the substrate diffuses into cells and fluorescence was thought to be more easily detectable. A host strain lacking, beta-galactosidase was used in order to decrease activity on the lactoside substrate. The lactoside substrate resulted in fewer hits and was deemed more specific than the cellobiose substrate. In addition, the lactoside substrate resulted in fewer beta-glucosidase hits. In order to test the feasibility of using these substrates in a screen, 14 libraries were chosen for screening based on the fact that these libraries yielded endoglucanase hits from a previous screening program. Of the libraries screened, there were a total of 50 primary hits from 11 of the libraries screened. Secondary screening consisted of plating the clones on agar plates and then colony picking into 384 well plates containing media and MUL. Active clones against MUL are differentiated from a background of inactive clones. Individual clones were then grown overnight and fluorescence was measured and the most active hits were picked for sequencing.

All genomic clone inserts from hits were sequenced. In general, the hits were from several different glycosyl hydrolase families including 1, 2, 5, 6, 10 and 16. Several other hits were discovered where the open reading frame was not homologous to any known glycosyl hydrolase families. In addition, some of the hits encoded GTP cyclohydrolase genes.

TABLE 1

Summary of GIGAMATRIX ™ hits

| Enzyme No. | Open Reading Frame SEQ ID NO: | nearest relevant BLAST |
|---|---|---|
| 1 | SEQ ID NO: 22 (encoded by, e.g. SEQ ID NO: 21) | ORF 001 - family 5 (cellulase) |
| 1a | SEQ ID NO: 24 (encoded by SEQ ID NO: 23) | ORF 003 - Family 16 + CBM |
| 2 | SEQ ID NO: 26 (encoded by, e.g. SEQ ID NO: 25) | ORF 001 - family 1 (β-glucosidase) |
| 3 | SEQ ID NO: 92 (encoded by, e.g. SEQ ID NO: 91) | ORF 001 - family 3 |
| 3a | SEQ ID NO: 94 (encoded by, e.g. SEQ ID NO: 93) | ORF 002 - alpha-rhamnosidase |
| 4 | SEQ ID NO: 96 (encoded by, e.g. SEQ ID NO: 95) | ORF 001 - family 3 |
| 4a | SEQ ID NO: 98 (encoded by, e.g. SEQ ID NO: 97) | ORF 003 - beta-glucuronidase |
| 5 | SEQ ID NO: 128 (encoded by, e.g. SEQ ID NO: 127) | ORF 004 - short chain dehydrogenase |
| 5a | SEQ ID NO: 130 (encoded by, e.g. SEQ ID NO: 129) | ORF 010 - short chain dehydrogenase |
| 6 | SEQ ID NO: 116 (encoded by, e.g. SEQ ID NO: 115) | ORF 004 - short chain dehydrogenase |
| 6a | SEQ ID NO: 118 (encoded by, e.g. SEQ ID NO: 117) | ORF 011 - short chain dehydrogenase |
| 7 | SEQ ID NO: 40 (encoded by, e.g. SEQ ID NO: 39) | ORF 004 - putative oxidoreductase |
| 8 | SEQ ID NO: 42 (encoded by, e.g. SEQ ID NO: 41) | ORF 004 - cysteinyl tRNA synthetase |
| 8a | SEQ ID NO: 44 (encoded by, e.g. SEQ ID NO: 43) | ORF 011 - hypothetical protein |
| 9 | SEQ ID NO: 54 (encoded by, e.g. SEQ ID NO: 53) | ORF 002 - Radical SAM family |
| 10 | SEQ ID NO: 134 (encoded by, e.g. SEQ ID NO: 133) | ORF 006 - family 1 (β-glucosidase) |
| 11 | SEQ ID NO: 58 (encoded by, e.g. SEQ ID NO: 57) | ORF 001 - subtilisin like protease |
| 12 | SEQ ID NO: 46 (encoded by, e.g. SEQ ID NO: 45) | ORF 006 - family 1 (β-glucosidase) |
| 13 | SEQ ID NO: 8 (encoded by, e.g. SEQ ID NO: 7) | ORF 003 - Isocitrate dehydrogenase |
| 13a | SEQ ID NO: 10 (encoded by, e.g. SEQ ID NO: 9) | ORF 004 - family 10 (xylanase) |
| 14 | SEQ ID NO: 48 (encoded by, e.g. SEQ ID NO: 47) | ORF 002 - family 1 (β-glucosidase) |
| 14a | SEQ ID NO: 50 (encoded by, e.g. SEQ ID NO: 49) | ORF 006 - fdhd/narq oxidoreductase |
| 15 | SEQ ID NO: 4 (encoded by, e.g. SEQ ID NO: 3) | ORF 008 - family 1 (β-glucosidase) |
| 15a | SEQ ID NO: 6 (encoded by, e.g. SEQ ID NO: 5) | ORF 012 - family 6 (cellulase) |
| 16 | SEQ ID NO: 136 (encoded by, e.g. SEQ ID NO: 135) | ORF 001 - cellulase (glycosyl hydrolase family 5) |
| 17 | SEQ ID NO: 56 (encoded by, e.g. SEQ ID NO: 55) | ORF 004 - family 1 (β-glucosidase) |
| 18 | SEQ ID NO: 126 (encoded by, e.g. SEQ ID NO: 125) | ORF 009 - family 1 (β-glucosidase) |
| 19 | SEQ ID NO: 120 (encoded by, e.g. SEQ ID NO: 119) | ORF 002 - oxidoreductase |
| 19a | SEQ ID NO: 122 (encoded by, e.g. SEQ ID NO: 121) | ORF 004 - family 5 (cellulase) |
| 20 | SEQ ID NO: 124 (encoded by, e.g. SEQ ID NO: 123) | ORF 006 - family 1 (β-glucosidase) |
| 21 | SEQ ID NO: 132 (encoded by, e.g. SEQ ID NO: 131) | ORF 007 - family 5 (cellulase) |
| 22 | SEQ ID NO: 38 (encoded by, e.g. SEQ ID NO: 37) | ORF 011 - family 1 (β-glucosidase) |
| 22a | SEQ ID NO: 36 (encoded by, e.g. SEQ ID NO: 35) | ORF 007 - family 5 (cellulase) |
| 23 | SEQ ID NO: 138 (encoded by, e.g. SEQ ID NO: 137) | ORF 001 - peptidase_M37 |
| 24 | SEQ ID NO: 146 (encoded by, e.g. SEQ ID NO: 145) | ORF 002 - family 1 (β-glucosidase) |
| 25 | SEQ ID NO: 52 (encoded by, e.g. SEQ ID NO: 51) | ORF 001 - family 5 (cellulase) |
| 26 | SEQ ID NO: 20 (encoded by, e.g. SEQ ID NO: 19) | ORF 008 - family 10 (xylanase) |
| 26a | SEQ ID NO: 18 (encoded by, e.g. SEQ ID NO: 17) | ORF 005 - β-lactamase |
| 27 | SEQ ID NO: 16 (encoded by, e.g. SEQ ID NO: 15) | ORF 007 - family 1 (β-glucosidase) |
| 27a | SEQ ID NO: 14 (encoded by, e.g. SEQ ID NO: 13) | ORF 005 - NADH dependent dehydrogenase |
| 27b | SEQ ID NO: 12 (encoded by, e.g. SEQ ID NO: 11) | ORF 003 - NAD binding oxidoreductase |
| 28 | SEQ ID NO: 28 (encoded by, e.g. SEQ ID NO: 27) | ORF 002 - family 1 (β-glucosidase) |
| 29 | SEQ ID NO: 114 (encoded by, e.g. SEQ ID NO: 113) | ORF 003 - family 10 |
| 30 | SEQ ID NO: 34 (encoded by, e.g. SEQ ID NO: 33) | ORF 006 - family 1 (β-glucosidase) |
| 30a | SEQ ID NO: 32 (encoded by, e.g. SEQ ID NO: 31) | ORF 002 - cellodextrin phosphorylase |
| 31 | SEQ ID NO: 30 (encoded by, e.g. SEQ ID NO: 29) | ORF 004 - family 1 (β-glucosidase) |
| 32 | SEQ ID NO: 100 (encoded by, e.g. SEQ ID NO: 99) | ORF 012 - family 1 (β-glucosidase) |
| 33 | SEQ ID NO: 84 (encoded by, e.g. SEQ ID NO: 83) | ORF 008 - dehydrogenase |
| 34 | SEQ ID NO: 102 (encoded by, e.g. SEQ ID NO: 101) | ORF 003 - family 5 (cellulase) |
| 35 | SEQ ID NO: 140 (encoded by, e.g. SEQ ID NO: 139) | ORF 001 - threonine dehydrogenase |
| 36 | SEQ ID NO: 142 (encoded by, e.g. SEQ ID NO: 141) | ORF 005 - family 1 (β-glucosidase) |
| 37 | SEQ ID NO: 144 (encoded by, e.g. SEQ ID NO: 143) | ORF 003 - family 1 (β-glucosidase) |

TABLE 1-continued

Summary of GIGAMATRIX ™ hits

| Enzyme No. | Open Reading Frame SEQ ID NO: | nearest relevant BLAST |
|---|---|---|
| 38 | SEQ ID NO: 2 (encoded by, e.g. SEQ ID NO: 1) | ORF 001 - family 1 (β-glucosidase) |
| 39 | SEQ ID NO: 86 (encoded by, e.g. SEQ ID NO: 85) | ORF 008 - family 1 (β-glucosidase) |

Abbreviations: CBM—carbohydrate binding module

Characterization Enzyme and Substrate Activity

The 39 hits (see Table 1, above) discovered in the GIGAMATRIX™ screen were first screened against cellohexaose to determine action pattern on a cellulose oligomer. Genomic clones are defined as clones that have an entire DNA insert potentially containing multiple open reading frames. For example, in Table 1, above, one such genomic clone contains two open reading frames annoted as Enzymes No. 22 and 22a, with said open reading frames having the sequences as depicted in SEQ ID NO:37 and SEQ ID NO:35, respectively. Another such genomic clone is contains three open reading frames, which are annotated as Enzymes 27, 27a and 27b. Subclones are derived from genomic clones and can contain only a single open reading frame. Genomic clones were grown overnight in TB media containing antibiotic, cells were lysed and lysates were clarified by centrifugation. Subclones are grown to an OD600=0.5 induced with an appropriate inducer and then grown an additional 3 h before lysing the cells and clarifying the lysate. Genomic clones will generally have less activity than a subclone, but are a more facile way of assessing activity in a large range of clones. Initial studies were performed using thin layer chromatography (TLC) for endpoint reactions usually run for 24 h. Enzymes were also tested on phosphoric acid swollen cellulose (PASC), which is crystalline cellulose that is made more amorphous through swelling by acid treatment.

Figure 6:
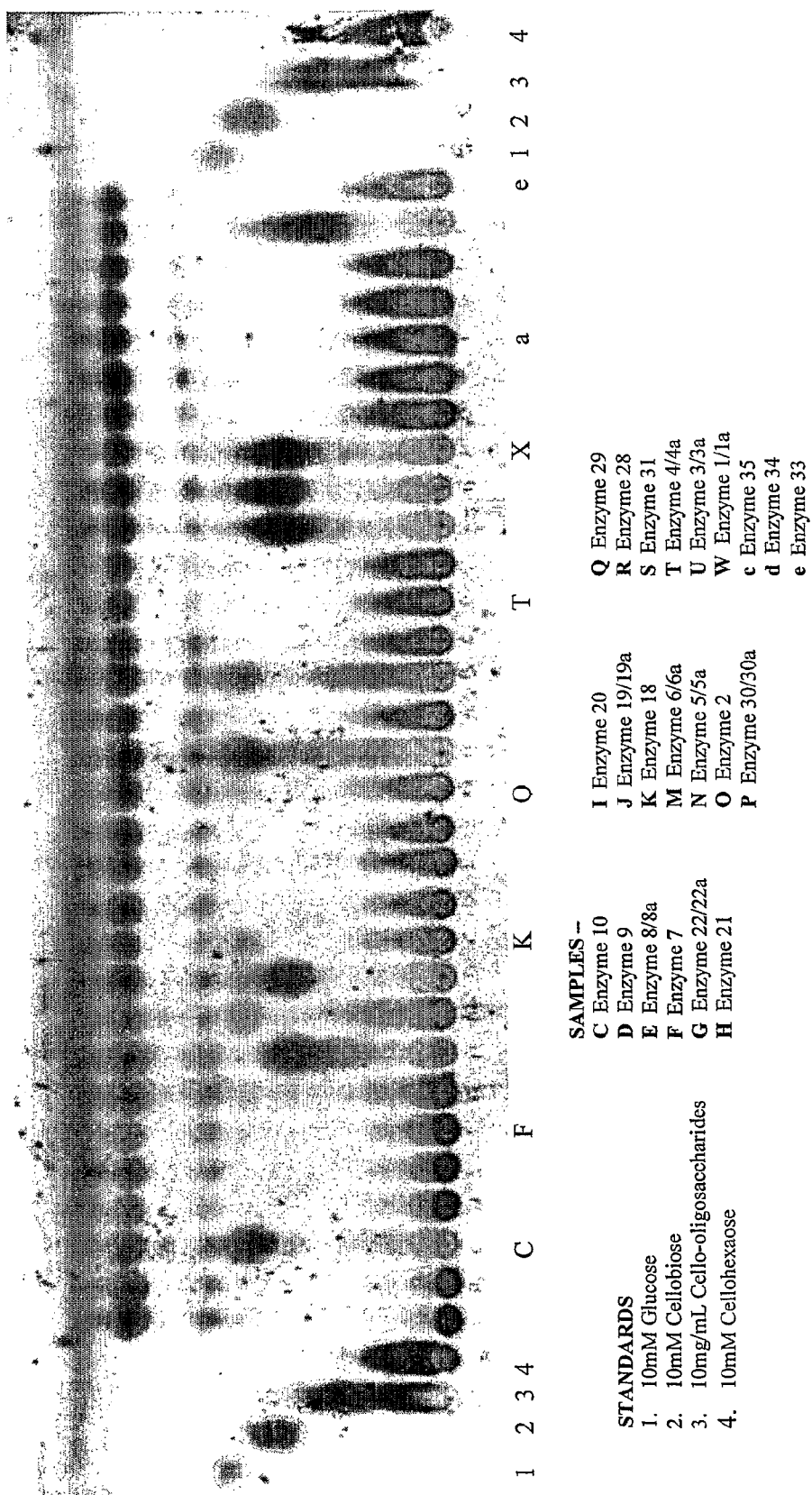
FIGS. 6 and 7 illustrate the results of a TLC analysis of reaction products from cellohexaose, as discussed in detail in Example 1, below.
Figure 7:
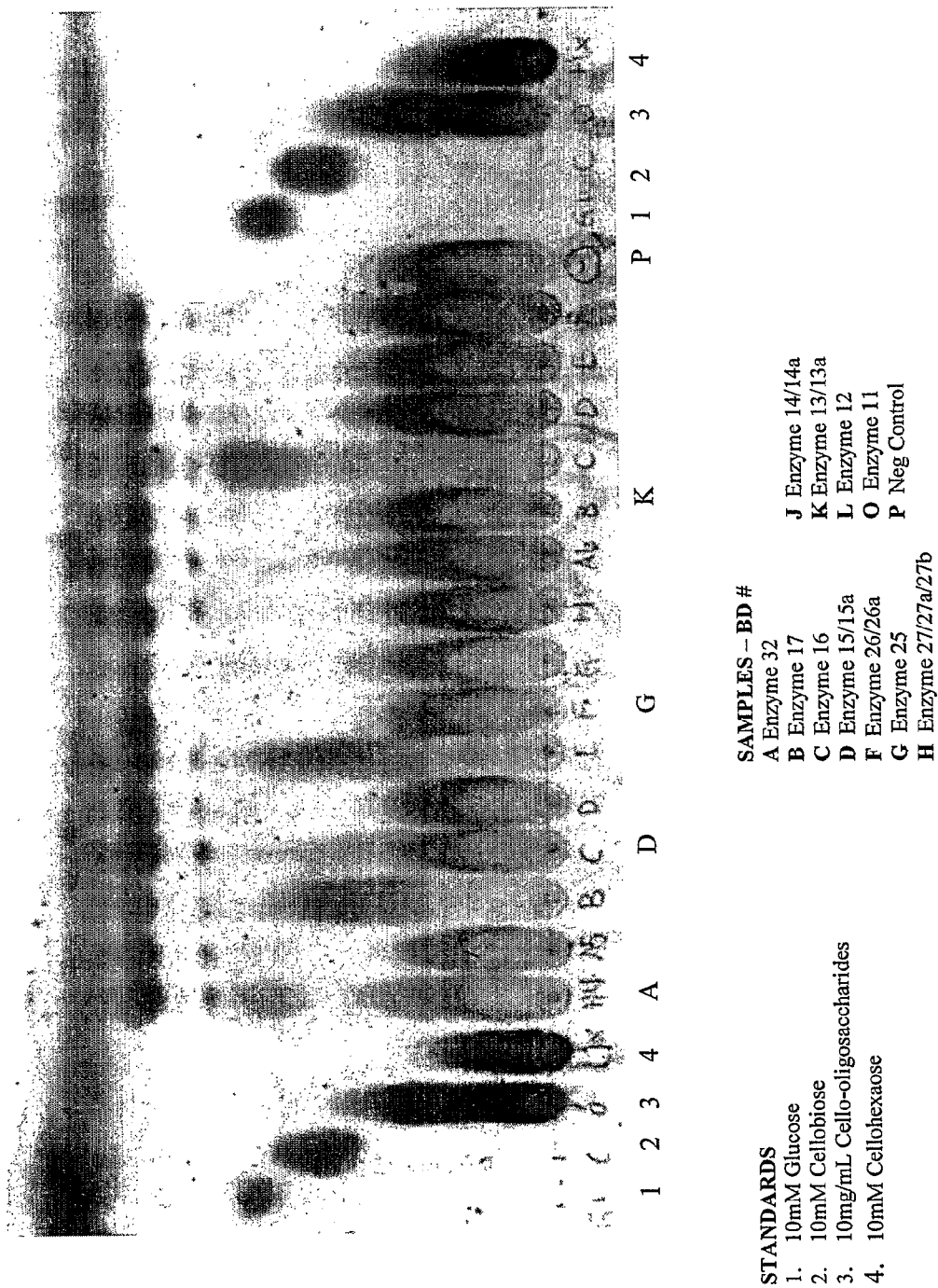

A number of cellulases which were cloned from environmental libraries were active against PASC, but released cellobiose as well as celltriose and/or glucose. The genomic clones from the GIGAMATRIX™ discovery effort were also tested against PASC and on cellulosic substrates such as cellohexaose (Seikagaku, Japan). Thin layer chromatography (TLC) experiments showed that several genomic clones were able to hydrolyze the cellohexaose, as illustrated in FIGS. 6 and 7. Of these clones, many were able to generate glucose as the final product which is consistent with the fact that they have sequence identity to glycosyl hydrolase family 1, which includes beta-glucosidases. Several enzymes produced cellobiose and/or larger fragments, but the exact nature of the product pattern could not be discerned from the TLC experiments, so a capillary electrophoresis (CE) method was developed.

Example 2

Capillary Electrophoresis

In some aspects, Capillary Electrophoresis (CE) is used in assays to screen for enzyme activity, e.g., CE is used in methods to determine if a polypeptide has cellulase activity and is within the scope of the invention, or, to identify and isolate a polypeptide having cellulase activity. Capillary Electrophoresis (CE) offers the advantages of faster run times and greater assay sensitivity. The CE method used 1-aminopyrene-3,6,8-trisulfonate (APTS) as the fluorophore and was optimized for use with sugars and sugar oligomers (Guttman (1996) High-resolution capillary gel electrophoresis of reducing oligosaccharides labeled with 1-aminopyrene-3,6, 8-trisulfonate. Anal. Biochem 233:234-242). Enzymes that were shown to be active on cellohexaose were subjected to tests on phosphoric acid swollen cellulose as well as cellohexaose. Genes were subcloned, expressed and partially purified using a nickel-chelating column. Enzymes were incubated with substrate for 1 h and the products were analyzed using a 10 cm or 48 cm capillary. Cellohexaose elutes at 2 and 9 minutes for the 10 and 48 cm capillaries respectively. The 48 cm capillary gives better separation of products in case there are low amounts of sugar or if there are contaminants in the mixture. The CE method was implemented for studies on enzymes from the GIGAMATRIX™ discovery that showed good activity on cellohexaose with TLC detection.

Figure 8:
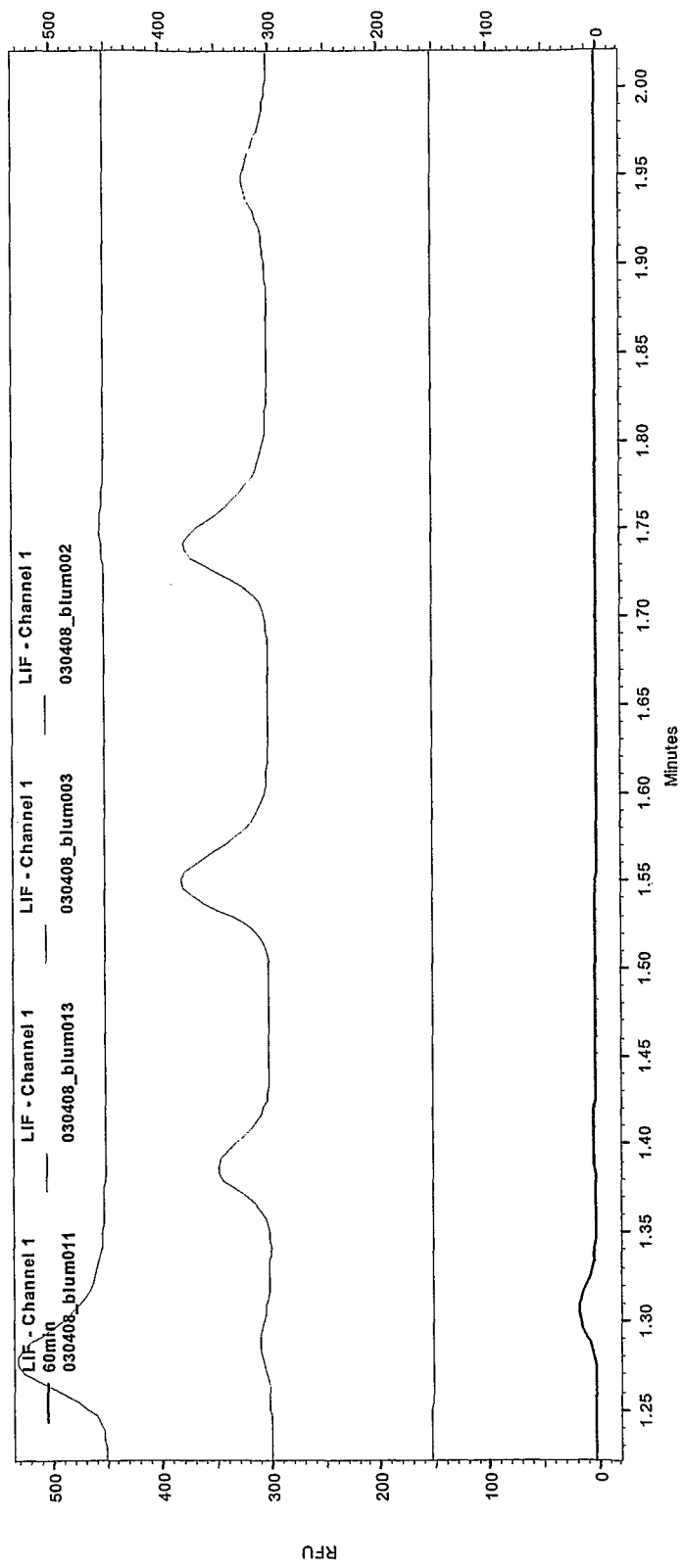
FIG. 8 illustrates in graph form data showing the release of cellobiose from PASC by the exemplary enzyme 22/22a (a CBH) of the invention, as discussed in detail in Example 2, below.
Figure 9:
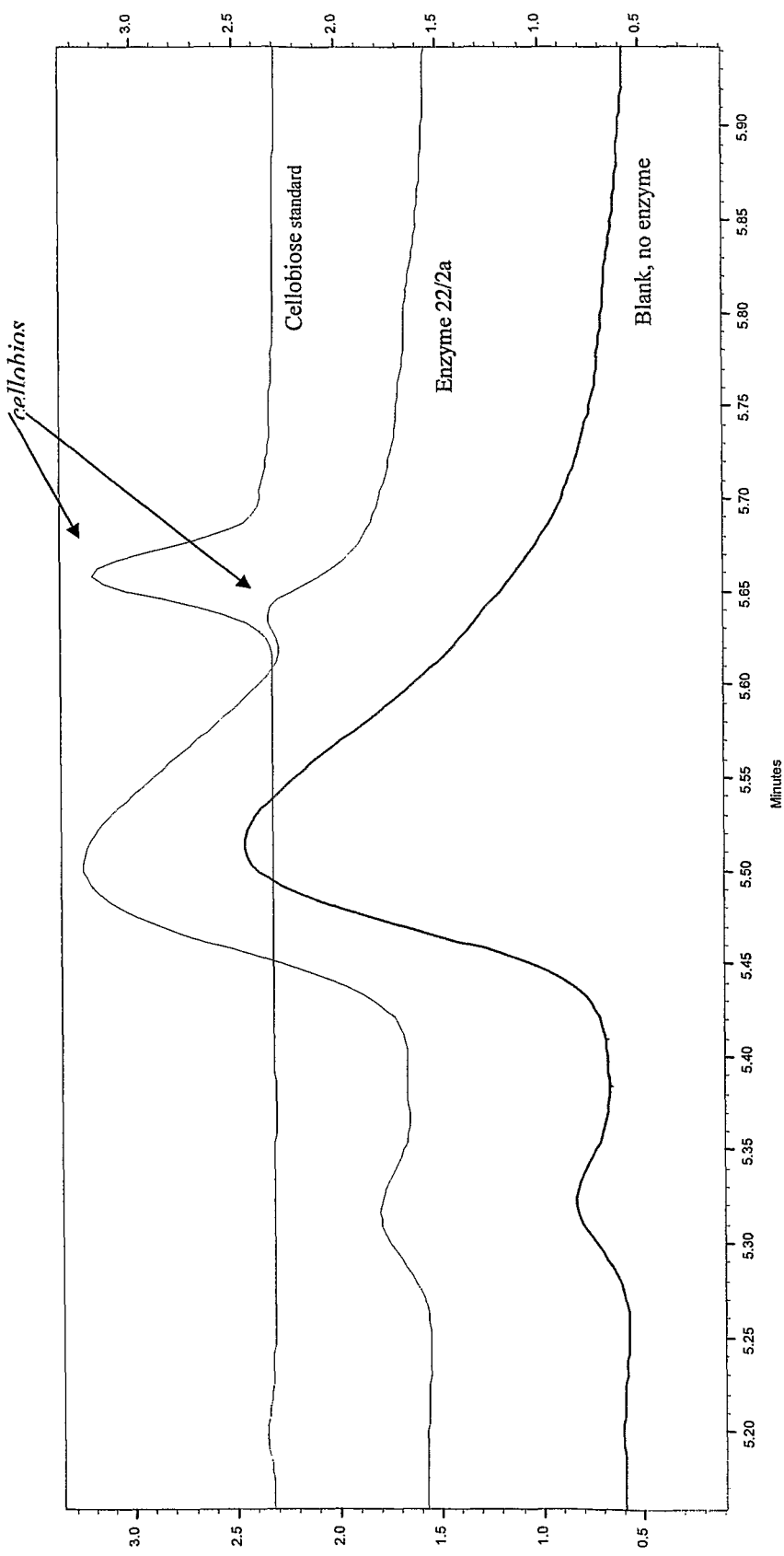
FIG. 9 illustrates in graph form data showing the release of cellobiose from AVICEL® MCC by the exemplary enzyme 22/22a (a CBH) of the invention, as discussed in detail in Example 2, below.

Enzyme 22/22a (see Table, 1 above) showed good performance on PASC (data summarized in graph form in FIG. 8), releasing mainly cellobiose. In addition, enzyme 22/22a was able to release cellobiose from AVICEL® Microcrystalline Cellulose (MCC) (FMC Corporation, Philadelphia, Pa.) (data summarized in graph form in FIG. 9). Sequence analysis showed that enzyme 22 and enzyme 21 are 92% identical and belong to glycosyl hydrolase family 5. Family 5 contains mainly endoglucanases, but there are examples of cellobiohydrolases. CelO from *Clostridium thermocellum* has been characterized as a cellobiohydrolase based on activity on release of only cellobiose from amorphic and crystalline cellulose (Zverlov (2002) A newly described cellulosomal cellobiohydrolase, CelO, from *Clostridium thermocellum*: investigation of the exo-mode of hydrolysis, and binding capacity to crystalline cellulose. Microbiology 148:247-255).

All three of these enzymes, when compared to the endoglucanase from *Acidothermus cellulolyticus* have an insertion that is in close proximity to the substrate binding site. This insertion could form a loop which encloses the substrate binding site thus converting this enzyme from an endoglucanase to a cellobiohydrolase. When these enzymes were tested on cellohexaose they produced mainly cellobiose with a smaller amount of cellotriose. These results are explained by the fact that cellobiohydrolases have the capability to produce both cellobiose and cellotriose from a cellohexaose substrate (Harjunpaa (1996) Cello-oligosaccharide hydrolysis by cellobiohydrolase II from *Trichoderma reesei*. Association and rate constants derived from an analysis of progress curves. Eur. J Biochem 240:584-591).

Example 3

Sequence Based Discovery

The invention provides methods for identifying and isolating cellulases, e.g., cellobiohydrolases, using sequences of the invention. In one exemplary method, primers that were homologous to conserved regions of three glycosyl hydrolase families that contain cellobiohydrolases were used to screen either polynucleotide libraries or DNA derived from fungal samples. Primers were designed towards family 48 conserved regions and 96 libraries were screened resulting in 1 confirmed hit. In addition, primers were designed towards family 6 and family 7. Fungal libraries were screened with these primers, resulting in 1 hit for family 6 and 56 hits for family 7. One of the family 7 hits was chosen for studies to extract the full length sequence. The full-length sequence was successfully obtained and showed 73% identity to exo-cellobiohydrolase I of *Penicillium janthinellum*.

Example 4

Genetic Engineering of an Enzyme with Cellobiohydrolase Activity

This example described the genetic engineering of an exemplary enzyme of the invention. This enzyme can be used in the conversion of biomass to fuels and chemicals, and for making effective and sustainable alternatives to petroleum-based products. This enzyme can be expressed in organisms (e.g., microorganisms, such as bacteria) for its participation in chemical cycles involving natural biomass conversion. In one aspect, this enzyme is used in "enzyme ensembles" for the efficient depolymerization of cellulosic and hemicellulosic polymers to metabolizable carbon moieties. As discussed above, the invention provides methods for discovering and implementing the most effective of enzymes to enable these important new "biomass conversion" and alternative energy industrial processes.

Using metagenomic discovery and a non-stochastic method of directed evolution (called "DIRECTEVOLU-TION®, as described, e.g., in U.S. Pat. No. 6,939,689, which includes Gene Site Saturation Mutagenesis (GSSM) (as discussed above, see also U.S. Pat. Nos. 6,171,820 and 6,579,258) and Tunable GeneReassembly (TGR) (see, e.g., U.S. Pat. No. 6,537,776) technologies. This effort focused on the discovery and optimization of an important enzyme component for cellulose reduction to glucose, cellobiohydrolase.

An enzyme discovery screen was implemented using Diversa Corporation's GIGAMATRIX™ high throughput expression screening platform (discussed above) to identify cellobiohydrolases using methylumbelliferyl cellobioside as substrate. A total of 100 complex environmental libraries were screened resulting in 25 confirmed cellobiohydrolase hits mainly from glycosyl hydrolase families 5 and 10. These hits were characterized for activity against AVICEL® Microcrystalline Cellulose (MCC) (FMC Corporation, Philadelphia, Pa.). Based on its performance characteristics, one enzyme, SEQ ID NO:162 (encoded by, e.g., SEQ ID NO:161) was chosen as a candidate for optimization using Gene Site Saturation Mutagenesis (GSSM) technology. However, before GSSM evolution was performed, the signal sequence (amino acids 1 through 30) was removed from SEQ ID NO:162 and a starting methionine was added. This signal-free sequence, hereinafter called the "wild-type" and represented by SEQ ID NO:164 (encoded by, e.g., SEQ ID NO:163), was the parental sequence that was optimized using GSSM technology. As discussed above, GSSM technology can rapidly mutate all amino acids in the protein to the 19 other amino acids in a sequential fashion. Mutants were screened using a fiber-based assay and potential upmutants representing single amino acid changes were identified. These upmutants were combined into a new library representing combinations of the upmutants. This library was screened resulting in identification of several candidate enzymes for commercialization.

Research Summary
GIGAMATRIX™ Screen

The GIGAMATRIX™ (GMx) screening platform is an ultra-high throughput method based on a 100,000 well microplate with the dimensions of a conventional 96 well plate (see Phase II application for details). The screen works with fluorescent substrates. The GMx screen was implemented using 2 substrates based on previously shown activity by cellulases. Methylumbelliferyl cellobioside (MUC) was used as the screening substrate. In addition, resorufin-beta-glucopyranoside was also included in the screen in order to eliminate clones that have activity on both substrates and are presumed to be beta-glucosidases.

Amplified phage or phagemid versions of the target libraries were screened. Two host strains (CEH6 & GAL631) lacking beta-galactosidase genes were used in order to decrease endogenous host activity on the substrates. 100 libraries were chosen for screening based on the fact that these libraries yielded cellulase hits from a previous screening program. Of the libraries screened, there were a total of 355 primary hits from 69 of the libraries screened.

Figure 10:
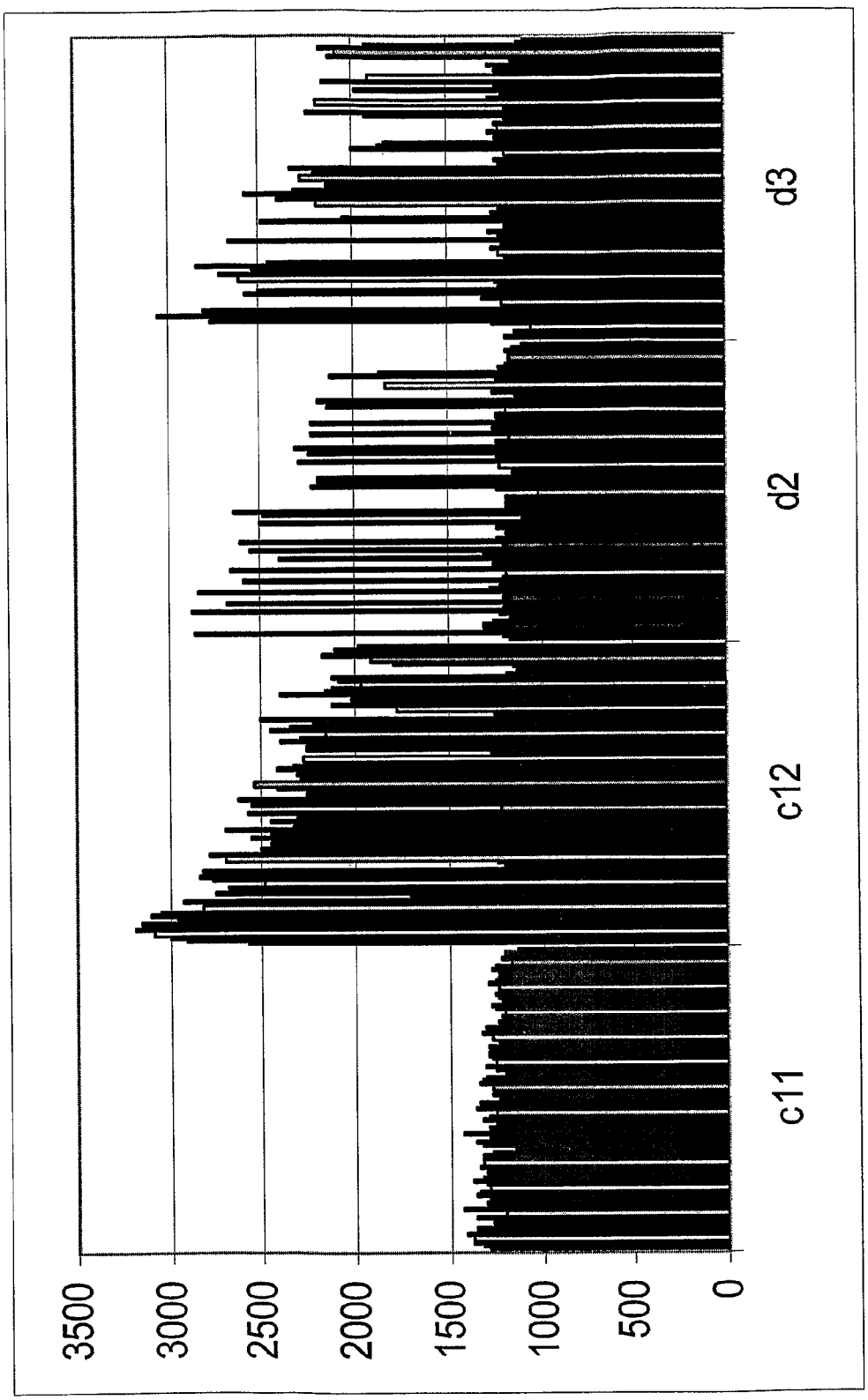
FIG. 10 illustrates in graphic form data showing a typical GIGAMATRIX™ breakout, where active clones expressing enzyme able to hydrolyze methylumbelliferyl cellobioside are identified, as discussed in detail in Example 4, below.

Secondary screening consisted of plating the clones on agar plates and then colony picking into 384 well plates containing media and methylumbelliferyl cellobioside (MUC) termed a "breakout". FIG. 10 illustrates in graphic form data showing a typical GIGAMATRIX™ (GMx) breakout. To generate this data, active clones against MUC (i.e., able to hydrolyze methylumbelliferyl cellobioside) are differentiated from a background of inactive clones. Individual clones were then grown overnight and fluorescence was measured and the most active hits were picked for sequencing. In FIG. 10, the X axis shows sample name; Y axis is relative fluorescent units. Positive "hits" were plated onto agar plates and then colony picked into 384 well plates containing LB+antibiotic plus 50 µM MUC and grown overnight.

TABLE 2

Summary of GIGAMATRIX ™ (GMx) hits

| Enzyme No. | Open Reading Frame SEQ ID NO: | Clone Family Characterization |
|---|---|---|
| 40 | SEQ ID NO: 104 (encoded by, e.g., SEQ ID NO: 103) | family 5 (cellulase) |
| 41 | SEQ ID NO: 108 (encoded by, e.g., SEQ ID NO: 107) | family 5 (cellulase) |
| 42 | SEQ ID NO: 112 (encoded by, e.g., SEQ ID NO: 111) | family 5 (cellulase) |
| H7 | SEQ ID NO: 60 (encoded by, e.g., SEQ ID NO: 59) | family 5 (cellulase) |
| 43 | SEQ ID NO: 82 (encoded by, e.g., SEQ ID NO: 81) | family 5 (cellulase) |
| 44 | SEQ ID NO: 78 (encoded by, e.g., SEQ ID NO: 77) | family 5 (cellulase) |
| 45 | SEQ ID NO: 68 (encoded by, e.g., SEQ ID NO: 67) | family 5 (cellulase)- ORF 2 |
| 45a | SEQ ID NO: 70 (encoded by, e.g., SEQ ID NO: 69) | family 26 (mannanase) - ORF4 |
| 46 | SEQ ID NO: 74 (encoded by, e.g., SEQ ID NO: 73) | family 10 (xylanase) |
| 47 | SEQ ID NO: 110 (encoded by, e.g., SEQ ID NO: 109) | family 10 (xylanase) |

TABLE 2-continued

Summary of GIGAMATRIX ™ (GMx) hits

| Enzyme No. | Open Reading Frame SEQ ID NO: | Clone Family Characterization |
|---|---|---|
| 48 | SEQ ID NO: 106 (encoded by, e.g., SEQ ID NO: 105) | family 5 (cellulase) |
| 49 | SEQ ID NO: 66 (encoded by, e.g., SEQ ID NO: 65) | family 10 (xylanase) |
| 50 | SEQ ID NO: 72 (encoded by, e.g., SEQ ID NO: 71) | family 5 (cellulase) |
| 51 | SEQ ID NO: 80 (encoded by, e.g., SEQ ID NO: 79) | family 5 (cellulase) |
| H8 | SEQ ID NO: 62 (encoded by, e.g., SEQ ID NO: 61) | family 5 (cellulase) ORF 1 |
| H8a | SEQ ID NO: 64 (encoded by, e.g., SEQ ID NO: 63) | family 5 (cellulase) ORF 4 |
| 52 | SEQ ID NO: 76 (encoded by, e.g., SEQ ID NO: 75) | family 5 (cellulase) |
| 53 | SEQ ID NO: 160 (encoded by, e.g., SEQ ID NO: 159) | family 10 (xylanase) |
| 54 | SEQ ID NO: 88 (encoded by, e.g., SEQ ID NO: 87) | family 5 (cellulase) |
| 55 | SEQ ID NO: 148 (encoded by, e.g., SEQ ID NO: 147) | family 10 (xylanase) |
| 56 | SEQ ID NO: 90 (encoded by, e.g., SEQ ID NO: 89) | family 5 (cellulase) |
| 57 | SEQ ID NO: 152 (encoded by, e.g., SEQ ID NO: 151) | family 5 (cellulase) |
| 58 | SEQ ID NO: 150 (encoded by, e.g., SEQ ID NO: 149) | family 5 (cellulase) |
| 59 | SEQ ID NO: 154 (encoded by, e.g., SEQ ID NO: 153) | family 5 (cellulase) |
| H6 | SEQ ID NO: 158 (encoded by, e.g., SEQ ID NO: 157) | family 5 (cellulase) |
| 60 | SEQ ID NO: 156 (encoded by, e.g., SEQ ID NO: 155) | family 5 (cellulase) |

All genomic clone inserts from hits were sequenced. As with Table 1 above, some genomic clones contained more than one open reading frame. For example, one such genomic clone contains two open reading frames annotated as Enzymes No. H8 and H8a, with said open reading frames having the sequences as depicted in SEQ ID NO:67 and SEQ ID NO:69, respectively. There was a total of 25 glycosyl hydrolase hits from 17 of the libraries screened. In general, the hits were from several different glycosyl hydrolase families including 5 and 10. Table 2 (above) lists the hits and their identities. Several other hits were discovered where the open reading frame was not homologous to any known glycosyl hydrolase families. In addition, some of the hits encoded GTP cyclohydrolase genes that are known false positives in this system as they create fluorescence regardless of substrate degradation. Overall the screen was successful in identifying enzymes that were active on MUC.

Characterization

Genes discovered in the GIGAMATRIX™ screen were sequenced and the data were analyzed. Open reading frames (ORFs) were annotated using a software system. The ORFs were subcloned into the appropriate vector(s) with the introduction of DNA encoding C-terminal His-tags. Construct DNA was transformed into the appropriate E. coli host(s) and expressed for characterization studies. The gene products were screened against phosphoric acid-swollen cellulose (PASC). PASC is crystalline cellulose that is made more amorphous through swelling by acid treatment. PASC was prepared from AVICEL® Microcrystalline Cellulose (MCC). Subclones were grown, expressed and lysed. Lysates were incubated with PASC and the reaction products were analyzed using the bicinchoninic acid (BCA) reducing sugar assay. The most active subclones were selected for larger scale growth and purification. The specific activity of these subclones was determined on PASC.

Figure 11:
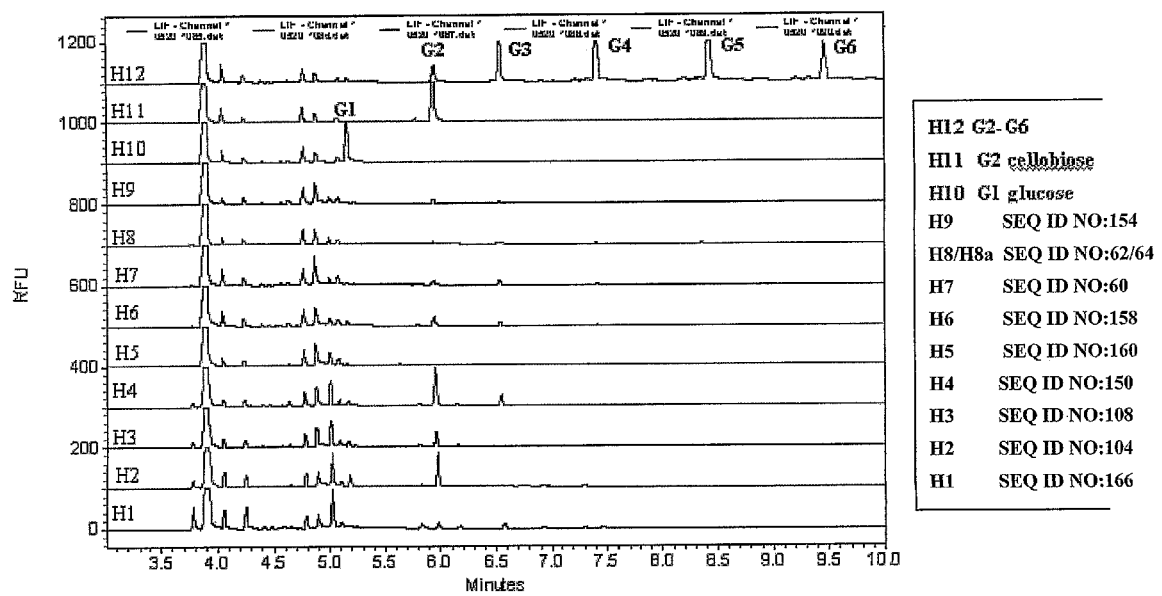
FIG. 11 illustrates in graph form data showing the activity of selected enzymes against phosphoric acid-swollen cellulose (PASC) by capillary electrophoresis (CE) analysis, as discussed in detail in Example 4, below.

The subclones were also analyzed by capillary electrophoresis (CE). Lysates were incubated with substrate for 30 hours. The reaction products were derivatized with the fluorophore 1-aminopyrene-3,6,8-trisulfonate (APTS). The products were analyzed using a 48 cm capillary. Cellobiose elutes at 6 minutes. FIG. 11 illustrates in graph form data showing the activity of selected enzymes against PASC by capillary electrophoresis (CE) analysis. Samples H9 through H1 are individual clones. In FIG. 11, a number of samples had reaction product profiles representative of processive enzymes. A processive enzyme is defined as having a ratio of cellobiose/(glucose+cellotriose) 10. Two potential processive enzymes that were the most active had specific activities on PASC of 0.35 and 0.04 U/mg, respectively.

Fungal CBHs in *Pichia*

Genes of newly discovered family 6 & 7 fungal cellobiohydrolases were transformed into *P. pastoris* and the transformations were spread onto solid agar plates. 160 colonies were selected for each construct. The samples were grown and induced and the supernatants were incubated with PASC in the presence of a β-glucosidase. The reaction products were analyzed using the glucose-oxidase assay. A glycosyl hydrolase family 6 cellobiohydrolase, was successfully heterologously expressed in *P. pastoris*.

Exo-Endo Acting Cellulase

Figure 12:
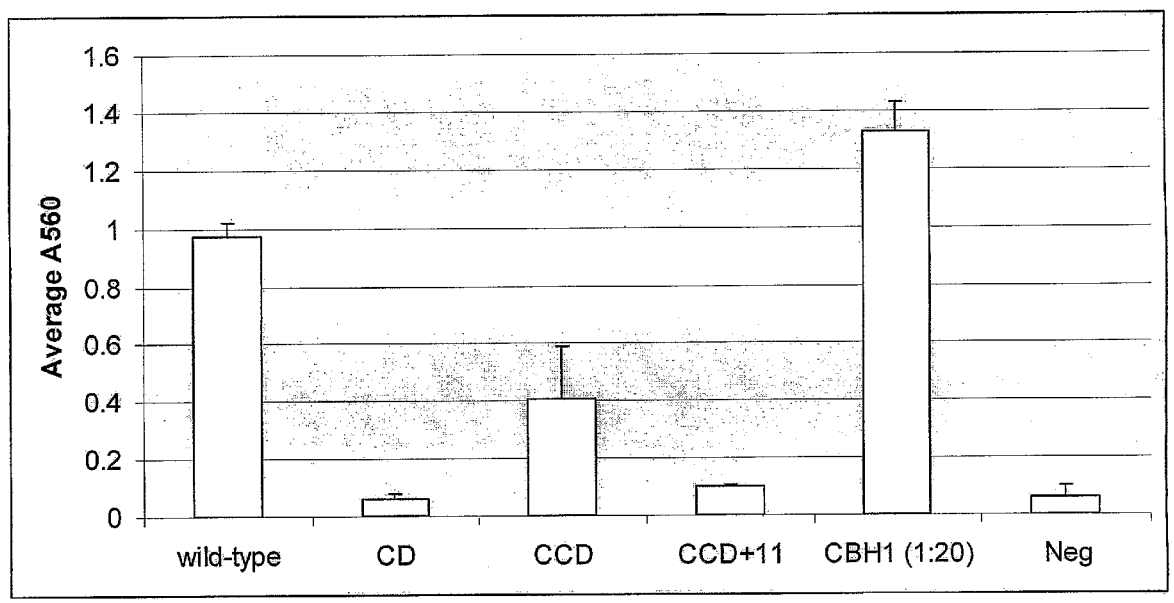
FIG. 12 illustrates in graph form data from assays of an exemplary enzyme of the invention and subclone variants in AVICEL® Microcrystalline Cellulose (MCC), where the reaction products were analyzed by the BCA reducing sugar assay, as discussed in detail in Example 4, below.

The wild-type enzyme, a family 9 glycosyl hydrolase discovered in an enzyme screen, is a homolog of *Thermomonospora fusca* E4. E4 has been shown to have both endo- and exo-activity. Initial tests of the wild-type enzyme showed it to be active on both PASC and AVICEL® Microcrystalline Cellulose (MCC). HPLC analysis of the reaction products showed the primary products to be glucose and cellobiose. The wild-type enzyme is a multi-domain protein which includes a glycosyl hydrolase family 9 catalytic domain, a family 3 cellulose binding domain, and three bacterial Ig-like domains that are believed to be involved in cell adhesion. Three additional subclone variants of the wild-type enzyme were tested to determine the effects of the domains on activity. The wild-type enzyme was subcloned with: 1) the catalytic domain alone (CD); 2) the catalytic and carbohydrate domain (CCD); and 3) the catalytic and carbohydrate binding domain plus the 11 downstream amino acids (CCD+11). The full-length protein and the 3 subclone variants were assayed on AVICEL® Microcrystalline Cellulose (MCC) and the reaction products were analyzed by the BCA reducing sugar assay, and the data is summarized in graphic form in FIG. 12. The data illustrated in FIG. 12 was generated by BCA of the wild-type enzyme and truncation mutants incubated with AVICEL® Microcrystalline Cellulose (MCC) for 74 hours, 37° C., pH 5. CBH1 is a positive control. The negative control is the host without insert.

The wild-type enzyme, the full-length protein (SEQ ID NO:164, encoded by, e.g., SEQ ID NO:163), was the most active. The full length protein was selected for GSSM evolution. The catalytic and the carbohydrate binding domain were evolved.

GSSM Screening

GSSM technology (discussed above) was used to rapidly and sequentially mutate the amino acids of the catalytic and carbohydrate binding domain of the target protein into the 19 other amino acids. The goal of the GSSM screen was to identify mutants that increased the extent of hydrolysis on insoluble microcrystalline cellulose. A robotic screening method was developed to facilitate the GSSM screening process.

DNA from the mutation constructs was transformed into DH10b host cells. Individual colonies were picked into 96 well (shallow) plates containing 150 uL LB/Ampicillin using the automatic colony picking system. The plates were incubated for 24 hours at 37° C., 400 rpm. 15 uL of culture was transferred from each well into an induction plate. Each well of the induction plate contained 135 uL LB/Ampicillin with 1.1 mM IPTG. The induction plates were incubated for 24 hours at 37° C., 400 rpm. The plates were centrifuged and the supernatant was discarded.

The automated portion of the assay began at this point. The cells were lysed and resuspended by the robot. 150 uL of lysis buffer (125 uL water plus 25 uL BPER containing 0.2 mg/ml lysozyme and 20 unit/ml DNase I) was added to each well. 15 uL lysate was transferred from each well to a reaction plate. Each well of the reaction plate contained 185 uL of a reaction mix (1% AVICEL® Microcrystalline Cellulose (MCC), 50 mM sodium acetate buffer pH5.0). The reaction plates were incubated at 37° C. for 30 hours with 95% humidity. After incubation, the plates were centrifuged and 15 uL supernatant was transferred to BCA plates. The BCA plates contained 50 uL reagent A, 50 uL reagent B, and 80 uL 400 mM Carbonate buffer, pH 10 per well. The plates were covered with rubber seals and incubated at 80° C. for 30 minutes, then cooled by centrifugation and the absorbance read at A560.

Results

Figure 13:
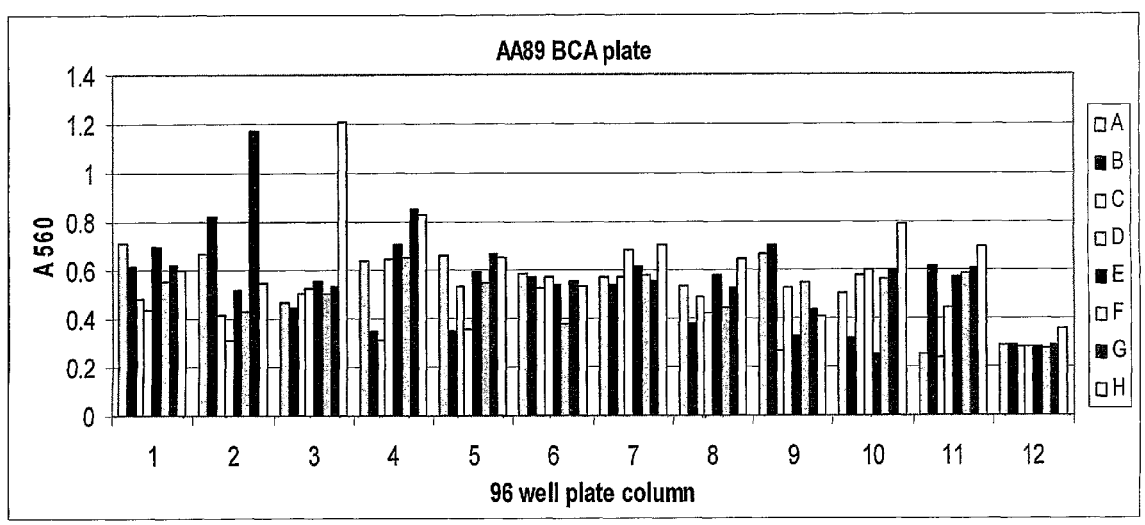
FIG. 13 illustrates in graph form data from primary GSSM screening assays, as discussed in detail in Example 4, below.

At least 80 random mutation colonies were screened for each amino acid site. An example of the primary GSSM™ screening data is graphically illustrated in FIG. 13. Column 6 contained the wildtype samples and column 12 contained the host/vector negative controls. After a 30 hour incubation with AVICEL® Microcrystalline Cellulose (MCC), the signal produced from the wildtype samples was around 0.53, with a standard deviation at 0.07. The negative control had an average signal at 0.29. Samples with signal higher than the average of positive controls plus 2 times the standard deviation were deemed primary hits. From this screening plate, about ten primary hits were selected for the secondary confirmation screening.

Figure 14:
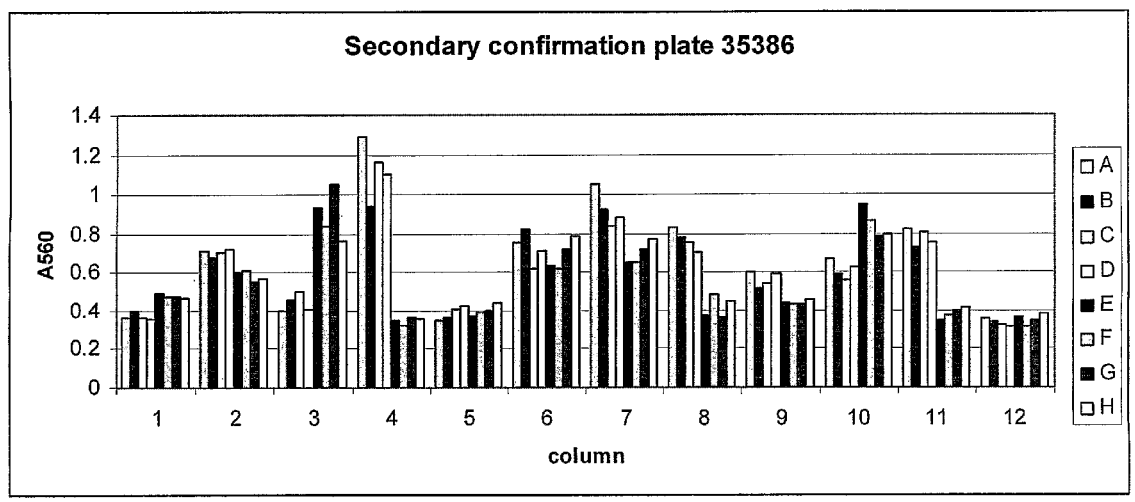
FIG. 14 illustrates in graph form data from secondary GSSM screening assays, as discussed in detail in Example 4, below.

Primary hits were reconfirmed in a secondary assay. This assay was the same as the primary screen. Samples were run in quadruplicate however. An example of the secondary GSSM screening data is graphically illustrated in FIG. 14. Samples in wells E3-H3, A4-D4, A7-D7 on average, had higher activity than the wildtype. These 12 wells correspond to 3 hits since the samples were run in quadruplicate. These samples were the primary hits shown in wells E4, G2, and H3 in FIG. 13 (plate 29805-AA89 BCA plate).

There were 77 hits from the secondary screening. These samples were sequenced. Thirty five of the samples had amino acid changes, 22 had transposon insertions, and the rest were wildtype or had deletions.

Hits from the secondary screen were further analyzed. The GSSM upmutants were mapped onto the crystal structure of T. fusca E4. Samples were prioritized based on amino acid location, amino acid change and the fold improvement score. Eight upmutants were selected from the GSSM screening and selected for gene reassembly evolution, i.e., Tunable GeneReassembly (TGR), discussed above, and also see, e.g., U.S. Pat. No. 6,537,776.

TABLE 2

Up-mutants selected for site directed mutagenesis reassembly.

| Residue | OLD AA | NEW AA |
|---------|--------|--------|
| 89 | M | R |
| 103 | F | G |
| 110 | P | G |
| 114 | Y | L |
| 157 | A | S |
| 481 | W | F |
| 550 | P | N |
| 590 | G | R |

Blending of Upmutants

Figure 15:
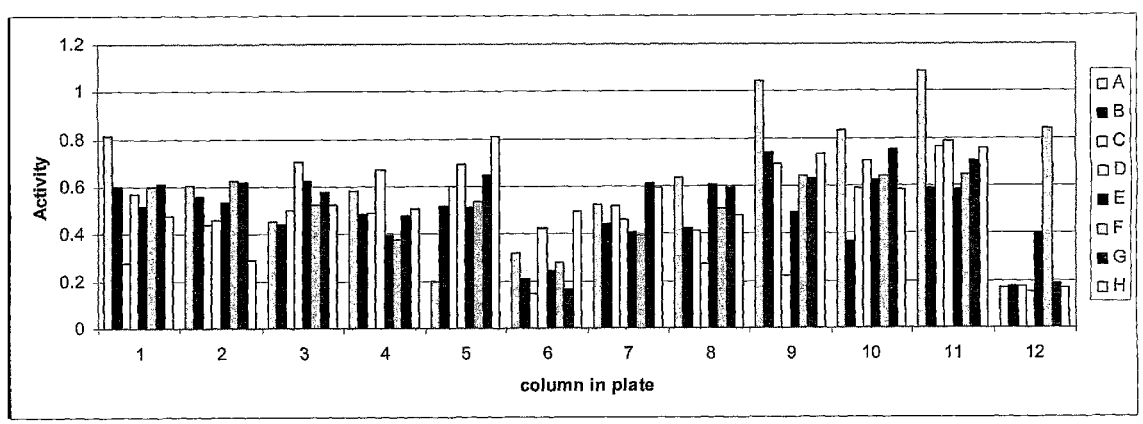
FIG. 15 illustrates in graph form data from mixed, or "blended", GSSM screening assays, as discussed in detail in Example 4, below.

Using gene reassembly (Tunable GeneReassembly (TGR)) technology, the upmutants shown in Table 2, above, were blended in order to identify the candidate with the best activity. Activity assays were the same as for the GSSM screening except reactions were further diluted to account for increased activity of upmutants over the wildtype enzyme. FIG. 15 illustrates in graph form data from mixed, or "blended", GSSM™ screening assays.

In summary, the invention provides enzymes having cellulase activity having the following sequences based on SEQ ID NO:164 (encoded by, e.g., SEQ ID NO:163):

| Residue | Original Amino Acid | Codons Encoding Original Amino Acid | New Amino Acid (after GSSM Evolution) | Codons Encodins New Amino Acid |
|---------|---------------------|-------------------------------------|---------------------------------------|--------------------------------|
| 89 | M | ATG | R | CGT, CGC, CGA, CGG, AGA, AGG |
| 103 | F | TTT, TTC | G | GGT, GGC, GGA, GGG |
| 110 | P | CCA, CCC, CCG, CCT | G | GGT, GGC, GGA, GGG |
| 114 | Y | TAT, TAC | L | TTA, TTG, CTT, CTC, CTA, CTG |
| 157 | A | GCT, GCC, GCA, GCG | S | TCT, TCC, TCA, TCG, AGT, AGC |
| 481 | W | TGG | F | TTT, TTC |
| 550 | P | CCA, CCC, CCG, CCT | N | AAT, AAC |
| 590 | G | GGT, GGC, GGA, GGG | R | CGT, CGC, CGA, CGG, AGA, AGG |

A number of aspects of the invention have been described. Nevertheless, it will be understood that various modifications may be made without departing from the spirit and scope of the invention. Accordingly, other aspects are within the scope of the following claims.

What is claimed is:

1. An isolated or recombinant nucleic acid comprising
(a) a nucleic acid sequence having at least 90%, 91%, 92%, 93%, 94%, 95%, 96%, 97%, 98%, 99%, or more or complete sequence identity to SEQ ID NO: 1, wherein the nucleic acid encodes at least one polypeptide having a cellulase activity,
and optionally the sequence identities are determined by analysis with a sequence comparison algorithm or by a visual inspection,
and optionally, the sequence comparison algorithm is a BLAST version 2.2.2 algorithm where a filtering setting is set to blastall -p blastp -d "nr pataa"-F F, and all other options are set to default; or
(b) a nucleic acid sequence that hybridizes under stringent conditions to the full-length complement of nucleic acid comprising SEQ ID NO:1, wherein the nucleic acid encodes a polypeptide having a cellulase activity, and the stringent conditions include a wash step comprising a wash in 0.2×SSC at a temperature of about 65° C. for about 15 minutes;
(c) a nucleic acid sequence encoding a polypeptide comprising the amino acid sequence of SEQ ID NO:2; or
(d) a nucleic acid sequence complementary to the full-length sequence of (a), (b) or (c);
optionally wherein the cellulase activity comprises an endoglucanase activity,
optionally wherein the cellulase activity comprises a cellobiohydrolase activity,
optionally wherein the cellulase activity comprises an beta-glucosidase or mannanase activity,
optionally wherein the cellulase activity comprises an endocellulase activity,
optionally wherein the cellulase activity comprises hydrolyzing a glucan to produce a smaller molecular weight polysaccharide or oligomer,
optionally wherein the cellulase activity comprises catalyzing hydrolysis of 1,4-beta-D-glycosidic linkages,
optionally wherein the endocellulase activity comprises an endo-1,4-beta-endocellulase activity,
optionally wherein the 1,4-beta-D-glycosidic linkage activity comprises hydrolysis of a 1,4-beta-D-glycosidic linkage in a cellulose, a cellulose derivative, a lichenin or a cereal,
optionally wherein the cellulose derivative comprises a carboxy methyl cellulose or a hydroxy ethyl cellulose,
optionally wherein the cereal comprises a beta-D-glucan or a xyloglucan,
optionally wherein the cellulase activity comprises catalyzing hydrolysis of glucanase linkages,
optionally wherein the cellulase activity comprises catalyzing hydrolysis of beta-1,4- or beta-1,3-glucanase linkages,
optionally wherein the cellulase activity comprises catalyzing hydrolysis of endo-glucanase linkages,
optionally wherein the cellulase activity comprises catalyzing hydrolysis of endo-1,4-beta-D-glucan 4-glucano hydrolase activity,
optionally wherein the cellulase activity comprises catalyzing hydrolysis of internal endo-beta-1,4-glucanase linkages or beta-1,3-glucanase linkages,
optionally wherein the cellulase activity comprises catalyzing hydrolysis of internal beta-1,3-glucosidic linkages,
optionally wherein the cellulase activity comprises hydrolyzing polysaccharides comprising glucopyranose,
optionally wherein the cellulase activity comprises hydrolyzing polysaccharides comprising 1,4-beta-glycoside-linked D-glucopyranoses,
optionally wherein the cellulase activity comprises hydrolyzing a cellulose, a cellulose derivative or a hemicellulose,
optionally wherein the cellulase activity comprises hydrolyzing a cellulose or a hemicellulose in a wood or paper pulp or a wood or paper product,
optionally wherein the cellulase activity comprises catalyzing hydrolysis of glucan in a feed, a food product or a beverage,
optionally wherein the feed, food product or beverage comprises a cereal-based animal feed, a wort or a beer, a dough, a fruit or a vegetable,
optionally wherein the cellulase activity comprises catalyzing hydrolysis of a glucan in a microbial cell, a fungal cell, a mammalian cell, a plant cell or any plant material comprising a cellulosic part,
optionally wherein the cellulase activity is thermostable,
optionally wherein the polypeptide retains a cellulase activity under conditions comprising a temperature range of between about 37° C. to about 95° C., or between about 55° C. to about 85° C., or between about 70° C. to about 75° C., or between about 70° C. to about 95° C., or between about 90° C. to about 95° C., or retains a cellulase activity in a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.,
optionally wherein the cellulase activity is thermotolerant, and
optionally wherein the polypeptide retains a cellulase activity after exposure to a temperature in the range from greater than 37° C. to about 95° C., from greater than 55° C. to about 85° C., or between about 70° C. to about 75° C., or from greater than 90° C. to about 95° C., or after exposure to a temperature in the range between about 1° C. to about 5° C., between about 5° C. to about 15° C., between about 15° C. to about 25° C., between about 25° C. to about 37° C., or between about 37° C. to about 95° C., 96° C., 98° C. or 99° C.

2. An expression cassette, a vector or a cloning vehicle comprising a nucleic acid comprising a sequence as set forth in claim 1,
wherein optionally the cloning vehicle comprises a viral vector, a plasmid, a phage, a phagemid, a cosmid, a fosmid, a bacteriophage or an artificial chromosome, and optionally the viral vector comprises an adenovirus vector, a retroviral vector or an adeno-associated viral vector, and optionally the cloning vehicle comprises a bacterial artificial chromosome (BAC), a plasmid, a bacteriophage P1-derived vector (PAC), a yeast artificial chromosome (YAC), or a mammalian artificial chromosome (MAC).

3. An isolated transformed cell comprising a nucleic acid comprising a sequence as set forth in claim 1, or the expression cassette, the vector, or the cloning vehicle as set forth in claim 2,
wherein optionally the cell is a bacterial cell, a fungal cell, a yeast cell, or a plant cell.

4. A transgenic plant or a transgenic seed comprising a sequence as set forth in claim 1,
wherein optionally the transgenic plant is a corn plant, a sorghum plant, a potato plant, a tomato plant, a wheat plant, an oilseed plant, a rapeseed plant, a soybean plant, a rice plant, a barley plant, a grass, or a tobacco plant, wherein optionally the transgenic seed is a corn seed, a wheat kernel, an oilseed, a rapeseed, a soybean seed, a palm kernel, a sunflower seed, a sesame seed, a rice, a barley, a peanut or a tobacco plant seed.

5. An isolated or recombinant polypeptide having a cellulase, endoglucanase, cellobiohydrolase, mannanase or beta-glucosidase activity
  (i) comprising an amino acid sequence having at least 90%, 91%, 92%, 93%, 94%, 95%, 96%, 97%, 98%, 99%, or more, or 100% sequence identity to SEQ ID NO:2, wherein optionally the sequence identities are determined by analysis with a sequence comparison algorithm or by a visual inspection, and optionally the sequence comparison algorithm is a BLAST version 2.2.2 algorithm where a filtering setting is set to blastall -p blastp -d "nr pataa"-F F, and all other options are set to default;
  (ii) comprising an amino acid sequence encoded by a nucleic acid as set forth in claim 1, wherein the polypeptide has a cellulase, endoglucanase, cellobiohydrolase, mannanase or beta-glucosidase activity or has immunogenic activity in that it is capable of generating an antibody that specifically binds to a polypeptide comprising the sequence of SEQ ID NO:2;
  (iii) having an amino acid sequence as set forth in (i) or (ii), or a polypeptide encoded by a nucleic acid as set forth in claim 1, and comprising at least one amino acid residue conservative substitution, wherein optionally conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, and optionally the aliphatic residue comprises Alanine, Valine, Leucine, Isoleucine or a synthetic equivalent thereof; the acidic residue comprises Aspartic acid, Glutamic acid or a synthetic equivalent thereof; the residue comprising an amide group comprises Aspartic acid, Glutamic acid or a synthetic equivalent thereof; the basic residue comprises Lysine, Arginine or a synthetic equivalent thereof; or, the aromatic residue comprises Phenylalanine, Tyrosine or a synthetic equivalent thereof,
  (iv) the polypeptide as set forth in (i), (ii) or (iii), wherein the polypeptide lacks a signal or leader sequence or a prepro sequence,
  (v) the polypeptide as set forth in (i), (ii), (iii), or (iv), having a heterologous signal or leader sequence or a heterologous prepro sequence,
  optionally wherein the cellulase activity comprises an endoglucanase activity,
  optionally wherein the cellulase activity comprises a cellobiohydrolase activity,
  optionally wherein the cellulase activity comprises an beta-glucosidase or mannanase activity,
  optionally wherein the cellulase activity comprises an endocellulase activity,
  optionally wherein the cellulase activity comprises hydrolyzing a glucan to produce a smaller molecular weight polysaccharide or oligomer,
  optionally wherein the cellulase activity comprises catalyzing hydrolysis of 1,4-beta-D-glycosidic linkages,
  optionally wherein the endocellulase activity comprises an endo-1,4-beta-endocellulase activity,
  optionally wherein the 1,4-beta-D-glycosidic linkage activity comprises hydrolysis of a 1,4-beta-D-glycosidic linkage in a cellulose, a cellulose derivative, a lichenin or a cereal,
  optionally wherein the cellulose derivative comprises a carboxy methyl cellulose or a hydroxy ethyl cellulose,
  optionally wherein the cereal comprises a beta-D-glucan or a xyloglucan,
  optionally wherein the cellulase activity comprises catalyzing hydrolysis of glucanase linkages,
  optionally wherein the cellulase activity comprises catalyzing hydrolysis of beta-1,4- or beta-1,3-glucanase linkages,
  optionally wherein the cellulase activity comprises catalyzing hydrolysis of endo-glucanase linkages,
  optionally wherein the cellulase activity comprises catalyzing hydrolysis of endo-1,4-beta-D-glucan 4-glucano hydrolase activity,
  optionally wherein the cellulase activity comprises catalyzing hydrolysis of internal endo-beta-1,4-glucanase linkages or beta-1,3-glucanase linkages,
  optionally wherein the cellulase activity comprises catalyzing hydrolysis of internal beta-1,3-glucosidic linkages,
  optionally wherein the cellulase activity comprises hydrolyzing polysaccharides comprising glucopyranose,
  optionally wherein the cellulase activity comprises hydrolyzing polysaccharides comprising 1,4-beta-glycoside-linked D-glucopyranoses,
  optionally wherein the cellulase activity comprises hydrolyzing a cellulose, a cellulose derivative or a hemicellulose,
  optionally wherein the cellulase activity comprises hydrolyzing a cellulose or a hemicellulose in a wood or paper pulp or a wood or paper product,
  optionally wherein the cellulase activity comprises catalyzing hydrolysis of glucan in a feed, a food product or a beverage,
  optionally wherein the feed, food product or beverage comprises a cereal-based animal feed, a wort or a beer, a dough, a fruit or a vegetable,
  optionally wherein the cellulase activity comprises catalyzing hydrolysis of a glucan in a microbial cell, a fungal cell, a mammalian cell, a plant cell or any plant material comprising a cellulosic part,
  optionally wherein the cellulase activity is thermostable,
  optionally wherein the polypeptide retains a cellulase activity under conditions comprising a temperature range of between about 37° C. to about 95° C., or between about 55° C. to about 85° C., or between about 70° C. to about 75° C., or between about 70° C. to about 95° C., or between about 90° C. to about 95° C., or retains a cellulase activity in a temperature in the range between about 1° C. to about 5° C., between about 5° C. to about 15° C., between about 15° C. to about 25° C., between about 25° C. to about 37° C., or between about 37° C. to about 95° C., 96° C., 97° C., 98° C. or 99° C.,
  optionally wherein the cellulase activity is thermotolerant, and
  optionally wherein the polypeptide retains a cellulase activity after exposure to a temperature in the range from greater than 37° C. to about 95° C., from greater than 55° C. to about 85° C., or between about 70° C. to about 75° C., or from greater than 90° C. to about 95° C., or after exposure to a temperature in the range between about 1°

C. to about 5° C., between about 5° C. to about 15° C., between about 15° C. to about 25° C., between about 25° C. to about 37° C., or between about 37° C. to about 95° C., 96° C., 97° C., 98° C. or 99° C.,
optionally wherein the cellulase activity comprises a specific activity at about 37° C. in the range from about 100 to about 1000 units per milligram of protein, from about 500 to about 750 units per milligram of protein, from about 500 to about 1200 units per milligram of protein, or from about 750 to about 1000 units per milligram of protein,
optionally wherein the thermotolerance comprises retention of at least half of the specific activity of the cellulase at 37° C. after being heated to an elevated temperature, or, wherein the thermotolerance comprises retention of specific activity at 37° C. in the range from about 500 to about 1200 units per milligram of protein after being heated to an elevated temperature,
optionally wherein the polypeptide comprises at least one glycosylation site, optionally the glycosylation is an N-linked glycosylation, and optionally the polypeptide is glycosylated after being expressed in a *P. pastoris* or a *S. pombe,*
optionally wherein the polypeptide retains a cellulase activity under conditions comprising about pH 6.5, pH 6.0, pH 5.5, 5.0, pH 4.5 or 4.0 or more acidic, or after exposure to conditions comprising about pH 6.5, pH 6.0, pH 5.5, 5.0, pH 4.5 or 4.0 or more acidic, and
optionally wherein the polypeptide retains a cellulase activity under conditions comprising about pH 7.5, pH 8.0, pH 8.5, pH 9, pH 9.5, pH 10 or pH 10.5 or more basic, or after exposure to conditions comprising about pH 7.5, pH 8.0, pH 8.5, pH 9, pH 9.5, pH 10 or pH 10.5 or more basic.

6. A method of making a transgenic plant comprising the following steps:
(a) introducing a heterologous nucleic acid sequence into the cell, wherein the heterologous nucleic sequence comprises a sequence as set forth in claim 1, thereby producing a transformed plant cell;
(b) producing a transgenic plant from the transformed cell.
wherein optionally the step (a) further comprises introducing the heterologous nucleic acid sequence by electroporation or microinjection of plant cell protoplasts,
and optionally step (a) comprises introducing the heterologous nucleic acid sequence directly to plant tissue by DNA particle bombardment or by using an *Agrobacterium tumefaciens* host.

7. A method of expressing a heterologous nucleic acid sequence in a plant cell comprising the following steps:
(a) transforming the plant cell with a heterologous nucleic acid sequence operably linked to a promoter, wherein the heterologous nucleic sequence comprises a sequence as set forth in claim 1;
(b) growing the plant under conditions wherein the heterologous nucleic acids sequence is expressed in the plant cell.

8. A method for hydrolyzing, breaking up or disrupting a glucan-, a hemicellulose, a cellulose, a lignin, or a saccharide comprising composition comprising the following steps:
(a) providing a polypeptide having a cellulase activity as set forth in claim 5, or a polypeptide encoded by a nucleic acid as set forth in claim 1;
(b) providing a composition comprising a cellulose, a hemicellulose, a lignin, a saccharide, or a glucan; and
(c) contacting the polypeptide of step (a) with the composition of step (b) under conditions wherein the cellulase hydrolyzes, breaks up or disrupts the glucan, hemicellulose-, cellulose, lignin, or sacharride comprising composition,
wherein optionally the composition comprises a plant cell, a bacterial cell, a yeast cell, an insect cell, or an animal cell,
and optionally the polypeptide has endoglucanase, cellobiohydrolase, mannanase or beta-glucosidase activity.

9. A method of dough conditioning comprising contacting a dough or a bread product with at least one polypeptide as set forth in claim 5, or a polypeptide encoded by a nucleic acid as set forth in claim 1, under conditions sufficient for conditioning the dough.

10. A method of beverage production comprising administration of at least one polypeptide as set forth in claim 5, or a polypeptide encoded by a nucleic acid as set forth in claim 1, to a beverage or a beverage precursor under conditions sufficient for decreasing the viscosity of the beverage,
wherein optionally the beverage or beverage precursor is a wort or a beer.

11. A method for utilizing a cellulase, an endoglucanase, a cellobiohydrolase, a mannanase or a beta-glucosidase, as a supplement in an animal diet, the method comprising:
(a) preparing a nutritional supplement containing a cellulase, an endoglucanase, a cellobiohydrolase, a mannanase or a beta-glucosidase, enzyme comprising a polypeptide as set forth in claim 5, or a polypeptide encoded by a nucleic acid as set forth in claim 1; and
(b) administering the supplement to an animal,
wherein optionally the animal is a human, or the animal is a ruminant or a monogastric animal,
and optionally the enzyme is prepared by expression of a polynucleotide encoding the cellulase, endoglucanase, cellobiohydrolase, mannanase or beta-glucosidase, in an organism selected from the group consisting of a bacterium, a yeast, a plant, an insect, a fungus and an animal, and optionally the organism is selected from the group consisting of an *S. pombe, S. cerevisiae, Pichia pastoris, E. coli, Streptomyces* sp., *Bacillus* sp, and *Lactobacillus* sp.

12. A method for reducing the amount of cellulose, hemicellulose, or lignin in a biomass, a paper, a wood or wood product comprising contacting the biomass, paper, wood or wood product with a cellulase as set forth in claim 5, or a cellulase encoded by a nucleic acid as set forth in claim 1,
wherein optionally the cellulase activity comprises endoglucanase, cellobiohydrolase, mannanase or beta-glucosidase activity.

13. A composition comprising a cellulase as set forth in claim 5, or a cellulase encoded by a nucleic acid as set forth in claim 1,
wherein optionally the composition is a pharmaceutical compostion, dieteray supplement, beverage, food, feed, nutritional supplement, dough, bread, detergent, fuel, dairy product, textile, fabric, waste product, disinfectant, biodefense agent, bio-detoxifying agent, biomass, wood, wood pulp, wood product, paper, paper pulp or paper product,
wherein optionally the cellulase is formulated in a non-aqueous liquid composition, a cast solid, a granular form, a particulate form, as a tablet, gel, pill, implant, liquid, spray, powder, paste, slurry, food, feed pellet or as an encapsulated formulation,
wherein optionally the fuel is derived from a plant material, which optionally comprises potatoes, soybean (rapeseed), barley, rye, corn, oats, wheat, beets or sugar cane, wherein optionally the fuel comprises a bioethanol or a gasoline-ethanol mix, wherein optionally the textile or fabric comprises a cellulose-containing fiber, wherein optionally the dairy product comprises a milk, an ice cream, a cheese or a yogurt, and optionally the cellulase activity comprises endoglucanase, cellobiohydrolase, mannanase or beta-glucosidase activity.

14. A method for making a fuel comprising contacting a composition comprising a cellulose, a hemicellulose, a lignin, or a fermentable sugar with a polypeptide as set forth in claim 5, or a polypeptide encoded by a nucleic acid as set forth in claim 1, wherein optionally the composition comprising a cellulose, a hemicellulose, a lignin, or a fermentable sugar comprises a plant, plant product or plant derivative, and optionally the plant or plant product comprises cane sugar plants or plant products, beets or sugarbeets, wheat, corn, soybeans, potato, rice or barley, and optionally the polypeptide has activity comprising cellulase, endoglucanase, cellobiohydrolase, mannanase or beta-glucosidase activity, and optionally the fuel comprises a bioethanol or a gasoline-ethanol mix.

15. An enzyme ensemble for depolymerization of cellulosic and hemicellulosic polymers to metabolizeable carbon moieties comprising a polypeptide as set forth in claim 5, or a polypeptide encoded by a nucleic acid as set forth in claim 1, wherein optionally the polypeptide has activity comprising cellulase, endoglucanase, cellobiohydrolase, mannanase or beta-glucosidase activity.

16. A method for processing a biomass comprising contacting a biomass with a polypeptide as set forth in claim 5, or a polypeptide encoded by a nucleic acid as set forth in claim 1, wherein optionally the biomass is derived from an agricultural crop, is a byproduct of a food or a feed production, is a lignocellulosic, cellulosic or lignin waste product, or is a plant residue or a waste paper or waste paper product, and optionally the polypeptide has activity comprising cellulase, endoglucanase, cellobiohydrolase, mannanase or beta-glucosidase activity, and optionally the plant residue comprise stems, leaves, hulls, husks, cobs, wood, wood chips, wood pulp and sawdust, and optionally the paper waste comprises discarded or used photocopy paper, computer printer paper, notebook paper, notepad paper, typewriter paper, newspapers, magazines, cardboard and paper-based packaging materials, and optionally the processing of the biomass material generates a bioethanol.

17. A method for treating solid or liquid animal waste products comprising the following steps:

(a) providing a polypeptide as set forth in claim 5, or a polypeptide encoded by a nucleic acid as set forth in claim 1, wherein optionally the polypeptide has activity comprising cellulase, endoglucanase, cellobiohydrolase, mannanase or beta-glucosidase activity;

(b) providing a solid or a liquid animal waste; and (c) contacting the polypeptide of step (a) and the solid or liquid waste of step (b) under conditions wherein the protease can treat the waste.

* * * * *

SEQUENCE LISTING

<160> NUMBER OF SEQ ID NOS: 166

<210> SEQ ID NO 1
<211> LENGTH: 1323
<212> TYPE: DNA
<213> ORGANISM: Unknown
<220> FEATURE:
<223> OTHER INFORMATION: Obtained from environmental sample

<400> SEQUENCE: 1

| | |
|---|---:|
| atgtcaacct ataaatttcc gcacaacttt ttttggggag ccgcaaccgc gtcttatcag | 60 |
| atcgaaggcg catggaacga ggatggcaaa ggcgaatcca tttggatcg cttcagccat | 120 |
| acgcccggaa aggtcaccaa tgccgatacc ggtgacatcg cctgtgacca ctatcaccgt | 180 |
| tgggaggaag atatcgccct tatgcgccaa cttgggttga aggcgtaccg cttttccact | 240 |
| tcatggcccc gtgtgatccc ggcggccgc agacgggtga atgtcaaagg gctggatttc | 300 |
| tacgatcgcc tggtggatgg tctgtgcgcc gcgaacatcg aaccgttcct cacccctgtat | 360 |
| cactgggacc tgccgcaggc tcttcaagac gaaggcggct gggataatcg caacaccgcc | 420 |
| catgcctttg ccgattatgc cgcattgatg gtgaaacgac ttggcgaccg tatccgctat | 480 |
| tggacgacgt tcaacgaacc cagcgttgtg gcgttcaatg gtcattactc aggctcgcac | 540 |
| gccccgggca ttcaagatgc ccgtgttacc cgccaggtgg tgcatcattt gctggtggcg | 600 |
| catgggttgg ctgtgcaggc gatccgcggc gcaaactcca aagtggatgt gggcatcgtg | 660 |
| cttaatttat ggcccgccga acccgattcg gactcccccg aagatgccgc cgccgccgaa | 720 |
| gccgcctgga accggcacga gaccctgttc cttgaccca tctttaaggc gcattatccc | 780 |
| gtatctgccc ttgatgcgat tggggaggat atgccccgca tccacgacgg cgatctggcg | 840 |
| ttgatctctc aggaattgga ttttgtcggc atcaactatt actccgcca tgtggtcagt | 900 |
| gccacaaaag aaataggcag gcttcccgaa tcggaataca ctgaaatggg ctgggaagta | 960 |
| tgcgccccg cactccgccg cctgctggtc aagatccata acgattaccg tttgccgccc | 1020 |
| atctatatca ccgaaaacgg atcggcattc aaggacgaag ttaacgcaga cggaaaggtt | 1080 |
| catgacccgc ggcggttgga ttacctgaaa caacacctga ttcaactttg ccttgccatg | 1140 |
| caggacggcg tggatgtgcg cggctacatg gcttggtccc tgctggataa tttcgagtgg | 1200 |
| ggtcacggct tttccaagcg ctttggcttg gtccatgtgg attacgagag ccagaagcgg | 1260 |
| attattaaag actcgggtga atggtatgca agtgtgatac ggaagaacga ggttgttgaa | 1320 |
| taa | 1323 |

<210> SEQ ID NO 2
<211> LENGTH: 440
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (2)...(438)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
    signature. Prosite id = PS00653
<220> FEATURE:
<221> NAME/KEY: SITE
<222> LOCATION: (351)...(354)
<223> OTHER INFORMATION: N-glycosylation site. Prosite id = PS00001

<400> SEQUENCE: 2

```
Met Ser Thr Tyr Lys Phe Pro His Asn Phe Phe Trp Gly Ala Ala Thr
1               5                   10                  15
Ala Ser Tyr Gln Ile Glu Gly Ala Trp Asn Glu Asp Gly Lys Gly Glu
            20                  25                  30
Ser Ile Trp Asp Arg Phe Ser His Thr Pro Gly Lys Val Thr Asn Ala
        35                  40                  45
Asp Thr Gly Asp Ile Ala Cys Asp His Tyr His Arg Trp Glu Glu Asp
50                  55                  60
Ile Ala Leu Met Arg Gln Leu Gly Leu Lys Ala Tyr Arg Phe Ser Thr
65                  70                  75                  80
Ser Trp Pro Arg Val Ile Pro Ala Gly Arg Arg Val Asn Val Lys
                85                  90                  95
Gly Leu Asp Phe Tyr Asp Arg Leu Val Asp Gly Leu Cys Ala Ala Asn
            100                 105                 110
Ile Glu Pro Phe Leu Thr Leu Tyr His Trp Asp Leu Pro Gln Ala Leu
        115                 120                 125
Gln Asp Glu Gly Gly Trp Asp Asn Arg Asn Thr Ala His Ala Phe Ala
130                 135                 140
Asp Tyr Ala Ala Leu Met Val Lys Arg Leu Gly Asp Arg Ile Arg Tyr
145                 150                 155                 160
Trp Thr Thr Phe Asn Glu Pro Ser Val Val Ala Phe Asn Gly His Tyr
                165                 170                 175
Ser Gly Ser His Ala Pro Gly Ile Gln Asp Ala Arg Val Thr Arg Gln
            180                 185                 190
Val Val His His Leu Leu Val Ala His Gly Leu Ala Val Gln Ala Ile
        195                 200                 205
Arg Gly Ala Asn Ser Lys Val Asp Val Gly Ile Val Leu Asn Leu Trp
210                 215                 220
Pro Ala Glu Pro Asp Ser Asp Ser Pro Glu Asp Ala Ala Ala Ala Glu
225                 230                 235                 240
Ala Ala Trp Asn Arg His Glu Thr Leu Phe Leu Asp Pro Ile Phe Lys
                245                 250                 255
Ala His Tyr Pro Val Ser Ala Leu Asp Ala Ile Gly Glu Asp Met Pro
            260                 265                 270
Arg Ile His Asp Gly Asp Leu Ala Leu Ile Ser Gln Glu Leu Asp Phe
        275                 280                 285
Val Gly Ile Asn Tyr Tyr Ser Arg His Val Val Ser Ala Thr Lys Glu
290                 295                 300
Ile Gly Arg Leu Pro Glu Ser Glu Tyr Thr Glu Met Gly Trp Glu Val
305                 310                 315                 320
Cys Ala Pro Ala Leu Arg Arg Leu Leu Val Lys Ile His Asn Asp Tyr
                325                 330                 335
Arg Leu Pro Pro Ile Tyr Ile Thr Glu Asn Gly Ser Ala Phe Lys Asp
            340                 345                 350
Glu Val Asn Ala Asp Gly Lys Val His Asp Pro Arg Arg Leu Asp Tyr
        355                 360                 365
Leu Lys Gln His Leu Ile Gln Leu Cys Leu Ala Met Gln Asp Gly Val
370                 375                 380
Asp Val Arg Gly Tyr Met Ala Trp Ser Leu Leu Asp Asn Phe Glu Trp
385                 390                 395                 400
Gly His Gly Phe Ser Lys Arg Phe Gly Leu Val His Val Asp Tyr Glu
                405                 410                 415
```

```
Ser Gln Lys Arg Ile Ile Lys Asp Ser Gly Glu Trp Tyr Ala Ser Val
            420                 425                 430

Ile Arg Lys Asn Glu Val Val Glu
        435                 440

<210> SEQ ID NO 3
<211> LENGTH: 1389
<212> TYPE: DNA
<213> ORGANISM: Unknown
<220> FEATURE:
<223> OTHER INFORMATION: Obtained from environmental sample

<400> SEQUENCE: 3
atgagcgctc cgagtcccgc ccgccccgtg tcctttcctc cccgcttcgt gtggggagcc      60
gcggccgcat cctatcaaat cgagggcgcc gtccggagg acgcaaggg cccttcggtg      120 tgggacatgt tctgcgagaa gccgggagcc gtcttcgagg gcacgacgg gcggtggct      180 tgcgatcact accaccgtta ccgggaagac gtggccctga tgcggcagat tgggctccag     240
gcttaccgcc tgagcgtgtg ctggcccagg gtgctgcccg aggggaccgg gcagcccaac     300 gagaagggc tcgacttcta ctcccggctc gtcgacgcct tgctcgaggc ggggatcacg      360
ccttgggtca cccttttttca ctgggactac ccactagccc tatatcaccg ggaggctgg    420 ctcaatcggg atagctcaga ctggttcggc gagtacgcgg tctgattgc ggagcgcctc    480 tccgatcggg tgagccactt cttcacccag aacgagcccc aggtgtacat cggcttcggg    540
cacctcgagg ggaaacacgc gccgggcgat acccttcccc tgtcgcagat gctgctggcc    600
ggtcaccaca gcctgctcgc ccatggaaag gccgtgcagg cgctgcgcgc ccacggcaag    660
cagcagctgc gggttggata cgctccggtg gggatgccgc tgcatccggt cagcgagtcc    720
gccgaagacg tggcggctgc acgcaccgcc actttccgcg tccgagagaa gaattcctgg    780
aacaacgctt ggtggatgga cccggtgtac ctcggtgagt accccgccca agggctcgag    840
ttctacgggc gagacgtccc cgcgatccgg tccggagaca tggaactcat ccggcaaccc    900
ttggactttt tcggcgtcaa catctaccag agcacgcccg tgcgcgccgc ggggcgcccc   960
caggggttcg aggtcgtccg gcatccgacg ggccacccca tcaccgcgtt caactggccg   1020
gttacgccac aggccttgta ttgggggccg cggttcttct acgagcgcta tgcaagccc    1080 atcgtcatta cggaaaacgg gctttcctgc cgagacgtga tcgcccttga cggcaaggtg   1140
cacgatccgt cccgcatcga cttcaccacg cgctacctgc gcgagctcca ccgcgccatc   1200
gccgaaggca acgaggtgga gggctacttc cactggtcca tcatggacaa cttcgaatgg   1260
gctgccggat accgagaacg cttcgggctc gttcacgtgg attacgagac cctggtgagg   1320
acacccaagg actctgcggc gtggtaccgc caggtcatcc agagcaacgg ggccgtgctg   1380
ttcgattga                                                            1389

<210> SEQ ID NO 4
<211> LENGTH: 462
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(458)
<223> OTHER INFORMATION: Glycosyl hydrolase family 1
<220> FEATURE:
<221> NAME/KEY: SITE
<222> LOCATION: (16)...(30)
<223> OTHER INFORMATION: Glycosyl hydrolases family 1 N-terminal
```

```
        signature. Prosite id = PS00653
<220> FEATURE:
<221> NAME/KEY: SITE
<222> LOCATION: (366)...(374)
<223> OTHER INFORMATION: Glycosyl hydrolases family 1 active site.
      Prosite id = PS00572

<400> SEQUENCE: 4

Met Ser Ala Pro Ser Pro Ala Arg Pro Val Ser Phe Pro Pro Arg Phe
1               5                   10                  15

Val Trp Gly Ala Ala Ala Ser Tyr Gln Ile Glu Gly Ala Val Arg
            20                  25                  30

Glu Asp Gly Lys Gly Pro Ser Val Trp Asp Met Phe Cys Glu Lys Pro
                35                  40                  45

Gly Ala Val Phe Glu Gly His Asp Gly Ala Val Ala Cys Asp His Tyr
50                  55                  60

His Arg Tyr Arg Glu Asp Val Ala Leu Met Arg Gln Ile Gly Leu Gln
65                  70                  75                  80

Ala Tyr Arg Leu Ser Val Cys Trp Pro Arg Val Leu Pro Glu Gly Thr
                85                  90                  95

Gly Gln Pro Asn Glu Lys Gly Leu Asp Phe Tyr Ser Arg Leu Val Asp
                100                 105                 110

Ala Leu Leu Glu Ala Gly Ile Thr Pro Trp Val Thr Leu Phe His Trp
            115                 120                 125

Asp Tyr Pro Leu Ala Leu Tyr His Arg Gly Gly Trp Leu Asn Arg Asp
130                 135                 140

Ser Ser Asp Trp Phe Gly Glu Tyr Ala Gly Leu Ile Ala Glu Arg Leu
145                 150                 155                 160

Ser Asp Arg Val Ser His Phe Phe Thr Gln Asn Glu Pro Gln Val Tyr
                165                 170                 175

Ile Gly Phe Gly His Leu Glu Gly Lys His Ala Pro Gly Asp Thr Leu
            180                 185                 190

Pro Leu Ser Gln Met Leu Leu Ala Gly His His Ser Leu Leu Ala His
        195                 200                 205

Gly Lys Ala Val Gln Ala Leu Arg Ala His Gly Lys Gln Gln Leu Arg
210                 215                 220

Val Gly Tyr Ala Pro Val Gly Met Pro Leu His Pro Val Ser Glu Ser
225                 230                 235                 240

Ala Glu Asp Val Ala Ala Ala Arg Thr Ala Thr Phe Arg Val Arg Glu
                245                 250                 255

Lys Asn Ser Trp Asn Asn Ala Trp Trp Met Asp Pro Val Tyr Leu Gly
                260                 265                 270

Glu Tyr Pro Ala Gln Gly Leu Glu Phe Tyr Gly Arg Asp Val Pro Ala
            275                 280                 285

Ile Arg Ser Gly Asp Met Glu Leu Ile Arg Gln Pro Leu Asp Phe Phe
            290                 295                 300

Gly Val Asn Ile Tyr Gln Ser Thr Pro Val Arg Ala Ala Gly Ala Pro
305                 310                 315                 320

Gln Gly Phe Glu Val Val Arg His Pro Thr Gly His Pro Ile Thr Ala
                325                 330                 335

Phe Asn Trp Pro Val Thr Pro Gln Ala Leu Tyr Trp Gly Pro Arg Phe
                340                 345                 350

Phe Tyr Glu Arg Tyr Gly Lys Pro Ile Val Ile Thr Glu Asn Gly Leu
            355                 360                 365

Ser Cys Arg Asp Val Ile Ala Leu Asp Gly Lys Val His Asp Pro Ser
370                 375                 380
```

```
Arg Ile Asp Phe Thr Thr Arg Tyr Leu Arg Glu Leu His Arg Ala Ile
385                 390                 395                 400

Ala Glu Gly Asn Glu Val Gly Tyr Phe His Trp Ser Ile Met Asp
            405                 410                 415

Asn Phe Glu Trp Ala Ala Gly Tyr Arg Glu Arg Phe Gly Leu Val His
            420                 425                 430

Val Asp Tyr Glu Thr Leu Val Arg Thr Pro Lys Asp Ser Ala Ala Trp
            435                 440                 445

Tyr Arg Gln Val Ile Gln Ser Asn Gly Ala Val Leu Phe Asp
            450                 455                 460

<210> SEQ ID NO 5
<211> LENGTH: 1098
<212> TYPE: DNA
<213> ORGANISM: Unknown
<220> FEATURE:
<223> OTHER INFORMATION: Obtained from environmental sample

<400> SEQUENCE: 5
atgactcgga ggtctatcgt gcgttcttct tccaacaagt ggcttgtcct tgccggtgcg      60
gcgctgctcg cctgcaccgc cctcgggtgc aagaaaaaag gcgagagcgg tgacgtcgcc     120
tcggccccgg ggcaggccca ggcgggcggc aagcagccgt tccccgacga tgcgccgatc     180
accgaaccgc ccgctccgcc ccctcgtagc ggcaatcctc tggtgggcgc caagctcttc     240
gtcgacccgg aatctttggc catgttgcag gcgaacaagc tgcggcgcac cgacccggag     300
aaggcggcga ttttggatcg catcgcccag cagccccagg ctttgtggat gggcgagtgg     360
aacacgaaca tcttccgcgc ggtcgagcat ttcgtggctc cgccaaggc ggagggcgcc      420 gtgcccgtca tgatcgccta caacatcccc caccgcgact gcgggcagta ctctcagggt     480
gggctttcct ccaaggaggc ttaccagcgc tggattcgga acgtcgccgc ggggattggc     540
agcgatgcag cggtcgtcgt gctcgagccc gacgcgctcg ccacttcca ggagtgtttg      600 accgaggagc agagcgccga gcgcatgttc ctgctcagcg acgccgtcaa ggtgctgcgc     660
caaaatccga gacggccgt gtacctggat gccgggcacg cgcgctgggt gccggtggag      720
gagatggccg agcgcctcaa gctcgcgggc atcgagcacg cccatggctt tcgctcaac      780 acctcgaact acgtgggcac cgaggagaac gccgcttacg ccacaagct cgtcgaggcc      840 ctgggtggga acgtgcgctt cgtcatcgac acgagccgca atggggcggg ccctacgag      900 gaggccaaga acgccgagga gagctggtgc aacccgccg tcgcaagat cggcaagccg       960 ccgaccaccg agacggggga tcccctcatc gacggattcc tttggctgaa cgcccgggc     1020 gagtcggacg tcagtgcaa cggcgggccc aaggccggtg tgttctggct ggagcaggct    1080
ctccagcagg cccagtaa                                                  1098

<210> SEQ ID NO 6
<211> LENGTH: 365
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(29)
<220> FEATURE:
<221> NAME/KEY: DOMAIN
<222> LOCATION: (81)...(358)
<223> OTHER INFORMATION: Glycosyl hydrolases family 6
<220> FEATURE:
<221> NAME/KEY: SITE
```

```
<222> LOCATION: (187)...(196)
<223> OTHER INFORMATION: Glycosyl hydrolases family 6 signature 2.
      Prosite id = PS00656
<220> FEATURE:
<221> NAME/KEY: SITE
<222> LOCATION: (263)...(266)
<223> OTHER INFORMATION: N-glycosylation site. Prosite id = PS00001

<400> SEQUENCE: 6
```

| | | | | | | | | | | | | | | |
|---|---|---|---|---|---|---|---|---|---|---|---|---|---|---|
| Met | Thr | Arg | Arg | Ser | Ile | Val | Arg | Ser | Ser | Asn | Lys | Trp | Leu | Val |
| 1 | | | | 5 | | | | | 10 | | | | | 15 |
| Leu | Ala | Gly | Ala | Ala | Leu | Leu | Ala | Cys | Thr | Ala | Leu | Gly | Cys | Lys | Lys |
| | | | 20 | | | | | 25 | | | | | 30 | | |
| Lys | Gly | Glu | Ser | Gly | Asp | Val | Ala | Ser | Ala | Pro | Gly | Gln | Ala | Gln | Ala |
| | | | 35 | | | | | 40 | | | | | 45 | | |
| Gly | Gly | Lys | Gln | Pro | Phe | Pro | Asp | Asp | Ala | Pro | Ile | Thr | Glu | Pro | Pro |
| 50 | | | | | 55 | | | | | 60 | | | | | |
| Ala | Pro | Pro | Arg | Ser | Gly | Asn | Pro | Leu | Val | Gly | Ala | Lys | Leu | Phe |
| 65 | | | | 70 | | | | | 75 | | | | | 80 |
| Val | Asp | Pro | Glu | Ser | Leu | Ala | Met | Leu | Gln | Ala | Asn | Lys | Leu | Arg | Arg |
| | | | | 85 | | | | | 90 | | | | | 95 | |
| Thr | Asp | Pro | Glu | Lys | Ala | Ala | Ile | Leu | Asp | Arg | Ile | Ala | Gln | Pro |
| | | | 100 | | | | | 105 | | | | | 110 | |
| Gln | Ala | Leu | Trp | Met | Gly | Glu | Trp | Asn | Thr | Asn | Ile | Phe | Arg | Ala | Val |
| | | | 115 | | | | | 120 | | | | | 125 | | |
| Glu | His | Phe | Val | Ala | Arg | Ala | Lys | Ala | Glu | Gly | Ala | Val | Pro | Val | Met |
| | 130 | | | | | 135 | | | | | 140 | | | | |
| Ile | Ala | Tyr | Asn | Ile | Pro | His | Arg | Asp | Cys | Gly | Gln | Tyr | Ser | Gln | Gly |
| 145 | | | | | 150 | | | | | 155 | | | | | 160 |
| Gly | Leu | Ser | Ser | Lys | Glu | Ala | Tyr | Gln | Arg | Trp | Ile | Arg | Asn | Val | Ala |
| | | | | 165 | | | | | 170 | | | | | 175 | |
| Ala | Gly | Ile | Gly | Ser | Asp | Ala | Ala | Val | Val | Val | Leu | Glu | Pro | Asp | Ala |
| | | | 180 | | | | | 185 | | | | | 190 | | |
| Leu | Gly | His | Phe | Gln | Glu | Cys | Leu | Thr | Glu | Glu | Gln | Ser | Ala | Glu | Arg |
| | | 195 | | | | | 200 | | | | | 205 | | | |
| Met | Phe | Leu | Leu | Ser | Asp | Ala | Val | Lys | Val | Leu | Arg | Gln | Asn | Pro | Lys |
| 210 | | | | | 215 | | | | | 220 | | | | | |
| Thr | Ala | Val | Tyr | Leu | Asp | Ala | Gly | His | Ala | Arg | Trp | Val | Pro | Val | Glu |
| 225 | | | | | 230 | | | | | 235 | | | | | 240 |
| Glu | Met | Ala | Glu | Arg | Leu | Lys | Leu | Ala | Gly | Ile | Glu | His | Ala | His | Gly |
| | | | | 245 | | | | | 250 | | | | | 255 | |
| Phe | Ser | Leu | Asn | Thr | Ser | Asn | Tyr | Val | Gly | Thr | Glu | Glu | Asn | Ala | Ala |
| | | | | 260 | | | | | 265 | | | | | 270 | |
| Tyr | Gly | His | Lys | Leu | Val | Glu | Ala | Leu | Gly | Gly | Asn | Val | Arg | Phe | Val |
| | | | 275 | | | | | 280 | | | | | 285 | | |
| Ile | Asp | Thr | Ser | Arg | Asn | Gly | Ala | Gly | Pro | Tyr | Glu | Glu | Ala | Lys | Asn |
| | 290 | | | | | 295 | | | | | 300 | | | | |
| Ala | Glu | Glu | Ser | Trp | Cys | Asn | Pro | Pro | Gly | Arg | Lys | Ile | Gly | Lys | Pro |
| 305 | | | | | 310 | | | | | 315 | | | | | 320 |
| Pro | Thr | Thr | Glu | Thr | Gly | Asp | Pro | Leu | Ile | Asp | Gly | Phe | Leu | Trp | Leu |
| | | | | 325 | | | | | 330 | | | | | 335 | |
| Lys | Arg | Pro | Gly | Glu | Ser | Asp | Gly | Gln | Cys | Asn | Gly | Gly | Pro | Lys | Ala |
| | | | 340 | | | | | 345 | | | | | 350 | | |
| Gly | Val | Phe | Trp | Leu | Glu | Gln | Ala | Leu | Gln | Gln | Ala | Gln |
| | | 355 | | | | | 360 | | | | | 365 |

<210> SEQ ID NO 7
<211> LENGTH: 2649
<212> TYPE: DNA
<213> ORGANISM: Unknown
<220> FEATURE:
<223> OTHER INFORMATION: Obtained from environmental sample

<400> SEQUENCE: 7

| | | | | | |
|---|---|---|---|---|---|
| atgcaaggaa | agaaaattga | tttcattaac | tcaaggttgt | tagttcctga | ttatccaatc | 60 |
| gttcccttca | ttgagggaga | tggtaccggc | cctgatatct | ggcgtgcttc | agtcagggtg | 120 |
| ctggatgttg | ctgttgacag | ggcatattcc | ggcaagcgaa | aacttctctg | gaaagaggtg | 180 |
| ctggctggcg | aaaaggcatt | tacaaatacc | gggtcctggc | ttccggagga | aactcttaga | 240 |
| gcatttcgtg | aatatcatgt | tggaattaaa | gggccactca | ctacgccagt | tggtggggga | 300 |
| attcgttctc | tcaatgtagc | cctcaggcaa | gagcttgact | tgtatgtttg | cctgaggcca | 360 |
| gtcaaatggt | ttaagggtgt | accaagtcct | ctaaaagatc | cttccaaagt | ggatatgcat | 420 |
| attttccgcg | aaaacactga | agatatttat | gcaggtattg | aatttatgca | tggtgaaccg | 480 |
| gaggccctga | agttaagaa | atttcttacc | gaagaaatgg | gaatcaagaa | gtttcggttt | 540 |
| cccgatacat | cctccattgg | tatcaagcct | atctcactcg | aaggaacaga | gcgtcttgta | 600 |
| agagcttcca | ttcaatatgc | acttgacagg | aagttgcctt | ccgtaacatt | ggttcataaa | 660 |
| ggcaatatca | tgaaattcac | cgaggggca | ttcaaaaaat | ggggttatga | acttgccgaa | 720 |
| agagaatttg | gcgacagggt | ttttacatgg | tcaatgtatg | accgtatcgc | cgatgaacat | 780 |
| ggaacggaag | aagctggcaa | agtgcaatcc | gaagcgattg | caaaaggtaa | actcctgata | 840 |
| aaggatgtga | ttgctgatgc | ttttctgcag | caaatactac | tcaggcctgc | cgagtacagc | 900 |
| gttatcgcaa | ccatgaacct | gaatggcgat | tatatcagcg | atgcactggc | agctatggtg | 960 |
| gggggtatag | gaattgctcc | cggagccaat | attaaccatc | aaactggcca | tgcagtctt | 1020 |
| gaagcaacac | acggcacggc | tcccaaatat | gccaaccttg | atcaggtaaa | ccctggctca | 1080 |
| gtaatactaa | gtggcgcgct | gatgctcgaa | tacatgggct | ggaacgaagc | cgctcagctc | 1140 |
| attaccaatg | gattggaggc | taccattcaa | cagaaactgg | taacctatga | tttccatcgc | 1200 |
| ttaatggaag | gtgctacaaa | gttgaagact | tcagaatttg | gcgatgctgt | gatccggccg | 1260 |
| gcacgttccg | cctgggcgga | cacggctgcc | gatgccctct | ccgggcggcg | cgtcgtgcg | 1320 |
| cggaacggcg | ggcttgttgc | cccgcccgcg | gcctgtcgcc | ggggcgggt | acgggactca | 1380 |
| gcgcttgcgc | gcctccttca | gggtggactg | cagggcgaag | aaggccggct | tgcggacgaa | 1440 |
| cttctccgtc | atgaccgtgg | cgctgccctc | accctcgaag | aagaccggca | cccacgagta | 1500 |
| cttgtcggtg | aagccccaga | tggtgaagga | gttgcagtcg | ttcacggcca | ggcaggccga | 1560 |
| cagtgcctgc | tggtagtagt | cggcctgctg | ccgcagctgc | tccttggtgg | gcttgccgct | 1620 |
| cgccggagg | tccatgcgga | cgtcgatctc | ggtgatggcg | gtctccagac | cgaggtcggc | 1680 |
| gaaccgctgc | aggttctgct | gcaggtcgcc | cgggaagccg | tagcgggtgc | tcaggtggcc | 1740 |
| ctgggcgccg | aatccgtgga | gcggcacgcc | ctgctccagc | atctcctggg | cgagctcgta | 1800 |
| gtaggcgtcc | tcttggcgt | tgatgccctc | gacgttgtag | tcgttgagga | acagcttggc | 1860 |
| ctcggggtcg | gcctcgtggg | cccagcggaa | ggcgtccgcg | acgatctccg | ggccgagctc | 1920 |
| acgtatccag | atgttctcgt | cggtgcgcag | ctcggcctgg | tcgttgaaga | tctcgttggc | 1980 |
| cacgtcccac | tgctggatct | tgccggcgta | gcggccgacg | accgtgtcga | tgtggtcctt | 2040 |
| gaggatggcg | cgcagttcct | ccttggtgaa | gtcgccctcc | tccagccatt | cggggttctg | 2100 |
| gctgtgccac | aggagggtgt | gcccgcgcac | ggcctggcgg | ttccgctggg | cgaactcgac | 2160 |

```
gatggcgtcg gcctcctcga agcggtactg gtcgcgctcg gggtggatga actcccactt    2220
catctggttc tcggcggaga ccgagttgaa ctgctggccc aggatcttcc ggtacttctt    2280
gtcgaaggtg aagggtccg ggtagtcctg ttcgaggtgg tggccgccgc cggccgccgc    2340
ggagcctatg aagaacccctt cggggggcggc ccagcgcagg cggtcgaact tggcgttgga    2400
gtggggcgcg gcctcgtggt cggcggacgg cttggccgtg gccgtcgacg tcaccagcgg    2460
gacggccagc gcggcggcga gagcaaaggt gacgatgcgg acggatctca tcagaggtcc    2520
ctcattcgat cgcggctccg aaagttttcg gaggattacc ggaatgtttc agggaccta    2580 aggcgcccgg agccgggtcg tcaacggttt ggcccggccc ggtcgaagct tctcccgacc    2640
aggcgttga                                                           2649
```

<210> SEQ ID NO 8
<211> LENGTH: 882
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (20)...(417)
<223> OTHER INFORMATION: Isocitrate/isopropylmalate dehydrogenase
<220> FEATURE:
<221> NAME/KEY: SITE
<222> LOCATION: (310)...(329)
<223> OTHER INFORMATION: Isocitrate and isopropylmalate dehydrogenases
      signature. Prosite id = PS00470
<220> FEATURE:
<221> NAME/KEY: SITE
<222> LOCATION: (868)...(871)
<223> OTHER INFORMATION: N-glycosylation site. Prosite id = PS00001

<400> SEQUENCE: 8

Met Gln Gly Lys Lys Ile Asp Phe Ile Asn Ser Arg Leu Leu Val Pro
1               5                   10                  15

Asp Tyr Pro Ile Val Pro Phe Ile Glu Gly Asp Gly Thr Gly Pro Asp
            20                  25                  30

Ile Trp Arg Ala Ser Val Arg Val Leu Asp Val Ala Val Asp Arg Ala
        35                  40                  45

Tyr Ser Gly Lys Arg Lys Leu Leu Trp Lys Glu Val Leu Ala Gly Glu
    50                  55                  60

Lys Ala Phe Thr Asn Thr Gly Ser Trp Leu Pro Glu Glu Thr Leu Arg
65                  70                  75                  80

Ala Phe Arg Glu Tyr His Val Gly Ile Lys Gly Pro Leu Thr Thr Pro
                85                  90                  95

Val Gly Gly Gly Ile Arg Ser Leu Asn Val Ala Leu Arg Gln Glu Leu
            100                 105                 110

Asp Leu Tyr Val Cys Leu Arg Pro Val Lys Trp Phe Lys Gly Val Pro
        115                 120                 125

Ser Pro Leu Lys Asp Pro Ser Lys Val Asp Met His Ile Phe Arg Glu
    130                 135                 140

Asn Thr Glu Asp Ile Tyr Ala Gly Ile Glu Phe Met His Gly Glu Pro
145                 150                 155                 160

Glu Ala Leu Lys Val Lys Lys Phe Leu Thr Glu Met Gly Ile Lys
                165                 170                 175

Lys Phe Arg Phe Pro Asp Thr Ser Ser Ile Gly Ile Lys Pro Ile Ser
                180                 185                 190

Leu Glu Gly Thr Glu Arg Leu Val Arg Ala Ser Ile Gln Tyr Ala Leu
        195                 200                 205

-continued

```
Asp Arg Lys Leu Pro Ser Val Thr Leu Val His Lys Gly Asn Ile Met
    210                 215                 220

Lys Phe Thr Glu Gly Ala Phe Lys Lys Trp Gly Tyr Glu Leu Ala Glu
225                 230                 235                 240

Arg Glu Phe Gly Asp Arg Val Phe Thr Trp Ser Met Tyr Asp Arg Ile
                245                 250                 255

Ala Asp Glu His Gly Thr Glu Ala Gly Lys Val Gln Ser Glu Ala
            260                 265                 270

Ile Ala Lys Gly Lys Leu Leu Ile Lys Asp Val Ile Ala Asp Ala Phe
        275                 280                 285

Leu Gln Gln Ile Leu Leu Arg Pro Ala Glu Tyr Ser Val Ile Ala Thr
    290                 295                 300

Met Asn Leu Asn Gly Asp Tyr Ile Ser Asp Ala Leu Ala Ala Met Val
305                 310                 315                 320

Gly Gly Ile Gly Ile Ala Pro Gly Ala Asn Ile Asn His Gln Thr Gly
                325                 330                 335

His Ala Val Phe Glu Ala Thr His Gly Thr Ala Pro Lys Tyr Ala Asn
            340                 345                 350

Leu Asp Gln Val Asn Pro Gly Ser Val Ile Leu Ser Gly Ala Leu Met
        355                 360                 365

Leu Glu Tyr Met Gly Trp Asn Glu Ala Ala Gln Leu Ile Thr Asn Gly
    370                 375                 380

Leu Glu Ala Thr Ile Gln Gln Lys Leu Val Thr Tyr Asp Phe His Arg
385                 390                 395                 400

Leu Met Glu Gly Ala Thr Lys Leu Lys Thr Ser Glu Phe Gly Asp Ala
                405                 410                 415

Val Ile Arg Pro Ala Arg Ser Ala Trp Ala Asp Thr Ala Ala Asp Ala
            420                 425                 430

Leu Ser Gly Arg Arg Arg Ala Arg Asn Gly Gly Leu Val Ala Pro
        435                 440                 445

Pro Ala Ala Cys Arg Arg Gly Arg Val Arg Asp Ser Ala Leu Ala Arg
    450                 455                 460

Leu Leu Gln Gly Gly Leu Gln Gly Glu Glu Gly Arg Leu Ala Asp Glu
465                 470                 475                 480

Leu Leu Arg His Asp Arg Gly Ala Ala Leu Thr Leu Glu Glu Asp Arg
                485                 490                 495

His Pro Arg Val Leu Val Gly Glu Ala Pro Asp Gly Glu Gly Val Ala
            500                 505                 510

Val Val His Gly Gln Ala Gly Arg Gln Cys Leu Leu Val Val Val Gly
        515                 520                 525

Leu Leu Pro Gln Leu Leu Leu Gly Gly Leu Ala Ala Arg Arg Glu Val
    530                 535                 540

His Ala Asp Val Asp Leu Gly Asp Gly Gly Leu Gln Thr Glu Val Gly
545                 550                 555                 560

Glu Pro Leu Gln Val Leu Leu Gln Val Ala Arg Glu Ala Val Ala Gly
                565                 570                 575

Ala Gln Val Ala Leu Gly Ala Glu Ser Val Glu Arg His Ala Leu Leu
            580                 585                 590

Gln His Leu Leu Gly Glu Leu Val Val Gly Val Ala Leu Gly Val Asp
        595                 600                 605

Ala Leu Asp Val Val Val Glu Glu Gln Leu Gly Leu Gly Val Gly
    610                 615                 620

Leu Val Gly Pro Ala Glu Gly Val Arg Asp Asp Leu Arg Ala Glu Leu
```

```
                        625                 630                 635                 640

Thr Tyr Pro Asp Val Leu Val Gly Ala Gln Leu Gly Leu Val Val Glu
                645                 650                 655

Asp Leu Val Gly His Val Pro Leu Leu Asp Leu Ala Gly Val Ala Ala
                660                 665                 670

Asp Asp Arg Val Asp Val Val Leu Glu Asp Gly Ala Gln Phe Leu Leu
                675                 680                 685

Gly Glu Val Ala Leu Leu Gln Pro Phe Gly Val Leu Ala Val Pro Gln
            690                 695                 700

Glu Gly Val Pro Ala His Gly Leu Ala Val Pro Leu Gly Glu Leu Asp
705                 710                 715                 720

Asp Gly Val Gly Leu Leu Glu Ala Val Leu Ala Leu Gly Val Asp
                725                 730                 735

Glu Leu Pro Leu His Leu Val Leu Gly Gly Asp Arg Val Glu Leu Leu
                740                 745                 750

Ala Gln Asp Leu Pro Val Leu Leu Val Glu Gly Glu Gly Val Arg Val
                755                 760                 765

Val Leu Phe Glu Val Val Ala Ala Gly Arg Arg Gly Ala Tyr Glu
        770                 775                 780

Glu Pro Phe Gly Gly Gly Pro Ala Gln Ala Val Glu Leu Gly Val Gly
785                 790                 795                 800

Val Gly Arg Gly Leu Val Val Gly Gly Arg Leu Gly Arg Gly Arg
                805                 810                 815

Arg His Gln Arg Asp Gly Gln Arg Gly Gly Glu Ser Lys Gly Asp Asp
                820                 825                 830

Ala Asp Gly Ser His Gln Arg Ser Leu Ile Arg Ser Arg Leu Arg Lys
                835                 840                 845

Phe Ser Glu Asp Tyr Arg Asn Val Ser Gly Thr Leu Arg Arg Pro Glu
        850                 855                 860

Pro Gly Arg Gln Arg Phe Gly Pro Ala Arg Ser Lys Leu Leu Pro Thr
865                 870                 875                 880

Arg Arg

<210> SEQ ID NO 9
<211> LENGTH: 1134
<212> TYPE: DNA
<213> ORGANISM: Unknown
<220> FEATURE:
<223> OTHER INFORMATION: Obtained from environmental sample

<400> SEQUENCE: 9
atgagatccg tccgcatcgt caccttttgct ctcgccgccg cgctggccgt cccgctggtg      60
acgtcgacgg ccacggccaa gccgtccgcc gaccacgagg ccgcgcccca ctccaacgcc     120
aagttcgacc gcctgcgctg gccgcccccc gaagggttct tcataggctc gcggcggcc     180 ggcggcggcc accacctcga acaggactac ccggaccccct tcaccttcga caagaagtac     240
cggaagatcc tgggccagca gttcaactcg gtctccgccg agaaccagat gaagtgggag     300
ttcatccacc ccgagcgcga ccagtaccgc ttcgaggagg ccgacgccat cgtcgagttc     360
gcccagcgga accgccaggc cgtgcgcggg cacaccctcc tgtggcacag ccagaacccc     420
gaatggctgg aggagggcga cttcaccaag gaggaactgc gcgccatcct caaggaccac     480
atcgacacgg tcgtcggccg ctacgccggc aagatccagc agtgggacgt ggccaacgag     540
atcttcaacg accaggccga gctgcgcacc gacgagaaca tctggatacg tgagctcggc     600
ccggagatcg tcgcggacgc cttccgctgg gcccacgagg ccgaccccga ggccaagctg     660
```

```
ttcctcaacg actacaacgt cgagggcatc aacgccaaga gcgacgccta ctacgagctc    720
gcccaggaga tgctggagca gggcgtgccg ctccacggat cggcgccca gggccacctg    780 agcacccgct acggcttccc gggcgacctg cagcagaacc tgcagcggtt cgccgacctc    840
ggtctggaga ccgccatcac cgagatcgac gtccgcatgg acctcccggc gagcggcaag    900
cccaccaagg agcagctgcg gcagcaggcc gactactacc agcaggcact gtcggcctgc    960
ctggccgtga cgactgcaa ctccttcacc atctggggct tcaccgacaa gtactcgtgg   1020
gtgccggtct tcttcgaggg tgagggcagc gccacggtca tgacggagaa gttcgtccgc   1080
aagccggcct tcttcgccct gcagtccacc ctgaaggagg cgcgcaagcg ctga        1134
```

```
<210> SEQ ID NO 10
<211> LENGTH: 377
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(26)
<220> FEATURE:
<221> NAME/KEY: DOMAIN
<222> LOCATION: (44)...(371)
<223> OTHER INFORMATION: Glycosyl hydrolase family 10

<400> SEQUENCE: 10
```

Met Arg Ser Val Arg Ile Val Thr Phe Ala Leu Ala Ala Ala Leu Ala
1               5                   10                  15

Val Pro Leu Val Thr Ser Thr Ala Thr Ala Lys Pro Ser Ala Asp His
                20                  25                  30

Glu Ala Ala Pro His Ser Asn Ala Lys Phe Asp Arg Leu Arg Trp Ala
            35                  40                  45

Ala Pro Glu Gly Phe Phe Ile Gly Ser Ala Ala Ala Gly Gly Gly His
        50                  55                  60

His Leu Glu Gln Asp Tyr Pro Asp Pro Phe Thr Phe Asp Lys Lys Tyr
65                  70                  75                  80

Arg Lys Ile Leu Gly Gln Gln Phe Asn Ser Val Ser Ala Glu Asn Gln
                85                  90                  95

Met Lys Trp Glu Phe Ile His Pro Glu Arg Asp Gln Tyr Arg Phe Glu
            100                 105                 110

Glu Ala Asp Ala Ile Val Glu Phe Ala Gln Arg Asn Arg Gln Ala Val
        115                 120                 125

Arg Gly His Thr Leu Leu Trp His Ser Gln Asn Pro Glu Trp Leu Glu
    130                 135                 140

Glu Gly Asp Phe Thr Lys Glu Glu Leu Arg Ala Ile Leu Lys Asp His
145                 150                 155                 160

Ile Asp Thr Val Val Gly Arg Tyr Ala Gly Lys Ile Gln Gln Trp Asp
                165                 170                 175

Val Ala Asn Glu Ile Phe Asn Asp Gln Ala Glu Leu Arg Thr Asp Glu
            180                 185                 190

Asn Ile Trp Ile Arg Glu Leu Gly Pro Glu Ile Val Ala Asp Ala Phe
        195                 200                 205

Arg Trp Ala His Glu Ala Asp Pro Glu Ala Lys Leu Phe Leu Asn Asp
    210                 215                 220

Tyr Asn Val Glu Gly Ile Asn Ala Lys Ser Asp Ala Tyr Tyr Glu Leu
225                 230                 235                 240

Ala Gln Glu Met Leu Glu Gln Gly Val Pro Leu His Gly Phe Gly Ala

```
                   245                 250                 255
Gln Gly His Leu Ser Thr Arg Tyr Gly Phe Pro Gly Asp Leu Gln Gln
            260                 265                 270

Asn Leu Gln Arg Phe Ala Asp Leu Gly Leu Glu Thr Ala Ile Thr Glu
        275                 280                 285

Ile Asp Val Arg Met Asp Leu Pro Ala Ser Gly Lys Pro Thr Lys Glu
    290                 295                 300

Gln Leu Arg Gln Gln Ala Asp Tyr Tyr Gln Ala Leu Ser Ala Cys
305                 310                 315                 320

Leu Ala Val Asn Asp Cys Asn Ser Phe Thr Ile Trp Gly Phe Thr Asp
                325                 330                 335

Lys Tyr Ser Trp Val Pro Val Phe Phe Glu Gly Glu Gly Ser Ala Thr
            340                 345                 350

Val Met Thr Glu Lys Phe Val Arg Lys Pro Ala Phe Phe Ala Leu Gln
        355                 360                 365

Ser Thr Leu Lys Glu Ala Arg Lys Arg
    370                 375

<210> SEQ ID NO 11
<211> LENGTH: 1080
<212> TYPE: DNA
<213> ORGANISM: Unknown
<220> FEATURE:
<223> OTHER INFORMATION: Obtained from environmental sample

<400> SEQUENCE: 11
atgccctgga gctcatcaac gggacctgca cctatgacga gtaacccgcc cctcaaacgc      60
cccctgcgta tcggtctggt cggcacgggc atcggctcac tgcacgccgc cggaatttcc     120
cggatgcctc agcttgccac gctggggccc atctgtgggc ttgataccca cgccgtgaat     180
gccctagcca cacgctacgg ggtagaaaaa accacatctc gctatgagga tttactgaac     240
gatcccggcc ttgatgtcat cgatctgtgc gttcctcacg atgaacacat gcccatggcc     300
attgccgccg cccgggccgg aaaacatctc ctcatcgaaa aacctttggc ccgcaccctg     360
gaagaggccg atgcaatcct cgaggccgtg aaaagcgccg gtgtaacgct gatgatggga     420
cacaaccagc gttactacgc ccatcacgcc agggctaaag cattggtcga cgccggggtc     480
atcgaaaaac cctacatgat cgtagcttcg gttcatgtgc acgggcagat tgatggtttt     540
cgccgctttc ttaagcacgc cggggggtgg acgttgatcg attcgggagt gcaccgcttc     600
gacctcattc gctggatcat gggtgaagtc gagaccgtct tcgctcaaac gggtcgcttc     660
ctccagatgc aaatggaagg agaagactgc gcggtggtca ccctccgctt ccgcagcgga     720
gccatcggga gcttctcatg cagctggagc gccaaaggcc ctgttccaga gaaacattg      780 caaattttcg gccctatgg ttcgatttat accgaagacc acaccgcac cttacgcctt       840 tacaccgaaa gacccacccc cgaactggaa gacgtaaggc agtttgtctt cccggtcgat     900
caggctgagt ccatccgccg catgattgaa gcgcacttca ccagcctgca cagggggtta     960 cccccctccga tcaccggtat ggacggacgc gcttcccttg agctcagcat ggcctcctat   1020
cgctcggctc aaaccggcca gctgttcat cttccccttc agagaggaaa ccagaaatga    1080

<210> SEQ ID NO 12
<211> LENGTH: 359
<212> TYPE: PRT
<213> ORGANISM: Unknown
<220> FEATURE:
<223> OTHER INFORMATION: Obtained from environmental sample
<220> FEATURE:
```

-continued

```
<221> NAME/KEY: DOMAIN
<222> LOCATION: (22)...(141)
<223> OTHER INFORMATION: Oxidoreductase family, NAD-binding Rossmann
      fold
<220> FEATURE:
<221> NAME/KEY: DOMAIN
<222> LOCATION: (153)...(260)
<223> OTHER INFORMATION: Oxidoreductase family, C-terminal alpha/beta
      domain

<400> SEQUENCE: 12

Met Pro Trp Ser Ser Ser Thr Gly Pro Ala Pro Met Thr Ser Asn Pro
1               5                   10                  15

Pro Leu Lys Arg Pro Leu Arg Ile Gly Leu Val Gly Thr Gly Ile Gly
                20                  25                  30

Ser Leu His Ala Ala Gly Ile Ser Arg Met Pro Gln Leu Ala Thr Leu
            35                  40                  45

Gly Ala Ile Cys Gly Leu Asp Thr His Ala Val Asn Ala Leu Ala Thr
        50                  55                  60

Arg Tyr Gly Val Glu Lys Thr Thr Ser Arg Tyr Glu Asp Leu Leu Asn
65                  70                  75                  80

Asp Pro Gly Leu Asp Val Ile Asp Leu Cys Val Pro His Asp Glu His
                85                  90                  95

Met Pro Met Ala Ile Ala Ala Arg Ala Gly Lys His Leu Leu Ile
                100                 105                 110

Glu Lys Pro Leu Ala Arg Thr Leu Glu Glu Ala Asp Ala Ile Leu Glu
            115                 120                 125

Ala Val Lys Ser Ala Gly Val Thr Leu Met Met Gly His Asn Gln Arg
130                 135                 140

Tyr Tyr Ala His His Ala Arg Ala Lys Ala Leu Val Asp Ala Gly Val
145                 150                 155                 160

Ile Gly Lys Pro Tyr Met Ile Val Ala Ser Val His Val His Gly Gln
                165                 170                 175

Ile Asp Gly Phe Arg Arg Phe Leu Lys His Ala Gly Gly Thr Leu
            180                 185                 190

Ile Asp Ser Gly Val His Arg Phe Asp Leu Ile Arg Trp Ile Met Gly
        195                 200                 205

Glu Val Glu Thr Val Phe Ala Gln Thr Gly Arg Phe Leu Gln Met Gln
210                 215                 220

Met Glu Gly Glu Asp Cys Ala Val Val Thr Leu Arg Phe Arg Ser Gly
225                 230                 235                 240

Ala Ile Gly Ser Phe Ser Cys Ser Trp Ser Ala Lys Gly Pro Val Pro
                245                 250                 255

Glu Glu Thr Leu Gln Ile Phe Gly Pro Tyr Gly Ser Ile Tyr Thr Glu
            260                 265                 270

Asp His Thr Arg Thr Leu Arg Leu Tyr Thr Glu Arg Pro Thr Pro Glu
        275                 280                 285

Leu Glu Asp Val Arg Gln Phe Val Phe Pro Val Asp Gln Ala Glu Ser
        290                 295                 300

Ile Arg Arg Met Ile Glu Ala His Phe Thr Ser Leu Gln Gln Gly Leu
305                 310                 315                 320

Pro Pro Pro Ile Thr Gly Met Asp Gly Arg Ala Ser Leu Glu Leu Ser
                325                 330                 335

Met Ala Ser Tyr Arg Ser Ala Gln Thr Gly Gln Pro Val His Leu Pro
            340                 345                 350

Leu Gln Arg Gly Asn Gln Lys
            355
```

-continued

<210> SEQ ID NO 13
<211> LENGTH: 1038
<212> TYPE: DNA
<213> ORGANISM: Unknown
<220> FEATURE:
<223> OTHER INFORMATION: Obtained from environmental sample

<400> SEQUENCE: 13

```
atgagcccgg tgcgcgttgc tgtcatcggc gccgggcaaa ttgcccagcg cgggcattta      60
cccgggcttc tggaagctgg cgccgaaatt accgttctgt gcgataattc ccttcctcag     120
cttgaagaaa ttggggccaa atttcacgtt caccgggtct accgcgactg gcacgccatg     180
ctggatgccg gcggattcga agccgtcacc atttgtaccc cgcccttcct ccatgccgag     240
atggccatcg aatgtgcccg cagagggttg catgtactgg tagaaaaacc catggctgta     300
aatctccaac aatgcgatca atgatcgcc gcgtctgaac aggccggaac catcttaatg     360
gtctcgcata accagcgctt tatggaggca catcgtctgg ccaaagaaat ccttgatgcc     420
ggcctcctcg gcaggctcta cctggcgcac ggggtctttg ccacggcgg cccggaggtt     480
tggagcccaa cccagcaatg gtacttccga cctgaccgcg ccggcgctgg cgtgatcgct     540
gacctggggt atcataaact tgacctgatc cgctggctca ccgggcaaga aattaccgcg     600
gtgggagcac tgggcgccac ctttgaaaag caaacctcgc ttgaagactc tgctgtgatg     660
ctggttcacc tttcggaggg tactctcgcc accatccagg taagctgggt gttcaggcct     720
gactgggaaa acagcctggt ccttcgagga aacgggggg tgctcgccat ccccactgat     780
gcctcgcaac ccctgcgggt ctcttacata tcttcttcgg gtcaggtcat tgaaagtacg     840
catcgttgcg actccggcga tacctccggc tggttcggag cgatccgggc atttctcacc     900
gcgatcgaaa aaagcgctcc cgctcccatt gacggaaaag aagggcgtgc tgtcatggcg     960
gcagttctgg cggccacacg ctccattcaa aaacatacga tcatttctat aaccgaggta    1020
gaaaccatcc atgactga                                                  1038
```

<210> SEQ ID NO 14
<211> LENGTH: 345
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (4)...(123)
<223> OTHER INFORMATION: Oxidoreductase family, NAD-binding Rossmann
      fold
<220> FEATURE:
<221> NAME/KEY: DOMAIN
<222> LOCATION: (135)...(248)
<223> OTHER INFORMATION: Oxidoreductase family, C-terminal alpha/beta
      domain

<400> SEQUENCE: 14

```
Met Ser Pro Val Arg Val Ala Val Ile Gly Ala Gly Gln Ile Ala Gln
1               5                   10                  15

Arg Gly His Leu Pro Gly Leu Leu Glu Ala Gly Ala Glu Ile Thr Val
            20                  25                  30

Leu Cys Asp Asn Ser Leu Pro Gln Leu Glu Glu Ile Gly Ala Lys Phe
        35                  40                  45

His Val His Arg Val Tyr Arg Asp Trp His Ala Met Leu Asp Ala Gly
    50                  55                  60

Gly Phe Glu Ala Val Thr Ile Cys Thr Pro Pro Phe Leu His Ala Glu
```

```
                65                  70                  75                  80
Met Ala Ile Glu Cys Ala Arg Arg Gly Leu His Val Leu Val Glu Lys
                    85                  90                  95
Pro Met Ala Val Asn Leu Gln Gln Cys Asp Gln Met Ile Ala Ala Ser
                100                 105                 110
Glu Gln Ala Gly Thr Ile Leu Met Val Ser His Asn Gln Arg Phe Met
            115                 120                 125
Glu Ala His Arg Leu Ala Lys Glu Ile Leu Asp Ala Gly Leu Leu Gly
        130                 135                 140
Arg Leu Tyr Leu Ala His Gly Val Phe Gly His Gly Pro Glu Val
145                 150                 155                 160
Trp Ser Pro Thr Gln Gln Trp Tyr Phe Arg Pro Asp Arg Ala Gly Ala
                165                 170                 175
Gly Val Ile Ala Asp Leu Gly Tyr His Lys Leu Asp Leu Ile Arg Trp
                180                 185                 190
Leu Thr Gly Gln Glu Ile Thr Ala Val Gly Ala Leu Gly Ala Thr Phe
            195                 200                 205
Glu Lys Gln Thr Ser Leu Glu Asp Ser Ala Val Met Leu Val His Leu
        210                 215                 220
Ser Glu Gly Thr Leu Ala Thr Ile Gln Val Ser Trp Val Phe Arg Pro
225                 230                 235                 240
Asp Trp Glu Asn Ser Leu Val Leu Arg Gly Glu Arg Gly Val Leu Ala
                245                 250                 255
Ile Pro Thr Asp Ala Ser Gln Pro Leu Arg Val Ser Tyr Ile Ser Ser
                260                 265                 270
Ser Gly Gln Val Ile Glu Ser Thr His Arg Cys Asp Ser Gly Asp Thr
            275                 280                 285
Ser Gly Trp Phe Gly Ala Ile Arg Ala Phe Leu Thr Ala Ile Glu Lys
        290                 295                 300
Ser Ala Pro Ala Pro Ile Asp Gly Lys Glu Gly Arg Ala Val Met Ala
305                 310                 315                 320
Ala Val Leu Ala Ala Thr Arg Ser Ile Gln Lys His Thr Ile Ile Ser
                325                 330                 335
Ile Thr Glu Val Glu Thr Ile His Asp
            340                 345

<210> SEQ ID NO 15
<211> LENGTH: 1347
<212> TYPE: DNA
<213> ORGANISM: Unknown
<220> FEATURE:
<223> OTHER INFORMATION: Obtained from environmental sample

<400> SEQUENCE: 15
atgactgacc atcgtttttcc aaaaggattc atctggggaa ccgctacggc gtctttccag      60
attgaaggcg ccacccgcga agatggccgg ggcgaatcca tctgggaccg cttctgcgcc     120
acgccgggga aaattgtcac gggcgaaacc ggcgatcctg cctgcgactc ctatcatcgt     180
tacccctgaag acatcgccct gatgaaggct atgtcgctca atggttaccg cttttcaatc     240
gcctggcctc gcgtcattcc tgacggagac ggtaaagtct gtcaggccgg gctcgactac     300
tacgatcgtg tggtagatgc tctcctggcg gagaatatcc aacctttat cacccctgtac     360
cactgggacc tgccccaggc attacaggat cggggtggct ggggcaaccg tgccacggtt     420
gaggcgttca ctcgctacgt agatattgtg gtttctcgcc tgggtgaccg cgtaaagtac     480
tggatgacac acaacgaacc ctggtgtgta tccattttga gccatgagct tggtgaacat     540
```

```
gcccccgggt tgaaggaccg aaaactggcc ctccaggtgg cgcaccatgt cctcgtttct   600
cacggcctgg ccgtgcccat catccgccag cgttgtaaag aggcgcaggt tggcatcgtg   660
ttgaattttt cacctgctta cccggccacc gatagcctgg ccgaccagat ggccacccgt   720
cagcaccacg cccggtttaa cctctggttc ctcgatccca tcgccgggcg cggctacccg   780
caggatgcct gggaagggta cggagccgat gttcccgcca tgaggcctga tgacatgcag   840
atcatcgccg cccccatcga cttcctgggc gtcaatttct acagtcgggc ggtctgccac   900
gatccggccg ggggcgaagg ttcccgggtg ctcaatgtgc gcagtaaaac cgaggccacc   960
gatcgagact gggagattta ccctcaggcg ctctacgatt tactcatctg gatccacaat  1020
ggataccagt tcagagatat ttacattacc gagaatggcg cctcatacaa cgatgtggtc  1080
tccccggatg ggaaagtgca cgatcctaaa cgtctggact atctgaaacg ccatctggcc  1140
atggctctgc gggccatcga agcgggcgtt ccactgcgtg ttatttctg ctggagcttg   1200
atggacaact tcgaatgggc catgggcacc agcagccgat tcgggttggc ctacaccgac  1260
ttcactaccc agaagcgtat tctcaaagac agtgggctct ggtttggcga agtggcacgg  1320
gcaaacgcct taatcgacct tccctga                                      1347
```

<210> SEQ ID NO 16
<211> LENGTH: 448
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (2)...(444)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
      signature. Prosite id = PS00653
<220> FEATURE:
<221> NAME/KEY: SITE
<222> LOCATION: (352)...(360)
<223> OTHER INFORMATION: Glycosyl hydrolases family 1 active site.
      Prosite id = PS00572

<400> SEQUENCE: 16

Met Thr Asp His Arg Phe Pro Lys Gly Phe Ile Trp Gly Thr Ala Thr
1               5                   10                  15

Ala Ser Phe Gln Ile Glu Gly Ala Thr Arg Glu Asp Gly Arg Gly Glu
            20                  25                  30

Ser Ile Trp Asp Arg Phe Cys Ala Thr Pro Gly Lys Ile Val Thr Gly
        35                  40                  45

Glu Thr Gly Asp Pro Ala Cys Asp Ser Tyr His Arg Tyr Pro Glu Asp
    50                  55                  60

Ile Ala Leu Met Lys Ala Met Ser Leu Asn Gly Tyr Arg Phe Ser Ile
65                  70                  75                  80

Ala Trp Pro Arg Val Ile Pro Asp Gly Asp Lys Val Cys Gln Ala
                85                  90                  95

Gly Leu Asp Tyr Tyr Asp Arg Val Val Asp Ala Leu Leu Ala Glu Asn
            100                 105                 110

Ile Gln Pro Phe Ile Thr Leu Tyr His Trp Asp Leu Pro Gln Ala Leu
        115                 120                 125

Gln Asp Arg Gly Gly Trp Gly Asn Arg Ala Thr Val Glu Ala Phe Thr
    130                 135                 140

Arg Tyr Val Asp Ile Val Ser Arg Leu Gly Asp Arg Val Lys Tyr
145                 150                 155                 160

Trp Met Thr His Asn Glu Pro Trp Cys Val Ser Ile Leu Ser His Glu
                165                 170                 175

Leu Gly Glu His Ala Pro Gly Leu Lys Asp Arg Lys Leu Ala Leu Gln
            180                 185                 190

Val Ala His His Val Leu Val Ser His Gly Leu Ala Val Pro Ile Ile
        195                 200                 205

Arg Gln Arg Cys Lys Glu Ala Gln Val Gly Ile Val Leu Asn Phe Ser
210                 215                 220

Pro Ala Tyr Pro Ala Thr Asp Ser Leu Ala Asp Gln Met Ala Thr Arg
225                 230                 235                 240

Gln His His Ala Arg Phe Asn Leu Trp Phe Leu Asp Pro Ile Ala Gly
                245                 250                 255

Arg Gly Tyr Pro Gln Asp Ala Trp Glu Gly Tyr Gly Ala Asp Val Pro
            260                 265                 270

Ala Met Arg Pro Asp Asp Met Gln Ile Ile Ala Ala Pro Ile Asp Phe
        275                 280                 285

Leu Gly Val Asn Phe Tyr Ser Arg Ala Val Cys His Asp Pro Ala Gly
290                 295                 300

Gly Glu Gly Ser Arg Val Leu Asn Val Arg Ser Lys Thr Glu Ala Thr
305                 310                 315                 320

Asp Arg Asp Trp Glu Ile Tyr Pro Gln Ala Leu Tyr Asp Leu Leu Ile
                325                 330                 335

Trp Ile His Asn Gly Tyr Gln Phe Arg Asp Ile Tyr Ile Thr Glu Asn
            340                 345                 350

Gly Ala Ser Tyr Asn Asp Val Val Ser Pro Asp Gly Lys Val His Asp
        355                 360                 365

Pro Lys Arg Leu Asp Tyr Leu Lys Arg His Leu Ala Met Ala Leu Arg
370                 375                 380

Ala Ile Glu Ala Gly Val Pro Leu Arg Gly Tyr Phe Cys Trp Ser Leu
385                 390                 395                 400

Met Asp Asn Phe Glu Trp Ala Met Gly Thr Ser Ser Arg Phe Gly Leu
                405                 410                 415

Ala Tyr Thr Asp Phe Thr Thr Gln Lys Arg Ile Leu Lys Asp Ser Gly
            420                 425                 430

Leu Trp Phe Gly Glu Val Ala Arg Ala Asn Ala Leu Ile Asp Leu Pro
        435                 440                 445

<210> SEQ ID NO 17
<211> LENGTH: 1215
<212> TYPE: DNA
<213> ORGANISM: Unknown
<220> FEATURE:
<223> OTHER INFORMATION: Obtained from environmental sample

<400> SEQUENCE: 17
atgcggtacg tgctgatttc ctgccttgcg ctggcttccc tgtgcgcgca gcctcttcct      60
gtttccacgc ctgaaaaaga gggcttctcg gcggagcgcc tcgggcggat gcaccggtat     120
ttcgagaacc tgacgaaaac cggagagcgg cctggcgcga tcacgctgat cgtgcgcaac     180
gggcgcatcg tggactggcg cacgttcggg ctgcgcgacg tcgagaacaa tctgccgatg     240
gagaaggaca cgatcgtcca catctactcg atgacgaagc cggtgacgtc cgtggccgtg     300
atgatgctgg tggaggaggg caggctggcg ctggacgacc gggtggacaa gttcattccc     360
gagttcaagg ggatgaaggt gtacaagggc ggcacggtgg agcggccgga gctggaggac     420

```
gcggcgcggc cgatcacggt gaagcatctg ctgacgcaca cgagcgggct gagctacggc    480
tggggcaacg acaacgtctc cgcgatgtac cgcaaggccg acccgctcgg cgcgccgagc    540
ctgaaagagt ttatcgacag gctggtgaaa ctgccgctgg cattccaccc gggcgagcgt    600
tacgagtatt cgatgtcgat cgacgtgctg ggctacctgg tggaggctgt ctccggcgag    660
ccgttcgatc agttcgtgga gaagcggatc acggggccgc tgaagatgaa cgacacgcat    720
ttcagactgc cggaggcgaa gcgggcgcgg ctggcgaaga tctactcgcg gcgcgagggg    780
aagctgacgg cgcagcgcgg cctgcagacg ggaggcgttc cgtacggcgg catgggcctg    840
tactcgacga tcggcgacta tcgcggttc gcgcagatgc tgttgaacgg cggccatctc    900
gacggagtgc gcctgctggg gcggaagacg gtggatctga tgatgatgaa ccatctgggc    960
ggactgtcga agccgacgat cggcggcgat gattcagcgg gattcggact gggcggagcg    1020
gtgcggatcg atccggcgaa atcgggccgt ccgggcacgg aaggactctt cggctgggac    1080
ggggcggctt cgacgtattt ccgggtggac cggaaagaga agctggcgat gctgctgttc    1140
ctgcaatgga tgccgtttga tcaggggacg ctgaacctgt acgagacgct ggtctaccaa    1200
gctctggtgg actga                                                    1215
```

<210> SEQ ID NO 18
<211> LENGTH: 404
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (37)...(400)
<223> OTHER INFORMATION: Beta-lactamase
<220> FEATURE:
<221> NAME/KEY: SITE
<222> LOCATION: (43)...(46)
<223> OTHER INFORMATION: N-glycosylation site. Prosite id = PS00001
<220> FEATURE:
<221> NAME/KEY: SITE
<222> LOCATION: (167)...(170)
<223> OTHER INFORMATION: N-glycosylation site. Prosite id = PS00001
<220> FEATURE:
<221> NAME/KEY: SITE
<222> LOCATION: (240)...(243)
<223> OTHER INFORMATION: N-glycosylation site. Prosite id = PS00001

<400> SEQUENCE: 18

Met Arg Tyr Val Leu Ile Ser Cys Leu Ala Leu Ala Ser Leu Cys Ala
1               5                   10                  15

Gln Pro Leu Pro Val Ser Thr Pro Glu Lys Glu Gly Phe Ser Ala Glu
            20                  25                  30

Arg Leu Gly Arg Met His Arg Tyr Phe Glu Asn Leu Thr Lys Thr Gly
        35                  40                  45

Glu Arg Pro Gly Ala Ile Thr Leu Ile Val Arg Asn Gly Arg Ile Val
    50                  55                  60

Asp Trp Arg Thr Phe Gly Leu Arg Asp Val Glu Asn Asn Leu Pro Met
65                  70                  75                  80

Glu Lys Asp Thr Ile Val His Ile Tyr Ser Met Thr Lys Pro Val Thr
                85                  90                  95

Ser Val Ala Val Met Met Leu Val Glu Glu Gly Arg Leu Ala Leu Asp
            100                 105                 110

Asp Arg Val Asp Lys Phe Ile Pro Glu Phe Lys Gly Met Lys Val Tyr
        115                 120                 125

Lys Gly Gly Thr Val Glu Arg Pro Glu Leu Glu Asp Ala Ala Arg Pro

```
                130                 135                 140
Ile Thr Val Lys His Leu Leu Thr His Thr Ser Gly Leu Ser Tyr Gly
145                 150                 155                 160

Trp Gly Asn Asp Asn Val Ser Ala Met Tyr Arg Lys Ala Asp Pro Leu
                165                 170                 175

Gly Ala Pro Ser Leu Lys Glu Phe Ile Asp Arg Leu Val Lys Leu Pro
            180                 185                 190

Leu Ala Phe His Pro Gly Glu Arg Tyr Glu Tyr Ser Met Ser Ile Asp
        195                 200                 205

Val Leu Gly Tyr Leu Val Glu Ala Val Ser Gly Glu Pro Phe Asp Gln
210                 215                 220

Phe Val Glu Lys Arg Ile Thr Gly Pro Leu Lys Met Asn Asp Thr His
225                 230                 235                 240

Phe Arg Leu Pro Glu Ala Lys Arg Ala Arg Leu Ala Lys Ile Tyr Ser
                245                 250                 255

Arg Arg Glu Gly Lys Leu Thr Ala Gln Arg Gly Leu Gln Thr Gly Gly
            260                 265                 270

Val Pro Tyr Gly Gly Met Gly Leu Tyr Ser Thr Ile Gly Asp Tyr Ala
        275                 280                 285

Arg Phe Ala Gln Met Leu Leu Asn Gly Gly His Leu Asp Gly Val Arg
    290                 295                 300

Leu Leu Gly Arg Lys Thr Val Asp Leu Met Met Met Asn His Leu Gly
305                 310                 315                 320

Gly Leu Ser Lys Pro Thr Ile Gly Gly Asp Asp Ser Ala Gly Phe Gly
                325                 330                 335

Leu Gly Gly Ala Val Arg Ile Asp Pro Ala Lys Ser Gly Arg Pro Gly
            340                 345                 350

Thr Glu Gly Leu Phe Gly Trp Asp Gly Ala Ala Ser Thr Tyr Phe Arg
        355                 360                 365

Val Asp Arg Lys Glu Lys Leu Ala Met Leu Leu Phe Leu Gln Trp Met
    370                 375                 380

Pro Phe Asp Gln Gly Thr Leu Asn Leu Tyr Glu Thr Leu Val Tyr Gln
385                 390                 395                 400

Ala Leu Val Asp

<210> SEQ ID NO 19
<211> LENGTH: 1794
<212> TYPE: DNA
<213> ORGANISM: Unknown
<220> FEATURE:
<223> OTHER INFORMATION: Obtained from environmental sample

<400> SEQUENCE: 19
atgccgtttt tgttcgccct gtttcttgtt gcctcgtcct gcgcggcgca gtcgctggcc    60
gggccggttt ccctgcttgg cggagatgcg ggcgcggcgt tccgctatac cgggccatcg   120
gcgggcgcgg cgagcggctc ggccgaatgg gtggcggtgg agaacatgcc gttcacgcac   180
gcctggcggc tgcgcacgaa tccgctgccg gagagcggcg caacgaatg gaccctgcgc   240 atccgcgccc gcggagcggc ggctgttccg gcaggggaca agatcctggc cgagttctgg   300
atgcgctgcg tggagcccga aaacggcgac tgcattctgc gcctgaacgt ggagcgcgac   360
gggtcgccgt ggaccaaatc catcagcaac ccctacccgg tgggccggga gtggcggcgg   420
ttccgcgtgc tgttcgagat gcgggagagc tacgccgccg gcggctacat gatcgatttc   480
tggatgggcc agcaggtgca gacggcggaa gtgggcggga tttccctgct gaattacggt   540
```

```
ccgcaggcca cggccgagca gcttggcctg gaccggtttt atgagggcgc ggcggcggac      600
gccgcgtggc ggcaggcggc cgagcagcgg atcgaggaga tccggaaagc gggcatgatc      660
atcgtggcgg tgacgccgga cggcgagccg atcgagggcg ctgaaatccg gcgaagctg       720 aagcggcacg cgttcgggtg gggcacggct gtggcggcat cacggcttct ggggacggga      780
acggacagcg agcgctaccg caacttcatc cgcgagaact tcaacatggc ggtgctcgag      840
aacgacctga atggggccc gttcgaagag aaccgcaacc gcgcgatgaa cgcgctgcgc       900
tggctgcatg agaacgggat cacgtggatc cgcgggcaca atctcgtctg gccgggctgg      960
cggtggatgc cgaacgacgt gcgcaacctg gcgaacaatc ccgaggcgct gcggcagcgg     1020
attctggacc gcatccggga cacggccacg gccacgcgcg ggctggtggt gcactgggac     1080
gtcgtcaacg agccggtggc cgagcgcgac gtgctgaaca ttctgggcga cgaggtgatg     1140
gcggactggt tccgcgccgc gaaggagtgc gatcccgagg cgaggatgtt catcaatgag     1200
tacgacattc tggcggcgaa cggggccaat ctgcggaagc agaacgcgta ttaccgcatg     1260
atcgagatgc tgttgaagct cgaggcgccg gtggagggca tcggcttcca gggccacttc     1320
gacacggcca cgccgccgga gcggatgctg gagatcatga accggtacgc ccggctcggg     1380
ctgccgatcg ccatcaccga gtacgatttc gccacggcgg acgaggagct gcaggcgcag     1440
ttcacgcgcg acctgatgat tctcgccttc agccatccgg cggtttcgga cttcctgatg     1500
tggggcttct gggaagggag ccactggaag ccgctgggcg ccatgatccg gcgcgactgg     1560
agcgagaagc cgatgtaccg cgtctggcgc gagctgatct tcgagcgctg gcagacggat     1620
gaaacaggcg tgacgccgga gcacggtgcc atctacgtgc ggggcttcaa gggcgactac     1680
gagatcacgg tgaaggcggg cgggcaggaa gtccgggtgc cgtacacgct gaaagaagac     1740
ggccaggtgc tgtgggtgac ggtgggcggg gcttctgaag agcgcgtgca gtaa          1794
```

<210> SEQ ID NO 20
<211> LENGTH: 597
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (235)...(533)
<223> OTHER INFORMATION: Glycosyl hydrolase family 10
<220> FEATURE:
<221> NAME/KEY: SITE
<222> LOCATION: (467)...(477)
<223> OTHER INFORMATION: Glycosyl hydrolases family 10 active site.
      Prosite id = PS00591

<400> SEQUENCE: 20

Met Pro Val Leu Phe Ala Leu Phe Leu Val Ala Ser Ser Cys Ala Ala
1               5                   10                  15

Gln Ser Leu Ala Gly Pro Val Ser Leu Leu Gly Gly Asp Ala Gly Ala
            20                  25                  30

Ala Phe Arg Tyr Thr Gly Pro Ser Ala Gly Ala Ala Ser Gly Ser Ala
        35                  40                  45

Glu Trp Val Ala Val Glu Asn Met Pro Phe Thr His Ala Trp Arg Leu
    50                  55                  60

Arg Thr Asn Pro Leu Pro Glu Ser Gly Gly Asn Glu Trp Asp Leu Arg
65                  70                  75                  80

Ile Arg Ala Arg Gly Ala Ala Ala Val Ser Ala Gly Asp Lys Ile Leu

```
                85                  90                  95
Ala Glu Phe Trp Met Arg Cys Val Glu Pro Glu Asn Gly Asp Cys Ile
            100                 105                 110

Leu Arg Leu Asn Val Glu Arg Asp Gly Ser Pro Trp Thr Lys Ser Ile
            115                 120                 125

Ser Asn Pro Tyr Pro Val Gly Arg Glu Trp Arg Arg Phe Arg Val Leu
            130                 135                 140

Phe Glu Met Arg Glu Ser Tyr Ala Ala Gly Tyr Met Ile Asp Phe
145                 150                 155                 160

Trp Met Gly Gln Gln Val Gln Thr Ala Glu Val Gly Gly Ile Ser Leu
                165                 170                 175

Leu Asn Tyr Gly Pro Gln Ala Thr Ala Glu Gln Leu Gly Leu Asp Arg
            180                 185                 190

Phe Tyr Glu Gly Ala Ala Ala Asp Ala Ala Trp Arg Gln Ala Ala Glu
            195                 200                 205

Gln Arg Ile Glu Glu Ile Arg Lys Ala Gly Met Ile Ile Val Ala Val
            210                 215                 220

Thr Pro Asp Gly Glu Pro Ile Glu Gly Ala Glu Ile Arg Ala Lys Leu
225                 230                 235                 240

Lys Arg His Ala Phe Gly Trp Gly Thr Ala Val Ala Ala Ser Arg Leu
                245                 250                 255

Leu Gly Thr Gly Thr Asp Ser Glu Arg Tyr Arg Asn Phe Ile Arg Glu
            260                 265                 270

Asn Phe Asn Met Ala Val Leu Glu Asn Asp Leu Lys Trp Gly Pro Phe
            275                 280                 285

Glu Glu Asn Arg Asn Arg Ala Met Asn Ala Leu Arg Trp Leu His Glu
            290                 295                 300

Asn Gly Ile Thr Trp Ile Arg Gly His Asn Leu Val Trp Pro Gly Trp
305                 310                 315                 320

Arg Trp Met Pro Asn Asp Val Arg Asn Leu Ala Asn Asn Pro Glu Ala
                325                 330                 335

Leu Arg Gln Arg Ile Leu Asp Arg Ile Arg Asp Thr Ala Thr Ala Thr
            340                 345                 350

Arg Gly Leu Val Val His Trp Asp Val Val Asn Glu Pro Val Ala Glu
            355                 360                 365

Arg Asp Val Leu Asn Ile Leu Gly Asp Glu Val Met Ala Asp Trp Phe
            370                 375                 380

Arg Ala Ala Lys Glu Cys Asp Pro Glu Ala Arg Met Phe Ile Asn Glu
385                 390                 395                 400

Tyr Asp Ile Leu Ala Ala Asn Gly Ala Asn Leu Arg Lys Gln Asn Ala
                405                 410                 415

Tyr Tyr Arg Met Ile Glu Met Leu Leu Lys Leu Glu Ala Pro Val Glu
            420                 425                 430

Gly Ile Gly Phe Gln Gly His Phe Asp Thr Ala Thr Pro Pro Glu Arg
            435                 440                 445

Met Leu Glu Ile Met Asn Arg Tyr Ala Arg Leu Gly Leu Pro Ile Ala
            450                 455                 460

Ile Thr Glu Tyr Asp Phe Ala Thr Ala Asp Glu Glu Leu Gln Ala Gln
465                 470                 475                 480

Phe Thr Arg Asp Leu Met Ile Leu Ala Phe Ser His Pro Ala Val Ser
                485                 490                 495

Asp Phe Leu Met Trp Gly Phe Trp Glu Gly Ser His Trp Lys Pro Leu
            500                 505                 510
```

-continued

Gly Ala Met Ile Arg Arg Asp Trp Ser Glu Lys Pro Met Tyr Arg Val
            515                 520                 525

Trp Arg Glu Leu Ile Phe Glu Arg Trp Gln Thr Asp Glu Thr Gly Val
        530                 535                 540

Thr Pro Glu His Gly Ala Ile Tyr Val Arg Gly Phe Lys Gly Asp Tyr
545                 550                 555                 560

Glu Ile Thr Val Lys Ala Gly Gly Gln Glu Val Arg Val Pro Tyr Thr
                565                 570                 575

Leu Lys Glu Asp Gly Gln Val Leu Trp Val Thr Val Gly Gly Ala Ser
            580                 585                 590

Glu Glu Arg Val Gln
        595

<210> SEQ ID NO 21
<211> LENGTH: 1032
<212> TYPE: DNA
<213> ORGANISM: Clostridium thermocellum

<400> SEQUENCE: 21
atggtgagtt ttaaagcagg tataaattta ggcggatgga tatcacaata tcaagttttc      60
agcaaagagc atttcgatac attcattacg gagaaggaca ttgaaactat tgcagaagca     120
gggtttgacc atgtcagact gccttttgat tatccaatta tcgagtctga tgacaatgtg     180
ggagaatata agaagatggg ctttcttat attgaccggt gccttgagtg gtgtaaaaaa     240
tacaatttgg ggcttgtgtt ggatatgcat cacgctcccg gtaccgcctt tcaagatttt     300
aagacaagca ccttgtttga agatccgaac cagcaaaaga gatttgttga catatggaga     360
ttttagccaa agcgttacat aaatgaacgg gaacatattg cctttgaact gttaaatgaa     420
gttgttgagc ctgacagtac ccgctggaac aagttgatgc ttgagtgtgt aaaagcaatc     480
agggaaattg attccaccag gtggctttac attgggggca ataactataa cagtcctgat     540
gagcttaaaa accttgcaga tattgatgat gattacatag tttacaatt ccatttttac     600 aatccttttt tctttacgca tcagaaagcc cactggtcgg aaagtgccat ggcgtacaac     660
aggactgtaa aatatccggg acaatatgag ggaattgaag agtttgtgaa aaataatcct     720
aagtacagtt ttatgatgga attgaataac ctgaagctga ataaagagct tttgcgcaaa     780
gatttaaaac cagcaattga gttcagggaa agaaaaaat gcaaactata ttgcggggag     840
tttggcgtaa ttgccattgc tgacctggag tccaggataa aatggcatga agattatata     900
agtcttctag aggagtatga tatccggcgg cgcggtgtgga actacaaaaa aatgattttt     960
gaaatttata tgaggatag aaaacctgtc tcgcaagaat tggtaaatat actggcgaga    1020
agaaaaactt ga                                                       1032

<210> SEQ ID NO 22
<211> LENGTH: 343
<212> TYPE: PRT
<213> ORGANISM: Clostridium thermocellum
<220> FEATURE:
<221> NAME/KEY: DOMAIN
<222> LOCATION: (1)...(323)
<223> OTHER INFORMATION: Cellulase (glycosyl hydrolase family 5)
<220> FEATURE:
<221> NAME/KEY: SITE
<222> LOCATION: (15)...(32)
<223> OTHER INFORMATION: Cytosolic fatty-acid binding proteins
    signature. Prosite id = PS00214
<220> FEATURE:
<221> NAME/KEY: SITE
<222> LOCATION: (135)...(144)
<223> OTHER INFORMATION: Glycosyl hydrolases family 5 signature.

```
                Prosite id = PS00659
<220> FEATURE:
<221> NAME/KEY: SITE
<222> LOCATION: (223)...(226)
<223> OTHER INFORMATION: N-glycosylation site. Prosite id = PS00001

<400> SEQUENCE: 22

Met Val Ser Phe Lys Ala Gly Ile Asn Leu Gly Gly Trp Ile Ser Gln
1               5                   10                  15

Tyr Gln Val Phe Ser Lys Glu His Phe Asp Thr Phe Ile Thr Glu Lys
            20                  25                  30

Asp Ile Glu Thr Ile Ala Glu Ala Gly Phe Asp His Val Arg Leu Pro
        35                  40                  45

Phe Asp Tyr Pro Ile Ile Glu Ser Asp Asp Asn Val Gly Glu Tyr Lys
    50                  55                  60

Glu Asp Gly Leu Ser Tyr Ile Asp Arg Cys Leu Glu Trp Cys Lys Lys
65                  70                  75                  80

Tyr Asn Leu Gly Leu Val Leu Asp Met His His Ala Pro Gly Tyr Arg
                85                  90                  95

Phe Gln Asp Phe Lys Thr Ser Thr Leu Phe Glu Asp Pro Asn Gln Gln
            100                 105                 110

Lys Arg Phe Val Asp Ile Trp Arg Phe Leu Ala Lys Arg Tyr Ile Asn
        115                 120                 125

Glu Arg Glu His Ile Ala Phe Glu Leu Leu Asn Glu Val Val Glu Pro
    130                 135                 140

Asp Ser Thr Arg Trp Asn Lys Leu Met Leu Glu Cys Val Lys Ala Ile
145                 150                 155                 160

Arg Glu Ile Asp Ser Thr Arg Trp Leu Tyr Ile Gly Gly Asn Asn Tyr
                165                 170                 175

Asn Ser Pro Asp Glu Leu Lys Asn Leu Ala Asp Ile Asp Asp Asp Tyr
            180                 185                 190

Ile Val Tyr Asn Phe His Phe Tyr Asn Pro Phe Phe Thr His Gln
        195                 200                 205

Lys Ala His Trp Ser Glu Ser Ala Met Ala Tyr Asn Arg Thr Val Lys
    210                 215                 220

Tyr Pro Gly Gln Tyr Glu Gly Ile Glu Glu Phe Val Lys Asn Asn Pro
225                 230                 235                 240

Lys Tyr Ser Phe Met Met Glu Leu Asn Asn Leu Lys Leu Asn Lys Glu
                245                 250                 255

Leu Leu Arg Lys Asp Leu Lys Pro Ala Ile Glu Phe Arg Glu Lys Lys
            260                 265                 270

Lys Cys Lys Leu Tyr Cys Gly Glu Phe Gly Val Ile Ala Ile Ala Asp
        275                 280                 285

Leu Glu Ser Arg Ile Lys Trp His Glu Asp Tyr Ile Ser Leu Leu Glu
    290                 295                 300

Glu Tyr Asp Ile Gly Gly Ala Val Trp Asn Tyr Lys Lys Met Asp Phe
305                 310                 315                 320

Glu Ile Tyr Asn Glu Asp Arg Lys Pro Val Ser Gln Glu Leu Val Asn
                325                 330                 335

Ile Leu Ala Arg Arg Lys Thr
            340

<210> SEQ ID NO 23
<211> LENGTH: 3966
<212> TYPE: DNA
<213> ORGANISM: Clostridium thermocellum
```

<400> SEQUENCE: 23

```
atgtataaaa gattattgtc gtcagtactg ataattatgc tgttattatc agcctggtcg      60
ccaatatccg tacaagcttc tgatggaatc aatgacatta gaggtcattg ggctgaagaa     120
gacttgaaca aatggatgga aaaaggtatt ttggtgggct accaggatgg gacgataagg     180
cccgataata atatcacaag agccgaattt gtcacattaa ttaacaaggt tttcgggctt     240
tatgaattaa gccgggagca attcgcagat gttgaagact caaaatggta ttcccgtgaa     300
atattaaaag ccagggctgc gggatatatt gcaggttatg gaagcaatgt tttcaaacct     360
gacaattata ttacaagaca agaagccgtt gttataatcg cgaaagtttt tgaacttcaa     420
agcggcagca attatacaag caagtttaaa gatggaagtc tggtaaagga atacgcaaaa     480
gattccgtta gcgcgttggt tgaaaaaggc tacatagcag gttatgaaga tggcactttc     540
aggccggaca actacattac ccgtgcagaa acaataaaaa ttctgaataa aattattcct     600
tccttgtata acgagaaagg agattataaa atgaagaag tagccggaaa cgctctgatt      660
aacaccgaag gagttatttt aaaagatacc gtaataaacg gggatttgta tcttgctcag     720
ggaattcaga acgcgatgt taccctgac ggtgtgaatg taaaggaac ggttttcgta        780
aatggtggag gaagcgacag catacatttt ataaatacga aaataaacag ggttgttgtc     840
aataaaacag gagttagaat tgtaacttcc ggcaatacct cggttgaaag tgttgtcgtt     900
aaatccggtg caaaacttga agaaaaagaa ttgacgggcg acggctttaa aaacgttaca     960
gtcgattctc aactttcagc cggcaatgaa ataatatttg tcggggattt tgaacaggtc    1020
gatgttctgg cggatgatgc cttgctggaa accaagagg caaaaatgaa actgagaata    1080
ttcggccaaa ggattaaagt aaatggaaag gcaatagaaa atcatcaaa gaactatatt     1140
gtaaacgggg aacttatatc aactgaggaa gaacccggtc cttccgacgc acccggtgcg    1200
gaagacgatc aaaattcagg tagtccgggc tcatcgacta atcctgcacc aaccaagaat    1260
ccgaatgaag agtggcgtct ggtttggagc gatgagttta acggttctga aataaatatg    1320
gctaattgga gctatgacga cccgaccaac ggaagatgga acggggaagt acaatcctac    1380
acacaaaaca atgcctatat caagacggc gcgttggtta ttgaagcaag aaaagaagac    1440
attacggaac caagcggtga gacttatcat tatacatcgt caaagctgat taccaaaggc    1500
aaaaagtcat ggaagtacgg aaaaatttga ataagggcaa aaatgccaca gggacaaggt    1560
atatggcctg caatctggat gatgccggaa gacgaaccct tctacggaac atggccaaag    1620
tgcggcgaaa tagatattat ggagcttttg ggccacgagc tgataaaat ttatggaacg      1680
atccattttg gagagcctca taaagaatcc cagggaacgt ataccttgcc ggaaggccag    1740
actttgctg atgatttcca cgtttattcg attgaatggg aaccgggaga atacgctgg       1800
tatatagacg gcaagctgta tcatgtcgct aatgactggt actcgaggga cccgtacctt    1860
gccgatgact acacttatcc cgcacctttt gaccagaatt tcttcttgat tctcaatata    1920
tccgttggtg gcggctggcc gggatatcct gacgaaacga cagttttccc gcagcaaatg    1980
gttgtggact atgtgagagt atatcaaaaa gataaatatc ctcacaggga aaaccggca    2040
aaggaagaag tgaagccaag agagcctctt gaggacggca attatatcta taacggcggt    2100
tttgatgtgg atgattctgc agcagttggt gtggacggtt ccctatac gtcttactgg      2160
acattcttaa cagcatccgg tggagctgcg acagtcaatg tagaggaagg tgttatgcac    2220
gtacagatag aaaacggagg gacaaccgac tacggcgtac aattgcttca agctccgatt    2280
catcttgaaa aaggcgcaaa atataaagca tcttttgaca tgaaagctga aaatccaagg    2340
```

-continued

```
caggtaaaac tgaaaatagg cggagacggc gacagggat ggaaagatta tgcggctatt    2400
ccaccgttta cggtctcaac agagatgacc aactatgagt tgagtttac tatgaaagat    2460 gataccgatg ttaaggcacg gtttgagttt aatatgggtt tggacgataa tgatgtctgg    2520
attgacaatg ttaaactgat taaaacagaa gatgcgccgg ttatagatcc ttccgaaata    2580
gcaagacctc cgcttctttc cggcaactat atatacaacg gtacctttga ccaaggtccg    2640
aacagaatgg gattctggaa ttttgttgtg gatagcactg caaaggctac atactatatt    2700
ggaagcgatg ttaatgagcg caggtttgaa acaagaatag aaaaaggcgg aacatcgagg    2760
ggagccataa gattggttca gccgggaatt aacattgaaa acggcaaaac atacaaggtt    2820
agcttcgaag ccagtgcggc aaatacaaga actattgagg tggaaattgc aagcaatctt    2880
cacaacagca gcattttttgc gacaactttt gaaataagca aagagagcaa gatatacgaa    2940
tttgagttta caatggacaa agattcggac aagaacggag aacttaggtt caatctgggc    3000
ggaagcaacg tgaacgtcta tattgataat gtcgttatga aaagagtaag taccgatgaa    3060
gttgaaggaa acctgatttt aaacggcgta tttaacggcc tggcaggctg gggatatgga    3120
gcgtatgaac ctggatcggc agattttgaa agtcatgagg aacaatttag gcaattatt    3180 agctctgtcg gtaatgaagg ttggaatgta cagttgtatc aggataatgt tccgctggaa    3240
caagggcaaa cctacgaagt ttctttttgat gcaaaatcaa cgattgacag aaagataatt    3300
gttcagctgc aaaggaacgg tacttcggat aataattggg actcctattt ctatcaagaa    3360
gttgaactta ctaatgaact taaaacattc aaatatgaat ttacaatgag taaacctaca    3420
gattcggcgt caagatttaa ttttgctttg ggtaatactg aaaacaaaac ttatgctcct    3480
catgaaataa taattgacaa tgttgtagta agaaaagttg cgactccttc tgcgctgata    3540
ttgaacggaa cctttgacga tggaatggat cattggctgc tatactgggg agacggtgaa    3600
ggcaattgcg atgtaactga cggagagctt gaaattaaca ttaccaaggt aggtaccgcg    3660
gattacatgc cgcagattaa acaggaaaac atagcgttgc aagagggtgt gacgtatact    3720
ttgtctctta agcgagagc gcttgaggca agaagtatta aagtggacat attggattct    3780
tcttataact ggtatggcgg aactatttc gatttaacaa cggaagatgc cgtatacacg    3840
tttacattta cccaaagcaa gtcgataaat aacggtgtct taactataaa tttaggtacc    3900
atagaaggta agacatccgc cgcaactact gtctatcttg atgatatttt gctggaacaa    3960
cagtaa                                                             3966
```

```
<210> SEQ ID NO 24
<211> LENGTH: 1321
<212> TYPE: PRT
<213> ORGANISM: Clostridium thermocellum
<220> FEATURE:
<221> NAME/KEY: SIGNAL
<222> LOCATION: (1)..(26)
<220> FEATURE:
<221> NAME/KEY: DOMAIN
<222> LOCATION: (30)..(71)
<223> OTHER INFORMATION: S-layer homology domain
<220> FEATURE:
<221> NAME/KEY: DOMAIN
<222> LOCATION: (88)..(130)
<223> OTHER INFORMATION: S-layer homology domain
<220> FEATURE:
<221> NAME/KEY: DOMAIN
<222> LOCATION: (149)..(192)
<223> OTHER INFORMATION: S-layer homology domain
<220> FEATURE:
<221> NAME/KEY: DOMAIN
<222> LOCATION: (445)..(666)
<223> OTHER INFORMATION: Glycosyl hydrolases family 16
```

```
<220> FEATURE:
<221> NAME/KEY: DOMAIN
<222> LOCATION: (693)...(849)
<223> OTHER INFORMATION: Carbohydrate binding domain
<220> FEATURE:
<221> NAME/KEY: DOMAIN
<222> LOCATION: (868)...(1016)
<223> OTHER INFORMATION: Carbohydrate binding domain
<220> FEATURE:
<221> NAME/KEY: DOMAIN
<222> LOCATION: (1023)...(1173)
<223> OTHER INFORMATION: Carbohydrate binding domain
<220> FEATURE:
<221> NAME/KEY: DOMAIN
<222> LOCATION: (1177)...(1321)
<223> OTHER INFORMATION: Carbohydrate binding domain
<220> FEATURE:
<221> NAME/KEY: SITE
<222> LOCATION: (146)...(149)
<223> OTHER INFORMATION: N-glycosylation site. Prosite id = PS00001
<220> FEATURE:
<221> NAME/KEY: SITE
<222> LOCATION: (285)...(288)
<223> OTHER INFORMATION: N-glycosylation site. Prosite id = PS00001
<220> FEATURE:
<221> NAME/KEY: SITE
<222> LOCATION: (296)...(299)
<223> OTHER INFORMATION: N-glycosylation site. Prosite id = PS00001
<220> FEATURE:
<221> NAME/KEY: SITE
<222> LOCATION: (322)...(325)
<223> OTHER INFORMATION: N-glycosylation site. Prosite id = PS00001
<220> FEATURE:
<221> NAME/KEY: SITE
<222> LOCATION: (440)...(443)
<223> OTHER INFORMATION: N-glycosylation site. Prosite id = PS00001
<220> FEATURE:
<221> NAME/KEY: SITE
<222> LOCATION: (448)...(451)
<223> OTHER INFORMATION: N-glycosylation site. Prosite id = PS00001
<220> FEATURE:
<221> NAME/KEY: SITE
<222> LOCATION: (648)...(651)
<223> OTHER INFORMATION: N-glycosylation site. Prosite id = PS00001
<220> FEATURE:
<221> NAME/KEY: SITE
<222> LOCATION: (886)...(889)
<223> OTHER INFORMATION: N-glycosylation site. Prosite id = PS00001
<220> FEATURE:
<221> NAME/KEY: SITE
<222> LOCATION: (976)...(979)
<223> OTHER INFORMATION: N-glycosylation site. Prosite id = PS00001
<220> FEATURE:
<221> NAME/KEY: SITE
<222> LOCATION: (1123)...(1126)
<223> OTHER INFORMATION: N-glycosylation site. Prosite id = PS00001
<220> FEATURE:
<221> NAME/KEY: SITE
<222> LOCATION: (1172)...(1175)
<223> OTHER INFORMATION: N-glycosylation site. Prosite id = PS00001
<220> FEATURE:
<221> NAME/KEY: SITE
<222> LOCATION: (1200)...(1203)
<223> OTHER INFORMATION: N-glycosylation site. Prosite id = PS00001
<220> FEATURE:
<221> NAME/KEY: SITE
<222> LOCATION: (1231)...(1234)
<223> OTHER INFORMATION: N-glycosylation site. Prosite id = PS00001

<400> SEQUENCE: 24

Met Tyr Lys Arg Leu Leu Ser Ser Val Leu Ile Ile Met Leu Leu Leu
1               5                   10                  15

Ser Ala Trp Ser Pro Ile Ser Val Gln Ala Ser Asp Gly Ile Asn Asp
                20                  25                  30

Ile Arg Gly His Trp Ala Glu Glu Asp Leu Asn Lys Trp Met Glu Lys
            35                  40                  45
```

```
Gly Ile Leu Val Gly Tyr Gln Asp Gly Thr Ile Arg Pro Asp Asn Asn
 50                  55                  60

Ile Thr Arg Ala Glu Phe Val Thr Leu Ile Asn Lys Val Phe Gly Leu
 65                  70                  75                  80

Tyr Glu Leu Ser Arg Glu Gln Phe Ala Asp Val Glu Asp Ser Lys Trp
                 85                  90                  95

Tyr Ser Arg Glu Ile Leu Lys Ala Arg Ala Gly Tyr Ile Ala Gly
            100                 105                 110

Tyr Gly Ser Asn Val Phe Lys Pro Asp Asn Tyr Ile Thr Arg Gln Glu
            115                 120                 125

Ala Val Val Ile Ile Ala Lys Val Phe Glu Leu Gln Ser Gly Ser Asn
        130                 135                 140

Tyr Thr Ser Lys Phe Lys Asp Gly Ser Leu Val Lys Glu Tyr Ala Lys
145                 150                 155                 160

Asp Ser Val Ser Ala Leu Val Glu Lys Gly Tyr Ile Ala Gly Tyr Glu
                165                 170                 175

Asp Gly Thr Phe Arg Pro Asp Asn Tyr Ile Thr Arg Ala Glu Thr Ile
            180                 185                 190

Lys Ile Leu Asn Lys Ile Ile Pro Ser Leu Tyr Asn Glu Lys Gly Asp
        195                 200                 205

Tyr Lys Asn Glu Glu Val Ala Gly Asn Ala Leu Ile Asn Thr Glu Gly
        210                 215                 220

Val Ile Leu Lys Asp Thr Val Ile Asn Gly Asp Leu Tyr Leu Ala Gln
225                 230                 235                 240

Gly Ile Gln Asn Gly Asp Val Thr Leu Asp Gly Val Asn Val Lys Gly
                245                 250                 255

Thr Val Phe Val Asn Gly Gly Ser Asp Ser Ile His Phe Ile Asn
            260                 265                 270

Thr Lys Ile Asn Arg Val Val Val Asn Lys Thr Gly Val Arg Ile Val
        275                 280                 285

Thr Ser Gly Asn Thr Ser Val Glu Ser Val Val Lys Ser Gly Ala
        290                 295                 300

Lys Leu Glu Glu Lys Glu Leu Thr Gly Asp Gly Phe Lys Asn Val Thr
305                 310                 315                 320

Val Asp Ser Gln Leu Ser Ala Gly Asn Glu Ile Ile Phe Val Gly Asp
                325                 330                 335

Phe Glu Gln Val Asp Val Leu Ala Asp Asp Ala Leu Leu Glu Thr Lys
            340                 345                 350

Glu Ala Lys Met Lys Leu Arg Ile Phe Gly Gln Arg Ile Lys Val Asn
        355                 360                 365

Gly Lys Ala Ile Glu Lys Ser Ser Lys Asn Tyr Ile Val Asn Gly Glu
        370                 375                 380

Leu Ile Ser Thr Glu Glu Pro Gly Pro Ser Asp Ala Pro Gly Ala
385                 390                 395                 400

Glu Asp Asp Gln Asn Ser Gly Ser Pro Gly Ser Ser Thr Asn Pro Ala
                405                 410                 415

Pro Thr Lys Asn Pro Asn Glu Glu Trp Arg Leu Val Trp Ser Asp Glu
            420                 425                 430

Phe Asn Gly Ser Glu Ile Asn Met Ala Asn Trp Ser Tyr Asp Asp Pro
        435                 440                 445

Thr Asn Gly Arg Trp Asn Gly Glu Val Gln Ser Tyr Thr Gln Asn Asn
        450                 455                 460

Ala Tyr Ile Lys Asp Gly Ala Leu Val Ile Glu Ala Arg Lys Glu Asp
465                 470                 475                 480
```

```
Ile Thr Glu Pro Ser Gly Glu Thr Tyr His Tyr Thr Ser Ser Lys Leu
            485                 490                 495

Ile Thr Lys Gly Lys Lys Ser Trp Lys Tyr Gly Lys Phe Glu Ile Arg
            500                 505                 510

Ala Lys Met Pro Gln Gly Gln Gly Ile Trp Pro Ala Ile Trp Met Met
            515                 520                 525

Pro Glu Asp Glu Pro Phe Tyr Gly Thr Trp Pro Lys Cys Gly Glu Ile
            530                 535                 540

Asp Ile Met Glu Leu Leu Gly His Glu Pro Asp Lys Ile Tyr Gly Thr
545                 550                 555                 560

Ile His Phe Gly Glu Pro His Lys Glu Ser Gln Gly Thr Tyr Thr Leu
            565                 570                 575

Pro Glu Gly Gln Thr Phe Ala Asp Asp Phe His Val Tyr Ser Ile Glu
            580                 585                 590

Trp Glu Pro Gly Glu Ile Arg Trp Tyr Ile Asp Gly Lys Leu Tyr His
            595                 600                 605

Val Ala Asn Asp Trp Tyr Ser Arg Asp Pro Tyr Leu Ala Asp Asp Tyr
            610                 615                 620

Thr Tyr Pro Ala Pro Phe Asp Gln Asn Phe Phe Leu Ile Leu Asn Ile
625                 630                 635                 640

Ser Val Gly Gly Gly Trp Pro Gly Tyr Pro Asp Glu Thr Thr Val Phe
            645                 650                 655

Pro Gln Gln Met Val Val Asp Tyr Val Arg Val Tyr Gln Lys Asp Lys
            660                 665                 670

Tyr Pro His Arg Glu Lys Pro Ala Lys Glu Val Lys Pro Arg Glu
            675                 680                 685

Pro Leu Glu Asp Gly Asn Tyr Ile Tyr Asn Gly Gly Phe Asp Val Asp
            690                 695                 700

Asp Ser Ala Ala Val Gly Val Asp Gly Val Pro Tyr Thr Ser Tyr Trp
705                 710                 715                 720

Thr Phe Leu Thr Ala Ser Gly Gly Ala Ala Thr Val Asn Val Glu Glu
            725                 730                 735

Gly Val Met His Val Gln Ile Glu Asn Gly Gly Thr Thr Asp Tyr Gly
            740                 745                 750

Val Gln Leu Leu Gln Ala Pro Ile His Leu Glu Lys Gly Ala Lys Tyr
            755                 760                 765

Lys Ala Ser Phe Asp Met Lys Ala Glu Asn Pro Arg Gln Val Lys Leu
            770                 775                 780

Lys Ile Gly Gly Asp Gly Asp Arg Gly Trp Lys Asp Tyr Ala Ala Ile
785                 790                 795                 800

Pro Pro Phe Thr Val Ser Thr Glu Met Thr Asn Tyr Glu Phe Glu Phe
            805                 810                 815

Thr Met Lys Asp Asp Thr Asp Val Lys Ala Arg Phe Glu Phe Asn Met
            820                 825                 830

Gly Leu Asp Asp Asn Asp Val Trp Ile Asp Asn Val Lys Leu Ile Lys
            835                 840                 845

Thr Glu Asp Ala Pro Val Ile Asp Pro Ser Glu Ile Ala Arg Pro Pro
            850                 855                 860

Leu Leu Ser Gly Asn Tyr Ile Tyr Asn Gly Thr Phe Asp Gln Gly Pro
865                 870                 875                 880

Asn Arg Met Gly Phe Trp Asn Phe Val Val Asp Ser Thr Ala Lys Ala
            885                 890                 895

Thr Tyr Tyr Ile Gly Ser Asp Val Asn Glu Arg Arg Phe Glu Thr Arg
```

-continued

```
              900                 905                 910
Ile Glu Lys Gly Gly Thr Ser Arg Gly Ala Ile Arg Leu Val Gln Pro
        915                 920                 925

Gly Ile Asn Ile Glu Asn Gly Lys Thr Tyr Lys Val Ser Phe Glu Ala
        930                 935                 940

Ser Ala Ala Asn Thr Arg Thr Ile Glu Val Glu Ile Ala Ser Asn Leu
945                 950                 955                 960

His Asn Ser Ser Ile Phe Ala Thr Thr Phe Glu Ile Ser Lys Glu Ser
                965                 970                 975

Lys Ile Tyr Glu Phe Glu Phe Thr Met Asp Lys Asp Ser Asp Lys Asn
            980                 985                 990

Gly Glu Leu Arg Phe Asn Leu Gly Gly Ser Asn Val Asn Val Tyr Ile
        995                 1000                1005

Asp Asn Val Val Met Lys Arg Val Ser Thr Asp Glu Val Glu Gly
        1010                1015                1020

Asn Leu Ile Leu Asn Gly Val Phe Asn Gly Leu Ala Gly Trp Gly
        1025                1030                1035

Tyr Gly Ala Tyr Glu Pro Gly Ser Ala Asp Phe Glu Ser His Glu
        1040                1045                1050

Glu Gln Phe Arg Ala Ile Ile Ser Ser Val Gly Asn Glu Gly Trp
        1055                1060                1065

Asn Val Gln Leu Tyr Gln Asp Asn Val Pro Leu Glu Gln Gly Gln
        1070                1075                1080

Thr Tyr Glu Val Ser Phe Asp Ala Lys Ser Thr Ile Asp Arg Lys
        1085                1090                1095

Ile Ile Val Gln Leu Gln Arg Asn Gly Thr Ser Asp Asn Asn Trp
        1100                1105                1110

Asp Ser Tyr Phe Tyr Gln Glu Val Glu Leu Thr Asn Glu Leu Lys
        1115                1120                1125

Thr Phe Lys Tyr Glu Phe Thr Met Ser Lys Pro Thr Asp Ser Ala
        1130                1135                1140

Ser Arg Phe Asn Phe Ala Leu Gly Asn Thr Glu Asn Lys Thr Tyr
        1145                1150                1155

Ala Pro His Glu Ile Ile Ile Asp Asn Val Val Val Arg Lys Val
        1160                1165                1170

Ala Thr Pro Ser Ala Leu Ile Leu Asn Gly Thr Phe Asp Asp Gly
        1175                1180                1185

Met Asp His Trp Leu Leu Tyr Trp Gly Asp Gly Glu Gly Asn Cys
        1190                1195                1200

Asp Val Thr Asp Gly Glu Leu Glu Ile Asn Ile Thr Lys Val Gly
        1205                1210                1215

Thr Ala Asp Tyr Met Pro Gln Ile Lys Gln Glu Asn Ile Ala Leu
        1220                1225                1230

Gln Glu Gly Val Thr Tyr Thr Leu Ser Leu Lys Ala Arg Ala Leu
        1235                1240                1245

Glu Ala Arg Ser Ile Lys Val Asp Ile Leu Asp Ser Ser Tyr Asn
        1250                1255                1260

Trp Tyr Gly Gly Thr Ile Phe Asp Leu Thr Thr Glu Asp Ala Val
        1265                1270                1275

Tyr Thr Phe Thr Phe Thr Gln Ser Lys Ser Ile Asn Asn Gly Val
        1280                1285                1290

Leu Thr Ile Asn Leu Gly Thr Ile Glu Gly Lys Thr Ser Ala Ala
        1295                1300                1305
```

```
Thr Thr Val Tyr Leu Asp Asp Ile Leu Leu Glu Gln Gln
    1310                1315                 1320

<210> SEQ ID NO 25
<211> LENGTH: 1347
<212> TYPE: DNA
<213> ORGANISM: Clostridium thermocellum

<400> SEQUENCE: 25
atgtcaaaga taactttccc aaaagatttc atatggggtt ctgcaacagc agcatatcag      60
attgaaggtg catacaacga agacggcaaa ggtgaatcta tatgggaccg ttttttcccac    120 acgccaggaa atatagcaga cggacatacc ggcgatgttg catgcgacca ctatcatcgt    180
tatgaagaag atatcaaaat aatgaaagaa atcggtatta atcatacag gttttccatc     240 tcatggccca gaatctttcc tgaaggaaca ggtaaattaa atcaaaaggg actggatttt    300
tacaaaaggc tcacaaatct gcttctggaa aacggaatta tgcctgcaat cactctttat    360
cactgggacc ttccccaaaa gcttcaggat aaaggcggat ggaaaaaccg ggacaccacc    420
gattatttta cagaatactc tgaagtaata tttaaaaatc tcggagatat cgttccaata    480
tggtttactc acaatgaacc cggtgttgtt tctttgcttg ccactttttt aggaattcat    540
gcccctggga taaaagacct ccgcacttca ttggaagtct cgcacaatct tcttttgtcc    600
cacggcaagg ccgtgaaact gtttagaaga atgaatattg acgcccaaat tggaatagct    660
ctcaatttat cttaccatta tcccgcatcc gaaaaagctg aggatattga agcagcggaa    720 ttgtcattt ctctggcggg aaggtggtat ctggatcctg tgctaaaagg ccggtatcct    780
gaaaacgcat tgaaacttta taaaaagaag ggtattgagc tttctttccc tgaagatgac    840
ctgaaactta tcagtcagcc aatagacttc atagcattca acaattattc ttcggaattt    900
ataaaatatg atccgtccag tgagtcaggt ttttcacctg caaactccat attagaaaag    960
ttcgaaaaaa cagatatggg ctggatcata tatcctgaag gcttgtatga tctgcttatg   1020
ctccttgaca gggattatgg aaagccaaac attgttatca gcgaaaacgg agccgccttc   1080
aaagatgaaa taggtagcaa cggaaagata gaagacacaa agagaatcca atatcttaaa   1140
gattatctga cccaggctca cagggcaatt caggacggtg taaacttaaa agcatactac   1200
ttgtggtcgc ttttggacaa cttttgaatgg gcttacgggt acaacaagag attcggaatc   1260
gttcacgtaa atttttgatac gttggaaaga aaaataaagg atagcggcta ctggtacaaa   1320
gaagtaatca aaacaacgg tttttaa                                         1347

<210> SEQ ID NO 26
<211> LENGTH: 448
<212> TYPE: PRT
<213> ORGANISM: Clostridium thermocellum
<220> FEATURE:
<221> NAME/KEY: DOMAIN
<222> LOCATION: (2)...(448)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
      signature. Prosite id = PS00653
<220> FEATURE:
<221> NAME/KEY: SITE
<222> LOCATION: (225)...(228)
<223> OTHER INFORMATION: N-glycosylation site. Prosite id = PS00001
<220> FEATURE:
<221> NAME/KEY: SITE
<222> LOCATION: (299)...(302)
<223> OTHER INFORMATION: N-glycosylation site. Prosite id = PS00001
<220> FEATURE:
```

```
<221> NAME/KEY: SITE
<222> LOCATION: (356)...(364)
<223> OTHER INFORMATION: Glycosyl hydrolases family 1 active site.
      Prosite id = PS00572

<400> SEQUENCE: 26
```

| | | | | | | | | | | | | | | |
|---|---|---|---|---|---|---|---|---|---|---|---|---|---|---|
| Met | Ser | Lys | Ile | Thr | Phe | Pro | Lys | Asp | Phe | Ile | Trp | Gly | Ser | Ala | Thr |
| 1 | | | | 5 | | | | | 10 | | | | | 15 | |
| Ala | Ala | Tyr | Gln | Ile | Glu | Gly | Ala | Tyr | Asn | Glu | Asp | Gly | Lys | Gly | Glu |
| | | | 20 | | | | | 25 | | | | | 30 | | |
| Ser | Ile | Trp | Asp | Arg | Phe | Ser | His | Thr | Pro | Gly | Asn | Ile | Ala | Asp | Gly |
| | | 35 | | | | | 40 | | | | | 45 | | | |
| His | Thr | Gly | Asp | Val | Ala | Cys | Asp | His | Tyr | His | Arg | Tyr | Glu | Glu | Asp |
| | 50 | | | | | 55 | | | | | 60 | | | | |
| Ile | Lys | Ile | Met | Lys | Glu | Ile | Gly | Ile | Lys | Ser | Tyr | Arg | Phe | Ser | Ile |
| 65 | | | | | 70 | | | | | 75 | | | | | 80 |
| Ser | Trp | Pro | Arg | Ile | Phe | Pro | Glu | Gly | Thr | Gly | Lys | Leu | Asn | Gln | Lys |
| | | | | 85 | | | | | 90 | | | | | 95 | |
| Gly | Leu | Asp | Phe | Tyr | Lys | Arg | Leu | Thr | Asn | Leu | Leu | Leu | Glu | Asn | Gly |
| | | | | 100 | | | | | 105 | | | | | 110 | |
| Ile | Met | Pro | Ala | Ile | Thr | Leu | Tyr | His | Trp | Asp | Leu | Pro | Gln | Lys | Leu |
| | | | 115 | | | | | 120 | | | | | 125 | | |
| Gln | Asp | Lys | Gly | Gly | Trp | Lys | Asn | Arg | Asp | Thr | Thr | Asp | Tyr | Phe | Thr |
| | 130 | | | | | 135 | | | | | 140 | | | | |
| Glu | Tyr | Ser | Glu | Val | Ile | Phe | Lys | Asn | Leu | Gly | Asp | Ile | Val | Pro | Ile |
| 145 | | | | | 150 | | | | | 155 | | | | | 160 |
| Trp | Phe | Thr | His | Asn | Glu | Pro | Gly | Val | Val | Ser | Leu | Leu | Gly | His | Phe |
| | | | | 165 | | | | | 170 | | | | | 175 | |
| Leu | Gly | Ile | His | Ala | Pro | Gly | Ile | Lys | Asp | Leu | Arg | Thr | Ser | Leu | Glu |
| | | | 180 | | | | | 185 | | | | | 190 | | |
| Val | Ser | His | Asn | Leu | Leu | Leu | Ser | His | Gly | Lys | Ala | Val | Lys | Leu | Phe |
| | | 195 | | | | | 200 | | | | | 205 | | | |
| Arg | Glu | Met | Asn | Ile | Asp | Ala | Gln | Ile | Gly | Ile | Ala | Leu | Asn | Leu | Ser |
| | 210 | | | | | 215 | | | | | 220 | | | | |
| Tyr | His | Tyr | Pro | Ala | Ser | Glu | Lys | Ala | Glu | Asp | Ile | Glu | Ala | Ala | Glu |
| 225 | | | | | 230 | | | | | 235 | | | | | 240 |
| Leu | Ser | Phe | Ser | Leu | Ala | Gly | Arg | Trp | Tyr | Leu | Asp | Pro | Val | Leu | Lys |
| | | | | 245 | | | | | 250 | | | | | 255 | |
| Gly | Arg | Tyr | Pro | Glu | Asn | Ala | Leu | Lys | Leu | Tyr | Lys | Lys | Lys | Gly | Ile |
| | | | 260 | | | | | 265 | | | | | 270 | | |
| Glu | Leu | Ser | Phe | Pro | Glu | Asp | Leu | Lys | Leu | Ile | Ser | Gln | Pro | Ile |
| | | 275 | | | | | 280 | | | | | 285 | | | |
| Asp | Phe | Ile | Ala | Phe | Asn | Asn | Tyr | Ser | Ser | Glu | Phe | Ile | Lys | Tyr | Asp |
| | 290 | | | | | 295 | | | | | 300 | | | | |
| Pro | Ser | Ser | Glu | Ser | Gly | Phe | Ser | Pro | Ala | Asn | Ser | Ile | Leu | Glu | Lys |
| 305 | | | | | 310 | | | | | 315 | | | | | 320 |
| Phe | Glu | Lys | Thr | Asp | Met | Gly | Trp | Ile | Ile | Tyr | Pro | Glu | Gly | Leu | Tyr |
| | | | 325 | | | | | 330 | | | | | 335 | | |
| Asp | Leu | Leu | Met | Leu | Leu | Asp | Arg | Asp | Tyr | Gly | Lys | Pro | Asn | Ile | Val |
| | | | 340 | | | | | 345 | | | | | 350 | | |
| Ile | Ser | Glu | Asn | Gly | Ala | Ala | Phe | Lys | Asp | Glu | Ile | Gly | Ser | Asn | Gly |
| | | 355 | | | | | 360 | | | | | 365 | | | |
| Lys | Ile | Glu | Asp | Thr | Lys | Arg | Ile | Gln | Tyr | Leu | Lys | Asp | Tyr | Leu | Thr |
| | 370 | | | | | 375 | | | | | 380 | | | | |
| Gln | Ala | His | Arg | Ala | Ile | Gln | Asp | Gly | Val | Asn | Leu | Lys | Ala | Tyr | Tyr |

```
                385                 390                 395                 400

Leu Trp Ser Leu Leu Asp Asn Phe Glu Trp Ala Tyr Gly Tyr Asn Lys
                    405                 410                 415

Arg Phe Gly Ile Val His Val Asn Phe Asp Thr Leu Glu Arg Lys Ile
                420                 425                 430

Lys Asp Ser Gly Tyr Trp Tyr Lys Glu Val Ile Lys Asn Asn Gly Phe
            435                 440                 445

<210> SEQ ID NO 27
<211> LENGTH: 1362
<212> TYPE: DNA
<213> ORGANISM: Unknown
<220> FEATURE:
<223> OTHER INFORMATION: Obtained from environmental sample

<400> SEQUENCE: 27
atggcaaaca agataacctt tcctgaaaat tttctgtggg gcgcggcaac ggcttcgtac      60
cagatcgaag gcgcctggaa caaacatggt aaaggcgaat ccacctggga tcgcttttca     120
cacacgcccg gtaagatcag gaacaacgat acgggcgatg tagcaaatga ccattatcgc     180
ctctggaaaa agacattggg cttgatgaag aagatcgggt tgaaggctta tcgattttcc     240
atttcgtggc gcgcgtattct tcctgctgga agaggcaagg tcaatcaaag agggctggat     300
ttttacaaca agatcgtaga tgagctgctg aaagcagata tcatcccatt tgttactctc     360
aatcactggg acctgcccca aaaactggaa gatgagggcg gctggccggc ccgttctact     420
gccgatgctt ttattgaata cagatgtg atcacccgct cccttggcga ccgcgcaaag      480
aattggatca ctcacaatga acctgccgtc gttgcctgga tgggatactc cactggccaa     540
cacgcacccg gactgaagga ctatgggctt ggtgcccgcg ccgcgcatca cctgttgctc     600
tcacatggac aggctgtacc ggtcattcgc agcaatagcg cggggggcaga agtgggaatt     660 acgctcgata ttagctggcg gatcgctgcc tcaaacagcc gcgccgaccg ggagctggtc     720
cgtgaggatg atgggaggtg gttccgctgg tttgccgacc cgcttttacgg gcgcggatat     780 ccctccgata aggtgtctga tttcactaag ttgggagcac tgcccaacgg acttgatttt     840
gtgcaggcag gcgacatgga cacgatcgcg acaccgactg attttatggg gctaaactac     900
tactcccgaa atgtctaccg cgcggacggt gcagataatg atccgcaaac tgttttccca     960
caaccgaaga tgcccgaaca ctggaccgag atgggctggg aaatttaccc ggatgggctg    1020
accaacattc tgggacgcgt ctatttcaac tatcagccgc gcaaactata cgtcacagaa    1080
aacggcgcca gttactccac gcctcctgat gataagggga atgtcgcgga tgaactccgc    1140
atccattatc tgaggacaca ttttgcagct gcctatcggg ccattcaaat gggcgtgcct    1200
ctggcaggat acttcgtctg gtccctcatg gacaactttg agtggtcatg gggctatatg    1260
caacgctttg gactcatctg ggtggattat gagacccaaa aacgcacttt aaaggatagc    1320
gcaaaatggt ataagcgcgt gatcaagaag aatgggctct aa                       1362

<210> SEQ ID NO 28
<211> LENGTH: 453
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(453)
<223> OTHER INFORMATION: Glycosyl hydrolase family 1
<220> FEATURE:
<221> NAME/KEY: SITE
```

<222> LOCATION: (11)...(25)
<223> OTHER INFORMATION: Glycosyl hydrolases family 1 N-terminal
     signature. Prosite id = PS00653
<220> FEATURE:
<221> NAME/KEY: SITE
<222> LOCATION: (49)...(52)
<223> OTHER INFORMATION: N-glycosylation site. Prosite id = PS00001
<220> FEATURE:
<221> NAME/KEY: SITE
<222> LOCATION: (361)...(369)
<223> OTHER INFORMATION: Glycosyl hydrolases family 1 active site.
     Prosite id = PS00572

<400> SEQUENCE: 28

Met Ala Asn Lys Ile Thr Phe Pro Glu Asn Phe Leu Trp Gly Ala Ala
1               5                   10                  15

Thr Ala Ser Tyr Gln Ile Glu Gly Ala Trp Asn Lys His Gly Lys Gly
            20                  25                  30

Glu Ser Thr Trp Asp Arg Phe Ser His Thr Pro Gly Lys Ile Arg Asn
        35                  40                  45

Asn Asp Thr Gly Asp Val Ala Asn Asp His Tyr Arg Leu Trp Lys Lys
    50                  55                  60

Asp Ile Gly Leu Met Lys Lys Ile Gly Leu Lys Ala Tyr Arg Phe Ser
65                  70                  75                  80

Ile Ser Trp Pro Arg Ile Leu Pro Ala Gly Arg Gly Lys Val Asn Gln
            85                  90                  95

Arg Gly Leu Asp Phe Tyr Asn Lys Ile Val Asp Glu Leu Leu Lys Ala
        100                 105                 110

Asp Ile Ile Pro Phe Val Thr Leu Asn His Trp Asp Leu Pro Gln Lys
    115                 120                 125

Leu Glu Asp Glu Gly Gly Trp Pro Ala Arg Ser Thr Ala Asp Ala Phe
130                 135                 140

Ile Glu Tyr Thr Asp Val Ile Thr Arg Ser Leu Gly Asp Arg Ala Lys
145                 150                 155                 160

Asn Trp Ile Thr His Asn Glu Pro Ala Val Val Ala Trp Met Gly Tyr
            165                 170                 175

Ser Thr Gly Gln His Ala Pro Gly Leu Lys Asp Tyr Gly Leu Gly Ala
        180                 185                 190

Arg Ala Ala His His Leu Leu Leu Ser His Gly Gln Ala Val Pro Val
    195                 200                 205

Ile Arg Ser Asn Ser Ala Gly Ala Glu Val Gly Ile Thr Leu Asp Ile
210                 215                 220

Ser Trp Arg Ile Ala Ala Ser Asn Ser Arg Ala Asp Arg Glu Leu Val
225                 230                 235                 240

Arg Glu Asp Asp Gly Arg Trp Phe Arg Trp Phe Ala Asp Pro Leu Tyr
            245                 250                 255

Gly Arg Gly Tyr Pro Ser Asp Lys Val Ser Asp Phe Thr Lys Leu Gly
        260                 265                 270

Ala Leu Pro Asn Gly Leu Asp Phe Val Gln Ala Gly Asp Met Asp Thr
    275                 280                 285

Ile Ala Thr Pro Thr Asp Phe Met Gly Leu Asn Tyr Tyr Ser Arg Asn
290                 295                 300

Val Tyr Arg Ala Asp Gly Ala Asp Asn Asp Pro Gln Thr Val Phe Pro
305                 310                 315                 320

Gln Pro Lys Met Pro Glu His Trp Thr Glu Met Gly Trp Glu Ile Tyr
            325                 330                 335

Pro Asp Gly Leu Thr Asn Ile Leu Gly Arg Val Tyr Phe Asn Tyr Gln
        340                 345                 350

```
Pro Arg Lys Leu Tyr Val Thr Glu Asn Gly Ala Ser Tyr Ser Thr Pro
        355                 360                 365

Pro Asp Asp Lys Gly Asn Val Ala Asp Glu Leu Arg Ile His Tyr Leu
    370                 375                 380

Arg Thr His Phe Ala Ala Ala Tyr Arg Ala Ile Gln Met Gly Val Pro
385                 390                 395                 400

Leu Ala Gly Tyr Phe Val Trp Ser Leu Met Asp Asn Phe Glu Trp Ser
                405                 410                 415

Trp Gly Tyr Met Gln Arg Phe Gly Leu Ile Trp Val Asp Tyr Glu Thr
                420                 425                 430

Gln Lys Arg Thr Leu Lys Asp Ser Ala Lys Trp Tyr Lys Arg Val Ile
                435                 440                 445

Lys Lys Asn Gly Leu
        450

<210> SEQ ID NO 29
<211> LENGTH: 1362
<212> TYPE: DNA
<213> ORGANISM: Unknown
<220> FEATURE:
<223> OTHER INFORMATION: Obtained from environmental sample

<400> SEQUENCE: 29
```

| | | | | | |
|---|---|---|---|---|---|
| atggcgaaca | aaattacctt | tcccgaaaat | tttctttggg | gcgcggcaac | agcctcctac | 60 |
| cagatcgaag | gtgcgtggga | caaacatggc | aagggtgaat | ccatctggga | tcgcttttcg | 120 |
| catacccctg | gcaagatcag | aaataatgat | acgggcgatg | ttgccaatga | tcattatcgt | 180 |
| ctctggaaaa | aagacattgg | cttgatgaag | aagatcggct | tgaaggcata | tcgtttttcc | 240 |
| atttcgtggc | cgcgtgttct | tcccgccgga | cgcggcaaag | tcaatcagaa | gggactggat | 300 |
| ttctataaca | ggctggtaga | tgctctgttg | aaagaagata | tcatcccatt | tgtgactctc | 360 |
| aatcactggg | acctgcccca | aaagctggag | gaggaaggcg | gttggccggt | tcgctccacc | 420 |
| gcagatgcct | tgtgtggaata | cacagacgtg | gtcacacgtt | ccctcggcga | ccgcgtaaag | 480 |
| aattggatca | cgcataatga | gcctgccgtc | gttgcctgga | tgggatattc | cacaggtcaa | 540 |
| cacgcacccg | gtttgaagga | ctatgggctt | ggtgtgcgcg | ccgcgcatca | tctgctgctc | 600 |
| tcccacgggc | aggcggtgcc | agtcatccgc | agtaacagcg | ccgatgcaga | agtgggcatt | 660 |
| acgctggata | ttagctggcg | gattcctgcc | tccaatagcc | gagcagaccg | ggaattggtc | 720 |
| cgtaaagatg | acggactatg | gttccgctgg | ttcgccgatc | cgctttatgg | gcgcggatac | 780 |
| ccctcggata | aagtcaccga | ttttacaaag | atcggcgcgc | tgcccaatgg | tctggacttt | 840 |
| atgcaagccg | gtgatatgga | tgcgatcgcc | acgccaaccg | atttcatggg | gctgaactat | 900 |
| tatttccgaa | atgtctaccg | cgcgaatggc | gaagacaatg | atccgcaggt | cgttttccca | 960 |
| caaccaaaga | tgcccgaaca | ctggacggag | atgggctggg | aaatctatcc | ggatggactg | 1020 |
| acgaacatcc | tgggacgcgt | ttatttcaat | taccagccac | ataaactgta | tatcacagag | 1080 |
| aacggcgcga | gctactccac | cccgcccgat | gaaaagggga | atgtcgccga | tgagctccgc | 1140 |
| actcattatt | tacggacaca | cttcgcggct | gcctaccggg | cgattcagat | gggcgtgcct | 1200 |
| ctggcaggat | actttgtctg | gtccctcatg | gacaactttg | agtggtcctg | ggatatatg | 1260 |
| cagcgctttg | ggctcatctg | ggtggactac | gagacacaga | aacgcaccct | gaaggatagc | 1320 |
| gccaagtggt | acaaacgtgt | gatcaggaag | aatgggtttt | ag | | 1362 |

```
<210> SEQ ID NO 30
```

```
<211> LENGTH: 453
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(453)
<223> OTHER INFORMATION: Glycosyl hydrolase family 1
<220> FEATURE:
<221> NAME/KEY: SITE
<222> LOCATION: (11)...(25)
<223> OTHER INFORMATION: Glycosyl hydrolases family 1 N-terminal
      signature. Prosite id = PS00653
<220> FEATURE:
<221> NAME/KEY: SITE
<222> LOCATION: (49)...(52)
<223> OTHER INFORMATION: N-glycosylation site. Prosite id = PS00001
<220> FEATURE:
<221> NAME/KEY: SITE
<222> LOCATION: (361)...(369)
<223> OTHER INFORMATION: Glycosyl hydrolases family 1 active site.
      Prosite id = PS00572

<400> SEQUENCE: 30

Met Ala Asn Lys Ile Thr Phe Pro Glu Asn Phe Leu Trp Gly Ala Ala
1               5                   10                  15

Thr Ala Ser Tyr Gln Ile Glu Gly Ala Trp Asp Lys His Gly Lys Gly
            20                  25                  30

Glu Ser Ile Trp Asp Arg Phe Ser His Thr Pro Gly Lys Ile Arg Asn
        35                  40                  45

Asn Asp Thr Gly Asp Val Ala Asn Asp His Tyr Arg Leu Trp Lys Lys
    50                  55                  60

Asp Ile Gly Leu Met Lys Lys Ile Gly Leu Lys Ala Tyr Arg Phe Ser
65                  70                  75                  80

Ile Ser Trp Pro Arg Val Leu Pro Ala Gly Arg Gly Lys Val Asn Gln
                85                  90                  95

Lys Gly Leu Asp Phe Tyr Asn Arg Leu Val Asp Ala Leu Leu Lys Glu
            100                 105                 110

Asp Ile Ile Pro Phe Val Thr Leu Asn His Trp Asp Leu Pro Gln Lys
        115                 120                 125

Leu Glu Glu Glu Gly Gly Trp Pro Val Arg Ser Thr Ala Asp Ala Phe
    130                 135                 140

Val Glu Tyr Thr Asp Val Val Thr Arg Ser Leu Gly Asp Arg Val Lys
145                 150                 155                 160

Asn Trp Ile Thr His Asn Glu Pro Ala Val Val Ala Trp Met Gly Tyr
                165                 170                 175

Ser Thr Gly Gln His Ala Pro Gly Leu Lys Asp Tyr Gly Leu Gly Val
            180                 185                 190

Arg Ala Ala His His Leu Leu Leu Ser His Gly Gln Ala Val Pro Val
        195                 200                 205

Ile Arg Ser Asn Ser Ala Asp Ala Glu Val Gly Ile Thr Leu Asp Ile
    210                 215                 220

Ser Trp Arg Ile Pro Ala Ser Asn Ser Arg Ala Asp Arg Glu Leu Val
225                 230                 235                 240

Arg Lys Asp Asp Gly Leu Trp Phe Arg Trp Phe Ala Asp Pro Leu Tyr
                245                 250                 255

Gly Arg Gly Tyr Pro Ser Asp Lys Val Thr Asp Phe Thr Lys Ile Gly
            260                 265                 270

Ala Leu Pro Asn Gly Leu Asp Phe Met Gln Ala Gly Asp Met Asp Ala
        275                 280                 285
```

```
Ile Ala Thr Pro Thr Asp Phe Met Gly Leu Asn Tyr Tyr Phe Arg Asn
        290                 295                 300

Val Tyr Arg Ala Asn Gly Glu Asp Asn Asp Pro Gln Val Val Phe Pro
305                 310                 315                 320

Gln Pro Lys Met Pro Glu His Trp Thr Glu Met Gly Trp Glu Ile Tyr
                325                 330                 335

Pro Asp Gly Leu Thr Asn Ile Leu Gly Arg Val Tyr Phe Asn Tyr Gln
            340                 345                 350

Pro His Lys Leu Tyr Ile Thr Glu Asn Gly Ala Ser Tyr Ser Thr Pro
        355                 360                 365

Pro Asp Glu Lys Gly Asn Val Ala Asp Glu Leu Arg Thr His Tyr Leu
    370                 375                 380

Arg Thr His Phe Ala Ala Ala Tyr Arg Ala Ile Gln Met Gly Val Pro
385                 390                 395                 400

Leu Ala Gly Tyr Phe Val Trp Ser Leu Met Asp Asn Phe Glu Trp Ser
                405                 410                 415

Trp Gly Tyr Met Gln Arg Phe Gly Leu Ile Trp Val Asp Tyr Glu Thr
            420                 425                 430

Gln Lys Arg Thr Leu Lys Asp Ser Ala Lys Trp Tyr Lys Arg Val Ile
        435                 440                 445

Arg Lys Asn Gly Phe
    450
```

<210> SEQ ID NO 31
<211> LENGTH: 1167
<212> TYPE: DNA
<213> ORGANISM: Unknown
<220> FEATURE:
<223> OTHER INFORMATION: Obtained from environmental sample

<400> SEQUENCE: 31

```
atggaagacc gcccgcacta ttacagcgac gaccatctct ggggtgtact gtgcgtgacc     60
gcctacatca aggaaactgg ggactttgca ttcctggacg agaaagttca cttttacgag    120
aaggacccgg tcgagggcgt gtctgtgctg atcacgttaa acgggcctt gacctttacc    180
cgcaacaaca tcgggaaaca tggtctgcct ctcctcggct tgcggattg gaacgacacg    240
atcaatctgg cgaagggcgc cgagtctctt ttcacgtcgc atctatatgg acgcgcgctg    300
ctggagttta ttgatctgct cacatatctt ggcaagaacg atgaagccga tgaatggcag    360
cgagcccacg ttgagatgca gtcccgcgtc gaaaaacatg cctgggatgg cgaatggtat    420
ttcatgtact ttgaccacga cggcagcccg gttgggtctc acacgaatca gtatggaaag    480
atccatctca acggacagag ctgggctgtg ctttcgggct tgcctctcc gcagcgcgcc    540
cgccaggcca tggactcggt ttacaagcat ctcaacacaa agcacggcat caagctctcc    600
acgccgggct acaatggcta tgaccccaac tacggcggcg tgaccaccta cccaccggga    660
gcaaaggaaa acggcggcat cttcctgcac ccgaatccct gggccatgat cgcagagacc    720
atgctcgggg atggcgatcg cgcctacgag tattactcgc agatcaaccc ggccggcaag    780
aacgatgaca tcgacctgta cgaggtcgag ccatatgttt acgctcaaaa catcctgggc    840
gatgagcatc gcagttcgg gctgggacgc aactcgtggc tctcgggtac ggcatcctgg    900
tgctatcagg ctgccacaca gtggatcctc ggaatccgcg ccgactatga agggctcgc    960
atcgacccgt gcattccgtc caagtgggat gggttcaagg caacgcgcct gtatcgcggc   1020
gtgaagtaca acattacggt caccaacccg aagcacatct gcaaaggcgt ggaaaaagtt   1080
ctggtcaacg gcaaaccggt tgagggggat gtggtccggg cagacgtggg tttgcgcgaa   1140
```
gtgaacgtgg aagttacctt aggataa                                    1167

<210> SEQ ID NO 32
<211> LENGTH: 388
<212> TYPE: PRT
<213> ORGANISM: Unknown
<220> FEATURE:
<223> OTHER INFORMATION: Obtained from environmental sample
<220> FEATURE:
<221> NAME/KEY: SITE
<222> LOCATION: (79)...(82)
<223> OTHER INFORMATION: N-glycosylation site. Prosite id = PS00001
<220> FEATURE:
<221> NAME/KEY: SITE
<222> LOCATION: (349)...(352)
<223> OTHER INFORMATION: N-glycosylation site. Prosite id = PS00001

<400> SEQUENCE: 32

```
Met Glu Asp Arg Pro His Tyr Tyr Ser Asp Asp His Leu Trp Gly Val
1               5                   10                  15

Leu Cys Val Thr Ala Tyr Ile Lys Glu Thr Gly Asp Phe Ala Phe Leu
            20                  25                  30

Asp Glu Lys Val His Phe Tyr Glu Lys Asp Pro Val Glu Gly Val Ser
        35                  40                  45

Val Leu Asp His Val Lys Arg Ala Leu Thr Phe Thr Arg Asn Asn Ile
50                  55                  60

Gly Lys His Gly Leu Pro Leu Leu Gly Phe Ala Asp Trp Asn Asp Thr
65                  70                  75                  80

Ile Asn Leu Ala Lys Gly Ala Glu Ser Leu Phe Thr Ser His Leu Tyr
                85                  90                  95

Gly Arg Ala Leu Leu Glu Phe Ile Asp Leu Leu Thr Tyr Leu Gly Lys
            100                 105                 110

Asn Asp Glu Ala Asp Glu Trp Gln Arg Ala His Val Glu Met Gln Ser
        115                 120                 125

Arg Val Glu Lys His Ala Trp Asp Gly Glu Trp Tyr Phe Met Tyr Phe
130                 135                 140

Asp His Asp Gly Ser Pro Val Gly Ser His Thr Asn Gln Tyr Gly Lys
145                 150                 155                 160

Ile His Leu Asn Gly Gln Ser Trp Ala Val Leu Ser Gly Phe Ala Ser
                165                 170                 175

Pro Gln Arg Ala Arg Gln Ala Met Asp Ser Val Tyr Lys His Leu Asn
            180                 185                 190

Thr Lys His Gly Ile Lys Leu Ser Thr Pro Gly Tyr Asn Gly Tyr Asp
        195                 200                 205

Pro Asn Tyr Gly Gly Val Thr Thr Tyr Pro Pro Gly Ala Lys Glu Asn
210                 215                 220

Gly Gly Ile Phe Leu His Pro Asn Pro Trp Ala Met Ile Ala Glu Thr
225                 230                 235                 240

Met Leu Gly Asp Gly Asp Arg Ala Tyr Glu Tyr Ser Gln Ile Asn
                245                 250                 255

Pro Ala Gly Lys Asn Asp Asp Ile Asp Leu Tyr Glu Val Glu Pro Tyr
            260                 265                 270

Val Tyr Ala Gln Asn Ile Leu Gly Asp Glu His Pro Gln Phe Gly Leu
        275                 280                 285

Gly Arg Asn Ser Trp Leu Ser Gly Thr Ala Ser Trp Cys Tyr Gln Ala
290                 295                 300

Ala Thr Gln Trp Ile Leu Gly Ile Arg Ala Asp Tyr Glu Gly Leu Arg
305                 310                 315                 320
```

Ile Asp Pro Cys Ile Pro Ser Lys Trp Asp Gly Phe Lys Ala Thr Arg
            325                 330                 335

Leu Tyr Arg Gly Val Lys Tyr Asn Ile Thr Val Thr Asn Pro Lys His
            340                 345                 350

Ile Cys Lys Gly Val Glu Lys Val Leu Val Asn Gly Lys Pro Val Glu
            355                 360                 365

Gly Asn Val Val Arg Ala Asp Val Gly Leu Arg Glu Val Asn Val Glu
        370                 375                 380

Val Thr Leu Gly
385

<210> SEQ ID NO 33
<211> LENGTH: 1362
<212> TYPE: DNA
<213> ORGANISM: Unknown
<220> FEATURE:
<223> OTHER INFORMATION: Obtained from environmental sample

<400> SEQUENCE: 33
atggcaaata aaattctctt ccccgagaac tttctctggg gcacggcgac cgcatcctac      60
cagatcgagg gggcttggga taaacatggt aagggcgagt cgacctggga ccgttttacg     120
catacacctg gaaagatcaa aaacaatgat acgggcgatg tagcagatga ccattatcga     180
ttatggaaaa agatatcgg cttgatgaag aagctcggct tgaaggctta tcgttttcg      240 acttcctggc cgcgggtgct gccggccggg cgcggtaaga gcaatcaaaa aggactcgat     300
ttctacagca agctggttga tgagttgcta aaagcaaata tcatcccatt cgtgacattg     360
aatcactggg acatcccaca aaagttggag gacgaggggtg gctgggccgt gcgctcaacg     420
gctgaggcat ttgtggaata tgccgatctc atgtcgcgca cgcttggaga ccgcgtcaag     480
aactggatca cgcacaacga accggccgtc gtcgcctgga tgggatacgg gatgggcatc     540
cacgcgccgg gcttaacgga tttctcgatt gcggtgccgg tctcgcatca tctgctcctt     600
tcgcacggat gggccgtgcc tgtgattcgc ggtaacagcc cggatgccga ggtgggcatt     660
accctcaaca ttcaatgggg cgaagcagca tccaacagcc gggccgacct aaacgccctg     720
cgcctgaacg atggacagtg gttccgctgg tttgccgatc cggtttatgg ccgcggctat     780
ccttccgacg tggtggctga tttcgagaaa atgggcgcgc tgccgaacgg catgaatttc     840
gtgcaacctg gcgatatgga tgtcatcgcc acgccaaccg atttcctcgg gctcaattat     900
tattcccgcc atgtgcatcg cgtcaacaca ccggataacg atcaacaggt tgtgtttgcc     960
aaacagcagg gtcccgagaa ctggaccgag atgggctggg agatccatcc tgatggattg    1020
gccggaattt tatccagagc gtatttcaat taccagccgc gcaaagtata tgtgactgaa    1080
aacggtgcca gctattccac cgcgcccgat gagaatggta ttgtcaacga cattcaccgc    1140
gtcaattatc tacggacgca cttcgcggct gcccatcgcg ccctgcaggc gggcgtgcca    1200
ttggcaggat acttcgtctg gtcaatgctc gataacttcg aatggagtca cgggtacagc    1260
cagcgctttg gcatcgttta tgtggactat caaacccaga gcgttacttt gaaagacagc    1320
gccaagtggt acaaaggtgt catcaaaaag aatgggttct aa                       1362

<210> SEQ ID NO 34
<211> LENGTH: 453
<212> TYPE: PRT
<213> ORGANISM: Unknown
<220> FEATURE:
<223> OTHER INFORMATION: Obtained from environmental sample
<220> FEATURE:

-continued

```
<221> NAME/KEY: DOMAIN
<222> LOCATION: (3)...(453)
<223> OTHER INFORMATION: Glycosyl hydrolase family 1
<220> FEATURE:
<221> NAME/KEY: SITE
<222> LOCATION: (11)...(25)
<223> OTHER INFORMATION: Glycosyl hydrolases family 1 N-terminal
      signature. Prosite id = PS00653
<220> FEATURE:
<221> NAME/KEY: SITE
<222> LOCATION: (49)...(52)
<223> OTHER INFORMATION: N-glycosylation site. Prosite id = PS00001
<220> FEATURE:
<221> NAME/KEY: SITE
<222> LOCATION: (332)...(335)
<223> OTHER INFORMATION: N-glycosylation site. Prosite id = PS00001
<220> FEATURE:
<221> NAME/KEY: SITE
<222> LOCATION: (361)...(369)
<223> OTHER INFORMATION: Glycosyl hydrolases family 1 active site.
      Prosite id = PS00572

<400> SEQUENCE: 34

Met Ala Asn Lys Ile Leu Phe Pro Glu Asn Phe Leu Trp Gly Thr Ala
1               5                   10                  15

Thr Ala Ser Tyr Gln Ile Glu Gly Ala Trp Asp Lys His Gly Lys Gly
            20                  25                  30

Glu Ser Thr Trp Asp Arg Phe Thr His Thr Pro Gly Lys Ile Lys Asn
        35                  40                  45

Asn Asp Thr Gly Asp Val Ala Asp His Tyr Arg Leu Trp Lys Lys
    50                  55                  60

Asp Ile Gly Leu Met Lys Lys Leu Gly Leu Lys Ala Tyr Arg Phe Ser
65                  70                  75                  80

Thr Ser Trp Pro Arg Val Leu Pro Ala Gly Arg Gly Lys Ser Asn Gln
                85                  90                  95

Lys Gly Leu Asp Phe Tyr Ser Lys Leu Val Asp Glu Leu Leu Lys Ala
            100                 105                 110

Asn Ile Ile Pro Phe Val Thr Leu Asn His Trp Asp Ile Pro Gln Lys
        115                 120                 125

Leu Glu Asp Glu Gly Gly Trp Ala Val Arg Ser Thr Ala Glu Ala Phe
    130                 135                 140

Val Glu Tyr Ala Asp Leu Met Ser Arg Thr Leu Gly Asp Arg Val Lys
145                 150                 155                 160

Asn Trp Ile Thr His Asn Glu Pro Ala Val Val Ala Trp Met Gly Tyr
                165                 170                 175

Gly Met Gly Ile His Ala Pro Gly Leu Thr Asp Phe Ser Ile Ala Val
            180                 185                 190

Pro Val Ser His His Leu Leu Leu Ser His Gly Trp Ala Val Pro Val
        195                 200                 205

Ile Arg Gly Asn Ser Pro Asp Ala Glu Val Gly Ile Thr Leu Asn Ile
    210                 215                 220

Gln Trp Gly Glu Ala Ala Ser Asn Ser Arg Ala Asp Leu Asn Ala Leu
225                 230                 235                 240

Arg Leu Asn Asp Gly Gln Trp Phe Arg Trp Phe Ala Asp Pro Val Tyr
                245                 250                 255

Gly Arg Gly Tyr Pro Ser Asp Val Val Ala Asp Phe Glu Lys Met Gly
            260                 265                 270

Ala Leu Pro Asn Gly Met Asn Phe Val Gln Pro Gly Asp Met Asp Val
        275                 280                 285

Ile Ala Thr Pro Thr Asp Phe Leu Gly Leu Asn Tyr Tyr Ser Arg His
    290                 295                 300
```

Val His Arg Val Asn Thr Pro Asp Asn Asp Gln Gln Val Val Phe Ala
305                 310                 315                 320

Lys Gln Gln Gly Pro Glu Asn Trp Thr Glu Met Gly Trp Glu Ile His
            325                 330                 335

Pro Asp Gly Leu Ala Gly Ile Leu Ser Arg Ala Tyr Phe Asn Tyr Gln
            340                 345                 350

Pro Arg Lys Val Tyr Val Thr Glu Asn Gly Ala Ser Tyr Ser Thr Ala
            355                 360                 365

Pro Asp Glu Asn Gly Ile Val Asn Asp Ile His Arg Val Asn Tyr Leu
            370                 375                 380

Arg Thr His Phe Ala Ala His Arg Ala Leu Gln Ala Gly Val Pro
385                 390                 395                 400

Leu Ala Gly Tyr Phe Val Trp Ser Met Leu Asp Asn Phe Glu Trp Ser
                405                 410                 415

His Gly Tyr Ser Gln Arg Phe Gly Ile Val Tyr Val Asp Tyr Gln Thr
            420                 425                 430

Gln Lys Arg Tyr Leu Lys Asp Ser Ala Lys Trp Tyr Lys Gly Val Ile
            435                 440                 445

Lys Lys Asn Gly Phe
    450

<210> SEQ ID NO 35
<211> LENGTH: 1116
<212> TYPE: DNA
<213> ORGANISM: Unknown
<220> FEATURE:
<223> OTHER INFORMATION: Obtained from environmental sample

<400> SEQUENCE: 35
atgaataaaa tcctcaaact cttcagcagc ctgctgcttt ttgcaggcat ctgtcccgcg        60
cttcaggcag agccagtaga aacctacttt cccctgtccc gcgggatcaa catgagccac       120
tggctctctc aagtgaatga aacattcccc gaccgttcca cctatgtgac ggagcgggat       180
ttgcaatttc tgcgggcagc cggtttcgac catgtgcgtc tgccaatcga tgaggtcgaa       240
ctctgggatg aagagggcaa tcagatcgag gaggcctggc aatacatgca taactttctc       300
cgttggagcc gaaagaacga tctccgggtc attctcgacc tgcacacggt attgtcccac       360
cacttcaacg cggtaaatat gggagaggtc aatacactct tcaatgatcc cagggaacag       420
gaaaagttcc tcaacctatg gaacaaatc atggatgccg tgggtcacca tccgaatgag       480
tttctcgcct atgaaatgct caatgaggcg gtcgcggaag atgatgaaga ctggaatctg       540
ctcctcaacc gcgccattgt ccgcatccgg gaccgtgagc cttatcgggt gctgattgcg       600
gggtcgaact ggtggcagca tgccgaccgg gtccccaacc tgaggctccc gaaaggagac       660
cccaatatca tcatcagttt tcattttat tcccctttc tcttcaccca ctaccgcagt        720
agctggactg cgatgcaggc gtaccagggc ttcgtccaat accctggcaa aaccatacct       780
tccatacatc tcgaaggcat gaactacccg gagtccttcg ttcatatgtg gaagcgcac       840 aatcggtact atgacatcca ttccatgtat gccgaaatgg tcccggcggt gcgttttgcc       900
gaaaagttgg gacttcggct ctattgcgga gaattcgggg ccatgaagac cgttgatcgc       960
gcccagatgc tgcagtggta tcgggatgtt gtcactgtat taataaaatt gggtattccc      1020
tatactgcct gggattatca gggaaccttc ggaatccgcg atgagctgac cggtgagccc      1080
gatcatgaaa tgatcgatat tctcctcggg cgctga                                1116

-continued

```
<210> SEQ ID NO 36
<211> LENGTH: 371
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(23)
<220> FEATURE:
<221> NAME/KEY: DOMAIN
<222> LOCATION: (39)...(350)
<223> OTHER INFORMATION: Cellulase (glycosyl hydrolase family 5)
<220> FEATURE:
<221> NAME/KEY: SITE
<222> LOCATION: (37)...(40)
<223> OTHER INFORMATION: N-glycosylation site. Prosite id = PS00001

<400> SEQUENCE: 36

Met Asn Lys Ile Leu Lys Leu Phe Ser Ser Leu Leu Leu Phe Ala Gly
1               5                   10                  15

Ile Cys Pro Ala Leu Gln Ala Glu Pro Val Glu Thr Tyr Phe Pro Leu
            20                  25                  30

Ser Arg Gly Ile Asn Met Ser His Trp Leu Ser Gln Val Asn Glu Asn
        35                  40                  45

Ile Pro Asp Arg Ser Thr Tyr Val Thr Glu Arg Asp Leu Gln Phe Leu
    50                  55                  60

Arg Ala Ala Gly Phe Asp His Val Arg Leu Pro Ile Asp Glu Val Glu
65                  70                  75                  80

Leu Trp Asp Glu Glu Gly Asn Gln Ile Glu Glu Ala Trp Gln Tyr Met
                85                  90                  95

His Asn Phe Leu Arg Trp Ser Arg Lys Asn Asp Leu Arg Val Ile Leu
            100                 105                 110

Asp Leu His Thr Val Leu Ser His His Phe Asn Ala Val Asn Met Gly
        115                 120                 125

Glu Val Asn Thr Leu Phe Asn Asp Pro Arg Glu Gln Glu Lys Phe Leu
    130                 135                 140

Asn Leu Trp Glu Gln Ile Met Asp Ala Val Gly His His Pro Asn Glu
145                 150                 155                 160

Phe Leu Ala Tyr Glu Met Leu Asn Glu Ala Val Ala Glu Asp Asp Glu
                165                 170                 175

Asp Trp Asn Leu Leu Asn Arg Ala Ile Val Arg Ile Arg Asp Arg
            180                 185                 190

Glu Pro Tyr Arg Val Leu Ile Ala Gly Ser Asn Trp Trp Gln His Ala
        195                 200                 205

Asp Arg Val Pro Asn Leu Arg Leu Pro Lys Gly Asp Pro Asn Ile Ile
    210                 215                 220

Ile Ser Phe His Phe Tyr Ser Pro Phe Leu Phe Thr His Tyr Arg Ser
225                 230                 235                 240

Ser Trp Thr Ala Met Gln Ala Tyr Gln Gly Phe Val Gln Tyr Pro Gly
                245                 250                 255

Lys Thr Ile Pro Ser Ile His Leu Glu Gly Met Asn Tyr Pro Glu Ser
            260                 265                 270

Phe Val His Met Trp Glu Ala His Asn Arg Tyr Tyr Asp Ile His Ser
        275                 280                 285

Met Tyr Ala Glu Met Val Pro Ala Val Arg Phe Ala Glu Lys Leu Gly
    290                 295                 300

Leu Arg Leu Tyr Cys Gly Glu Phe Gly Ala Met Lys Thr Val Asp Arg
305                 310                 315                 320
```

```
Ala Gln Met Leu Gln Trp Tyr Arg Asp Val Thr Val Phe Asn Lys
            325                 330                 335

Leu Gly Ile Pro Tyr Thr Ala Trp Asp Tyr Gln Gly Thr Phe Gly Ile
        340                 345                 350

Arg Asp Glu Leu Thr Gly Glu Pro Asp His Glu Met Ile Asp Ile Leu
        355                 360                 365

Leu Gly Arg
    370

<210> SEQ ID NO 37
<211> LENGTH: 1383
<212> TYPE: DNA
<213> ORGANISM: Unknown
<220> FEATURE:
<223> OTHER INFORMATION: Obtained from environmental sample

<400> SEQUENCE: 37
atgagcaaac tccccaaatt cctctttgga gccggcacct caagttatca gatcgaaggt      60
gcctggaata tagatggcaa aggtccctcc atttgggatt ccacactcg ccatcccggc      120 gcggtttatc ggatgcacaa cggggatatg gcctgcgatc attatcatcg gtatcgaacg      180
gatatcgagc tgatgcagaa gatcggccta gaggcttacc gcttttccat aaactggccc      240
cgggttctgc cggaagggac cggtgccgcc aatgaagcag gtctggactt ttacgaccgg      300
ctggtggacg cactgttgga agcgggaatt cagccttgga tcacccttta tcactgggaa      360 ctccccctggg ctctccacct cgcgggggt tggctcaatc gggacatgcc cgaccacatt      420
gagaactacg ccgccttggt cgccaggtgc ctcggtgacc gggtgaaaaa ctggattact      480
ttgaatgagc tcaggttttt catcgggctt ggctatgcca gcggggttca tgccccggc      540 tataagttgt ccttgcggga gtgcctggtc ggttcccacc atgccgtgct tcccaccac      600 cgggcagtca aggcgatccg ggccaactgc gaaggcagcg tccagatcgg ctcagccccg      660
gtgggtgttg tctgccgacc ggaaacggag tcggcagcag acattgaggc tgcccgccag      720
gccacctacc atatcaacac tcccagcacc cacactcccg acaatctgat cggctgcctc      780
tggaacagca cttggtggat agatccaatg gttctgggga gtatccgga acacgggctg      840 aaagcctttg aaagctatct gccggacaac attcaggccg aactggatgc cgtattcgaa      900
ccgacggact ttgtcggttc caacatctac acggccgca cggtgcgggc caagcaggat      960
ggtggttttg agtttatcga ccttccgccc ggcagccccc gcaccaccat gggctgggac      1020
atcaccccgg acatcctcta ctggggagga aagtatcttt acgaacgcta tggcaagccg      1080
atgtttatca cggaaaacgg cattgccgtc ccggaactgg tgaatgatga aggccaggtc      1140
gaggataccg tccgtgagca atacatgaag ctgcacctgc gtgggctgca gcgggcccgc      1200
gatgaaggca tccctatgc cggatacttc cactggtccc tgctcgacaa cttcgagtgg      1260
gaacaaggct actcccagcg ctttggcatg gtctacgtcg actaccagac ccaggaacgt      1320
atcctcaaac gttcgggcca gcatttcgct gccatcgtcc gggaaatcac cggaaccgcc      1380
taa                                                                   1383

<210> SEQ ID NO 38
<211> LENGTH: 460
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (1)...(458)
```

```
<223> OTHER INFORMATION: Glycosyl hydrolase family 1
<220> FEATURE:
<221> NAME/KEY: SITE
<222> LOCATION: (7)...(21)
<223> OTHER INFORMATION: Glycosyl hydrolases family 1 N-terminal
      signature. Prosite id = PS00653
<220> FEATURE:
<221> NAME/KEY: SITE
<222> LOCATION: (266)...(269)
<223> OTHER INFORMATION: N-glycosylation site. Prosite id = PS00001
<220> FEATURE:
<221> NAME/KEY: SITE
<222> LOCATION: (366)...(374)
<223> OTHER INFORMATION: Glycosyl hydrolases family 1 active site.
      Prosite id = PS00572

<400> SEQUENCE: 38
```

| | | | | | | | | | | | | | | |
|---|---|---|---|---|---|---|---|---|---|---|---|---|---|---|
| Met | Ser | Lys | Leu | Pro | Lys | Phe | Leu | Phe | Gly | Ala | Gly | Thr | Ser | Ser | Tyr |
| 1 | | | | 5 | | | | | 10 | | | | | 15 | |
| Gln | Ile | Glu | Gly | Ala | Trp | Asn | Ile | Asp | Gly | Lys | Gly | Pro | Ser | Ile | Trp |
| | | | | 20 | | | | | 25 | | | | | 30 | |
| Asp | Phe | His | Thr | Arg | His | Pro | Gly | Ala | Val | Tyr | Arg | Met | His | Asn | Gly |
| | | | 35 | | | | | 40 | | | | | 45 | | |
| Asp | Met | Ala | Cys | Asp | His | Tyr | His | Arg | Tyr | Arg | Thr | Asp | Ile | Glu | Leu |
| | 50 | | | | | 55 | | | | | 60 | | | | |
| Met | Gln | Lys | Ile | Gly | Leu | Glu | Ala | Tyr | Arg | Phe | Ser | Ile | Asn | Trp | Pro |
| 65 | | | | | 70 | | | | | 75 | | | | | 80 |
| Arg | Val | Leu | Pro | Glu | Gly | Thr | Gly | Ala | Ala | Asn | Glu | Ala | Gly | Leu | Asp |
| | | | | 85 | | | | | 90 | | | | | 95 | |
| Phe | Tyr | Asp | Arg | Leu | Val | Asp | Ala | Leu | Leu | Glu | Ala | Gly | Ile | Gln | Pro |
| | | | 100 | | | | | 105 | | | | | 110 | | |
| Trp | Ile | Thr | Leu | Tyr | His | Trp | Glu | Leu | Pro | Trp | Ala | Leu | His | Leu | Arg |
| | | 115 | | | | | 120 | | | | | 125 | | | |
| Gly | Gly | Trp | Leu | Asn | Arg | Asp | Met | Pro | Asp | His | Ile | Glu | Asn | Tyr | Ala |
| 130 | | | | | 135 | | | | | 140 | | | | | |
| Ala | Leu | Val | Ala | Arg | Cys | Leu | Gly | Asp | Arg | Val | Lys | Asn | Trp | Ile | Thr |
| 145 | | | | | 150 | | | | | 155 | | | | | 160 |
| Leu | Asn | Glu | Pro | Gln | Val | Phe | Ile | Gly | Leu | Gly | Tyr | Ala | Ser | Gly | Val |
| | | | | 165 | | | | | 170 | | | | | 175 | |
| His | Ala | Pro | Gly | Tyr | Lys | Leu | Ser | Leu | Arg | Glu | Cys | Leu | Val | Gly | Ser |
| | | | 180 | | | | | 185 | | | | | 190 | | |
| His | His | Ala | Val | Leu | Ser | His | His | Arg | Ala | Val | Lys | Ala | Ile | Arg | Ala |
| | | 195 | | | | | 200 | | | | | 205 | | | |
| Asn | Cys | Glu | Gly | Ser | Val | Gln | Ile | Gly | Ser | Ala | Pro | Val | Gly | Val | Val |
| 210 | | | | | 215 | | | | | 220 | | | | | |
| Cys | Arg | Pro | Glu | Thr | Glu | Ser | Ala | Ala | Asp | Ile | Glu | Ala | Ala | Arg | Gln |
| 225 | | | | | 230 | | | | | 235 | | | | | 240 |
| Ala | Thr | Tyr | His | Ile | Asn | Thr | Pro | Ser | Thr | His | Thr | Pro | Asp | Asn | Leu |
| | | | | 245 | | | | | 250 | | | | | 255 | |
| Ile | Gly | Cys | Leu | Trp | Asn | Ser | Thr | Trp | Trp | Ile | Asp | Pro | Met | Val | Leu |
| | | | 260 | | | | | 265 | | | | | 270 | | |
| Gly | Lys | Tyr | Pro | Glu | His | Gly | Leu | Lys | Ala | Phe | Glu | Ser | Tyr | Leu | Pro |
| | | 275 | | | | | 280 | | | | | 285 | | | |
| Asp | Asn | Ile | Gln | Ala | Glu | Leu | Asp | Ala | Val | Phe | Glu | Pro | Thr | Asp | Phe |
| 290 | | | | | 295 | | | | | 300 | | | | | |
| Val | Gly | Ser | Asn | Ile | Tyr | His | Gly | Arg | Thr | Val | Arg | Ala | Lys | Gln | Asp |
| 305 | | | | | 310 | | | | | 315 | | | | | 320 |
| Gly | Gly | Phe | Glu | Phe | Ile | Asp | Leu | Pro | Pro | Gly | Ser | Pro | Arg | Thr | Thr |
| | | | | 325 | | | | | 330 | | | | | 335 | |

```
Met Gly Trp Asp Ile Thr Pro Asp Ile Leu Tyr Trp Gly Lys Tyr
            340                 345                 350

Leu Tyr Glu Arg Tyr Gly Lys Pro Met Phe Ile Thr Glu Asn Gly Ile
        355                 360                 365

Ala Val Pro Glu Leu Val Asn Asp Glu Gly Gln Val Glu Asp Thr Val
    370                 375                 380

Arg Glu Gln Tyr Met Lys Leu His Leu Arg Gly Leu Gln Arg Ala Arg
385                 390                 395                 400

Asp Glu Gly Ile Pro Tyr Ala Gly Tyr Phe His Trp Ser Leu Leu Asp
                405                 410                 415

Asn Phe Glu Trp Glu Gln Gly Tyr Ser Gln Arg Phe Gly Met Val Tyr
            420                 425                 430

Val Asp Tyr Gln Thr Gln Glu Arg Ile Leu Lys Arg Ser Gly Gln His
        435                 440                 445

Phe Ala Ala Ile Val Arg Glu Ile Thr Gly Thr Ala
    450                 455                 460
```

<210> SEQ ID NO 39
<211> LENGTH: 1521
<212> TYPE: DNA
<213> ORGANISM: Unknown
<220> FEATURE:
<223> OTHER INFORMATION: Obtained from environmental sample

<400> SEQUENCE: 39

```
gtgctcgccc ataaccgctc gcaccgtgaa gaactcctca atcgccggcc ggttgaattc      60
atcagcgccc tggaggcccg ggcgagctc cagcgcatca ccgccgaggt ggaccctac      120
ctcgagatca ccgagatctg cgatcgcacc ctgcgcgccg gcgggcccggc gctgctgttc      180
gagaacgtca aggggcacga catgcctctg ctcggcaacc tcttcggcac gccgaagcgg      240
gttgccctcg gcatgggcca ggactccgtg gccgccctgc gcgaagtggg cgagctgctc      300
gccttcctca aggagccgga gcctcccaag ggctttcgcg acgcctggga caagctgccg      360
atcttcaagc aggtgatgag catggggccg aagaaggtcc gctcggcgcc ggtgcaggaa      420
aaggtgtacg agggcgacga ggtcgacctc gaccgcctgc cgatccagca ctgctggccc      480
ggcgacgccg cgcccctggt cacctggccg ctggtgatca cccgcgggcc ccacaagaag      540
cgccagaacc tcggcatcta ccgccagcag aagctgtcga gaaccggct gatcatgcgc      600
tggctctccc accgcggcgg ggcgctggac ttcctggagt tccagaaggc ccaccccggc      660
gagcccttcc cggtggcggt ggcgctgggc gccgacccgg cgaccatcct cggcgcggtg      720
acccccggtgc cggattcgct ctccgagtac gccttcgccg gctgctgcg cggctcgcgc      780
accgagctgg tcaagtgcgg ccacgccgac ctggacgtgc cggcctcggc ggagatcatc      840
ctggaggggt tcatctaccc ggatgacatg gccccgagg gccccgtacgg cgaccatacc      900
ggctactaca cgaggtgga taccttcccg gtcttcacgg tgacgcgtat gaccatgcgc      960
cgcgatgcca tctatcactc cacctacacc ggccggccgc cgacgagcc ggcgatcctt      1020
gggctggcgc tcaacgaggt gttcgtgccg atcctgcgcc gccagttccc ggagatcgtc      1080
gacttctacc tgccgccgga gggctgctcc taccgcatgg cggtggtgac catgaagaag      1140
cagtacccgg ccacgccaa gcgggtgatg atgggcgtgt ggagcttcct gccgccagttc      1200
atgtacacca gttcgtggt ggtgctcgac gacgacgtca gcgcccggga ctgggaggac      1260
gtgatctggg ccatcaccac ccgcatggac cggcccgggg acaccgtggt ggtggagaac      1320
accccccatcg actacctgga cttcgcctcg ccggtctccg gcctcggttc caagatgggc      1380
```

```
ctggatgcca ccagcaagtg gcccggcgag accgaccgcg agtgggggt gcccatcgtc    1440 atggacgagg ccgtcaaggc cgcgtcagc gagcgctgga acgagctggg catcgagctc    1500
cccgacaaca cgacccctg a                                              1521
```

<210> SEQ ID NO 40
<211> LENGTH: 506
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (21)...(445)
<223> OTHER INFORMATION: 3-octaprenyl-4-hydroxybenzoate carboxy-lyase
<220> FEATURE:
<221> NAME/KEY: SITE
<222> LOCATION: (5)...(8)
<223> OTHER INFORMATION: N-glycosylation site. Prosite id = PS00001

<400> SEQUENCE: 40

```
Met Leu Ala His Asn Arg Ser His Arg Glu Glu Leu Leu Asn Arg Arg
1               5                   10                  15

Pro Val Glu Phe Ile Ser Ala Leu Glu Ala Arg Gly Glu Leu Gln Arg
            20                  25                  30

Ile Thr Ala Glu Val Asp Pro Tyr Leu Glu Ile Thr Glu Ile Cys Asp
        35                  40                  45

Arg Thr Leu Arg Ala Gly Gly Pro Ala Leu Leu Phe Glu Asn Val Lys
    50                  55                  60

Gly His Asp Met Pro Leu Leu Gly Asn Leu Phe Gly Thr Pro Lys Arg
65                  70                  75                  80

Val Ala Leu Gly Met Gly Gln Asp Ser Val Ala Ala Leu Arg Glu Val
                85                  90                  95

Gly Glu Leu Leu Ala Phe Leu Lys Glu Pro Glu Pro Lys Gly Phe
            100                 105                 110

Arg Asp Ala Trp Asp Lys Leu Pro Ile Phe Lys Gln Val Met Ser Met
        115                 120                 125

Gly Pro Lys Lys Val Arg Ser Ala Pro Val Gln Glu Lys Val Tyr Glu
    130                 135                 140

Gly Asp Glu Val Asp Leu Asp Arg Leu Pro Ile Gln His Cys Trp Pro
145                 150                 155                 160

Gly Asp Ala Ala Pro Leu Val Thr Trp Pro Leu Val Ile Thr Arg Gly
                165                 170                 175

Pro His Lys Lys Arg Gln Asn Leu Gly Ile Tyr Arg Gln Gln Lys Leu
            180                 185                 190

Ser Lys Asn Arg Leu Ile Met Arg Trp Leu Ser His Arg Gly Gly Ala
        195                 200                 205

Leu Asp Phe Leu Glu Phe Gln Lys Ala His Pro Gly Glu Pro Phe Pro
    210                 215                 220

Val Ala Val Ala Leu Gly Ala Asp Pro Ala Thr Ile Leu Gly Ala Val
225                 230                 235                 240

Thr Pro Val Pro Asp Ser Leu Ser Glu Tyr Ala Phe Ala Gly Leu Leu
                245                 250                 255

Arg Gly Ser Arg Thr Glu Leu Val Lys Cys Gly His Ala Asp Leu Asp
            260                 265                 270

Val Pro Ala Ser Ala Glu Ile Ile Leu Glu Gly Phe Ile Tyr Pro Asp
        275                 280                 285

Asp Met Ala Pro Glu Gly Pro Tyr Gly Asp His Thr Gly Tyr Tyr Asn
```

```
               290                 295                 300
Glu Val Asp Thr Phe Pro Val Phe Thr Val Thr Arg Met Thr Met Arg
305                 310                 315                 320

Arg Asp Ala Ile Tyr His Ser Thr Tyr Thr Gly Arg Pro Pro Asp Glu
                325                 330                 335

Pro Ala Ile Leu Gly Leu Ala Leu Asn Glu Val Phe Val Pro Ile Leu
                340                 345                 350

Arg Arg Gln Phe Pro Glu Ile Val Asp Phe Tyr Leu Pro Pro Glu Gly
            355                 360                 365

Cys Ser Tyr Arg Met Ala Val Val Thr Met Lys Lys Gln Tyr Pro Gly
        370                 375                 380

His Ala Lys Arg Val Met Met Gly Val Trp Ser Phe Leu Arg Gln Phe
385                 390                 395                 400

Met Tyr Thr Lys Phe Val Val Leu Asp Asp Val Ser Ala Arg
                405                 410                 415

Asp Trp Glu Asp Val Ile Trp Ala Ile Thr Thr Arg Met Asp Pro Ala
            420                 425                 430

Arg Asp Thr Val Val Val Glu Asn Thr Pro Ile Asp Tyr Leu Asp Phe
        435                 440                 445

Ala Ser Pro Val Ser Gly Leu Gly Ser Lys Met Gly Leu Asp Ala Thr
    450                 455                 460

Ser Lys Trp Pro Gly Glu Thr Asp Arg Glu Trp Gly Val Pro Ile Val
465                 470                 475                 480

Met Asp Glu Ala Val Lys Ala Arg Val Ser Glu Arg Trp Asn Glu Leu
                485                 490                 495

Gly Ile Glu Leu Pro Asp Asn Thr Thr Pro
                500                 505

<210> SEQ ID NO 41
<211> LENGTH: 1410
<212> TYPE: DNA
<213> ORGANISM: Unknown
<220> FEATURE:
<223> OTHER INFORMATION: Obtained from environmental sample

<400> SEQUENCE: 41
atgaagacgc cttcgatcta cgataccatg acgcggtcgg tgcagccgtt gacacccgcc      60
gacggcgaca ccttccgctt ttattgctgc ggccccaccg tctacgggcc ggcgcatgtc     120
ggcaatttcc gcaccttcat cattcaggac gtgctgcgac gcgttatcga agggtcgggc     180
ctcaaaacga gacacgtacg caacatcacc gatgtggacg acaaaaccat ccgccaatcg     240
caagcggaag gaaatctctc tgaaaatctt cacagggtact ggctggaacg gttccacgcc     300
gattgcgacg cgctgaatct gctgcgcccg cacgtcgagc ccggcgccgt tgaccatatc     360
ccggcgcaaa tccggatgat cgaacaactg atcgaaaaag ccacgcccta cgtggcggac     420
gacaactcgg tctattatcg cgttgcttcg ttcgaagcgt acggccggtt gtcacgcctg     480
caagaacgac acatcaccac cggctgcgcc gaacacgcgc ataccgacga tgaatacgag     540
cgcgaatcgg ccgccgactt cgccttgtgg aaagcgcata atccgaggga cggcccgaac     600
gcgtggccga gccgtggggg cgacggacga cccggctggc acatcgagtg cagcgccatg     660
tccgtcgagt atctgggcga gacattcgat ctgcacggcg gcggcgtgga cctgaccttc     720
ccccaccacg aaaacgaaat cgcgcaaagc gaagccgcca ccggcaagcc cttcgcgcgt     780
atctggttcc attccgcgca tctcatggtc gaaggccaca agatgtccaa gagcctcggc     840
aacctgttta cgctcgacga tatccgcgcg cgcggattcg acgccatgac cctgcgctat     900
```

```
gtcctgcttt cgggcaatta ccgccaaccc ctcaatttca cgtgggactc ccttaacgcc    960
gcgcaaagcg ccttacgccg cctgcgtcag ctcaaccacg atctccagca ggcggcgggc   1020
aagacggtcg cgcccgctga tacttcgtgg gggccgttcg aaccggtgta cgacgcgctt   1080
gccgacaacc tgaacacgcc cgacgccctc ggccgcttat tctccgccct gcacagcatc   1140
gagcgcgcgc ttaacggcaa ggaaaggacg gccgaagagg ccgccctcgc ccgtgcgcag   1200
ttcctgcggg tcatggacct tttcggtttc agcctggacg cgccgccgac cgccgaagcg   1260
cccgaagaag tgcgtgcgct ggcgcagcag cgatgggacg ctaaacaagc gcgcgatttc   1320
gtccgcgccg acgccttgcg caaacaggtc accgacctcg gctggaccat ccgcgacgcc   1380
aaagacggct acgaactcgt ccaagagtaa                                    1410
```

<210> SEQ ID NO 42
<211> LENGTH: 469
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (16)...(323)
<223> OTHER INFORMATION: tRNA synthetases class I (C) catalytic domain
<220> FEATURE:
<221> NAME/KEY: SITE
<222> LOCATION: (69)...(72)
<223> OTHER INFORMATION: N-glycosylation site. Prosite id = PS00001
<220> FEATURE:
<221> NAME/KEY: SITE
<222> LOCATION: (316)...(319)
<223> OTHER INFORMATION: N-glycosylation site. Prosite id = PS00001

<400> SEQUENCE: 42

Met Lys Thr Pro Ser Ile Tyr Asp Thr Met Thr Arg Ser Val Gln Pro
1               5                   10                  15

Leu Thr Pro Ala Asp Gly Asp Thr Phe Arg Phe Tyr Cys Cys Gly Pro
            20                  25                  30

Thr Val Tyr Gly Pro Ala His Val Gly Asn Phe Arg Thr Phe Ile Ile
        35                  40                  45

Gln Asp Val Leu Arg Arg Val Ile Glu Gly Ser Gly Leu Lys Thr Arg
    50                  55                  60

His Val Arg Asn Ile Thr Asp Val Asp Asp Lys Thr Ile Arg Gln Ser
65                  70                  75                  80

Gln Ala Glu Gly Lys Ser Leu Lys Ile Phe Thr Gly Tyr Trp Leu Glu
                85                  90                  95

Arg Phe His Ala Asp Cys Asp Ala Leu Asn Leu Leu Arg Pro His Val
            100                 105                 110

Glu Pro Gly Ala Val Asp His Ile Pro Ala Gln Ile Arg Met Ile Glu
        115                 120                 125

Gln Leu Ile Glu Lys Gly His Ala Tyr Val Ala Asp Asp Asn Ser Val
    130                 135                 140

Tyr Tyr Arg Val Ala Ser Phe Glu Ala Tyr Gly Arg Leu Ser Arg Leu
145                 150                 155                 160

Gln Glu Arg His Ile Thr Thr Gly Cys Ala Glu His Ala His Thr Asp
                165                 170                 175

Asp Glu Tyr Glu Arg Glu Ser Ala Ala Asp Phe Ala Leu Trp Lys Ala
            180                 185                 190

His Lys Ser Glu Asp Gly Pro Asn Ala Trp Pro Ser Pro Trp Gly Asp
        195                 200                 205

```
Gly Arg Pro Gly Trp His Ile Glu Cys Ser Ala Met Ser Val Glu Tyr
        210                 215                 220
Leu Gly Glu Thr Phe Asp Leu His Gly Gly Val Asp Leu Thr Phe
225                 230                 235                 240
Pro His His Glu Asn Glu Ile Ala Gln Ser Glu Ala Ala Thr Gly Lys
                    245                 250                 255
Pro Phe Ala Arg Ile Trp Phe His Ser Ala His Leu Met Val Glu Gly
                260                 265                 270
His Lys Met Ser Lys Ser Leu Gly Asn Leu Phe Thr Leu Asp Asp Ile
            275                 280                 285
Arg Ala Arg Gly Phe Asp Ala Met Thr Leu Arg Tyr Val Leu Leu Ser
        290                 295                 300
Gly Asn Tyr Arg Gln Pro Leu Asn Phe Thr Trp Asp Ser Leu Asn Ala
305                 310                 315                 320
Ala Gln Ser Ala Leu Arg Arg Leu Arg Gln Leu Asn His Asp Leu Gln
                    325                 330                 335
Gln Ala Ala Gly Lys Thr Val Ala Pro Ala Asp Thr Ser Trp Gly Pro
                340                 345                 350
Phe Glu Pro Val Tyr Asp Ala Leu Ala Asp Asn Leu Asn Thr Pro Asp
            355                 360                 365
Ala Leu Gly Arg Leu Phe Ser Ala Leu His Ser Ile Glu Arg Ala Leu
        370                 375                 380
Asn Gly Lys Glu Arg Thr Ala Glu Glu Ala Leu Ala Arg Ala Gln
385                 390                 395                 400
Phe Leu Arg Val Met Asp Leu Phe Gly Phe Ser Leu Asp Ala Pro Pro
                    405                 410                 415
Thr Ala Glu Ala Pro Glu Glu Val Arg Ala Leu Ala Gln Gln Arg Trp
                420                 425                 430
Asp Ala Lys Gln Ala Arg Asp Phe Val Arg Asp Ala Leu Arg Lys
            435                 440                 445
Gln Val Thr Asp Leu Gly Trp Thr Ile Arg Asp Ala Lys Asp Gly Tyr
        450                 455                 460
Glu Leu Val Gln Glu
465
```

<210> SEQ ID NO 43
<211> LENGTH: 984
<212> TYPE: DNA
<213> ORGANISM: Unknown
<220> FEATURE:
<223> OTHER INFORMATION: Obtained from environmental sample

<400> SEQUENCE: 43

```
atgacgactg aaaccaaatc caaactgtac ttgcataaag tgaacggcca gaaaggactg    60
gacctgcgcc agacctatca gcgcgacttc accgtgaccg aggcgtatcg cgatacgctg   120
ccggatatgc agaacgcttc cgaggcgttg caggggcca atgtcgccat ccagaaagtc    180
ggcgtatcca atttcaagct gccactcaag taccgcaccc acacgggcga accgaccacg   240
ctggaaacca gcgtaaccgg cagcgtatcc ctgaagccgg gctgaaggg catcaacatg   300
tcccgcgtca tgcggacctt ctacgacttc aggacgacg tgttcacgct cgacacgctg   360
gcccgtatac tggaagcgta caacgggat gtcgacagca cgacgcaca tcttcggctg   420
agtttctcct acccgctgct tcaaaaaagt ctgcgcagcg aattattcgg ctggcaatat   480
taccaggtcg cattcgaggg acggatcgat gccgaaaatc gagtccgcac gttcattcat   540
tttgacttcg tgtattcctc cgcctgtccc tgttcggctg aactggccga acacgcgcgg   600
```

```
gaagtgcgcg gcctatacag catcccccac tcgcaacgca gcaaggcgcg cgtcttcgtg    660
gaagttcagc ccggcgccga actcaccatc gaagacgtgc acatgcactg cctgaacgcg    720
ctccaaacgg aaacgcaagt gatggtcaaa cgcgaagacg agcaggcgtt cgctgaaatg    780
aacggcgccg ccatcaaatt cgtcgaagac gccgcccgtc tgatctatga gcagttcgac    840
caggatccgc gcatcaagga tttcgaaatc gcctgcgcgc atctggaatc cttgcactcg    900
cacgacgccg tatcggtcat cgccaaaggc gtgcccggcg gcttccgcgc cgacttctcg    960
gacttcaaga gtctgatctg ctaa                                           984
```

```
<210> SEQ ID NO 44
<211> LENGTH: 327
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (39)...(308)
<223> OTHER INFORMATION: Uncharacterized ACR, COG1469
<220> FEATURE:
<221> NAME/KEY: SITE
<222> LOCATION: (45)...(48)
<223> OTHER INFORMATION: N-glycosylation site. Prosite id = PS00001
<220> FEATURE:
<221> NAME/KEY: SITE
<222> LOCATION: (100)...(103)
<223> OTHER INFORMATION: N-glycosylation site. Prosite id = PS00001

<400> SEQUENCE: 44

Met Thr Thr Glu Thr Lys Ser Lys Leu Tyr Leu His Lys Val Asn Gly
1               5                   10                  15

Gln Lys Gly Leu Asp Leu Arg Gln Thr Tyr Gln Arg Asp Phe Thr Val
            20                  25                  30

Thr Glu Ala Tyr Arg Asp Thr Leu Pro Asp Met Gln Asn Ala Ser Glu
        35                  40                  45

Ala Leu Gln Gly Ala Asn Val Ala Ile Gln Lys Val Gly Val Ser Asn
    50                  55                  60

Phe Lys Leu Pro Leu Lys Tyr Arg Thr His Thr Gly Glu Pro Thr Thr
65                  70                  75                  80

Leu Glu Thr Ser Val Thr Gly Ser Val Ser Leu Lys Pro Gly Leu Lys
                85                  90                  95

Gly Ile Asn Met Ser Arg Val Met Arg Thr Phe Tyr Asp Phe Gln Asp
            100                 105                 110

Asp Val Phe Thr Leu Asp Thr Leu Ala Arg Ile Leu Glu Ala Tyr Lys
        115                 120                 125

Arg Asp Val Asp Ser Asn Asp Ala His Leu Arg Leu Ser Phe Ser Tyr
    130                 135                 140

Pro Leu Leu Gln Lys Ser Leu Arg Ser Glu Leu Phe Gly Trp Gln Tyr
145                 150                 155                 160

Tyr Gln Val Ala Phe Glu Gly Arg Ile Asp Ala Glu Asn Arg Val Arg
                165                 170                 175

Thr Phe Ile His Phe Asp Phe Val Tyr Ser Ser Ala Cys Pro Cys Ser
            180                 185                 190

Ala Glu Leu Ala Glu His Ala Arg Glu Val Arg Gly Leu Tyr Ser Ile
        195                 200                 205

Pro His Ser Gln Arg Ser Lys Ala Arg Val Phe Val Glu Val Gln Pro
    210                 215                 220

Gly Ala Glu Leu Thr Ile Glu Asp Val His Met His Cys Leu Asn Ala
```

```
                225                 230                 235                 240
Leu Gln Thr Glu Thr Gln Val Met Val Lys Arg Glu Asp Glu Gln Ala
                245                 250                 255

Phe Ala Glu Met Asn Gly Ala Ala Ile Lys Phe Val Glu Asp Ala Ala
            260                 265                 270

Arg Leu Ile Tyr Glu Gln Phe Asp Gln Asp Pro Arg Ile Lys Asp Phe
        275                 280                 285

Glu Ile Ala Cys Ala His Leu Glu Ser Leu His Ser His Asp Ala Val
    290                 295                 300

Ser Val Ile Ala Lys Gly Val Pro Gly Gly Phe Arg Ala Asp Phe Ser
305                 310                 315                 320

Asp Phe Lys Ser Leu Ile Cys
                325

<210> SEQ ID NO 45
<211> LENGTH: 1377
<212> TYPE: DNA
<213> ORGANISM: Unknown
<220> FEATURE:
<223> OTHER INFORMATION: Obtained from environmental sample

<400> SEQUENCE: 45
atgacacaac tggcttttcc atctaacttc atctggggaa cagctacttc cgcttaccaa      60
atcgaaggcg cctggaacgc agacggcaag ggcgaatcta tttgggatcg cttttcccat     120
acgcagggga agatcattga cggcagcaac ggcgatgtgg cctgcgatca ctaccaccgc     180
tggcgcgagg acgtggccct catgagagac ttgggtatgc aggcatatcg cttctccatc     240
tcctggccac gcatcctgcc caccggtcat ggacagatca atcaggctgg gctggacttt     300
tacaatcgcc tggtggacgg gttgctggaa gctggcatca agccctttgc caccctctac     360
cactgggacc tgccgctggc gctacaggct gacggcggct ggccggagcg ctccacggcc     420
aaggcctttg tcgaatacgc cgacgtggtc agccgcgcgc tgggcgatcg ggtgaagagc     480
tggatcaccc ataacgaacc gtggtgcatc agcatgctga ccatcaaat ggggagcat      540
gcgcccggct ggcgggactg gcaggctgcg ttggcggccg cgcaccacgt cctccttcg      600
catggttggg ccgtgccgga actgcgtcgc aacagccgcg atgcagaaat cggcatcacg     660
ttgaacttta ccccggcgga gccagcttcg aacagcgcag ccgatttcaa ggcctatcgc     720
cagttcgatg gctacttcaa ccgctggttc ctggacccgc tctatggccg ccactatccg     780
gcagatatgg tgcacgatta tcgcgcaa ggctacctgc catcacaggg tttgactttc      840
gtggaagctg gtgacctgga cgcgatcgcg acgcgcaccg atttcctggg tgtgaactat     900
tacacgcgcg aagtggtccg tagccaggaa atcccagaga gtgagaacgc gccgcgcaca     960
gtcttgcgcg cgccacagga agagtggaca gagatgggct gggaagtgta tcctgagggc    1020
ctctacaggt tgctcaatcg gttgcacttt gaataccagc cgcgcaagct ctacgtgacc    1080
gagagcggtt gcagctactc cgatggaccc ggccccaacg gtcggatacc ggaccaacgc    1140
cgtatcaact acctgcgcga tcacttcgca gcggcgcatc aggcgataca atgcggcgtc    1200
ccgctggccg gctacttcgt ctggtcgttc atggacaact tcgagtgggc caaagggtac    1260
acccaacgtt tggtatcgt atgggtggat tatcaatcgc aacgacggat accgaaagac    1320
agcgcctact ggtatcgcga tgtcgtcgcc gccaacgcgg tgcaagttcc tgattag       1377

<210> SEQ ID NO 46
<211> LENGTH: 458
<212> TYPE: PRT
```

```
<213> ORGANISM: Unknown
<220> FEATURE:
<223> OTHER INFORMATION: Obtained from environmental sample
<220> FEATURE:
<221> NAME/KEY: DOMAIN
<222> LOCATION: (2)...(454)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
      signature. Prosite id = PS00653

<400> SEQUENCE: 46
```

| Met | Thr | Gln | Leu | Ala | Phe | Pro | Ser | Asn | Phe | Ile | Trp | Gly | Thr | Ala | Thr |
|---|---|---|---|---|---|---|---|---|---|---|---|---|---|---|---|
| 1 | | | | 5 | | | | | 10 | | | | | 15 | |

| Ser | Ala | Tyr | Gln | Ile | Glu | Gly | Ala | Trp | Asn | Ala | Asp | Gly | Lys | Gly | Glu |
|---|---|---|---|---|---|---|---|---|---|---|---|---|---|---|---|
| | | | 20 | | | | | 25 | | | | | 30 | | |

| Ser | Ile | Trp | Asp | Arg | Phe | Ser | His | Thr | Gln | Gly | Lys | Ile | Ile | Asp | Gly |
|---|---|---|---|---|---|---|---|---|---|---|---|---|---|---|---|
| | | | 35 | | | | | 40 | | | | | 45 | | |

| Ser | Asn | Gly | Asp | Val | Ala | Cys | Asp | His | Tyr | His | Arg | Trp | Arg | Glu | Asp |
|---|---|---|---|---|---|---|---|---|---|---|---|---|---|---|---|
| | 50 | | | | | 55 | | | | | 60 | | | | |

| Val | Ala | Leu | Met | Arg | Asp | Leu | Gly | Met | Gln | Ala | Tyr | Arg | Phe | Ser | Ile |
|---|---|---|---|---|---|---|---|---|---|---|---|---|---|---|---|
| 65 | | | | | 70 | | | | | 75 | | | | | 80 |

| Ser | Trp | Pro | Arg | Ile | Leu | Pro | Thr | Gly | His | Gly | Gln | Ile | Asn | Gln | Ala |
|---|---|---|---|---|---|---|---|---|---|---|---|---|---|---|---|
| | | | | 85 | | | | | 90 | | | | | 95 | |

| Gly | Leu | Asp | Phe | Tyr | Asn | Arg | Leu | Val | Asp | Gly | Leu | Leu | Glu | Ala | Gly |
|---|---|---|---|---|---|---|---|---|---|---|---|---|---|---|---|
| | | | | 100 | | | | | 105 | | | | | 110 | |

| Ile | Lys | Pro | Phe | Ala | Thr | Leu | Tyr | His | Trp | Asp | Leu | Pro | Leu | Ala | Leu |
|---|---|---|---|---|---|---|---|---|---|---|---|---|---|---|---|
| | | | 115 | | | | | 120 | | | | | 125 | | |

| Gln | Ala | Asp | Gly | Gly | Trp | Pro | Glu | Arg | Ser | Thr | Ala | Lys | Ala | Phe | Val |
|---|---|---|---|---|---|---|---|---|---|---|---|---|---|---|---|
| | 130 | | | | | 135 | | | | | 140 | | | | |

| Glu | Tyr | Ala | Asp | Val | Val | Ser | Arg | Ala | Leu | Gly | Asp | Arg | Val | Lys | Ser |
|---|---|---|---|---|---|---|---|---|---|---|---|---|---|---|---|
| 145 | | | | | 150 | | | | | 155 | | | | | 160 |

| Trp | Ile | Thr | His | Asn | Glu | Pro | Trp | Cys | Ile | Ser | Met | Leu | Ser | His | Gln |
|---|---|---|---|---|---|---|---|---|---|---|---|---|---|---|---|
| | | | | 165 | | | | | 170 | | | | | 175 | |

| Ile | Gly | Glu | His | Ala | Pro | Gly | Trp | Arg | Asp | Trp | Gln | Ala | Ala | Leu | Ala |
|---|---|---|---|---|---|---|---|---|---|---|---|---|---|---|---|
| | | | 180 | | | | | 185 | | | | | 190 | | |

| Ala | Ala | His | His | Val | Leu | Leu | Ser | His | Gly | Trp | Ala | Val | Pro | Glu | Leu |
|---|---|---|---|---|---|---|---|---|---|---|---|---|---|---|---|
| | | | 195 | | | | | 200 | | | | | 205 | | |

| Arg | Arg | Asn | Ser | Arg | Asp | Ala | Glu | Ile | Gly | Ile | Thr | Leu | Asn | Phe | Thr |
|---|---|---|---|---|---|---|---|---|---|---|---|---|---|---|---|
| | 210 | | | | | 215 | | | | | 220 | | | | |

| Pro | Ala | Glu | Pro | Ala | Ser | Asn | Ser | Ala | Ala | Asp | Phe | Lys | Ala | Tyr | Arg |
|---|---|---|---|---|---|---|---|---|---|---|---|---|---|---|---|
| 225 | | | | | 230 | | | | | 235 | | | | | 240 |

| Gln | Phe | Asp | Gly | Tyr | Phe | Asn | Arg | Trp | Phe | Leu | Asp | Pro | Leu | Tyr | Gly |
|---|---|---|---|---|---|---|---|---|---|---|---|---|---|---|---|
| | | | | 245 | | | | | 250 | | | | | 255 | |

| Arg | His | Tyr | Pro | Ala | Asp | Met | Val | His | Asp | Tyr | Ile | Ala | Gln | Gly | Tyr |
|---|---|---|---|---|---|---|---|---|---|---|---|---|---|---|---|
| | | | 260 | | | | | 265 | | | | | 270 | | |

| Leu | Pro | Ser | Gln | Gly | Leu | Thr | Phe | Val | Glu | Ala | Gly | Asp | Leu | Asp | Ala |
|---|---|---|---|---|---|---|---|---|---|---|---|---|---|---|---|
| | | 275 | | | | | 280 | | | | | 285 | | | |

| Ile | Ala | Thr | Arg | Thr | Asp | Phe | Leu | Gly | Val | Asn | Tyr | Tyr | Thr | Arg | Glu |
|---|---|---|---|---|---|---|---|---|---|---|---|---|---|---|---|
| | 290 | | | | | 295 | | | | | 300 | | | | |

| Val | Val | Arg | Ser | Gln | Glu | Ile | Pro | Glu | Ser | Glu | Asn | Ala | Pro | Arg | Thr |
|---|---|---|---|---|---|---|---|---|---|---|---|---|---|---|---|
| 305 | | | | | 310 | | | | | 315 | | | | | 320 |

| Val | Leu | Arg | Ala | Pro | Gln | Glu | Glu | Trp | Thr | Glu | Met | Gly | Trp | Glu | Val |
|---|---|---|---|---|---|---|---|---|---|---|---|---|---|---|---|
| | | | | 325 | | | | | 330 | | | | | 335 | |

| Tyr | Pro | Glu | Gly | Leu | Tyr | Arg | Leu | Leu | Asn | Arg | Leu | His | Phe | Glu | Tyr |
|---|---|---|---|---|---|---|---|---|---|---|---|---|---|---|---|
| | | | | 340 | | | | | 345 | | | | | 350 | |

```
Gln Pro Arg Lys Leu Tyr Val Thr Glu Ser Gly Cys Ser Tyr Ser Asp
        355                 360                 365

Gly Pro Gly Pro Asn Gly Arg Ile Pro Asp Gln Arg Arg Ile Asn Tyr
    370                 375                 380

Leu Arg Asp His Phe Ala Ala His Gln Ala Ile Gln Cys Gly Val
385                 390                 395                 400

Pro Leu Ala Gly Tyr Phe Val Trp Ser Phe Met Asp Asn Phe Glu Trp
                405                 410                 415

Ala Lys Gly Tyr Thr Gln Arg Phe Gly Ile Val Trp Val Asp Tyr Gln
            420                 425                 430

Ser Gln Arg Arg Ile Pro Lys Asp Ser Ala Tyr Trp Tyr Arg Asp Val
        435                 440                 445

Val Ala Ala Asn Ala Val Gln Val Pro Asp
    450                 455
```

<210> SEQ ID NO 47
<211> LENGTH: 1353
<212> TYPE: DNA
<213> ORGANISM: Unknown
<220> FEATURE:
<223> OTHER INFORMATION: Obtained from environmental sample

<400> SEQUENCE: 47

```
atgaaaaaat accttttcc tgaaaatttt ttatggggtg ctgccacagc ttcgtatcaa      60
atcgaaggtt ctccctctgc tgatggcaaa ggtgaatcga tatgggaccg tttttctcac    120
acaccgggga acatttggaa cgctgaaacc ggggatatcg cctgcgatca ttaccggcgt    180
tacgtggatg atgtaaagct gatttcacaa atcgggctta acgcgtaccg ttttcaatt     240
tcctggccca gggtatttcc agaggggaga ggaaaagcaa atgaaaaagg actcgatttt    300
taccgcaggt tgattgaaca gctgcagcaa catcgaatca aaacggcagt gacactttac    360
cactgggatc ttccacaagt tctgcaggat cgcggcgggt gggcaaaccg tgatacggcg    420
aagtattttt ctgagtatgc cacctttctc tttgaaaaac tcgatctccc cgttgacatg    480
tggattactc ttaacgaacc atgggttatc gctattctgg ggcatgcttt tggtatccac    540
gctccaggga tgagtgactt cagcacagcc ctccaggtct cgcataacct gcttctgggg    600
cacgggttgg cggttaaagc atttcgggag tctaagaggg gtgatgaacc ggtaggtatt    660
acccttaacc ttgccccggt tgaaccgctg accgaaaagc ccgccgatct aaaggcagct    720
ttactttctg acggttttat gaaccgctgg taccttgatc ccctgttcaa aggtggttac    780
cctgaagata tgatggatat ctattcccgg aactttgaac tgcccaaaat tgaaaagggg    840
gatgctcagg ttattgccga accgatcgac ttcctgggca taataactat accaggggtt    900
ctcgtggaag ccagcggtga tgaaaatgcc tttatgggca accctgtcaa cccccagggc    960
tctgaatata ctgaaatggg ttgggaggtt tatccgcagg gtctctacga cctgctgacc   1020
agggttcacc gggattacgg gccaatgccg ctatatataa ctgaaaacgg ggcagccttt   1080
cccgatgaac ttgacagcaa tgggcagata tgatgatcca ggcggataaa ttacctggaa   1140
acttatcttc atcagtgctg gaaggcagtt caggacggtg tgcctctaaa aggctatttt   1200
gtctggaccc tgatggataa cttcgagtgg gctttcggtt tcagcaagcg atttgggctc   1260
atatacgtag attaccagga tcagaaacgt tacttgaaaa acagcgccta ctggtatagc   1320
aaggttattg ggcgaaacgg cctcgagcta taa                                1353
```

<210> SEQ ID NO 48

```
<211> LENGTH: 450
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (4)...(448)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
      signature. Prosite id = PS00653
<220> FEATURE:
<221> NAME/KEY: SITE
<222> LOCATION: (300)...(303)
<223> OTHER INFORMATION: N-glycosylation site. Prosite id = PS00001
<220> FEATURE:
<221> NAME/KEY: SITE
<222> LOCATION: (356)...(364)
<223> OTHER INFORMATION: Glycosyl hydrolases family 1 active site.
      Prosite id = PS00572

<400> SEQUENCE: 48

Met Lys Lys Tyr Leu Phe Pro Glu Asn Phe Leu Trp Gly Ala Ala Thr
1               5                   10                  15

Ala Ser Tyr Gln Ile Glu Gly Ser Pro Ser Ala Asp Gly Lys Gly Glu
            20                  25                  30

Ser Ile Trp Asp Arg Phe Ser His Thr Pro Gly Asn Ile Trp Asn Ala
        35                  40                  45

Glu Thr Gly Asp Ile Ala Cys Asp His Tyr Arg Arg Tyr Val Asp Asp
50                  55                  60

Val Lys Leu Ile Ser Gln Ile Gly Leu Asn Ala Tyr Arg Phe Ser Ile
65                  70                  75                  80

Ser Trp Pro Arg Val Phe Pro Glu Gly Arg Gly Lys Ala Asn Glu Lys
                85                  90                  95

Gly Leu Asp Phe Tyr Arg Arg Leu Ile Glu Gln Leu Gln His Arg
            100                 105                 110

Ile Lys Thr Ala Val Thr Leu Tyr His Trp Asp Leu Pro Gln Val Leu
        115                 120                 125

Gln Asp Arg Gly Gly Trp Ala Asn Arg Asp Thr Ala Lys Tyr Phe Ser
130                 135                 140

Glu Tyr Ala Thr Phe Leu Phe Glu Lys Leu Asp Leu Pro Val Asp Met
145                 150                 155                 160

Trp Ile Thr Leu Asn Glu Pro Trp Val Ile Ala Ile Leu Gly His Ala
                165                 170                 175

Phe Gly Ile His Ala Pro Gly Met Ser Asp Phe Ser Thr Ala Leu Gln
            180                 185                 190

Val Ser His Asn Leu Leu Leu Gly His Gly Leu Ala Val Lys Ala Phe
        195                 200                 205

Arg Glu Ser Lys Arg Gly Asp Glu Pro Val Gly Ile Thr Leu Asn Leu
210                 215                 220

Ala Pro Val Glu Pro Leu Thr Glu Lys Pro Ala Asp Leu Lys Ala Ala
225                 230                 235                 240

Leu Leu Ser Asp Gly Phe Met Asn Arg Trp Tyr Leu Asp Pro Leu Phe
                245                 250                 255

Lys Gly Gly Tyr Pro Glu Asp Met Met Asp Ile Tyr Ser Arg Asn Phe
            260                 265                 270

Glu Leu Pro Lys Ile Glu Lys Gly Asp Ala Gln Val Ile Ala Glu Pro
        275                 280                 285
```

```
Ile Asp Phe Leu Gly Ile Asn Asn Tyr Thr Arg Val Leu Val Glu Ala
        290                 295                 300

Ser Gly Asp Glu Asn Ala Phe Met Gly Asn Pro Val Asn Pro Gln Gly
305                 310                 315                 320

Ser Glu Tyr Thr Glu Met Gly Trp Glu Val Tyr Pro Gln Gly Leu Tyr
                325                 330                 335

Asp Leu Leu Thr Arg Val His Arg Asp Tyr Gly Pro Met Pro Leu Tyr
                340                 345                 350

Ile Thr Glu Asn Gly Ala Ala Phe Pro Asp Glu Leu Asp Ser Asn Gly
        355                 360                 365

Gln Ile Asp Asp Pro Arg Ile Asn Tyr Leu Glu Thr Tyr Leu His
    370                 375                 380

Gln Cys Trp Lys Ala Val Gln Asp Gly Val Pro Leu Lys Gly Tyr Phe
385                 390                 395                 400

Val Trp Thr Leu Met Asp Asn Phe Glu Trp Ala Phe Gly Phe Ser Lys
                405                 410                 415

Arg Phe Gly Leu Ile Tyr Val Asp Tyr Gln Asp Gln Lys Arg Tyr Leu
                420                 425                 430

Lys Asn Ser Ala Tyr Trp Tyr Ser Lys Val Ile Gly Arg Asn Gly Leu
        435                 440                 445

Glu Leu
    450

<210> SEQ ID NO 49
<211> LENGTH: 591
<212> TYPE: DNA
<213> ORGANISM: Unknown
<220> FEATURE:
<223> OTHER INFORMATION: Obtained from environmental sample

<400> SEQUENCE: 49
atggactttg agcgggcagt tgacaggaat atcattagat tacgctcttc gttaaaggaa      60
gaaatgaagg atctagttgc agttgaagct ccggtaacaa tattttttaaa tggcagcgag     120 ctggtaaccc tgctctgcac cccggagaaa attgatcgtt tggccctcgg tttccttcat     180
tcagaagggc tgcttaactc acttgatgat cttagtatga tcaggaccag ggagagcgaa     240
ggcctggttg aaattgaact taagagggcc tcgccggcac ttgataaatt atacgggaag     300
aggacaatta cttccggttg cggtaaggga acaattttttt ttaatgttct cgattctctg     360
cgcagtaaac cactcgacgg aaagcttgtg attacaaccg aagagattca taaattaatg     420
gatgacctgc aggggcgggc ggaactgttc aaggctaccg ggggtgttca cagcgctgcg     480
cttgccgaca gaaaggaaat actcttttc agtgaagata tcggccgcca taatgctatc     540
gataaaattg tgggagagtg tttgctggag ggggtatctc ctgaagataa g              591

<210> SEQ ID NO 50
<211> LENGTH: 197
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (17)...(195)
<223> OTHER INFORMATION: FdhD/NarQ family
<220> FEATURE:
<221> NAME/KEY: SITE
<222> LOCATION: (37)...(40)
<223> OTHER INFORMATION: N-glycosylation site. Prosite id = PS00001

<400> SEQUENCE: 50
```

```
Met Asp Phe Glu Arg Ala Val Asp Arg Asn Ile Ile Arg Leu Arg Ser
1               5                   10                  15

Ser Leu Lys Glu Glu Met Lys Asp Leu Val Ala Val Glu Ala Pro Val
            20                  25                  30

Thr Ile Phe Leu Asn Gly Ser Glu Leu Val Thr Leu Leu Cys Thr Pro
        35                  40                  45

Glu Lys Ile Asp Arg Leu Ala Leu Gly Phe Leu His Ser Glu Gly Leu
    50                  55                  60

Leu Asn Ser Leu Asp Asp Leu Ser Met Ile Arg Thr Arg Glu Ser Glu
65                  70                  75                  80

Gly Leu Val Glu Ile Glu Leu Lys Glu Ala Ser Pro Ala Leu Asp Lys
                85                  90                  95

Leu Tyr Gly Lys Arg Thr Ile Thr Ser Gly Cys Gly Lys Gly Thr Ile
            100                 105                 110

Phe Phe Asn Val Leu Asp Ser Leu Arg Ser Lys Pro Leu Asp Gly Lys
        115                 120                 125

Leu Val Ile Thr Thr Glu Glu Ile His Lys Leu Met Asp Asp Leu Gln
    130                 135                 140

Gly Arg Ala Glu Leu Phe Lys Ala Thr Gly Gly Val His Ser Ala Ala
145                 150                 155                 160

Leu Ala Asp Arg Lys Glu Ile Leu Phe Phe Ser Glu Asp Ile Gly Arg
                165                 170                 175

His Asn Ala Ile Asp Lys Ile Val Gly Glu Cys Leu Leu Glu Gly Val
            180                 185                 190

Ser Pro Glu Asp Lys
        195

<210> SEQ ID NO 51
<211> LENGTH: 1014
<212> TYPE: DNA
<213> ORGANISM: Unknown
<220> FEATURE:
<223> OTHER INFORMATION: Obtained from environmental sample

<400> SEQUENCE: 51
atgtccaggg gcatcctgat cctcgtcatg ctgtctgttc tgagcggcgc ggcgctggcc    60
caaccggccg ggctgccgcc gcgttcgccg gtgcagcgct gcatcaacct gggcaatatg    120
ctggaagcgc cggaggaggg ctggtggggg ctgcgcgtcg agcgcgacta cctgacgacg    180
atcgccgggg ccgggttcga tgcggtgcgc atcccgataa gctggtcaac ccatgctgcc    240
agcgagccgc cctacaccat cgatccggct ttcttcgccc gcgttgatga agtcgtcggc    300
tgggcgctgg cggacgggct gaaggccatc atcaacgtgc accactacga ggagatgatg    360
agcgatccgg cggggcattt ccccggctg cgcgcgctgt gggcgcagat cgcggagcac    420
tacgccgact acccgcccgc gctgatgttc gagctgctca cgaaccgtt cgaggcgctg    480 acgccgctgc ggtggaacga gtacgccgcc gatctgatcg cgctgatccg ccagaccaac    540
ccggggcgca ccctgatcgt cggcggggc tggtggaaca gtgtggaagg gctgatgcag    600
ctccgcctgc cggatgatcc cgatctgctg gcgacgttcc attactacca cccgttcgag    660
ttcacgcatc aggggcgga gtggtcaccg gaagtgactg acctgagcgg gatcgcctgg    720
gggacgggcg aggaacggct cgatctggag tccaatatcc gtattgcggc ggcctgggcg    780
gtgtacaacc ggcgcccgct gctgttgggc gaattcggcg tctatggccg ggtgccgat    840 ctcgattcgc gcctgcgctg gacgacggcg gtgcgcgccg aggccgaggc gcagggcatc    900
```

```
ggctggtgct actgggaatt cgccgccggc ttcggcattt acgacccgga aagccggacg      960
ttcaacccgc tgtaccgcgc gctgatcccg caggccgggc cggcgcgccc ctga           1014
```

<210> SEQ ID NO 52
<211> LENGTH: 337
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (38)...(314)
<223> OTHER INFORMATION: Cellulase (glycosyl hydrolase family 5)
<220> FEATURE:
<221> NAME/KEY: SITE
<222> LOCATION: (150)...(159)
<223> OTHER INFORMATION: Glycosyl hydrolases family 5 signature. Prosite
      id = PS00659

<400> SEQUENCE: 52

```
Met Ser Arg Gly Ile Leu Ile Leu Val Met Leu Ser Val Leu Ser Gly
1               5                   10                  15

Ala Ala Leu Ala Gln Pro Ala Gly Leu Pro Pro Arg Ser Pro Val Gln
            20                  25                  30

Arg Cys Ile Asn Leu Gly Asn Met Leu Glu Ala Pro Glu Gly Trp
        35                  40                  45

Trp Gly Leu Arg Val Glu Arg Asp Tyr Leu Thr Thr Ile Ala Gly Ala
    50                  55                  60

Gly Phe Asp Ala Val Arg Ile Pro Ile Ser Trp Ser Thr His Ala Ala
65                  70                  75                  80

Ser Glu Pro Pro Tyr Thr Ile Asp Pro Ala Phe Phe Ala Arg Val Asp
                85                  90                  95

Glu Val Val Gly Trp Ala Leu Ala Asp Gly Leu Lys Ala Ile Ile Asn
            100                 105                 110

Val His His Tyr Glu Glu Met Met Ser Asp Pro Ala Gly His Phe Pro
        115                 120                 125

Arg Leu Arg Ala Leu Trp Ala Gln Ile Ala Glu His Tyr Ala Asp Tyr
130                 135                 140

Pro Pro Ala Leu Met Phe Glu Leu Leu Asn Glu Pro Phe Glu Ala Leu
145                 150                 155                 160

Thr Pro Leu Arg Trp Asn Glu Tyr Ala Ala Asp Leu Ile Ala Leu Ile
                165                 170                 175

Arg Gln Thr Asn Pro Gly Arg Thr Leu Ile Val Gly Gly Trp Trp
            180                 185                 190

Asn Ser Val Glu Gly Leu Met Gln Leu Arg Leu Pro Asp Asp Pro Asp
        195                 200                 205

Leu Leu Ala Thr Phe His Tyr Tyr His Pro Phe Glu Phe Thr His Gln
    210                 215                 220

Gly Ala Glu Trp Ser Pro Glu Val Thr Asp Leu Ser Gly Ile Ala Trp
225                 230                 235                 240

Gly Thr Gly Glu Glu Arg Leu Asp Leu Glu Ser Asn Ile Arg Ile Ala
                245                 250                 255

Ala Ala Trp Ala Val Tyr Asn Arg Arg Pro Leu Leu Leu Gly Glu Phe
            260                 265                 270

Gly Val Tyr Gly Arg Val Ala Asp Leu Asp Ser Arg Leu Arg Trp Thr
        275                 280                 285
```

-continued

```
         Thr Ala Val Arg Ala Glu Ala Glu Ala Gln Gly Ile Gly Trp Cys Tyr
                 290                 295                 300

Trp Glu Phe Ala Ala Gly Phe Gly Ile Tyr Asp Pro Glu Ser Arg Thr
         305                 310                 315                 320

Phe Asn Pro Leu Tyr Arg Ala Leu Ile Pro Gln Ala Gly Pro Ala Arg
                         325                 330                 335

Pro

<210> SEQ ID NO 53
<211> LENGTH: 1377
<212> TYPE: DNA
<213> ORGANISM: Unknown
<220> FEATURE:
<223> OTHER INFORMATION: Obtained from environmental sample

<400> SEQUENCE: 53
atgtggatgg ttcaagcgac atctttaatt caaaaataca atgtgcctgg cccacgctac      60
accagttatc caacggttcc ttattgggaa agtgagaatt tttcactaaa gcagtggcaa     120
caaacgctca aaaatccttt gatgagtcg aatcaaagtg aaggcatcag tctgtatatc     180
catttgccat tttgcgaaag tttatgcacc ttctgtggtt gccataaacg tgtgactaaa     240
aagcatgaga tggaaaagcc ttatatccaa gcggtattaa agaatggga tttatattgc     300 caacttttgg tggataaacc tgtcattaaa gaaattcatt gggtgggggg aactccgaca     360
ttttttagtc ctgaacattt aacgcagctg attaagggga tattggctaa gccgaagtt     420 gcagatgagc atgagtttag ttttgaagga catcccaaca atacgacacg tgaacatttg     480
caagcgctct atgatgttgg atttcgacgt gtcagttatg gcgtgcagga ctataacgaa     540
actgtgcaaa aagccattca ccgcattcag ccctatgaaa atgttaaaaa tgtcaccgag     600
tgggcgcgtg agattggcta ccctctatt tcgcatgatt tggtctttgg cctgccgttt     660
caaagtttag acgatgtctt aaatacgatt gatcaaacca ataccttaat gccggatcgt     720
ttggctttgt atagctatgc ccatgtgcca tggattaaag gcaatggtca acgcggtttt     780
aaagatgctg atgtcccgaa agacgagatt aaacgtcaat gttatgagga aggcaaaaaa     840
aaattattag acatggcta tcatgaaatt ggtatggatc attttgctct agaacaagac     900
agtatgtatc agtcttttaa gcagggagc ttgcatcgta atttcatggg ttataccgca     960
tcgaaaacgc aagtgatgat tgggcttggg atttcatcaa ttagtgacag ttggtacagc    1020
tttgcgcaaa acgtgaaaac attagatgaa tattatacct tgctagaaaa aaatcagatt    1080 cccgtgtttta aagggcatgt cttgaatcag gaagatttga tcatccgtaa acatattta    1140 aatttgatgt gtggcttcca aacctcatgg gcaaatcccg atatgcaatt tcctgaaatt    1200
cagtctgttt tggcacaatt agcagaaatg cagcaagatg gttgattca aattgaagac    1260 gcatcggtca cagttttaga agcgggcaag ccttttgttc gaaatatttg tatggccttt    1320
gatttaagac tcaagcgcaa caagcctgag aatcggattt tttcgatgac gatttaa      1377

<210> SEQ ID NO 54
<211> LENGTH: 458
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (59)...(233)
<223> OTHER INFORMATION: Radical SAM superfamily
<220> FEATURE:
<221> NAME/KEY: DOMAIN
```

```
<222> LOCATION: (316)...(431)
<223> OTHER INFORMATION: HemN C-terminal region
<220> FEATURE:
<221> NAME/KEY: SITE
<222> LOCATION: (33)...(36)
<223> OTHER INFORMATION: N-glycosylation site. Prosite id = PS00001
<220> FEATURE:
<221> NAME/KEY: SITE
<222> LOCATION: (51)...(54)
<223> OTHER INFORMATION: N-glycosylation site. Prosite id = PS00001
<220> FEATURE:
<221> NAME/KEY: SITE
<222> LOCATION: (155)...(158)
<223> OTHER INFORMATION: N-glycosylation site. Prosite id = PS00001
<220> FEATURE:
<221> NAME/KEY: SITE
<222> LOCATION: (181)...(184)
<223> OTHER INFORMATION: N-glycosylation site. Prosite id = PS00001
<220> FEATURE:
<221> NAME/KEY: SITE
<222> LOCATION: (200)...(203)
<223> OTHER INFORMATION: N-glycosylation site. Prosite id = PS00001

<400> SEQUENCE: 54

Met Trp Met Val Gln Ala Thr Ser Leu Ile Gln Lys Tyr Asn Val Pro
1               5                   10                  15

Gly Pro Arg Tyr Thr Ser Tyr Pro Thr Val Pro Tyr Trp Glu Ser Glu
            20                  25                  30

Asn Phe Ser Leu Lys Gln Trp Gln Gln Thr Leu Lys Lys Ser Phe Asp
        35                  40                  45

Glu Ser Asn Gln Ser Glu Gly Ile Ser Leu Tyr Ile His Leu Pro Phe
    50                  55                  60

Cys Glu Ser Leu Cys Thr Phe Cys Gly Cys His Lys Arg Val Thr Lys
65                  70                  75                  80

Lys His Glu Met Glu Lys Pro Tyr Ile Gln Ala Val Leu Lys Glu Trp
                85                  90                  95

Asp Leu Tyr Cys Gln Leu Leu Val Asp Lys Pro Val Ile Lys Glu Ile
            100                 105                 110

His Leu Gly Gly Gly Thr Pro Thr Phe Phe Ser Pro Glu His Leu Thr
        115                 120                 125

Gln Leu Ile Lys Gly Ile Leu Ala Lys Ala Glu Val Ala Asp Glu His
    130                 135                 140

Glu Phe Ser Phe Glu Gly His Pro Asn Asn Thr Thr Arg Glu His Leu
145                 150                 155                 160

Gln Ala Leu Tyr Asp Val Gly Phe Arg Arg Val Ser Tyr Gly Val Gln
                165                 170                 175

Asp Tyr Asn Glu Thr Val Gln Lys Ala Ile His Arg Ile Gln Pro Tyr
            180                 185                 190

Glu Asn Val Lys Asn Val Thr Glu Trp Ala Arg Glu Ile Gly Tyr Thr
        195                 200                 205

Ser Ile Ser His Asp Leu Val Phe Gly Leu Pro Phe Gln Ser Leu Asp
    210                 215                 220

Asp Val Leu Asn Thr Ile Asp Gln Thr Asn Thr Leu Met Pro Asp Arg
225                 230                 235                 240

Leu Ala Leu Tyr Ser Tyr Ala His Val Pro Trp Ile Lys Gly Asn Gly
                245                 250                 255

Gln Arg Gly Phe Lys Asp Ala Asp Val Pro Lys Asp Glu Ile Lys Arg
            260                 265                 270

Gln Cys Tyr Glu Glu Gly Lys Lys Lys Leu Leu Glu His Gly Tyr His
        275                 280                 285

Glu Ile Gly Met Asp His Phe Ala Leu Glu Gln Asp Ser Met Tyr Gln
```

```
                    290                   295                   300
Ser Phe Lys Ala Gly Ser Leu His Arg Asn Phe Met Gly Tyr Thr Ala
305                 310                 315                 320

Ser Lys Thr Gln Val Met Ile Gly Leu Gly Ile Ser Ser Ile Ser Asp
                325                 330                 335

Ser Trp Tyr Ser Phe Ala Gln Asn Val Lys Thr Leu Asp Glu Tyr Tyr
                340                 345                 350

Thr Leu Leu Glu Lys Asn Gln Ile Pro Val Phe Lys Gly His Val Leu
                355                 360                 365

Asn Gln Glu Asp Leu Ile Ile Arg Lys His Ile Leu Asn Leu Met Cys
370                 375                 380

Gly Phe Gln Thr Ser Trp Ala Asn Pro Asp Met Gln Phe Pro Glu Ile
385                 390                 395                 400

Gln Ser Val Leu Ala Gln Leu Ala Glu Met Gln Gln Asp Gly Leu Ile
                405                 410                 415

Gln Ile Glu Asp Ala Ser Val Thr Val Leu Glu Ala Gly Lys Pro Phe
                420                 425                 430

Val Arg Asn Ile Cys Met Ala Phe Asp Leu Arg Leu Lys Arg Asn Lys
                435                 440                 445

Pro Glu Asn Arg Ile Phe Ser Met Thr Ile
450                 455

<210> SEQ ID NO 55
<211> LENGTH: 1389
<212> TYPE: DNA
<213> ORGANISM: Unknown
<220> FEATURE:
<223> OTHER INFORMATION: Obtained from environmental sample

<400> SEQUENCE: 55
atgagcgctt cgagtccctc ccgcccctg tccttcccag agcagttcgt ctggggtgct      60
gccgcggcct cctaccaagt cgagggcgcc gtccacgagg acgggaaggg ccctccgtc    120 tgggacatgt tctgcgagaa gcccggagcg gtcttccagg gcacgacgg gcggtggct     180 tgcgaccact atcaccgcta ccgagaggac gtggcgttga tgcgacaggt gggcctgcac    240
gcctaccgcc tgagcgtgtg ctggccccga gtgctcccgg agggcgtcgg gcagcccaac    300
gagaagggcc tcgacttcta ctcgcggttg gtggacgcgc tgctcgaggc agggattacg    360
ccctgggtaa cgcttttca ttgggactac cccttggctc tctatcaccg ggggggctgg    420
ctcaaccggg atagcgcgga ttggtttgcc gagtacgcgg gctaatcgc cgatcgcctc    480 tccgaccggg tgcagcattt cttcactcag aacgagcccc aggtctatat cggcttcgga    540
cacctcgagg gtaagcatgc tccaggagac accttgccca tgtcccaggt gctgcttgcg    600
gggcatcata gcctactggc gcacggcaag gccgtgcagg cgctccgcgc ccaggcgaag    660
cagcagctgc gcgtcggcta cgctcccgtc ggcatgcccc tccatccctt cacggactcg    720
gccgaggacg tggccgctgc gcggaaggcg accttttggg ttcgggagaa gaactcctgg    780
aacaacgcct ggtggatgga cccggtgttc ttgggtgagt acccggctca gggcctcgcc    840
ttcttcggcc gggacgtgcc gcaggtgcgc gagggagaca tgcagctcat cgcgcagccc    900
ttggacttct ttgggggtcaa catctaccag agcacccccg tgcgcgcgtc tagcgccgaa    960
agcggcttcg aggtcgtccc ccatccaacg ggctatccta tcactgcctt caactggccg   1020
atcacgcccc aggccctcta ctggggtccg gcttcttct acgagcgcta ccagaagccg   1080
atcgtcatca cggagaacgg actgtcctgt cgggacgtcg tcgctgtgga cgggaaggtt   1140
```

```
cacgatccgg ctcgcatcga tttcaccacc cgctatctgc gcgagctcca ccgagccgtc    1200
gcggacggcg tcgcggtcga gggctacttc cactggtcca tcatggacaa cttcgaatgg    1260
gctgccggct accgcgagcg gttcgggctc attcacgtcg actacgagac cctggcgcgg    1320
acgcccaagg cgtccgctgc gtggtatcgc aaggtaatcg agagcaacgg agcgacccct    1380
ttcggatga                                                            1389
```

<210> SEQ ID NO 56
<211> LENGTH: 462
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(458)
<223> OTHER INFORMATION: Glycosyl hydrolase family 1
<220> FEATURE:
<221> NAME/KEY: SITE
<222> LOCATION: (16)...(30)
<223> OTHER INFORMATION: Glycosyl hydrolases family 1 N-terminal
      signature. Prosite id = PS00653
<220> FEATURE:
<221> NAME/KEY: SITE
<222> LOCATION: (366)...(374)
<223> OTHER INFORMATION: Glycosyl hydrolases family 1 active site.
      Prosite id = PS00572

<400> SEQUENCE: 56

Met Ser Ala Ser Ser Pro Ser Arg Pro Leu Ser Phe Pro Glu Gln Phe
1               5                   10                  15

Val Trp Gly Ala Ala Ala Ala Ser Tyr Gln Val Glu Gly Ala Val His
            20                  25                  30

Glu Asp Gly Lys Gly Pro Ser Val Trp Asp Met Phe Cys Glu Lys Pro
        35                  40                  45

Gly Ala Val Phe Gln Gly His Asp Gly Ala Val Ala Cys Asp His Tyr
    50                  55                  60

His Arg Tyr Arg Glu Asp Val Ala Leu Met Arg Gln Val Gly Leu His
65                  70                  75                  80

Ala Tyr Arg Leu Ser Val Cys Trp Pro Arg Val Leu Pro Glu Gly Val
                85                  90                  95

Gly Gln Pro Asn Glu Lys Gly Leu Asp Phe Tyr Ser Arg Leu Val Asp
            100                 105                 110

Ala Leu Leu Glu Ala Gly Ile Thr Pro Trp Val Thr Leu Phe His Trp
        115                 120                 125

Asp Tyr Pro Leu Ala Leu Tyr His Arg Gly Gly Trp Leu Asn Arg Asp
    130                 135                 140

Ser Ala Asp Trp Phe Ala Glu Tyr Ala Gly Leu Ile Ala Asp Arg Leu
145                 150                 155                 160

Ser Asp Arg Val Gln His Phe Phe Thr Gln Asn Glu Pro Gln Val Tyr
                165                 170                 175

Ile Gly Phe Gly His Leu Glu Gly Lys His Ala Pro Gly Asp Thr Leu
            180                 185                 190

Pro Met Ser Gln Val Leu Leu Ala Gly His His Ser Leu Leu Ala His
        195                 200                 205

Gly Lys Ala Val Gln Ala Leu Arg Ala Gln Ala Lys Gln Gln Leu Arg
    210                 215                 220

Val Gly Tyr Ala Pro Val Gly Met Pro Leu His Pro Phe Thr Asp Ser
225                 230                 235                 240

Ala Glu Asp Val Ala Ala Ala Arg Lys Ala Thr Phe Trp Val Arg Glu 245                 250                 255
Lys Asn Ser Trp Asn Asn Ala Trp Trp Met Asp Pro Val Phe Leu Gly
                260                 265                 270

Glu Tyr Pro Ala Gln Gly Leu Ala Phe Phe Gly Arg Asp Val Pro Gln
            275                 280                 285

Val Arg Glu Gly Asp Met Gln Leu Ile Ala Gln Pro Leu Asp Phe Phe
        290                 295                 300

Gly Val Asn Ile Tyr Gln Ser Thr Pro Val Arg Ala Ser Ser Ala Glu
305                 310                 315                 320

Ser Gly Phe Glu Val Val Pro His Pro Thr Gly Tyr Pro Ile Thr Ala
                325                 330                 335

Phe Asn Trp Pro Ile Thr Pro Gln Ala Leu Tyr Trp Gly Pro Arg Phe
            340                 345                 350

Phe Tyr Glu Arg Tyr Gln Lys Pro Ile Val Ile Thr Glu Asn Gly Leu
        355                 360                 365

Ser Cys Arg Asp Val Val Ala Val Asp Gly Lys Val His Asp Pro Ala
370                 375                 380

Arg Ile Asp Phe Thr Thr Arg Tyr Leu Arg Glu Leu His Arg Ala Val
385                 390                 395                 400

Ala Asp Gly Val Ala Val Glu Gly Tyr Phe His Trp Ser Ile Met Asp
                405                 410                 415

Asn Phe Glu Trp Ala Ala Gly Tyr Arg Glu Arg Phe Gly Leu Ile His
            420                 425                 430

Val Asp Tyr Glu Thr Leu Ala Arg Thr Pro Lys Ala Ser Ala Ala Trp
        435                 440                 445

Tyr Arg Lys Val Ile Glu Ser Asn Gly Ala Thr Leu Phe Gly
450                 455                 460

<210> SEQ ID NO 57
<211> LENGTH: 414
<212> TYPE: DNA
<213> ORGANISM: Unknown
<220> FEATURE:
<223> OTHER INFORMATION: Obtained from environmental sample

<400> SEQUENCE: 57
atgattgctt catctatgtt ctatggaacg gttcgtggaa tacaagagct aactcaaaac    60
gttattgcat tggataccgc aatggtttcg cttaccagag ttgctgacgg aagtgatttt   120
gagtttgata gagttattga acgctcgatt gaaaacgtaa ccgaactatc aggtaagcta   180
actgattaca tggatttagt aacggagttt gctagaactg gtaaaacaat agatgaatct   240
tttaatttag ctaatacaac acaaatgtta atgaatattt ctgaattaac agcagatgaa   300
tcagtaaata gtttaactgc cgcaatgatt gcttttaata ttaacgcaga tgatagtatt   360
agaattgctg ataagttgaa tgaggttaac aatatcagcc tccttttgtg gtaa         414

<210> SEQ ID NO 58
<211> LENGTH: 137
<212> TYPE: PRT
<213> ORGANISM: Unknown
<220> FEATURE:
<223> OTHER INFORMATION: Obtained from environmental sample
<220> FEATURE:
<221> NAME/KEY: SITE
<222> LOCATION: (52)...(55)
<223> OTHER INFORMATION: N-glycosylation site. Prosite id = PS00001
<220> FEATURE:
<221> NAME/KEY: SITE
<222> LOCATION: (86)...(89)
<223> OTHER INFORMATION: N-glycosylation site. Prosite id = PS00001

```
<220> FEATURE:
<221> NAME/KEY: SITE
<222> LOCATION: (93)...(96)
<223> OTHER INFORMATION: N-glycosylation site. Prosite id = PS00001
<220> FEATURE:
<221> NAME/KEY: SITE
<222> LOCATION: (133)...(136)
<223> OTHER INFORMATION: N-glycosylation site. Prosite id = PS00001

<400> SEQUENCE: 58

Met Ile Ala Ser Ser Met Phe Tyr Gly Thr Val Arg Gly Ile Gln Glu
  1               5                  10                  15

Leu Thr Gln Asn Val Ile Ala Leu Asp Thr Ala Met Val Ser Leu Thr
                 20                  25                  30

Arg Val Ala Asp Gly Ser Asp Phe Glu Phe Asp Arg Val Ile Glu Arg
             35                  40                  45

Ser Ile Glu Asn Val Thr Glu Leu Ser Gly Lys Leu Thr Asp Tyr Met
 50                  55                  60

Asp Leu Val Thr Glu Phe Ala Arg Thr Gly Lys Thr Ile Asp Glu Ser
 65                  70                  75                  80

Phe Asn Leu Ala Asn Thr Thr Gln Met Leu Met Asn Ile Ser Glu Leu
                 85                  90                  95

Thr Ala Asp Glu Ser Val Asn Ser Leu Thr Ala Ala Met Ile Ala Phe
            100                 105                 110

Asn Ile Asn Ala Asp Asp Ser Ile Arg Ile Ala Asp Lys Leu Asn Glu
            115                 120                 125

Val Asn Asn Ile Ser Leu Leu Leu Trp
130                 135

<210> SEQ ID NO 59
<211> LENGTH: 1044
<212> TYPE: DNA
<213> ORGANISM: Unknown
<220> FEATURE:
<223> OTHER INFORMATION: Obtained from environmental sample

<400> SEQUENCE: 59
atgagaattt tgaaggatt tcagcgaggt gtaaaccttg gcggctggat ctcccagttc     60
gacaagtacg accatgagca tttccgcagc tttattacgg aaaatgacat cgccgccatt    120
gcagctcttg gttttgacca tgtccgcgtg ccggtggatt ataacgtgct ggaggatgag    180
gagggcaacc gcatcgacag cggatttgtc tacctgagaa gctgctacga gtggtgccgc    240
aaacacgacc tgaacatgct ggtggatctt cacgagtgct acggctactc cttcgatccg    300
ctgaaaaaag atatggaccg caaacgcttc ttctatgccg aagctctgca ggagcgtttt    360
ctgaagctct gggagcagat ctgtgaaacc tttaaagacg atcctgtgca cgtggcattc    420
gagccgctga atgagatcgt tttaggagag gtcgcagacg cctggaacgt gatgatccgc    480
aaatatatca agaccgtccg cgccatctgc ccggagcact atctggtcct ggaagcgtg    540 cactacagcc acgttaccac catccctctt cttgaggcac cggcagatga caagatcgtc    600
ttcaacttcc actgctacga gccgctggtc ttcacccacc agggcgcata ctggctggag    660
gatatgattc cggatttccg catgacctat cctgccacca tggaagagtt ctacgaagca    720
acaaagaaga tcctgccaaa catgagtccg gatggattta aggatttcga tcaggagatg    780
ggtccgggct tctttgagaa gatcttcaca ccggccctga acgtgccga gcaggacaat    840 gtagccctct actgcggcga gtacggcgtg attgatctgg cagataacca tgccaagatc    900
cgctggctca agacatcca caccaccttc tccaaatacg gcatcggaag tgccctctgg    960
```

```
aactacaagg gcaaggattt cggctatgta gatgatcgct tcgccgagtg cagagaagca      1020
tttatcgagt gcctgaaggc ctga                                            1044
```

<210> SEQ ID NO 60
<211> LENGTH: 347
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (14)...(330)
<223> OTHER INFORMATION: Cellulase (glycosyl hydrolase family 5)

<400> SEQUENCE: 60

```
Met Arg Ile Phe Glu Gly Phe Gln Arg Gly Val Asn Leu Gly Gly Trp
1               5                   10                  15

Ile Ser Gln Phe Asp Lys Tyr Asp His Glu His Phe Arg Ser Phe Ile
            20                  25                  30

Thr Glu Asn Asp Ile Ala Ala Ile Ala Leu Gly Phe Asp His Val
        35                  40                  45

Arg Val Pro Val Asp Tyr Asn Val Leu Glu Asp Glu Gly Asn Arg
50                  55                  60

Ile Asp Ser Gly Phe Val Tyr Leu Arg Ser Cys Tyr Glu Trp Cys Arg
65                  70                  75                  80

Lys His Asp Leu Asn Met Leu Val Asp Leu His Glu Cys Tyr Gly Tyr
                85                  90                  95

Ser Phe Asp Pro Leu Lys Lys Asp Met Asp Arg Lys Arg Phe Phe Tyr
            100                 105                 110

Ala Glu Ala Leu Gln Glu Arg Phe Leu Lys Leu Trp Glu Gln Ile Cys
        115                 120                 125

Glu Thr Phe Lys Asp Asp Pro Val His Val Ala Phe Glu Pro Leu Asn
130                 135                 140

Glu Ile Val Leu Gly Glu Val Ala Asp Ala Trp Asn Val Met Ile Arg
145                 150                 155                 160

Lys Tyr Ile Lys Thr Val Arg Ala Ile Cys Pro Glu His Tyr Leu Val
                165                 170                 175

Leu Gly Ser Val His Tyr Ser His Val Thr Thr Ile Pro Leu Leu Glu
            180                 185                 190

Ala Pro Ala Asp Asp Lys Ile Val Phe Asn Phe His Cys Tyr Glu Pro
        195                 200                 205

Leu Val Phe Thr His Gln Gly Ala Tyr Trp Leu Glu Asp Met Ile Pro
210                 215                 220

Asp Phe Arg Met Thr Tyr Pro Ala Thr Met Glu Glu Phe Glu Ala
225                 230                 235                 240

Thr Lys Lys Ile Leu Pro Asn Met Ser Pro Asp Gly Phe Lys Asp Phe
                245                 250                 255

Asp Gln Glu Met Gly Pro Gly Phe Phe Glu Lys Ile Phe Thr Pro Ala
            260                 265                 270

Leu Lys Arg Ala Glu Gln Asp Asn Val Ala Leu Tyr Cys Gly Glu Tyr
        275                 280                 285

Gly Val Ile Asp Leu Ala Asp Asn His Ala Lys Ile Arg Trp Leu Lys
290                 295                 300

Asp Ile His Thr Thr Phe Ser Lys Tyr Gly Ile Gly Ser Ala Leu Trp
305                 310                 315                 320

Asn Tyr Lys Gly Lys Asp Phe Gly Tyr Val Asp Asp Arg Phe Ala Glu
                325                 330                 335
```

```
Cys Arg Glu Ala Phe Ile Glu Cys Leu Lys Ala
        340                 345
```

<210> SEQ ID NO 61
<211> LENGTH: 1230
<212> TYPE: DNA
<213> ORGANISM: Unknown
<220> FEATURE:
<223> OTHER INFORMATION: Obtained from environmental sample

<400> SEQUENCE: 61

```
ttggtatgga caccagctcg atcaacgctt gctggatctt ctgaaatccc actaatgaca      60
atgaatatat tccccaatag aaaagactca cgaatgtccc tctggatcaa gcttggcata     120
ctttgtatga tggctggaac ggtgatggtt cacggagcgc agactggtca aggagaagca     180
acaatgaatc aagcaaatgg cttcaaggta agcaacggga ccaatatcag ccattggttg     240
tcccagtgtt ttgaaacaat gccacccccgg cgcggatttt tctccgaact ggatgttatc     300
ttcatccgct cgctggggat ggatcatttc cgtcttccgg tggacgagaa ggaactttgg     360
acggaggatc ttgagaagat tcccgaagcg tgggattacc tcaggaatgc tctaagctgg     420
gctagaaagc atgagcttcg tgtgattgtg atcttcacg tcgtgcggtc ccatcacttt     480
aatgcggcaa atgaaggggg aaccaacact ctgtgggatg atccggaggc gcaggaaagt     540
ttcctcaacc tttggaggca gctttcggca gagctcgcct acaccgatgt ggactgggtg     600
gcctatgaga tcatgaatga ggccgtcgcg gatgatccgg aggactggaa tcgtctcatc     660
gccaaagccc actccttgat ccgcgagcgt gagccaaggc gcacactcgt catcggatcc     720
aaccggtggc aaattccgtc aacgttcccg gatctgaaga ttccggacgg agatccgaac     780
atcctcctga gtttccattt ctacgcgcct ctgcttttca cccactatcg ggcaacctgg     840
gttgccttt acgattatga tgggccggtt cctatcctg caggatcgt tgatgatgca     900
gctcttgaga aaaatgatta tactcctgca ttcaaagaca agattcgtgc gttgaatggt     960
gtgtatgaca tcgacgctct cgaaaaagaa atgcagccgg ctatcgaata cgcaaaacag    1020
aaagggttac cactgtattg cggagagtgg ggatgttttc atgctgtgga agaaaacaa    1080
cgcttgcaat ggtacaaaga tatatccact attttgaaac gcaatgggat cgcccatgcc    1140
acatgggatt acaagggcga gttcggcatt gtggacactt ggacactagg tgttgattgg    1200
aatttggtag gagcaatcct gtcagagtag                                    1230
```

<210> SEQ ID NO 62
<211> LENGTH: 409
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (62)...(390)
<223> OTHER INFORMATION: Cellulase (glycosyl hydrolase family 5)
<220> FEATURE:
<221> NAME/KEY: SITE
<222> LOCATION: (73)...(76)
<223> OTHER INFORMATION: N-glycosylation site. Prosite id = PS00001

<400> SEQUENCE: 62

```
Met Val Trp Thr Pro Ala Arg Ser Thr Leu Ala Gly Ser Ser Glu Ile
1               5                   10                  15

Pro Leu Met Thr Met Asn Ile Phe Pro Asn Arg Lys Asp Ser Arg Met
            20                  25                  30
```

Ser Leu Trp Ile Lys Leu Gly Ile Leu Cys Met Met Ala Gly Thr Val
    35                  40                  45

Met Val His Gly Ala Gln Thr Gly Gln Gly Glu Ala Thr Met Asn Gln
 50                  55                  60

Ala Asn Gly Phe Lys Val Ser Asn Gly Thr Asn Ile Ser His Trp Leu
 65                  70                  75                  80

Ser Gln Cys Phe Glu Thr Met Pro Pro Arg Arg Gly Phe Phe Ser Glu
                 85                  90                  95

Leu Asp Val Ile Phe Ile Arg Ser Leu Gly Met Asp His Phe Arg Leu
                100                 105                 110

Pro Val Asp Glu Lys Glu Leu Trp Thr Glu Asp Leu Glu Lys Ile Pro
                115                 120                 125

Glu Ala Trp Asp Tyr Leu Arg Asn Ala Leu Ser Trp Ala Arg Lys His
                130                 135                 140

Glu Leu Arg Val Ile Val Asp Leu His Val Val Arg Ser His His Phe
145                 150                 155                 160

Asn Ala Ala Asn Glu Gly Gly Thr Asn Thr Leu Trp Asp Asp Pro Glu
                165                 170                 175

Ala Gln Glu Ser Phe Leu Asn Leu Trp Arg Gln Leu Ser Ala Glu Leu
                180                 185                 190

Ala Tyr Thr Asp Val Asp Trp Val Ala Tyr Glu Ile Met Asn Glu Ala
                195                 200                 205

Val Ala Asp Asp Pro Glu Asp Trp Asn Arg Leu Ile Ala Lys Ala His
210                 215                 220

Ser Leu Ile Arg Glu Arg Glu Pro Arg Arg Thr Leu Val Ile Gly Ser
225                 230                 235                 240

Asn Arg Trp Gln Ile Pro Ser Thr Phe Pro Asp Leu Lys Ile Pro Asp
                245                 250                 255

Gly Asp Pro Asn Ile Leu Leu Ser Phe His Phe Tyr Ala Pro Leu Leu
                260                 265                 270

Phe Thr His Tyr Arg Ala Thr Trp Val Ala Phe Tyr Asp Tyr Asp Gly
                275                 280                 285

Pro Val Ser Tyr Pro Gly Arg Ile Val Asp Asp Ala Ala Leu Glu Lys
                290                 295                 300

Asn Asp Tyr Thr Pro Ala Phe Lys Asp Lys Ile Arg Ala Leu Asn Gly
305                 310                 315                 320

Val Tyr Asp Ile Asp Ala Leu Glu Lys Glu Met Gln Pro Ala Ile Glu
                325                 330                 335

Tyr Ala Lys Gln Lys Gly Leu Pro Leu Tyr Cys Gly Glu Trp Gly Cys
                340                 345                 350

Phe His Ala Val Glu Arg Lys Gln Arg Leu Gln Trp Tyr Lys Asp Ile
                355                 360                 365

Ser Thr Ile Leu Lys Arg Asn Gly Ile Ala His Ala Thr Trp Asp Tyr
370                 375                 380

Lys Gly Glu Phe Gly Ile Val Asp Thr Trp Thr Leu Gly Val Asp Trp
385                 390                 395                 400

Asn Leu Val Gly Ala Ile Leu Ser Glu
                405

<210> SEQ ID NO 63
<211> LENGTH: 1152
<212> TYPE: DNA
<213> ORGANISM: Unknown
<220> FEATURE:
<223> OTHER INFORMATION: Obtained from environmental sample

<400> SEQUENCE: 63

```
atgaaacgga gggaattcat gttgggggggt gcgggtgttg ctgcgttggc atcgactctt      60
ggagtctccg ccggttccac ttccgggcag ggagtgaacg agaatgtgag ggtataccgg     120
aatgcgattc cccgttggag ggggttcaac ctcatgccct ttttctcggc aatgagcacc     180
aacccggaat acaatggtct gacggtgccg gaggatgacc taaactggat ccgcgactgg     240
ggttttgact atgtccggct tccgattgat tactggattc tggttgattc cgattggcga     300
gatgcaaagc gcatgcgggt agaggatgtt cgcaaggccg accagaaggg atattcacgg     360
ctggacgctg tgattgaagc ctgtatcgcg aagggtttgc acctcaacct gaatatgcat     420
cggtgtcccg gtattgcat caatggctgg gaactggagc cctataacct cttcaaggat     480
gagcaggcgg aggatgattt tgtctaccat tgggagttgc tcgcgagacg ctataaggga     540
atcgatcctt cgctgctgag tttcaatctg ctgaatgagg ctcccaatcc tggagacaag     600
atgtcgtcgg aggattatcg tcgggtgatg cttcgatccg ctgctgttat tcggggggata     660
agcccggacc gcatgattat tgtggacggg ctggaaatcg gtaaatcagt tgttccaggg     720
ctgatgcatg agccatttgc ccaagctgtt catgcctacg agcccacga gttgagccat     780
tataatgcgc cttggacgtc ggtgtttatg ggtattcctg agccatcctg gccgacagtt     840
cgtttggatg gttctctgtt cgaccgcaag cgactggagt tgtatttcgc gccgtggggg     900
gagttggtcc gccaggggggt aggggtccac tgtggggaga ccggttgcta cattcatacg     960
ccccatcggg tgtttctgtc ctggttcgaa gatgttttgg atatcctgac cggatacgac    1020
atagggtggg ctctatggaa tttccgggga gatttcggaa tacttgattc caaacgcaag    1080
gatgtgcaat atgtcgattg gtatggacac cagctcgatc aacgcttgct ggatcttctg    1140
aaatcccact aa                                                         1152
```

<210> SEQ ID NO 64
<211> LENGTH: 383
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(24)
<220> FEATURE:
<221> NAME/KEY: DOMAIN
<222> LOCATION: (48)...(357)
<223> OTHER INFORMATION: Cellulase (glycosyl hydrolase family 5)

<400> SEQUENCE: 64

```
Met Lys Arg Arg Glu Phe Met Leu Gly Gly Ala Gly Val Ala Ala Leu
1               5                   10                  15
Ala Ser Thr Leu Gly Val Ser Ala Gly Ser Thr Ser Gly Gln Gly Val
            20                  25                  30
Asn Glu Asn Val Arg Val Tyr Arg Asn Ala Ile Pro Arg Trp Arg Gly
        35                  40                  45
Phe Asn Leu Met Pro Phe Phe Ser Ala Met Ser Thr Asn Pro Glu Tyr
    50                  55                  60
Asn Gly Leu Thr Val Pro Glu Asp Asp Leu Asn Trp Ile Arg Asp Trp
65                  70                  75                  80
Gly Phe Asp Tyr Val Arg Leu Pro Ile Asp Tyr Trp Ile Leu Val Asp
                85                  90                  95
Ser Asp Trp Arg Asp Ala Lys Arg Met Arg Val Glu Asp Val Arg Lys
            100                 105                 110
```

```
Ala Asp Gln Lys Gly Tyr Ser Arg Leu Asp Ala Val Ile Glu Ala Cys
        115                 120                 125

Ile Ala Lys Gly Leu His Leu Asn Leu Asn Met His Arg Cys Pro Gly
130                 135                 140

Tyr Cys Ile Asn Gly Trp Glu Leu Glu Pro Tyr Asn Leu Phe Lys Asp
145                 150                 155                 160

Glu Gln Ala Glu Asp Asp Phe Val Tyr His Trp Leu Leu Ala Arg
                165                 170                 175

Arg Tyr Lys Gly Ile Asp Pro Ser Leu Leu Ser Phe Asn Leu Leu Asn
            180                 185                 190

Glu Ala Pro Asn Pro Gly Asp Lys Met Ser Ser Glu Asp Tyr Arg Arg
        195                 200                 205

Val Met Leu Arg Ser Ala Ala Val Ile Arg Gly Ile Ser Pro Asp Arg
210                 215                 220

Met Ile Ile Val Asp Gly Leu Glu Ile Gly Lys Ser Val Val Pro Gly
225                 230                 235                 240

Leu Met His Glu Pro Phe Ala Gln Ala Val His Ala Tyr Glu Pro His
                245                 250                 255

Glu Leu Ser His Tyr Asn Ala Pro Trp Thr Ser Val Phe Met Gly Ile
            260                 265                 270

Pro Glu Pro Ser Trp Pro Thr Val Arg Leu Asp Gly Ser Leu Phe Asp
        275                 280                 285

Arg Lys Arg Leu Glu Leu Tyr Phe Ala Pro Trp Gly Glu Leu Val Arg
290                 295                 300

Gln Gly Val Gly Val His Cys Gly Glu Thr Gly Cys Tyr Ile His Thr
305                 310                 315                 320

Pro His Arg Val Phe Leu Ser Trp Phe Glu Asp Val Leu Asp Ile Leu
                325                 330                 335

Thr Gly Tyr Asp Ile Gly Trp Ala Leu Trp Asn Phe Arg Gly Asp Phe
            340                 345                 350

Gly Ile Leu Asp Ser Lys Arg Lys Asp Val Gln Tyr Val Asp Trp Tyr
        355                 360                 365

Gly His Gln Leu Asp Gln Arg Leu Leu Asp Leu Leu Lys Ser His
370                 375                 380

<210> SEQ ID NO 65
<211> LENGTH: 1131
<212> TYPE: DNA
<213> ORGANISM: Unknown
<220> FEATURE:
<223> OTHER INFORMATION: Obtained from environmental sample

<400> SEQUENCE: 65
atgaacacac tcctaccacg gcggcgactg tggtcctcca cggcgatcct gcgcacgctg      60
gcggccgggg cgctggcggc cggtatggtc ctggcacccg tcagtgccgc caacgcggcc     120
accaccctcg gtgcctcggc ggcggagaag ggccggtact cggtgcggc cgtcgggacg      180 tacaagttca cgacagcac ctacatgtcg gtgctgaacc gcgagttcaa cagcctggtc      240
gccgagaacg agatgaagtg ggacgcgacc gagccccagc gcggcgtgtt caactacagc     300 gccgggacc gcatcgtcaa ccacgcccga tcccagggca tgaaggtacg cggacacgcc      360
ctgttgtggc acgccagca gccacgctgg acgagggcc tgtccggcgg cgacctgcgc      420
aacgccgcga tcaaccatgt cacccaggtg gccagccact ccgggggca gatctactcc      480 tgggacgtgg tgaacgaggc tttcgccgac ggtggcagcg tgcccggcg ggactcgaac      540 ctccagcgca ccggcaacga ctggatcgag gcggcgttcc gtgccgcccg ggcagccgat     600
```

| | | |
|---|---|---|
| cccaacgcca agctctgcta caacgactac aacaccgacg ggatcaacgc gaagtccacc | 660 | |
| ggcgtctaca acatggtgcg tgacttcaag tcccgtgggg tgccgatcga ctgcgtgggc | 720 | |
| ttccagtcac acctgggcac caccctcccc ggtgactacc aggccaacct tcagcgcttc | 780 | |
| gccgacctgg gcgtcgacgt ggagatcacc gagctggaca tcacccaggg cggaaaccag | 840 | |
| gccaacatgt acggcgccgt cacccgcgcc tgcctggcga tctcgcgctg caccggcatc | 900 | |
| accgtgtggg gggtacggga ctgcgactcc tggcgtggtg gggacaacgc cctgctgttc | 960 | |
| gactgcgccg gcaacaagaa gcccgcgtac acggccgtcc tcgacgccct caacagcggc | 1020 |
| tcgaacccga accccaaccc caccggcaac cggctgcgca acgaggcctc cggtcgatgc | 1080 |
| ctggacgtca acggcgcaag ctccgccaac gggtcacaaa tgatccaaag a | 1131 |

```
<210> SEQ ID NO 66
<211> LENGTH: 377
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(39)
<220> FEATURE:
<221> NAME/KEY: DOMAIN
<222> LOCATION: (42)...(337)
<223> OTHER INFORMATION: Glycosyl hydrolase family 10
<220> FEATURE:
<221> NAME/KEY: SITE
<222> LOCATION: (99)...(102)
<223> OTHER INFORMATION: N-glycosylation site. Prosite id = PS00001
<220> FEATURE:
<221> NAME/KEY: SITE
<222> LOCATION: (268)...(278)
<223> OTHER INFORMATION: Glycosyl hydrolases family 10 active site.
      Prosite id = PS00591
<220> FEATURE:
<221> NAME/KEY: SITE
<222> LOCATION: (375)...(378)
<223> OTHER INFORMATION: N-glycosylation site. Prosite id = PS00001

<400> SEQUENCE: 66
```

Met Asn Thr Leu Leu Pro Arg Arg Arg Leu Trp Ser Ser Thr Ala Ile
1               5                   10                  15

Leu Arg Thr Leu Ala Ala Gly Ala Leu Ala Ala Gly Met Val Leu Ala
            20                  25                  30

Pro Val Ser Ala Ala Asn Ala Ala Thr Thr Leu Gly Ala Ser Ala Ala
        35                  40                  45

Glu Lys Gly Arg Tyr Phe Gly Ala Ala Val Gly Thr Tyr Lys Phe Asn
    50                  55                  60

Asp Ser Thr Tyr Met Ser Val Leu Asn Arg Glu Phe Asn Ser Leu Val
65                  70                  75                  80

Ala Glu Asn Glu Met Lys Trp Asp Ala Thr Glu Pro Gln Arg Gly Val
                85                  90                  95

Phe Asn Tyr Ser Ala Gly Asp Arg Ile Val Asn His Ala Arg Ser Gln
            100                 105                 110

Gly Met Lys Val Arg Gly His Ala Leu Leu Trp His Ala Gln Gln Pro
        115                 120                 125

Arg Trp Thr Glu Gly Leu Ser Gly Gly Asp Leu Arg Asn Ala Ala Ile
    130                 135                 140

Asn His Val Thr Gln Val Ala Ser His Phe Arg Gly Gln Ile Tyr Ser
145                 150                 155                 160

Trp Asp Val Val Asn Glu Ala Phe Ala Asp Gly Gly Ser Gly Ala Arg

-continued

```
                        165                 170                 175
Arg Asp Ser Asn Leu Gln Arg Thr Gly Asn Asp Trp Ile Glu Ala Ala
            180                 185                 190

Phe Arg Ala Ala Arg Ala Ala Asp Pro Asn Ala Lys Leu Cys Tyr Asn
        195                 200                 205

Asp Tyr Asn Thr Asp Gly Ile Asn Ala Lys Ser Thr Gly Val Tyr Asn
    210                 215                 220

Met Val Arg Asp Phe Lys Ser Arg Gly Val Pro Ile Asp Cys Val Gly
225                 230                 235                 240

Phe Gln Ser His Leu Gly Thr Thr Leu Pro Gly Asp Tyr Gln Ala Asn
                245                 250                 255

Leu Gln Arg Phe Ala Asp Leu Gly Val Asp Val Glu Ile Thr Glu Leu
            260                 265                 270

Asp Ile Thr Gln Gly Gly Asn Gln Ala Asn Met Tyr Gly Ala Val Thr
        275                 280                 285

Arg Ala Cys Leu Ala Ile Ser Arg Cys Thr Gly Ile Thr Val Trp Gly
    290                 295                 300

Val Arg Asp Cys Asp Ser Trp Arg Gly Gly Asp Asn Ala Leu Leu Phe
305                 310                 315                 320

Asp Cys Ala Gly Asn Lys Lys Pro Ala Tyr Thr Ala Val Leu Asp Ala
                325                 330                 335

Leu Asn Ser Gly Ser Asn Pro Asn Pro Asn Pro Thr Gly Asn Arg Leu
            340                 345                 350

Arg Asn Glu Ala Ser Gly Arg Cys Leu Asp Val Asn Gly Ala Ser Ser
        355                 360                 365

Ala Asn Gly Ser Gln Met Ile Gln Arg
    370                 375

<210> SEQ ID NO 67
<211> LENGTH: 1023
<212> TYPE: DNA
<213> ORGANISM: Unknown
<220> FEATURE:
<223> OTHER INFORMATION: Obtained from environmental sample

<400> SEQUENCE: 67
atgaaatata tattttcgta tataataatg atgattttaa tcggttttat accggtctat     60
ggattcggcg attcacctga ccaaacatac tctctcccct tcctcagcgt agaaggaaat    120
tcattcgtcg atgaaaacgg tgaggaggtt attttgcggg gtgtatcgtt tcccgatccc    180
aatcgattgg atgatgctac tcaatggaac aaacggtatt ccaggcagc aaaagattgg     240 aactgtaatg tcgtcagaat accggttcat ccgcaaagat ggcgggaaag gggaaaagaa    300
aattatctga acttttaga taagggtatc gagtgggccg gtgaactcgg tatgtacgtg     360
atcattgact ggcacactat cggcaatccg attccgaag tgttcttcgg cgagctctat     420
aatacgaccc agaccgaaac gttccggttc tggagaacaa tagcggagcg atatgcaggt    480
aatcccgttg ttgcatttta tgaattgttt aatgaaccga ccgattataa cggtcggctc    540
gggaggatga cctgggatca atataaagaa ttcatcgaag agatcattta tataatttat    600
gcacacgacg aaaccgtgat accgcttgta ggcggtttcg attggggata tgatctcagg    660
aatgttagag ataatccgat aaatgccccg ggtatcgcgt atgttactca cccgtatccg    720
caaaagcggg accaaccgtg ggaagaaaaa tgggaaaggg attccggttt cgtagccgac    780 acctacccctg tgtttgctac cgagttcgga tttatgagtg aggatggttt gggtgcacat    840
attcccgtta tcggtgatga acatacggt gaagcgatca tcagttactt caatgagaaa    900
```

```
ggtatatcgt ggacggcctg ggtgttcgat ccgctctggt cgccgcagct tattaaagac    960
tggtatttta ccccgacccg gcagggacag ttttttaaag agaagctaat ggagttgaat   1020
taa                                                                1023
```

```
<210> SEQ ID NO 68
<211> LENGTH: 340
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(23)
<220> FEATURE:
<221> NAME/KEY: DOMAIN
<222> LOCATION: (40)...(317)
<223> OTHER INFORMATION: Cellulase (glycosyl hydrolase family 5)
<220> FEATURE:
<221> NAME/KEY: SITE
<222> LOCATION: (143)...(146)
<223> OTHER INFORMATION: N-glycosylation site. Prosite id = PS00001

<400> SEQUENCE: 68
```

Met Lys Tyr Ile Phe Ser Tyr Ile Ile Met Met Ile Leu Ile Gly Phe
1               5                   10                  15

Ile Pro Val Tyr Gly Phe Gly Asp Ser Pro Asp Gln Thr Tyr Ser Leu
            20                  25                  30

Pro Phe Leu Ser Val Glu Gly Asn Ser Phe Val Asp Glu Asn Gly Glu
        35                  40                  45

Glu Val Ile Leu Arg Gly Val Ser Phe Pro Asp Pro Asn Arg Leu Asp
    50                  55                  60

Asp Ala Thr Gln Trp Asn Lys Arg Tyr Phe Gln Ala Ala Lys Asp Trp
65                  70                  75                  80

Asn Cys Asn Val Val Arg Ile Pro Val His Pro Gln Arg Trp Arg Glu
                85                  90                  95

Arg Gly Lys Glu Asn Tyr Leu Lys Leu Leu Asp Lys Gly Ile Glu Trp
            100                 105                 110

Ala Gly Glu Leu Gly Met Tyr Val Ile Ile Asp Trp His Thr Ile Gly
        115                 120                 125

Asn Pro Ile Thr Glu Val Phe Phe Gly Glu Leu Tyr Asn Thr Thr Gln
    130                 135                 140

Thr Glu Thr Phe Arg Phe Trp Arg Thr Ile Ala Glu Arg Tyr Ala Gly
145                 150                 155                 160

Asn Pro Val Val Ala Phe Tyr Glu Leu Phe Asn Glu Pro Thr Asp Tyr
                165                 170                 175

Asn Gly Arg Leu Gly Arg Met Thr Trp Asp Gln Tyr Lys Glu Phe Ile
            180                 185                 190

Glu Glu Ile Ile Tyr Ile Ile Tyr Ala His Asp Glu Thr Val Ile Pro
        195                 200                 205

Leu Val Gly Gly Phe Asp Trp Gly Tyr Asp Leu Arg Asn Val Arg Asp
    210                 215                 220

Asn Pro Ile Asn Ala Pro Gly Ile Ala Tyr Val Thr His Pro Tyr Pro
225                 230                 235                 240

Gln Lys Arg Asp Gln Pro Trp Glu Glu Lys Trp Glu Arg Asp Phe Gly
                245                 250                 255

Phe Val Ala Asp Thr Tyr Pro Val Phe Ala Thr Glu Phe Gly Phe Met
            260                 265                 270

Ser Glu Asp Gly Leu Gly Ala His Ile Pro Val Ile Gly Asp Glu Thr

Tyr Gly Glu Ala Ile Ile Ser Tyr Phe Asn Glu Lys Gly Ile Ser Trp
        275                 280                 285

Thr Ala Trp Val Phe Asp Pro Leu Trp Ser Pro Gln Leu Ile Lys Asp
290                 295                 300

Trp Tyr Phe Thr Pro Thr Arg Gln Gly Gln Phe Phe Lys Gly Lys Leu
305                 310                 315                 320

Met Glu Leu Asn
            325                 330                 335

340

<210> SEQ ID NO 69
<211> LENGTH: 1182
<212> TYPE: DNA
<213> ORGANISM: Unknown
<220> FEATURE:
<223> OTHER INFORMATION: Obtained from environmental sample

<400> SEQUENCE: 69

```
atgagtttta aaaccacat acttttgtcg ctcctcatag tattgctttt cttttcagcg      60
tgcgatatcg aagaaccgat cgccggagat tatcatacac ttgtggatca aaacgctata    120
tcgcacaccc gcgcattatt caccaacctc gaacgtatcc gtcacgatca tatcctcttc    180
ggtcatcagg atgcgcttgc atacggtgtt cactggcgca acgatgagcc gggtcgatcg    240
gatgtattcg aagtaaccgg ttcgtatcct gcggtgtatg gctgggagat tggcgatatt    300
gaacttggtg caccggaaaa tctggataac gtaaacttcg atcaaatgca gggctggatt    360
cgcgaagggt acgaacgcgg cggtataatt acgattagct ggcatatgaa caatccggca    420
tcgggtggtg attcgtggga tgtgaatgga ggtcataaag cggtaactaa gatacttccc    480
ggcggagaac ttcacgatac gtttaaagaa tggctggata cgtttgcaaa attcgcgaag    540
agccagattg cttttcccga aacaaataat gaacaccttaa tcccggtcat attccggccg    600
tatcatgaaa acaccggaag ctggttctgg tggggcgccg accactgtac acctgaagaa    660
tataaaaagt tatggcgatt taccgtcgaa tacctgcgcg atgtaaaagg tgttcacaat    720
ctcctctggg cgtattcacc tgccggcaat gctgcggatt cagaggaagc atattttgct    780
cggtatcccg gcgacgacta tgttgatatt attggattcg acgattacgg cagtgtgcgg    840
aaaccgtatc aaatcgaacg ttttactaac cggattcgaa cgattgtaaa cttcgccgaa    900
gcacgaaata aaatcccggc aataacggaa accggctatg aaactatccc cgatccgcaa    960
tggtggacgg gtacattgct tagtgcactt gatcacgatt tgacaacccg gaaatagca   1020 tacgtacttg tgtggcgaaa ttcaaacaat gctaccgacc ggcagaatca ttattacgct   1080
ccgtatcccg gacatccaag tgctgacgat tttatcgcgt tcaggaatca cccgttgata   1140
gttttcgaag atgatctgcc gggtatgtat acactaccgt aa                     1182
```

<210> SEQ ID NO 70
<211> LENGTH: 393
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (35)...(351)
<223> OTHER INFORMATION: Glycosyl hydrolase family 26
<220> FEATURE:
<221> NAME/KEY: SITE
<222> LOCATION: (355)...(358)
<223> OTHER INFORMATION: N-glycosylation site. Prosite id = PS00001

<400> SEQUENCE: 70

```
Met Ser Phe Lys Asn His Ile Leu Leu Ser Leu Leu Ile Val Leu Leu
1               5                   10                  15

Phe Phe Ser Ala Cys Asp Ile Glu Glu Pro Ile Ala Gly Asp Tyr His
            20                  25                  30

Thr Leu Val Asp Gln Asn Ala Ile Ser His Thr Arg Ala Leu Phe Thr
        35                  40                  45

Asn Leu Glu Arg Ile Arg His Asp His Ile Leu Phe Gly His Gln Asp
50                  55                  60

Ala Leu Ala Tyr Gly Val His Trp Arg Asn Asp Glu Pro Gly Arg Ser
65                  70                  75                  80

Asp Val Phe Glu Val Thr Gly Ser Tyr Pro Ala Val Tyr Gly Trp Glu
                85                  90                  95

Ile Gly Asp Ile Glu Leu Gly Ala Pro Glu Asn Leu Asp Asn Val Asn
            100                 105                 110

Phe Asp Gln Met Gln Gly Trp Ile Arg Glu Gly Tyr Glu Arg Gly Gly
        115                 120                 125

Ile Ile Thr Ile Ser Trp His Met Asn Asn Pro Ala Ser Gly Gly Asp
130                 135                 140

Ser Trp Asp Val Asn Gly Gly His Lys Ala Val Thr Lys Ile Leu Pro
145                 150                 155                 160

Gly Gly Glu Leu His Asp Thr Phe Lys Glu Trp Leu Asp Thr Phe Ala
                165                 170                 175

Lys Phe Ala Lys Ser Gln Ile Ala Phe Pro Glu Thr Asn Asn Glu His
            180                 185                 190

Leu Ile Pro Val Ile Phe Arg Pro Tyr His Glu Asn Thr Gly Ser Trp
        195                 200                 205

Phe Trp Trp Gly Ala Asp His Cys Thr Pro Glu Glu Tyr Lys Lys Leu
210                 215                 220

Trp Arg Phe Thr Val Glu Tyr Leu Arg Asp Val Lys Gly Val His Asn
225                 230                 235                 240

Leu Leu Trp Ala Tyr Ser Pro Ala Gly Asn Ala Ala Asp Ser Glu Glu
                245                 250                 255

Ala Tyr Phe Ala Arg Tyr Pro Gly Asp Asp Tyr Val Asp Ile Ile Gly
            260                 265                 270

Phe Asp Asp Tyr Gly Ser Val Arg Lys Pro Tyr Gln Ile Glu Arg Phe
        275                 280                 285

Thr Asn Arg Ile Arg Thr Ile Val Asn Phe Ala Glu Ala Arg Asn Lys
290                 295                 300

Ile Pro Ala Ile Thr Glu Thr Gly Tyr Glu Thr Ile Pro Asp Pro Gln
305                 310                 315                 320

Trp Trp Thr Gly Thr Leu Leu Ser Ala Leu Asp His Asp Leu Thr Thr
                325                 330                 335

Arg Arg Ile Ala Tyr Val Leu Val Trp Arg Asn Ser Asn Asn Ala Thr
            340                 345                 350

Asp Arg Gln Asn His Tyr Tyr Ala Pro Tyr Pro Gly His Pro Ser Ala
        355                 360                 365

Asp Asp Phe Ile Ala Phe Arg Asn His Pro Leu Ile Val Phe Glu Asp
370                 375                 380

Asp Leu Pro Gly Met Tyr Thr Leu Pro
385                 390
```

-continued

<210> SEQ ID NO 71
<211> LENGTH: 1089
<212> TYPE: DNA
<213> ORGANISM: Unknown
<220> FEATURE:
<223> OTHER INFORMATION: Obtained from environmental sample

<400> SEQUENCE: 71

| | |
|---|---|
| atgaaacttt taaaactttt aatctttctc cttattacgg taattttttc tgatgtttcg | 60 |
| gctcaaactt ttcaaataca aaaaggcaag aacattagcc attggctgtc ccaaagtaaa | 120 |
| agaaggggag aagagcgaaa agagttcttt actaagaatg acgtagaatt tattgcaggc | 180 |
| atcggcttcg atcatattcg tattcctatt gacgaggagc aaatgtggga tgaaaaggc | 240 |
| aacaaagagc ctgaagcgtt tcagttgctg cacaacgcga tagaatggag caggcaatcg | 300 |
| aacttaaaag ttattgtgga cctgcatatt tgaggtcgc attatttcaa cgcggaagaa | 360 |
| aaaccgcttt ttacggaccc taaagctcag gaacgttttt accaatgttg ggcggatctg | 420 |
| tctggtgaat tgaaaaaata tccgaataca ctggtggctt atgaattaat gaacgaacct | 480 |
| gtagccgatg atccggaaga ctggaataga attgtaagag aatcagtaaa aaggctaagg | 540 |
| gtgcttgagc ccaatagggt tattgtaatc gggtctaacc gatggcagca ttatgacact | 600 |
| ctgaaggatt tatacgtgcc ggaaaacgac aaaaacatca tttttaagctt tcattttat | 660 |
| aaccctatgt tgcttacgca ttcagggcc agctgggtaa atttcggcga ttaccaggt | 720 |
| cccgttaact acccgggaca gttggtagac tcaaagcatt tgtcgggact gagcgaagat | 780 |
| ttaagaaaga aagtcgagca aaacaatggc gtttataata aggctcggat tgagaaaatg | 840 |
| atagccgaag ccgttgctgt agcaaaaaag cacaacctcc ctttgtattg tggtgaatgg | 900 |
| ggtgcctacg aaaagcgcc aagggagccc aggctacaat ggtacagaga catggtggat | 960 |
| gtgttgaaca aaaacaatat tgcctggact acctgggact ataaaggagg cttcggcata | 1020 |
| gttgacgcca aaggaaacaa agacgaacag ttgatcaatg tattaacagg aaaagagaaa | 1080 |
| aaaatgtaa | 1089 |

<210> SEQ ID NO 72
<211> LENGTH: 362
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(21)
<220> FEATURE:
<221> NAME/KEY: DOMAIN
<222> LOCATION: (22)...(340)
<223> OTHER INFORMATION: Cellulase (glycosyl hydrolase family 5)
<220> FEATURE:
<221> NAME/KEY: SITE
<222> LOCATION: (31)...(34)
<223> OTHER INFORMATION: N-glycosylation site. Prosite id = PS00001
<220> FEATURE:
<221> NAME/KEY: SITE
<222> LOCATION: (154)...(163)
<223> OTHER INFORMATION: Glycosyl hydrolases family 5 signature. Prosite
    id = PS00659

<400> SEQUENCE: 72

Met Lys Leu Leu Lys Leu Leu Ile Phe Leu Leu Ile Thr Val Ile Phe
1               5                   10                  15

Ser Asp Val Ser Ala Gln Thr Phe Gln Ile Gln Lys Gly Lys Asn Ile
            20                  25                  30

Ser His Trp Leu Ser Gln Ser Lys Arg Arg Gly Glu Glu Arg Lys Glu
         35                  40                  45

Phe Phe Thr Lys Asn Asp Val Glu Phe Ile Ala Ile Gly Phe Asp
 50                  55                  60

His Ile Arg Ile Pro Ile Asp Glu Glu Gln Met Trp Asp Glu Lys Gly
 65                  70                  75                  80

Asn Lys Glu Pro Glu Ala Phe Gln Leu Leu His Asn Ala Ile Glu Trp
                 85                  90                  95

Ser Arg Gln Ser Asn Leu Lys Val Ile Val Asp Leu His Ile Leu Arg
            100                 105                 110

Ser His Tyr Phe Asn Ala Glu Glu Lys Pro Leu Phe Thr Asp Pro Lys
        115                 120                 125

Ala Gln Glu Arg Phe Tyr Gln Cys Trp Ala Asp Leu Ser Gly Glu Leu
    130                 135                 140

Lys Lys Tyr Pro Asn Thr Leu Val Ala Tyr Glu Leu Met Asn Glu Pro
145                 150                 155                 160

Val Ala Asp Asp Pro Glu Asp Trp Asn Arg Ile Val Arg Glu Ser Val
                165                 170                 175

Lys Arg Leu Arg Val Leu Glu Pro Asn Arg Val Ile Val Ile Gly Ser
            180                 185                 190

Asn Arg Trp Gln His Tyr Asp Thr Leu Lys Asp Leu Tyr Val Pro Glu
        195                 200                 205

Asn Asp Lys Asn Ile Ile Leu Ser Phe His Phe Tyr Asn Pro Met Leu
    210                 215                 220

Leu Thr His Tyr Arg Ala Ser Trp Val Asn Phe Gly Asp Tyr Gln Gly
225                 230                 235                 240

Pro Val Asn Tyr Pro Gly Gln Leu Val Asp Ser Lys His Leu Ser Gly
                245                 250                 255

Leu Ser Glu Asp Leu Arg Lys Lys Val Glu Gln Asn Asn Gly Val Tyr
            260                 265                 270

Asn Lys Ala Arg Ile Glu Lys Met Ile Ala Glu Ala Val Ala Val Ala
        275                 280                 285

Lys Lys His Asn Leu Pro Leu Tyr Cys Gly Glu Trp Gly Ala Tyr Glu
    290                 295                 300

Lys Ala Pro Arg Glu Pro Arg Leu Gln Trp Tyr Arg Asp Met Val Asp
305                 310                 315                 320

Val Leu Asn Lys Asn Asn Ile Ala Trp Thr Thr Trp Asp Tyr Lys Gly
                325                 330                 335

Gly Phe Gly Ile Val Asp Ala Lys Gly Asn Lys Asp Glu Gln Leu Ile
            340                 345                 350

Asn Val Leu Thr Gly Lys Glu Lys Lys Met
        355                 360

<210> SEQ ID NO 73
<211> LENGTH: 1146
<212> TYPE: DNA
<213> ORGANISM: Unknown
<220> FEATURE:
<223> OTHER INFORMATION: Obtained from environmental sample

<400> SEQUENCE: 73
gtggatatta ccggacatcc cgaccacatc gccttcgcgc gggaagttgc cgagcaaagc      60
atggtcttgc tgcaaaaccg tgcgaacctc gccccccttt cggtatctga ctattccacc     120
attgccgtga tcgccccgaa tgccaatgac actttgctgg ttcttacag cggcgttccg      180 aaaacctact acacggtact cgacgggata cggtcctatg tcggtgaccg ggcgaatgtg     240

```
gtttacgctc aggggccgaa gataaccaaa cccggccatc gggaggacaa tgaagtattt      300
ccaccggatc ctgaaaacga ccggagacga ctggccgaag cgatagctgt cgccgagaac      360
gccgacctga tcatcctcgc gatcggcggc aatgaactga cgggacgaga ggcatgggcg      420
gcgcatcatc ccggtgatcg accggatctg tcgttgctcg gtttgcagga ggatcttgtt      480
gacgcagttg gagcgatggg ggttccatct gtcgcattgg ttttcggtgc acggccgctg      540
gacctcggca atgtcgccga aaaaattgat gtggtcttcc aaaactggta cctgggccag      600
gaaaccggca atgccgtcgc caatgtgctg tttggcgagg tgtcaccgtc cgccaaactc      660
cccatcagct tcccgcggac tgccgggcac attcctgcct actacaatta caaaccatcg      720
gctcgacggg tctacctttt tgacgatgtc actccgcgtt accatttcgg tacggcctc       780 agctatacga cgtttgaata cggggaaccg cagctatcgg atacactact gtctggcgat      840
ggtgaaataa ccctctacgt tgaagttacc aacaccggag agcgaggcgg ttcggaagtc      900
gtgcaactgt acatcaacca cgaatacaga tccgtcaccc ggccggtaaa ggagctcaag      960
ggattcgaaa aggtgtatct cgagccgaat gaaactgccg gtgtatcgtt caccatcact     1020
tcagatcagt tgaggttctg gaatatcgac atggagttta ccgctgaatc cggtaaagtg     1080
aacctgatgg tcggctcatc cagccgtgac gaagacctgc agacgacggc aattttttctt    1140 gaataa                                                                 1146

<210> SEQ ID NO 74
<211> LENGTH: 381
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (21)...(264)
<223> OTHER INFORMATION: Glycosyl hydrolase family 3 C terminal domain
<220> FEATURE:
<221> NAME/KEY: SITE
<222> LOCATION: (49)...(52)
<223> OTHER INFORMATION: N-glycosylation site. Prosite id = PS00001
<220> FEATURE:
<221> NAME/KEY: SITE
<222> LOCATION: (335)...(338)
<223> OTHER INFORMATION: N-glycosylation site. Prosite id = PS00001

<400> SEQUENCE: 74

Met Asp Ile Thr Gly His Pro Asp His Ile Ala Phe Ala Arg Glu Val
1               5                   10                  15

Ala Glu Gln Ser Met Val Leu Leu Gln Asn Arg Ala Asn Leu Ala Pro
            20                  25                  30

Leu Ser Val Ser Asp Tyr Ser Thr Ile Ala Val Ile Gly Pro Asn Ala
        35                  40                  45

Asn Asp Thr Leu Leu Gly Ser Tyr Ser Gly Val Pro Lys Thr Tyr Tyr
    50                  55                  60

Thr Val Leu Asp Gly Ile Arg Ser Tyr Val Gly Asp Arg Ala Asn Val
65                  70                  75                  80

Val Tyr Ala Gln Gly Pro Lys Ile Thr Lys Pro Gly His Arg Glu Asp
                85                  90                  95

Asn Glu Val Phe Pro Pro Asp Pro Glu Asn Asp Arg Arg Arg Leu Ala
            100                 105                 110

Glu Ala Ile Ala Val Ala Glu Asn Ala Asp Leu Ile Ile Leu Ala Ile
        115                 120                 125

Gly Gly Asn Glu Leu Thr Gly Arg Glu Ala Trp Ala Ala His His Pro
```

```
            130                 135                 140
Gly Asp Arg Pro Asp Leu Ser Leu Leu Gly Leu Gln Glu Asp Leu Val
145                 150                 155                 160

Asp Ala Val Gly Ala Met Gly Val Pro Ser Val Ala Leu Val Phe Gly
                165                 170                 175

Ala Arg Pro Leu Asp Leu Gly Asn Val Ala Glu Lys Ile Asp Val Val
            180                 185                 190

Phe Gln Asn Trp Tyr Leu Gly Gln Glu Thr Gly Asn Ala Val Ala Asn
        195                 200                 205

Val Leu Phe Gly Glu Val Ser Pro Ser Ala Lys Leu Pro Ile Ser Phe
210                 215                 220

Pro Arg Thr Ala Gly His Ile Pro Ala Tyr Tyr Asn Tyr Lys Pro Ser
225                 230                 235                 240

Ala Arg Arg Val Tyr Leu Phe Asp Asp Val Thr Pro Arg Tyr His Phe
                245                 250                 255

Gly Tyr Gly Leu Ser Tyr Thr Thr Phe Glu Tyr Gly Glu Pro Gln Leu
            260                 265                 270

Ser Asp Thr Leu Leu Ser Gly Asp Gly Glu Ile Thr Leu Tyr Val Glu
        275                 280                 285

Val Thr Asn Thr Gly Glu Arg Gly Gly Ser Glu Val Val Gln Leu Tyr
290                 295                 300

Ile Asn His Glu Tyr Arg Ser Val Thr Arg Pro Val Lys Glu Leu Lys
305                 310                 315                 320

Gly Phe Glu Lys Val Tyr Leu Glu Pro Asn Glu Thr Ala Gly Val Ser
                325                 330                 335

Phe Thr Ile Thr Ser Asp Gln Leu Arg Phe Trp Asn Ile Asp Met Glu
            340                 345                 350

Phe Thr Ala Glu Ser Gly Lys Val Asn Leu Met Val Gly Ser Ser Ser
        355                 360                 365

Arg Asp Glu Asp Leu Gln Thr Thr Ala Ile Phe Leu Glu
370                 375                 380

<210> SEQ ID NO 75
<211> LENGTH: 1014
<212> TYPE: DNA
<213> ORGANISM: Unknown
<220> FEATURE:
<223> OTHER INFORMATION: Obtained from environmental sample

<400> SEQUENCE: 75
atgctgcgca agttgatcgt ctcggtcttc ggcttcgtca tgctgactag tgcggcagcg      60
gcgcagactc ctcccgcctt agcggaatcc gcgcctgctc tccggcgcgg aatgaacgtt     120
ctgggctacg acccaatctg gcacgacccg aagaaaggtc ggttcgaaga gcggcacttc     180
gccgagattc gcaagggcgg cttcgacttc gttcgggtga acctccacgg gttcaaacat     240
atgaacgccg cggacaaact cagtccggag ttcctgagcc gcgtggactg gatcgtgaag     300
cacgccagtg cggcgggcct gtcggtcatc ctagacgagc atgaatatga ggaatgctcg     360
gacgacgtcg caatgtgccg gcggcgtttg gcggcattct ggacgcaggt cgcgccgcgc     420
tacaagggcg cgcccgatac ggttctgttc gagcttctca atgagccgca cgacaagttg     480
gatgccgaca cctggaacgc cttgtttccc gacatcctgg ccatcgtgcg gcagtcgaac     540
ccgaagcgcc gcgtggtgat cggcccgact cagtggaaca acttcagcca gctggacacg     600
ctcaagctgc cggcagacga ccggaacatc gtcgtcacct ccattatta cgatccgttc     660 ccgtttaccc accagggcgc gccgtggggtt ccggacatgc tcaaggtgaa aggcatcgag     720
```

```
tggaagcccg agcagagggc gaagatcgcc gaggacttcg gcaaggtcgc ggaatggtcg     780
cagaaaaccg gccgcgaaat cttgctcggc gagttcgggg cctacgatgt gagcggtacg     840
ccaaccgcca tgcgttcagc ttatacggaa gcggtggcgc gcgaggcgga acgccacggc     900
ttcgcttggg cctactggca gttcgacagc aatttcctgg cttgggacat gaagacaaac     960
ggctgggtcg agccgatcca caaggcactc atccccgagg cgaagcagcc ttag          1014
```

<210> SEQ ID NO 76
<211> LENGTH: 337
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (37)...(316)
<223> OTHER INFORMATION: Cellulase (glycosyl hydrolase family 5)
<220> FEATURE:
<221> NAME/KEY: SITE
<222> LOCATION: (150)...(159)
<223> OTHER INFORMATION: Glycosyl hydrolases family 5 signature. Prosite
      id = PS00659

<400> SEQUENCE: 76

Met Leu Arg Lys Leu Ile Val Ser Val Phe Gly Phe Val Met Leu Thr
1               5                   10                  15

Ser Ala Ala Ala Ala Gln Thr Pro Pro Ala Leu Ala Glu Ser Ala Pro
            20                  25                  30

Ala Leu Arg Arg Gly Met Asn Val Leu Gly Tyr Asp Pro Ile Trp His
        35                  40                  45

Asp Pro Lys Lys Gly Arg Phe Glu Glu Arg His Phe Ala Glu Ile Arg
    50                  55                  60

Lys Gly Gly Phe Asp Phe Val Arg Val Asn Leu His Gly Phe Lys His
65                  70                  75                  80

Met Asn Ala Ala Asp Lys Leu Ser Pro Glu Phe Leu Ser Arg Val Asp
                85                  90                  95

Trp Ile Val Lys His Ala Ser Ala Ala Gly Leu Ser Val Ile Leu Asp
            100                 105                 110

Glu His Glu Tyr Glu Glu Cys Ser Asp Asp Val Ala Met Cys Arg Arg
        115                 120                 125

Arg Leu Ala Ala Phe Trp Thr Gln Val Ala Pro Arg Tyr Lys Gly Ala
    130                 135                 140

Pro Asp Thr Val Leu Phe Glu Leu Leu Asn Glu Pro His Asp Lys Leu
145                 150                 155                 160

Asp Ala Asp Thr Trp Asn Ala Leu Phe Pro Asp Ile Leu Ala Ile Val
                165                 170                 175

Arg Gln Ser Asn Pro Lys Arg Arg Val Val Ile Gly Pro Thr Gln Trp
            180                 185                 190

Asn Asn Phe Ser Gln Leu Asp Thr Leu Lys Leu Pro Ala Asp Asp Arg
        195                 200                 205

Asn Ile Val Val Thr Phe His Tyr Tyr Asp Pro Phe Pro Phe Thr His
    210                 215                 220

Gln Gly Ala Pro Trp Val Pro Asp Met Leu Lys Val Lys Gly Ile Glu
225                 230                 235                 240

Trp Lys Pro Glu Gln Arg Ala Lys Ile Ala Glu Asp Phe Gly Lys Val
                245                 250                 255

Ala Glu Trp Ser Gln Lys Thr Gly Arg Glu Ile Leu Leu Gly Glu Phe
            260                 265                 270

-continued

```
Gly Ala Tyr Asp Val Ser Gly Thr Pro Thr Ala Met Arg Ser Ala Tyr
            275                 280                 285

Thr Glu Ala Val Ala Arg Glu Ala Glu Arg His Gly Phe Ala Trp Ala
        290                 295                 300

Tyr Trp Gln Phe Asp Ser Asn Phe Leu Ala Trp Asp Met Lys Thr Asn
305                 310                 315                 320

Gly Trp Val Glu Pro Ile His Lys Ala Leu Ile Pro Glu Ala Lys Gln
                325                 330                 335

Pro

<210> SEQ ID NO 77
<211> LENGTH: 1125
<212> TYPE: DNA
<213> ORGANISM: Unknown
<220> FEATURE:
<223> OTHER INFORMATION: Obtained from environmental sample

<400> SEQUENCE: 77
atgaaaagga acgggtttt tattcattct ctaatcgtat ttttttttaat gattggttct     60 tttacttctt gtggatcagt cgccgatgat gccgaagaag ggtttgatat ttttagagga   120
accaatatcg ctcattggtt atcacaaagt aatgcaaggg gcgaagagcg aaaaaatttc   180
tttaccgaaa atgatataaa atttattgct gatgctggtt ttgatcatat tcgtttgcca   240
attgacgagg ttcatttctg ggatgagaat atgaaccggc accaagatgc atttgatctt   300
atgcatgact gtattaagtg gtcagagaaa catggtctta gggttgtagt ggatttgcat   360
attattcgtt cacattattt tgttggagat gataatacac tatgggatga agacatgaa    420 caggaaaagt ttgttgatat ttggatggag ttatcatctg aactatctca atattcaaac   480
tcattagtag cttatgagtt aatgaatgaa cctgtagccc cttctcatga tgattggaat   540
agtttggttg cggaaactat agaggcaatt cgtaaagttg aacctgagag atatattgta   600
gttggatcaa atatgtggca aggtattgat acatttgagt atttggaagt tcccgaaaat   660
gatgatagaa taattcttag ttttcatttt tatgatcct  ttattttgac tcattatact   720
gcatcttggg ggtatttaag agattactca gggcctgtta actatccggg atatcttgtt   780
acaaatgacc agctgttgga tatgtcaaac gaaatgcaaa agttaattag ggagtttcag   840
acaaattttg atatttatac cattgaagaa ctgatatcta ttccatatag tattgcaaag   900 gaaaagggt tgaaattata ttgtggagag tttggtgcaa ttgatcaggc tccaagagat   960
gcgagattgg catggtacag agatgttgtt caggttttg agcgatatgg tatagctcat  1020
gccaactgga attacaaaga ttatggtacg tttgggataa agaactatag cgaggagata  1080
gatcaggaac tgtttgaaat cttaattgga acaaaacata aatag                  1125

<210> SEQ ID NO 78
<211> LENGTH: 374
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(28)
<220> FEATURE:
<221> NAME/KEY: DOMAIN
<222> LOCATION: (25)...(353)
<223> OTHER INFORMATION: Cellulase (glycosyl hydrolase family 5)
<220> FEATURE:
<221> NAME/KEY: SITE
<222> LOCATION: (165)...(174)
```

<223> OTHER INFORMATION: Glycosyl hydrolases family 5 signature. Prosite
id = PS00659
<220> FEATURE:
<221> NAME/KEY: SITE
<222> LOCATION: (360)...(363)
<223> OTHER INFORMATION: N-glycosylation site. Prosite id = PS00001

<400> SEQUENCE: 78

```
Met Lys Arg Lys Arg Val Phe Ile His Ser Leu Ile Val Phe Phe Leu
1               5                   10                  15

Met Ile Gly Ser Phe Thr Ser Cys Gly Ser Val Ala Asp Asp Ala Glu
            20                  25                  30

Glu Gly Phe Asp Ile Phe Arg Gly Thr Asn Ile Ala His Trp Leu Ser
        35                  40                  45

Gln Ser Asn Ala Arg Gly Glu Glu Arg Lys Asn Phe Phe Thr Glu Asn
    50                  55                  60

Asp Ile Lys Phe Ile Ala Asp Ala Gly Phe Asp His Ile Arg Leu Pro
65                  70                  75                  80

Ile Asp Glu Val His Phe Trp Asp Glu Asn Met Asn Arg His Gln Asp
                85                  90                  95

Ala Phe Asp Leu Met His Asp Cys Ile Lys Trp Ser Glu Lys His Gly
            100                 105                 110

Leu Arg Val Val Asp Leu His Ile Ile Arg Ser His Tyr Phe Val
        115                 120                 125

Gly Asp Asp Asn Thr Leu Trp Asp Glu Arg His Glu Gln Glu Lys Phe
130                 135                 140

Val Asp Ile Trp Met Glu Leu Ser Ser Glu Leu Ser Gln Tyr Ser Asn
145                 150                 155                 160

Ser Leu Val Ala Tyr Glu Leu Met Asn Glu Pro Val Ala Pro Ser His
                165                 170                 175

Asp Asp Trp Asn Ser Leu Val Ala Glu Thr Ile Glu Ala Ile Arg Lys
            180                 185                 190

Val Glu Pro Glu Arg Tyr Ile Val Val Gly Ser Asn Met Trp Gln Gly
        195                 200                 205

Ile Asp Thr Phe Glu Tyr Leu Glu Val Pro Gly Asn Asp Asp Arg Ile
    210                 215                 220

Ile Leu Ser Phe His Phe Tyr Asp Pro Phe Ile Leu Thr His Tyr Thr
225                 230                 235                 240

Ala Ser Trp Gly Tyr Leu Arg Asp Tyr Ser Gly Pro Val Asn Tyr Pro
                245                 250                 255

Gly Tyr Leu Val Thr Asn Asp Gln Leu Leu Asp Met Ser Asn Glu Met
            260                 265                 270

Gln Lys Leu Ile Arg Glu Phe Gln Thr Asn Phe Asp Ile Tyr Thr Ile
        275                 280                 285

Glu Glu Leu Ile Ser Ile Pro Tyr Ser Ile Ala Lys Glu Lys Gly Leu
    290                 295                 300

Lys Leu Tyr Cys Gly Glu Phe Gly Ala Ile Asp Gln Ala Pro Arg Asp
305                 310                 315                 320

Ala Arg Leu Ala Trp Tyr Arg Asp Val Val Gln Val Phe Glu Arg Tyr
                325                 330                 335

Gly Ile Ala His Ala Asn Trp Ser Tyr Lys Asp Tyr Gly Thr Phe Gly
            340                 345                 350

Ile Lys Asn Tyr Ser Glu Glu Ile Asp Gln Glu Leu Phe Glu Ile Leu
        355                 360                 365

Ile Gly Thr Lys His Lys
    370
```

<210> SEQ ID NO 79
<211> LENGTH: 1017
<212> TYPE: DNA
<213> ORGANISM: Unknown
<220> FEATURE:
<223> OTHER INFORMATION: Obtained from environmental sample

<400> SEQUENCE: 79

```
atgaaatata aagctatttt tatatacctt attgttttga ttctatttta ctcaattaat    60
atttatgcta atgcagaaaa caacccctc cccttcctca gtgtcgaagg aaacaggttc   120
gtcgatgaag atggaaatac ggtaatcctg cgaggtgtat cgttcccga tcccgaccgg   180
ctggctgagg caactcaatg gaacaagcga tacttccagg cggcaaaaga ctggaactgt   240
aatgtcgtcc ggattcctgt ccatccacag aaatggcggg aaagaggcga ggaaaattat   300
ctgaaacttt tagataaggg aattcaatgg gcgggtgaac tcgggatgta tgtaatcatc   360
gactggcata ccatcggtaa tccgataacc gaagtatttt tccgcgaact atacaatacg   420
tcacgtgcgg agaccttcca gttctggaga caatcgctg agcgctatgc cggtaacccg   480
gttgttgctt tctatgaact gttcaatgaa ccgaccgact acaacggccg tctcggaaga   540
atgaactggg atcagtataa agagtttatc gaggagataa ttcacatcat ctattctcac   600
gacgatacag ttatccctct cgttgccggt ttcgactggg cgtatgaact ccgccatata   660
aaagataaac ctatagattt tcccggcatc gcttatgtga ctcacccta tccccagaaa   720
cgcgatccgc catgggaaga aaatgggaa gaggatttcg ggtttgccgc cgatatgtat   780
ccggtgtttg caaccgagtt cggtttcatg ggggaggatg aattaggtgc acacataccc   840
gtcatcggcg atgaaacata cggcgaagcc attatcgatt acttttataa aaagggggata   900
tcgtggactg catgggtatt cgatccgctt tggtcgccgc agcttattag agactggtat   960
tttaccccgt cccgacaggg gcagtttttt aagagaagt tgatggagtt gaattag     1017
```

<210> SEQ ID NO 80
<211> LENGTH: 338
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(25)
<220> FEATURE:
<221> NAME/KEY: DOMAIN
<222> LOCATION: (38)...(315)
<223> OTHER INFORMATION: Cellulase (glycosyl hydrolase family 5)
<220> FEATURE:
<221> NAME/KEY: SITE
<222> LOCATION: (141)...(144)
<223> OTHER INFORMATION: N-glycosylation site. Prosite id = PS00001

<400> SEQUENCE: 80

```
Met Lys Tyr Lys Ala Ile Phe Ile Tyr Leu Ile Val Leu Ile Leu Phe
1               5                   10                  15

Tyr Ser Ile Asn Ile Tyr Ala Asn Ala Glu Asn Asn Pro Leu Pro Phe
            20                  25                  30

Leu Ser Val Glu Gly Asn Arg Phe Val Asp Glu Asp Gly Asn Thr Val
        35                  40                  45

Ile Leu Arg Gly Val Ser Phe Pro Asp Pro Asp Arg Leu Ala Glu Ala
    50                  55                  60

Thr Gln Trp Asn Lys Arg Tyr Phe Gln Ala Ala Lys Asp Trp Asn Cys
65                  70                  75                  80
```

Asn Val Val Arg Ile Pro Val His Pro Gln Lys Trp Arg Glu Arg Gly
                85                  90                  95

Glu Glu Asn Tyr Leu Lys Leu Leu Asp Lys Gly Ile Gln Trp Ala Gly
            100                 105                 110

Glu Leu Gly Met Tyr Val Ile Ile Asp Trp His Thr Ile Gly Asn Pro
        115                 120                 125

Ile Thr Glu Val Phe Phe Arg Glu Leu Tyr Asn Thr Ser Arg Ala Glu
    130                 135                 140

Thr Phe Gln Phe Trp Arg Thr Ile Ala Glu Arg Tyr Ala Gly Asn Pro
145                 150                 155                 160

Val Val Ala Phe Tyr Glu Leu Phe Asn Glu Pro Thr Asp Tyr Asn Gly
                165                 170                 175

Arg Leu Gly Arg Met Asn Trp Asp Gln Tyr Lys Glu Phe Ile Glu Glu
            180                 185                 190

Ile Ile His Ile Ile Tyr Ser His Asp Asp Thr Val Ile Pro Leu Val
        195                 200                 205

Ala Gly Phe Asp Trp Ala Tyr Glu Leu Arg His Ile Lys Asp Lys Pro
    210                 215                 220

Ile Asp Phe Pro Gly Ile Ala Tyr Val Thr His Pro Tyr Pro Gln Lys
225                 230                 235                 240

Arg Asp Pro Pro Trp Glu Glu Lys Trp Glu Glu Asp Phe Gly Phe Ala
                245                 250                 255

Ala Asp Met Tyr Pro Val Phe Ala Thr Glu Phe Gly Phe Met Gly Glu
            260                 265                 270

Asp Glu Leu Gly Ala His Ile Pro Val Ile Gly Asp Glu Thr Tyr Gly
        275                 280                 285

Glu Ala Ile Ile Asp Tyr Phe Tyr Lys Lys Gly Ile Ser Trp Thr Ala
    290                 295                 300

Trp Val Phe Asp Pro Leu Trp Ser Pro Gln Leu Ile Arg Asp Trp Tyr
305                 310                 315                 320

Phe Thr Pro Ser Arg Gln Gly Gln Phe Phe Lys Glu Lys Leu Met Glu
                325                 330                 335

Leu Asn

<210> SEQ ID NO 81
<211> LENGTH: 1119
<212> TYPE: DNA
<213> ORGANISM: Unknown
<220> FEATURE:
<223> OTHER INFORMATION: Obtained from environmental sample

<400> SEQUENCE: 81
atgaatttac ttgctcaata cttttccgga ctatttctga ttttttttgat ctcaattttt    60 ttcgttagtt ctgcagcgaa tcatcattat gaaaaaaata cagtcaacga attttctgat   120
gatgtaaatc aaacaacatt agtccttcaa cccgggatat ccgaagccca gaatactcaa   180
aacctgccgc ggattcggt tgaaggaaac caatttgtgg atgaatcggg aaacacagtc   240
acatttcagg gtgtcagtgt tgccgatccg cacaggctta ataatgccgg ccaatggaaa   300
cgggaactgt ttgaagaaat cgcaaactgg ggagcaaacg tcgttcgtct gcccatacac   360
ccgctctggt ggcgggaacg gggagaggag caatacctcg aatggattga tgaagccgtg   420
gagtgggcca agagctggga gatgtacctc atcatcgact ggcacagtat cgggaacctg   480
cggacagaac tcttttttcag ggatatctac aacaccaccc gccgtgaaac ttatgaattc   540
tggaggctga tttcggatcg ctatgctgat gaaaccacaa ttgccttta cgaaatcttt   600

```
aatgaaccca cacggcagca gggcaggctg ggaaccatga cctggaagca atggaaggaa      660
attctaaccg acattatcac aatcatttat gcccacaatc ctgatgcgat tccgctggta      720
gcaggtttta actgggcgta tgaccttact ccggtccgcc actcacccct cgattttgaa      780
ggtattgcct atgttaccca cccatatccg caaaaaagaa gcaggccctg ggttccaaaa      840
tgggaagaag atttcggttt tgtggctgac aaatatcctg tatttgccac tgaattcggc      900
tatatgaggg agtatgagcg gggcgctcat gtgcccgtaa tcggggacga agaatatggg      960
gaaatcctca tcaattattt ccgcgaaaaa gggatttcgt ggacagcctg gtattcgat     1020 ccaagctggt cgccacagct cattcaggat tgggattata cacccacacg ctcaggtgag     1080
tttttcagaa atgcgatgag aacgaaaaac aatgaataa                            1119
```

```
<210> SEQ ID NO 82
<211> LENGTH: 372
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(25)
<220> FEATURE:
<221> NAME/KEY: DOMAIN
<222> LOCATION: (70)...(347)
<223> OTHER INFORMATION: Cellulase (glycosyl hydrolase family 5)
<220> FEATURE:
<221> NAME/KEY: SITE
<222> LOCATION: (43)...(46)
<223> OTHER INFORMATION: N-glycosylation site. Prosite id = PS00001
<220> FEATURE:
<221> NAME/KEY: SITE
<222> LOCATION: (173)...(176)
<223> OTHER INFORMATION: N-glycosylation site. Prosite id = PS00001

<400> SEQUENCE: 82

Met Asn Leu Leu Ala Gln Tyr Phe Ser Gly Leu Phe Leu Ile Phe Leu
1               5                   10                  15

Ile Ser Ile Phe Phe Val Ser Ser Ala Ala Asn His His Tyr Glu Lys
            20                  25                  30

Asn Thr Val Asn Glu Phe Ser Asp Asp Val Asn Gln Thr Thr Leu Val
        35                  40                  45

Leu Gln Pro Gly Ile Ser Glu Ala Gln Asn Thr Gln Asn Leu Pro Arg
    50                  55                  60

Ile Ser Val Glu Gly Asn Gln Phe Val Asp Glu Ser Gly Asn Thr Val
65                  70                  75                  80

Thr Phe Gln Gly Val Ser Val Ala Asp Pro His Arg Leu Asn Asn Ala
                85                  90                  95

Gly Gln Trp Lys Arg Glu Leu Phe Glu Glu Ile Ala Asn Trp Gly Ala
            100                 105                 110

Asn Val Val Arg Leu Pro Ile His Pro Leu Trp Trp Arg Glu Arg Gly
        115                 120                 125

Glu Glu Gln Tyr Leu Glu Trp Ile Asp Glu Ala Val Glu Trp Ala Lys
    130                 135                 140

Glu Leu Glu Met Tyr Leu Ile Ile Asp Trp His Ser Ile Gly Asn Leu
145                 150                 155                 160

Arg Thr Glu Leu Phe Phe Arg Asp Ile Tyr Asn Thr Thr Arg Arg Glu
                165                 170                 175

Thr Tyr Glu Phe Trp Arg Leu Ile Ser Asp Arg Tyr Ala Asp Glu Thr
            180                 185                 190
```

```
Thr Ile Ala Phe Tyr Glu Ile Phe Asn Glu Pro Thr Arg Gln Gln Gly
        195                 200                 205

Arg Leu Gly Thr Met Thr Trp Lys Gln Trp Lys Glu Ile Leu Thr Asp
    210                 215                 220

Ile Ile Thr Ile Ile Tyr Ala His Asn Pro Asp Ala Ile Pro Leu Val
225                 230                 235                 240

Ala Gly Phe Asn Trp Ala Tyr Asp Leu Thr Pro Val Arg His Ser Pro
            245                 250                 255

Leu Asp Phe Glu Gly Ile Ala Tyr Val Thr His Pro Tyr Pro Gln Lys
        260                 265                 270

Arg Ser Arg Pro Trp Val Pro Lys Trp Glu Asp Phe Gly Phe Val
    275                 280                 285

Ala Asp Lys Tyr Pro Val Phe Ala Thr Glu Phe Gly Tyr Met Arg Glu
        290                 295                 300

Tyr Glu Arg Gly Ala His Val Pro Val Ile Gly Asp Glu Tyr Gly
305                 310                 315                 320

Glu Ile Leu Ile Asn Tyr Phe Arg Glu Lys Gly Ile Ser Trp Thr Ala
            325                 330                 335

Trp Val Phe Asp Pro Ser Trp Ser Pro Gln Leu Ile Gln Asp Trp Asp
        340                 345                 350

Tyr Thr Pro Thr Arg Ser Gly Glu Phe Phe Arg Asn Ala Met Arg Thr
        355                 360                 365

Lys Asn Asn Glu
    370

<210> SEQ ID NO 83
<211> LENGTH: 1089
<212> TYPE: DNA
<213> ORGANISM: Unknown
<220> FEATURE:
<223> OTHER INFORMATION: Obtained from environmental sample

<400> SEQUENCE: 83
atgagccttg gcctgactgc aatcgagttg atcaatcgcg cccgcgccga tctgcgactg      60
ggcgtgccga tcgttctgcg cgagggcgac gtgcaggcgc tggtgctggc ggtcgagcca     120
gtaaccgagg cgcggctggg tgggctgcgc gggctggggc cagggctggt gcttgcaatc     180
acgcagcgcc gcgccacgac actgaaggcg cgcgcctatg atgaggatct tgcgcgagtg     240
gtggtgcccg aggggtaggc tgcgactggc tgcgggcgg tggcggaccc ctccgacgat     300
ctgcgctttc cgatgaaggg cccgctgatg accgctcgcg agggcacggc cgcgctgcat     360
cgcgctgcac ttcaactggt gaaatccgcg cagcttcttc cggccgcact tgttcagccg     420
cttgcggatc ccgaggcgct gcccgtcacg gggctgacag tgctcgatat cgccgatgtc     480
agccgtgaat ggcgcgcga cagtgttg tatccagtgg tgcatgcgcg cttgccgatg     540
ctggcggcgc aagcgggccg cgtgcatatc ttccgacccc gcgacggcgg cgttgagcat     600
tacgccatcg agatcggcca gcccgaccgt gccgcgcccg tgctcacgcg gctgcattcg     660
cctgttttca caggcgatgt gctgggctcg ctcaaatgcg attgcggccc gcaactgcag     720
gcagcactcg cgcagatggg cgaggaaggc gcggggggtgc tgctctatct caatcaggag     780
ggtcgcggca tcgggcttgc caacaagatg cgcgcctatt cgctgcagga tcagggcttt     840
gacacggtcg aggccaatca ccgtctgggg ttcgaggatg acgagcggga tttccgcatc     900
ggggccgcgc ttctgcggcg gatgggttc tctcggcgc ggctgctgac caacaaccct     960
cggaaggtga acatgctgaa tgcgcatcgg gtcgaagtgg tggaacgggt gccgcttcgg    1020
```

```
gtgggcgaga cggtcgagaa ccgcgcctat cttgccacca aggccgccaa atccgggcat    1080
ctgttgtga                                                            1089
```

<210> SEQ ID NO 84
<211> LENGTH: 362
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (168)...(339)
<223> OTHER INFORMATION: GTP cyclohydrolase II

<400> SEQUENCE: 84

```
Met Ser Leu Gly Leu Thr Ala Ile Glu Leu Ile Asn Arg Ala Arg Ala
1               5                   10                  15

Asp Leu Arg Leu Gly Val Pro Ile Val Leu Arg Glu Gly Asp Val Gln
                20                  25                  30

Ala Leu Val Leu Ala Val Glu Pro Val Thr Glu Ala Arg Leu Gly Gly
            35                  40                  45

Leu Arg Gly Leu Gly Pro Gly Leu Val Leu Ala Ile Thr Gln Arg Arg
        50                  55                  60

Ala Thr Thr Leu Lys Ala Arg Ala Tyr Asp Glu Asp Leu Ala Arg Val
65                  70                  75                  80

Val Val Pro Glu Gly Val Gly Cys Asp Trp Leu Arg Ala Val Ala Asp
                85                  90                  95

Pro Ser Asp Asp Leu Arg Phe Pro Met Lys Gly Pro Leu Met Thr Ala
            100                 105                 110

Arg Glu Gly Thr Ala Ala Leu His Arg Ala Ala Leu Gln Leu Val Lys
        115                 120                 125

Ser Ala Gln Leu Leu Pro Ala Ala Leu Val Gln Pro Leu Ala Asp Pro
    130                 135                 140

Glu Ala Leu Pro Val Thr Gly Leu Thr Val Leu Asp Ile Ala Asp Val
145                 150                 155                 160

Ser Arg Glu Leu Ala Arg Glu Thr Val Leu Tyr Pro Val Val His Ala
                165                 170                 175

Arg Leu Pro Met Leu Ala Ala Gln Ala Gly Arg Val His Ile Phe Arg
            180                 185                 190

Pro Arg Asp Gly Gly Val Glu His Tyr Ala Ile Glu Ile Gly Gln Pro
        195                 200                 205

Asp Arg Ala Ala Pro Val Leu Thr Arg Leu His Ser Ala Cys Phe Thr
    210                 215                 220

Gly Asp Val Leu Gly Ser Leu Lys Cys Asp Cys Gly Pro Gln Leu Gln
225                 230                 235                 240

Ala Ala Leu Ala Gln Met Gly Glu Glu Gly Ala Gly Val Leu Leu Tyr
                245                 250                 255

Leu Asn Gln Glu Gly Arg Gly Ile Gly Leu Ala Asn Lys Met Arg Ala
            260                 265                 270

Tyr Ser Leu Gln Asp Gln Gly Phe Asp Thr Val Glu Ala Asn His Arg
        275                 280                 285

Leu Gly Phe Glu Asp Asp Glu Arg Asp Phe Arg Ile Gly Ala Ala Leu
    290                 295                 300

Leu Arg Arg Met Gly Phe Ser Arg Ala Arg Leu Leu Thr Asn Asn Pro
305                 310                 315                 320

Arg Lys Val Asn Met Leu Asn Ala His Arg Val Glu Val Val Glu Arg
                325                 330                 335
```

Val Pro Leu Arg Val Gly Glu Thr Val Glu Asn Arg Ala Tyr Leu Ala
            340                 345                 350

Thr Lys Ala Ala Lys Ser Gly His Leu Leu
            355                 360

<210> SEQ ID NO 85
<211> LENGTH: 1284
<212> TYPE: DNA
<213> ORGANISM: Unknown
<220> FEATURE:
<223> OTHER INFORMATION: Obtained from environmental sample

<400> SEQUENCE: 85

| | | | | | |
|---|---|---|---|---|---|
| gtgaacaccg | cgcatcgcat | cgaattccct | cggcaattta | tcttcggttc | cgccactgct | 60 |
| gctcaccaag | tggagggcaa | caacgttcac | aatgattggt | gggcccacga | gcatgccacc | 120 |
| gacacgaatg | ccgtggagcc | gtcgggcctc | gcctgcgacc | actttcggcg | ctttgccgac | 180 |
| gacttccgcc | tcttacgcca | actcggacag | ccagcgcacc | gcctgtcgct | ggaatggagc | 240 |
| cgcatcgaac | cggcacccgg | tgaaatcgat | cgttcggcat | tgtcccacta | ccgccgagtc | 300 |
| ctgggtactt | tgcgagacct | cggaatcgag | ccatgggtca | ccatccacca | cttcacttgc | 360 |
| cctcgctggt | tcgtggaaca | gggagggttt | acacgcatgg | attcagcgcg | ctctctcgtt | 420 |
| cgccataccg | aacgcgtggc | gagggagttc | tccgacctag | tcacaaactg | gtgcaccata | 480 |
| aatgagccaa | acgtcgtggc | agaactcggt | tatcgcttcg | gatactttcc | gccgcggttg | 540 |
| caggacgatg | agctggcagc | ggaagtgctc | accaacttct | ttcgcttaca | cgctgaaatg | 600 |
| gcagaagttt | tgcgcgctca | cgcgcagaga | tcggcgcaaa | tcggtatcac | ccttgcgatg | 660 |
| caagcacacg | agccgctgcg | catcgaaagc | gaagcggacc | gcgcactggc | ggcgcggcgc | 720 |
| gacgccgaga | ccaacggcgt | catgctcaac | gccttgcgaa | ccggtgtatt | cgcctacccg | 780 |
| ggacgggagc | cggtggaaat | ccctggactg | aaaacgtcat | cgaccttcgt | ggggtccag | 840 |
| tactattcgc | gggtccgcta | cgacgccgag | tcgcaaggtc | cagcaatgcc | cgacttcgag | 900 |
| cgcacccctca | gccaaatggg | atgggaggtg | tatcctgagg | ggttcggccc | cttgctcgag | 960 |
| cgcgcagcag | aaactggact | cgaagtgatc | gtcacagaga | acgggatggc | gcacgacgat | 1020 |
| gaccgtgtgc | gcgtgcgttt | tatcgccgac | cacttgcggg | tcgttcaccg | ccttctggaa | 1080 |
| cgcggtgtgc | gcatcggagg | gtactttttac | tggtcgacca | tggacaactt | cgaatggaac | 1140 |
| ttcgggtacg | gaccgaagtt | cggcctgatc | gaagtggacc | gttctaccct | ggaacgcagg | 1200 |
| ccgcggcgaa | gcgcgtattt | cttccgtgac | atgatccagc | agcgagtgct | cgacgacgac | 1260 |
| ctggtcgagc | actggactcg | ctga | | | | 1284 |

<210> SEQ ID NO 86
<211> LENGTH: 427
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (5)...(417)
<223> OTHER INFORMATION: Glycosyl hydrolase family 1
<220> FEATURE:
<221> NAME/KEY: SITE
<222> LOCATION: (334)...(342)
<223> OTHER INFORMATION: Glycosyl hydrolases family 1 active site.
       Prosite id = PS00572

<400> SEQUENCE: 86

-continued

```
Met Asn Thr Ala His Arg Ile Glu Phe Pro Arg Gln Phe Ile Phe Gly
1               5                   10                  15

Ser Ala Thr Ala Ala His Gln Val Glu Gly Asn Asn Val His Asn Asp
            20                  25                  30

Trp Trp Ala His Glu His Ala Thr Asp Thr Asn Ala Val Glu Pro Ser
            35                  40                  45

Gly Leu Ala Cys Asp His Phe Arg Arg Phe Ala Asp Asp Phe Arg Leu
        50                  55                  60

Leu Arg Gln Leu Gly Gln Pro Ala His Arg Leu Ser Leu Glu Trp Ser
65                  70                  75                  80

Arg Ile Glu Pro Ala Pro Gly Glu Ile Asp Arg Ser Ala Leu Ser His
                85                  90                  95

Tyr Arg Arg Val Leu Gly Thr Leu Arg Asp Leu Gly Ile Glu Pro Trp
                100                 105                 110

Val Thr Ile His His Phe Thr Cys Pro Arg Trp Phe Val Glu Gln Gly
                115                 120                 125

Gly Phe Thr Arg Met Asp Ser Ala Arg Ser Leu Val Arg His Thr Glu
        130                 135                 140

Arg Val Ala Arg Glu Phe Ser Asp Leu Val Thr Asn Trp Cys Thr Ile
145                 150                 155                 160

Asn Glu Pro Asn Val Val Ala Glu Leu Gly Tyr Arg Phe Gly Tyr Phe
                165                 170                 175

Pro Pro Arg Leu Gln Asp Asp Glu Leu Ala Ala Glu Val Leu Thr Asn
            180                 185                 190

Phe Phe Arg Leu His Ala Glu Met Ala Glu Val Leu Arg Ala His Ala
        195                 200                 205

Gln Arg Ser Ala Gln Ile Gly Ile Thr Leu Ala Met Gln Ala His Glu
210                 215                 220

Pro Leu Arg Ile Glu Ser Glu Ala Asp Arg Ala Leu Ala Ala Arg Arg
225                 230                 235                 240

Asp Ala Glu Thr Asn Gly Val Met Leu Asn Ala Leu Arg Thr Gly Val
                245                 250                 255

Phe Ala Tyr Pro Gly Arg Glu Pro Val Glu Ile Pro Gly Leu Lys Thr
            260                 265                 270

Ser Ser Thr Phe Val Gly Val Gln Tyr Tyr Ser Arg Val Arg Tyr Asp
        275                 280                 285

Ala Glu Ser Gln Gly Pro Ala Met Pro Asp Phe Glu Arg Thr Leu Ser
        290                 295                 300

Gln Met Gly Trp Glu Val Tyr Pro Glu Gly Phe Gly Pro Leu Leu Glu
305                 310                 315                 320

Arg Ala Ala Glu Thr Gly Leu Glu Val Ile Val Thr Glu Asn Gly Met
                325                 330                 335

Ala His Asp Asp Arg Val Arg Val Arg Phe Ile Ala Asp His Leu
        340                 345                 350

Arg Val Val His Arg Leu Leu Glu Arg Gly Val Arg Ile Gly Gly Tyr
            355                 360                 365

Phe Tyr Trp Ser Thr Met Asp Asn Phe Glu Trp Asn Phe Gly Tyr Gly
        370                 375                 380

Pro Lys Phe Gly Leu Ile Glu Val Asp Arg Ser Thr Leu Glu Arg Arg
385                 390                 395                 400

Pro Arg Arg Ser Ala Tyr Phe Phe Arg Asp Met Ile Gln Gln Arg Val
            405                 410                 415

Leu Asp Asp Asp Leu Val Glu His Trp Thr Arg
            420                 425
```

<210> SEQ ID NO 87
<211> LENGTH: 1167
<212> TYPE: DNA
<213> ORGANISM: Unknown
<220> FEATURE:
<223> OTHER INFORMATION: Obtained from environmental sample

<400> SEQUENCE: 87

| | | | | | |
|---|---|---|---|---|---|
| atgagaaaga | gtgtgttcac | cctcgccgtg | tttttgtcgg | cactgtttgc | attcacgtct | 60 |
| tgtcagaaca | agagccagaa | cgaggctcaa | gaccaggcag | acaagtcaa | taacttccgc | 120 |
| atcaagcgcg | gcacgaacat | cagccactgg | ctgtcgcagt | cggagcagcg | cggtgaggct | 180 |
| cgcagactgc | atatccagga | ggacgacttc | gcccgtctgg | aagagctggg | cttcgacttc | 240 |
| gtgcgcatcc | ccatcgacga | ggtgcagttc | tgggacgagc | agggcaacaa | gctgcccgag | 300 |
| gcgtgggatc | tgctgaacaa | cgccctcgac | tggagcaaga | agcacaacct | gcgtgccatc | 360 |
| gtcgacctgc | acatcatccg | tgcgcactat | ttcaatgccg | tgaatgaggc | agaccaggcc | 420 |
| gccaataccc | tcttcacctc | tgaggaggca | caggaaggac | tccttaacct | gtggcgccag | 480 |
| ctctccgagt | tcctgaagga | ccgcagcaac | gactgggtgg | cctacgagtt | catgaacgag | 540 |
| ccggtagccc | ctgagcacga | gatgtggaac | cagctggtag | ccaaggtaca | caaggccctg | 600 |
| cgcgaactgg | aacccagcg | tacactcgtc | gtcggctcga | acatgtggca | gggacacgag | 660 |
| acgatgaagt | atctgaaagt | gcccgagggc | gataagaaca | tcatcctctc | gttccactac | 720 |
| tacaacccga | tgctgctgac | gcactacggt | gcctggtggt | cgccgctgtg | tgctgcctac | 780 |
| aagggtaagg | tgaactatcc | cggtgtgctc | gtgtcgaagg | aagactacga | tgccgctcct | 840 |
| gctgccatca | aggatcagct | gaagcccttt | accgaggaag | tatggaacat | cgacaagatc | 900 |
| cgtgagcagt | tcaaggatgc | catcgaggcc | gccaagaaat | atgacctgca | actgttctgc | 960 |
| ggcgagtggg | gtgtctatga | gcccgtggac | cgtgagctgg | cctacaaatg | gtatcgtgac | 1020 |
| gtgctgacgg | tgttcgacga | gttcaacatc | gcctggacga | cctggtgcta | cgatgctgac | 1080 |
| ttcggttttct | gggatcagca | gcgccactgc | tacaaagact | atccgctggt | ggagctcctg | 1140 |
| atgtcaggaa | agaaactggg | agaatag | | | | 1167 |

<210> SEQ ID NO 88
<211> LENGTH: 388
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(23)
<220> FEATURE:
<221> NAME/KEY: DOMAIN
<222> LOCATION: (48)...(365)
<223> OTHER INFORMATION: Cellulase (glycosyl hydrolase family 5)
<220> FEATURE:
<221> NAME/KEY: SITE
<222> LOCATION: (23)...(26)
<223> OTHER INFORMATION: N-glycosylation site. Prosite id = PS00001
<220> FEATURE:
<221> NAME/KEY: SITE
<222> LOCATION: (46)...(49)
<223> OTHER INFORMATION: N-glycosylation site. Prosite id = PS00001

<400> SEQUENCE: 88

Met Arg Lys Ser Val Phe Thr Leu Ala Val Phe Leu Ser Ala Leu Phe
1               5                   10                  15

Ala Phe Thr Ser Cys Gln Asn Lys Ser Gln Asn Glu Ala Gln Asp Gln

```
            20                  25                  30
Ala Gly Gln Val Asn Asn Phe Arg Ile Lys Arg Gly Thr Asn Ile Ser
        35                  40                  45
His Trp Leu Ser Gln Ser Glu Gln Arg Gly Glu Ala Arg Arg Leu His
    50                  55                  60
Ile Gln Glu Asp Asp Phe Ala Arg Leu Glu Glu Leu Gly Phe Asp Phe
65                  70                  75                  80
Val Arg Ile Pro Ile Asp Glu Val Gln Phe Trp Asp Glu Gln Gly Asn
                85                  90                  95
Lys Leu Pro Glu Ala Trp Asp Leu Leu Asn Asn Ala Leu Asp Trp Ser
            100                 105                 110
Lys Lys His Asn Leu Arg Ala Ile Val Asp Leu His Ile Ile Arg Ala
        115                 120                 125
His Tyr Phe Asn Ala Val Asn Glu Ala Asp Gln Ala Ala Asn Thr Leu
    130                 135                 140
Phe Thr Ser Glu Glu Ala Gln Glu Gly Leu Leu Asn Leu Trp Arg Gln
145                 150                 155                 160
Leu Ser Glu Phe Leu Lys Asp Arg Ser Asn Asp Trp Val Ala Tyr Glu
                165                 170                 175
Phe Met Asn Glu Pro Val Ala Pro Glu His Glu Met Trp Asn Gln Leu
            180                 185                 190
Val Ala Lys Val His Lys Ala Leu Arg Glu Leu Glu Pro Gln Arg Thr
        195                 200                 205
Leu Val Val Gly Ser Asn Met Trp Gln Gly His Glu Thr Met Lys Tyr
    210                 215                 220
Leu Lys Val Pro Glu Gly Asp Lys Asn Ile Ile Leu Ser Phe His Tyr
225                 230                 235                 240
Tyr Asn Pro Met Leu Leu Thr His Tyr Gly Ala Trp Trp Ser Pro Leu
                245                 250                 255
Cys Ala Ala Tyr Lys Gly Lys Val Asn Tyr Pro Gly Val Leu Val Ser
            260                 265                 270
Lys Glu Asp Tyr Asp Ala Ala Pro Ala Ala Ile Lys Asp Gln Leu Lys
        275                 280                 285
Pro Phe Thr Glu Glu Val Trp Asn Ile Asp Lys Ile Arg Glu Gln Phe
    290                 295                 300
Lys Asp Ala Ile Glu Ala Lys Lys Tyr Asp Leu Gln Leu Phe Cys
305                 310                 315                 320
Gly Glu Trp Gly Val Tyr Glu Pro Val Asp Arg Glu Leu Ala Tyr Lys
                325                 330                 335
Trp Tyr Arg Asp Val Leu Thr Val Phe Asp Glu Phe Asn Ile Ala Trp
            340                 345                 350
Thr Thr Trp Cys Tyr Asp Ala Asp Phe Gly Phe Trp Asp Gln Gln Arg
        355                 360                 365
His Cys Tyr Lys Asp Tyr Pro Leu Val Glu Leu Leu Met Ser Gly Lys
    370                 375                 380
Lys Leu Gly Glu
385

<210> SEQ ID NO 89
<211> LENGTH: 1500
<212> TYPE: DNA
<213> ORGANISM: Unknown
<220> FEATURE:
<223> OTHER INFORMATION: Obtained from environmental sample

<400> SEQUENCE: 89
```

```
atgaaacgtt cagtctctat ctttatcgca tgtttattaa tgacagtatt aacaattagc      60
ggtgtcgcgg caccagaagc atctgcagca ggggcgaaaa cgcctgtagc ccttaatggc     120
cagcttagca ttaaaggtac tcagctagtc aatcaaaacg gaaaaccggt gcagctgaag     180
gggatcagct cacacggttt gcagtggttc ggcgattatg tcaataaaga cactttaaaa     240
tggctaagag acgattgggg aattaccgtc ttccgggcgg caatgtacac ggctgacggc     300
ggttatatcg agaatccgtc tgtgaaaaat aaagtcaaag aagctgttga agcggcaaaa     360
gagctcggga tatatgtcat cattgactgg catattttaa atgacggcaa tccaaatcaa     420
aataaagaga aggcgaagga attctttaag gaaatgtcaa gcctttacgg aagctcacca     480
aacgttatat atgaaattgc taatgaaccg aacggtgatg taaattggaa gcgcgatatc     540
aaaccgtatg cggaagaagt gatttctgtt atccgtaaaa atgacccgga taacatcatt     600
attaccggaa caggcacttg gagccaggat gtcaacgatg ctgcggatga tcagcttaag     660
gatgcaaacg tcatgtacgc gcttcatttt tatgccggta cacacggcca gttttaagg     720
gataaagcgg actatgcgct cagcaaagga gctccgattt tgtaacgga atggggacg      780
agtgacgctt ccggaaatgg aggggtatac cttgaccagt cgagggaatg gctgaattat     840
ctcgacagca agaaaatcag ctgggtaaac tggaaccttt ctgataagca ggaatcatcc     900
tcagctttaa agccggggc atctaaaaca ggcggctggc cgttatcaga tttatccgct     960
tcagggacat ttgtaagaga aaacattcgc ggctcccaaa attcgagtga agacagatct    1020
gagacaccaa gcaagagaa acccgcacag gaaaacagca tctctgtgca atacagaaca     1080
ggggatggaa gtgtgaacag caaccaaatc cgtcctcaga tcaatgtgaa aacaacagc     1140
aagaccaccg ttaacttaaa aaatgtaact gtccgctact ggtataacac gaaaaacaaa    1200
ggccaaaact tcgactgtga ttacgcgaag atcggatgca gcaatgtgac gcacaagttt    1260
gtgacattac ataaacctgt aaaaggtgca gatgcctatc tggaacttgg gtttagaaac    1320
gggacgctgt caccgggagc aagcaccgga gaaattcaaa ttcgtcttca caatgaggac    1380
tggagcaatt attcacaagc cggggattat tcttttttcc agtcgaatac gtttaaagat    1440
acaaaaaaaa tcacattata taataacgga aaactgattt ggggaacaga acccaaatag    1500
```

<210> SEQ ID NO 90
<211> LENGTH: 499
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(29)
<220> FEATURE:
<221> NAME/KEY: DOMAIN
<222> LOCATION: (47)...(301)
<223> OTHER INFORMATION: Cellulase (glycosyl hydrolase family 5)
<220> FEATURE:
<221> NAME/KEY: DOMAIN
<222> LOCATION: (356)...(437)
<223> OTHER INFORMATION: Cellulose binding domain
<220> FEATURE:
<221> NAME/KEY: SITE
<222> LOCATION: (164)...(173)
<223> OTHER INFORMATION: Glycosyl hydrolases family 5 signature. Prosite
      id = PS00659
<220> FEATURE:
<221> NAME/KEY: SITE
<222> LOCATION: (296)...(299)
<223> OTHER INFORMATION: N-glycosylation site. Prosite id = PS00001
<220> FEATURE:
<221> NAME/KEY: SITE

```
<222> LOCATION: (339)...(342)
<223> OTHER INFORMATION: N-glycosylation site. Prosite id = PS00001
<220> FEATURE:
<221> NAME/KEY: SITE
<222> LOCATION: (383)...(386)
<223> OTHER INFORMATION: N-glycosylation site. Prosite id = PS00001
<220> FEATURE:
<221> NAME/KEY: SITE
<222> LOCATION: (393)...(396)
<223> OTHER INFORMATION: N-glycosylation site. Prosite id = PS00001
<220> FEATURE:
<221> NAME/KEY: SITE
<222> LOCATION: (421)...(424)
<223> OTHER INFORMATION: N-glycosylation site. Prosite id = PS00001
<220> FEATURE:
<221> NAME/KEY: SITE
<222> LOCATION: (446)...(449)
<223> OTHER INFORMATION: N-glycosylation site. Prosite id = PS00001
<220> FEATURE:
<221> NAME/KEY: SITE
<222> LOCATION: (470)...(473)
<223> OTHER INFORMATION: N-glycosylation site. Prosite id = PS00001

<400> SEQUENCE: 90

Met Lys Arg Ser Val Ser Ile Phe Ile Ala Cys Leu Leu Met Thr Val
1               5                   10                  15

Leu Thr Ile Ser Gly Val Ala Ala Pro Glu Ala Ser Ala Ala Gly Ala
            20                  25                  30

Lys Thr Pro Val Ala Leu Asn Gly Gln Leu Ser Ile Lys Gly Thr Gln
        35                  40                  45

Leu Val Asn Gln Asn Gly Lys Pro Val Gln Leu Lys Gly Ile Ser Ser
    50                  55                  60

His Gly Leu Gln Trp Phe Gly Asp Tyr Val Asn Lys Asp Thr Leu Lys
65                  70                  75                  80

Trp Leu Arg Asp Asp Trp Gly Ile Thr Val Phe Arg Ala Ala Met Tyr
                85                  90                  95

Thr Ala Asp Gly Gly Tyr Ile Glu Asn Pro Ser Val Lys Asn Lys Val
            100                 105                 110

Lys Glu Ala Val Glu Ala Ala Lys Glu Leu Gly Ile Tyr Val Ile Ile
        115                 120                 125

Asp Trp His Ile Leu Asn Asp Gly Asn Pro Asn Gln Asn Lys Glu Lys
    130                 135                 140

Ala Lys Glu Phe Phe Lys Glu Met Ser Ser Leu Tyr Gly Ser Ser Pro
145                 150                 155                 160

Asn Val Ile Tyr Glu Ile Ala Asn Glu Pro Asn Gly Asp Val Asn Trp
                165                 170                 175

Lys Arg Asp Ile Lys Pro Tyr Ala Glu Glu Val Ile Ser Val Ile Arg
            180                 185                 190

Lys Asn Asp Pro Asp Asn Ile Ile Ile Thr Gly Thr Gly Thr Trp Ser
        195                 200                 205

Gln Asp Val Asn Asp Ala Ala Asp Asp Gln Leu Lys Asp Ala Asn Val
    210                 215                 220

Met Tyr Ala Leu His Phe Tyr Ala Gly Thr His Gly Gln Phe Leu Arg
225                 230                 235                 240

Asp Lys Ala Asp Tyr Ala Leu Ser Lys Gly Ala Pro Ile Phe Val Thr
                245                 250                 255

Glu Trp Gly Thr Ser Asp Ala Ser Gly Asn Gly Gly Val Tyr Leu Asp
            260                 265                 270

Gln Ser Arg Glu Trp Leu Asn Tyr Leu Asp Ser Lys Lys Ile Ser Trp
        275                 280                 285

Val Asn Trp Asn Leu Ser Asp Lys Gln Glu Ser Ser Ser Ala Leu Lys
```

```
                    290                 295                 300
Pro Gly Ala Ser Lys Thr Gly Gly Trp Pro Leu Ser Asp Leu Ser Ala
305                 310                 315                 320

Ser Gly Thr Phe Val Arg Glu Asn Ile Arg Gly Ser Gln Asn Ser Ser
                325                 330                 335

Glu Asp Arg Ser Glu Thr Pro Lys Gln Glu Lys Pro Ala Gln Glu Asn
            340                 345                 350

Ser Ile Ser Val Gln Tyr Arg Thr Gly Asp Gly Ser Val Asn Ser Asn
        355                 360                 365

Gln Ile Arg Pro Gln Ile Asn Val Lys Asn Asn Ser Lys Thr Thr Val
    370                 375                 380

Asn Leu Lys Asn Val Thr Val Arg Tyr Trp Tyr Asn Thr Lys Asn Lys
385                 390                 395                 400

Gly Gln Asn Phe Asp Cys Asp Tyr Ala Lys Ile Gly Cys Ser Asn Val
                405                 410                 415

Thr His Lys Phe Val Thr Leu His Lys Pro Val Lys Gly Ala Asp Ala
            420                 425                 430

Tyr Leu Glu Leu Gly Phe Arg Asn Gly Thr Leu Ser Pro Gly Ala Ser
        435                 440                 445

Thr Gly Glu Ile Gln Ile Arg Leu His Asn Glu Asp Trp Ser Asn Tyr
    450                 455                 460

Ser Gln Ala Gly Asp Tyr Ser Phe Phe Gln Ser Asn Thr Phe Lys Asp
465                 470                 475                 480

Thr Lys Lys Ile Thr Leu Tyr Asn Asn Gly Lys Leu Ile Trp Gly Thr
                485                 490                 495

Glu Pro Lys

<210> SEQ ID NO 91
<211> LENGTH: 1725
<212> TYPE: DNA
<213> ORGANISM: Unknown
<220> FEATURE:
<223> OTHER INFORMATION: Obtained from environmental sample

<400> SEQUENCE: 91
atgctgaaat taagtgataa cctaactttc ttgaaaagca aaccattttt tcttaatgaa      60
aaagaaatga gtgggtggga gaaaacactt caatccatgt ccttacatga aaaagtaggg     120
caattatttt gtcccattgg cggttcagat aataaacaag aattagaagc ctttattaag     180
gaatatcatc ctggcggcat catgtaccgt cctaatacag gagcaaaaat acaggaaaca     240
catcggttgt tacaagagct atccccggta cctttattaa tttctgctaa cttagaggcc     300
ggtggtaatg ggattgctac ggatggtact tacttcggaa agcaaatgca ggtggctgca     360
acagataatg aagaaatggc ctataaatta ggattagttg ctggccgtga aggccgtgtg     420
gccggttgta actgggcttt tgcaccaatt gttgatattg atatgaacta tcgaaaccca     480
attacaaacg taagaacgta tgggtctgac ccaattagag ttgcccaaat gtctaaagct     540
tttatgaagg gaattcatga aagcggactc gcagcagctg ttaagcattt cccaggggat     600
ggagtggatg atagagatca gcatcttta tcatctgtaa acaccttatc taccgaagaa     660
tgggatcaaa cctttgggat ggtttatcaa gaaatgatag acagtggggc aaaatcgatt     720
atggcgggcc atatcatgct ccctgaatat tcaagagaac tattgccggg tattgaagac     780
gaacaaatca tgcccgccac actagcacca gagttactta atggtttatt aagggaaaag     840
ttaggtttta atggtttaat cgtgactgat gcatccccta tgttagggtt cactacttcg     900
```

```
gaaagaagag aaattgctgt tcctaaggcg attgcttcgg gctgtgatat gtttctcttc    960
aaccgtaaca taaagaaga ttatgagttc atgctgaatg gaattgaaac tggaattcta   1020
accttggaaa gagtagatga agctgttact agagtacttg ctcttaaagc atctctaggt   1080
ctgaatgtac aaaaggaatt gggaatatta gtacctgaag aagcggaatt gtcggtatta   1140
caatctgaag aacatttgga ttgggcaaga gaatgtgcag accaatcggt tacattagta   1200
aaggatacac aaaaactgct gcctattagt gctgatcagt ataaacgggt tcgactttat   1260
gtattgggtg atcaagaagg agggctaaag gaaggcggct ccgtcactca accgtttatc   1320
gattctctta aaaatgctgg ctttgaagta gatttatata atgacaagca agttaatttc   1380
caagaactgt ttatgagtgt aaacgagttt aaaaagaact atgatctgat catttatgtc   1440
gccaaccttg aaaccgctag taaccaaacg acagtcagaa ttaattggca gcagccgcta   1500
aatgccaacg ctccatggtt tgttaaagat ataccgacat tatttatttc ggttgctaac   1560
ccataccatc tacaggacgt accaatggtt aagacctata taaatgctta ttcatctaat   1620
gaatatgtgg tagaagcaat tgtagataaa atcttaggaa aatcagagtt taaagggaag   1680
aatcccgtcg atccgttttg tgggaaatgg gataccagac tttaa               1725
```

<210> SEQ ID NO 92
<211> LENGTH: 574
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (87)...(320)
<223> OTHER INFORMATION: Glycosyl hydrolase family 3 N terminal domain
<220> FEATURE:
<221> NAME/KEY: SITE
<222> LOCATION: (7)...(10)
<223> OTHER INFORMATION: N-glycosylation site. Prosite id = PS00001
<220> FEATURE:
<221> NAME/KEY: SITE
<222> LOCATION: (495)...(498)
<223> OTHER INFORMATION: N-glycosylation site. Prosite id = PS00001

<400> SEQUENCE: 92

```
Met Leu Lys Leu Ser Asp Asn Leu Thr Phe Leu Lys Ser Lys Pro Phe
1               5                   10                  15

Phe Leu Asn Glu Lys Glu Met Lys Trp Val Lys Thr Leu Gln Ser
            20                  25                  30

Met Ser Leu His Glu Lys Val Gly Gln Leu Phe Cys Pro Ile Gly Gly
        35                  40                  45

Ser Asp Asn Lys Gln Glu Leu Glu Ala Phe Ile Lys Glu Tyr His Pro
    50                  55                  60

Gly Gly Ile Met Tyr Arg Pro Asn Thr Gly Ala Lys Ile Gln Glu Thr
65                  70                  75                  80

His Arg Leu Leu Gln Glu Leu Ser Pro Val Pro Leu Leu Ile Ser Ala
                85                  90                  95

Asn Leu Glu Ala Gly Gly Asn Gly Ile Ala Thr Asp Gly Thr Tyr Phe
            100                 105                 110

Gly Lys Gln Met Gln Val Ala Ala Thr Asp Asn Glu Glu Met Ala Tyr
        115                 120                 125

Lys Leu Gly Leu Val Ala Gly Arg Glu Gly Arg Val Ala Gly Cys Asn
    130                 135                 140

Trp Ala Phe Ala Pro Ile Val Asp Ile Asp Met Asn Tyr Arg Asn Pro
145                 150                 155                 160
```

```
Ile Thr Asn Val Arg Thr Tyr Gly Ser Asp Pro Ile Arg Val Ala Gln
            165                 170                 175

Met Ser Lys Ala Phe Met Lys Gly Ile His Glu Ser Gly Leu Ala Ala
        180                 185                 190

Ala Val Lys His Phe Pro Gly Asp Gly Val Asp Asp Arg Asp Gln His
        195                 200                 205

Leu Leu Ser Ser Val Asn Thr Leu Ser Thr Glu Glu Trp Asp Gln Thr
        210                 215                 220

Phe Gly Met Val Tyr Gln Glu Met Ile Asp Ser Gly Ala Lys Ser Ile
225                 230                 235                 240

Met Ala Gly His Ile Met Leu Pro Glu Tyr Ser Arg Glu Leu Leu Pro
                245                 250                 255

Gly Ile Glu Asp Glu Gln Ile Met Pro Ala Thr Leu Ala Pro Glu Leu
            260                 265                 270

Leu Asn Gly Leu Leu Arg Glu Lys Leu Gly Phe Asn Gly Leu Ile Val
        275                 280                 285

Thr Asp Ala Ser Pro Met Leu Gly Phe Thr Thr Ser Glu Arg Arg Glu
        290                 295                 300

Ile Ala Val Pro Lys Ala Ile Ala Ser Gly Cys Asp Met Phe Leu Phe
305                 310                 315                 320

Asn Arg Asn Ile Lys Glu Asp Tyr Glu Phe Met Leu Asn Gly Ile Glu
                325                 330                 335

Thr Gly Ile Leu Thr Leu Glu Arg Val Asp Glu Ala Val Thr Arg Val
            340                 345                 350

Leu Ala Leu Lys Ala Ser Leu Gly Leu Asn Val Gln Lys Glu Leu Gly
        355                 360                 365

Ile Leu Val Pro Glu Glu Ala Glu Leu Ser Val Leu Gln Ser Glu Glu
        370                 375                 380

His Leu Asp Trp Ala Arg Glu Cys Ala Asp Gln Ser Val Thr Leu Val
385                 390                 395                 400

Lys Asp Thr Gln Lys Leu Leu Pro Ile Ser Ala Asp Gln Tyr Lys Arg
                405                 410                 415

Val Arg Leu Tyr Val Leu Gly Asp Gln Glu Gly Gly Leu Lys Glu Gly
            420                 425                 430

Gly Ser Val Thr Gln Pro Phe Ile Asp Ser Leu Lys Asn Ala Gly Phe
        435                 440                 445

Glu Val Asp Leu Tyr Asn Asp Lys Gln Val Asn Phe Gln Glu Leu Phe
        450                 455                 460

Met Ser Val Asn Glu Phe Lys Lys Asn Tyr Asp Leu Ile Ile Tyr Val
465                 470                 475                 480

Ala Asn Leu Glu Thr Ala Ser Asn Gln Thr Thr Val Arg Ile Asn Trp
                485                 490                 495

Gln Gln Pro Leu Asn Ala Asn Ala Pro Trp Phe Val Lys Asp Ile Pro
            500                 505                 510

Thr Leu Phe Ile Ser Val Ala Asn Pro Tyr His Leu Gln Asp Val Pro
        515                 520                 525

Met Val Lys Thr Tyr Ile Asn Ala Tyr Ser Ser Asn Glu Tyr Val Val
        530                 535                 540

Glu Ala Ile Val Asp Lys Ile Leu Gly Lys Ser Glu Phe Lys Gly Lys
545                 550                 555                 560

Asn Pro Val Asp Pro Phe Cys Gly Lys Trp Asp Thr Arg Leu
                565                 570
```

<210> SEQ ID NO 93

```
<211> LENGTH: 546
<212> TYPE: DNA
<213> ORGANISM: Unknown
<220> FEATURE:
<223> OTHER INFORMATION: Obtained from environmental sample

<400> SEQUENCE: 93
atgagaataa aaaatttaaa acgaaccgt  atcacaaacc cgctgggatt tgatatagga      60
aaaccacgta tatcttttgt cacttatgac actacggcta aaaagcaaac agcagcgcaa     120
atacaggttg cgctagatca agagtttacg aacctaacat ttgacagtgg gaaaagcacg     180
gagatagata gtctagcata cgaactgcca tttcaattag agtcttacac tcgctactac     240
tggcgtgtga ccgtttgggc ggataatggg gatgtggcca caagtgaaat tgcttggttt     300
gaaacagcca aactaggcga ttcttgggag gccaagtgga ttaccccccga ttttgataag     360 gaaatccatc ccgtactatc aagggaattt gatttgtcaa agaagtcgt  ttctgcccgt     420 gcctatgttt gcggtttggg attatatgaa atggagatta tggtctaaa  ggctggggat     480 gaatatctga cccctaattt caacgcctat gataaatggc tgcagtacca gacctatgat     540
attaca                                                                546

<210> SEQ ID NO 94
<211> LENGTH: 182
<212> TYPE: PRT
<213> ORGANISM: Unknown
<220> FEATURE:
<223> OTHER INFORMATION: Obtained from environmental sample
<220> FEATURE:
<221> NAME/KEY: SITE
<222> LOCATION: (51)...(54)
<223> OTHER INFORMATION: N-glycosylation site. Prosite id = PS00001

<400> SEQUENCE: 94

Met Arg Ile Lys Asn Leu Lys Thr Asn Arg Ile Thr Asn Pro Leu Gly
1               5                   10                  15

Phe Asp Ile Gly Lys Pro Arg Ile Ser Phe Val Thr Tyr Asp Thr Thr
            20                  25                  30

Ala Lys Lys Gln Thr Ala Ala Gln Ile Gln Val Ala Leu Asp Gln Glu
        35                  40                  45

Phe Thr Asn Leu Thr Phe Asp Ser Gly Lys Ser Thr Glu Ile Asp Ser
    50                  55                  60

Leu Ala Tyr Glu Leu Pro Phe Gln Leu Glu Ser Tyr Thr Arg Tyr Tyr
65                  70                  75                  80

Trp Arg Val Thr Val Trp Ala Asp Asn Gly Asp Val Ala Thr Ser Glu
                85                  90                  95

Ile Ala Trp Phe Glu Thr Ala Lys Leu Gly Asp Ser Trp Glu Ala Lys
            100                 105                 110

Trp Ile Thr Pro Asp Phe Asp Lys Glu Ile His Pro Val Leu Ser Arg
        115                 120                 125

Glu Phe Asp Leu Ser Lys Glu Val Val Ser Ala Arg Ala Tyr Val Cys
    130                 135                 140

Gly Leu Gly Leu Tyr Glu Met Glu Ile Asn Gly Leu Lys Ala Gly Asp
145                 150                 155                 160

Glu Tyr Leu Thr Pro Asn Phe Asn Ala Tyr Asp Lys Trp Leu Gln Tyr
                165                 170                 175

Gln Thr Tyr Asp Ile Thr
            180

<210> SEQ ID NO 95
```

<211> LENGTH: 2298
<212> TYPE: DNA
<213> ORGANISM: Unknown
<220> FEATURE:
<223> OTHER INFORMATION: Obtained from environmental sample

<400> SEQUENCE: 95

| | | | | | |
|---|---|---|---|---|---|
| atgatcaatc | aagatataaa | acaattaatc | tcacaaatga | ccttggaaga | aaaagctggt | 60 |
| ctttgttctg | gattagattt | ttggaattta | aaaggtatcg | aaagactggg | aatacccctcg | 120 |
| ataatggtaa | ccgatggtcc | gcatggactc | cgtaaacaaa | aatgggagc | agatcattta | 180 |
| gggctgtttg | acagtattcc | tgcgacatgt | ttcccatctg | cagccggttt | agctagtact | 240 |
| tggaataaag | agttaatata | tgaagttggg | gttgcattag | gaaaggaatg | ccaggcagag | 300 |
| gatgtggcaa | tacttcttgg | ccctggagca | aacattaagc | gctcaccct | ttgtggcaga | 360 |
| aactttgaat | atttttcgga | agatccattc | ctttcatcag | aaatggctgc | gtcccatatc | 420 |
| aagggtgttc | aaagtgaggg | ggttgggaca | tcacttaagc | acttcgctgc | aaataatcaa | 480 |
| gaacaccgaa | gaatgtcgac | agatgctatt | gtggatgaaa | ggacgttgcg | agaaatatat | 540 |
| ttggccagct | ttgaaaacgc | tgtaaagaaa | gcgcagccat | ggactgtgat | gtgcgcctac | 600 |
| aacaaggtca | atggagactt | tgcatcagaa | aataaaacat | tgttaactga | catcctgcga | 660 |
| gatgagtggg | gctttgaagg | aattgttgtt | tctgactggg | gggcggttaa | tgaacctgtt | 720 |
| gacggattaa | atgccgggtt | agacctggaa | atgccttcaa | gtagtgggat | tggtgaaaag | 780 |
| aaaatcatca | atgctgtaag | aaatggtcag | cttttagaag | ataaactaga | tcaggcagtt | 840 |
| gaaagaattc | tacgtattat | cttaatggca | gtagaaaaca | agaaagaaac | cgctgactat | 900 |
| gataaagaac | aacatcataa | gcttgcaaga | aaagcagcaa | gtgaaagtat | ggttttatta | 960 |
| aagaatgaag | ataatatcct | gccgttaaag | aaagaaggaa | ccatttcgat | tattggttca | 1020 |
| tttgccaaaa | aaccaaggta | tcaaggcggt | ggaagctcac | acattaaccc | gacaaagctt | 1080 |
| gaaaatatct | atgaagaaat | agagaaaaca | gcgggccaaa | atgtgaacgt | tttatacgcg | 1140 |
| gaaggatatc | atcttgaaaa | ggatttaatc | gatgatcaat | taattgaaga | ggcaaaaaaa | 1200 |
| acggcagcaa | aatccgatgt | aaccgtattg | tttgtaggtc | ttcctgaccg | atatgaatct | 1260 |
| gaaggatatg | atagagagca | cctgaatata | ccggagaatc | accgtctttt | agtcgaagcg | 1320 |
| gttgcggaag | tacaaaagaa | tatagttgtt | gtactaagta | atggggcacc | gcttgttatg | 1380 |
| ccatggcttg | ataaggtgaa | ggggctgctg | gaaagttacc | tgggaggtca | ggcactagga | 1440 |
| ggtgcgattg | cagacatcct | attcggagaa | gttaatccaa | gtgaaagct | tgccgaaact | 1500 |
| tttcccgtaa | aattaggtga | caatccttct | tatctcaact | ttccaggaga | gagggataaa | 1560 |
| gttgagtata | agaaggcat | ctttgttggt | tatcgttatt | acgatacaaa | acagattgag | 1620 |
| ccgctgtttc | catttggata | tggtttaagc | tatacaaact | ttgaatataa | aaaccttgta | 1680 |
| attgataaaa | aagaaataaa | agatacagaa | attgtcacag | ttaccgtgaa | tgtgaaaaat | 1740 |
| acaggaaaag | tgcctgggaa | agaaatcatc | cagttatatg | taaaagatat | aaaaagcagt | 1800 |
| gtagttcgtc | ctgaaaaaga | gttaaaaggc | tttggaaagg | tttccttaca | gcctggggaa | 1860 |
| gacaaaacta | tttcctttaa | attggataaa | cgcgcatttg | catattacaa | cacgaattg | 1920 |
| aaggattggt | atgtagaatc | aggagaattt | gaaattttgg | tggggaaatc | gtccagagaa | 1980 |
| attgaactaa | cagaaaaaat | tatggttcac | tctacttccc | cagttttctt | ggaggttcac | 2040 |
| cgaaattcca | cggtcggaga | tcttttaact | gatccaattc | taggtgaaaa | agctaatgct | 2100 |
| ctaattagag | agctaacaaa | aggaagtcca | ttatttgatg | ctgggtcaga | tcacggagag | 2160 |

-continued

```
ggtgcagaaa tgatggaagc gatgttaaaa tacatgcctt tgcgtgctct tatgaatttt    2220
agtggtggag acattaccga agagaaacta actgaattta ttaaggaact taattcaact    2280
aattttgtaa gcctttaa                                                  2298
```

<210> SEQ ID NO 96
<211> LENGTH: 765
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (30)...(252)
<223> OTHER INFORMATION: Glycosyl hydrolase family 3 N terminal domain
<220> FEATURE:
<221> NAME/KEY: DOMAIN
<222> LOCATION: (317)...(531)
<223> OTHER INFORMATION: Glycosyl hydrolase family 3 C terminal domain
<220> FEATURE:
<221> NAME/KEY: SITE
<222> LOCATION: (214)...(217)
<223> OTHER INFORMATION: N-glycosylation site. Prosite id = PS00001
<220> FEATURE:
<221> NAME/KEY: SITE
<222> LOCATION: (221)...(238)
<223> OTHER INFORMATION: Glycosyl hydrolases family 3 active site.
      Prosite id = PS00775
<220> FEATURE:
<221> NAME/KEY: SITE
<222> LOCATION: (692)...(695)
<223> OTHER INFORMATION: N-glycosylation site. Prosite id = PS00001
<220> FEATURE:
<221> NAME/KEY: SITE
<222> LOCATION: (750)...(753)
<223> OTHER INFORMATION: N-glycosylation site. Prosite id = PS00001
<220> FEATURE:
<221> NAME/KEY: SITE
<222> LOCATION: (769)...(772)
<223> OTHER INFORMATION: N-glycosylation site. Prosite id = PS00001

<400> SEQUENCE: 96

Met Ile Asn Gln Asp Ile Lys Gln Leu Ile Ser Gln Met Thr Leu Glu
1               5                   10                  15

Glu Lys Ala Gly Leu Cys Ser Gly Leu Asp Phe Trp Asn Leu Lys Gly
            20                  25                  30

Ile Glu Arg Leu Gly Ile Pro Ser Ile Met Val Thr Asp Gly Pro His
        35                  40                  45

Gly Leu Arg Lys Gln Lys Met Gly Ala Asp His Leu Gly Leu Phe Asp
    50                  55                  60

Ser Ile Pro Ala Thr Cys Phe Pro Ser Ala Gly Leu Ala Ser Thr
65                  70                  75                  80

Trp Asn Lys Glu Leu Ile Tyr Glu Val Gly Val Ala Leu Gly Lys Glu
                85                  90                  95

Cys Gln Ala Glu Asp Val Ala Ile Leu Leu Gly Pro Gly Ala Asn Ile
            100                 105                 110

Lys Arg Ser Pro Leu Cys Gly Arg Asn Phe Glu Tyr Phe Ser Glu Asp
        115                 120                 125

Pro Phe Leu Ser Ser Glu Met Ala Ala Ser His Ile Lys Gly Val Gln
    130                 135                 140

Ser Glu Gly Val Gly Thr Ser Leu Lys His Phe Ala Ala Asn Asn Gln
145                 150                 155                 160

Glu His Arg Arg Met Ser Thr Asp Ala Ile Val Asp Glu Arg Thr Leu
                165                 170                 175

Arg Glu Ile Tyr Leu Ala Ser Phe Glu Asn Ala Val Lys Lys Ala Gln
            180                 185                 190

-continued

Pro Trp Thr Val Met Cys Ala Tyr Asn Lys Val Asn Gly Asp Phe Ala
        195                 200                 205

Ser Glu Asn Lys Thr Leu Leu Thr Asp Ile Leu Arg Asp Glu Trp Gly
        210                 215                 220

Phe Glu Gly Ile Val Val Ser Asp Trp Gly Ala Val Asn Glu Pro Val
225                 230                 235                 240

Asp Gly Leu Asn Ala Gly Leu Asp Leu Glu Met Pro Ser Ser Ser Gly
                245                 250                 255

Ile Gly Glu Lys Lys Ile Ile Asn Ala Val Arg Asn Gly Gln Leu Leu
            260                 265                 270

Glu Asp Lys Leu Asp Gln Ala Val Glu Arg Ile Leu Arg Ile Ile Leu
        275                 280                 285

Met Ala Val Glu Asn Lys Lys Glu Thr Ala Asp Tyr Asp Lys Glu Gln
        290                 295                 300

His His Lys Leu Ala Arg Lys Ala Ala Ser Glu Ser Met Val Leu Leu
305                 310                 315                 320

Lys Asn Glu Asp Asn Ile Leu Pro Leu Lys Lys Glu Gly Thr Ile Ser
                325                 330                 335

Ile Ile Gly Ser Phe Ala Lys Lys Pro Arg Tyr Gln Gly Gly Gly Ser
            340                 345                 350

Ser His Ile Asn Pro Thr Lys Leu Glu Asn Ile Tyr Glu Glu Ile Glu
        355                 360                 365

Lys Thr Ala Gly Gln Asn Val Asn Val Leu Tyr Ala Glu Gly Tyr His
        370                 375                 380

Leu Glu Lys Asp Leu Ile Asp Asp Gln Leu Ile Glu Glu Ala Lys Lys
385                 390                 395                 400

Thr Ala Ala Lys Ser Asp Val Thr Val Leu Phe Val Gly Leu Pro Asp
                405                 410                 415

Arg Tyr Glu Ser Glu Gly Tyr Asp Arg Glu His Leu Asn Ile Pro Glu
            420                 425                 430

Asn His Arg Leu Leu Val Glu Ala Val Ala Glu Val Gln Lys Asn Ile
        435                 440                 445

Val Val Val Leu Ser Asn Gly Ala Pro Leu Val Met Pro Trp Leu Asp
        450                 455                 460

Lys Val Lys Gly Leu Leu Glu Ser Tyr Leu Gly Gly Gln Ala Leu Gly
465                 470                 475                 480

Gly Ala Ile Ala Asp Ile Leu Phe Gly Glu Val Asn Pro Ser Gly Lys
                485                 490                 495

Leu Ala Glu Thr Phe Pro Val Lys Leu Gly Asp Asn Pro Ser Tyr Leu
            500                 505                 510

Asn Phe Pro Gly Glu Arg Asp Lys Val Glu Tyr Lys Glu Gly Ile Phe
        515                 520                 525

Val Gly Tyr Arg Tyr Tyr Asp Thr Lys Gln Ile Glu Pro Leu Phe Pro
        530                 535                 540

Phe Gly Tyr Gly Leu Ser Tyr Thr Asn Phe Glu Tyr Lys Asn Leu Val
545                 550                 555                 560

Ile Asp Lys Lys Glu Ile Lys Asp Thr Glu Ile Val Thr Val Thr Val
                565                 570                 575

Asn Val Lys Asn Thr Gly Lys Val Pro Gly Lys Glu Ile Ile Gln Leu
            580                 585                 590

Tyr Val Lys Asp Ile Lys Ser Ser Val Arg Pro Glu Lys Glu Leu
        595                 600                 605

Lys Gly Phe Gly Lys Val Ser Leu Gln Pro Gly Glu Asp Lys Thr Ile

```
                610              615              620
Ser Phe Lys Leu Asp Lys Arg Ala Phe Ala Tyr Tyr Asn Thr Glu Leu
625                 630                 635                 640

Lys Asp Trp Tyr Val Glu Ser Gly Glu Phe Glu Ile Leu Val Gly Lys
                645                 650                 655

Ser Ser Arg Glu Ile Glu Leu Thr Glu Lys Ile Met Val His Ser Thr
                660                 665                 670

Ser Pro Val Phe Leu Glu Val His Arg Asn Ser Thr Val Gly Asp Leu
                675                 680                 685

Leu Thr Asp Pro Ile Leu Gly Glu Lys Ala Asn Ala Leu Ile Arg Glu
690                 695                 700

Leu Thr Lys Gly Ser Pro Leu Phe Asp Ala Gly Ser Asp His Gly Glu
705                 710                 715                 720

Gly Ala Glu Met Met Glu Ala Met Leu Lys Tyr Met Pro Leu Arg Ala
                725                 730                 735

Leu Met Asn Phe Ser Gly Gly Asp Ile Thr Glu Glu Lys Leu Thr Glu
                740                 745                 750

Phe Ile Lys Glu Leu Asn Ser Thr Asn Phe Val Ser Leu
                755                 760                 765

<210> SEQ ID NO 97
<211> LENGTH: 615
<212> TYPE: DNA
<213> ORGANISM: Unknown
<220> FEATURE:
<223> OTHER INFORMATION: Obtained from environmental sample

<400> SEQUENCE: 97
atgttatacc caattataac tgaaactcgc agtatcatcg atttaaatgg tatctggaaa        60
tttaaattag ataatggtga aggactgcag gaaaaatggt atgaaaacgg attaacagac       120
acgatcagta tggctgtacc atcttccttt aatgatattg gagtaaatgc cagtatacgc       180
gatcatgttg gctgggtatg gtatgagcgg gaattttctg tccccgccat ccttcaatct       240
gagcgtgtgg ttttgcgatt cggttccgca acacatctag ctaaggtttt cgtaaatggt       300
gaacttgttg ttgaacataa gggcggtttt ttaccgtttg aagcagaaat aaataagttt       360
ttacaaaaag ggaaaaatcg aataacggtt gctgtcaaca atattcttga ttactcaact       420
ttacccgttg gcacagtaat agaaaaggat attcctggag ttggcaaagt aatacgcaat       480
cagccaaatt ttgacttctt caactacgct ggcttgcacc gtccagtgaa aatatatact       540
acaccgacta cttatgtgaa ggatgtaacc attgtaacgg aaatagatgg acaggttcac       600
tattcaattg attaa                                                       615

<210> SEQ ID NO 98
<211> LENGTH: 204
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (9)...(182)
<223> OTHER INFORMATION: Glycosyl hydrolases family 2, sugar binding
      domain
<220> FEATURE:
<221> NAME/KEY: SITE
<222> LOCATION: (56)...(59)
<223> OTHER INFORMATION: N-glycosylation site. Prosite id = PS00001

<400> SEQUENCE: 98
```

```
Met Leu Tyr Pro Ile Ile Thr Glu Thr Arg Ser Ile Ile Asp Leu Asn
1               5                  10                 15

Gly Ile Trp Lys Phe Lys Leu Asp Asn Gly Gly Leu Gln Glu Lys
            20                  25                  30

Trp Tyr Glu Asn Gly Leu Thr Asp Thr Ile Ser Met Ala Val Pro Ser
            35                  40                  45

Ser Phe Asn Asp Ile Gly Val Asn Ala Ser Ile Arg Asp His Val Gly
    50                  55                  60

Trp Val Trp Tyr Glu Arg Glu Phe Ser Val Pro Ala Ile Leu Gln Ser
65                  70                  75                  80

Glu Arg Val Val Leu Arg Phe Gly Ser Ala Thr His Leu Ala Lys Val
                85                  90                  95

Phe Val Asn Gly Glu Leu Val Val Glu His Lys Gly Gly Phe Leu Pro
                100                 105                 110

Phe Glu Ala Glu Ile Asn Lys Phe Leu Gln Lys Gly Lys Asn Arg Ile
            115                 120                 125

Thr Val Ala Val Asn Asn Ile Leu Asp Tyr Ser Thr Leu Pro Val Gly
            130                 135                 140

Thr Val Ile Glu Lys Asp Ile Pro Gly Val Gly Lys Val Ile Arg Asn
145                 150                 155                 160

Gln Pro Asn Phe Asp Phe Phe Asn Tyr Ala Gly Leu His Arg Pro Val
            165                 170                 175

Lys Ile Tyr Thr Thr Pro Thr Thr Tyr Val Lys Asp Val Thr Ile Val
            180                 185                 190

Thr Glu Ile Asp Gly Gln Val His Tyr Ser Ile Asp
            195                 200

<210> SEQ ID NO 99
<211> LENGTH: 1404
<212> TYPE: DNA
<213> ORGANISM: Unknown
<220> FEATURE:
<223> OTHER INFORMATION: Obtained from environmental sample

<400> SEQUENCE: 99
atgaatcatt cccttttcatt tccgccatcc tttgtatggg gcgcggcaac cgcaagctac      60
caactggaag atcaaccca aggcgtggac ggctgcgccg agtccgtctg ggatatgcac      120
tgccgaagat ccggcgcgat caaggacggc tcgaacggat tcgtcgcctg cgatcactac      180
catcgctatc gcgaggatgt ggcgctcatg aacgagcttg gcttgaatgc ctatcgattc      240
tcaatcatgt ggccccgcgt catgcccgaa ggcaccggcg cggtgaacga aagggcatg      300 gatttctacg atcggttggt tgatgaactg ctcgccgccg gcatcacacc ttgggttact      360
ttgttccact gggactttcc cctagccttg ttccaacgcg gtggctggct gaatgcggat      420
tccccgcaat ggtttgagga ttacactcgg gaagtggtta acgcttgtc ggatcgtgtg      480 catcactggc taacgctcaa cgaaccggcg tgcttcattg agtttggcca ccgtaccggc      540
atgcatgcac ccggcttgca actggcggac aaggaagcct gccgggtctg caccatgcc      600 atgctggccc acggtcgcgc cgttcgcgct attcgccagg aatccgtgca tccatcaccc      660
caggtcggct acgcgccggt cttccgcact accatcccgg acactgaaga tcctgccgac      720
atcgaagcgg cccggacctc gatgtttgct catcaggccg caacctgtt cgatacgcgg      780 tggaacctcg acccctgctt tcggggcgcg tatccggaga tcatgatgca gtattgggc      840 gatgccgcgc cgcgcatcca ggacggcgac atggagttga tccgtcagga actcgatttt      900
ctcggcctga atatttacca gtccgagcgc attcgggccg gtgcggatgg cgcacccgag      960
```

```
gtggtgccat accctgcgga ttatccgcgc aaccagctcg gttggcccat cacgccggag    1020
gccctgcgct gggcgacccct ctttctcttt gaggagtacg ggaaacccct gatcatcaca   1080
gaaaacggaa tcaccctcga cgacaagccc aatgcagacg cgcgaggtgaa tgatgtccag   1140 cggatcgctt ttctgaatga ctatcttagc ggtctccagc gcagcgtgga cgacggcatc   1200
cctgtactgg gctatttcca ctggtcgctg tgcgacaact ttgagtgggc agaaggctat   1260
gtccctcgct tcggcctgat ccatgtggac tatgccagtc aacgcagaac catcaaggcc   1320
tcaggacggt tttaccgcga catcattcgg ggccagacag ccacgccctg catcgcccaa   1380
tccagtcagc cggaaacaac ctaa                                          1404
```

<210> SEQ ID NO 100
<211> LENGTH: 467
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(454)
<223> OTHER INFORMATION: Glycosyl hydrolase family 1
<220> FEATURE:
<221> NAME/KEY: SITE
<222> LOCATION: (2)...(5)
<223> OTHER INFORMATION: N-glycosylation site. Prosite id = PS00001
<220> FEATURE:
<221> NAME/KEY: SITE
<222> LOCATION: (11)...(25)
<223> OTHER INFORMATION: Glycosyl hydrolases family 1 N-terminal
      signature. Prosite id = PS00653

<400> SEQUENCE: 100

```
Met Asn His Ser Leu Ser Phe Pro Pro Ser Phe Val Trp Gly Ala Ala
1               5                   10                  15

Thr Ala Ser Tyr Gln Leu Glu Gly Ser Thr Gln Gly Val Asp Gly Cys
            20                  25                  30

Ala Glu Ser Val Trp Asp Met His Cys Arg Arg Ser Gly Ala Ile Lys
        35                  40                  45

Asp Gly Ser Asn Gly Phe Val Ala Cys Asp His Tyr His Arg Tyr Arg
    50                  55                  60

Glu Asp Val Ala Leu Met Asn Glu Leu Gly Leu Asn Ala Tyr Arg Phe
65                  70                  75                  80

Ser Ile Met Trp Pro Arg Val Met Pro Glu Gly Thr Gly Ala Val Asn
                85                  90                  95

Glu Lys Gly Met Asp Phe Tyr Asp Arg Leu Val Asp Glu Leu Leu Ala
            100                 105                 110

Ala Gly Ile Thr Pro Trp Val Thr Leu Phe His Trp Asp Phe Pro Leu
        115                 120                 125

Ala Leu Phe Gln Arg Gly Gly Trp Leu Asn Ala Asp Ser Pro Gln Trp
    130                 135                 140

Phe Glu Asp Tyr Thr Arg Glu Val Val Lys Arg Leu Ser Asp Arg Val
145                 150                 155                 160

His His Trp Leu Thr Leu Asn Glu Pro Ala Cys Phe Ile Glu Phe Gly
                165                 170                 175

His Arg Thr Gly Met His Ala Pro Gly Leu Gln Leu Ala Asp Lys Glu
            180                 185                 190

Ala Cys Arg Val Trp His His Ala Met Leu Ala His Gly Arg Ala Val
        195                 200                 205

Arg Ala Ile Arg Gln Glu Ser Val His Pro Ser Pro Gln Val Gly Tyr
```

```
                210                 215                 220
Ala Pro Val Phe Arg Thr Thr Ile Pro Asp Thr Glu Asp Pro Ala Asp
225                 230                 235                 240

Ile Glu Ala Ala Arg Thr Ser Met Phe Ala His Gln Ala Gly Asn Leu
            245                 250                 255

Phe Asp Thr Arg Trp Asn Leu Asp Pro Cys Phe Arg Gly Ala Tyr Pro
        260                 265                 270

Glu Ile Met Met Gln Tyr Trp Gly Asp Ala Ala Pro Arg Ile Gln Asp
    275                 280                 285

Gly Asp Met Glu Leu Ile Arg Gln Glu Leu Asp Phe Leu Gly Leu Asn
290                 295                 300

Ile Tyr Gln Ser Glu Arg Ile Arg Ala Gly Ala Asp Gly Ala Pro Glu
305                 310                 315                 320

Val Val Pro Tyr Pro Ala Asp Tyr Pro Arg Asn Gln Leu Gly Trp Pro
            325                 330                 335

Ile Thr Pro Glu Ala Leu Arg Trp Ala Thr Leu Phe Leu Phe Glu Glu
        340                 345                 350

Tyr Gly Lys Pro Leu Ile Ile Thr Glu Asn Gly Ile Thr Leu Asp Asp
    355                 360                 365

Lys Pro Asn Ala Asp Gly Glu Val Asn Asp Val Gln Arg Ile Ala Phe
370                 375                 380

Leu Asn Asp Tyr Leu Ser Gly Leu Gln Arg Ser Val Asp Asp Gly Ile
385                 390                 395                 400

Pro Val Leu Gly Tyr Phe His Trp Ser Leu Cys Asp Asn Phe Glu Trp
            405                 410                 415

Ala Glu Gly Tyr Val Pro Arg Phe Gly Leu Ile His Val Asp Tyr Ala
        420                 425                 430

Ser Gln Arg Arg Thr Ile Lys Ala Ser Gly Arg Phe Tyr Arg Asp Ile
    435                 440                 445

Ile Arg Gly Gln Thr Ala Thr Pro Cys Ile Ala Gln Ser Ser Gln Pro
450                 455                 460

Glu Thr Thr
465

<210> SEQ ID NO 101
<211> LENGTH: 1101
<212> TYPE: DNA
<213> ORGANISM: Unknown
<220> FEATURE:
<223> OTHER INFORMATION: Obtained from environmental sample

<400> SEQUENCE: 101
atgagaaatc atctgaatgt acccttttac tttatcttct tttttttaat agcgtcaata      60
tttacagtct gttcatcatc aactgcttct gataacaatg agcatccacc gccagtggaa     120
gtcgcggatc aggacgcttt tcgtgatgct tttgaagtga atgaattact tggacgcgtt     180
attaatctgg gtaatgccct tgaagcgccc aatgaaggcg aatggggaat ggtaatccag     240
gaagagtttc ttgatctgat acttgcagca ggttttgagt ctgtacgaat tccgattcgc     300
tggaatgccc atgccagtga agtcacccct tcaccattc aacgatcgtt ttttgatcgg     360
gttgatgaag tcatccaatg gtcgctggat cgtggccttt ctgtaatgat caatattcat     420
cactacaatg aactgatgca aaacccgcag cagcaccggc agcggttttt gcgactctgg     480
aaccagattg ctacacacta taaagattat ccggataatc tggttttga atccttaat      540 gaacctcatg ataatctgac tccttctatc tggaatagtt atttgaggga tgctattggc     600
```

```
atgattcgcc agacaaaccc acgcagggtt atcgctatcg aacagcaaa ctggggtggt      660 ttcggagcat tatcacaact tgaaatcccc tcaaacgatc gccagatcat tgcaactgtt     720
cattattatg aaccccttcag gttcacccat caggggggctg aatgggcagg accggaaaca   780
aacgattggc tggggacacg atgggatgga tcgatgagg aaaaatttga tattgaaagt     840
ggttttgatg ccgtacagtc ctgggcagtg acaaataacc ggcctgttca tctcggagaa    900
ttcggtgctt acagtactgc cgataatgaa tcacgcgaac gctggacaac ctttgttcgg    960
gaatccgctg agcaacgcaa tttcagctgg gcatactggg aatttgcagc cggttttggg    1020
atctatgacc gtaatcagtg gcaatggagg gattatctgt tgagggcttt gataccggat    1080
agcccggtcc tgttggagta a                                              1101
```

<210> SEQ ID NO 102
<211> LENGTH: 366
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(29)
<220> FEATURE:
<221> NAME/KEY: DOMAIN
<222> LOCATION: (64)...(342)
<223> OTHER INFORMATION: Cellulase (glycosyl hydrolase family 5)
<220> FEATURE:
<221> NAME/KEY: SITE
<222> LOCATION: (176)...(185)
<223> OTHER INFORMATION: Glycosyl hydrolases family 5 signature. Prosite
      id = PS00659
<220> FEATURE:
<221> NAME/KEY: SITE
<222> LOCATION: (313)...(316)
<223> OTHER INFORMATION: N-glycosylation site. Prosite id = PS00001
<220> FEATURE:
<221> NAME/KEY: SITE
<222> LOCATION: (332)...(335)
<223> OTHER INFORMATION: N-glycosylation site. Prosite id = PS00001

<400> SEQUENCE: 102

```
Met Arg Asn His Leu Asn Val Pro Phe Tyr Phe Ile Phe Phe Leu
1               5                   10                  15

Ile Ala Ser Ile Phe Thr Val Cys Ser Ser Thr Ala Ser Asp Asn
                20                  25                  30

Asn Glu His Pro Pro Pro Val Glu Val Ala Asp Gln Asp Ala Phe Arg
                35                  40                  45

Asp Ala Phe Glu Val Asn Glu Leu Leu Gly Arg Gly Ile Asn Leu Gly
            50                  55                  60

Asn Ala Leu Glu Ala Pro Asn Glu Gly Glu Trp Gly Met Val Ile Gln
65                  70                  75                  80

Glu Glu Phe Leu Asp Leu Ile Leu Ala Ala Gly Phe Glu Ser Val Arg
                85                  90                  95

Ile Pro Ile Arg Trp Asn Ala His Ala Ser Glu Ser His Pro Phe Thr
            100                 105                 110

Ile Gln Arg Ser Phe Phe Asp Arg Val Asp Glu Val Ile Gln Trp Ser
        115                 120                 125

Leu Asp Arg Gly Leu Ser Val Met Ile Asn Ile His His Tyr Asn Glu
    130                 135                 140

Leu Met Gln Asn Pro Gln Gln His Arg Gln Arg Phe Leu Arg Leu Trp
145                 150                 155                 160

Asn Gln Ile Ala Thr His Tyr Lys Asp Tyr Pro Asp Asn Leu Val Phe
                165                 170                 175
```

Glu Ile Leu Asn Glu Pro His Asp Asn Leu Thr Pro Ser Ile Trp Asn
            180                 185                 190

Ser Tyr Leu Arg Asp Ala Ile Gly Met Ile Arg Gln Thr Asn Pro Arg
        195                 200                 205

Arg Val Ile Ala Ile Gly Thr Ala Asn Trp Gly Gly Phe Gly Ala Leu
    210                 215                 220

Ser Gln Leu Glu Ile Pro Ser Asn Asp Arg Gln Ile Ile Ala Thr Val
225                 230                 235                 240

His Tyr Tyr Glu Pro Phe Arg Phe Thr His Gln Gly Ala Glu Trp Ala
                245                 250                 255

Gly Pro Glu Thr Asn Asp Trp Leu Gly Thr Arg Trp Asp Gly Ser Asp
            260                 265                 270

Glu Glu Lys Phe Asp Ile Glu Ser Gly Phe Asp Ala Val Gln Ser Trp
        275                 280                 285

Ala Val Thr Asn Asn Arg Pro Val His Leu Gly Glu Phe Gly Ala Tyr
    290                 295                 300

Ser Thr Ala Asp Asn Glu Ser Arg Glu Arg Trp Thr Thr Phe Val Arg
305                 310                 315                 320

Glu Ser Ala Glu Gln Arg Asn Phe Ser Trp Ala Tyr Trp Glu Phe Ala
                325                 330                 335

Ala Gly Phe Gly Ile Tyr Asp Arg Asn Gln Trp Gln Trp Arg Asp Tyr
            340                 345                 350

Leu Leu Arg Ala Leu Ile Pro Asp Ser Pro Val Leu Leu Glu
        355                 360                 365

<210> SEQ ID NO 103
<211> LENGTH: 1101
<212> TYPE: DNA
<213> ORGANISM: Unknown
<220> FEATURE:
<223> OTHER INFORMATION: Obtained from environmental sample

<400> SEQUENCE: 103
atgctgataa ttggaggcct tcttgtttta ctgggatttt cttcttgcgg gcggcaggca      60
gaacctgctg ctgactcttt caggggggttt catgactttg acatcaggcg tggggtgaac    120
atcagccact ggttgtcgca gagtggaagg cgtggtgctg atcgggaggc gttctttacc     180
agggcggatg tggaggccat cgccggcttc ggttatgatc acattcgttt gcccattgat    240
gaggagcaga tgtgggatga gtcgggcaac aaggaaccac gtgcctttga attgctgcat     300
gaagccattg gctgggcttt ggacaatgag ctcagggtca ttgtcgacct gcacatcatc    360
aggtcgcact atttaatgc gcctgagaac ccgctttgga ccgatcgtgc tgaacagttg     420
aaatttgttg agatgtggcg acagttgtct gatgagctgc agggctatcc gctcgatagg    480
gtggcctatg aattgatgaa tgaggccgtg gctgatgatc cggacgattg gaaccggctt    540
gtggctgaga cgatggaggc gctacggatg ctggaaccgg agcgcaagat tgtcattggc    600
tccaaccgct ggcagtctgt gcatacattt cctgacctgg tgatcccgga taatgacccg    660
catatcatat tgagttttca cttctacgaa ccatttctgc tgacgcacca caaggcctcc    720
tggacacaca tccgtgatta caccggtccg gtgaactatc cgggttttgac tgtagacccg    780 acccacctgg aggggttgtc tgaagaactg gtgacccgga ttggccatca aatgggggtg    840
tatacaaaag aaacgatgga ggagatgatc atgatcccac tgcaatatgc caaagaccgg    900
gggctccccc tttattgtgg agagtgggga tgtttcccga ccatgcccca ggagatgcgc    960
ctgcaatggt acgccgatgt gcgtgcgatc ctggaaaagc atgagattgc ctgggcaaac   1020

```
tgggattaca agggtggttt cggtgtggtt gaccgcaacg gcgaacccca ccatgattta   1080
ttggaagtgc tcttaaaata a                                             1101
```

<210> SEQ ID NO 104
<211> LENGTH: 366
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(20)
<220> FEATURE:
<221> NAME/KEY: DOMAIN
<222> LOCATION: (42)...(349)
<223> OTHER INFORMATION: Cellulase (glycosyl hydrolase family 5)
<220> FEATURE:
<221> NAME/KEY: SITE
<222> LOCATION: (40)...(43)
<223> OTHER INFORMATION: N-glycosylation site. Prosite id = PS00001

<400> SEQUENCE: 104

```
Met Leu Ile Ile Gly Gly Leu Leu Val Leu Gly Phe Ser Ser Cys
1               5                   10                  15

Gly Arg Gln Ala Glu Pro Ala Ala Asp Ser Phe Arg Gly Phe His Asp
            20                  25                  30

Phe Asp Ile Arg Arg Gly Val Asn Ile Ser His Trp Leu Ser Gln Ser
        35                  40                  45

Gly Arg Arg Gly Ala Asp Arg Glu Ala Phe Phe Thr Arg Ala Asp Val
    50                  55                  60

Glu Ala Ile Ala Gly Phe Gly Tyr Asp His Ile Arg Leu Pro Ile Asp
65                  70                  75                  80

Glu Glu Gln Met Trp Asp Ser Gly Asn Lys Glu Pro Arg Ala Phe
                85                  90                  95

Glu Leu Leu His Glu Ala Ile Gly Trp Ala Leu Asp Asn Glu Leu Arg
            100                 105                 110

Val Ile Val Asp Leu His Ile Ile Arg Ser His Tyr Phe Asn Ala Pro
        115                 120                 125

Glu Asn Pro Leu Trp Thr Asp Arg Ala Glu Gln Leu Lys Phe Val Glu
    130                 135                 140

Met Trp Arg Gln Leu Ser Asp Glu Leu Gln Gly Tyr Pro Leu Asp Arg
145                 150                 155                 160

Val Ala Tyr Glu Leu Met Asn Glu Ala Val Ala Asp Pro Asp Asp
                165                 170                 175

Trp Asn Arg Leu Val Ala Glu Thr Met Glu Ala Leu Arg Met Leu Glu
            180                 185                 190

Pro Glu Arg Lys Ile Val Ile Gly Ser Asn Arg Trp Gln Ser Val His
        195                 200                 205

Thr Phe Pro Asp Leu Val Ile Pro Asp Asn Asp Pro His Ile Ile Leu
    210                 215                 220

Ser Phe His Phe Tyr Glu Pro Phe Leu Leu Thr His His Lys Ala Ser
225                 230                 235                 240

Trp Thr His Ile Arg Asp Tyr Thr Gly Pro Val Asn Tyr Pro Gly Leu
                245                 250                 255

Thr Val Asp Pro Thr His Leu Glu Gly Leu Ser Glu Leu Val Thr
            260                 265                 270

Arg Ile Gly His His Asn Gly Val Tyr Thr Lys Glu Thr Met Glu Glu
        275                 280                 285
```

```
Met Ile Met Ile Pro Leu Gln Tyr Ala Lys Asp Arg Gly Leu Pro Leu
            290                 295                 300

Tyr Cys Gly Glu Trp Gly Cys Phe Pro Thr Met Pro Gln Glu Met Arg
305                 310                 315                 320

Leu Gln Trp Tyr Ala Asp Val Arg Ala Ile Leu Glu Lys His Glu Ile
                325                 330                 335

Ala Trp Ala Asn Trp Asp Tyr Lys Gly Gly Phe Gly Val Val Asp Arg
            340                 345                 350

Asn Gly Glu Pro His His Asp Leu Leu Glu Val Leu Leu Lys
            355                 360                 365

<210> SEQ ID NO 105
<211> LENGTH: 1047
<212> TYPE: DNA
<213> ORGANISM: Unknown
<220> FEATURE:
<223> OTHER INFORMATION: Obtained from environmental sample

<400> SEQUENCE: 105
atgcaacact tcatcaacgg cgtcaacctg ggaggctggc tctcccaata ccagaaatac      60
gaccatgagc acttccgcac cttcatcacc cggcgcgata tcgaacaaat cgcatcctgg     120
ggcttcgacc acatccgcct gccggtcgat tatccggttc tcgaatcgga cgacgcgccc     180
ggtatctatc atgaagatgg ctttgcctat cttgactctt gcctggaatg gtgccaggcc     240
gctgggctgg cagtcgtctt cgacctgcat catgcccccg gctacagttt cacgaacacg     300
ctcaagcctg aaaccctgca cctgaacgta ctcttcgagc aggaaatcgc caaaatcga     360
tttatcgccc tctgggaaac cattgttcgg cgctaccagg ccgccggctt gcctatcatc     420
tttgaactac tgaatgaaat ggtgctgcca gacagcggcc cctggaacgc cctggcccac     480
aaaaccgtcg ccgccctgcg acagatttcg cccgattgca aaatcatgat tggcggcaat     540
aactacaacg ccgcatccga actcaaaaac ataaccctgc acaacgaccc caacatccta     600
tacaccttcc atttctacga accggccctg ttcacccacc agaaagcccc ctgggtgcag     660
attgctgtcg aatacaacca ggaactcgaa taccctggct cgtacaccaa cctggccgcc     720
tttctccggc gcaatcccca ctatcaagaa tcctatggat ggcaggtcaa ccgccgtatc     780
gaccgcgacc tcctgctcga attcacccaa cccgccctgg actttgtcca gcagaccggg     840
cgcgacctgt actgcggtga attcggcgtc attgaatacg tcgagcctgc cagccgccaa     900
aactggcacg ccgacctgct ggacatcctg cgccagcaga agattggccg cgccgtctgg     960
acttataaac aaatggattt tggcctggtg gacgcggacg gcaaggtggt cgaccccaaa    1020
cttctcgaaa tcttgtgtca atcctga                                        1047

<210> SEQ ID NO 106
<211> LENGTH: 348
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (2)...(330)
<223> OTHER INFORMATION: Cellulase (glycosyl hydrolase family 5)
<220> FEATURE:
<221> NAME/KEY: SITE
<222> LOCATION: (192)...(195)
<223> OTHER INFORMATION: N-glycosylation site. Prosite id = PS00001

<400> SEQUENCE: 106

Met Gln His Phe Ile Asn Gly Val Asn Leu Gly Gly Trp Leu Ser Gln
```

```
              1               5                  10                 15
Tyr Gln Lys Tyr Asp His Glu His Phe Arg Thr Phe Ile Thr Arg Arg
                           20                 25                  30

Asp Ile Glu Gln Ile Ala Ser Trp Gly Phe Asp His Ile Arg Leu Pro
                35                 40                 45

Val Asp Tyr Pro Val Leu Glu Ser Asp Ala Pro Gly Ile Tyr His
     50                 55                 60

Glu Asp Gly Phe Ala Tyr Leu Asp Ser Cys Leu Glu Trp Cys Gln Ala
65                 70                 75                 80

Ala Gly Leu Ala Val Val Phe Asp Leu His His Ala Pro Gly Tyr Ser
                85                 90                 95

Phe Thr Asn Thr Leu Lys Pro Glu Thr Leu His Leu Asn Val Leu Phe
                 100                105                110

Glu Gln Glu Ile Ala Gln Asn Arg Phe Ile Ala Leu Trp Glu Thr Ile
             115                120                125

Val Arg Arg Tyr Gln Ala Ala Gly Leu Pro Ile Ile Phe Glu Leu Leu
     130                135                140

Asn Glu Met Val Leu Pro Asp Ser Gly Pro Trp Asn Ala Leu Ala His
145                150                155                160

Lys Thr Val Ala Ala Leu Arg Gln Ile Ser Pro Asp Cys Lys Ile Met
                 165                170                175

Ile Gly Gly Asn Asn Tyr Asn Ala Ala Ser Glu Leu Lys Asn Ile Thr
                 180                185                190

Leu His Asn Asp Pro Asn Ile Leu Tyr Thr Phe His Phe Tyr Glu Pro
         195                200                205

Ala Leu Phe Thr His Gln Lys Ala Pro Trp Val Gln Ile Ala Val Glu
     210                215                220

Tyr Asn Gln Glu Leu Glu Tyr Pro Gly Ser Tyr Thr Asn Leu Ala Ala
225                230                235                240

Phe Leu Arg Arg Asn Pro His Tyr Gln Glu Ser Tyr Gly Trp Gln Val
                 245                250                255

Asn Arg Arg Ile Asp Arg Asp Leu Leu Leu Glu Phe Thr Gln Pro Ala
             260                265                270

Leu Asp Phe Val Gln Gln Thr Gly Arg Asp Leu Tyr Cys Gly Glu Phe
     275                280                285

Gly Val Ile Glu Tyr Val Glu Pro Ala Ser Arg Gln Asn Trp His Ala
     290                295                300

Asp Leu Leu Asp Ile Leu Arg Gln Gln Lys Ile Gly Arg Ala Val Trp
305                310                315                320

Thr Tyr Lys Gln Met Asp Phe Gly Leu Val Asp Ala Asp Gly Lys Val
                 325                330                335

Val Asp Pro Lys Leu Leu Glu Ile Leu Cys Gln Ser
                 340                345

<210> SEQ ID NO 107
<211> LENGTH: 1137
<212> TYPE: DNA
<213> ORGANISM: Unknown
<220> FEATURE:
<223> OTHER INFORMATION: Obtained from environmental sample

<400> SEQUENCE: 107
atggaaaagc aaatctgttc aaatgttttc agtacgatgc tgataattgg aggccttctt      60
gttttactgg gattttcttc ttgcgggcgg caggcagaac ctgctgctga ctctttcagg     120
gggtttcacg actttgacat caggcgcggg gtgaacatca gccattggtt gtcgcagagt     180
```

```
ggaaggcgtg gtgctgatcg ggaggcgttc tttaccaggg cggatgtgga ggccatcgcc    240
ggcttcggtt atgatcacat tcgtttgccc atcgatgaag agcagatgtg ggatgagtcg    300
ggcaacaagg agccacgtgc ctttgaattg ctgcatgagg ccattggctg ggctttggac    360
aatgagctca gggtcattgt tgacctgcac atcatcaggt cgcactattt taatgcgcct    420
gagaacccgc tttggaccga tcgtgctgaa cagttgaaat tgttgagat gtggcgacag     480 ttgtctgatg agctgcaggg ctatccgctc gataggtgg cctatgaatt gatgaatgag     540
gccgtggctg atgatccgga cgattggaac cggcttgtgg ctgagacgat ggaggcgcta    600
cggatgctgg aaccggagcg caagattgtc attggctcca accgctggca gtctgtgcat    660
acatttcctg acctggtgat cccggataat gacccgcata tcatattgag ttttcacttc    720
tacgaaccat ttctgctgac gcaccacaag gcctcctgga cacacatccg tgattacacc    780
ggtccggtga actatccggg tttgactgta gacccgaccc acctggaggg gttgtctgaa    840
gaactggtga cccggattgg ccatcacaat ggggtgtata caaaagaaac gatggaggag    900
atgatcatga tcccactgca atatgccaaa gaacgggggc tcccctgta ttgcggggag     960 tggggatgtt tcccgaccat gccccaggag atgcgcctgc aatggtacgc cgatgtgcgt    1020
gcgatcctgg aaaagcatga gattgcctgg gcaaactggg attacaaggg tggtttcggt    1080
gtggttgacc gcaacggcga accccaccat gatttattgg aagtcttact aaaataa      1137
```

<210> SEQ ID NO 108
<211> LENGTH: 378
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(32)
<220> FEATURE:
<221> NAME/KEY: DOMAIN
<222> LOCATION: (54)...(361)
<223> OTHER INFORMATION: Cellulase (glycosyl hydrolase family 5)
<220> FEATURE:
<221> NAME/KEY: SITE
<222> LOCATION: (52)...(55)
<223> OTHER INFORMATION: N-glycosylation site. Prosite id = PS00001

<400> SEQUENCE: 108

```
Met Glu Lys Gln Ile Cys Ser Asn Val Phe Ser Thr Met Leu Ile Ile
1               5                   10                  15

Gly Gly Leu Leu Val Leu Leu Gly Phe Ser Ser Cys Gly Arg Gln Ala
            20                  25                  30

Glu Pro Ala Ala Asp Ser Phe Arg Gly Phe His Asp Phe Asp Ile Arg
        35                  40                  45

Arg Gly Val Asn Ile Ser His Trp Leu Ser Gln Ser Gly Arg Arg Gly
    50                  55                  60

Ala Asp Arg Glu Ala Phe Phe Thr Arg Ala Asp Val Glu Ala Ile Ala
65                  70                  75                  80

Gly Phe Gly Tyr Asp His Ile Arg Leu Pro Ile Asp Glu Glu Gln Met
                85                  90                  95

Trp Asp Glu Ser Gly Asn Lys Glu Pro Arg Ala Phe Glu Leu Leu His
            100                 105                 110

Glu Ala Ile Gly Trp Ala Leu Asp Asn Glu Leu Arg Val Ile Val Asp
        115                 120                 125

Leu His Ile Ile Arg Ser His Tyr Phe Asn Ala Pro Glu Asn Pro Leu
    130                 135                 140
```

Trp Thr Asp Arg Ala Glu Gln Leu Lys Phe Val Glu Met Trp Arg Gln
145                 150                 155                 160

Leu Ser Asp Glu Leu Gln Gly Tyr Pro Leu Asp Arg Val Ala Tyr Glu
            165                 170                 175

Leu Met Asn Glu Ala Val Ala Asp Pro Asp Asp Trp Asn Arg Leu
            180                 185                 190

Val Ala Glu Thr Met Glu Ala Leu Arg Met Leu Glu Pro Glu Arg Lys
            195                 200                 205

Ile Val Ile Gly Ser Asn Arg Trp Gln Ser Val His Thr Phe Pro Asp
    210                 215                 220

Leu Val Ile Pro Asp Asn Asp Pro His Ile Ile Leu Ser Phe His Phe
225                 230                 235                 240

Tyr Glu Pro Phe Leu Leu Thr His His Lys Ala Ser Trp Thr His Ile
                245                 250                 255

Arg Asp Tyr Thr Gly Pro Val Asn Tyr Pro Gly Leu Thr Val Asp Pro
            260                 265                 270

Thr His Leu Glu Gly Leu Ser Glu Glu Leu Val Thr Arg Ile Gly His
        275                 280                 285

His Asn Gly Val Tyr Thr Lys Glu Thr Met Glu Glu Met Ile Met Ile
    290                 295                 300

Pro Leu Gln Tyr Ala Lys Glu Arg Gly Leu Pro Leu Tyr Cys Gly Glu
305                 310                 315                 320

Trp Gly Cys Phe Pro Thr Met Pro Gln Glu Met Arg Leu Gln Trp Tyr
                325                 330                 335

Ala Asp Val Arg Ala Ile Leu Glu Lys His Glu Ile Ala Trp Ala Asn
            340                 345                 350

Trp Asp Tyr Lys Gly Gly Phe Gly Val Val Asp Arg Asn Gly Glu Pro
        355                 360                 365

His His Asp Leu Leu Glu Val Leu Leu Lys
    370                 375

<210> SEQ ID NO 109
<211> LENGTH: 1248
<212> TYPE: DNA
<213> ORGANISM: Unknown
<220> FEATURE:
<223> OTHER INFORMATION: Obtained from environmental sample

<400> SEQUENCE: 109
atgaagacac atagcttcaa cctcagatca cggatcacct tgttgaccgc ggcactgctt      60
ttcatcgggg caacggccgg ggccgccacg acacctatca ccctcaaaga cgcctacaaa     120
gaccatttcc ttatgggtgt agccatcaac cgcctgattg caatgggcga tacgaatgtc     180
cgggccgaca cgccagccga gaccccggaa cagctcaagg gggacattgc cctggtcaag     240
gcgcagttca acctgatcgt caatgagaac gatctgaaac cgattctcat tcacccgagg     300
ccaggaccgg acgggtacga cttcgcccca gcggatgcct tcgtgaagtt cggcatggac     360
aacaatatgt atatcgtggg ccacacccte ctctggcaca gccaggtgcc caactggttc     420
ttccaagggt ctgctccggc gactccggaa acgccacctg ctgccacgga cgcggcggtc     480
gcaccccgcg gcggacgagg aggtcgcggc gggattaccg gccccctggc gacccgcgag     540
gagttgatcg aacgcatgcg cgagcacatt cacaccgtcg tcggccgcta agggaaag      600 atcaaggtct gggacgtcgt caacgaagcc ctcgccgacg gcggcaccga gaccctgcga     660
agcacgtact ggacccaaat catcgggccg gaattcatcg ccatggcctt tcgattcgcc     720

```
cacgaagccg atccggatgc gatccttcgt tacaacgatt atggcctgga gaaccctgcc    780
aagcgtgaga aactcaagaa gctgatcgcg tcgctccagg agcagaacgt tccggttcat    840
gccatcggca cgcaaaccca tatcagcgtc tccacgacgt tcgaaagaat ggatgagacc    900
ttgagggacc tggcatccat cgggcttccc gtccacatca ccgaactgga tgtcaacgcc    960
gccgcggggg gccagagggg caccaatgcg acattgccg gcactgccga gcgtacggcg   1020
ggcggcgtgg tcagtgaagc cgacaagcgg ctggccgacg cctacgcgaa tctcttccgc   1080
gcgatcatga agcacaagga ctcggtgaag atggtcacgt tctgggcgt caatgacgcg   1140 gtttcgtggc tcgcacgcgg caccccgctg ctgttcgacg caacaatca gcccaagccg   1200 gctttcgatg cggtcattcg cgtcgccacg gaggcggcac agaactga              1248
```

<210> SEQ ID NO 110
<211> LENGTH: 415
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(28)
<220> FEATURE:
<221> NAME/KEY: DOMAIN
<222> LOCATION: (34)...(409)
<223> OTHER INFORMATION: Glycosyl hydrolase family 10
<220> FEATURE:
<221> NAME/KEY: SITE
<222> LOCATION: (312)...(322)
<223> OTHER INFORMATION: Glycosyl hydrolases family 10 active site.
       Prosite id = PS00591

<400> SEQUENCE: 110

Met Lys Thr His Ser Phe Asn Leu Arg Ser Arg Ile Thr Leu Leu Thr
1               5                   10                  15

Ala Ala Leu Leu Phe Ile Gly Ala Thr Ala Gly Ala Ala Thr Thr Pro
            20                  25                  30

Ile Thr Leu Lys Asp Ala Tyr Lys Asp His Phe Leu Met Gly Val Ala
        35                  40                  45

Ile Asn Arg Leu Ile Ala Met Gly Asp Thr Asn Val Arg Ala Asp Asn
    50                  55                  60

Ala Ser Arg Thr Pro Glu Gln Leu Lys Gly Asp Ile Ala Leu Val Lys
65                  70                  75                  80

Ala Gln Phe Asn Leu Ile Val Asn Glu Asn Asp Leu Lys Pro Ile Leu
                85                  90                  95

Ile His Pro Arg Pro Gly Pro Asp Gly Tyr Asp Phe Ala Pro Ala Asp
            100                 105                 110

Ala Phe Val Lys Phe Gly Met Asp Asn Asn Met Tyr Ile Val Gly His
        115                 120                 125

Thr Leu Leu Trp His Ser Gln Val Pro Asn Trp Phe Phe Gln Gly Ser
    130                 135                 140

Ala Pro Ala Thr Pro Glu Thr Pro Pro Ala Ala Thr Asp Ala Ala Val
145                 150                 155                 160

Ala Pro Arg Gly Gly Arg Gly Gly Arg Gly Gly Ile Thr Gly Pro Leu
                165                 170                 175

Ala Thr Arg Glu Glu Leu Ile Glu Arg Met Arg Glu His Ile His Thr
            180                 185                 190

Val Val Gly Arg Tyr Lys Gly Lys Ile Lys Val Trp Asp Val Val Asn
        195                 200                 205

Glu Ala Leu Ala Asp Gly Gly Thr Glu Thr Leu Arg Ser Thr Tyr Trp

```
                    210                 215                 220
Thr Gln Ile Ile Gly Pro Glu Phe Ile Ala Met Ala Phe Arg Phe Ala
225                 230                 235                 240

His Glu Ala Asp Pro Asp Ala Ile Leu Arg Tyr Asn Asp Tyr Gly Leu
                245                 250                 255

Glu Asn Pro Ala Lys Arg Glu Lys Leu Lys Lys Leu Ile Ala Ser Leu
            260                 265                 270

Gln Glu Gln Asn Val Pro Val His Ala Ile Gly Thr Gln Thr His Ile
            275                 280                 285

Ser Val Ser Thr Thr Phe Glu Arg Met Asp Glu Thr Leu Arg Asp Leu
290                 295                 300

Ala Ser Ile Gly Leu Pro Val His Ile Thr Glu Leu Asp Val Asn Ala
305                 310                 315                 320

Ala Ala Gly Gly Gln Arg Gly Thr Asn Ala Asp Ile Ala Gly Thr Ala
                325                 330                 335

Glu Arg Thr Ala Gly Gly Val Val Ser Glu Ala Asp Lys Arg Leu Ala
            340                 345                 350

Asp Ala Tyr Ala Asn Leu Phe Arg Ala Ile Met Lys His Lys Asp Ser
            355                 360                 365

Val Lys Met Val Thr Phe Trp Gly Val Asn Asp Ala Val Ser Trp Leu
370                 375                 380

Ala Arg Gly Thr Pro Leu Leu Phe Asp Gly Asn Asn Gln Pro Lys Pro
385                 390                 395                 400

Ala Phe Asp Ala Val Ile Arg Val Ala Thr Glu Ala Ala Gln Asn
                405                 410                 415

<210> SEQ ID NO 111
<211> LENGTH: 1131
<212> TYPE: DNA
<213> ORGANISM: Unknown
<220> FEATURE:
<223> OTHER INFORMATION: Obtained from environmental sample

<400> SEQUENCE: 111
atgcgaagac tgatcaccat catccttgcg acggctgtcg caatcttatc gaccacatca      60
tgctccaaga ccgctgaacg agagggcttc ttgatcaagc gaggaaccaa cctcagccat     120
tggctctccc agagcaagga aaggggagag gctcgcaggc tccatatcca ggaggatgac     180
tttgctcgcc tcgacagcct cggtttcgac catgtgcgca tccctgtcga cgaggaacaa     240
ctctgggacg aggatggcaa caagctcaca gaagcatggg aactgctcga tttcgccctc     300
gacatggcgc gcaagtacaa cctgcgcgct atcgtggacc ttcacatcat ccgcgcccat     360
tacttcaacg ccgtcaacga aggcgcgtcg aatactctct tcaccagcga ggaggcgcag     420
cagggcctga tcaacctttg gtaccagctt ccgacttcc tcaaggaccg cagcgtcgac     480
tgggttgcct acgagttcat gaacgagcca gtcgctcctg agcatgagca atggaacgcc     540
ctcgtcgcaa aggtgcacaa ggcgcttcgt gagcgtgaac cggagcgtac cctcgtgatc     600
ggttctaacc tgtggcaggg tcaccagacc ttcaagtacc tccgcgtacc tgagaatgac     660
ccgaacatca tcctgagctt ccactactac aacccttcga tcctcaccca acatggct     720 ccgtggactc cggtgggcaa atataccggt tccatcaatt atccgggcgt catcgtctct     780
gctgaggatt acgctgcgca gagccctgag gtgcaggccg aggtgaagca gtatacggag     840
atggtctgga accgcgacac gatctacagc cagatgaagg atgcgatcga ggtggctgcc     900
agctatggac tgcagctctt ctgcggcgaa tgggcgtgt atgaacctgt cgaccgtgag     960
```

-continued

```
cttgcatacg catggaccaa ggatatgctg tcggtgttcg acgagttcga catcgcatgg   1020
acgacctggt gttacgatgc cgacttcggc ttctgggacc aggcgaaaca tgatttcaag   1080
gacaagcctc ttgtcgatct cctgatgggt tccaagggtc ttgaacaata g            1131
```

<210> SEQ ID NO 112
<211> LENGTH: 376
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(22)
<220> FEATURE:
<221> NAME/KEY: DOMAIN
<222> LOCATION: (39)...(353)
<223> OTHER INFORMATION: Cellulase (glycosyl hydrolase family 5)
<220> FEATURE:
<221> NAME/KEY: SITE
<222> LOCATION: (37)...(40)
<223> OTHER INFORMATION: N-glycosylation site. Prosite id = PS00001

<400> SEQUENCE: 112

```
Met Arg Arg Leu Ile Thr Ile Ile Leu Ala Thr Ala Val Ala Ile Leu
1               5                   10                  15

Ser Thr Thr Ser Cys Ser Lys Thr Ala Glu Arg Glu Gly Phe Leu Ile
            20                  25                  30

Lys Arg Gly Thr Asn Leu Ser His Trp Leu Ser Gln Ser Lys Glu Arg
        35                  40                  45

Gly Glu Ala Arg Arg Leu His Ile Gln Glu Asp Asp Phe Ala Arg Leu
    50                  55                  60

Asp Ser Leu Gly Phe Asp His Val Arg Ile Pro Val Asp Glu Glu Gln
65                  70                  75                  80

Leu Trp Asp Glu Asp Gly Asn Lys Leu Thr Glu Ala Trp Glu Leu Leu
                85                  90                  95

Asp Phe Ala Leu Asp Met Ala Arg Lys Tyr Asn Leu Arg Ala Ile Val
            100                 105                 110

Asp Leu His Ile Ile Arg Ala His Tyr Phe Asn Ala Val Asn Glu Gly
        115                 120                 125

Ala Ser Asn Thr Leu Phe Thr Ser Glu Glu Ala Gln Gln Gly Leu Ile
    130                 135                 140

Asn Leu Trp Tyr Gln Leu Ser Asp Phe Leu Lys Asp Arg Ser Val Asp
145                 150                 155                 160

Trp Val Ala Tyr Glu Phe Met Asn Glu Pro Val Ala Pro Glu His Glu
                165                 170                 175

Gln Trp Asn Ala Leu Val Ala Lys Val His Lys Ala Leu Arg Glu Arg
            180                 185                 190

Glu Pro Glu Arg Thr Leu Val Ile Gly Ser Asn Leu Trp Gln Gly His
        195                 200                 205

Gln Thr Phe Lys Tyr Leu Arg Val Pro Glu Asn Asp Pro Asn Ile Ile
    210                 215                 220

Leu Ser Phe His Tyr Tyr Asn Pro Ser Ile Leu Thr His Asn Met Ala
225                 230                 235                 240

Pro Trp Thr Pro Val Gly Lys Tyr Thr Gly Ser Ile Asn Tyr Pro Gly
                245                 250                 255

Val Ile Val Ser Ala Glu Asp Tyr Ala Ala Gln Ser Pro Glu Val Gln
            260                 265                 270

Ala Glu Val Lys Gln Tyr Thr Glu Met Val Trp Asn Arg Asp Thr Ile
        275                 280                 285
```

```
Tyr Ser Gln Met Lys Asp Ala Ile Glu Val Ala Ala Ser Tyr Gly Leu
    290                 295                 300

Gln Leu Phe Cys Gly Glu Trp Gly Val Tyr Glu Pro Val Asp Arg Glu
305                 310                 315                 320

Leu Ala Tyr Ala Trp Thr Lys Asp Met Leu Ser Val Phe Asp Glu Phe
                325                 330                 335

Asp Ile Ala Trp Thr Thr Trp Cys Tyr Asp Ala Asp Phe Gly Phe Trp
            340                 345                 350

Asp Gln Ala Lys His Asp Phe Lys Asp Lys Pro Leu Val Asp Leu Leu
        355                 360                 365

Met Gly Ser Lys Gly Leu Glu Gln
    370                 375

<210> SEQ ID NO 113
<211> LENGTH: 1095
<212> TYPE: DNA
<213> ORGANISM: Unknown
<220> FEATURE:
<223> OTHER INFORMATION: Obtained from environmental sample

<400> SEQUENCE: 113
```

| | | | | | |
|---|---|---|---|---|---|
| atgaaggtga | cccgaacagc | tgtcgcgggc | attgtcgccg | cagcggtcct | catcacgatc | 60 |
| ggcacgtcga | ccgcgtcggc | tgaggatgaa | ccaaccagcg | agaacacgtc | gacggatcag | 120 |
| ccgttgcgcg | tcctggcagc | caaagccggg | atcgcgttcg | gcacggccgt | cgacatgaac | 180 |
| gcgtacaaca | cgacgcgac | ctaccgtgag | ctcgtcggcc | aggagttctc | gagcgtcacg | 240 |
| gccgagaacg | tcatgaagtg | gcagctcctc | gagccgcagc | gaggggtcta | caactggggt | 300 |
| ccggccgatc | agctcgtgcg | cgtagccaac | gagaacggcc | agaaggtgcg | cgggcacacg | 360 |
| ctcatctggc | acaaccagct | gcccacctgg | cttaccagcg | gagtcgcctc | cggtgagatc | 420 |
| acaccggacg | agtccggca | gctcctgagg | aaccacatct | tcacggtgat | gcgccacttc | 480 |
| aagggcgaga | tccaccagtg | ggatgtcgcc | aacgaggtca | tcgacgacag | cggcaacctg | 540 |
| cgcaacacga | tctggctgca | gaacctgggt | ccgagctaca | tcgcggacgc | gttccggtgg | 600 |
| gctcgcaagg | ccgacccgga | cgccgccctc | tatctgaacg | actacaacgt | cgagggcccg | 660 |
| aacgccaagg | ccgatgcgta | ctacgccctg | gtcaagcagc | tcctcgccga | cgacgtgccg | 720 |
| gtggacggct | tcggaataca | ggggcacctc | ggtgtgcagt | tcggcttctg | gcccgcgagt | 780 |
| gcggtggccg | acaacatggg | gcgcttcgag | gcactcggcc | tgcagacggc | ggtcaccgag | 840 |
| gcggatgtcc | ggatgatcat | gccgcccgac | gaggacaagc | tggccgcaca | ggcacgtggc | 900 |
| tacagcacgt | tggtccaggg | ctgcctgatg | gccaagcgtt | gcaggtcgtt | caccgtctgg | 960 |
| ggcttcaccg | acaagtactc | ctgggttccg | ggcaccttcc | ccggccaggg | cgcggcgaac | 1020 |
| ctcctggccg | aggacttcca | gcccaagccg | gcttactacg | ccgtccagga | tgacctcgcg | 1080 |
| cgcgccggac | ggtag | | | | | 1095 |

```
<210> SEQ ID NO 114
<211> LENGTH: 364
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(27)
<220> FEATURE:
<221> NAME/KEY: DOMAIN
<222> LOCATION: (41)...(359)
```

<223> OTHER INFORMATION: Glycosyl hydrolase family 10
<220> FEATURE:
<221> NAME/KEY: SITE
<222> LOCATION: (35)...(38)
<223> OTHER INFORMATION: N-glycosylation site. Prosite id = PS00001

<400> SEQUENCE: 114

```
Met Lys Val Thr Arg Thr Ala Val Ala Gly Ile Val Ala Ala Val
1               5                   10                  15

Leu Ile Thr Ile Gly Thr Ser Thr Ala Ser Ala Glu Asp Glu Pro Thr
                20                  25                  30

Ser Glu Asn Thr Ser Thr Asp Gln Pro Leu Arg Val Leu Ala Ala Lys
                35                  40                  45

Ala Gly Ile Ala Phe Gly Thr Ala Val Asp Met Asn Ala Tyr Asn Asn
            50                  55                  60

Asp Ala Thr Tyr Arg Glu Leu Val Gly Gln Glu Phe Ser Ser Val Thr
65                  70                  75                  80

Ala Glu Asn Val Met Lys Trp Gln Leu Leu Pro Gln Arg Gly Val
                85                  90                  95

Tyr Asn Trp Gly Pro Ala Asp Gln Leu Val Arg Val Ala Asn Glu Asn
            100                 105                 110

Gly Gln Lys Val Arg Gly His Thr Leu Ile Trp His Asn Gln Leu Pro
        115                 120                 125

Thr Trp Leu Thr Ser Gly Val Ala Ser Gly Glu Ile Thr Pro Asp Glu
    130                 135                 140

Leu Arg Gln Leu Leu Arg Asn His Ile Phe Thr Val Met Arg His Phe
145                 150                 155                 160

Lys Gly Glu Ile His Gln Trp Asp Val Ala Asn Glu Val Ile Asp Asp
                165                 170                 175

Ser Gly Asn Leu Arg Asn Thr Ile Trp Leu Gln Asn Leu Gly Pro Ser
            180                 185                 190

Tyr Ile Ala Asp Ala Phe Arg Trp Ala Arg Lys Ala Asp Pro Asp Ala
        195                 200                 205

Ala Leu Tyr Leu Asn Asp Tyr Asn Val Glu Gly Pro Asn Ala Lys Ala
    210                 215                 220

Asp Ala Tyr Tyr Ala Leu Val Lys Gln Leu Leu Ala Asp Val Pro
225                 230                 235                 240

Val Asp Gly Phe Gly Ile Gln Gly His Leu Gly Val Gln Phe Gly Phe
                245                 250                 255

Trp Pro Ala Ser Ala Val Ala Ser Asn Met Gly Arg Phe Glu Ala Leu
            260                 265                 270

Gly Leu Gln Thr Ala Val Thr Glu Ala Asp Val Arg Met Ile Met Pro
        275                 280                 285

Pro Asp Glu Asp Lys Leu Ala Ala Gln Ala Arg Gly Tyr Ser Thr Leu
    290                 295                 300

Val Gln Gly Cys Leu Met Ala Lys Arg Cys Arg Ser Phe Thr Val Trp
305                 310                 315                 320

Gly Phe Thr Asp Lys Tyr Ser Trp Val Pro Gly Thr Phe Pro Gly Gln
                325                 330                 335

Gly Ala Ala Asn Leu Leu Ala Glu Asp Phe Gln Pro Lys Pro Ala Tyr
            340                 345                 350

Tyr Ala Val Gln Asp Asp Leu Ala Arg Ala Gly Arg
        355                 360
```

<210> SEQ ID NO 115
<211> LENGTH: 774

-continued

```
<212> TYPE: DNA
<213> ORGANISM: Unknown
<220> FEATURE:
<223> OTHER INFORMATION: Obtained from environmental sample

<400> SEQUENCE: 115
atggacttgc agctaggcgg aaagcgcgtg ctgatcacgg gtgcgtccaa aggcatcggc      60
ctggcctgcg ccgtcgcctt tgcgcgcgag ggtgccgacc cgattctggt ggcgcgcgat     120
gatgcggcgt tgcatcacgc cacgtccgcc atccgcgaac aaagcggccg cgcggcacat     180
gccatcacgc tggacctggc cctgcctggc gcggcgaaa agctggccaa ggaaaccggc      240
cccatcgaca tactggtcaa caacgcgggc gcggtgcccg gcggcgcgct ggaccaggtg     300
caagacgaac gctggcgcgc gggctgggaa ttgaaagtgc acggctacat cagcctggcg     360
cgctgctact acccgcacat gcgcgaagcg ggcgcggggcg tcatcgccaa catcatcggc    420
atggcgggcg cggcgccccg cgccgactac atctgcggcg cggcggccaa tgcctcactg     480
attgccttta cccgcgcgct gggtggcgaa gcgccccgcc acggcgtgcg cgtctttggc     540
gtcaacccct cgcgcacgcg gaccgaccgc gtgctgaccc tggcccggca acgcgcgcag     600
gcgcgctggg gcgacgaaac ccgttggcag gaaacgctgt cggacctgcc cttcaaccgg     660
ctgatggaac ccgccgaagt ggccgacatg attgtgttcg gcgcctcgcc gcgcgcgggt     720
tacctgagcg gcacggtcat cgacctggac ggcggcgaac agtacgcgaa atag           774

<210> SEQ ID NO 116
<211> LENGTH: 257
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(172)
<223> OTHER INFORMATION: short chain dehydrogenase
<220> FEATURE:
<221> NAME/KEY: SITE
<222> LOCATION: (159)...(162)
<223> OTHER INFORMATION: N-glycosylation site. Prosite id = PS00001

<400> SEQUENCE: 116

Met Asp Leu Gln Leu Gly Gly Lys Arg Val Leu Ile Thr Gly Ala Ser
1               5                   10                  15

Lys Gly Ile Gly Leu Ala Cys Ala Val Ala Phe Ala Arg Glu Gly Ala
            20                  25                  30

Asp Pro Ile Leu Val Ala Arg Asp Asp Ala Ala Leu His His Ala Thr
        35                  40                  45

Ser Ala Ile Arg Glu Gln Ser Gly Arg Ala Ala His Ala Ile Thr Leu
    50                  55                  60

Asp Leu Ala Leu Pro Gly Ala Ala Glu Lys Leu Ala Lys Glu Thr Gly
65                  70                  75                  80

Pro Ile Asp Ile Leu Val Asn Asn Ala Gly Ala Val Pro Gly Gly Ala
                85                  90                  95

Leu Asp Gln Val Gln Asp Glu Arg Trp Arg Ala Gly Trp Glu Leu Lys
            100                 105                 110

Val His Gly Tyr Ile Ser Leu Ala Arg Cys Tyr Tyr Pro His Met Arg
        115                 120                 125

Glu Ala Gly Ala Gly Val Ile Ala Asn Ile Ile Gly Met Ala Gly Ala
    130                 135                 140

Ala Pro Arg Ala Asp Tyr Ile Cys Gly Ala Ala Ala Asn Ala Ser Leu
145                 150                 155                 160
```

```
Ile Ala Phe Thr Arg Ala Leu Gly Gly Glu Ala Pro Arg His Gly Val
            165                 170                 175

Arg Val Phe Gly Val Asn Pro Ser Arg Thr Arg Thr Asp Arg Val Leu
            180                 185                 190

Thr Leu Ala Arg Gln Arg Ala Gln Ala Arg Trp Gly Asp Glu Thr Arg
            195                 200                 205

Trp Gln Glu Thr Leu Ser Asp Leu Pro Phe Asn Arg Leu Met Glu Pro
    210                 215                 220

Ala Glu Val Ala Asp Met Ile Val Phe Gly Ala Ser Pro Arg Ala Gly
225                 230                 235                 240

Tyr Leu Ser Gly Thr Val Ile Asp Leu Asp Gly Gly Glu Gln Tyr Ala
            245                 250                 255

Lys
```

<210> SEQ ID NO 117
<211> LENGTH: 747
<212> TYPE: DNA
<213> ORGANISM: Unknown
<220> FEATURE:
<223> OTHER INFORMATION: Obtained from environmental sample

<400> SEQUENCE: 117

```
atgcccaaag tcatgctcgt taccggcggc agccgtggca tcggcgccgc cgtcgccaag      60
ctggccgcgc gccgcggcta cgcggtcggc atcaactacc gcacccattc cgacgccgcc     120
gacgccgtcg tggccgagat ccagcaggcg ggcggcaccg cgctggccat ccaggccgac     180
gtgtcgcaag aagatgacgt gctgcacatg ttccgcacgc tggacgagcg cctgggccgc     240
atcgacgcgc tggtcaataa cgccggcatc ctggaaacgc agatgcgcct ggaccagatg     300
gaagcggacc gcctgctgcg cgtgctgtcc accaacgtca tcggcgcttt cctgtgtgcg     360
cgcgaagcgg tgcgcaggat gtcgacgcgc atggcggcg  tgggcggcgc catcgtcaac     420
gtgtcttcgg cggcggcgcg cctgggctcg cccaatgaat acgtggatta cgcggcctcc     480
aagggcgcgc tggacacgat gaccatcggc ctgtccaaag aggtagcgcc cgaaggtatc     540
cgcgtgaatg gcgtgcgccc cggcaccatc tacaccgaca tgcacgcaag cggcggcgag     600
ccgggccggg tggatcgcct gaaaagcgtg atcccgctgc ggcgcggcgg ctcggtggaa     660
gaagtggcgg gcgccgtcat gtggctgttt tccgaagaag ccggctatac cagcggctcg     720
ttcatcgacg tgtccggcgg tagttga                                         747
```

<210> SEQ ID NO 118
<211> LENGTH: 248
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(176)
<223> OTHER INFORMATION: short chain dehydrogenase
<220> FEATURE:
<221> NAME/KEY: SITE
<222> LOCATION: (142)...(145)
<223> OTHER INFORMATION: N-glycosylation site. Prosite id = PS00001
<220> FEATURE:
<221> NAME/KEY: SITE
<222> LOCATION: (146)...(174)
<223> OTHER INFORMATION: Short-chain dehydrogenases/reductases family
      signature. Prosite id = PS00061

<400> SEQUENCE: 118

```
Met Pro Lys Val Met Leu Val Thr Gly Gly Ser Arg Ile Gly Ala
1               5                   10                  15

Ala Val Ala Lys Leu Ala Ala Arg Arg Gly Tyr Ala Val Gly Ile Asn
            20                  25                  30

Tyr Arg Thr His Ser Asp Ala Ala Asp Ala Val Val Ala Glu Ile Gln
        35                  40                  45

Gln Ala Gly Gly Thr Ala Leu Ala Ile Gln Ala Asp Val Ser Gln Glu
    50                  55                  60

Asp Asp Val Leu His Met Phe Arg Thr Leu Asp Glu Arg Leu Gly Arg
65              70                  75                  80

Ile Asp Ala Leu Val Asn Asn Ala Gly Ile Leu Glu Thr Gln Met Arg
                85                  90                  95

Leu Asp Gln Met Glu Ala Asp Arg Leu Leu Arg Val Leu Ser Thr Asn
            100                 105                 110

Val Ile Gly Ala Phe Leu Cys Ala Arg Glu Ala Val Arg Arg Met Ser
        115                 120                 125

Thr Arg His Gly Gly Val Gly Gly Ala Ile Val Asn Val Ser Ser Ala
    130                 135                 140

Ala Ala Arg Leu Gly Ser Pro Asn Glu Tyr Val Asp Tyr Ala Ala Ser
145                 150                 155                 160

Lys Gly Ala Leu Asp Thr Met Thr Ile Gly Leu Ser Lys Glu Val Ala
                165                 170                 175

Pro Glu Gly Ile Arg Val Asn Gly Val Arg Pro Gly Thr Ile Tyr Thr
            180                 185                 190

Asp Met His Ala Ser Gly Gly Glu Pro Gly Arg Val Asp Arg Leu Lys
        195                 200                 205

Ser Val Ile Pro Leu Arg Arg Gly Gly Ser Val Glu Glu Val Ala Gly
    210                 215                 220

Ala Val Met Trp Leu Phe Ser Glu Glu Ala Gly Tyr Thr Ser Gly Ser
225                 230                 235                 240

Phe Ile Asp Val Ser Gly Gly Ser
                245

<210> SEQ ID NO 119
<211> LENGTH: 1611
<212> TYPE: DNA
<213> ORGANISM: Unknown
<220> FEATURE:
<223> OTHER INFORMATION: Obtained from environmental sample

<400> SEQUENCE: 119
atgcaaaagc ggtatgacgt cattgtcgtg ggcagcggga tcgccggcct cagttttgcg     60
ctaaaagtcg ccaaggcggg gcatcgcgta gggattttga ccaaaaaaga ccgtgctgaa    120
agcaacacca attatgccca aggcggcatc gcggcagtca cttcgcagac agatgatttc    180
gagctgcatg tgcaggacac attgaccgcg ggagatggac tctgcgacga ggcagtcgtc    240
cgcacgatta tcggcgaggc tcccgcccga atccaggagc tgatcgattt gggggtggcc    300
ttctcacatt tggaagatgg acgggttttcc ctccatcgcg aaggggtca ctcgaaaagg    360 cgcattcttc acgttcagga tgtcaccggc aaagcgattg aagaagccct cctccatgcc    420
atcgaacagt cgccgctgat cgacctgaat gagcacgtct tgccatcga cttactgact    480 gaacgcaagc tggcgctggc gggctttgag gtggaaggtg ctaaaaaccg ggtggtcgga    540
ctctatgcgc tcgatgaagc cactcaggag gttcacgtat ttgaggctcc agtcgtcatg    600
ctggcaacgg gaggcgtcgg gcaggtctac ctctacagca ccaacccaag gatcgcgacc    660
```

-continued

```
ggtgatggat tggccatggc ttaccgggct ggcgccgaaa tccgcaacct cgagtgtatc    720
caatttcatc ctacagcgct ataccaccac caatgacc gctttctgat cagcgaagcc      780
gtccggggtg aagggccat cctccgcaat caggagggag aggctttcat ggctcgctac     840
gatgaccgca aggacctcgc ccccgggat attgtggcca gagcaattga cagtgaaatg    900
aagcagtccg gctcatccca tgtctggctc gacatcactc atcgggatga aaccgatctg   960
cgggagcgtt tccccaacat tttcgaggcc tgcctgaagg tcggagtcaa catggcgcaa   1020
tcctccatcc cggtggttcc ggcgatgcac tacctctgcg gaggcgtagc caccgacctc   1080
aatgcggcca ccgacatcac tggactgttt gcctgtgggg aagttgcctg cacgggattg   1140
catggtgcca accgtctcgc cagcaacagc ctgctggagg cagtggtcat ggcgcaccgg   1200
gcctccgtcg cagtggatgc atacctcaac agcaaacctc accgctatgc acaattgccg   1260
gaatggacgg atggcaacgt gcaggacagc gacgagcgtg tcgtgatcag ccacaactgg   1320
gatgaactca aacgcacgat gtgggactac gtgggcatcg tccgcaccac caagcggctt   1380
cagcgcgcgc aacgacgcat tcgtcacctc cagcaggaaa tcgaagagta ttactggaat   1440
ttcaaggttg agtcctccct tctggagtta cggaatctgg ttgtggtggc ggatctggtt   1500
atccactgtg ccctccaacg ccatgagagc cgtggcctgc attgcacccg ggattatccc   1560
ggcaagttgc ccaccccgat caataccgcc gttcgcagaa gaaccggtta a            1611
```

<210> SEQ ID NO 120
<211> LENGTH: 536
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (6)...(260)
<223> OTHER INFORMATION: FAD dependent oxidoreductase
<220> FEATURE:
<221> NAME/KEY: DOMAIN
<222> LOCATION: (6)...(380)
<223> OTHER INFORMATION: Pyridine nucleotide-disulphide oxidoreductase
<220> FEATURE:
<221> NAME/KEY: DOMAIN
<222> LOCATION: (6)...(391)
<223> OTHER INFORMATION: FAD binding domain
<220> FEATURE:
<221> NAME/KEY: DOMAIN
<222> LOCATION: (440)...(534)
<223> OTHER INFORMATION: Fumarate reductase/succinate dehydrogenase flavoprotein C-terminal domain

<400> SEQUENCE: 120

```
Met Gln Lys Arg Tyr Asp Val Ile Val Val Gly Ser Gly Ile Ala Gly
1               5                   10                  15

Leu Ser Phe Ala Leu Lys Val Ala Lys Ala Gly His Arg Val Gly Ile
                20                  25                  30

Leu Thr Lys Lys Asp Arg Ala Glu Ser Asn Thr Asn Tyr Ala Gln Gly
            35                  40                  45

Gly Ile Ala Ala Val Thr Ser Gln Thr Asp Asp Phe Glu Leu His Val
        50                  55                  60

Gln Asp Thr Leu Thr Ala Gly Asp Gly Leu Cys Asp Glu Ala Val Val
65                  70                  75                  80

Arg Thr Ile Ile Gly Glu Ala Pro Ala Arg Ile Gln Glu Leu Ile Asp
                85                  90                  95

Leu Gly Val Ala Phe Ser His Leu Glu Asp Gly Arg Val Ser Leu His
                100                 105                 110
```

```
Arg Glu Gly Gly His Ser Lys Arg Arg Ile Leu His Val Gln Asp Val
        115                 120                 125

Thr Gly Lys Ala Ile Glu Glu Ala Leu Leu His Ala Ile Glu Gln Ser
130                 135                 140

Pro Leu Ile Asp Leu Asn Glu His Val Phe Ala Ile Asp Leu Leu Thr
145                 150                 155                 160

Glu Arg Lys Leu Ala Leu Ala Gly Phe Glu Val Glu Gly Ala Lys Asn
                165                 170                 175

Arg Val Val Gly Leu Tyr Ala Leu Asp Glu Ala Thr Gln Glu Val His
                180                 185                 190

Val Phe Glu Ala Pro Val Val Met Leu Ala Thr Gly Gly Val Gly Gln
            195                 200                 205

Val Tyr Leu Tyr Ser Thr Asn Pro Arg Ile Ala Thr Gly Asp Gly Leu
210                 215                 220

Ala Met Ala Tyr Arg Ala Gly Ala Glu Ile Arg Asn Leu Glu Cys Ile
225                 230                 235                 240

Gln Phe His Pro Thr Ala Leu Tyr Thr Thr Thr Asn Asp Arg Phe Leu
                245                 250                 255

Ile Ser Glu Ala Val Arg Gly Glu Gly Ala Ile Leu Arg Asn Gln Glu
                260                 265                 270

Gly Glu Ala Phe Met Ala Arg Tyr Asp Asp Arg Lys Asp Leu Ala Pro
            275                 280                 285

Arg Asp Ile Val Ala Arg Ala Ile Asp Ser Glu Met Lys Gln Ser Gly
        290                 295                 300

Ser Ser His Val Trp Leu Asp Ile Thr His Arg Asp Glu Thr Asp Leu
305                 310                 315                 320

Arg Glu Arg Phe Pro Asn Ile Phe Glu Ala Cys Leu Lys Val Gly Val
                325                 330                 335

Asn Met Ala Gln Ser Ser Ile Pro Val Val Pro Ala Met His Tyr Leu
                340                 345                 350

Cys Gly Gly Val Ala Thr Asp Leu Asn Ala Ala Thr Asp Ile Thr Gly
            355                 360                 365

Leu Phe Ala Cys Gly Glu Val Ala Cys Thr Gly Leu His Gly Ala Asn
370                 375                 380

Arg Leu Ala Ser Asn Ser Leu Leu Glu Ala Val Val Met Ala His Arg
385                 390                 395                 400

Ala Ser Val Ala Val Asp Ala Tyr Leu Asn Ser Lys Pro His Arg Tyr
                405                 410                 415

Ala Gln Leu Pro Glu Trp Thr Asp Gly Asn Val Gln Ser Asp Glu
                420                 425                 430

Arg Val Val Ile Ser His Asn Trp Asp Glu Leu Lys Arg Thr Met Trp
            435                 440                 445

Asp Tyr Val Gly Ile Val Arg Thr Thr Lys Arg Leu Gln Arg Ala Gln
450                 455                 460

Arg Arg Ile Arg His Leu Gln Gln Glu Ile Glu Tyr Tyr Trp Asn
465                 470                 475                 480

Phe Lys Val Glu Ser Ser Leu Leu Glu Leu Arg Asn Leu Val Val Val
                485                 490                 495

Ala Asp Leu Val Ile His Cys Ala Leu Gln Arg His Glu Ser Arg Gly
            500                 505                 510

Leu His Cys Thr Arg Asp Tyr Pro Gly Lys Leu Pro Thr Pro Ile Asn
        515                 520                 525

Thr Ala Val Arg Arg Thr Gly
530                 535
```

<210> SEQ ID NO 121
<211> LENGTH: 990
<212> TYPE: DNA
<213> ORGANISM: Unknown
<220> FEATURE:
<223> OTHER INFORMATION: Obtained from environmental sample

<400> SEQUENCE: 121

| | | | | | |
|---|---|---|---|---|---|
| atgcctttg | atgccattgg | agaaagcttc | cgtgccagcc | agcaactccc | gctgatcaag | 60 |
| gtcgacggca | accgtttcgt | gattgcggag | accggtgagc | cgatcgtctt | ccggggcgtc | 120 |
| tccgcctccg | acccggctgc | gctactggaa | cgcggtcaat | ggggtcgccg | ttactttgaa | 180 |
| gagatggcca | agtggaatgc | caacgttgtg | cgcattcctg | ttcacccggc | agactggcgt | 240 |
| aatctcggcg | aagacatcta | tctcgcccta | ctcgaccagg | cgattgaatg | gtcggctgaa | 300 |
| ctcggcatgc | acgtcatcat | cgactggcac | actatcggca | atattctgac | cggtatttat | 360 |
| caccgcgaca | tttatgaaac | cacccgtgat | gagacttacc | gttttggta | caccatcgcc | 420 |
| attcgttatc | agggtaaccc | gacagtggcc | ttttatgaac | tctacaatga | gcccaccaac | 480 |
| cgaggcggtc | gcatgggccc | ccttccctgg | aagaatatg | cccagttcat | cgaagggctg | 540 |
| atttccatgc | tctacgccat | cgacgacacc | gttattccac | tggtcgctgg | cttcgactgg | 600 |
| ggatatgatt | tgagctatgt | tgcggaacgc | ccgatccgtt | ttccaggagt | cgcctatgtc | 660 |
| acccacccct | acccgcagaa | gcgccccgag | ccttgggaac | cgatctggca | ggaggaatgg | 720 |
| ggttttgtcg | ccgacaccta | tcccatgatc | gccactgagt | ttggcttcat | gagtgaggac | 780 |
| ggtcccggag | cccacaaccc | ggttatcggg | gatgaacact | atggcgaatc | ggtcatccgc | 840 |
| ttttcgagg | aacgcggcat | ttcctggacg | gcctgggtgt | tgatcctct | ctggtcaccc | 900 |
| cagcttttcg | aagactggga | aacctatacc | cccacccggc | aaggccgatt | ctttaaacag | 960 |
| aaaatgatgg | aactgaatcc | cccgcgttga | | | | 990 |

<210> SEQ ID NO 122
<211> LENGTH: 329
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (25)...(302)
<223> OTHER INFORMATION: Cellulase (glycosyl hydrolase family 5)

<400> SEQUENCE: 122

Met Pro Phe Asp Ala Ile Gly Glu Ser Phe Arg Ala Ser Gln Gln Leu
1               5                   10                  15

Pro Leu Ile Lys Val Asp Gly Asn Arg Phe Val Ile Ala Glu Thr Gly
            20                  25                  30

Glu Pro Ile Val Phe Arg Gly Val Ser Ala Ser Asp Pro Ala Ala Leu
        35                  40                  45

Leu Glu Arg Gly Gln Trp Gly Arg Arg Tyr Phe Glu Glu Met Ala Lys
    50                  55                  60

Trp Asn Ala Asn Val Val Arg Ile Pro Val His Pro Ala Asp Trp Arg
65                  70                  75                  80

Asn Leu Gly Glu Asp Ile Tyr Leu Ala Leu Leu Asp Gln Ala Ile Glu
                85                  90                  95

Trp Ser Ala Glu Leu Gly Met His Val Ile Ile Asp Trp His Thr Ile
            100                 105                 110

-continued

```
Gly Asn Ile Leu Thr Gly Ile Tyr His Arg Asp Ile Tyr Glu Thr Thr
            115                 120                 125
Arg Asp Glu Thr Tyr Arg Phe Trp Tyr Thr Ile Ala Ile Arg Tyr Gln
        130                 135                 140
Gly Asn Pro Thr Val Ala Phe Tyr Glu Leu Tyr Asn Glu Pro Thr Asn
145                 150                 155                 160
Arg Gly Gly Arg Met Gly Pro Leu Pro Trp Glu Glu Tyr Ala Gln Phe
                165                 170                 175
Ile Glu Gly Leu Ile Ser Met Leu Tyr Ala Ile Asp Asp Thr Val Ile
            180                 185                 190
Pro Leu Val Ala Gly Phe Asp Trp Gly Tyr Asp Leu Ser Tyr Val Ala
        195                 200                 205
Glu Arg Pro Ile Arg Phe Pro Gly Val Ala Tyr Val Thr His Pro Tyr
    210                 215                 220
Pro Gln Lys Arg Pro Glu Pro Trp Glu Pro Ile Trp Gln Glu Glu Trp
225                 230                 235                 240
Gly Phe Val Ala Asp Thr Tyr Pro Met Ile Ala Thr Glu Phe Gly Phe
                245                 250                 255
Met Ser Glu Asp Gly Pro Gly Ala His Asn Pro Val Ile Gly Asp Glu
            260                 265                 270
His Tyr Gly Glu Ser Val Ile Arg Phe Phe Glu Glu Arg Gly Ile Ser
        275                 280                 285
Trp Thr Ala Trp Val Phe Asp Pro Leu Trp Ser Pro Gln Leu Phe Glu
    290                 295                 300
Asp Trp Glu Thr Tyr Thr Pro Thr Arg Gln Gly Arg Phe Phe Lys Gln
305                 310                 315                 320
Lys Met Met Glu Leu Asn Pro Pro Arg
                325
```

<210> SEQ ID NO 123
<211> LENGTH: 1398
<212> TYPE: DNA
<213> ORGANISM: Unknown
<220> FEATURE:
<223> OTHER INFORMATION: Obtained from environmental sample

<400> SEQUENCE: 123

```
atgccgatga gcacagaaac gacttttcct tctgatttca cctggggcgc agcaacagcc      60
gcctaccaga tcgaaggggg cgatcgcgct ggcgggcgcg ccgttccgt gtgggacatg      120
ttttgcgaga aacgaggagc tatttgggag gggcatacgg ggcagcgagc gagtctgcat      180
cttcagcgct ggcgtgagga cgtaatgttg atgcaacagc tcggactgcg gggctatcgt      240
tttagcgtca gctggccgcg cgtcttcccg acaggagtcg gcaaagtcaa ccgtgaaggg      300
ttggcctttt acgatcagct cgtagacgcc ttgctcgagg ccggcatcac ccccttata      360
acgctatttc attgggactt cccgctcgat ttgtaccacc gaggcggctg gttgaatcgc      420
gacagcgccg actggtttgc ctcctacgcc gagtgcctcg gcaaggcact gggcgacagg      480
gtcaagcact gggtgaccct caacgagccg caggttttca taggcctcgg tcattacgaa      540
gggcgtcatg ccccggggtt gaagctctcc atcgcggaaa tgctgcgctg cgggcaccac      600
gccttgctcg cgcacgggaa ggccgtgcaa gccctgcgcg cttccgtcga cggccctgc      660
aagattggat tgctccggt ggggattccc aagcttccgg cgagtgagag ctcagaggat      720
atcgccgcgg cacgaaaggc ccagttcgcg gcgggagcgc cgccgtattg acgctgagc      780
tggtgggcgg atccggtgtt tcaggggaca tatcccgctg atgcctgcca ggctctcgga      840
```

```
gcggacgcgc cgcaggtggc cgatcacgac atgagcatca tcagcgagcc gactgatttc    900
ctgggcctca acctttatca aggggtggtg gtgcgtgccg atcacacggg tcaaccagaa    960
acggtgccgt ttccgccggg attccccgtg actgcgctca actgggccgt aaccccagag   1020
gcgctgtatt ggggcccgcg ctttgccttc gaacgctaca aaaagccgat tcacatcacg   1080
gaaaacgggc tatcctgtcg tgactggccg tcgctcgacg ggcacgtcca cgacgccgac   1140
cgcatcgact tcatggcccg gcacttcgcg cagcgcatc gagccattcg cgatgggata   1200
ccgatcgaag ctacttcca ctggtctgcg atcgacaact tcgagtgggc agaaggctac   1260
aaggaacgct tcgggctcat ttacgtcgac tatacgagcg gcgagcgcat tccgaaggac   1320
tcgtaccact ggtaccagaa ggtcattgcc tccgaggggc gggcagcgct cggcgcgccc   1380
agtgctgctc gcccataa                                                 1398
```

<210> SEQ ID NO 124
<211> LENGTH: 465
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (5)...(454)
<223> OTHER INFORMATION: Glycosyl hydrolase family 1
<220> FEATURE:
<221> NAME/KEY: SITE
<222> LOCATION: (13)...(27)
<223> OTHER INFORMATION: Glycosyl hydrolases family 1 N-terminal
    signature. Prosite id = PS00653

<400> SEQUENCE: 124

```
Met Pro Met Ser Thr Glu Thr Thr Phe Pro Ser Asp Phe Thr Trp Gly
1               5                   10                  15

Ala Ala Thr Ala Ala Tyr Gln Ile Glu Gly Gly Asp Arg Ala Gly Gly
                20                  25                  30

Arg Gly Arg Ser Val Trp Asp Met Phe Cys Glu Lys Arg Gly Ala Ile
            35                  40                  45

Trp Glu Gly His Thr Gly Gln Arg Ala Ser Leu His Leu Gln Arg Trp
        50                  55                  60

Arg Glu Asp Val Met Leu Met Gln Gln Leu Gly Leu Arg Gly Tyr Arg
65                  70                  75                  80

Phe Ser Val Ser Trp Pro Arg Val Phe Pro Thr Gly Val Gly Lys Val
                85                  90                  95

Asn Arg Glu Gly Leu Ala Phe Tyr Asp Gln Leu Val Asp Ala Leu Leu
            100                 105                 110

Glu Ala Gly Ile Thr Pro Phe Ile Thr Leu Phe His Trp Asp Phe Pro
        115                 120                 125

Leu Asp Leu Tyr His Arg Gly Gly Trp Leu Asn Arg Asp Ser Ala Asp
    130                 135                 140

Trp Phe Ala Ser Tyr Ala Glu Cys Leu Gly Lys Ala Leu Gly Asp Arg
145                 150                 155                 160

Val Lys His Trp Val Thr Leu Asn Glu Pro Gln Val Phe Ile Gly Leu
                165                 170                 175

Gly His Tyr Glu Gly Arg His Ala Pro Gly Leu Lys Leu Ser Ile Ala
            180                 185                 190

Glu Met Leu Arg Cys Gly His His Ala Leu Leu Ala His Gly Lys Ala
        195                 200                 205

Val Gln Ala Leu Arg Ala Ser Val Asp Gly Pro Cys Lys Ile Gly Phe
    210                 215                 220
```

```
Ala Pro Val Gly Ile Pro Lys Leu Pro Ala Ser Glu Ser Ser Glu Asp
225                 230                 235                 240

Ile Ala Ala Ala Arg Lys Ala Gln Phe Ala Gly Ala Pro Pro Tyr
            245                 250                 255

Trp Thr Leu Ser Trp Trp Ala Asp Pro Val Phe Gln Gly Thr Tyr Pro
                260                 265                 270

Ala Asp Ala Cys Gln Ala Leu Gly Ala Asp Ala Pro Gln Val Ala Asp
            275                 280                 285

His Asp Met Ser Ile Ile Ser Glu Pro Thr Asp Phe Leu Gly Leu Asn
290                 295                 300

Leu Tyr Gln Gly Val Val Arg Ala Asp His Thr Gly Gln Pro Glu
305                 310                 315                 320

Thr Val Pro Phe Pro Pro Gly Phe Pro Val Thr Ala Leu Asn Trp Ala
                325                 330                 335

Val Thr Pro Glu Ala Leu Tyr Trp Gly Pro Arg Phe Ala Phe Glu Arg
            340                 345                 350

Tyr Lys Lys Pro Ile His Ile Thr Glu Asn Gly Leu Ser Cys Arg Asp
            355                 360                 365

Trp Pro Ser Leu Asp Gly His Val His Asp Ala Asp Arg Ile Asp Phe
        370                 375                 380

Met Ala Arg His Leu Arg Ala Ala His Arg Ala Ile Arg Asp Gly Ile
385                 390                 395                 400

Pro Ile Glu Gly Tyr Phe His Trp Ser Ala Ile Asp Asn Phe Glu Trp
                405                 410                 415

Ala Glu Gly Tyr Lys Glu Arg Phe Gly Leu Ile Tyr Val Asp Tyr Thr
            420                 425                 430

Ser Gly Glu Arg Ile Pro Lys Asp Ser Tyr His Trp Tyr Gln Lys Val
        435                 440                 445

Ile Ala Ser Glu Gly Arg Ala Ala Leu Gly Ala Pro Ser Ala Ala Arg
    450                 455                 460

Pro
465

<210> SEQ ID NO 125
<211> LENGTH: 1350
<212> TYPE: DNA
<213> ORGANISM: Unknown
<220> FEATURE:
<223> OTHER INFORMATION: Obtained from environmental sample

<400> SEQUENCE: 125
atgtcagatg ccgccccgac tgatccgaaa tccgcaatgc ccagacgctc ggacttcccc    60
gagggttttg tcttcggcgc ggccaccgcg gcctatcaga tcgagggcca tgccttcggc   120
ggcgcgggcc cctgccattg gacagcttc gccgcaaccg gcgtaacgt ggtcggcaat    180 gaggatggcg cgcgcgcctg cgagcattac acccgctggc gcaggatct ggacctgatc    240 cgcgaggccg gctcgacgc ctaccgcttc tcgacctcct gggcgcgggt gatgcccgat   300
ggcgtgaccc tgaaccccga ggggctggat ttctacgacc gcctcgtcga tggcatgctc   360
gagcgcgggc taaagcccta tctcaccctc taccattggg aattgccctc ggcgcttgcc   420
gacaggggcg gctggaccaa tcgcgacacg gccgagcgct tgccgatttt cgcagcggtg   480
gtgatggagc ggttgggcag ccgcgtcgcc cgcacggcca ccatcaacga gccatggtgc   540
gtgagctggc tctcgcattt cgaaggccat cacgcgccgg gctgcgcga catccgtgcc   600 accgcacgcg ccatgcatca tgtgcaactg gcgcacggcc tcgcgctcgg gaagctgcgc   660
```

-continued

```
gcgcaggggc atggcaatct cggcatcgtg ctgaatttct cggaaatcat tcccgccggg    720
cgagagcacg cgaaggcggc tgatctcggc gacgcaatct cgaaccgctg gttcatcgag    780
tcagtcgcgc gtggcaccta tcccgatgtg gtcctcgagg gtctgggcaa gcacatgccc    840
gagggctggc aggatgacat gaaaaccatc gcggcccgc tcgactggct gggtgtgaac     900
tactacaccc gcggcatcgt cgcgcatgac ccggacgcgt cctggccctc gacccgagcg    960 gaggagggc ccctgcccaa gacgcagatg ggctgggaga tctaccccga gggcttgcgc    1020
aacctgctgg tgcgcatggc gcgcgactat gtgggcgacc ttcccatggt cgtgaccgaa   1080
aacgggatgg cctgggccga cgaggtcgcg gatggcgccg tcagagatac gatccgcacc   1140
gaatatgtcg cagcccatct caacgcgacc cgcgaggcgc tggccggcgg ggcgaatatc   1200
gaaggtttct tctattggtc gctgctcgac aattacgaat gggccttcgg ctatgccaag   1260
cgcttcggcc tcgtccatgt cgatttcgac acgatggcac gcacgccgaa agcctcctac   1320
cacgcgctga gggccgcgct gcagggttga                                    1350
```

<210> SEQ ID NO 126
<211> LENGTH: 449
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (15)...(443)
<223> OTHER INFORMATION: Glycosyl hydrolase family 1
<220> FEATURE:
<221> NAME/KEY: SITE
<222> LOCATION: (235)...(238)
<223> OTHER INFORMATION: N-glycosylation site. Prosite id = PS00001
<220> FEATURE:
<221> NAME/KEY: SITE
<222> LOCATION: (361)...(369)
<223> OTHER INFORMATION: Glycosyl hydrolases family 1 active site.
      Prosite id = PS00572
<220> FEATURE:
<221> NAME/KEY: SITE
<222> LOCATION: (393)...(396)
<223> OTHER INFORMATION: N-glycosylation site. Prosite id = PS00001

<400> SEQUENCE: 126

```
Met Ser Asp Ala Ala Pro Thr Asp Pro Lys Ser Ala Met Pro Arg Arg
1               5                   10                  15

Ser Asp Phe Pro Glu Gly Phe Val Phe Gly Ala Ala Thr Ala Ala Tyr
                20                  25                  30

Gln Ile Glu Gly His Ala Phe Gly Gly Ala Gly Pro Cys His Trp Asp
            35                  40                  45

Ser Phe Ala Ala Thr Gly Arg Asn Val Val Gly Asn Glu Asp Gly Ala
        50                  55                  60

Arg Ala Cys Glu His Tyr Thr Arg Trp Pro Gln Asp Leu Asp Leu Ile
65                  70                  75                  80

Arg Glu Ala Gly Leu Asp Ala Tyr Arg Phe Ser Thr Ser Trp Ala Arg
                85                  90                  95

Val Met Pro Asp Gly Val Thr Leu Asn Pro Glu Gly Leu Asp Phe Tyr
            100                 105                 110

Asp Arg Leu Val Asp Gly Met Leu Glu Arg Gly Leu Lys Pro Tyr Leu
        115                 120                 125

Thr Leu Tyr His Trp Glu Leu Pro Ser Ala Leu Ala Asp Arg Gly Gly
    130                 135                 140

Trp Thr Asn Arg Asp Thr Ala Glu Arg Phe Ala Asp Phe Ala Ala Val
```

```
                145                 150                 155                 160
Val Met Glu Arg Leu Gly Ser Arg Val Ala Arg Thr Ala Thr Ile Asn
                    165                 170                 175
Glu Pro Trp Cys Val Ser Trp Leu Ser His Phe Glu Gly His His Ala
                180                 185                 190
Pro Gly Leu Arg Asp Ile Arg Ala Thr Ala Arg Ala Met His His Val
                195                 200                 205
Gln Leu Ala His Gly Leu Ala Leu Gly Lys Leu Arg Ala Gln Gly His
                210                 215                 220
Gly Asn Leu Gly Ile Val Leu Asn Phe Ser Glu Ile Ile Pro Ala Gly
225                 230                 235                 240
Arg Glu His Ala Lys Ala Ala Asp Leu Gly Asp Ala Ile Ser Asn Arg
                245                 250                 255
Trp Phe Ile Glu Ser Val Ala Arg Gly Thr Tyr Pro Asp Val Val Leu
                260                 265                 270
Glu Gly Leu Gly Lys His Met Pro Glu Gly Trp Gln Asp Asp Met Lys
                275                 280                 285
Thr Ile Ala Ala Pro Leu Asp Trp Leu Gly Val Asn Tyr Tyr Thr Arg
                290                 295                 300
Gly Ile Val Ala His Asp Pro Asp Ala Ser Trp Pro Ser Thr Arg Ala
305                 310                 315                 320
Glu Glu Gly Pro Leu Pro Lys Thr Gln Met Gly Trp Glu Ile Tyr Pro
                325                 330                 335
Glu Gly Leu Arg Asn Leu Leu Val Arg Met Ala Arg Asp Tyr Val Gly
                340                 345                 350
Asp Leu Pro Met Val Val Thr Glu Asn Gly Met Ala Trp Ala Asp Glu
                355                 360                 365
Val Ala Asp Gly Ala Val Arg Asp Thr Ile Arg Thr Glu Tyr Val Ala
                370                 375                 380
Ala His Leu Asn Ala Thr Arg Glu Ala Leu Ala Gly Gly Ala Asn Ile
385                 390                 395                 400
Glu Gly Phe Phe Tyr Trp Ser Leu Leu Asp Asn Tyr Glu Trp Ala Phe
                405                 410                 415
Gly Tyr Ala Lys Arg Phe Gly Leu Val His Val Asp Phe Asp Thr Met
                420                 425                 430
Ala Arg Thr Pro Lys Ala Ser Tyr His Ala Leu Arg Ala Ala Leu Gln
                435                 440                 445
Gly

<210> SEQ ID NO 127
<211> LENGTH: 774
<212> TYPE: DNA
<213> ORGANISM: Unknown
<220> FEATURE:
<223> OTHER INFORMATION: Obtained from environmental sample

<400> SEQUENCE: 127
atggacttgc agctaggcgg aaagcgcgtg ctgatcacgg gtgcgtccaa aggcatcggc    60
ctggcctgcg ccgtcgcctt tgcgcgcgag ggtgccgacc cgattctggt ggcgcgcgat   120
gatgcggcgt tgcatcacgc cacgtccgcc atccgcgaac aaagcggccg cgcggcacat   180
gccatcacgc tggacctggc cctgcctggc gcggcggaaa agctggccaa ggaaaccggc   240
cccatcgaca tactggtcaa caacgcgggc gcggtgcccg gcggcgcgct ggaccaggtg   300
caagacgaac gctggcgcgc gggctgggaa ttgaaagtgc acggctacat cagcctggcg   360
```

```
cgctgctact acccgcacat gcgcgaagcg ggcgcgggcg tcatcgccaa catcatcggc    420
atggcgggcg cggcgccccg cgccgactac atctgcggcg cggcggccaa tgcctcactg    480
attgccttta cccgcgcgct gggtggcgaa gcgccccgcc acggcgtgcg cgtctttggc    540
gtcaacccct cgcgcacgcg gaccgaccgc gtgctgaccc tggcccggca acgcgcgcag    600
gcgcgctggg gcgacgaaac gcgttggcag gaaacgctgt cggacctgcc cttcaaccgg    660
ctgatggaac ccgccgaagt ggccgacatg attgtgttcg gcgcctcgcc acgcgcgggt    720
tacctgagcg gcacggtcat cgacctggac ggcggcgaac agtacgcgaa atag          774
```

<210> SEQ ID NO 128
<211> LENGTH: 257
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (8)...(172)
<223> OTHER INFORMATION: short chain dehydrogenase
<220> FEATURE:
<221> NAME/KEY: SITE
<222> LOCATION: (159)...(162)
<223> OTHER INFORMATION: N-glycosylation site. Prosite id = PS00001

<400> SEQUENCE: 128

Met Asp Leu Gln Leu Gly Gly Lys Arg Val Leu Ile Thr Gly Ala Ser
1               5                   10                  15

Lys Gly Ile Gly Leu Ala Cys Ala Val Ala Phe Ala Arg Glu Gly Ala
            20                  25                  30

Asp Pro Ile Leu Val Ala Arg Asp Ala Ala Leu His His Ala Thr
        35                  40                  45

Ser Ala Ile Arg Glu Gln Ser Gly Arg Ala Ala His Ala Ile Thr Leu
    50                  55                  60

Asp Leu Ala Leu Pro Gly Ala Ala Glu Lys Leu Ala Lys Glu Thr Gly
65                  70                  75                  80

Pro Ile Asp Ile Leu Val Asn Asn Ala Gly Ala Val Pro Gly Gly Ala
                85                  90                  95

Leu Asp Gln Val Gln Asp Glu Arg Trp Arg Ala Gly Trp Glu Leu Lys
            100                 105                 110

Val His Gly Tyr Ile Ser Leu Ala Arg Cys Tyr Tyr Pro His Met Arg
        115                 120                 125

Glu Ala Gly Ala Gly Val Ile Ala Asn Ile Ile Gly Met Ala Gly Ala
    130                 135                 140

Ala Pro Arg Ala Asp Tyr Ile Cys Gly Ala Ala Asn Ala Ser Leu
145                 150                 155                 160

Ile Ala Phe Thr Arg Ala Leu Gly Gly Glu Ala Pro Arg His Gly Val
                165                 170                 175

Arg Val Phe Gly Val Asn Pro Ser Arg Thr Arg Thr Asp Arg Val Leu
            180                 185                 190

Thr Leu Ala Arg Gln Arg Ala Gln Ala Arg Trp Gly Asp Glu Thr Arg
        195                 200                 205

Trp Gln Glu Thr Leu Ser Asp Leu Pro Phe Asn Arg Leu Met Glu Pro
    210                 215                 220

Ala Glu Val Ala Asp Met Ile Val Phe Gly Ala Ser Pro Arg Ala Gly
225                 230                 235                 240

Tyr Leu Ser Gly Thr Val Ile Asp Leu Asp Gly Gly Glu Gln Tyr Ala
                245                 250                 255

-continued

Lys

<210> SEQ ID NO 129
<211> LENGTH: 747
<212> TYPE: DNA
<213> ORGANISM: Unknown
<220> FEATURE:
<223> OTHER INFORMATION: Obtained from environmental sample

<400> SEQUENCE: 129

```
atgcccaaag tcatgctcgt taccggcggc agccgtggca tcggcgccgc cgtcgccaag    60
ctggccgcgc gccgcggcta cgcggtcggc atcaactacc gcacccattc cgacgccgcc   120
gacgccgtcg tggccgaaat ccagcaggcg ggcggcaccg cgctggccat ccaggccgac   180
gtgtcgcagg aagacgatgt gctgcacatg ttccgcacgc tggacgagcg cctgggccgc   240
atcgacgcgc tggtcaataa cgccggcatc ctggaaacgc agatgcgcct ggaccagatg   300
gaagccgacc gcctgctgcg cgtgctgtcc accaacgtca tcggcgcttt cctatgtgcg   360
cgcgaagccg tgcgcaggat gtcgacgcgc catggcggcg tgggcggcgc catcgtcaac   420
gtgtcttcgg cggcggcgcg cctgggctcg cccaatgaat acgtggatta cgcggcctcc   480
aagggcgcgc tggacacgat gaccatcggc ctgtcgaaag aggtggcgcc cgaaggtatc   540
cgcgtgaatg gcgtgcgccc cggcaccatc tacaccgaca tgcacgcaag cggcggcgag   600
ccgggccggg tggatcgcct gaaaagcgtg atcccgctgc ggcgcggcgg ctcggtggaa   660
gaagtggcgg gcgccgtcat gtggctgttt tccgaagaag ccggctatac agcggttcg    720
ttcatcgacg tgtccggcgg tagttga                                       747
```

<210> SEQ ID NO 130
<211> LENGTH: 248
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (3)...(176)
<223> OTHER INFORMATION: short chain dehydrogenase
<220> FEATURE:
<221> NAME/KEY: SITE
<222> LOCATION: (142)...(145)
<223> OTHER INFORMATION: N-glycosylation site. Prosite id = PS00001
<220> FEATURE:
<221> NAME/KEY: SITE
<222> LOCATION: (146)...(174)
<223> OTHER INFORMATION: Short-chain dehydrogenases/reductases family
      signature. Prosite id = PS00061

<400> SEQUENCE: 130

```
Met Pro Lys Val Met Leu Val Thr Gly Gly Ser Arg Gly Ile Gly Ala
  1               5                  10                  15

Ala Val Ala Lys Leu Ala Ala Arg Arg Gly Tyr Ala Val Gly Ile Asn
             20                  25                  30

Tyr Arg Thr His Ser Asp Ala Ala Asp Ala Val Val Ala Glu Ile Gln
         35                  40                  45

Gln Ala Gly Gly Thr Ala Leu Ala Ile Gln Ala Asp Val Ser Gln Glu
     50                  55                  60

Asp Asp Val Leu His Met Phe Arg Thr Leu Asp Glu Arg Leu Gly Arg
 65                  70                  75                  80

Ile Asp Ala Leu Val Asn Asn Ala Gly Ile Leu Glu Thr Gln Met Arg
                 85                  90                  95

Leu Asp Gln Met Glu Ala Asp Arg Leu Leu Arg Val Leu Ser Thr Asn
```

```
                100                 105                 110
Val Ile Gly Ala Phe Leu Cys Ala Arg Glu Ala Val Arg Arg Met Ser
            115                 120                 125

Thr Arg His Gly Gly Val Gly Gly Ala Ile Val Asn Val Ser Ser Ala
        130                 135                 140

Ala Ala Arg Leu Gly Ser Pro Asn Glu Tyr Val Asp Tyr Ala Ala Ser
145                 150                 155                 160

Lys Gly Ala Leu Asp Thr Met Thr Ile Gly Leu Ser Lys Glu Val Ala
                165                 170                 175

Pro Glu Gly Ile Arg Val Asn Gly Val Arg Pro Gly Thr Ile Tyr Thr
            180                 185                 190

Asp Met His Ala Ser Gly Gly Glu Pro Gly Arg Val Asp Arg Leu Lys
        195                 200                 205

Ser Val Ile Pro Leu Arg Arg Gly Gly Ser Val Glu Glu Val Ala Gly
    210                 215                 220

Ala Val Met Trp Leu Phe Ser Glu Glu Ala Gly Tyr Thr Ser Gly Ser
225                 230                 235                 240

Phe Ile Asp Val Ser Gly Gly Ser
            245

<210> SEQ ID NO 131
<211> LENGTH: 1041
<212> TYPE: DNA
<213> ORGANISM: Unknown
<220> FEATURE:
<223> OTHER INFORMATION: Obtained from environmental sample

<400> SEQUENCE: 131
gtggaaacct attttcccct gcaccgcggg atcaacatga gccactggct ttcgcaagtg      60
aatgaaaaca ttcccgaccg ttccacctat gtgacggagc gggacctgca attttgcgg     120 gcagcgggct cgaccatgt gcgtctgccg atcgatgaga tcgaactctg ggatgaggag     180
ggccatcaga tcgaggaggc ctggcaatac atgcacaact ttatgcgctg gagccgaaag     240
aatgacctcc gggttattct cgacctgcac acggtattgt cccaccactt caacgcgatc     300
aacatgggag aggtcaacac cctctttaat gatcccaagg aacaggaaaa attcctcaat     360
ctctgggagc aaatcatgga tgccgtaggg caccacccca acgagtttct cgcttatgaa     420
atgctcaatg aggcggtcgc ggaagatgat gaagactgga acctgctcct caaccgtgcg     480
attgaacgca tccgggaacg tgagccgcat cgcgttctga ttgccggggc caactggtgg     540
cagcatgccg cccgcgttcc caacctgagg cttcccctg gtgatcccaa catcatcatc     600
agttttcact tttactcacc ctttctcttc acgcactatc gcagcagctg gactgccatg     660
cgggcatacc agggtttcgt ccaataccc ggcattacca ttcccgccat ccatctcgaa     720
ggaatgaact atccggagtc ctttgtccaa atgtgggaag agcacaatca gtattacgac     780
atccattcaa tgtatgccga aatggtcccg gcggtgcgtt ttgccgaaaa gctgggcctt     840
cggctctatt gcggcgaatt tggagccatg aagaccgttg atcgtgccca aatgctgcag     900
tggtatcggg atgtggtcag agtctttgaa atgttggaca tttccctacac tgcctgggat     960 tatcagggaa cctttggaat ccgcgatgag ctgaccggtg agcctgatca tgaactgatc    1020
gacattctcc tcggccgcta a                                             1041

<210> SEQ ID NO 132
<211> LENGTH: 346
<212> TYPE: PRT
<213> ORGANISM: Unknown
```

-continued

```
<220> FEATURE:
<223> OTHER INFORMATION: Obtained from environmental sample
<220> FEATURE:
<221> NAME/KEY: DOMAIN
<222> LOCATION: (14)...(325)
<223> OTHER INFORMATION: Cellulase (glycosyl hydrolase family 5)
<220> FEATURE:
<221> NAME/KEY: SITE
<222> LOCATION: (12)...(15)
<223> OTHER INFORMATION: N-glycosylation site. Prosite id = PS00001

<400> SEQUENCE: 132

Met Glu Thr Tyr Phe Pro Leu His Arg Gly Ile Asn Met Ser His Trp
1               5                   10                  15

Leu Ser Gln Val Asn Glu Asn Ile Pro Asp Arg Ser Thr Tyr Val Thr
                20                  25                  30

Glu Arg Asp Leu Gln Phe Leu Arg Ala Ala Gly Phe Asp His Val Arg
            35                  40                  45

Leu Pro Ile Asp Glu Ile Glu Leu Trp Asp Glu Glu Gly His Gln Ile
    50                  55                  60

Glu Glu Ala Trp Gln Tyr Met His Asn Phe Met Arg Trp Ser Arg Lys
65                  70                  75                  80

Asn Asp Leu Arg Val Ile Leu Asp Leu His Thr Val Leu Ser His
                85                  90                  95

Phe Asn Ala Ile Asn Met Gly Glu Val Asn Thr Leu Phe Asn Asp Pro
                100                 105                 110

Lys Glu Gln Glu Lys Phe Leu Asn Leu Trp Glu Gln Ile Met Asp Ala
            115                 120                 125

Val Gly His His Pro Asn Glu Phe Leu Ala Tyr Glu Met Leu Asn Glu
    130                 135                 140

Ala Val Ala Glu Asp Asp Glu Asp Trp Asn Leu Leu Asn Arg Ala
145                 150                 155                 160

Ile Glu Arg Ile Arg Glu Arg Glu Pro His Arg Val Leu Ile Ala Gly
                165                 170                 175

Ala Asn Trp Trp Gln His Ala Ala Arg Val Pro Asn Leu Arg Leu Pro
                180                 185                 190

Pro Gly Asp Pro Asn Ile Ile Ile Ser Phe His Phe Tyr Ser Pro Phe
            195                 200                 205

Leu Phe Thr His Tyr Arg Ser Ser Trp Thr Ala Met Arg Ala Tyr Gln
    210                 215                 220

Gly Phe Val Gln Tyr Pro Gly Ile Thr Ile Pro Ala Ile His Leu Glu
225                 230                 235                 240

Gly Met Asn Tyr Pro Glu Ser Phe Val Gln Met Trp Glu Glu His Asn
                245                 250                 255

Gln Tyr Tyr Asp Ile His Ser Met Tyr Ala Glu Met Val Pro Ala Val
                260                 265                 270

Arg Phe Ala Glu Lys Leu Gly Leu Arg Leu Tyr Cys Gly Glu Phe Gly
            275                 280                 285

Ala Met Lys Thr Val Asp Arg Ala Gln Met Leu Gln Trp Tyr Arg Asp
    290                 295                 300

Val Val Arg Val Phe Glu Met Leu Asp Ile Pro Tyr Thr Ala Trp Asp
305                 310                 315                 320

Tyr Gln Gly Thr Phe Gly Ile Arg Asp Glu Leu Thr Gly Glu Pro Asp
                325                 330                 335

His Glu Leu Ile Asp Ile Leu Leu Gly Arg
            340                 345
```

```
<210> SEQ ID NO 133
<211> LENGTH: 1377
<212> TYPE: DNA
<213> ORGANISM: Unknown
<220> FEATURE:
<223> OTHER INFORMATION: Obtained from environmental sample

<400> SEQUENCE: 133
atgacacaac tggctttcc atctaacttc atctggggaa cagctacttc cgcttaccaa      60
atcgaaggcg cctggaacgc agacggcaag ggcgaatcta tttgggatcg cttttcccat    120
acgcagggga agatcattga cggcagcaac ggcgatgtgg cctgcgatca ctaccaccgc    180
tggcgcgagg acgtggccct catgagagac ttggtatgc aggcatatcg cttctccatc    240
tcctggccac gcatcctgcc caccggtcat ggacagatca atcaggctgg gctggacttt    300
tacaatcgcc tggtggacgg gttgctggaa gctggcatca agccctttgc caccctctac    360
cactgggacc tgccgctggc gctacaggct gacggcggct ggccggagcg ctccacggcc    420
aaggcctttg tcgaatacgc cgacgtggtc agccgcgcgc tggcgatcg ggtgaagagc    480
tggatcaccc ataacgaacc gtggtgcatc agcatgctga ccatcaaat tggggagcat    540
gcgcccggct ggcgggactg gcaggctgcg ttggcggccg cgcaccacgt cctcctttcg    600
catggttggg ccgtgccgga actgcgtcgc aacagccgcg atgcagaaat cggcatcacg    660
ttgaactta ccccggcgga gccagcttcg aacagcgcag ccgatttcaa ggcctatcgc    720
cagttcgatg gctacttcaa ccgctggttc ctggaccgc tctatggccg ccactatccg    780
gcagatatgg tgcacgatta atcgcgcaa ggctacctgc catcacaggg tttgactttc    840
gtggaagctg gtgacctgga cgcgatcgcg acgcgcaccg atttcctggg tgtgaactat    900
tacacgcgcg aagtggtccg tagccaggaa atcccagaga gtgagaacgc gccgcgcaca    960
gtcttgcgcg cgccacagga agagtggaca gagatgggct gggaagtgta tcctgagggc   1020
ctctacaggt tgctcaatcg gttgcacttt gaataccagc cgcgcaagct ctacgtgacc   1080
gagagcggtt gcagctactc cgatggaccc ggccccaacg gtcggatacc ggaccaacgc   1140
cgtatcaact acctgcgcga tcacttcgca gcggcgcatc aggcgataca atgcggcgtc   1200
ccgctggccg gctacttcgt ctggtcgttc atggacaact tcgagtgggc caaagggtac   1260
acccaacgtt tggtatcgt atgggtggat tatcaatcgc aacgacggat accgaaagac   1320
agcgcctact ggtatcgcga tgtcgtcgcc gccaacgcgg tgcaagttcc tgattag      1377

<210> SEQ ID NO 134
<211> LENGTH: 458
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (2)...(454)
<223> OTHER INFORMATION: Glycosyl hydrolase family 1
<220> FEATURE:
<221> NAME/KEY: SITE
<222> LOCATION: (10)...(24)
<223> OTHER INFORMATION: Glycosyl hydrolases family 1 N-terminal
      signature. Prosite id = PS00653

<400> SEQUENCE: 134

Met Thr Gln Leu Ala Phe Pro Ser Asn Phe Ile Trp Gly Thr Ala Thr
1               5                   10                  15
Ser Ala Tyr Gln Ile Glu Gly Ala Trp Asn Ala Asp Gly Lys Gly Glu
            20                  25                  30
```

-continued

```
Ser Ile Trp Asp Arg Phe Ser His Thr Gln Gly Lys Ile Asp Gly
         35                  40                  45

Ser Asn Gly Asp Val Ala Cys Asp His Tyr His Arg Trp Arg Glu Asp
 50                  55                  60

Val Ala Leu Met Arg Asp Leu Gly Met Gln Ala Tyr Arg Phe Ser Ile
 65                  70                  75                  80

Ser Trp Pro Arg Ile Leu Pro Thr Gly His Gly Gln Ile Asn Gln Ala
                 85                  90                  95

Gly Leu Asp Phe Tyr Asn Arg Leu Val Asp Gly Leu Leu Glu Ala Gly
                100                 105                 110

Ile Lys Pro Phe Ala Thr Leu Tyr His Trp Asp Leu Pro Leu Ala Leu
                115                 120                 125

Gln Ala Asp Gly Gly Trp Pro Glu Arg Ser Thr Ala Lys Ala Phe Val
130                 135                 140

Glu Tyr Ala Asp Val Val Ser Arg Ala Leu Gly Asp Arg Val Lys Ser
145                 150                 155                 160

Trp Ile Thr His Asn Glu Pro Trp Cys Ile Ser Met Leu Ser His Gln
                165                 170                 175

Ile Gly Glu His Ala Pro Gly Trp Arg Asp Trp Gln Ala Ala Leu Ala
                180                 185                 190

Ala Ala His His Val Leu Leu Ser His Gly Trp Ala Val Pro Glu Leu
                195                 200                 205

Arg Arg Asn Ser Arg Asp Ala Glu Ile Gly Ile Thr Leu Asn Phe Thr
210                 215                 220

Pro Ala Glu Pro Ala Ser Asn Ser Ala Ala Asp Phe Lys Ala Tyr Arg
225                 230                 235                 240

Gln Phe Asp Gly Tyr Phe Asn Arg Trp Phe Leu Asp Pro Leu Tyr Gly
                245                 250                 255

Arg His Tyr Pro Ala Asp Met Val His Asp Tyr Ile Ala Gln Gly Tyr
                260                 265                 270

Leu Pro Ser Gln Gly Leu Thr Phe Val Glu Ala Gly Asp Leu Asp Ala
                275                 280                 285

Ile Ala Thr Arg Thr Asp Phe Leu Gly Val Asn Tyr Tyr Thr Arg Glu
290                 295                 300

Val Val Arg Ser Gln Glu Ile Pro Glu Ser Glu Asn Ala Pro Arg Thr
305                 310                 315                 320

Val Leu Arg Ala Pro Gln Glu Glu Trp Thr Glu Met Gly Trp Glu Val
                325                 330                 335

Tyr Pro Glu Gly Leu Tyr Arg Leu Leu Asn Arg Leu His Phe Glu Tyr
                340                 345                 350

Gln Pro Arg Lys Leu Tyr Val Thr Glu Ser Gly Cys Ser Tyr Ser Asp
                355                 360                 365

Gly Pro Gly Pro Asn Gly Arg Ile Pro Asp Gln Arg Ile Asn Tyr
370                 375                 380

Leu Arg Asp His Phe Ala Ala His Gln Ala Ile Gln Cys Gly Val
385                 390                 395                 400

Pro Leu Ala Gly Tyr Phe Val Trp Ser Phe Met Asp Asn Phe Glu Trp
                405                 410                 415

Ala Lys Gly Tyr Thr Gln Arg Phe Gly Ile Val Trp Val Asp Tyr Gln
                420                 425                 430

Ser Gln Arg Arg Ile Pro Lys Asp Ser Ala Tyr Trp Tyr Arg Asp Val
                435                 440                 445

Val Ala Ala Asn Ala Val Gln Val Pro Asp
450                 455
```

<210> SEQ ID NO 135
<211> LENGTH: 987
<212> TYPE: DNA
<213> ORGANISM: Unknown
<220> FEATURE:
<223> OTHER INFORMATION: Obtained from environmental sample

<400> SEQUENCE: 135

```
atggttgagc ctgccgatca gagtcatttt tcagatgctt ttcaggtaaa tcgcactctt      60
ggaaaaggca tcaatcttgg taacacactg gaggctccaa atgaaggcga gtggggattg     120
acaattcgcg aggagtattt tgatgaagtg aaacaagccg gatttgaatc cgtgcgtatt     180
ccgatacgat ggaatgctca tgctctggaa ggttttccat atacgataga tgaatctttt     240
tttgaccggg ttgatgaagt tattggctgg gcttttgatc gtgatcttgc agtcatgatt     300
aacattcatc actacaacga attgatggag cagccacagg atcaccggga tcgcttttg      360
aaactttggg agcaaattgc tgcgcactat aaagagtacc cggaagaact ggtattcgag     420
attttaaacg aaccccacga taatctgacc ccggctatct ggaatagctt tttggctgat     480
gctctcggta ttatacgcca aaccaatcca ggaagggtta ttgcagtcgg aacagctgaa     540
tggggcggtt tcgggagttt gcaggatctt gagctgcctg ataatgaccg ccagataatc     600
accaccgttc attactataa cccatttcat ttcacgcatc aggggcaga ttgggttgga      660
gatgaagcgg atcagtggct ggaaccgaa tgggatggag cagatcatga aaaagctgaa      720
gttgacagcg attttgactc tgtggaacag tgggcccgaa atcatgaccg ccaatacac      780
gtgggagagt tcggagcttt cagcgccgca gatgatttgt cacgtgaaca gtggacggca     840
tacgtacgtg agtcttcgga gaaccggcag tttagctggg cgtattggga gtttgggtca     900
gggttcggtg cctatgatcc cggttccgga gaatggcgtg aatatttact ccgggcgtta     960
atccccgaca gtccggtgat tgattaa                                         987
```

<210> SEQ ID NO 136
<211> LENGTH: 328
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (27)...(306)
<223> OTHER INFORMATION: Cellulase (glycosyl hydrolase family 5)
<220> FEATURE:
<221> NAME/KEY: SITE
<222> LOCATION: (17)...(20)
<223> OTHER INFORMATION: N-glycosylation site. Prosite id = PS00001
<220> FEATURE:
<221> NAME/KEY: SITE
<222> LOCATION: (139)...(148)
<223> OTHER INFORMATION: Glycosyl hydrolases family 5 signature. Prosite
      id = PS00659

<400> SEQUENCE: 136

Met Val Glu Pro Ala Asp Gln Ser His Phe Ser Asp Ala Phe Gln Val
1               5                   10                  15

Asn Arg Thr Leu Gly Lys Gly Ile Asn Leu Gly Asn Thr Leu Glu Ala
            20                  25                  30

Pro Asn Glu Gly Glu Trp Gly Leu Thr Ile Arg Glu Glu Tyr Phe Asp
        35                  40                  45

Glu Val Lys Gln Ala Gly Phe Glu Ser Val Arg Ile Pro Ile Arg Trp
    50                  55                  60

```
Asn Ala His Ala Leu Glu Gly Phe Pro Tyr Thr Ile Asp Glu Ser Phe
 65                  70                  75                  80

Phe Asp Arg Val Asp Glu Val Ile Gly Trp Ala Phe Arg Asp Leu
                 85                  90                  95

Ala Val Met Ile Asn Ile His His Tyr Asn Glu Leu Met Glu Gln Pro
            100                 105                 110

Gln Asp His Arg Asp Arg Phe Leu Lys Leu Trp Glu Gln Ile Ala Ala
        115                 120                 125

His Tyr Lys Glu Tyr Pro Glu Glu Leu Val Phe Glu Ile Leu Asn Glu
130                 135                 140

Pro His Asp Asn Leu Thr Pro Ala Ile Trp Asn Ser Phe Leu Ala Asp
145                 150                 155                 160

Ala Leu Gly Ile Ile Arg Gln Thr Asn Pro Gly Arg Val Ile Ala Val
                165                 170                 175

Gly Thr Ala Glu Trp Gly Gly Phe Gly Ser Leu Gln Asp Leu Glu Leu
            180                 185                 190

Pro Asp Asn Asp Arg Gln Ile Ile Thr Thr Val His Tyr Tyr Asn Pro
        195                 200                 205

Phe His Phe Thr His Gln Gly Ala Asp Trp Val Gly Asp Glu Ala Asp
210                 215                 220

Gln Trp Leu Gly Thr Glu Trp Asp Gly Ala Asp His Glu Lys Ala Glu
225                 230                 235                 240

Val Asp Ser Asp Phe Asp Ser Val Glu Gln Trp Ala Arg Asn His Asp
                245                 250                 255

Arg Pro Ile His Val Gly Glu Phe Gly Ala Phe Ser Ala Ala Asp Asp
            260                 265                 270

Leu Ser Arg Glu Gln Trp Thr Ala Tyr Val Arg Glu Ser Ser Glu Asn
        275                 280                 285

Arg Gln Phe Ser Trp Ala Tyr Trp Glu Phe Gly Ser Gly Phe Gly Ala
        290                 295                 300

Tyr Asp Pro Gly Ser Gly Glu Trp Arg Glu Tyr Leu Leu Arg Ala Leu
305                 310                 315                 320

Ile Pro Asp Ser Pro Val Ile Asp
                325

<210> SEQ ID NO 137
<211> LENGTH: 702
<212> TYPE: DNA
<213> ORGANISM: Unknown
<220> FEATURE:
<223> OTHER INFORMATION: Obtained from environmental sample

<400> SEQUENCE: 137
atgagccacc gatcgcagga attcaacggc cagccactga tggtgtccga agacggccac      60
ttcgtgctcg gattcggcg cgacgacgag gccacccacc gactgcgcgt tcagctaccg     120
gatgagcgag tctgggagaa gaatctgcgt ccggaatcgc gcgagttcga tattcagcgg     180
atcgacggct tgccgcaaga ccaggtcacc ccaccccact ccgtgctggc gagaatccga     240
gaggacgctt cgctgtcgcg ccgtgcccgc gaacgacgcg atccgcggac cgactggacc     300
gatggctgga tctggccggc cgagggccgc atttccggcg tgtacggcag ccagcgcatc     360
ctcaacggtg agcctcgcaa cccgcactgg gggctgata tcgccgcgcc aaccggcagc      420
ccggtcgtgg cgcctgccgg cggcatcgtc agcctgactc atccggacat gtattttcc      480 ggcggcaccc tgttaatcga ccacggtcac ggctggtgt ctgcgttcct ccacctgagt      540
gaaatcctgg tcgaggaagg gcagcgggtc gagcagggg atctgatcgc acgcattggc      600
```

```
gccaccggtc gtgccaccgg gccgcacctg gactggcgga tcaatctcgg cgatgtacgc    660
gtggacccac agctgctgct gccgccgatg gacgcgcagt ga                        702
```

<210> SEQ ID NO 138
<211> LENGTH: 233
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (127)...(223)
<223> OTHER INFORMATION: Peptidase family M23

<400> SEQUENCE: 138

```
Met Ser His Arg Ser Gln Glu Phe Asn Gly Gln Pro Leu Met Val Ser
1               5                   10                  15

Glu Asp Gly His Phe Val Leu Gly Phe Gly Arg Asp Asp Glu Ala Thr
            20                  25                  30

His Arg Leu Arg Val Gln Leu Pro Asp Glu Arg Val Trp Glu Lys Asn
        35                  40                  45

Leu Arg Pro Glu Ser Arg Glu Phe Asp Ile Gln Arg Ile Asp Gly Leu
    50                  55                  60

Pro Gln Asp Gln Val Thr Pro Pro His Ser Val Leu Ala Arg Ile Arg
65                  70                  75                  80

Glu Asp Ala Ser Leu Ser Arg Arg Ala Arg Glu Arg Asp Pro Arg
            85                  90                  95

Thr Asp Trp Thr Asp Gly Trp Ile Trp Pro Ala Glu Gly Arg Ile Ser
            100                 105                 110

Gly Val Tyr Gly Ser Gln Arg Ile Leu Asn Gly Glu Pro Arg Asn Pro
        115                 120                 125

His Trp Gly Leu Asp Ile Ala Ala Pro Thr Gly Ser Pro Val Val Ala
    130                 135                 140

Pro Ala Gly Gly Ile Val Ser Leu Thr His Pro Asp Met Tyr Phe Ser
145                 150                 155                 160

Gly Gly Thr Leu Leu Ile Asp His Gly His Gly Leu Val Ser Ala Phe
            165                 170                 175

Leu His Leu Ser Glu Ile Leu Val Glu Glu Gln Arg Val Glu Gln
        180                 185                 190

Gly Asp Leu Ile Ala Arg Ile Gly Ala Thr Gly Arg Ala Thr Gly Pro
    195                 200                 205

His Leu Asp Trp Arg Ile Asn Leu Gly Asp Val Arg Val Asp Pro Gln
    210                 215                 220

Leu Leu Leu Pro Pro Met Asp Ala Gln
225                 230
```

<210> SEQ ID NO 139
<211> LENGTH: 351
<212> TYPE: DNA
<213> ORGANISM: Unknown
<220> FEATURE:
<223> OTHER INFORMATION: Obtained from environmental sample

<400> SEQUENCE: 139

```
atggaaaaaa ttctcgttat cggatgcgcg ggccagatag gctcagagct tacgctcgaa    60
cttcgtaaga tttatggtga tgacaatgtg gtggctactg acattaagcc ggccagcaag   120
gaaattaccg agggcggccc ctttgaaatt cttgatgtgc tcgacaccca ccggctttt    180
```

```
ggcactgtaa gccgcaacaa gatcacccag atttatcacc ttgcagccat cctttcgggc        240
aatgccgaga aaaaaccact tgcaagctgg cacattaaca tggagagttt gctcaacgtg        300
cttgaactgg cccgtgaact gaagcttcat aaaattttct ggccaagctc a                 351
```

<210> SEQ ID NO 140
<211> LENGTH: 117
<212> TYPE: PRT
<213> ORGANISM: Unknown
<220> FEATURE:
<223> OTHER INFORMATION: Obtained from environmental sample

<400> SEQUENCE: 140

```
Met Glu Lys Ile Leu Val Ile Gly Cys Ala Gly Gln Ile Gly Ser Glu
1               5                   10                  15

Leu Thr Leu Glu Leu Arg Lys Ile Tyr Gly Asp Asp Asn Val Val Ala
            20                  25                  30

Thr Asp Ile Lys Pro Ala Ser Lys Glu Ile Thr Glu Gly Gly Pro Phe
        35                  40                  45

Glu Ile Leu Asp Val Leu Asp Thr His Arg Leu Phe Gly Thr Val Ser
    50                  55                  60

Arg Asn Lys Ile Thr Gln Ile Tyr His Leu Ala Ala Ile Leu Ser Gly
65                  70                  75                  80

Asn Ala Glu Lys Lys Pro Leu Ala Ser Trp His Ile Asn Met Glu Ser
                85                  90                  95

Leu Leu Asn Val Leu Glu Leu Ala Arg Glu Leu Lys Leu His Lys Ile
            100                 105                 110

Phe Trp Pro Ser Ser
        115
```

<210> SEQ ID NO 141
<211> LENGTH: 1350
<212> TYPE: DNA
<213> ORGANISM: Unknown
<220> FEATURE:
<223> OTHER INFORMATION: Obtained from environmental sample

<400> SEQUENCE: 141

```
atgctgtcct atacgagtcc gttcccaaag aactttgtct ggggtgtggc gacggcggcg         60
ccgcagatcg agggcgctgc gcgagaagac ggaaagggcg aatcgatatg ggatcgcttt        120
tgccgcgtgc ccggaaaggt ccacaatggc gatactctcg atgttgcgtg cgaccactac        180
caccggttcc gggaggattt cgcgctcatg cgagacttgg gcgtgcgcca ctaccggctt        240
tcgcttgcct ggccccgcat attcccggac ggcgacggcg cattgaacca gcgcggagtg        300
gatttctacc accggctctt tgaggccatg atcgagcacg ggattacgcc ttgggtgacg        360
ctctttcact gggatttgcc gcaggcgctc gaggaccgcg gcggctggtg tgagcgtctc        420
accgtcgatg cattcgggcg ctacgctgac ccgtggtga aggcgtttgg cgatcgcgtg        480
aagaattgga tcaccctgaa cgaaatccgc tgcttcacgt tgctcgctta cgatctctgc        540
atcaaggccc cgggccgcaa ggtctcgcgg gcgcagctca accagaccta tcatcacgcg        600
ctgatctgcc atgggcatgg cgtccgggcg gtccgcgaac acggcgggcg aggcgctcgc        660
gtcgggctta ccgacaacag cgacgtatgc gtgcccgtca ccgagaccgc gcccgacatc        720
attgcggcca gatcctggta tgcgtcgcga atattcatc tgctcgatcc gatctatcgc        780
ggcgagtatg cgccggaata cctcgaacgc tgccgtgcgg acgcgccccca ggtggccgag        840 gacgatttcg cgctgatttc aatgccgacg gattttctcg gctgaatgt atatacggcg        900
```

```
acctttgtgc gtgccgacgc ggagggcagg ccggaggaga ttaaactgcc gcggaattac    960
ccgcgcgcgg atagcgcgtg gttgaatatt gtgccccagt cgatgtactg ggccacacgg   1020
ctggcgcggg aaacctacgg cgtgagatca atctacatca ccgaaaacgg ctgcggctac   1080
gacgacgagc ccgtcgacgg cggcgaggtg ctcgacctgc atcgacgcga ttttctgcgc   1140
aaccaccttc gggaattgca tcgcgccata ggcgacggcg tgcccgttga cgggtatttt   1200
ctctggtcct tcatggacaa ctacgagtgg gaggacgggt atgcgcggcg gttcggcatc   1260
gttcacgtcg acttcgaaag ccagaaacgg actccaaaac tctcggcgcg ctattacgcg   1320
caggtaatga agaaaaccg gatcctgtga                                     1350
```

<210> SEQ ID NO 142
<211> LENGTH: 449
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (4)...(448)
<223> OTHER INFORMATION: Glycosyl hydrolase family 1

<400> SEQUENCE: 142

```
Met Leu Ser Tyr Thr Ser Pro Phe Pro Lys Asn Phe Val Trp Gly Val
 1               5                  10                  15

Ala Thr Ala Ala Pro Gln Ile Glu Gly Ala Ala Arg Glu Asp Gly Lys
             20                  25                  30

Gly Glu Ser Ile Trp Asp Arg Phe Cys Arg Val Pro Gly Lys Val His
         35                  40                  45

Asn Gly Asp Thr Leu Asp Val Ala Cys Asp His Tyr His Arg Phe Arg
     50                  55                  60

Glu Asp Phe Ala Leu Met Arg Asp Leu Gly Val Arg His Tyr Arg Leu
 65                  70                  75                  80

Ser Leu Ala Trp Pro Arg Ile Phe Pro Asp Gly Asp Gly Ala Leu Asn
                 85                  90                  95

Gln Arg Gly Val Asp Phe Tyr His Arg Leu Phe Glu Ala Met Ile Glu
            100                 105                 110

His Gly Ile Thr Pro Trp Val Thr Leu Phe His Trp Asp Leu Pro Gln
        115                 120                 125

Ala Leu Glu Asp Arg Gly Gly Trp Cys Glu Arg Leu Thr Val Asp Ala
    130                 135                 140

Phe Gly Arg Tyr Ala Asp Thr Val Val Lys Ala Phe Gly Asp Arg Val
145                 150                 155                 160

Lys Asn Trp Ile Thr Leu Asn Glu Ile Arg Cys Phe Thr Leu Leu Ala
                165                 170                 175

Tyr Asp Leu Cys Ile Lys Ala Pro Gly Arg Lys Val Ser Arg Ala Gln
            180                 185                 190

Leu Asn Gln Thr Tyr His His Ala Leu Ile Cys His Gly His Gly Val
        195                 200                 205

Arg Ala Val Arg Glu His Gly Gly Arg Gly Ala Arg Val Gly Leu Thr
    210                 215                 220

Asp Asn Ser Asp Val Cys Val Pro Val Thr Glu Thr Ala Pro Asp Ile
225                 230                 235                 240

Ile Ala Ala Arg Ser Trp Tyr Ala Ser Arg Asn Ile His Leu Leu Asp
                245                 250                 255

Pro Ile Tyr Arg Gly Glu Tyr Ala Pro Glu Tyr Leu Glu Arg Cys Gly
            260                 265                 270
```

Ala Asp Ala Pro Gln Val Ala Glu Asp Asp Phe Ala Leu Ile Ser Met
    275                 280                 285

Pro Thr Asp Phe Leu Gly Leu Asn Val Tyr Thr Ala Thr Phe Val Arg
    290                 295                 300

Ala Asp Ala Glu Gly Arg Pro Glu Glu Ile Lys Leu Pro Arg Asn Tyr
305                 310                 315                 320

Pro Arg Ala Asp Ser Ala Trp Leu Asn Ile Val Pro Gln Ser Met Tyr
                325                 330                 335

Trp Ala Thr Arg Leu Ala Arg Glu Thr Tyr Gly Val Arg Ser Ile Tyr
            340                 345                 350

Ile Thr Glu Asn Gly Cys Gly Tyr Asp Asp Glu Pro Val Asp Gly Gly
        355                 360                 365

Glu Val Leu Asp Leu His Arg Arg Asp Phe Leu Arg Asn His Leu Arg
    370                 375                 380

Glu Leu His Arg Ala Ile Gly Asp Gly Val Pro Val Asp Gly Tyr Phe
385                 390                 395                 400

Leu Trp Ser Phe Met Asp Asn Tyr Glu Trp Glu Asp Gly Tyr Ala Arg
                405                 410                 415

Arg Phe Gly Ile Val His Val Asp Phe Glu Ser Gln Lys Arg Thr Pro
            420                 425                 430

Lys Leu Ser Ala Arg Tyr Tyr Ala Gln Val Met Lys Glu Asn Arg Ile
        435                 440                 445

Leu

<210> SEQ ID NO 143
<211> LENGTH: 1188
<212> TYPE: DNA
<213> ORGANISM: Unknown
<220> FEATURE:
<223> OTHER INFORMATION: Obtained from environmental sample

<400> SEQUENCE: 143
atgaccatca ccttccccga cgggttctgg tgggggacgg cgacggccgc ccaccaggtg      60
gagggcggca actggaacac cgactggtgg gcctacgagc acgccccggg cacccgctgc     120
gcggagccgt ccggcgatgc gtgcgaccac tggcaccgct acccggagga catcgccctc     180
ctcgccgcgc tcgggttcag tgcctaccgc ttctcggtgg aatgggctcg catcgagccc     240
gaggaagggc atttctcccg cgccacccte gaccactacc ggcgcatgat cgcctgctgc     300
cgcgaccacg gctggcccc gtggtgacc ttccaccact tcaccacccc ccgctgggcc      360
gcggccgggg gctgctggtc cgacccggtc accgccgagc gcttcgcccg ttactgcgag     420
cgcaccgtgg ccgccctcgg cgacgagatc gcgatggcct gcacgatcaa cgagccgaac     480
atcgtggcca cctcgggta cttcctcggc gagttcccgc cggccgtcgc cgaccccgac     540
cgctaccgga aggcgaacga cacgctgatc gcgcccatc gcctcgccta cgaggcgctg     600
aaggccgggc ccggcgagtt ccccgtcggc ctcaccctgt cgatggccga gttcgtcgcc     660
gagcccggcg cgaggcccca cctcgcccag gtccggcaca cgatggagga catcttcctg     720
gaggccgccc ggggcgacga cttcatcggg gtgcagacct acagccgcat gcgcttcggt     780
cccgactcgc cgatcccgct cgggccggcc gagggcgtcg aggtcgtcca gatgggggtac     840
gagtactggc cgtgggcgct cgaggcgacg atccggcgcg ccgccgaggt caccggcacg     900
gcggtccacg tcaccgagaa cggcatcggg accgccgacg acacgcagcg ggtcgcctac     960
gtcaccgagg ccctccgggg gctgcggcgc tgcctcgacg acggcatcga cgtccgcagc    1020

-continued

```
tacttctact ggacgctgct cgacaacttc gagtggacgc gcggctacgt gccgacgttc    1080
gggctcgtcg ccgtcgaccg caccacccag cgccggtcgg tgaagccgag cgcggtgtgg    1140
ctcggcgagg tcgcccgcac gaaccgcctc gagctcccgg accgctga                1188
```

<210> SEQ ID NO 144
<211> LENGTH: 395
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (1)...(390)
<223> OTHER INFORMATION: Glycosyl hydrolase family 1
<220> FEATURE:
<221> NAME/KEY: SITE
<222> LOCATION: (9)...(23)
<223> OTHER INFORMATION: Glycosyl hydrolases family 1 N-terminal
    signature. Prosite id = PS00653
<220> FEATURE:
<221> NAME/KEY: SITE
<222> LOCATION: (188)...(191)
<223> OTHER INFORMATION: N-glycosylation site. Prosite id = PS00001

<400> SEQUENCE: 144

```
Met Thr Ile Thr Phe Pro Asp Gly Phe Trp Trp Gly Thr Ala Thr Ala
1               5                   10                  15

Ala His Gln Val Glu Gly Gly Asn Trp Asn Thr Asp Trp Ala Tyr
            20                  25                  30

Glu His Ala Pro Gly Thr Arg Cys Ala Glu Pro Ser Gly Asp Ala Cys
            35                  40                  45

Asp His Trp His Arg Tyr Pro Glu Asp Ile Ala Leu Leu Ala Ala Leu
        50                  55                  60

Gly Phe Ser Ala Tyr Arg Phe Ser Val Glu Trp Ala Arg Ile Glu Pro
65                  70                  75                  80

Glu Glu Gly His Phe Ser Arg Ala Thr Leu Asp His Tyr Arg Arg Met
                85                  90                  95

Ile Ala Cys Cys Arg Asp His Gly Leu Ala Pro Val Val Thr Phe His
            100                 105                 110

His Phe Thr Thr Pro Arg Trp Ala Ala Gly Gly Cys Trp Ser Asp
            115                 120                 125

Pro Val Thr Ala Glu Arg Phe Ala Arg Tyr Cys Glu Arg Thr Val Ala
        130                 135                 140

Ala Leu Gly Asp Glu Ile Ala Met Ala Cys Thr Ile Asn Glu Pro Asn
145                 150                 155                 160

Ile Val Ala Thr Leu Gly Tyr Phe Leu Gly Glu Phe Pro Pro Ala Val
                165                 170                 175

Ala Asp Pro Asp Arg Tyr Arg Gln Ala Asn Asp Thr Leu Ile Arg Ala
            180                 185                 190

His Arg Leu Ala Tyr Glu Ala Leu Lys Ala Gly Pro Gly Glu Phe Pro
        195                 200                 205

Val Gly Leu Thr Leu Ser Met Ala Glu Phe Val Ala Glu Pro Gly Gly
    210                 215                 220

Glu Ala His Leu Ala Gln Val Arg His Thr Met Glu Asp Ile Phe Leu
225                 230                 235                 240

Glu Ala Ala Arg Gly Asp Asp Phe Ile Gly Val Gln Thr Tyr Ser Arg
                245                 250                 255

Met Arg Phe Gly Pro Asp Ser Pro Ile Pro Leu Gly Pro Ala Glu Gly
            260                 265                 270
```

| Val | Glu | Val | Val | Gln | Met | Gly | Tyr | Glu | Tyr | Trp | Pro | Trp | Ala | Leu | Glu |
| | 275 | | | | | 280 | | | | | 285 | | | | |

Ala Thr Ile Arg Arg Ala Ala Glu Val Thr Gly Thr Ala Val His Val
   290                 295                 300

Thr Glu Asn Gly Ile Gly Thr Ala Asp Asp Thr Gln Arg Val Ala Tyr
305                 310                 315                 320

Val Thr Glu Ala Leu Arg Gly Leu Arg Arg Cys Leu Asp Asp Gly Ile
            325                 330                 335

Asp Val Arg Ser Tyr Phe Tyr Trp Thr Leu Leu Asp Asn Phe Glu Trp
                340                 345                 350

Thr Arg Gly Tyr Val Pro Thr Phe Gly Leu Val Ala Val Asp Arg Thr
        355                 360                 365

Thr Gln Arg Arg Ser Val Lys Pro Ser Ala Val Trp Leu Gly Glu Val
370                 375                 380

Ala Arg Thr Asn Arg Leu Glu Leu Pro Asp Arg
385                 390                 395

<210> SEQ ID NO 145
<211> LENGTH: 1386
<212> TYPE: DNA
<213> ORGANISM: Unknown
<220> FEATURE:
<223> OTHER INFORMATION: Obtained from environmental sample

<400> SEQUENCE: 145
atgtcgtttc cgagaaattt cctgtgggga tcagccacct cctcctacca aatcgaaggc      60
gcctggcaag aagacggcaa aggcccaaat atctgggacg tgttttcaca caccccgggg     120
aaagtcgcca atggcgacac cggtgatatc gccatcgacc actaccacgg ataccgagac     180
gacgttgccc tgatggctga gcttggactt caggcatacc gtttctcgtt ctcctgggcc     240
agaataatgc cggaaggagc aggccccatc gagcaacggg gtctggactt ctacgaccgc     300
ctcattgatg cactgctgga gaaaaacatc caacccatgg ccaccctcta ccactgggat     360
ttaccagccg cactgcaaga cagagggggg tggactaacc gcgacagcgc gtcctggttt     420
gctgactact cagccgttgt tcacgacgct ttttctgacc gggtgggaat gtgggcaacg     480
ttgaacgagc cgtgggtgtc tgcattttg ggccacggaa ctggcatcca cgcacctggc     540
atcacaagcc cccacgcggc gttcgccgcg ggcatcacc tgcttctggg gcatggcaag     600
gccatccaag cgatgcgcgc tcaatcgtct agcacccaac tgggaattgt tttgaacctc     660 gccccgtgt atctcgaagg tgacacccct gctgaccacc cggctcacac ctccgtggca     720
ctacacgatg ccatttgaa tgggttgtgg acagagccgc ttctgcgctc cagatacccc     780
gacctgcttc ttcaactagg cgacatggtg acaaaaaaca tccacgacgg tgacctcgcc     840
atcatggccg agccgattga ctggatgggc atcaactact accaggacat tagatttgtg     900
gccactgatg ttgccccac ggctaacccg atggccccctc cgggtaacga cctgccgggc     960
accgtcgggg tggagcctgc gccagcaatc ggaaacatca ccagctttgg ctggtccacc    1020 accccccgacg gactgcgagt actgttggtg ggcctggatg aggaatacga caacctcccg    1080
ccgatattca ttaccgaaaa cgggtgtgct tacgattacc ccgtcgagga cggtgtcgtc    1140
aacgacaccc ttcgtgtcac atacatgcga gaacacctca ccgcgttgtc gcaggccatt    1200
gaggcgggtg tgaatgtccg gggctatatg cactggtctc tgttcgacaa cttcgagtgg    1260
gccgaagggt atcgccaacg ctttggcatg gtgcacgtcg actttgagac cttggagcgg    1320
actcccaaag cctcagctca ctactattca cgtgtcatca caaataacgc cctctctgac    1380

-continued

```
gactga                                                      1386
```

<210> SEQ ID NO 146
<211> LENGTH: 461
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (1)...(458)
<223> OTHER INFORMATION: Glycosyl hydrolase family 1
<220> FEATURE:
<221> NAME/KEY: SITE
<222> LOCATION: (7)...(21)
<223> OTHER INFORMATION: Glycosyl hydrolases family 1 N-terminal
      signature. Prosite id = PS00653
<220> FEATURE:
<221> NAME/KEY: SITE
<222> LOCATION: (337)...(340)
<223> OTHER INFORMATION: N-glycosylation site. Prosite id = PS00001
<220> FEATURE:
<221> NAME/KEY: SITE
<222> LOCATION: (386)...(389)
<223> OTHER INFORMATION: N-glycosylation site. Prosite id = PS00001

<400> SEQUENCE: 146

Met Ser Phe Pro Arg Asn Phe Leu Trp Gly Ser Ala Thr Ser Ser Tyr
1               5                   10                  15

Gln Ile Glu Gly Ala Trp Gln Glu Asp Gly Lys Gly Pro Asn Ile Trp
            20                  25                  30

Asp Val Phe Ser His Thr Pro Gly Lys Val Ala Asn Gly Asp Thr Gly
        35                  40                  45

Asp Ile Ala Ile Asp His Tyr His Arg Tyr Arg Asp Val Ala Leu
    50                  55                  60

Met Ala Glu Leu Gly Leu Gln Ala Tyr Arg Phe Ser Phe Ser Trp Ala
65                  70                  75                  80

Arg Ile Met Pro Glu Gly Ala Gly Pro Ile Glu Gln Arg Gly Leu Asp
                85                  90                  95

Phe Tyr Asp Arg Leu Ile Asp Ala Leu Leu Glu Lys Asn Ile Gln Pro
            100                 105                 110

Met Ala Thr Leu Tyr His Trp Asp Leu Pro Ala Ala Leu Gln Asp Arg
        115                 120                 125

Gly Gly Trp Thr Asn Arg Asp Ser Ala Ser Trp Phe Ala Asp Tyr Ser
    130                 135                 140

Ala Val Val His Asp Ala Phe Ser Asp Arg Val Gly Met Trp Ala Thr
145                 150                 155                 160

Leu Asn Glu Pro Trp Val Ser Ala Phe Leu Gly His Gly Thr Gly Ile
                165                 170                 175

His Ala Pro Gly Ile Thr Ser Pro His Ala Ala Phe Ala Ala Gly His
            180                 185                 190

His Leu Leu Leu Gly His Gly Lys Ala Ile Gln Ala Met Arg Ala Gln
        195                 200                 205

Ser Ser Ser Thr Gln Leu Gly Ile Val Leu Asn Leu Ala Pro Val Tyr
    210                 215                 220

Leu Glu Gly Asp Thr Pro Ala Asp His Pro Ala His Thr Ser Val Ala
225                 230                 235                 240

Leu His Asp Ala Ile Leu Asn Gly Leu Trp Thr Glu Pro Leu Leu Arg
                245                 250                 255

Ser Arg Tyr Pro Asp Leu Leu Leu Gln Leu Gly Asp Met Val Thr Lys
            260                 265                 270

```
Asn Ile His Asp Gly Asp Leu Ala Ile Met Ala Glu Pro Ile Asp Trp
    275                 280                 285
Met Gly Ile Asn Tyr Tyr Gln Asp Ile Arg Phe Val Ala Thr Asp Val
    290                 295                 300
Ala Pro Thr Ala Asn Pro Met Ala Pro Pro Gly Asn Asp Leu Pro Gly
305                 310                 315                 320
Thr Val Gly Val Glu Pro Ala Pro Ala Ile Gly Asn Ile Thr Ser Phe
                325                 330                 335
Gly Trp Ser Thr Thr Pro Asp Gly Leu Arg Val Leu Val Gly Leu
            340                 345                 350
Asp Glu Glu Tyr Asp Asn Leu Pro Pro Ile Phe Ile Thr Glu Asn Gly
                355                 360                 365
Cys Ala Tyr Asp Tyr Pro Val Glu Asp Gly Val Val Asn Asp Thr Leu
370                 375                 380
Arg Val Thr Tyr Met Arg Glu His Leu Thr Ala Leu Ser Gln Ala Ile
385                 390                 395                 400
Glu Ala Gly Val Asn Val Arg Gly Tyr Met His Trp Ser Leu Phe Asp
                405                 410                 415
Asn Phe Glu Trp Ala Glu Gly Tyr Arg Gln Arg Phe Gly Met Val His
            420                 425                 430
Val Asp Phe Glu Thr Leu Glu Arg Thr Pro Lys Ala Ser Ala His Tyr
        435                 440                 445
Tyr Ser Arg Val Ile Thr Asn Asn Ala Leu Ser Asp Asp
450                 455                 460

<210> SEQ ID NO 147
<211> LENGTH: 1242
<212> TYPE: DNA
<213> ORGANISM: Unknown
<220> FEATURE:
<223> OTHER INFORMATION: Obtained from environmental sample

<400> SEQUENCE: 147
atgctaaaag ttttacgtaa acctattatt tctggattag ctttagctct attattgccg      60
gcaggggcag ctggtgccga actaatatt tcaaagaagc caaatataag tggattaacc     120
gcgccgcaat tagaccaaag atataaagat tctttcacca ttggtgctgc ggttgagccg     180
tatcaattat tagatgcaaa agattcacaa atgctaaagc ggcattttaa tagtatcgta     240
gcagagaatg tcatgaagcc tagtagttta cagccagtag aaggacaatt caactgggag     300
ccggctgata aacttgttca gtttgcgaag gaaaatggaa tggacatgcg aggtcatacg     360
cttgtctggc atagccaggt accggattgg ttctttgaag atgcggcagg aaatccaatg     420
gttgtttggg aaaatggcag gcaagtggtt gccgatccat caaagcttca ggaaaacaaa     480
gagctcttac ttagccgatt acaaaatcat attcaggcag tcgtaacgcg ttataaagat     540
gatataaaat cttgggatgt tgtcaatgaa gtaatcgatg aatggggcgg acattctgaa     600
gggctgcgtc aatctccatg gttcctcatc accggaacgg actatattaa agttgctttt     660
gaaactgcaa gagaatatgc agctccagac gctaagctgt atatcaatga ttacaataca     720
gaagtagaac caaaaaggac gcacctttat aacttagtaa aaagtttaaa agaagaacag     780
aacgttccga ttgatggtgt tgggcatcag tctcacattc aaattggctg gccttcagaa     840
aaagaaattg aagatactat taatatgttt gcagatcttg gtttagataa ccaaatcacc     900
gagcttgatg ttagtatgta tggctggccg gtaaggtcgt atccaactta tgatgcgatc     960
ccagaactta aattcatgga tcaagcagct cgttatgatc gtttatttaa gttatatgag    1020
```

-continued

```
aaattaggag ataaaatcag taatgtgaca ttctggggta ttgcggataa ccatacatgg   1080
ctgaatgacc gcgcagatgt ttactatgat gaaaatggaa atgttgtatt agatagagaa   1140
acaccaagag tagaaagagg agcaggaaaa gatgcgccat ttgtatttga tcctgaatac   1200
aatgtaaaac cagcttattg ggcaattatc gatcacaaat aa                      1242
```

<210> SEQ ID NO 148
<211> LENGTH: 413
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(26)
<220> FEATURE:
<221> NAME/KEY: DOMAIN
<222> LOCATION: (43)...(413)
<223> OTHER INFORMATION: Glycosyl hydrolase family 10
<220> FEATURE:
<221> NAME/KEY: SITE
<222> LOCATION: (29)...(32)
<223> OTHER INFORMATION: N-glycosylation site. Prosite id = PS00001
<220> FEATURE:
<221> NAME/KEY: SITE
<222> LOCATION: (35)...(38)
<223> OTHER INFORMATION: N-glycosylation site. Prosite id = PS00001
<220> FEATURE:
<221> NAME/KEY: SITE
<222> LOCATION: (298)...(308)
<223> OTHER INFORMATION: Glycosyl hydrolases family 10 active site.
    Prosite id = PS00591
<220> FEATURE:
<221> NAME/KEY: SITE
<222> LOCATION: (353)...(356)
<223> OTHER INFORMATION: N-glycosylation site. Prosite id = PS00001
<220> FEATURE:
<221> NAME/KEY: SITE
<222> LOCATION: (362)...(365)
<223> OTHER INFORMATION: N-glycosylation site. Prosite id = PS00001

<400> SEQUENCE: 148

```
Met Leu Lys Val Leu Arg Lys Pro Ile Ile Ser Gly Leu Ala Leu Ala
1               5                   10                  15

Leu Leu Leu Pro Ala Gly Ala Ala Gly Ala Glu Thr Asn Ile Ser Lys
            20                  25                  30

Lys Pro Asn Ile Ser Gly Leu Thr Ala Pro Gln Leu Asp Gln Arg Tyr
        35                  40                  45

Lys Asp Ser Phe Thr Ile Gly Ala Ala Val Glu Pro Tyr Gln Leu Leu
    50                  55                  60

Asp Ala Lys Asp Ser Gln Met Leu Lys Arg His Phe Asn Ser Ile Val
65                  70                  75                  80

Ala Glu Asn Val Met Lys Pro Ser Ser Leu Gln Pro Val Glu Gly Gln
                85                  90                  95

Phe Asn Trp Glu Pro Ala Asp Lys Leu Val Gln Phe Ala Lys Glu Asn
            100                 105                 110

Gly Met Asp Met Arg Gly His Thr Leu Val Trp His Ser Gln Val Pro
        115                 120                 125

Asp Trp Phe Phe Glu Asp Ala Ala Gly Asn Pro Met Val Val Trp Glu
    130                 135                 140

Asn Gly Arg Gln Val Val Ala Asp Pro Ser Lys Leu Gln Glu Asn Lys
145                 150                 155                 160

Glu Leu Leu Leu Ser Arg Leu Gln Asn His Ile Gln Ala Val Val Thr
                165                 170                 175

Arg Tyr Lys Asp Asp Ile Lys Ser Trp Asp Val Val Asn Glu Val Ile
```

```
                  180              185                 190
Asp Glu Trp Gly Gly His Ser Glu Gly Leu Arg Gln Ser Pro Trp Phe
        195                     200                 205

Leu Ile Thr Gly Thr Asp Tyr Ile Lys Val Ala Phe Glu Thr Ala Arg
    210                     215                 220

Glu Tyr Ala Ala Pro Asp Ala Lys Leu Tyr Ile Asn Asp Tyr Asn Thr
225                 230                 235                 240

Glu Val Glu Pro Lys Arg Thr His Leu Tyr Asn Leu Val Lys Ser Leu
                245                 250                 255

Lys Glu Glu Gln Asn Val Pro Ile Asp Gly Val Gly His Gln Ser His
            260                 265                 270

Ile Gln Ile Gly Trp Pro Ser Glu Lys Glu Ile Glu Asp Thr Ile Asn
        275                 280                 285

Met Phe Ala Asp Leu Gly Leu Asp Asn Gln Ile Thr Glu Leu Asp Val
    290                 295                 300

Ser Met Tyr Gly Trp Pro Val Arg Ser Tyr Pro Thr Tyr Asp Ala Ile
305                 310                 315                 320

Pro Glu Leu Lys Phe Met Asp Gln Ala Ala Arg Tyr Asp Arg Leu Phe
                325                 330                 335

Lys Leu Tyr Glu Lys Leu Gly Asp Lys Ile Ser Asn Val Thr Phe Trp
            340                 345                 350

Gly Ile Ala Asp Asn His Thr Trp Leu Asn Asp Arg Ala Asp Val Tyr
        355                 360                 365

Tyr Asp Glu Asn Gly Asn Val Val Leu Asp Arg Glu Thr Pro Arg Val
    370                 375                 380

Glu Arg Gly Ala Gly Lys Asp Ala Pro Phe Val Phe Asp Pro Glu Tyr
385                 390                 395                 400

Asn Val Lys Pro Ala Tyr Trp Ala Ile Ile Asp His Lys
                405                 410

<210> SEQ ID NO 149
<211> LENGTH: 1068
<212> TYPE: DNA
<213> ORGANISM: Unknown
<220> FEATURE:
<223> OTHER INFORMATION: Obtained from environmental sample

<400> SEQUENCE: 149
atgacccgaa tgcgcgggat aaacatgggc ggctggctca gccaaattga cgccatacag     60
gaaaaagacc ctgatacatt tcccggaaca gacaaacata tggaacttta tatccagcag    120
aaggattttg ccaatgtcag gagatggggt ttcgatcatg tgcgaattcc aattgacgcg    180
tatctgttct ttaccgaaaa aggagagccg attgaaaaca ggcttgccaa tcttgaccgc    240
gccgtagagt atgcgctgcc cgccggcctc aacatgatat tggacctcca cgagtgtccg    300 ggcacgatt tttcggaagc agtaaaaagc cctgtccaaa acttttctc gggagatgac      360 acctggataa ggaaaactga aaaatatgg gcttgccttg ccgagcgtta ttctcaaaag    420
ggccacgtcc ttttgagac gctcaatgag cctgtcgctc caccgcgga gatttggaac      480 aatgttaagg acaggctctg ccgcgaaata cggctccacg ccccctggtc gactataatc    540
accggctcca acatgtggaa ctcagcggca accttgaca gcctcacgcc ctttgacgac     600
gacaacatga tctacagcgt acatttttac gagccgctgc ttttcacgca ccagaacgca    660
ttgtggatcg acaatccgga atcaggatc gcaaggccgt atccgggcga ttacggtccc     720
ggctttgtcc ccaaagacgg tttgacgctg tcggacggcg tctggaacag ggatcgtctc    780
```

-continued

```
gccggcgcat tagcgcccgt gaacgcgttc aggaaaaagt acaatgcgaa gattatctgt      840
aacgagttcg gcgtttacgc gcccgtagac cttcaatcgc agctgcgctg gtatgaagat      900
ctgctctcaa tcctcaatga gacggggatc ggtttcacgt actggaacta taaaaatctc      960
gacttcggga taatttccat aggggagaag ctgcacgaag cccttccgca gtacgacaat     1020
agcgatcgaa taaataaatc ggttcttgaa gtgttaaaaa agtattag                  1068
```

<210> SEQ ID NO 150
<211> LENGTH: 355
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (24)...(325)
<223> OTHER INFORMATION: Cellulase (glycosyl hydrolase family 5)
<220> FEATURE:
<221> NAME/KEY: SITE
<222> LOCATION: (145)...(154)
<223> OTHER INFORMATION: Glycosyl hydrolases family 5 signature. Prosite
    id = PS00659
<220> FEATURE:
<221> NAME/KEY: SITE
<222> LOCATION: (310)...(313)
<223> OTHER INFORMATION: N-glycosylation site. Prosite id = PS00001
<220> FEATURE:
<221> NAME/KEY: SITE
<222> LOCATION: (350)...(353)
<223> OTHER INFORMATION: N-glycosylation site. Prosite id = PS00001

<400> SEQUENCE: 150

```
Met Thr Arg Met Arg Gly Ile Asn Met Gly Gly Trp Leu Ser Gln Ile
1               5                   10                  15

Asp Ala Ile Gln Glu Lys Asp Pro Asp Thr Phe Pro Gly Thr Asp Lys
            20                  25                  30

His Met Glu Thr Phe Ile Gln Gln Lys Asp Phe Ala Asn Val Arg Arg
        35                  40                  45

Trp Gly Phe Asp His Val Arg Ile Pro Ile Asp Ala Tyr Leu Phe Phe
    50                  55                  60

Thr Glu Lys Gly Glu Pro Ile Glu Asn Arg Leu Ala Asn Leu Asp Arg
65                  70                  75                  80

Ala Val Glu Tyr Ala Leu Pro Ala Gly Leu Asn Met Ile Leu Asp Leu
                85                  90                  95

His Glu Cys Pro Gly His Asp Phe Ser Glu Ala Val Lys Ser Pro Val
            100                 105                 110

Gln Lys Leu Phe Ser Gly Asp Asp Thr Trp Ile Arg Lys Thr Glu Lys
        115                 120                 125

Ile Trp Ala Cys Leu Ala Glu Arg Tyr Ser Gln Lys Gly His Val Leu
    130                 135                 140

Phe Glu Thr Leu Asn Glu Pro Val Ala Pro Thr Ala Glu Ile Trp Asn
145                 150                 155                 160

Asn Val Lys Asp Arg Leu Cys Arg Glu Ile Arg Leu His Ala Pro Trp
                165                 170                 175

Ser Thr Ile Ile Thr Gly Ser Asn Met Trp Asn Ser Ala Ala Thr Phe
            180                 185                 190

Asp Ser Leu Thr Pro Phe Asp Asp Asn Met Ile Tyr Ser Val His
        195                 200                 205

Phe Tyr Glu Pro Leu Leu Phe Thr His Gln Asn Ala Leu Trp Ile Asp
    210                 215                 220

Asn Pro Glu Ile Arg Ile Ala Arg Pro Tyr Pro Gly Asp Tyr Gly Pro
```

```
                225                 230                 235                 240
Gly Phe Val Pro Lys Asp Gly Leu Thr Leu Ser Asp Gly Val Trp Asn
                    245                 250                 255

Arg Asp Arg Leu Ala Gly Ala Leu Ala Pro Val Asn Ala Phe Arg Lys
                260                 265                 270

Lys Tyr Asn Ala Lys Ile Ile Cys Asn Glu Phe Gly Val Tyr Ala Pro
            275                 280                 285

Val Asp Leu Gln Ser Gln Leu Arg Trp Tyr Glu Asp Leu Leu Ser Ile
        290                 295                 300

Leu Asn Glu Thr Gly Ile Gly Phe Thr Tyr Trp Asn Tyr Lys Asn Leu
305                 310                 315                 320

Asp Phe Gly Ile Ile Ser Ile Gly Glu Lys Leu His Glu Ala Leu Pro
                325                 330                 335

Gln Tyr Asp Asn Ser Asp Arg Ile Asn Lys Ser Val Leu Glu Val Leu
            340                 345                 350

Lys Lys Tyr
        355

<210> SEQ ID NO 151
<211> LENGTH: 1068
<212> TYPE: DNA
<213> ORGANISM: Unknown
<220> FEATURE:
<223> OTHER INFORMATION: Obtained from environmental sample

<400> SEQUENCE: 151
atgaccagaa tgcgcggaat aaacatgggc ggctggctca gccagattga cgccatacag      60
gaaaaagacc ccgataaatt tcccggaata gacaaacaca tggaaacatt tatcggttcc     120
aatgattttt ccaatgtcag gaaatggggt ttcgatcatg tgcgaatccc gattgacgcg     180 taccttttt ttaccgatca ggaagccccg attgaaaaca ggcttgtcca tattgacaac      240
gccgtaaaat acgcgcggag caacggcctc aaggtgatat tggacctcca cgagtgtccg     300
gggcatgatt tttcggacgc ggcaaaaggc cctgtccaga aactttttctc cggagatgac    360 acttatataa aaagaccga aaaaatatgg gcatgtctgg ccgagcgtta ttcgaaaaac     420
gacaacgtcc tctatgagac tctcaacgag cctgtcgccc ccacgcctga gatttggaac     480
actgttaagg acaggctctg ccgggaaata cgcctgcacg ccccctgggc gacgataatc     540
accggttcca atatgtggaa ttggccgagc acctttgaca gcctgacgcc ctttgacgac     600
gacaacgtga tctacagcgt gcatttttac gagccgctgc ttttttacgca ccagaacgcg    660 ccctggatca caattctgaa atcaggatc acaaggccgt atccgggcga ttacggcccc      720
ggctttgtcc gcaaatacgg cttaactctg tcagccggcg tctggaacag gacaggctg      780 gcgaaggaat cgcgcccgt gaacgcgttc aggaaaaaat acaaggcgca ggttatatgc      840
gacgaattcg gcgtttacgc gcctgtcgag attaatcgc agcttcgatg gtatgaggat      900
ttgctctcga tcctcaggga gatgggtata gggttttcgt actggaacta taaaaacctg    960
gactttggga taattcccat aggggagaag ctgcacgaaa gccttctgca gtacggcaac   1020
ggcgacagga taaatcatat ggttcttgac ttgctaaaga agtactaa                 1068

<210> SEQ ID NO 152
<211> LENGTH: 355
<212> TYPE: PRT
<213> ORGANISM: Unknown
<220> FEATURE:
<223> OTHER INFORMATION: Obtained from environmental sample
<220> FEATURE:
```

```
<221> NAME/KEY: DOMAIN
<222> LOCATION: (19)...(325)
<223> OTHER INFORMATION: Cellulase (glycosyl hydrolase family 5)
<220> FEATURE:
<221> NAME/KEY: SITE
<222> LOCATION: (145)...(154)
<223> OTHER INFORMATION: Glycosyl hydrolases family 5 signature. Prosite
      id = PS00659
<220> FEATURE:
<221> NAME/KEY: SITE
<222> LOCATION: (227)...(230)
<223> OTHER INFORMATION: N-glycosylation site. Prosite id = PS00001

<400> SEQUENCE: 152

Met Thr Arg Met Arg Gly Ile Asn Met Gly Gly Trp Leu Ser Gln Ile
1               5                   10                  15

Asp Ala Ile Gln Glu Lys Asp Pro Asp Lys Phe Pro Gly Ile Asp Lys
            20                  25                  30

His Met Glu Thr Phe Ile Gly Ser Asn Asp Phe Ser Asn Val Arg Lys
        35                  40                  45

Trp Gly Phe Asp His Val Arg Ile Pro Ile Asp Ala Tyr Leu Phe Phe
    50                  55                  60

Thr Asp Gln Glu Ala Pro Ile Glu Asn Arg Leu Val His Ile Asp Asn
65                  70                  75                  80

Ala Val Lys Tyr Ala Arg Ser Asn Gly Leu Lys Val Ile Leu Asp Leu
                85                  90                  95

His Glu Cys Pro Gly His Asp Phe Ser Asp Ala Ala Lys Gly Pro Val
            100                 105                 110

Gln Lys Leu Phe Ser Gly Asp Asp Thr Tyr Ile Lys Lys Thr Glu Lys
        115                 120                 125

Ile Trp Ala Cys Leu Ala Glu Arg Tyr Ser Lys Asn Asp Asn Val Leu
    130                 135                 140

Tyr Glu Thr Leu Asn Glu Pro Val Ala Pro Thr Pro Glu Ile Trp Asn
145                 150                 155                 160

Thr Val Lys Asp Arg Leu Cys Arg Glu Ile Arg Leu His Ala Pro Trp
                165                 170                 175

Ala Thr Ile Ile Thr Gly Ser Asn Met Trp Asn Trp Pro Ser Thr Phe
            180                 185                 190

Asp Ser Leu Thr Pro Phe Asp Asp Asn Val Ile Tyr Ser Val His
        195                 200                 205

Phe Tyr Glu Pro Leu Leu Phe Thr His Gln Asn Ala Pro Trp Ile Asn
    210                 215                 220

Asn Ser Glu Ile Arg Ile Thr Arg Pro Tyr Pro Gly Asp Tyr Gly Pro
225                 230                 235                 240

Gly Phe Val Arg Lys Tyr Gly Leu Thr Leu Ser Ala Gly Val Trp Asn
                245                 250                 255

Arg Asp Arg Leu Ala Lys Glu Phe Ala Pro Val Asn Ala Phe Arg Lys
            260                 265                 270

Lys Tyr Lys Ala Gln Val Ile Cys Asp Glu Phe Gly Val Tyr Ala Pro
        275                 280                 285

Val Glu Ile Glu Ser Gln Leu Arg Trp Tyr Gly Asp Leu Leu Ser Ile
    290                 295                 300

Leu Arg Glu Met Gly Ile Gly Phe Ser Tyr Trp Asn Tyr Lys Asn Leu
305                 310                 315                 320

Asp Phe Gly Ile Ile Ser Ile Gly Glu Lys Leu His Glu Ser Leu Leu
                325                 330                 335

Gln Tyr Gly Asn Gly Asp Arg Ile Asn His Met Val Leu Asp Leu Leu
            340                 345                 350
```

Lys Lys Tyr
    355

<210> SEQ ID NO 153
<211> LENGTH: 1068
<212> TYPE: DNA
<213> ORGANISM: Unknown
<220> FEATURE:
<223> OTHER INFORMATION: Obtained from environmental sample

<400> SEQUENCE: 153

```
atgcaaagaa tgcgaggctt aaatattggc ggctggctca gccagattga cgccatacag      60
gaaaaggacc ctgagggctt tcccggaata gacaaacaca tggaaacatt cattgtttcc     120
ggagattttt acaatatcag gaatgggggt ttcgaccatg tgcggcttcc cattgactcg     180
tacctgttct ttacggaaga cgatgccccc attgagaaca ggtttgccca tcttgaccgc     240
gccgtacaat cgcgaagag caacagcctc aagctgatat tggacctcca cgagtgtccg     300
ggacacgatt tttccgaagc cgcgaaagga cccgtccaga acttttttc gggagatgac     360
gtttacataa aaaaaaccga aaaatctgg gcctgcctcg ccgagcgtta ttcgaaaaac     420
gaccatgtac tctttgagac tctcaacgaa cctgtcgctc ccactgccga aatttggaac     480
aaggttaagg acaggctctg cagagtaatc cgcatccacg cgccctggtc gaccataatc     540
accggctcca atatgtggaa ctcgccgtcc gccttcgacg tcttacgcc ctttgacgat      600
ggcaacgtga tctacagcgt gcattttac gagccgctgc tttttacgca tcagaacgcg     660
ccgtggatcg acaatccgga gatcaggacg gcaaggccct atccgggcga ttacggcccc     720
ggccttgtcc gcaaatacgg tatggcgcag tcggccggca tctggaacaa gaaacggctt     780
gcaaaagaat ttgagcccgt ggacgcgttc aggaaaaat acaaggcgcg cgttatctgt      840
aacgagtttg gcgtgtacgc ccccgccgat ctggaatcgc agcttcgctg gtatgaggat     900
ctgctctcaa tcctcaacgg gatgcagata ggttactcgt actggaacta caaaaatctg     960
gatttcggaa taatttccat aggggagaaa ctgcacgaaa gactttcgca gtatgacaac    1020
gacgagcgga taaccaccc ggtgctgaat gtgctgaaga aatattaa                  1068
```

<210> SEQ ID NO 154
<211> LENGTH: 355
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (19)...(325)
<223> OTHER INFORMATION: Cellulase (glycosyl hydrolase family 5)
<220> FEATURE:
<221> NAME/KEY: SITE
<222> LOCATION: (145)...(154)
<223> OTHER INFORMATION: Glycosyl hydrolases family 5 signature. Prosite
      id = PS00659

<400> SEQUENCE: 154

Met Gln Arg Met Arg Gly Leu Asn Ile Gly Gly Trp Leu Ser Gln Ile
1               5                   10                  15

Asp Ala Ile Gln Glu Lys Asp Pro Glu Gly Phe Pro Gly Ile Asp Lys
            20                  25                  30

His Met Glu Thr Phe Ile Val Ser Gly Asp Phe Tyr Asn Ile Arg Lys
        35                  40                  45

Trp Gly Phe Asp His Val Arg Leu Pro Ile Asp Ser Tyr Leu Phe Phe
    50                  55                  60

| | | | | | | | | | | | | | | | |
|---|---|---|---|---|---|---|---|---|---|---|---|---|---|---|---|
|Thr|Glu|Asp|Asp|Ala|Pro|Ile|Glu|Asn|Arg|Phe|Ala|His|Leu|Asp|Arg|
|65| | | |70| | | |75| | | |80| | | |

Ala Val Gln Phe Ala Lys Ser Asn Ser Leu Lys Leu Ile Leu Asp Leu
                   85                 90                95

His Glu Cys Pro Gly His Asp Phe Ser Glu Ala Ala Lys Gly Pro Val
           100                 105                110

Gln Lys Leu Phe Ser Gly Asp Val Tyr Ile Lys Lys Thr Glu Lys
      115                120              125

Ile Trp Ala Cys Leu Ala Glu Arg Tyr Ser Lys Asn Asp His Val Leu
     130              135              140

Phe Glu Thr Leu Asn Glu Pro Val Ala Pro Thr Ala Glu Ile Trp Asn
145              150                155            160

Lys Val Lys Asp Arg Leu Cys Arg Val Ile Arg Ile His Ala Pro Trp
             165                170            175

Ser Thr Ile Ile Thr Gly Ser Asn Met Trp Asn Ser Pro Ser Ala Phe
         180                185              190

Asp Gly Leu Thr Pro Phe Asp Asp Gly Asn Val Ile Tyr Ser Val His
        195              200              205

Phe Tyr Glu Pro Leu Leu Phe Thr His Gln Asn Ala Pro Trp Ile Asp
     210              215              220

Asn Pro Glu Ile Arg Thr Ala Arg Pro Tyr Pro Gly Asp Tyr Gly Pro
225              230              235            240

Gly Leu Val Arg Lys Tyr Gly Met Ala Gln Ser Ala Gly Ile Trp Asn
             245                250            255

Lys Lys Arg Leu Ala Lys Glu Phe Glu Pro Val Asp Ala Phe Arg Lys
         260                265              270

Lys Tyr Lys Ala Arg Val Ile Cys Asn Glu Phe Gly Val Tyr Ala Pro
     275              280              285

Ala Asp Leu Glu Ser Gln Leu Arg Trp Tyr Glu Asp Leu Leu Ser Ile
         290             295              300

Leu Asn Gly Met Gln Ile Gly Tyr Ser Tyr Trp Asn Tyr Lys Asn Leu
305              310              315            320

Asp Phe Gly Ile Ile Ser Ile Gly Glu Lys Leu His Glu Arg Leu Ser
             325                330            335

Gln Tyr Asp Asn Asp Glu Arg Ile Asn His Pro Val Leu Asn Val Leu
         340                345              350

Lys Lys Tyr
     355

<210> SEQ ID NO 155
<211> LENGTH: 954
<212> TYPE: DNA
<213> ORGANISM: Unknown
<220> FEATURE:
<223> OTHER INFORMATION: Obtained from environmental sample

<400> SEQUENCE: 155

```
atgttaaagg attccggttt ttataagggc atcaatctcg gcggctggct gtcccagtgc    60
gactacagcg aggagcgcct gaacagcttc atcaccgaaa aggactttga ggtgatcgcc   120
tcctggggtt ttgaccacgt ccgcctcccg gtggactata atgtcatcca ggatgcggaa   180
ggccgcatga tggagaaagg ccttgcacgc atcgacgccg cgcttcggtt tgtgagaag    240 accgggcttc acatggttct cgacctgcat aagacaccgg ctttttcctt cgacccgcag   300
gagcaggaga tgggattctt ccggtcggcg cccgaccagc agctcttcta cacgatctgg   360
```

```
gagagccttg ctgcccggta tgcagacaaa tcggagatac tcatgttcga tcttctgaac    420
gagatcacgg agccggcgta tctggaggac tggaaccgga tttccgcgga atgcatccgc    480
cgcatccggc gtacgatgcc ggacgtccga attctggtcg aagctatca ccacaatgcc    540
gtcagcgcgt aaaggacct gcctgcgccg gcagacgata aggtttttta cagctttcac    600
tgttacgacc ctcacaccta tacccaccag ggcgcttact ggatgccgga tgactttgac    660
atcgatgcaa gagtttcctt ccgcgacacc ggcgttaccc ccgtcttctt cgaaaagctg    720
tttgcctccg ccgttgaaaa ggcgcaggcg aagggacgg aactgtactg cggagaatac     780
ggcgtcatcg acattgttcc gccggaggat gccgttctct ggttccggac cattcatgag    840
gtctttgaag cattcgggat tgcaagaagc gtctggagct ataaggaaat ggatttcggt    900
ctcgccgacc cccgcatgga tgcggtccgg gcagagctgc tgacctgtct ctga          954
```

<210> SEQ ID NO 156
<211> LENGTH: 317
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (14)...(302)
<223> OTHER INFORMATION: Cellulase (glycosyl hydrolase family 5)

<400> SEQUENCE: 156

```
Met Leu Lys Asp Ser Gly Phe Tyr Lys Gly Ile Asn Leu Gly Gly Trp
1               5                   10                  15
Leu Ser Gln Cys Asp Tyr Ser Glu Glu Arg Leu Asn Ser Phe Ile Thr
            20                  25                  30
Glu Lys Asp Phe Glu Val Ile Ala Ser Trp Gly Phe Asp His Val Arg
        35                  40                  45
Leu Pro Val Asp Tyr Asn Val Ile Gln Asp Ala Glu Gly Arg Met Met
    50                  55                  60
Glu Lys Gly Leu Ala Arg Ile Asp Ala Ala Leu Arg Phe Cys Glu Lys
65                  70                  75                  80
Thr Gly Leu His Met Val Leu Asp Leu His Lys Thr Pro Gly Phe Ser
                85                  90                  95
Phe Asp Pro Gln Glu Gln Glu Met Gly Phe Phe Arg Ser Ala Pro Asp
            100                 105                 110
Gln Gln Leu Phe Tyr Thr Ile Trp Glu Ser Leu Ala Ala Arg Tyr Ala
        115                 120                 125
Asp Lys Ser Glu Ile Leu Met Phe Asp Leu Leu Asn Glu Ile Thr Glu
    130                 135                 140
Pro Ala Tyr Leu Glu Asp Trp Asn Arg Ile Ser Ala Glu Cys Ile Arg
145                 150                 155                 160
Arg Ile Arg Arg Thr Met Pro Asp Val Arg Ile Leu Val Gly Ser Tyr
                165                 170                 175
His His Asn Ala Val Ser Ala Val Lys Asp Leu Pro Ala Pro Ala Asp
            180                 185                 190
Asp Lys Val Phe Tyr Ser Phe His Cys Tyr Asp Pro His Thr Tyr Thr
        195                 200                 205
His Gln Gly Ala Tyr Trp Met Pro Asp Phe Asp Ile Asp Ala Arg
    210                 215                 220
Val Ser Phe Arg Asp Thr Gly Val Thr Pro Val Phe Glu Lys Leu
225                 230                 235                 240
Phe Ala Ser Ala Val Glu Lys Ala Gln Ala Glu Gly Thr Glu Leu Tyr
```

```
                245                 250                 255
Cys Gly Glu Tyr Gly Val Ile Asp Ile Val Pro Pro Glu Asp Ala Val
            260                 265                 270

Leu Trp Phe Arg Thr Ile His Glu Val Phe Glu Ala Phe Gly Ile Ala
        275                 280                 285

Arg Ser Val Trp Ser Tyr Lys Glu Met Asp Phe Gly Leu Ala Asp Pro
    290                 295                 300

Arg Met Asp Ala Val Arg Ala Glu Leu Leu Thr Cys Leu
305                 310                 315

<210> SEQ ID NO 157
<211> LENGTH: 954
<212> TYPE: DNA
<213> ORGANISM: Unknown
<220> FEATURE:
<223> OTHER INFORMATION: Obtained from environmental sample

<400> SEQUENCE: 157
atgttaaagg attccggttt ttataagggc atcaatctcg gcggctggct gtcccagtgc      60
gactacagcg aggagcgcct gaacagcttc atcaccgaaa aagactttga ggtgatcgcc     120
tcctggggtt ttgaccacgt ccgtctgccg gtggactata atgtcatcca ggatgcggaa     180
ggccgcatga tggaggaagg cctcgcacgc atcgacgccg cgcttcggtt ttgtgaaaag     240
accgggcttc acatggttct cgacctgcat aagacaccgg gcttttcctt cgacccgcag     300
gagcaggaga tgggattctt ccggtcggcg cccgaccagc agcgcttcta cacgatctgg     360
gagagccttg ctgcccggta tgcagacaaa tcggagatgc tcatgttcga tcttctgaac     420
gagatcacgg agccggcgta tctgaaggac tggaaccgga tttccgcgga atgcatccgc     480
cgcatccggc gtacgatgcc ggacgtccgg attctggtcg gaagctatca ccacaatgcc     540
gtcagcgcgg taaaggacct gcctgcgccg gcggacgacc gggtttttta cagctttcac     600
tgttacgacc ctcacaccta tacccaccag ggcgcttact ggatgccgga tgactttgac     660
atcgatgcaa gagtttcctt ccgcgacatc ggcgtcaccc ccgccttctt cgaagagctg     720
tttgcatctg ccgttgaaaa ggcgaaggtg gaagggacgg aactgtactg cggagaatac     780
ggcgtcatcg acattgttcc gccggaggat gccgttctct ggttccggac cattcatgag     840
gtctttgaga aatacgggat tgcaagaagc gtctggagct ataaggaaat ggatttcggt     900
ctctccgacc cccgcatgga cgcggtccgg gcagagctgc tgacctgtct ctga           954

<210> SEQ ID NO 158
<211> LENGTH: 317
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (14)...(302)
<223> OTHER INFORMATION: Cellulase (glycosyl hydrolase family 5)

<400> SEQUENCE: 158

Met Leu Lys Asp Ser Gly Phe Tyr Lys Gly Ile Asn Leu Gly Gly Trp
1               5                   10                  15

Leu Ser Gln Cys Asp Tyr Ser Glu Glu Arg Leu Asn Ser Phe Ile Thr
            20                  25                  30

Glu Lys Asp Phe Glu Val Ile Ala Ser Trp Gly Phe Asp His Val Arg
        35                  40                  45

Leu Pro Val Asp Tyr Asn Val Ile Gln Asp Ala Glu Gly Arg Met Met
```

```
                  50                  55                  60
Glu Glu Gly Leu Ala Arg Ile Asp Ala Ala Leu Arg Phe Cys Glu Lys
 65                  70                  75                  80

Thr Gly Leu His Met Val Leu Asp Leu His Lys Thr Pro Gly Phe Ser
                 85                  90                  95

Phe Asp Pro Gln Glu Gln Met Gly Phe Phe Arg Ser Ala Pro Asp
            100                 105                 110

Gln Gln Arg Phe Tyr Thr Ile Trp Glu Ser Leu Ala Ala Arg Tyr Ala
            115                 120                 125

Asp Lys Ser Glu Met Leu Met Phe Asp Leu Leu Asn Glu Ile Thr Glu
130                 135                 140

Pro Ala Tyr Leu Lys Asp Trp Asn Arg Ile Ser Ala Glu Cys Ile Arg
145                 150                 155                 160

Arg Ile Arg Arg Thr Met Pro Asp Val Arg Ile Leu Val Gly Ser Tyr
                165                 170                 175

His His Asn Ala Val Ser Ala Val Lys Asp Leu Pro Ala Pro Ala Asp
            180                 185                 190

Asp Arg Val Phe Tyr Ser Phe His Cys Tyr Asp Pro His Thr Tyr Thr
            195                 200                 205

His Gln Gly Ala Tyr Trp Met Pro Asp Asp Phe Asp Ile Asp Ala Arg
210                 215                 220

Val Ser Phe Arg Asp Ile Gly Val Thr Pro Ala Phe Phe Glu Glu Leu
225                 230                 235                 240

Phe Ala Ser Ala Val Glu Lys Ala Lys Val Glu Gly Thr Glu Leu Tyr
                245                 250                 255

Cys Gly Glu Tyr Gly Val Ile Asp Ile Val Pro Pro Glu Asp Ala Val
            260                 265                 270

Leu Trp Phe Arg Thr Ile His Glu Val Phe Glu Lys Tyr Gly Ile Ala
            275                 280                 285

Arg Ser Val Trp Ser Tyr Lys Glu Met Asp Phe Gly Leu Ser Asp Pro
            290                 295                 300

Arg Met Asp Ala Val Arg Ala Glu Leu Leu Thr Cys Leu
305                 310                 315

<210> SEQ ID NO 159
<211> LENGTH: 1023
<212> TYPE: DNA
<213> ORGANISM: Unknown
<220> FEATURE:
<223> OTHER INFORMATION: Obtained from environmental sample

<400> SEQUENCE: 159
atgaatccaa cattcagttc cgtaccggca ttaaaggagc tgtttgcggc ggacttcaac      60 atcgggcgg cggtgaatcc gacgacgatc cggacgcagg aggcgttgct ggcttatcat     120
tttaacagcc tgactgcgga gaacgagatg aagttcgtca gcgtgcatcc ggaggagcag     180
acctatacct tcgaggcggc ggaccggctg gtcgaattcg cccgagagca cggcatggcc     240
atgcggggac acacgctcgt atggcataac cagacgtccg attggctgtt ccaggatcgc     300
caaggcggga gggtaagcaa ggaggtgctg ctcggaaggc tccgggagca tattcatacc     360
atagtaggcc ggtacaagaa cgagatctac gcctgggacg tcgtcaacga ggtcatcgcg     420
gacgaagggg aggcgctgct gcgcacttcc aaatggacgg aaatcgcggg acctgaattt     480
atcgctaaag cgttcgagta tgcacatgag gcggatccac aggcgctgtt gttttataac     540
gactacaacg aatcgaatcc tctgaaacgc gataaaattt acacactcgt tcattcgctg     600
```

-continued

```
ctggagcaag gggtgccgat ccatggcatc ggattacaag cgcactggaa cctgtacgat    660
ccatcgttgg atgagattaa ggcagcgatt gagaagtatg cttcgctggg tttgcagctg    720
cagctgacgg agctggatct ctcgatgttc cgcttcgatg accggcgaac cgatttgacc    780
gcgccagagc cggggatgct ggagcaacag gccgagcgtt atgaagccgt gttccggctg    840
ttgctggagt atcgtgacgt catcagcggc gttaccttct ggggagcggc ggatgattat    900
acctggctgg acaattttcc ggtgcgcggc cggaagaact ggccgtttct gttcgatgcc    960
cagcaccagc cgaaggcagc ttatcaccgt gtggcggcat ggctgcgga gcaacgagca   1020 taa                                                                 1023
```

<210> SEQ ID NO 160
<211> LENGTH: 340
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (10)...(335)
<223> OTHER INFORMATION: Glycosyl hydrolase family 10
<220> FEATURE:
<221> NAME/KEY: SITE
<222> LOCATION: (91)...(94)
<223> OTHER INFORMATION: N-glycosylation site. Prosite id = PS00001
<220> FEATURE:
<221> NAME/KEY: SITE
<222> LOCATION: (185)...(188)
<223> OTHER INFORMATION: N-glycosylation site. Prosite id = PS00001

<400> SEQUENCE: 160

```
Met Asn Pro Thr Phe Ser Ser Val Pro Ala Leu Lys Glu Leu Phe Ala
1               5                   10                  15

Ala Asp Phe Asn Ile Gly Ala Ala Val Asn Pro Thr Thr Ile Arg Thr
            20                  25                  30

Gln Glu Ala Leu Leu Ala Tyr His Phe Asn Ser Leu Thr Ala Glu Asn
        35                  40                  45

Glu Met Lys Phe Val Ser Val His Pro Glu Glu Gln Thr Tyr Thr Phe
    50                  55                  60

Glu Ala Ala Asp Arg Leu Val Glu Phe Ala Arg Glu His Gly Met Ala
65                  70                  75                  80

Met Arg Gly His Thr Leu Val Trp His Asn Gln Thr Ser Asp Trp Leu
                85                  90                  95

Phe Gln Asp Arg Gln Gly Gly Arg Val Ser Lys Glu Val Leu Leu Gly
            100                 105                 110

Arg Leu Arg Glu His Ile His Thr Ile Val Gly Arg Tyr Lys Asn Glu
        115                 120                 125

Ile Tyr Ala Trp Asp Val Val Asn Glu Val Ile Ala Asp Glu Gly Glu
    130                 135                 140

Ala Leu Leu Arg Thr Ser Lys Trp Thr Glu Ile Ala Gly Pro Glu Phe
145                 150                 155                 160

Ile Ala Lys Ala Phe Glu Tyr Ala His Glu Ala Asp Pro Gln Ala Leu
                165                 170                 175

Leu Phe Tyr Asn Asp Tyr Asn Glu Ser Asn Pro Leu Lys Arg Asp Lys
            180                 185                 190

Ile Tyr Thr Leu Val His Ser Leu Leu Glu Gln Gly Val Pro Ile His
        195                 200                 205

Gly Ile Gly Leu Gln Ala His Trp Asn Leu Tyr Asp Pro Ser Leu Asp
    210                 215                 220
```

```
Glu Ile Lys Ala Ala Ile Glu Lys Tyr Ala Ser Leu Gly Leu Gln Leu
225                 230                 235                 240

Gln Leu Thr Glu Leu Asp Leu Ser Met Phe Arg Phe Asp Asp Arg Arg
            245                 250                 255

Thr Asp Leu Thr Ala Pro Glu Pro Gly Met Leu Glu Gln Gln Ala Glu
            260                 265                 270

Arg Tyr Glu Ala Val Phe Arg Leu Leu Leu Glu Tyr Arg Asp Val Ile
        275                 280                 285

Ser Gly Val Thr Phe Trp Gly Ala Ala Asp Asp Tyr Thr Trp Leu Asp
    290                 295                 300

Asn Phe Pro Val Arg Gly Arg Lys Asn Trp Pro Phe Leu Phe Asp Ala
305                 310                 315                 320

Gln His Gln Pro Lys Ala Ala Tyr His Arg Val Ala Ala Leu Ala Ala
            325                 330                 335

Glu Gln Arg Ala
        340

<210> SEQ ID NO 161
<211> LENGTH: 2820
<212> TYPE: DNA
<213> ORGANISM: Unknown
<220> FEATURE:
<223> OTHER INFORMATION: Obtained from environmental sample

<400> SEQUENCE: 161
atgtcctgcc gcaccctgat gagtaggcgt gtaggatggg gacttttatt gtggggaggt      60
ttattcctca gaaccggttc ggttacagga caaacttaca attatgccga agtcctgcag     120
aaatctatgt ttttctacga atgtcaggag tctaaaattg ccccgggcaa tcgggtgaca     180
tggcgagcta atgcagccat gaacgatggg agcgatgttg aaaagacct gacaggagga      240 tggtttgatg caggtgacca tgtgaaattt aatttttccca tggcgtttac cgctacgggcg    300 ctggcgtggg gagctattga ctttgctcag ggatacatta gttccgggca aatgcaatac     360
ctgaaacgta atctgcgcta cgtcaatgac tatttcatta atgtcacaca agcccccaac     420
gaattgtatg gtcaggtggg taatggaggc cttgaccatg cctttgggg accacccgaa      480 gtcatgcgca tggctaggcc tgcctataaa attgatgcgt caaaacccgg atcagatctg     540
gctgccgaaa cagctgctgc aatggctgcc gccagcattg ttttcaaatc cgacgatcct     600
acctatagcg ctactttgct gaatcatgca aaacagctgt tttcttttgc cgaaacctat     660
aaaggaaaat attccgacgc tattaccgat gctgcaggat attataactc ctggagcggc     720
tataacgatg aactggtatg gggagctata tggctttacc gggctaccgg cgatgcaacc     780
tatctatcta aggcagaatc ctattacgac aatctgggta tcagggtca ggaacccgtt      840 aaagcctaca atggaccatt gcatgggat gacaaatcct atggctgtta tgccctactg     900
gccaaattga caggtaagga aaaatacaaa attgacgccg aacgttttct cgactattgg    960
accgatggtt ataatggttc ccggattact tatacccccgg aggactcgc tttcctcgat   1020 atatggggat cgttgcgcta tgctatgaat actgcctttg ttgctgccta ctatgccgat    1080
gcagccactt cagctgctaa aaccacaaaa tatctcaact ttgctaaaca acaactgcat    1140
tatgctcttg gatccaatcc gagcaacaga agctatgtct gtggctttgg caataatcct    1200
cccgttaatc ctcaccatag aggtgcacac ggagcatggt ctaataatgt tcaaggacct    1260
cctaccgaaa cacgacatat cctctacggc gcattagtgg gtggaccagg cagtaatgac    1320
tcctatactg acgaccgatc caattacacc aataacgaag tagcatgtga ctacaatgct    1380
```

-continued

```
cttttctccg gactgcttgc aaagttcgtc attgattatg gaggcacacc gttagccaac    1440
ttccctgttc gtgaaacccc aaaagatgaa tatttcgttg aagcaaaagc aaacgctaca    1500
ggaaccaatt tctccgaatg gacggtatgg gtatacaacc acactgcatg gccagcccgt    1560
gaaggttctg aatataaatt cagattatac gtaaatattt cggaaggact ggctgcaggc    1620
tatactgcct caaattatgt tgtgcaaacc aataatgccg gtgtggtaaa cttacccaa     1680 cttttagctg ctgatgcagc taacggcatc tattataccg aagtaacctt taaacctggt    1740
accgaaattt atcctggcgg gcaacagtat gacaagaagg aagctcagat gcgtattagt    1800
ttgcccaatg ctccggcttc tgcatgggat ccgactaacg cccgtcatg ggcgggaatc     1860 acctctacct tgaaacaaat gccgggtata cccatgtatg tagatggtgt aaaggtattt    1920
ggtaatgagc ctgtcccagg tcagacagtt cccgtcaccg gagtaaccgt atcgcctacc    1980
accctgagtc tgactgtagg acagaccagt acactcaccg ctaccgtatc gccggctaat    2040
gctaccaaca aaaacgtcac ctggagcagc agcaatacca gcgtagccac ggtaagctca    2100
acaggcgttg tcacagccgt agcagccggt tcggccacca tcaccgtaac cacagtcgat    2160
ggcgctaaaa cagccacctg cgccgtaacg gtaacaggca gcaccaacgt tcccgtcacc    2220
ggagtaaccg tatcgcccac cacgctgagt ctgaccgtag gcagaccgc tacccctcacc    2280 gctaccgtat cgccggctaa tgctaccaac aagaacgtta cctggagcag cagcaatacc    2340
agcgtagcca cggtaagttc aacaggcgta gttactgccg tagcggccgg ttcggccacc    2400
atcaccgtaa ccaccgtcga tggagctaaa accgctacct gcaccgtaac ggtaacgggc    2460
agcactaccg tacccgtcac cggcgtaact gtatcgccta ccaccctgag tctgaccgtt    2520
ggacaaaccg ctaccctgac cgctaccgta tcgccagctg atgctaccaa caagaacgtc    2580
acctggagca gcagcaatac cagcgtagcc acggtaagct caacaggcgt agtcactgcc    2640
gtagcggccg gttcagctac catcaccgtg accacagtcg atggggctaa aactgctacc    2700
tgtgccgtga ccgtaaccgc cggaggttcc accacccct gcagtaatcc ggtaagcaaa     2760 accctaccte tggtacagga tggtgccggc gaattcaggt tgagtaatag ttttaattaa    2820
```

<210> SEQ ID NO 162
<211> LENGTH: 939
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(30)
<220> FEATURE:
<221> NAME/KEY: DOMAIN
<222> LOCATION: (34)...(469)
<223> OTHER INFORMATION: Glycosyl hydrolase family 9
<220> FEATURE:
<221> NAME/KEY: DOMAIN
<222> LOCATION: (491)...(576)
<223> OTHER INFORMATION: Cellulose binding domain
<220> FEATURE:
<221> NAME/KEY: DOMAIN
<222> LOCATION: (738)...(816)
<223> OTHER INFORMATION: Bacterial Ig-like domain (group 2)
<220> FEATURE:
<221> NAME/KEY: DOMAIN
<222> LOCATION: (825)...(903)
<223> OTHER INFORMATION: Bacterial Ig-like domain (group 2)
<220> FEATURE:
<221> NAME/KEY: DOMAIN
<222> LOCATION: (651)...(729)
<223> OTHER INFORMATION: Bacterial Ig-like domain (group 2)

<400> SEQUENCE: 162

```
Met Ser Cys Arg Thr Leu Met Ser Arg Val Gly Trp Gly Leu Leu
1               5                   10                  15

Leu Trp Gly Gly Leu Phe Leu Arg Thr Gly Ser Val Thr Gly Gln Thr
            20                  25                  30

Tyr Asn Tyr Ala Glu Val Leu Gln Lys Ser Met Phe Phe Tyr Glu Cys
        35                  40                  45

Gln Glu Ser Lys Ile Ala Pro Gly Asn Arg Val Thr Trp Arg Ala Asn
    50                  55                  60

Ala Ala Met Asn Asp Gly Ser Asp Val Gly Lys Asp Leu Thr Gly Gly
65              70                  75                  80

Trp Phe Asp Ala Gly Asp His Val Lys Phe Asn Phe Pro Met Ala Phe
                85                  90                  95

Thr Ala Thr Ala Leu Ala Trp Gly Ala Ile Asp Phe Ala Gln Gly Tyr
            100                 105                 110

Ile Ser Ser Gly Gln Met Gln Tyr Leu Lys Arg Asn Leu Arg Tyr Val
        115                 120                 125

Asn Asp Tyr Phe Ile Lys Cys His Thr Ala Pro Asn Glu Leu Tyr Gly
    130                 135                 140

Gln Val Gly Asn Gly Gly Leu Asp His Ala Phe Trp Gly Pro Pro Glu
145                 150                 155                 160

Val Met Arg Met Ala Arg Pro Ala Tyr Lys Ile Asp Ala Ser Lys Pro
                165                 170                 175

Gly Ser Asp Leu Ala Ala Glu Thr Ala Ala Ala Met Ala Ala Ala Ser
            180                 185                 190

Ile Val Phe Lys Ser Asp Asp Pro Thr Tyr Ser Ala Thr Leu Leu Asn
        195                 200                 205

His Ala Lys Gln Leu Phe Ser Phe Ala Glu Thr Tyr Lys Gly Lys Tyr
    210                 215                 220

Ser Asp Ala Ile Thr Asp Ala Ala Gly Tyr Tyr Asn Ser Trp Ser Gly
225                 230                 235                 240

Tyr Asn Asp Glu Leu Val Trp Gly Ala Ile Trp Leu Tyr Arg Ala Thr
                245                 250                 255

Gly Asp Ala Thr Tyr Leu Ser Lys Ala Glu Ser Tyr Tyr Asp Asn Leu
            260                 265                 270

Gly Asn Gln Gly Gln Glu Pro Val Lys Ala Tyr Lys Trp Thr Ile Ala
        275                 280                 285

Trp Asp Asp Lys Ser Tyr Gly Cys Tyr Ala Leu Leu Ala Lys Leu Thr
    290                 295                 300

Gly Lys Glu Lys Tyr Lys Ile Asp Ala Glu Arg Phe Leu Asp Tyr Trp
305                 310                 315                 320

Thr Asp Gly Tyr Asn Gly Ser Arg Ile Thr Tyr Thr Pro Gly Gly Leu
                325                 330                 335

Ala Phe Leu Asp Ile Trp Gly Ser Leu Arg Tyr Ala Met Asn Thr Ala
            340                 345                 350

Phe Val Ala Ala Tyr Tyr Ala Asp Ala Thr Ser Ala Ala Lys Thr
        355                 360                 365

Thr Lys Tyr Leu Asn Phe Ala Lys Gln Gln Leu His Tyr Ala Leu Gly
    370                 375                 380

Ser Asn Pro Ser Asn Arg Ser Tyr Val Cys Gly Phe Gly Asn Asn Pro
385                 390                 395                 400

Pro Val Asn Pro His His Arg Gly Ala His Gly Ala Trp Ser Asn Asn
                405                 410                 415

Val Gln Gly Pro Pro Thr Glu Thr Arg His Ile Leu Tyr Gly Ala Leu
```

-continued

```
                420                 425                 430
Val Gly Gly Pro Gly Ser Asn Asp Ser Tyr Thr Asp Asp Arg Ser Asn
            435                 440                 445

Tyr Thr Asn Asn Glu Val Ala Cys Asp Tyr Asn Ala Leu Phe Ser Gly
    450                 455                 460

Leu Leu Ala Lys Phe Val Ile Asp Tyr Gly Gly Thr Pro Leu Ala Asn
465                 470                 475                 480

Phe Pro Val Arg Glu Thr Pro Lys Asp Glu Tyr Phe Val Glu Ala Lys
                485                 490                 495

Ala Asn Ala Thr Gly Thr Asn Phe Ser Glu Trp Thr Val Trp Val Tyr
            500                 505                 510

Asn His Thr Ala Trp Pro Ala Arg Glu Gly Ser Glu Tyr Lys Phe Arg
    515                 520                 525

Leu Tyr Val Asn Ile Ser Glu Gly Leu Ala Ala Gly Tyr Thr Ala Ser
530                 535                 540

Asn Tyr Val Val Gln Thr Asn Asn Ala Gly Val Val Asn Phe Thr Gln
545                 550                 555                 560

Leu Leu Ala Ala Asp Ala Ala Asn Gly Ile Tyr Tyr Thr Glu Val Thr
                565                 570                 575

Phe Lys Pro Gly Thr Glu Ile Tyr Pro Gly Gly Gln Gln Tyr Asp Lys
            580                 585                 590

Lys Glu Ala Gln Met Arg Ile Ser Leu Pro Asn Ala Pro Ala Ser Ala
    595                 600                 605

Trp Asp Pro Thr Asn Asp Pro Ser Trp Ala Gly Ile Thr Ser Thr Leu
610                 615                 620

Lys Gln Met Pro Gly Ile Pro Met Tyr Val Asp Gly Val Lys Val Phe
625                 630                 635                 640

Gly Asn Glu Pro Val Pro Gly Gln Thr Val Pro Val Thr Gly Val Thr
                645                 650                 655

Val Ser Pro Thr Thr Leu Ser Leu Thr Val Gly Gln Thr Ser Thr Leu
            660                 665                 670

Thr Ala Thr Val Ser Pro Ala Asn Ala Thr Asn Lys Asn Val Thr Trp
    675                 680                 685

Ser Ser Ser Asn Thr Ser Val Ala Thr Val Ser Ser Thr Gly Val Val
690                 695                 700

Thr Ala Val Ala Ala Gly Ser Ala Thr Ile Thr Val Thr Thr Val Asp
705                 710                 715                 720

Gly Ala Lys Thr Ala Thr Cys Ala Val Thr Val Thr Gly Ser Thr Asn
                725                 730                 735

Val Pro Val Thr Gly Val Thr Val Ser Pro Thr Thr Leu Ser Leu Thr
            740                 745                 750

Val Gly Gln Thr Ala Thr Leu Thr Ala Thr Val Ser Pro Ala Asn Ala
    755                 760                 765

Thr Asn Lys Asn Val Thr Trp Ser Ser Ser Asn Thr Ser Val Ala Thr
770                 775                 780

Val Ser Ser Thr Gly Val Val Thr Ala Val Ala Ala Gly Ser Ala Thr
785                 790                 795                 800

Ile Thr Val Thr Thr Val Asp Gly Ala Lys Thr Ala Thr Cys Thr Val
                805                 810                 815

Thr Val Thr Gly Ser Thr Thr Val Pro Val Thr Gly Val Thr Val Ser
            820                 825                 830

Pro Thr Thr Leu Ser Leu Thr Val Gly Gln Thr Ala Thr Leu Thr Ala
    835                 840                 845
```

```
Thr Val Ser Pro Ala Asp Ala Thr Asn Lys Asn Val Thr Trp Ser Ser
        850                 855                 860
Ser Asn Thr Ser Val Ala Thr Val Ser Thr Gly Val Val Thr Ala
865                 870                 875                 880
Val Ala Ala Gly Ser Ala Thr Ile Thr Val Thr Val Asp Gly Ala
                885                 890                 895
Lys Thr Ala Thr Cys Ala Val Thr Val Thr Ala Gly Gly Ser Thr Thr
                    900                 905                 910
Pro Cys Ser Asn Pro Val Ser Lys Thr Leu Pro Leu Val Gln Asp Gly
            915                 920                 925
Ala Gly Glu Phe Arg Leu Ser Asn Ser Phe Asn
        930                 935

<210> SEQ ID NO 163
<211> LENGTH: 2733
<212> TYPE: DNA
<213> ORGANISM: Unknown
<220> FEATURE:
<223> OTHER INFORMATION: Obtained from environmental sample

<400> SEQUENCE: 163
```

| | | | | | |
|---|---|---|---|---|---|
| atgcaaactt | acaattatgc | cgaagtcctg | cagaaatcta | tgtttttcta | cgaatgtcag | 60 |
| gagtctaaaa | ttgccccggg | caatcgggtg | acatggcgag | ctaatgcagc | catgaacgat | 120 |
| gggagcgatg | ttggaaaaga | cctgacagga | ggatggtttg | atgcaggtga | ccatgtgaaa | 180 |
| tttaattttc | ccatggcgtt | taccgctacg | gcgctggcgt | ggggagctat | tgactttgct | 240 |
| cagggataca | ttagttccgg | gcaaatgcaa | tacctgaaac | gtaatctgcg | ctacgtcaat | 300 |
| gactatttca | ttaaatgtca | cacagccccc | aacgaattgt | atggtcaggt | gggtaatgga | 360 |
| ggccttgacc | atgccttttg | ggaccacccc | gaagtcatgc | gcatggctag | gcctgcctat | 420 |
| aaaattgatg | cgtcaaaacc | cggatcagat | ctggctgccg | aaacagctgc | tgcaatggct | 480 |
| gccgccagca | ttgttttcaa | atccgacgat | cctacctata | gcgctacttt | gctgaatcat | 540 |
| gcaaaacagc | tgttttcttt | tgccgaaacc | tataaaggaa | atattccga | cgctattacc | 600 |
| gatgctgcag | atattataa | ctcctggagc | ggctataacg | atgaactggt | atggggagct | 660 |
| atatggcttt | accgggctac | cggcgatgca | acctatctat | ctaaggcaga | atcctattac | 720 |
| gacaatctgg | gtaatcaggg | tcaggaaccc | gttaaagcct | acaaatggac | cattgcatgg | 780 |
| gatgacaaat | cctatggctg | ttatgcccta | ctggccaaat | tgacaggtaa | ggaaaaatac | 840 |
| aaaattgacg | ccgaacgttt | tctcgactat | tggaccgatg | gttataatgg | ttcccggatt | 900 |
| acttatatccc | cggaggact | cgctttcctc | gatatatggg | gatcgttgcg | ctatgctatg | 960 |
| aatactgcct | ttgttgctgc | ctactatgcc | gatgcagcca | cttcagctgc | taaaaccaca | 1020 |
| aaatatctca | actttgctaa | caacaactg | cattatgctc | ttggatccaa | tccgagcaac | 1080 |
| agaagctatg | tctgtggctt | tggcaataat | cctcccgtta | atcctcacca | tagaggtgca | 1140 |
| cacggagcat | ggtctaataa | tgttcaagga | cctcctaccg | aaacacgaca | tatcctctac | 1200 |
| ggcgcattag | tgggtggacc | aggcagtaat | gactcctata | ctgacgaccg | atccaattac | 1260 |
| accaataacg | aagtagcatg | tgactacaat | gctcttttct | ccggactgct | tgcaaagttc | 1320 |
| gtcattgatt | atgaggcac | accgttagcc | aacttccctg | ttcgtgaaac | cccaaaagat | 1380 |
| gaatatttcg | ttgaagcaaa | agcaaacgct | acaggaacca | atttctccga | atggacggta | 1440 |
| tgggtataca | accacactgc | atggccagcc | cgtgaaggtt | ctgaatataa | attcagatta | 1500 |
| tacgtaaata | tttcggaagg | actggctgca | ggctatactg | cctcaaatta | tgttgtgcaa | 1560 |

-continued

```
accaataatg ccggtgtggt aaactttacc caacttttag ctgctgatgc agctaacggc    1620
atctattata ccgaagtaac ctttaaacct ggtaccgaaa tttatcctgg cgggcaacag    1680
tatgacaaga aggaagctca gatgcgtatt agtttgccca atgctccggc ttctgcatgg    1740
gatccgacta acgacccgtc atgggcggga atcacctcta ccttgaaaca aatgccgggt    1800
atacccatgt atgtagatgg tgtaaaggta tttggtaatg agcctgtccc aggtcagaca    1860
gttcccgtca ccggagtaac cgtatcgcct accaccctga gtctgactgt aggacagacc    1920
agtacactca ccgctaccgt atcgccggct aatgctacca caaaaacgt cacctggagc    1980
agcagcaata ccagcgtagc cacggtaagc tcaacaggcg ttgtcacagc cgtagcagcc    2040
ggttcggcca ccatcaccgt aaccacagtc gatggcgcta aacagccac ctgcgccgta    2100
acggtaacag gcagcaccaa cgttcccgtc accggagtaa ccgtatcgcc caccacgctg    2160
agtctgaccg tagggcagac cgctacccte accgctaccg tatcgccggc taatgctacc    2220
aacaagaacg ttacctggag cagcagcaat accagcgtag ccacggtaag ttcaacaggc    2280
gtagttactg ccgtagcggc cggttcggcc accatcaccg taaccaccgt cgatggagct    2340
aaaaccgcta cctgcaccgt aacggtaacg gcagcacta ccgtacccgt caccggcgta    2400
actgtatcgc ctaccaccct gagtctgacc gttggacaaa ccgctaccct gaccgctacc    2460
gtatcgccag ctgatgctac caacaagaac gtcacctgga gcagcagcaa taccagcgta    2520
gccacggtaa gctcaacagg cgtagtcact gccgtagcgg ccggttcagc taccatcacc    2580
gtgaccacag tcgatggggc taaaactgct acctgtgccg tgaccgtaac cgccggaggt    2640
tccaccaccc cctgcagtaa tccggtaagc aaaaccctac ctctggtaca ggatggtgcc    2700
ggcgaattca ggttgagtaa tagtttaat taa                                 2733
```

<210> SEQ ID NO 164
<211> LENGTH: 910
<212> TYPE: PRT
<213> ORGANISM: Unknown
<220> FEATURE:
<223> OTHER INFORMATION: Obtained from environmental sample
<220> FEATURE:
<221> NAME/KEY: DOMAIN
<222> LOCATION: (5)...(440)
<223> OTHER INFORMATION: Glycosyl hydrolase family 9
<220> FEATURE:
<221> NAME/KEY: DOMAIN
<222> LOCATION: (462)...(547)
<223> OTHER INFORMATION: Cellulose binding domain
<220> FEATURE:
<221> NAME/KEY: DOMAIN
<222> LOCATION: (709)...(787)
<223> OTHER INFORMATION: Bacterial Ig-like domain (group 2)
<220> FEATURE:
<221> NAME/KEY: DOMAIN
<222> LOCATION: (796)...(874)
<223> OTHER INFORMATION: Bacterial Ig-like domain (group 2)
<220> FEATURE:
<221> NAME/KEY: DOMAIN
<222> LOCATION: (622)...(700)
<223> OTHER INFORMATION: Bacterial Ig-like domain (group 2)

<400> SEQUENCE: 164

Met Gln Thr Tyr Asn Tyr Ala Glu Val Leu Gln Lys Ser Met Phe Phe
1               5                   10                  15

Tyr Glu Cys Gln Glu Ser Lys Ile Ala Pro Gly Asn Arg Val Thr Trp
            20                  25                  30

Arg Ala Asn Ala Ala Met Asn Asp Gly Ser Asp Val Gly Lys Asp Leu
        35                  40                  45

Thr Gly Gly Trp Phe Asp Ala Gly Asp His Val Lys Phe Asn Phe Pro

-continued

```
             50                  55                  60
Met Ala Phe Thr Ala Thr Ala Leu Ala Trp Gly Ala Ile Asp Phe Ala
 65                  70                  75                  80

Gln Gly Tyr Ile Ser Ser Gly Gln Met Gln Tyr Leu Lys Arg Asn Leu
                 85                  90                  95

Arg Tyr Val Asn Asp Tyr Phe Ile Lys Cys His Thr Ala Pro Asn Glu
            100                 105                 110

Leu Tyr Gly Gln Val Gly Asn Gly Gly Leu Asp His Ala Phe Trp Gly
            115                 120                 125

Pro Pro Glu Val Met Arg Met Ala Arg Pro Ala Tyr Lys Ile Asp Ala
130                 135                 140

Ser Lys Pro Gly Ser Asp Leu Ala Ala Glu Thr Ala Ala Ala Met Ala
145                 150                 155                 160

Ala Ala Ser Ile Val Phe Lys Ser Asp Asp Pro Thr Tyr Ser Ala Thr
                165                 170                 175

Leu Leu Asn His Ala Lys Gln Leu Phe Ser Phe Ala Glu Thr Tyr Lys
            180                 185                 190

Gly Lys Tyr Ser Asp Ala Ile Thr Asp Ala Ala Gly Tyr Tyr Asn Ser
            195                 200                 205

Trp Ser Gly Tyr Asn Asp Glu Leu Val Trp Gly Ala Ile Trp Leu Tyr
        210                 215                 220

Arg Ala Thr Gly Asp Ala Thr Tyr Leu Ser Lys Ala Glu Ser Tyr Tyr
225                 230                 235                 240

Asp Asn Leu Gly Asn Gln Gly Gln Glu Pro Val Lys Ala Tyr Lys Trp
                245                 250                 255

Thr Ile Ala Trp Asp Asp Lys Ser Tyr Gly Cys Tyr Ala Leu Leu Ala
            260                 265                 270

Lys Leu Thr Gly Lys Glu Lys Tyr Lys Ile Asp Ala Glu Arg Phe Leu
        275                 280                 285

Asp Tyr Trp Thr Asp Gly Tyr Asn Gly Ser Arg Ile Thr Tyr Thr Pro
        290                 295                 300

Gly Gly Leu Ala Phe Leu Asp Ile Trp Gly Ser Leu Arg Tyr Ala Met
305                 310                 315                 320

Asn Thr Ala Phe Val Ala Ala Tyr Tyr Ala Asp Ala Ala Thr Ser Ala
                325                 330                 335

Ala Lys Thr Thr Lys Tyr Leu Asn Phe Ala Lys Gln Gln Leu His Tyr
            340                 345                 350

Ala Leu Gly Ser Asn Pro Ser Asn Arg Ser Tyr Val Cys Gly Phe Gly
            355                 360                 365

Asn Asn Pro Pro Val Asn Pro His His Arg Gly Ala His Gly Ala Trp
        370                 375                 380

Ser Asn Asn Val Gln Gly Pro Pro Thr Glu Thr Arg His Ile Leu Tyr
385                 390                 395                 400

Gly Ala Leu Val Gly Gly Pro Gly Ser Asn Asp Ser Tyr Thr Asp Asp
                405                 410                 415

Arg Ser Asn Tyr Thr Asn Asn Glu Val Ala Cys Asp Tyr Asn Ala Leu
            420                 425                 430

Phe Ser Gly Leu Leu Ala Lys Phe Val Ile Asp Tyr Gly Gly Thr Pro
            435                 440                 445

Leu Ala Asn Phe Pro Val Arg Glu Thr Pro Lys Asp Glu Tyr Phe Val
        450                 455                 460

Glu Ala Lys Ala Asn Ala Thr Gly Thr Asn Phe Ser Glu Trp Thr Val
465                 470                 475                 480
```

```
Trp Val Tyr Asn His Thr Ala Trp Pro Ala Arg Glu Gly Ser Glu Tyr
                485                 490                 495

Lys Phe Arg Leu Tyr Val Asn Ile Ser Glu Gly Leu Ala Ala Gly Tyr
            500                 505                 510

Thr Ala Ser Asn Tyr Val Val Gln Thr Asn Asn Ala Gly Val Val Asn
        515                 520                 525

Phe Thr Gln Leu Leu Ala Ala Asp Ala Ala Asn Gly Ile Tyr Tyr Thr
    530                 535                 540

Glu Val Thr Phe Lys Pro Gly Thr Glu Ile Tyr Pro Gly Gly Gln Gln
545                 550                 555                 560

Tyr Asp Lys Lys Glu Ala Gln Met Arg Ile Ser Leu Pro Asn Ala Pro
                565                 570                 575

Ala Ser Ala Trp Asp Pro Thr Asn Asp Pro Ser Trp Ala Gly Ile Thr
            580                 585                 590

Ser Thr Leu Lys Gln Met Pro Gly Ile Pro Met Tyr Val Asp Gly Val
        595                 600                 605

Lys Val Phe Gly Asn Glu Pro Val Pro Gly Gln Thr Val Pro Val Thr
    610                 615                 620

Gly Val Thr Val Ser Pro Thr Thr Leu Ser Leu Thr Val Gly Gln Thr
625                 630                 635                 640

Ser Thr Leu Thr Ala Thr Val Ser Pro Ala Asn Ala Thr Asn Lys Asn
                645                 650                 655

Val Thr Trp Ser Ser Asn Thr Ser Val Ala Thr Val Ser Ser Thr
            660                 665                 670

Gly Val Val Thr Ala Val Ala Ala Gly Ser Ala Thr Ile Thr Val Thr
        675                 680                 685

Thr Val Asp Gly Ala Lys Thr Ala Thr Cys Ala Val Thr Val Thr Gly
    690                 695                 700

Ser Thr Asn Val Pro Val Thr Gly Val Thr Val Ser Pro Thr Thr Leu
705                 710                 715                 720

Ser Leu Thr Val Gly Gln Thr Ala Thr Leu Thr Ala Thr Val Ser Pro
                725                 730                 735

Ala Asn Ala Thr Asn Lys Asn Val Thr Trp Ser Ser Ser Asn Thr Ser
            740                 745                 750

Val Ala Thr Val Ser Ser Thr Gly Val Val Thr Ala Val Ala Ala Gly
        755                 760                 765

Ser Ala Thr Ile Thr Val Thr Thr Val Asp Gly Ala Lys Thr Ala Thr
    770                 775                 780

Cys Thr Val Thr Val Thr Gly Ser Thr Thr Val Pro Val Thr Gly Val
785                 790                 795                 800

Thr Val Ser Pro Thr Thr Leu Ser Leu Thr Val Gly Gln Thr Ala Thr
                805                 810                 815

Leu Thr Ala Thr Val Ser Pro Ala Asp Ala Thr Asn Lys Asn Val Thr
            820                 825                 830

Trp Ser Ser Ser Asn Thr Ser Val Ala Thr Val Ser Ser Thr Gly Val
        835                 840                 845

Val Thr Ala Val Ala Ala Gly Ser Ala Thr Ile Thr Val Thr Thr Val
    850                 855                 860

Asp Gly Ala Lys Thr Ala Thr Cys Ala Val Thr Val Thr Ala Gly Gly
865                 870                 875                 880

Ser Thr Thr Pro Cys Ser Asn Pro Val Ser Lys Thr Leu Pro Leu Val
                885                 890                 895

Gln Asp Gly Ala Gly Glu Phe Arg Leu Ser Asn Ser Phe Asn
            900                 905                 910
```

<210> SEQ ID NO 165
<211> LENGTH: 1347
<212> TYPE: DNA
<213> ORGANISM: Unknown
<220> FEATURE:
<223> OTHER INFORMATION: Obtained from environmental sample

<400> SEQUENCE: 165

```
atgacaatta acaacaaaac tacagcgagt cctagtattc ccagcaccca caattccctc      60
ccgtcgcttc gcacactgtt taccaccagc ctgctcacgc tggccctgac cgcctgcggt     120
ggttcttcca gcagcgacaa ggacccttca agctccagct ccagtgaatc atcaagttcc     180
agcgaatcct cgagctcagc ttccagcgaa tcctcgagca gtgagtccag cagtagctct     240
tccgcgggcc atttctccat cgagccggac ttccagctct acagcctggc caacttcccg     300
gtgggcgtgg cggtctccgc cgccaacgag aacgacagca tcttcaacag tccggatgcc     360
gccgaacgtc aggccgttat tattgagcac ttctctcagc tcaccgccgg caacatcatg     420
aaaatgagct acctgcagcc gagtcaaggc aacttcacct tcgatgacgc cgacgagttg     480
gttaacttcg cccaagccaa tggcatgacc gtacacggcc actccaccat ctggcacgcg     540
gactaccaag taccgaactt catgagaaac tttgaaggtg accaggagga atgggcagaa     600
attctgaccg atcacgtcac taccatcatc gagcacttcc ccgacgatgt ggtcatcagc     660
tgggacgtgg tgaacgaggc tgtcgatcaa ggcacggcga acggctggcg ccattcggtg     720
ttctacaatg cattcgacgc cccggaagaa ggcgacattc ccgaatacat caaagtcgct     780
ttccgcgccg cgcgcgaggc tgacgccaac gtagacctct actacaacga ctacgacaat     840
accgccaatg cccagcgcct ggccaaaaca ctgcaaattg ccgaggtact ggacgccgaa     900
ggcaccattg acggcgtcgg tttccagatg cacgcctaca tggattaccc gagcctgacc     960
cattttgaaa acgccttccg gcaagtcgtc gacctggggc tcaaagtgaa agttaccgag    1020
ctggacgtat ccgtagtcaa cccctacggc ggcgaagcac ctccacaacc ggaatacgac    1080
aaagaactgg ccggcgcgca aaaactgcgc ttctgccaaa tcgccgaagt ttacatgaac    1140
actgtacccg aggagttacg cggtggcttc accgtctggg gcctgaccga tgatgaaagt    1200
tggctgatgc aacagttcag aaacgccacc ggcgccgact acgacgacgt ctggccgtta    1260
ctgttcaatg ccgacaaatc cgccaaaccg gcactgcaag gcgtggccga cgcctttacc    1320
ggacaaacct gcacctccga gttctaa                                        1347
```

<210> SEQ ID NO 166
<211> LENGTH: 448
<212> TYPE: PRT
<213> ORGANISM: Unknown
<220> FEATURE:
<223> OTHER INFORMATION: Obtained from environmental sample
<220> FEATURE:
<221> NAME/KEY: SIGNAL
<222> LOCATION: (1)...(45)

<400> SEQUENCE: 166

```
Met Thr Ile Asn Asn Lys Thr Thr Ala Ser Pro Ser Ile Pro Ser Thr
1               5                   10                  15

His Asn Ser Leu Pro Ser Leu Arg Thr Leu Phe Thr Thr Ser Leu Leu
            20                  25                  30

Thr Leu Ala Leu Thr Ala Cys Gly Gly Ser Ser Ser Asp Lys Asp
        35                  40                  45

Pro Ser Ser Ser Ser Ser Ser Glu Ser Ser Ser Ser Glu Ser Ser
```

```
                    50                  55                  60
Ser Ser Ala Ser Ser Glu Ser Ser Ser Glu Ser Ser Ser Ser Ser Ser
65                  70                  75                  80

Ser Ala Gly His Phe Ser Ile Glu Pro Asp Phe Gln Leu Tyr Ser Leu
                85                  90                  95

Ala Asn Phe Pro Val Gly Val Ala Val Ser Ala Ala Asn Glu Asn Asp
                100                 105                 110

Ser Ile Phe Asn Ser Pro Asp Ala Ala Glu Arg Gln Ala Val Ile Ile
                115                 120                 125

Glu His Phe Ser Gln Leu Thr Ala Gly Asn Ile Met Lys Met Ser Tyr
                130                 135                 140

Leu Gln Pro Ser Gln Gly Asn Phe Thr Phe Asp Asp Ala Asp Glu Leu
145                 150                 155                 160

Val Asn Phe Ala Gln Ala Asn Gly Met Thr Val His Gly His Ser Thr
                165                 170                 175

Ile Trp His Ala Asp Tyr Gln Val Pro Asn Phe Met Arg Asn Phe Glu
                180                 185                 190

Gly Asp Gln Glu Glu Trp Ala Glu Ile Leu Thr Asp His Val Thr Thr
                195                 200                 205

Ile Ile Glu His Phe Pro Asp Asp Val Val Ile Ser Trp Asp Val Val
                210                 215                 220

Asn Glu Ala Val Asp Gln Gly Thr Ala Asn Gly Trp Arg His Ser Val
225                 230                 235                 240

Phe Tyr Asn Ala Phe Asp Ala Pro Glu Glu Gly Asp Ile Pro Glu Tyr
                245                 250                 255

Ile Lys Val Ala Phe Arg Ala Ala Arg Glu Ala Asp Ala Asn Val Asp
                260                 265                 270

Leu Tyr Tyr Asn Asp Tyr Asp Asn Thr Ala Asn Ala Gln Arg Leu Ala
                275                 280                 285

Lys Thr Leu Gln Ile Ala Glu Val Leu Asp Ala Glu Gly Thr Ile Asp
290                 295                 300

Gly Val Gly Phe Gln Met His Ala Tyr Met Asp Tyr Pro Ser Leu Thr
305                 310                 315                 320

His Phe Glu Asn Ala Phe Arg Gln Val Val Asp Leu Gly Leu Lys Val
                325                 330                 335

Lys Val Thr Glu Leu Asp Val Ser Val Val Asn Pro Tyr Gly Gly Glu
                340                 345                 350

Ala Pro Pro Gln Pro Glu Tyr Asp Lys Glu Leu Ala Gly Ala Gln Lys
                355                 360                 365

Leu Arg Phe Cys Gln Ile Ala Glu Val Tyr Met Asn Thr Val Pro Glu
                370                 375                 380

Glu Leu Arg Gly Gly Phe Thr Val Trp Gly Leu Thr Asp Asp Glu Ser
385                 390                 395                 400

Trp Leu Met Gln Gln Phe Arg Asn Ala Thr Gly Ala Asp Tyr Asp Asp
                405                 410                 415

Val Trp Pro Leu Leu Phe Asn Ala Asp Lys Ser Ala Lys Pro Ala Leu
                420                 425                 430

Gln Gly Val Ala Asp Ala Phe Thr Gly Gln Thr Cys Thr Ser Glu Phe
                435                 440                 445
```